(12) United States Patent
Corey

(10) Patent No.: US 11,708,423 B2
(45) Date of Patent: Jul. 25, 2023

(54) CHIMERIC ENGULFMENT RECEPTOR MOLECULES AND METHODS OF USE

(71) Applicant: CERO THERAPEUTICS, INC., South San Francisco, CA (US)

(72) Inventor: Daniel Mark Corey, Menlo Park, CA (US)

(73) Assignee: CERO THERAPEUTICS, INC., South San Francisco, CA (US)

( * ) Notice: Subject to any disclaimer, the term of this patent is extended or adjusted under 35 U.S.C. 154(b) by 186 days.

(21) Appl. No.: 16/646,530

(22) PCT Filed: Sep. 21, 2018

(86) PCT No.: PCT/US2018/052297
§ 371 (c)(1),
(2) Date: Mar. 11, 2020

(87) PCT Pub. No.: WO2019/067328
PCT Pub. Date: Apr. 4, 2019

(65) Prior Publication Data
US 2020/0308305 A1  Oct. 1, 2020

Related U.S. Application Data

(60) Provisional application No. 62/652,822, filed on Apr. 4, 2018, provisional application No. 62/649,529, filed on Mar. 28, 2018, provisional application No. 62/563,615, filed on Sep. 26, 2017.

(51) Int. Cl.
| | |
|---|---|
| C07K 16/44 | (2006.01) |
| A61P 35/00 | (2006.01) |
| A61K 35/17 | (2015.01) |
| C07K 14/705 | (2006.01) |
| C07K 14/735 | (2006.01) |
| C07K 16/28 | (2006.01) |

(52) U.S. Cl.
CPC ............. *C07K 16/44* (2013.01); *A61K 35/17* (2013.01); *A61P 35/00* (2018.01); *C07K 14/70503* (2013.01); *C07K 14/70535* (2013.01); *C07K 14/70596* (2013.01); *C07K 16/2803* (2013.01); *C07K 2317/53* (2013.01); *C07K 2317/622* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 5,019,368 A | 5/1991 | Epstein et al. |
| 5,283,173 A | 2/1994 | Fields et al. |
| 5,468,614 A | 11/1995 | Fields et al. |
| 5,641,863 A | 6/1997 | Schreiber et al. |
| 5,641,875 A | 6/1997 | Schreiber et al. |
| 5,747,498 A | 5/1998 | Schnur et al. |
| 5,776,910 A | 7/1998 | Schreiber et al. |
| 5,821,071 A | 10/1998 | Schreiber et al. |
| 6,068,983 A | 5/2000 | Schreiber et al. |
| 6,475,997 B1 | 11/2002 | Schreiber et al. |
| 6,630,313 B2 | 10/2003 | Fadok et al. |
| 7,195,761 B2 | 3/2007 | Holtzman et al. |
| 7,247,303 B2 | 7/2007 | Thorpe et al. |
| 7,892,544 B2 | 2/2011 | Pfeifer et al. |
| 7,910,333 B2 | 3/2011 | Chilcote et al. |
| 8,025,878 B2 | 9/2011 | Gellerfors et al. |
| 8,119,772 B2 | 2/2012 | Yang et al. |
| 8,496,938 B2 | 7/2013 | Smith et al. |
| 8,940,276 B2 | 1/2015 | Weihofen et al. |
| 8,956,616 B2 | 2/2015 | Thorpe et al. |
| 10,093,717 B2 | 10/2018 | Li et al. |
| 10,980,836 B1 | 4/2021 | Getts et al. |
| 2003/0072743 A1 | 4/2003 | Albert et al. |
| 2003/0095962 A1 | 5/2003 | Ueda et al. |
| 2003/0124114 A1 | 7/2003 | McIntire et al. |
| 2003/0130218 A1 | 7/2003 | Schreiber et al. |
| 2006/0002940 A1 | 1/2006 | Stevenson |
| 2006/0257359 A1 | 11/2006 | Francois et al. |
| 2007/0258897 A1 | 11/2007 | Devitt et al. |
| 2008/0213216 A1 | 9/2008 | Schreiber et al. |
| 2011/0165649 A1 | 7/2011 | Tyler et al. |
| 2013/0071414 A1 | 3/2013 | Dotti et al. |
| 2014/0162290 A1 | 6/2014 | Watanabe et al. |
| 2015/0023986 A1 | 1/2015 | Jones et al. |
| 2017/0058024 A1 | 3/2017 | West et al. |
| 2017/0151281 A1* | 6/2017 | Wagner ............... C12N 5/0645 |

(Continued)

FOREIGN PATENT DOCUMENTS

| | | |
|---|---|---|
| EP | 0566226 B1 | 11/1995 |
| EP | 0520722 B1 | 12/1996 |

(Continued)

OTHER PUBLICATIONS

Moeller-Tank et al. (J. Virology Jun. 2014 88(12): 6702-6713) (Year: 2014).*
Aderem, "Phagocytosis and the Inflammatory Response," *JID* 187(Suppl 2):S340-S345, 2003.
Agaugue et al., "224. Development of Safer & Optimized CAR-T Cells Using Lentiviral Vectors," *Mol. Ther.* 23(Suppl. 1):S88, May 2015.
Aggen et al., "Single-chain V(alpha)V(beta) T-cell receptors function without mispairing with endogenous TCR chains," *Gene Therapy* 19:365-374, 2012.
Albert et al., "αvβ5 integrin recruits the CrkII-Dock180-Rac1 complex for phagocytosis of apoptotic cells," *Nature Cell Biology* 2:899-905, Dec. 2000.

(Continued)

*Primary Examiner* — Peter J Reddig
(74) *Attorney, Agent, or Firm* — Seed Intellectual Property Law Group LLP

(57) ABSTRACT

The present disclosure relates to chimeric engulfment receptor molecules, host cells modified to include the phagocytic engulfment molecules, and methods of making and using such receptor molecules and modified cells.

27 Claims, 98 Drawing Sheets

Specification includes a Sequence Listing.

(56) References Cited

U.S. PATENT DOCUMENTS

| | | |
|---|---|---|
| 2017/0166622 A1 | 6/2017 | Baeuerle et al. |
| 2017/0166657 A1 | 6/2017 | O'Neill et al. |
| 2018/0186855 A1 | 7/2018 | Rosenthal |
| 2018/0186878 A1 | 7/2018 | Rosenthal |
| 2018/0291089 A1 | 10/2018 | Epstein et al. |
| 2018/0319862 A1 | 11/2018 | Thompson et al. |
| 2018/0334653 A1 | 11/2018 | O'Neill |
| 2019/0350972 A1 | 11/2019 | Mason et al. |
| 2020/0002402 A1 | 1/2020 | Emtage et al. |
| 2020/0055917 A1 | 2/2020 | Corey |
| 2021/0015865 A1 | 1/2021 | Corey |
| 2021/0023135 A1 | 1/2021 | Corey |
| 2021/0024607 A1 | 1/2021 | Corey et al. |
| 2021/0087251 A1 | 3/2021 | Corey |
| 2021/0253696 A1 | 8/2021 | Corey et al. |
| 2022/0098273 A1 | 3/2022 | Corey |

FOREIGN PATENT DOCUMENTS

| | | |
|---|---|---|
| EP | 0787722 A1 | 8/1997 |
| EP | 0837063 A1 | 4/1998 |
| EP | 0564409 B1 | 1/2000 |
| WO | WO 9633980 A1 | 10/1996 |
| WO | WO 9702266 A1 | 1/1997 |
| WO | WO 9709433 A1 | 3/1997 |
| WO | WO 9730034 A1 | 8/1997 |
| WO | WO 9738983 A1 | 10/1997 |
| WO | WO 9749688 A1 | 12/1997 |
| WO | WO 9810767 A2 | 3/1998 |
| WO | WO 9903854 A1 | 1/1999 |
| WO | WO 0168709 A1 | 9/2001 |
| WO | WO 0185207 A2 | 11/2001 |
| WO | WO 02066470 A1 | 8/2002 |
| WO | WO 03064383 A2 | 8/2003 |
| WO | WO 2004067569 A1 | 8/2004 |
| WO | WO 2005019429 A2 | 3/2005 |
| WO | WO 2005090573 A1 | 9/2005 |
| WO | WO 2005097211 A2 | 10/2005 |
| WO | WO 2006122806 A2 | 11/2006 |
| WO | WO 2007084786 A1 | 7/2007 |
| WO | WO 2009036082 A2 | 3/2009 |
| WO | WO 2009055730 A1 | 4/2009 |
| WO | WO 2013074916 A1 | 5/2013 |
| WO | WO 2013192294 A1 | 12/2013 |
| WO | WO 2014031687 A1 | 2/2014 |
| WO | WO 2014059173 A2 | 4/2014 |
| WO | WO 2015066262 A1 | 5/2015 |
| WO | WO 2015123642 A1 | 8/2015 |
| WO | WO 2015184228 A1 | 12/2015 |
| WO | WO 2016019300 A1 | 2/2016 |
| WO | WO 2016044605 A1 | 3/2016 |
| WO | WO 2016126608 A1 | 8/2016 |
| WO | WO 2017019848 A1 | 2/2017 |
| WO | WO 2017025944 A2 | 2/2017 |
| WO | WO 2017083700 A1 | 5/2017 |
| WO | WO 2017205747 A1 | 11/2017 |
| WO | WO 2017219916 A1 | 12/2017 |
| WO | WO 2018031419 A1 | 2/2018 |
| WO | WO 2018064076 A1 | 4/2018 |
| WO | WO 2018132695 A1 | 7/2018 |
| WO | WO 2018212770 A1 | 11/2018 |
| WO | WO 2018220224 A1 | 12/2018 |
| WO | WO 2019067328 A1 | 4/2019 |
| WO | WO 2019079529 A1 | 4/2019 |
| WO | WO 2019086512 A1 | 5/2019 |
| WO | WO 2019091478 A1 | 5/2019 |
| WO | WO 2019157440 A1 | 8/2019 |
| WO | WO 2019191332 A1 | 10/2019 |
| WO | WO 2019191334 A1 | 10/2019 |
| WO | WO 2019191339 A1 | 10/2019 |
| WO | WO 2019191340 A1 | 10/2019 |
| WO | WO 2020114518 A1 | 6/2020 |
| WO | WO 2020223550 A1 | 11/2020 |
| WO | WO 2021003428 A1 | 1/2021 |
| WO | WO 2021067875 A1 | 4/2021 |
| WO | WO2022/036265 | 2/2022 |
| WO | WO2022/036285 | 2/2022 |
| WO | WO2022/036287 | 2/2022 |
| WO | WO 2022036265 A1 | 2/2022 |
| WO | WO 2022036285 A1 | 2/2022 |
| WO | WO 2022036287 A1 | 2/2022 |
| WO | WO 2023010097 A1 | 2/2023 |

OTHER PUBLICATIONS

Alder et al., "Antibody responses of variable lymphocyte receptors in the lamprey," Nature Immunology 9(3):319-327, Mar. 2008.

Altman et al., "Phenotypic Analysis of Antigen-Specific T Lymphocytes," Science 274:94-96, 1996.

Arandjelovic et al., "Phagocytosis of apoptotic cells in homeostasis," Nat. Immunol. 16(9):907-917, Sep. 2015.

Baral et al., "Experimental therapy of African trypanosomiasis with a nanobody-conjugated human trypanolytic factor," Nature Medicine 12(5):580-584, May 2006.

Barthelemy et al., "Comprehensive Analysis of the Factors Contributing to the Stability and Solubility of Autonomous Human VH Domains," J. Biol. Chem. 283(6):3639-3654, Feb. 8, 2008.

Belzile et al., "Antibody targeting of phosphatidylserine for the detection and immunotherapy of cancer," ImmunoTargets and Therapy, (7) pp. 1-14, 2018.

Blackburn et al., "Coregulation of CD8+ T cell exhaustion by multiple inhibitory receptors during chronic viral infection," Nature Immunology 10(1):29-37, Jan. 2009.

Burns et al., "A high molecular weight-melanoma associated antigen-specific chimeric antigen receptor redirects lymphocytes to target human melanomas," Cancer Res. 70(8):3027-3033, Apr. 15, 2010.

Castellano et al., "Membrane recruitment of Rae1 triggers phagocytosis," Journal of Cell Science 113:2955-2961, 2000.

Chen et al., "Fusion Protein Linkers: Property, Design and Functionality," Adv. Drug Deliv. Rev. 65(10):1357-1369, Oct. 15, 2013.

Clackson et al., "Making antibody fragments using phage display libraries," Nature 352:624-628, Aug. 1991.

Colman, "Effects of amino acid sequence changes on antibody-antigen interactions," Research in Immunology 145(1):33-36, 1994.

Cordoba et al., "The large ectodomains of CD45 and CD 148 regulate their segregation from and inhibition of ligated T-cell receptor," Blood 121(21):4295-4302, 2013.

Cortez-Retamozo et al., "Efficient Cancer Therapy with a Nanobody-Based Conjugate," Cancer Research 64:2853-2857, Apr. 2004.

Delgado Tascón et al., "The granulocyte orphan receptor CEACAM4 is able to trigger phagocytosis of bacteria," Journal of Leukocyte Biology 97:521-531, Mar. 2015.

Dillon et al., "Annexin V Binds to Viable B Cells and Colocalizes with a Marker of Lipid Rafts upon B Cell Receptor Activation," The Journal of Immunology 164:1322-1332, 2000.

Dolezal et al., "ScFv multimers of the anti-neuraminidase antibody NC10: shortening of the linker in single-chain Fv fragment assembled in V(L) to V(H) orientation drives the formation of dimers, trimers, tetramers and higher molecular mass multimers," Protein Engineering 13(8):565-574, 2000.

Duclos et al., "Rab5 regulates the kiss and run fusion between phagosomes and endosomes and the acquisition of phagosome leishmanicidal properties in RAW 264.7 macrophages," Journal of Cell Science 113:3531-3541, 2000.

Engels et al., "Retroviral Vectors for High-Level Transgene Expression in T Lymphocytes," Human Gene Therapy 14:1155-1168, Aug. 2003.

Feng et al., "Interleukin-6 increases prostate cancer cells resistance to bicalutamide via TIF2," Mol. Cancer Ther. 8(3):665-671, Mar. 2009.

Fesnak et al., "Engineered T Cells: The Promise and Challenges of Cancer Immunotherapy," Nature Reviews Cancer 16(9):566-581, Sep. 2016.

Frecha et al., "Advances in the Field of Lentivector-based Transduction of T and B Lymphocytes for Gene Therapy," Molecular Therapy 18(10):1748-1757, Oct. 2010.

Gerber et al., "Tumor-specific targeting by Bavituximab, a phosphatidylserine-targeting monoclonal antibody with vascular

(56) References Cited

OTHER PUBLICATIONS targeting and immune modulating properties, in lung cancer xenografts," *Am. J. Nucl. Med. Mol. Imaging* 5(5):493-503, 2015.
Ghahroudi et al., "Selection and identification of single domain antibody fragments from camel heavy-chain antibodies," *FEBS Letters* 414:521-526, 1997.
Green et al., "Mitochondria and Apoptosis," *Science* 281(5381):1309-1312, Aug. 1998.
Greenberg et al., "Clustered syk tyrosine kinase domains trigger phagocytosis," *Proc. Natl. Acad. Sci. USA* 93:1103-1107, Feb. 1996.
Greenberg, "Programmed cell death: A way of life for plants," *Proc. Natl. Acad. Sci. USA* 93:12094-12097, Oct. 1996.
Guest et al., "The Role of Extracellular Spacer Regions in the Optimal Design of Chimeric Immune Receptors: Evaluation of Four Different scFvs and Antigens," *Journal of Immunotherapy* 28(3):203-211, May/Jun. 2005.
Hamers-Casterman et al., "Naturally occurring antibodies devoid of light chains," *Nature* 363:446-448, Jun. 1993.
Hanayama et al., "Identification of a factor that links apoptotic cells to phagocytes," *Nature* 417:182-187, May 2002.
Hartt Meyers et al., "TIM-4 is the ligand for TIM-1, and the TIM-1-TIM-4 interaction regulates T cell proliferation," *Nat. Immunol.* 6(5):455-464, May 2005.
Herrin et al., "Structure and specificity of lamprey monoclonal antibodies," *PNAS* 105(6):2040-2045, Feb. 2008.
Hochreiter-Hufford et al., "Clearing the Dead: Apoptotic Cell Sensing, Recognition, Engulfment, and Digestion," *Cold Spring Harb Perspect Biol* 5:a008748, 2013. (21 pages).
Hudecek et al., "Receptor Affinity and Extracellular Domain Modifications Affect Tumor Recognition by ROR1-Specific Chimeric Antigen Receptor T Cells," *Clin. Cancer Res.* 19(12):3153-31564, 2013.
Hudecek et al., "The Nonsignaling Extracellular Spacer Domain of Chimeric Antigen Receptors Is Decisive for In Vivo Antitumor Activity," *Cancer Immunol. Res.* 3(2):125-135, Feb. 2015.
Hull et al., "The Mononuclear Phagocyte System in Homeostasis and Disease: A Role for Heme Oxygenase-1," *Antioxidants & Redox Signaling* 20(11):1770-1788, 2014.
International Search Report and Written Opinion, dated Aug. 19, 2019, for International Application No. PCT/US2019/024441, 13 pages.
International Search Report and Written Opinion, dated Feb. 6, 2018, for International Application No. PCT/US17/53553, 13 pages.
International Search Report and Written Opinion, dated Jun. 28, 2019, for International Application No. PCT/US2019/024442, 12 pages.
International Search Report and Written Opinion, dated Jun. 7, 2019, for International Application No. PCT/US2019/024433, 13 pages.
International Search Report and Written Opinion, dated Mar. 25, 2019, for International Application No. PCT/US2018/052297, 10 pages.
International Search Report and Written Opinion, dated May 29, 2019, for International Application No. PCT/US2019/024435, 12 pages.
Jespers et al., "Aggregation-resistant domain antibodies selected on phage by heat denaturation," *Nature Biotechnology* 22(9):1161-1165, Sep. 2004.
Jolly, "9: Emerging Viral Vectors," *Cold Spring Harbor Monograph Archive* 36:209-240, 1999.
Jones et al., "Lentiviral Vector Design for Optimal T Cell Receptor Gene Expression in the Transduction of Peripheral Blood Lymphocytes and Tumor-Infiltrating Lymphocytes," *Human Gene Therapy* 20:630-640, Jun. 2009.
June, "Adoptive T cell therapy for cancer in the clinic," *The Journal of Clinical Investigation* 117(6):1466-1476, Jun. 2007.
Khogeer et al., "Antiphosphatidylserine antibodies as diagnostic indicators of antiphospholipid syndrome," *Lupus* 24:186-190, 2015.

Kitchen et al., "Engineering Antigen-Specific T Cells from Genetically Modified Human Hematopoietic Stem Cells in Immunodeficient Mice," *PLoS One* 4(12):e8208, Dec. 2009.
Kobayashi et al., "TIM-1 and TIM-4 Glycoproteins Bind Phosphatidylserine and Mediate Uptake of Apoptotic Cells," *Immunity* 27:927-940, Dec. 2007.
Kochenderfer et al., "Construction and Pre-clinical Evaluation of an Anti-CD19 Chimeric Antigen Receptor," *J. Immunother.* 32(7):689-702, 2009.
Krisky et al., "Development of herpes simplex virus replication-defective multigene vectors for combination gene therapy applications," *Gene Therapy* 5:1517-1530, 1998.
Kruskal et al., "Phagocytic Chimeric Receptors Require Both Transmembrane and Cytoplasmic Domains from the Mannose Receptor," *J. Exp. Med.* 176:1673-1680, Dec. 1992.
Luo et al., "Development of genetically engineered $CD4^+$ and $CD8^+$ T cells expressing TCRs specific for a *M. tuberculosis* 38-kDa antigen," *Journal of Molecular Medicine* 89:903-913, 2011.
Maeda et al., "Engineering of Functional Chimeric Protein G-Vargula Luciferase," *Analytical Biochemistry* 249:147-152, 1997.
Miksa et al., "A novel method to determine the engulfment of apoptotic cells by macrophages using pHrodo succinimidyl ester," *J Immunol Methods* 342:71-77, 2009.
Misyurin, "Structure and Functions of Main Apoptosis Receptors and Ligands," *Russian Journal of Biotherapy* 14(2):23-30, 2015.
Miyanishi et al., "Identification of Tim4 as a phosphatidylserine receptor," *Nature* 450:435-439, Nov. 2007.
Morgan et al., "Cancer Regression in Patients After Transfer of Genetically Engineered Lymphocytes," *Science* 314(5796):126-129, Oct. 2006.
Morrissey et al., "Chimeric antigen receptors that trigger phagocytosis," eLife, 2018. (21 pages).
Muller et al., "Spliceosomal Peptide P140 for Immunotherapy of Systemic Lupus Erythematosus: Results of an Early Phase II Clinical Trial," *Arthritis & Rheumatism* 58(12):3873-3883, Dec. 2008.
Nguyen et al., "Heavy-chain antibodies in Camelidae; a case of evolutionary innovation," *Immunogenetics* 54:39-47, 2002.
Nguyen et al., "The Specific Variable Domain of Camel Heavy-chain Antibodies is Encoded in the Germline," *J. Mol. Biol.* 275:413-418, 1998.
Nishi et al., "Systematic characterization of deubiquitylating enzymes for roles in maintaining genome integrity," *Nat Cell Biol.* 16(10):1016-8, Oct. 2014. (27 pages).
Nishi et al., "Tim4- and MerTK-Mediated Engulftnent of Apoptotic Cells by Mouse Resident Peritoneal Macrophages," *Molecular and Cellular Biology* 34(8):1512-1520, Apr. 2014.
Penberthy et al., "Apoptotic cell recognition receptors and scavenger receptors," *Immunological Reviews* 269:44-59, 2016.
Pfeifer et al., "Gene Therapy: Promises and Problems," *Annu. Rev. Genomics Hum. Genet.* 2:177-211, 2001.
Portolano et al., "Lack of Promiscuity in Autoantigen-Specific H and L Chain Combinations as Revealed by Human H and L Chain "Roulette"," *J. Immunol.* 150(3):880-887, Feb. 1993.
Ravichandran "Find-me and eat-me signals in apoptotic cell clearance: progress and conundrums," *J. Exp. Med.* 207(9):1807-1817, 2017.
Rossi et al., "Genetic therapies against HIV," *Nat. Biotechnol.* 25(12):1444-1454, Dec. 2007.
Roux et al., "Structural analysis of the nurse shark (new) antigen receptor (NAR): Molecular convergence of NAR and unusual mammalian immunoglobulins," *PNAS* 95:11804-11809, Sep. 1998.
Safdari et al., "Antibody humanization methods—a review and update," *Biotechnology and Genetic Engineering Reviews* 29(2):175-186, 2013.
Sandberg et al., "Human T-cell lines with well-defined T-cell receptor gene rearrangements as controls for the BIOMED-2 multiplex polymerase chain reaction tubes," *Leukemia* 21:230-237, 2007.
Sato et al., "Enhancement of Fcγ Receptor-Mediated Phagocytosis by Transforming Mutants of Cbl1," *The Journal of Immunology* 163(11):6123-6131, 1999.

(56) References Cited

OTHER PUBLICATIONS

Scatchard et al., "The Attractions of Proteins for Small Molecules and Ions," *Ann. N.Y. Acad. Sci.* 51:660-672, 1949.
Schmitt et al., "T Cell Receptor Gene Therapy for Cancer," *Human Gene Therapy* 20:1240-1248, Nov. 2009.
Scholten et al., "Codon modification of T cell receptors allows enhanced functional expression in transgenic human T cells," *Clin. Immunol.* 119:135-145, 2006.
Schutters et al., "Phosphatidylserine targeting for diagnosis and treatment of human diseases," *Apoptosis* 15:1072-1082, 2010.
Srivastava et al., "Engineering CAR-T Cells: Design Concepts," *Trends Immunol.* 36(8):494-502, 2015.
Stone et al., "A novel T cell receptor single-chain signaling complex mediates antigen-specific T cell activity and tumor control," *Cancer Immunol. Immunother.* 63(11):1163-1176, Nov. 2014.
Teplyakov et al., "Antibody modeling assessment II. Structures and models," *Proteins* 82(8):1563-1582, 2014. (20 pages).
Vallabhapurapu et al., "Variation in human cancer cell external phosphatidylserine is regulated by flippase activity and intracellular calcium," *Oncotarget* 6(33):34375-34388, 2015.
Verhoeyen et al., "Chapter 8: Lentiviral Vector Gene Transfer into Human T Cells," *Methods Mol. Biol.* 506:97-114, 2009.
Vincke et al., "General Strategy to Humanize a Camelid Single-domain Antibody and Identification of a Universal Humanized Nanobody Scaffold," *J. Biol. Chem.* 284(5):3273-3284, Jan. 2009.
Walseng et al., "A TCR-based Chimeric Antigen Receptor," *Scientific Reports* 7:10713, 2017. (10 pages).
Wang et al., "A transgene-encoded cell surface polypeptide for selection, in vivo tracking, and ablation of engineered cells," *Blood* 118(5):1255-1263, Aug. 2011.
Williamson et al., "Abstract A165: Engineering approaches to uncover the mechanism of apoptotic cell clearance by a conserved signaling system," *CRI-CIMT-EATI-AACR Inaugural International Cancer Immunotherapy Conference: Translating Science into Survival*, New York, New York, Sep. 16-19, 2015. (6 pages).
Williamson et al., "Abstract PR15: Engineering phagocytic signaling," *CRI-CIMT-EATI-AACR International Cancer Immunotherapy Conference: Translating Science into Survival*, New York, New York, Sep. 25-28, 2016. (4 pages).
Williamson et al., "Cellular reconstitution of apoptotic cell clearance reveals a multi-step phosphorylation mechanism for Draper receptor triggering," *bioRxiv*:1-48, 2017. (58 pages).
Williamson et al., "Spatial control of Draper receptor signaling initiates apoptotic cell engulfment," *J. Cell Biol.* 217(11):3977-3992, 2018.
Wilson, "Analyzing Biomolecular Interactions," *Science* 295(5562):2103-2105, 2002.
Wolff et al., "Monoclonal Antibody Homodimers: Enhanced Antitumor Activity in Nude Mice," *Cancer Res.* 53:2560-2565, Jun. 1993.
Wälchli et al., "A Practical Approach to T-Cell Receptor Cloning and Expression," *PLoS One* 6(11):e27930, 2011. (11 pages).
Zaritskaya et al., "New flow cytometric assays for monitoring cell-mediated cytotoxicity," *Expert Review of Vaccines* 9(6):601-616, Jun. 2010. (26 pages).
Zhang et al., "Transduction of Human T Cells with a Novel T-Cell Receptor Confers Anti-HCV Reactivity," *PLoS Pathogens* 6(7):e1001018, Jul. 2010. (13 pages).
Zhao et al., "Primary Human Lymphocytes Transduced with NY-ESO-1 Antigen-Specific TCR Genes Recognize and Kill Diverse Human Tumor Cell Lines," *J. Immunol.* 174:(7):4415-4423, Apr. 2005. (25 pages).
U.S. Appl. No. 16/785,485, filed Feb. 7, 2020.
U.S. Appl. No. 17/156,445, filed Jan. 22, 2021.
U.S. Appl. No. 17/543,567, filed Dec. 6, 2021.
U.S. Appl. No. 17/683,190, filed Feb. 28, 2022.
U.S. Appl. No. 17/766,173, filed Apr. 1, 2022.
U.S. Appl. No. 17/812,653, filed Jul. 14, 2022.
Hayashi et al., "The innate immune response to bacterial flagellin is mediated by Toll-like receptor 5," *Nature* 410(6832):1099-1103, Apr. 2001.
Nakaya, "Research on Molecular Mechanisms of Engulfinent of Apoptotic Cells," *The Pharmaceutical Society of Japan* 135(8):949-954, 2015. (w/ English Abstract).
Ortiz et al., "The evolutionary history of the CD209 (DC-Sign) family in humans and non-human primates," *Genes and Immunity* 9:483-492, Jun. 2008.
Takeshi et al., "Regulation of Immunity by Toll-like Receptor Functions: Their Physiological and Pathological Roles," *Journal of Gifu Dental Society* 37:138-158, 2011. (w/ English Abstract).

\* cited by examiner

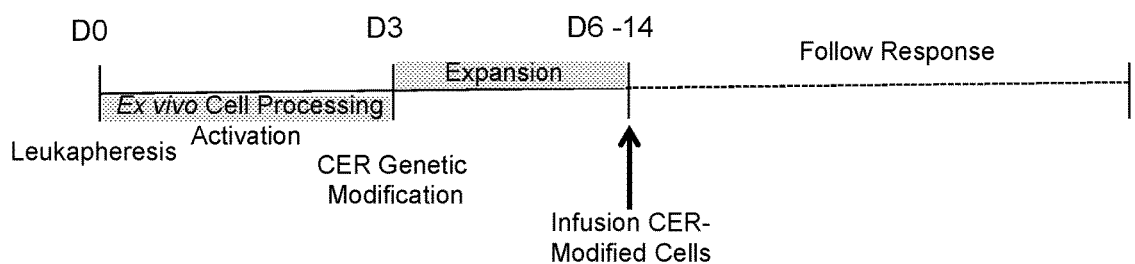
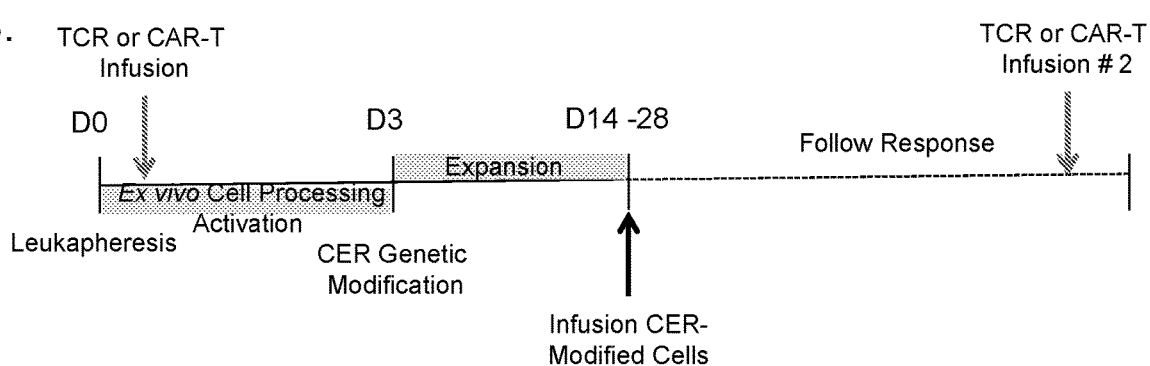
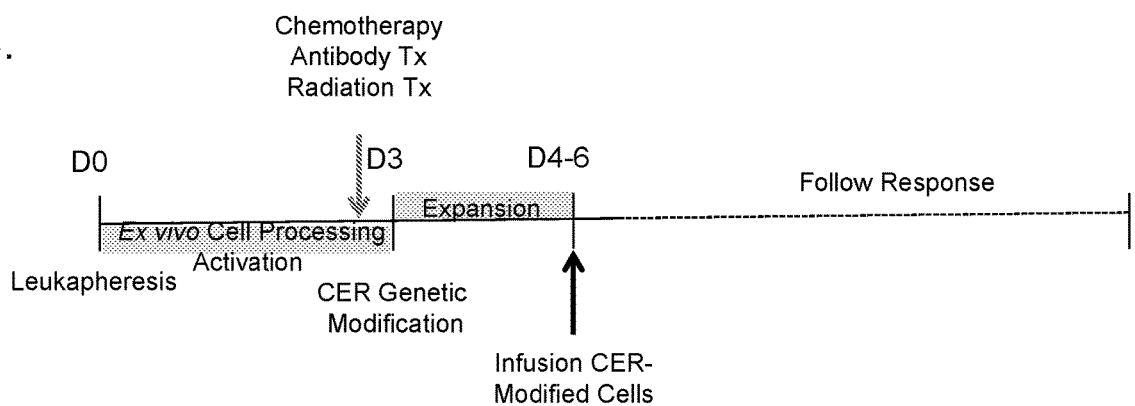
FIG. 4

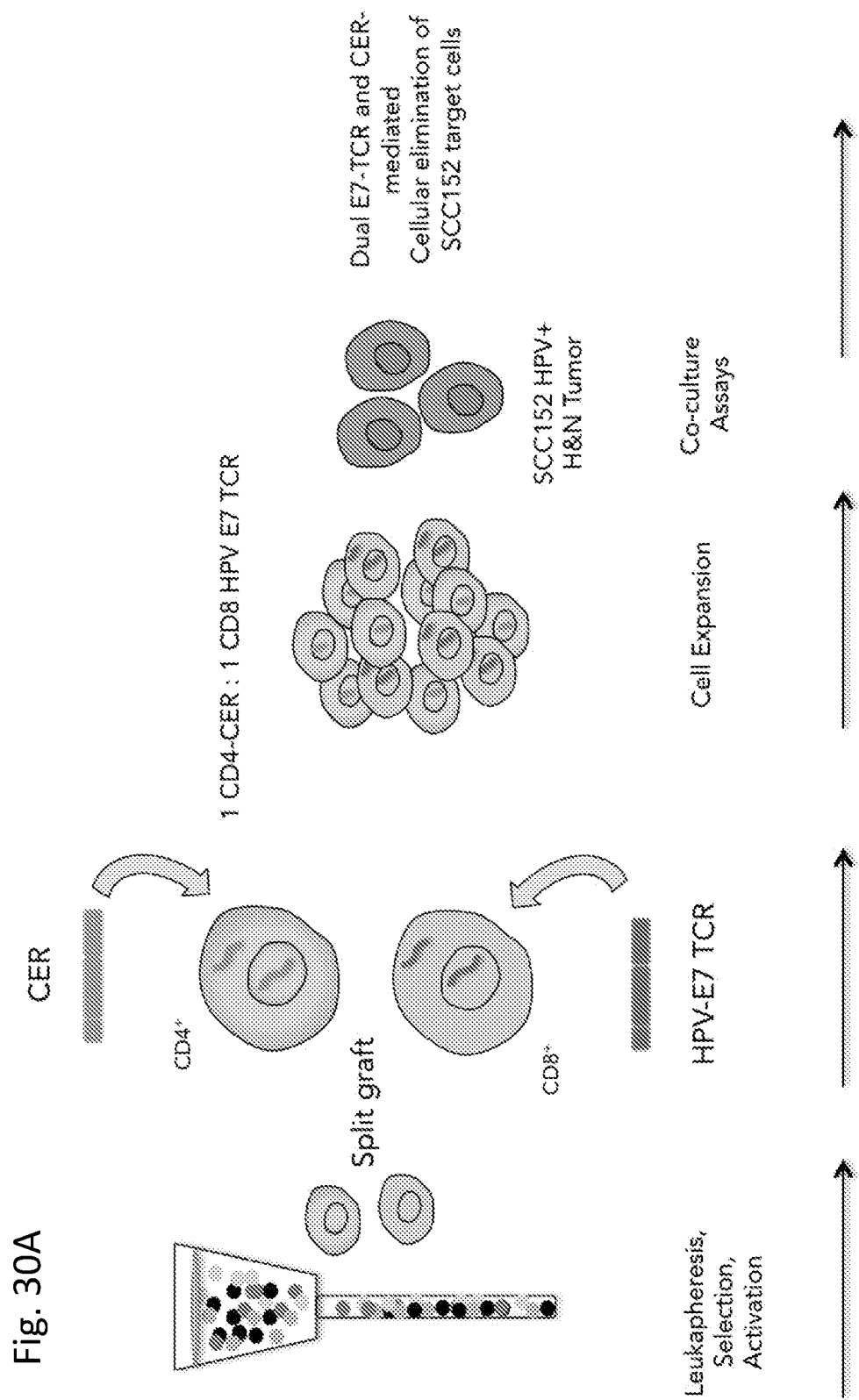

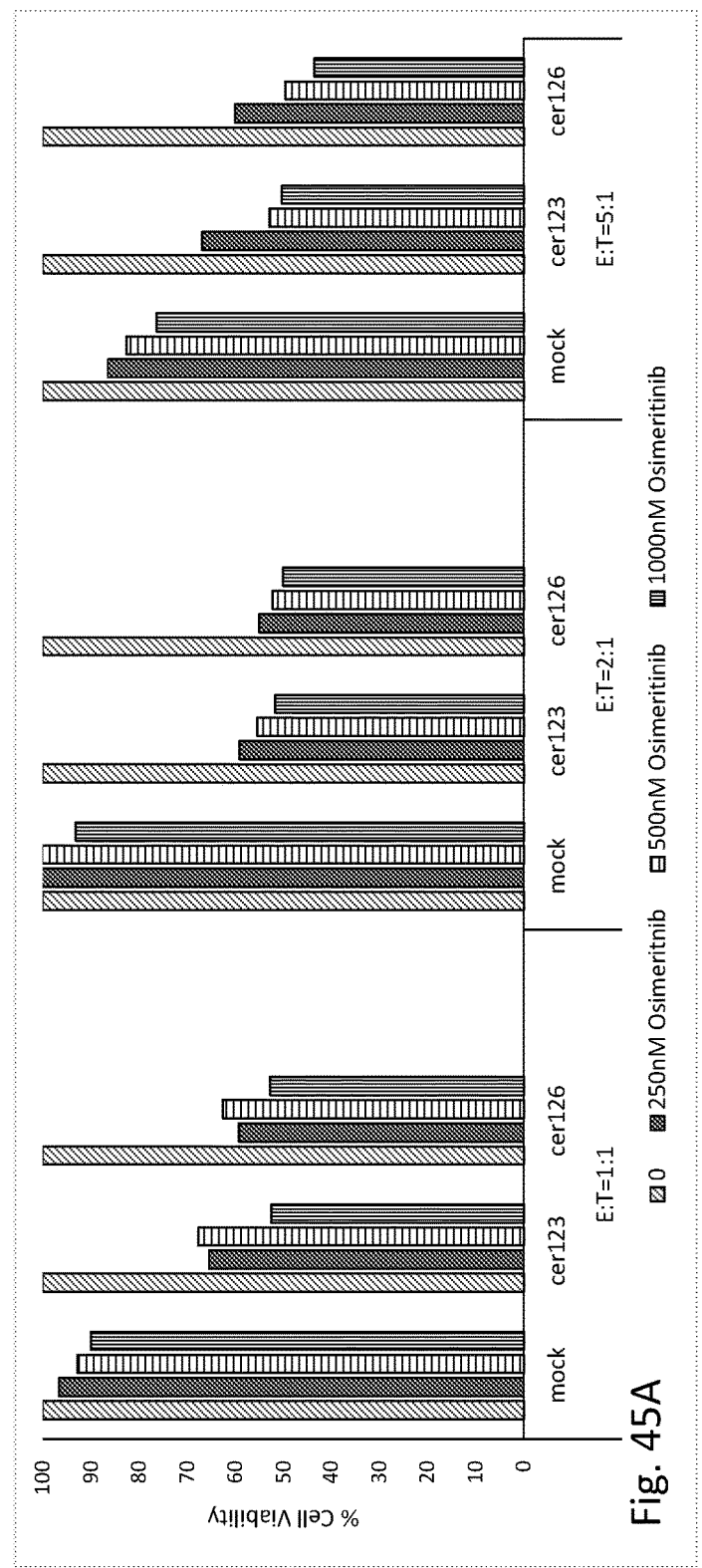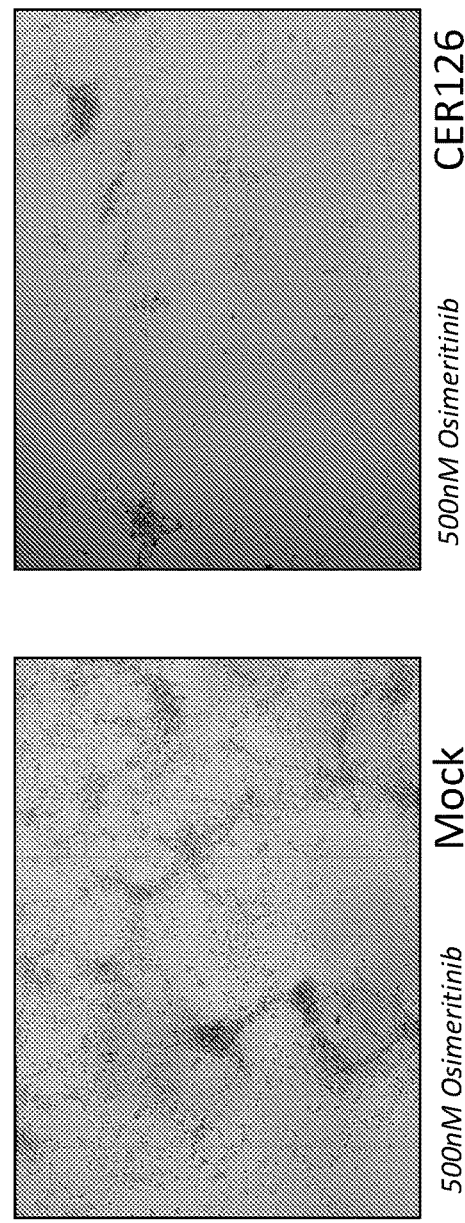
Fig. 45A
Fig. 45B

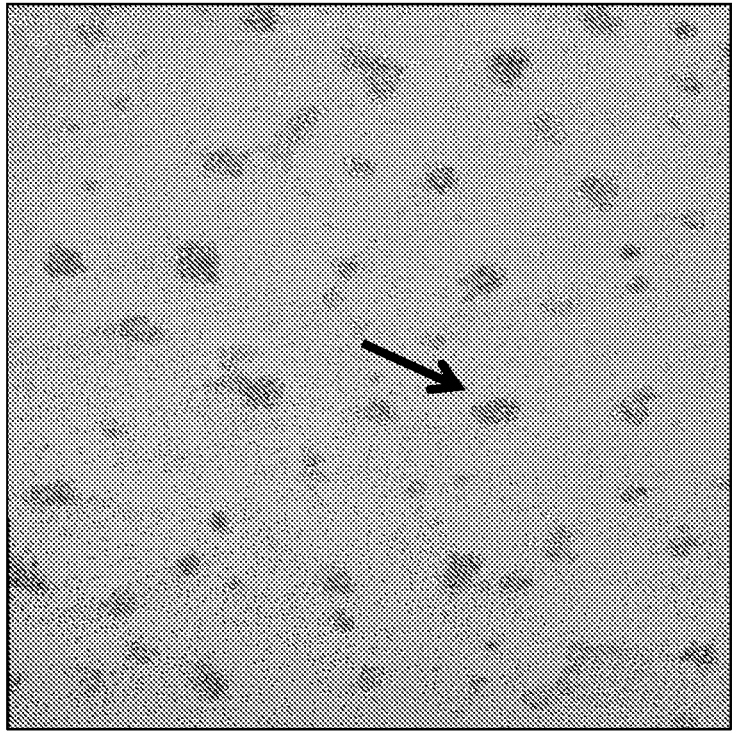
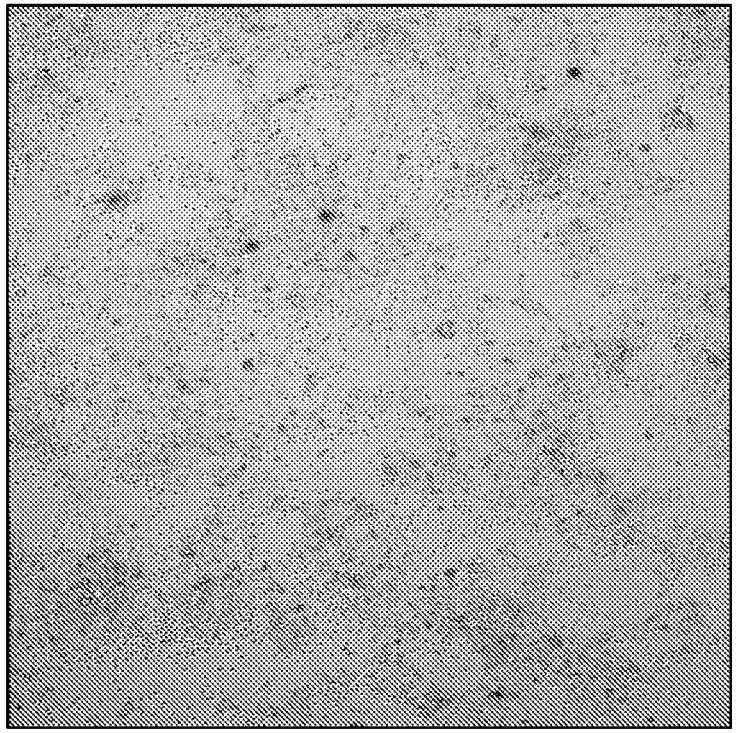
Fig. 54

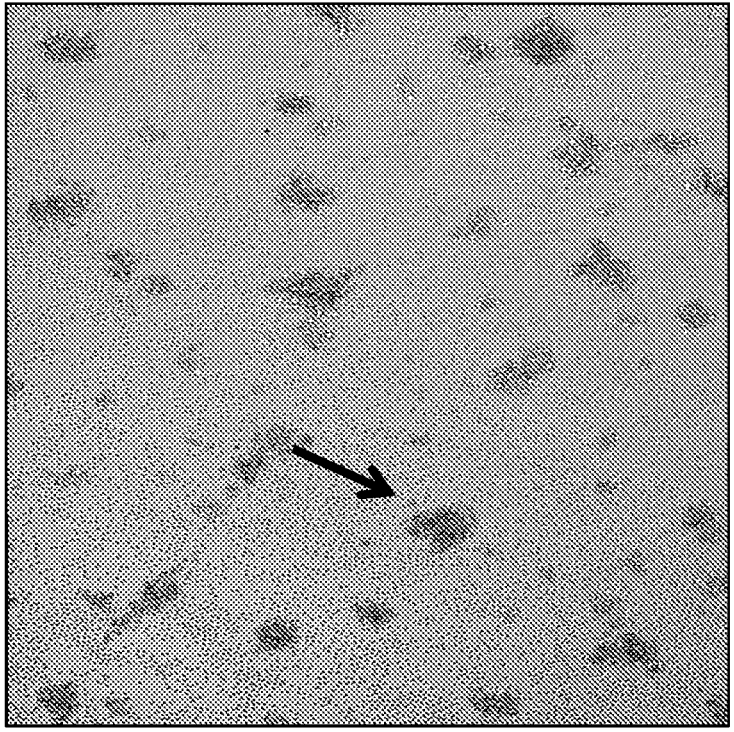
Fig. 55

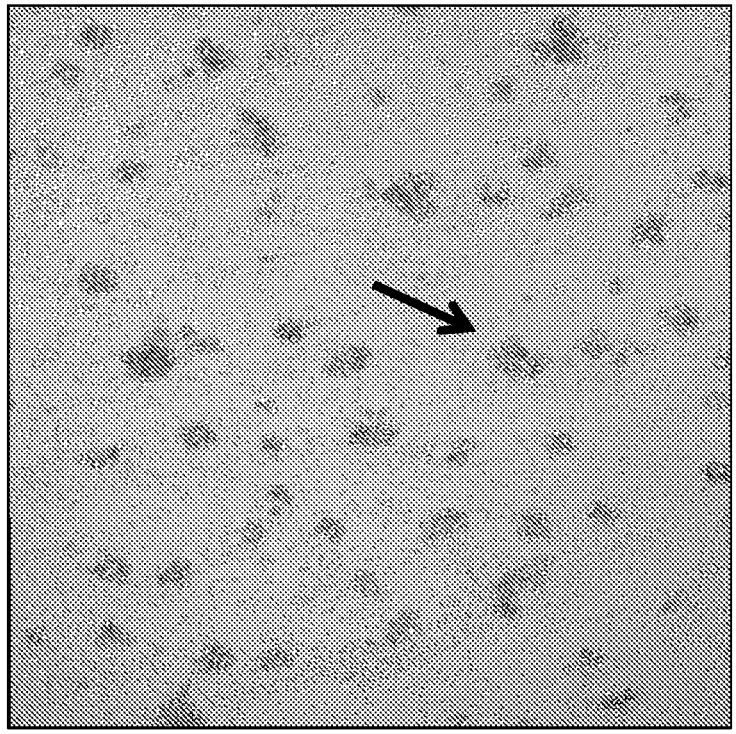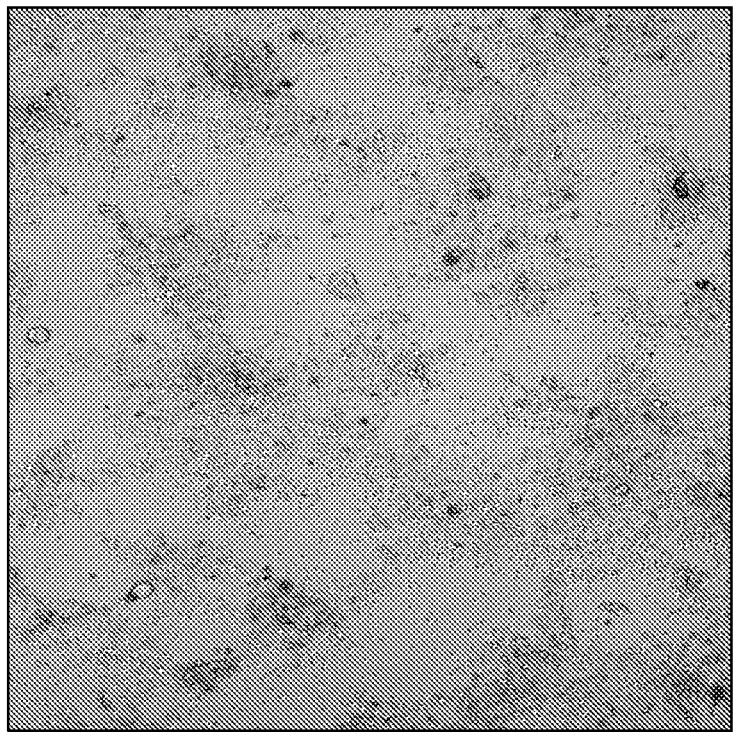
Fig. 56

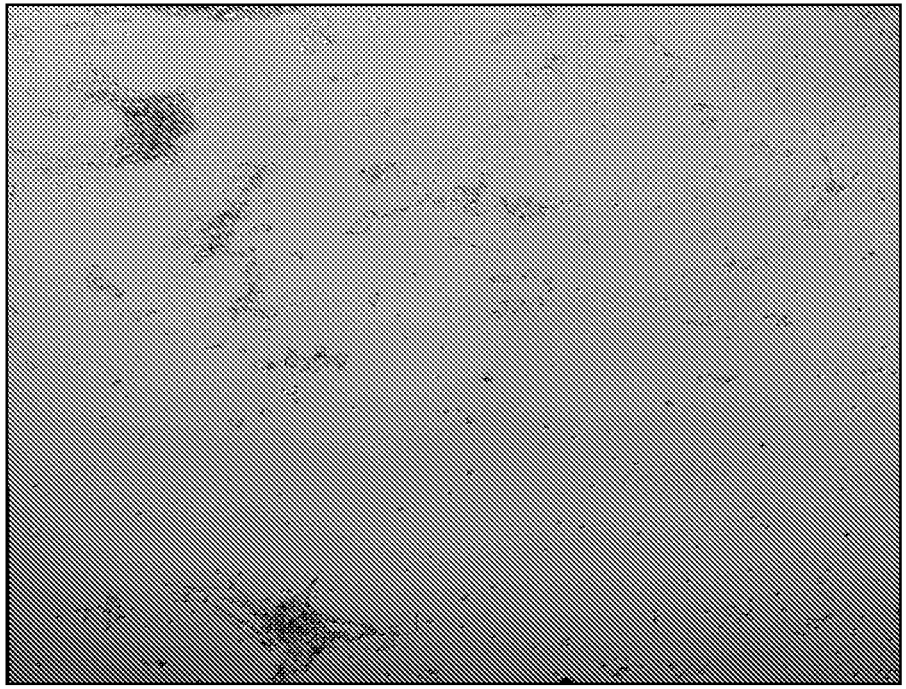
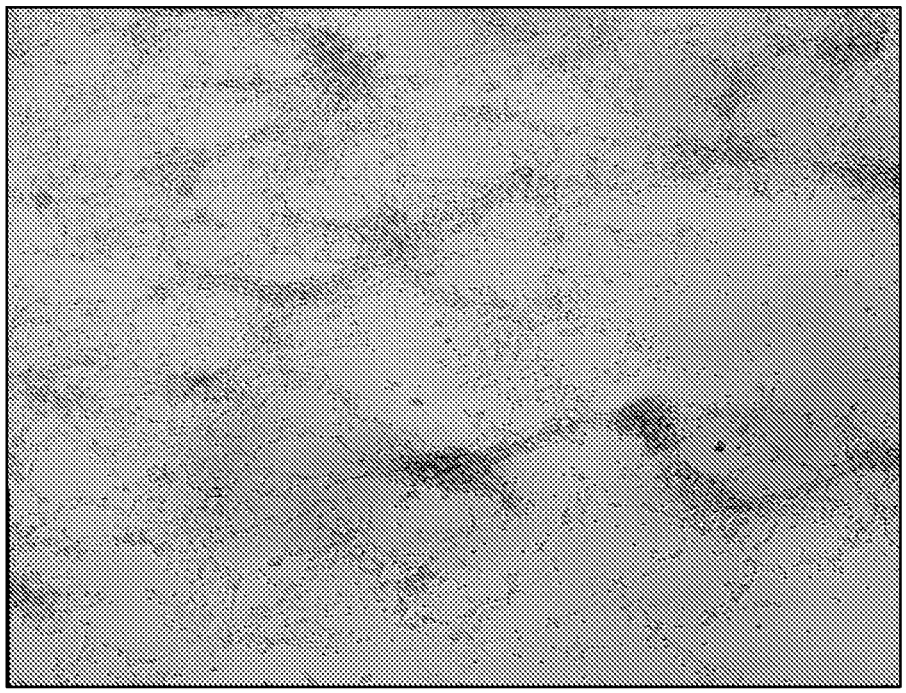
Fig. 58

48h post treatment 48h post treatment 72h post treatment 72h post treatment

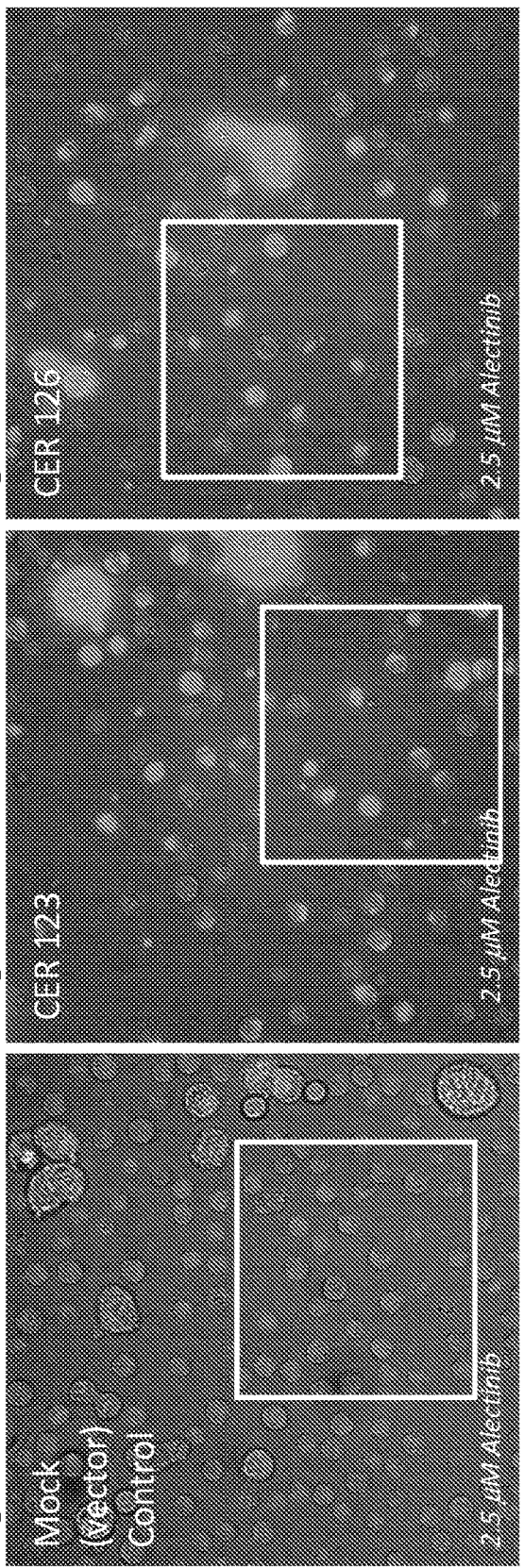

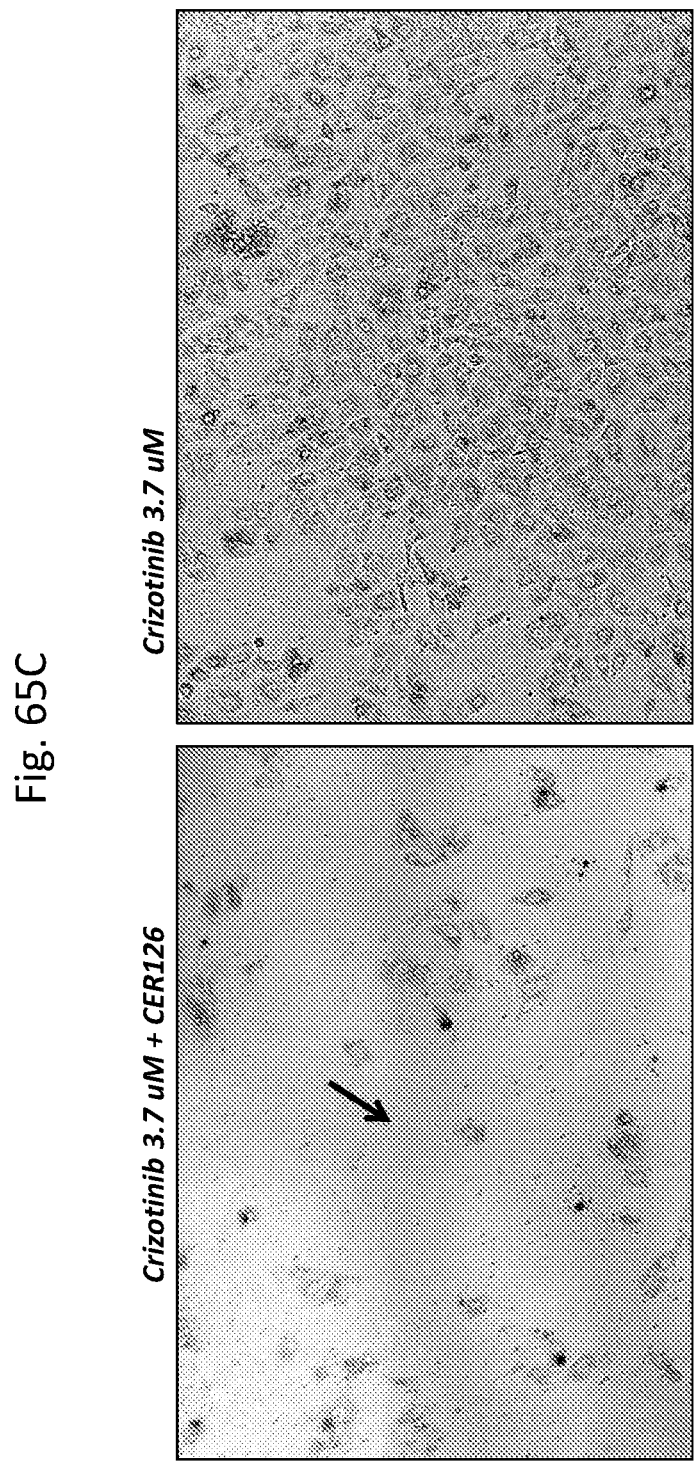

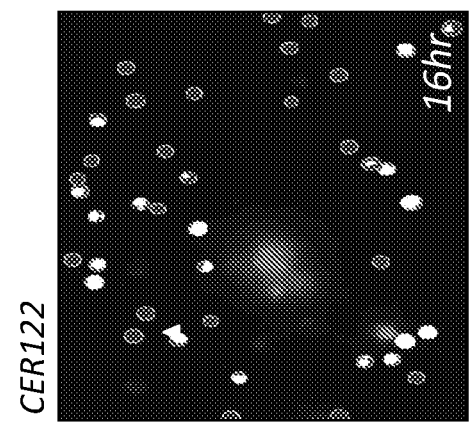
Fig. 72B
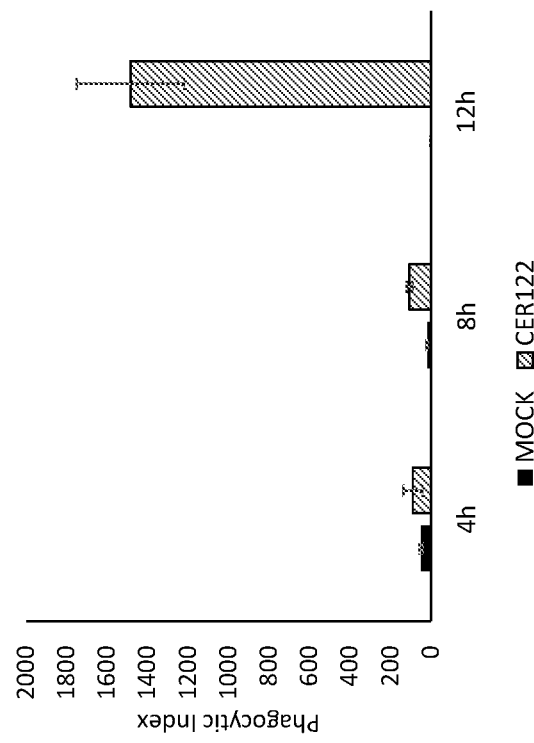
Fig. 72A
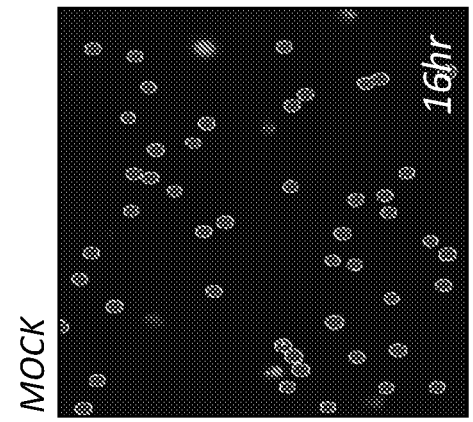
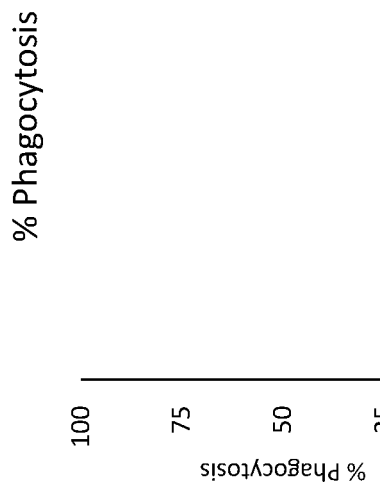
Fig. 72C

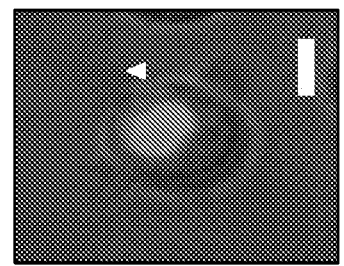
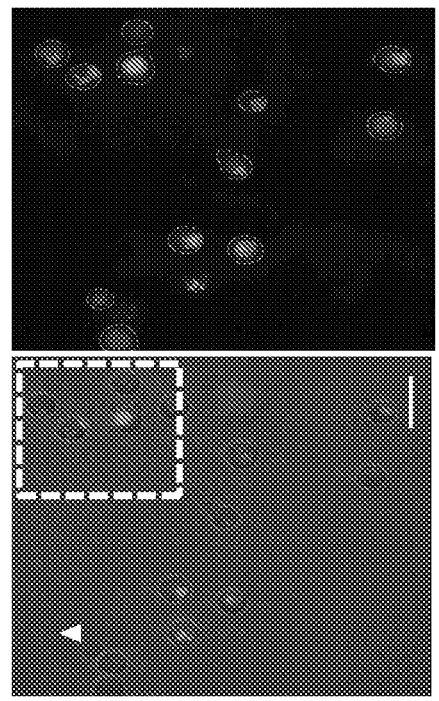
Fig. 80B

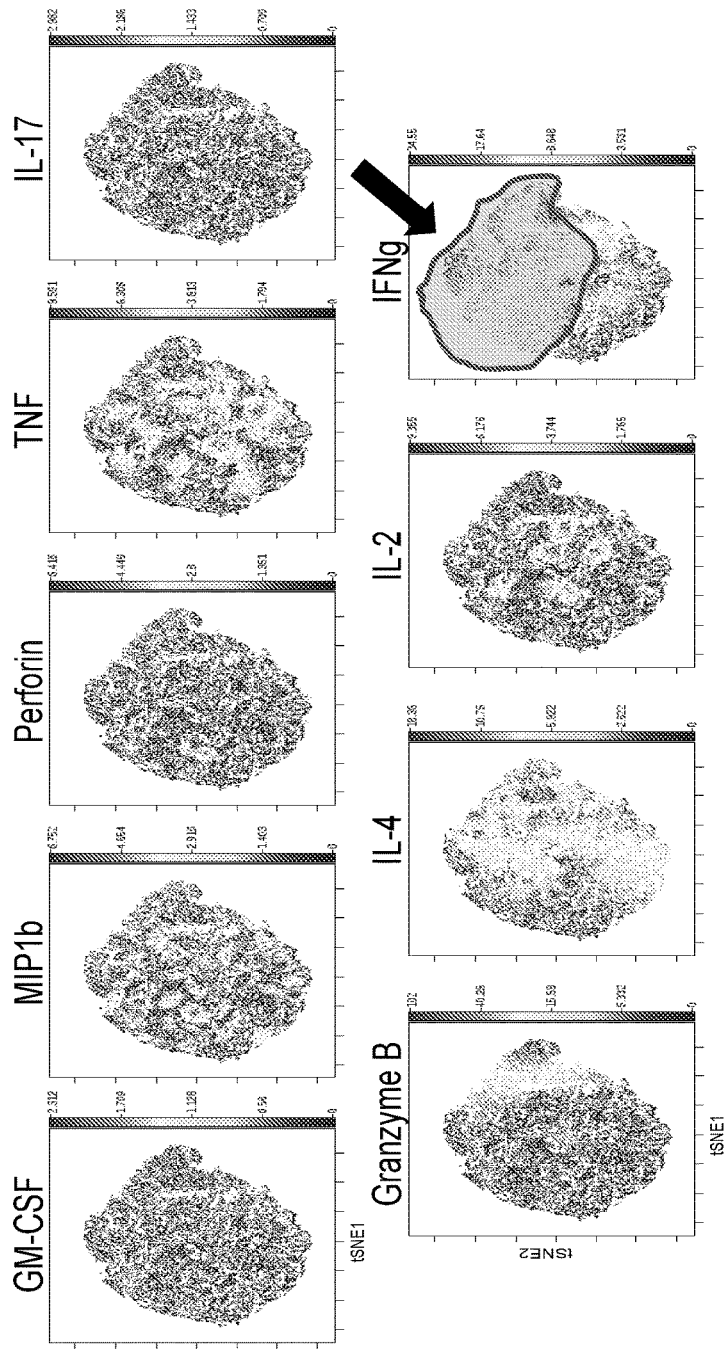
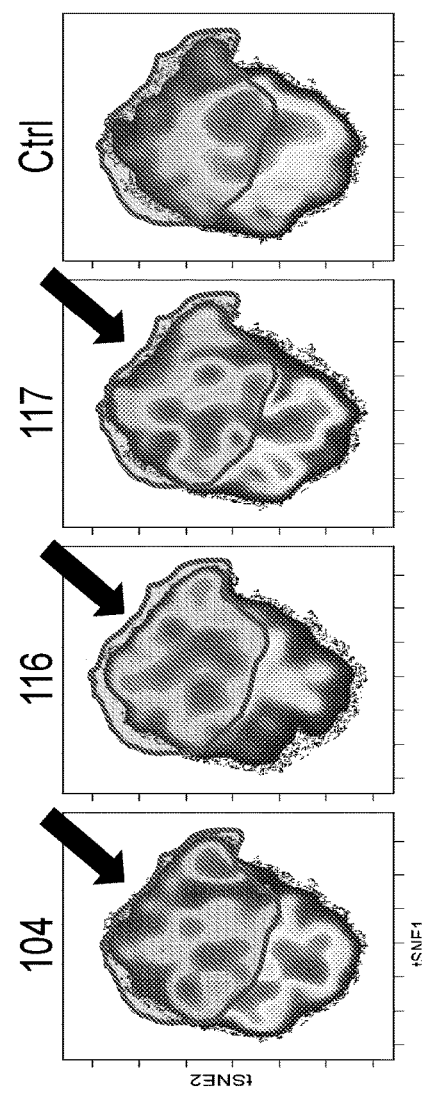
Fig. 82A
Fig. 82B

CHIMERIC ENGULFMENT RECEPTOR MOLECULES AND METHODS OF USE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200265_402USPC_SEQUENCE_LISTING.txt. The text file is 407 KB, was created on Oct. 26, 2021, and is being submitted electronically via EFS-Web.

BACKGROUND

There are two principle types of phagocytosis, which are influenced by the target, cell-type and surrounding milieu. Anti-microbe phagocytosis clears and degrades disease-causing microbes, induces pro-inflammatory signaling through cytokine and chemokine secretion, and recruits immune cells to mount an effective inflammatory response. This type of phagocytosis is often referred to as "inflammatory phagocytosis" (or "immunogenic phagocytosis"). However, in some instances, such as with certain persistent infections, anti-inflammatory responses may follow microbial uptake. Anti-microbe phagocytosis is commonly performed by professional phagocytes of the myeloid lineage, such as immature dendritic cells (DCs) and macrophages and by tissue-resident immune cells.

Phagocytosis of damaged, self-derived apoptotic cells or cell debris (e.g., efferocytosis), in contrast, is typically a non-inflammatory (also referred to as a "non-immunogenic") process. Billions of damaged, dying, and unwanted cells undergo apoptosis each day. Unwanted cells include, for example, excess cells generated during development, senescent cells, infected cells (intracellular bacteria or viruses), transformed or malignant cells, and cells irreversibly damaged by cytotoxic agents. Phagocytes execute specific, swift removal of apoptotic cells without causing damage to the surrounding tissues or inducing a pro-inflammatory immune response. Steps for apoptotic cell clearance include: (1) release of "find me" signals from apoptotic cells to recruit phagocytes to the location of apoptotic cells; (2) "eat me" signals exposed on the surface of apoptotic cells are bound by phagocytes via specific receptors; (3) cytoskeletal rearrangement to engulf the apoptotic cell; and (4) the ingested apoptotic cell is digested and specific phagocytic responses are elicited (e.g., secretion of anti-inflammatory cytokines).

There is an ongoing need for new compositions and methods of treating infections, inflammatory diseases, immune diseases, and various cancers. The methods and compositions disclosed herein meets such needs by enhancing the removal of infected, transformed, malignant, apoptotic, damaged or necrotic cells from the body in treatment of various cancers, acute and chronic infections, inflammatory, immune and selected neurological diseases.

BRIEF SUMMARY

Chimeric, engulfment receptors are described herein. In certain embodiments, the chimeric engulfment receptors ("CER" in the singular and "CERs" in the plural) include an extracellular domain, a transmembrane domain, and an intracellular engulfment signaling domain. The transmembrane domain is positioned between and connects the extracellular domain and the engulfment signaling domain. The extracellular domain comprises a binding domain and an optional extracellular spacer domain positioned between and connecting the binding domain and transmembrane domain. In certain embodiments, the chimeric engulfment receptors described herein are chimeric proteins having (a) and extracellular domain that targets a pro-engulfment marker or a target antigen associated with a disease, disorder, condition, or infection, (b) a transmembrane domain, and (c) an engulfment signaling domain that comprises a toll-like receptor (TLR) signaling domain, a Traf6 signaling domain, aTraf2 signaling domain, or a Traf3 signaling domain. In certain embodiments, the engulfment signaling domain comprises a primary engulfment signaling domain and a secondary engulfment signaling domain. In particular embodiments, the chimeric engulfment receptors are single chain chimeric proteins. Chimeric engulfment receptors may be designed to generate an inflammatory response to a target cell/organ/tissue/area. While apoptotic cell clearance is typically a non-inflammatory process, inflammation can be beneficial to the host in certain contexts, such as, for example, in the context of clearance of apoptotic tumor cells to induce an immune response to residual tumor cells.

In some embodiments, the extracellular domain of the CER includes a binding domain specific to a pro-engulfment marker. In certain such embodiments, the extracellular domain includes a phosphatidylserine (PtdSer) binding domain. In embodiments of the CERs described herein, a PtdSer binding domain can include all or a portion of the extracellular domain of T cell immunoglobulin and mucin domain 1 (Tim1), T cell immunoglobulin and mucin domain 4 (Tim4), or T cell immunoglobulin and mucin domain 3 (Tim3). In other embodiments a PtdSer binding domain can include all or a portion of a binding domain derived from FA58C2, GAS6, protein S, Factor VII, Factor IX, Factor X, or prothrombin PS.

In further embodiments, the extracellular domain binds to a target antigen. In certain such embodiments, the extracellular domain includes all or part of the extracellular domain of an Fc receptor (FcR), such as, for example, FcγR1, FcγR2A, FcγR2B2, FcγR2C, FcγR3A, FcER1, and FcaR1. In still other embodiments where the extracellular domain binds a target antigen, the extracellular domain can include an antibody or an antigen-binding domain thereof. For example, the extracellular domain can include an antibody or an antigen-binding domain selected from intrabodies, peptibodies, nanobodies, single domain antibodies, SMIPs, and multispecific antibodies. In certain such embodiments, the extracellular domain includes a Fab binding domain. In yet other such embodiments, the extracellular domain includes a scFv.

Upon binding of the extracellular domain of the CER to the pro-engulfment marker or targeted antigen, the engulfment signaling domain stimulates engulfment signaling activity. Thus, upon activation, the engulfment signaling domain included in the CER transduces effector functional signals that direct the host cell to engulf. In certain embodiments, the engulfment signaling domain comprises: a primary engulfment signaling domain comprising a TLR signaling domain, a Traf6 signaling domain, a Traf2 signaling domain, or a Traf3 signaling domain; and a secondary engulfment signaling domain. Examples of secondary engulfment signaling domains include FcγR1, FcγR2A, FcγR2B2, FcγR2C, FcγR3A, FcER1, FcaR1, BAFF-R, NFAM1, DAP12, MERTK, CD79b, TLR, Traf2, Traf3, and Traf6 signaling domains.

In further aspects, the present disclosure is directed to cells genetically modified to express a CER. In specific embodiments, the CER confers an engulfment phenotype not exhibited by a single, naturally-occurring receptor protein. In other embodiments, a CER according to the present description confers an engulfment phenotype to a cell that does not naturally exhibit engulfment activity. In one embodiment, antigen binding by a CER induces phagocytic signal transduction cascade in a cell that does not naturally exhibit phagocytic signal transduction activity. In another embodiment, a CER-expressing cell that does not naturally exhibit engulfment activity and that engulfs a target cell is capable of degrading the target cell. In other embodiments, a CER according to the present disclosure further confers a phenotype to the host cell, such as enhanced proliferative activity, expansion activity, activation, cytolytic activity, antigen presentation activity, memory formation, persistence, or a combination thereof that may otherwise not be present in a host cell that does not express the CER. In certain embodiments, cells are genetically modified to express a CER that targets a pro-engulfment marker associated with dead, dying, damaged, infected, or necrotic cells. In other embodiments, cells are genetically modified to express a CER that targets a marker, such as an antibody, associated with an infectious microbe or molecule induced by an infectious particle. In such embodiments, the genetically modified cells promote clearance or degradation of the targeted cells or microbes upon binding by the CER of the marker associated with the targeted infectious microbe or the targeted molecule induced by an infectious particle. In other specific embodiments, cells are genetically modified to express a CER that targets an antigenic marker that does not normally trigger engulfment. For example, in such embodiments, the extracellular domain of the CER can include an antibody or antigen-binding portion of an antibody, such as a Fab binding domain or a scFv specific to an antigenic marker. In certain such embodiments, the antigenic marker can be, a surface protein, glycoprotein, or glycolipid characteristic of aberrant cells associated with a disease, disorder, or other undesirable condition. In such embodiments, the genetically modified cells promote clearance or degradation of the aberrant cells upon binding of the antigenic marker by the CER. In certain embodiments, cells that are genetically modified to express a CER that targets an antigenic marker that does not normally trigger engulfment are B cells.

In yet further aspects, the present disclosure is directed to a method treating a subject suffering from a disease, disorder or undesired condition. Embodiments of these methods include administering to a subject a therapeutically effective amount of a pharmaceutical composition including one or more CERs or a population of cells genetically modified to express one or more CERs according to the present description.

In other aspects, the present disclosure provides methods for altering the engulfment phenotype of a host cell. In certain embodiments, such methods include one or more of the following: methods for producing a population of cells exhibiting an engulfment phenotype by introducing into and expressing a CER in host cells that do not naturally exhibit an engulfment phenotype; methods for altering the engulfment phenotype of a population of cells by introducing into and expressing a CER in the host cells, wherein the CER confers an engulfment phenotype specific to a pro-engulfment marker or antigenic marker not naturally targeted by the host cells; and methods for enhancing the engulfment phenotype of a population of cells by introducing into and expressing a CER in the host cells, wherein the CER is specific to a pro-engulfment marker or antigenic marker naturally targeted by the host cells and expression of the CER by the host cells enhances the engulfment by the host cells of cells, microbes, or particles exhibiting the targeted pro-engulfment or antigenic marker.

BRIEF DESCRIPTION OF THE SEVERAL VIEWS OF THE DRAWINGS

FIG. 1A shows an illustrative CER having an extracellular domain specific for a pro-engulfment marker (e.g., Tim4 binding domain for phosphatidylserine), a transmembrane domain, an engulfment signaling domain comprising a TLR signaling domain, Traf6 signaling domain, Traf2 signaling domain, or Traf3 signaling domain, and optionally, a secondary engulfment signaling domain. FIG. 1B shows an illustrative CER having an extracellular domain comprising a scFv binding domain, a transmembrane domain, an engulfment signaling domain comprising a TLR signaling domain, Traf6 signaling domain, Traf2 signaling domain, or Traf3 signaling domain, and optionally, a secondary engulfment signaling domain.

FIG. 2A shows an endogenous lymphocyte. FIG. 2B shows a lymphocyte modified with a CER of the present disclosure.

FIGS. 4A-4C show illustrative treatment timelines. FIG. 4A shows a treatment scheme for therapy with cells modified with a CER. FIG. 4B shows a treatment scheme for CER-modified cells used in combination with non-phagocytic T cellular immune therapies. FIG. 4C shows a treatment scheme for CER-modified cells used in combination with monoclonal antibodies, conventional chemotherapy, or radiation therapy.

FIGS. 30A-30B show in vitro co-culture assay schematic and data from CD4+ T cells transduced with selected CER+CD8+ T cells transduced with HPV16 E7 specific TCR. FIG. 30A is a schematic for exemplary in vitro co-culture experiments. CD8 T cells were activated and transduced with a lentivirus cassette encoding a human papilloma virus 16 (HPV16) E7 protein-specific TCR, while CD4 T cells from the same graft were activated and transduced with a lentivirus encoding a CER. Both sets of cells were expanded ex vivo and combined at a 1:1 ratio and co-cultured with HPV16 E7+ head and neck squamous cell carcinoma cells (SCC152). FIG. 30B is a bar graph showing that combination of CD4 T cell/CER of the present disclosure with a CD8+/HPV16 E7 TCR (see, PCT Published Application No. WO2015/184228; SEQ ID NO:158) enhances cytolysis of target cells as measured by caspase induction compared to administration of the HPV16 E7 TCR alone. SCC152 is a head and neck squamous carcinoma that is HPV16+. Human primary CD8+ cells transduced with a HPV16 E7 TCR were co-cultured alone with SCC152 cells or in combination with CD4+ T cells transduced with various CERs of the present disclosure (CERS, CER17, CER19, CER21, CER23, CER26, CER27, CER103B, CER104, CER105, CER106, or CER116) at a 1:1 ratio. The number of caspase positive SCC152 target cells in the co-culture assay was measured by quantifying the intensity of red fluorescence from a caspase 3/7 apoptosis reagent that couples the activated caspase 3/7 recognition motif with a red reagent that fluoresces upon cleavage. The caspase 3/7 apoptosis reagent was added to the co-culture assay after 6 hours, and fluorescence was detected using BZ-X710 Keyence microscope and using hybrid capture software. The target SCC152 cells (transduced with green fluorescent protein (GFP)) were determined similarly. The Y-axis represents % caspase positive targets (# of caspase events/# of GFP target cells)*100.

FIG. 38A shows an exemplary tandem expression cassette comprising a polynucleotide encoding a chimeric engulfment receptor (CER) 5 construct and a polynucleotide encoding a HPV16 E7 specific TCR. CER5 is positioned upstream of the HPV16 E7 specific TCR. The sequences encoding CER5 and HPV16 E7 TCR are operably linked to a EF-lα promoter and separated by a T2A peptide. CER5 comprises a Tim4 binding domain, a Tim4 transmembrane domain, and a TLR4 engulfment signaling domain. FIG. 38B shows an exemplary tandem expression cassette comprising a polynucleotide encoding a chimeric engulfment receptor (CER) 19 construct and a polynucleotide encoding an HPV16 E7 specific TCR. CER19 is positioned upstream of the HPV16

E7 specific TCR. The sequences encoding CER19 and HPV16 E7 TCR are operably linked to a EF-1α promoter and separated by a T2A peptide. CER19 comprises a Tim4 binding domain, a Tim4 transmembrane domain, and a TLR5 signaling domain. FIG. 38C shows an exemplary tandem expression cassette comprising a polynucleotide encoding a CER21 construct and a polynucleotide encoding an HPV16 E7 specific TCR. CER21 is positioned upstream of the HPV16 E7 specific TCR. The sequences encoding CER21 and HPV16 E7 TCR are operably linked to a EF-1α promoter and separated by a T2A peptide. CER21 comprises a Tim4 binding domain, a Tim4 transmembrane domain, and a TLR8 signaling domain. FIG. 38D shows an exemplary tandem expression cassette comprising a polynucleotide encoding CER27 construct and a polynucleotide encoding an HPV16 E7 specific TCR. CER27 is positioned upstream of the HPV16 E7 specific TCR. The sequences encoding CER27 and HPV16 E7 TCR are operably linked to a EF-1α promoter and separated by a T2A peptide. CER27 comprises a Tim4 binding domain, a Tim4 transmembrane domain, and a TLR2 signaling domain. FIG. 38E shows an exemplary tandem expression cassette comprising a polynucleotide encoding CER29 construct and a polynucleotide encoding an HPV16 E7 specific TCR. CER29 is positioned upstream of the HPV16 E7 specific TCR. The sequences encoding CER29 and HPV16 E7 TCR are operably linked to a EF-1α promoter and separated by a T2A peptide. CER29 comprises a Tim4 binding domain, a Tim4 transmembrane domain, and a Traf6 signaling domain. FIG. 38F shows an exemplary tandem expression cassette comprising a polynucleotide encoding CER31 construct and a polynucleotide encoding an HPV16 E7 specific TCR. CER31 is positioned upstream of the HPV16 E7 specific TCR. The sequences encoding CER31 and HPV16 E7 TCR are operably linked to a EF-1α promoter and separated by a T2A peptide. CER31 comprises a Tim4 binding domain, a Tim4 transmembrane domain, and a Traf3 signaling domain.

FIGS. 45A-45B show that when EGFR inhibitor Osimeritinib (250 nM, 500 nM, and 1000 nM) was combined with phosphatidylserine-specific CER123- or CER126-expressing cells, growth of NSCLC cells harboring EGFR rearrangements was synergistically suppressed in vitro as measured by MTT assay (FIG. 45A) or microscopy (500 nM osimeritinib+CER126) (FIG. 45B). In FIG. 45A, the left bar graph shows data using an effector:target cell ratio of 1:1, the middle bar graph shows data using an effector:target ratio of 2:1, and the right bar graph shows data using an effector:target ratio of 5:1.

In FIG. 48A, the left bar graph shows data using an effector:target cell ratio of 1:1, the middle bar graph shows data using an effector:target ratio of 2:1, and the right bar graph shows data using an effector:target ratio of 5:1.

FIG. 51A shows % viability for HCC827 cells incubated with Osimeritinib+CER21, CER108, CER104, or CER129-expressing T cells. FIG. 51B shows % viability for HCC827 cells incubated with Osimeritinib+CER27, CER120, CER122, CER123, CER124, or CER126-expressing T cells.

FIG. 54 shows bright field microscopy images from co-culture experiments of HCC827+ cells. HCC827 cells were treated with CER104-transduced CD4+ T cells with Osimeritinib (1 nM) for 48 hours (right image) or without Osimeritinib (left image). Arrow indicates cluster of dead HCC827 EGFR$^+$ cells surrounded by phagocytic CER104$^+$ T cells.

FIG. 55 shows bright field microscopy images from co-culture experiments of HCC827+ cells. HCC827 cells were treated with CER21-transduced CD4+ T cells with Osimeritinib (1 nM) for 48 hours (right image) or without Osimeritinib (left image). Arrow indicates cluster of dead HCC827 EGFR$^+$ cells surrounded by phagocytic CER21$^+$ T cells.

FIG. 56 shows bright field microscopy images from co-culture experiments of HCC827+ cells. HCC827 cells were treated with CER122-transduced CD4+ T cells with Osimeritinib (1 nM) for 48 hours (right image) or without Osimeritinib (left image). Arrow indicates cluster of dead HCC827 EGFR$^+$ cells surrounded by phagocytic CER122$^+$ T cells.

FIG. 58 shows bright field microscopy images from co-culture experiments of H1975 cells. H1975 cells were treated with CER126-transduced T cells +Osimeritinib (500 nM) for 48 hours (right image) or mock-transduced (vector only) T cells +Osimeritinib (500 nM) (left image).

FIG. 60A and FIG. 60B show effects of Alectinib (250 nM, 500 nM, 1 µM, 2.5 µM, 3.7 µM, 7 µM, or 10 µM)+CER104- or CER122-modified T cells on A549 cell viability after 48 hours co-culture at effector:target cell ratio of 2:1 (FIG. 60A) and 5:1 (FIG. 60B). FIG. 60C and FIG. 60D show effects of Crizotinib (250 nM, 500 nM, 1 µM, 2.5 µM, 3.7 µM, 7 µM, or 10 µM)+CER104- or CER122-modified T cells on A549 cell viability after 48 hours co-culture at effector:target cell ratio of 2:1 (FIG. 60C) and 5:1 (FIG. 60D). Mock transduced (vector only) T cells were used as control.

FIG. 61A and FIG. 61B show effects of Alectinib (250 nM, 500 nM, 1 µM, 2.5 µM, 3.7 µM, 7 µM, or 10 µM)+CER104- or CER122-modified T cells on A549 cell viability after 72 hours co-culture at effector:target cell ratio of 2:1 (FIG. 61A) and 5:1 (FIG. 61B). FIG. 61C and FIG. 61D show effects of Crizotinib (250 nM, 500 nM, 1 µM, 2.5 µM, 3.7 µM, 7 µM, or 10 µM)+CER104- or CER122-modified T cells on A549 cell viability after 72 hours co-culture at effector:target cell ratio of 2:1 (FIG. 61C) and 5:1 (FIG. 61D). Mock transduced (vector only) T cells were used as control.

FIG. 62A shows mock-transduced (vector only) T cells do not exhibit phagocytosis of A549 cells. FIGS. 62B-62C show that CER104-expressing T cells phagocytosed A549 cells when co-cultured with 1 µM Alectinib (FIG. 62B) or 1 µM Crizotinib (FIG. 62C). FIGS. 62D-62E show that CER117-expressing T cells phagocytosed A549 cells when co-cultured with 1 µM Alectinib (FIG. 62D) or 1 µM Crizotinib (FIG. 62E). White arrows indicate examples of phagocytic events (pHrodo red target cells within CT-violet labeled CD4 T cells).

FIGS. 63A-63F show fluorescent micrographs (63× magnification) of phagocytic elimination of ALK-positive A549 NSCLC cells treated with ALK inhibitor (alectinib). A549 cells were labeled with pHrodo red dye, a pH sensing dye to indicate localization in low-PH retaining endosomes. CD4 T cells were labeled with CT-violet. FIG. 63A shows mock-transduced (vector only) T cells do not exhibit phagocytosis of A549 cells. FIG. 63D is an enlarged view of the area in FIG. 63A outlined by the white square. FIG. 63B shows that CER123-expressing T cells phagocytosed A549 cells when co-cultured with 2.504 Alectinib (FIG. 63B). FIG. 63E is an enlarged view of the area in FIG. 63B outlined by the white square. FIG. 63C shows that CER126-expressing T cells phagocytosed A549 cells when co-cultured with 2.504 Alectinib (FIG. 63C). FIG. 63F is an enlarged view of the area in FIG. 63C outlined by the white square. White arrows indicate examples of phagocytic events (pHrodo red target cells within CELLTRACE-violet labeled CD4 T cells).

FIGS. 65A-65C show that CER-expressing T cells demonstrate dose-dependent, inducible cell killing responses in the presence of ALK inhibitors Crizotinib and Alectinib. FIG. 65A shows that in the presence of Crizotinib (0, 2500, or 3700 nM), CER123- or CER126-expressing cells demonstrate inducible, dose-dependent killing of A549 cells. The left bar graph shows data using an effector:target cell ratio of 5:1, and the right bar graph shows data using an effector:target ratio of 2:1. FIG. 65B shows that in the presence of Alectinib (0, 2500, or 3700 nM), CER123- or CER126-expressing cells demonstrate inducible, dose-dependent killing of A549 cells. The left bar graph shows data using an effector:target cell ratio of 5:1, and the right bar graph shows data using an effector:target ratio of 2:1. FIG. 65C shows micrograph images from co-culture experiments with near complete loss of Crizotinib (3700 nM) treated A549 cells in the presence of CER126-transduced T cells (left panel) as compared to control (right panel).

FIG. 67A shows % cell viability of A549 ALK+ cells co-cultured with Alectinib+CER21−, CER108−, CER104−, or CER129-expressing T cells. FIG. 67B shows % cell viability of A549 ALK+ cells co-cultured with Alectinib+ CER27−, CER120−, CER122, CER123−, CER124−, or CER126-expressing T-cells.

FIGS. 72A-72C show time course (4 hours, 8 hours, and 12 hours) of phagocytic uptake of Alectinib-treated A549 ALK+ cells by CER122-expressing T cells as % phagocytosis (FIG. 72A) and phagocytic index (FIG. 72B). FIG. 72C shows fluorescent micrograph images obtained at 16 hours co-culture. Yellow arrows indicate phagocytic events (pHrodo red targets within CT-violet-labeled CD4 T cells) (FIG. 72C right image). Mock-transduced (vector only) controls exhibit no phagocytic activity (FIG. 72C left image).

FIG. 75A: T cells were enriched, activated, and transduced with a CER122-T2A-tEGFR lentiviral construct and phenotyped for surface tEGFR and T cell markers CD4 and CD8 by FACS. FIG. 75B: The total number of transduced and control T cells in unselected cultures were determined after CD3 and CD28 bead activation. FIG. 75C: 2D fluorescence droplet digital PCR plot from DNA of CER122-expressing T cell demonstrates amplification of a region from the CER cassette. The blue cluster on the plot (upper left) represents droplets that are positive for CER122 only, and the orange cluster (top right) represents clusters that are positive for both CER122 and RPP30. FIG. 75D: Table showing copy number value (CNV) for CER122-transduced T cells determined by droplet digital PCR.

FIG. 76A shows tumor volume measurements post-adoptive transfer in untreated, Alectinib only +mock transduced T cells (vector only), and Alectinib+ CER122-transduced T cells (n=5/treatment group) NSG mice. FIG. 76B shows growth of A549/luciferase+/ALK+ cells in NSG mice, as evaluated by bioluminescence imaging. FIG. 76C shows bioluminescence imaging of A549-positive tumor burden at day 8 post-adoptive transfer.

FIG. 77B shows expansion of CER122 transduced T cells post-adoptive transfer as measured by an APC-conjugated, anti-human CD45 antibody at days 4, 8, 16, and 25 post-transfer.

FIGS. 80A-80B shows analysis of phagocytosis of HPV+ SCC152 cells by CER-expressing CD4+ T cells. FIG. 80A shows a magnitude breadth curve of CD4+ T cell phagocytosis by CER type. FIG. 80B shows fluorescent micrograph images of SCC152 target cells engulfed by CD4+CER126- transduced T cells. Top image is an enlargement of a cell in the lower left image showing a SCC152 cell engulfed by CER126-transduced CD4+ T cell. Lower left image shows SCC152 cells (stained with pHrodo red) engulfed by CE126R-transduced CD4+ T cells; lower right image is the same micrograph, showing CER126-transduced CD4+ T cells illuminated with CELLTRACE violet. White arrow indicates CD8+ T cell transduced with E7-specific TCR and that is pHrodo Red negative (lower left panel of FIG. 80B). Software rendition of phagocytosis (lower right panel of FIG. 80B).

FIGS. 82A-82B show viSNE maps of mass cytometry data of CER-transduced CD4+ T cells upon antigen encounter. CER-transduced CD4+ T cells were co-cultured with E7-specific TCR-transduced CD8+ T cells and HPV+ SCC152 target cells and then interrogated by mass cytometry (CyTof). Intact CER-CD4+ T cells are shown in plots displaying tSNE1 and tSNE2 axes. Nine intracellular markers were used for the viSNE analysis. Each dot represents a single cell. FIG. 82A: Coloring the plots by a few of the measured markers (GM-CSF, MIPlb, Perforin, TNF, IL-17, Granzyme B, IL-4, IL-2, and IFNγ) shows the phenotype across viSNE 'islands.' Red represents high expression and blue represents low expression for each marker. FIG. 82B: Populations of CD4+ T cells were generated using a clustering algorithm from all 32 markers and overlaid onto the viSNE map. Arrows indicate enrichment of islands expressing the intracellular marker IFNγ in samples containing CER104, CER116, and CER117.

FIG. 83A: Populations of CD4+ T cells were generated using a clustering algorithm from all 18 markers and overlaid onto the viSNE map. Arrows indicate enrichment of islands expressing the T cell activation marker CD69 in samples containing CER104 and CER116. FIG. 83B: Color plots show the phenotype across viSNE 'islands.' Red represents high expression and blue represents low expression for each marker. Highlighted region indicates cells expressing T cell activation marker CD69.

FIG. 84A: Populations of CD4+ T cells were generated using a clustering algorithm from all 18 markers and overlaid onto the viSNE map. Arrows indicate loss of islands expressing the naïve T cell marker CD45RA within the CCR7+ population among CER104 and CER116 samples compared to controls. FIG. 84B: Color plots show the phenotype across viSNE 'islands.' Red represents high expression and blue represents low expression for each marker. Highlighted region indicates cells the naïve T cell marker CD45RA. CER104 and CER116-transduced CD4 T cells were associated with memory formation after antigen encounter.

FIG. 85A: Ba/F3 cell lines harboring CER21, CER116, or an empty plasmid (mock) were co-cultured with dexamethasone pre-treated thymocytes for 2 hours. The Rac1 inhibitor NSC23766 (Selleck Chem) was added during the co-culture in appropriate wells. Cells were then collected, solubilized in lysis buffer, and protein lysates underwent immunoprecipitation for phospho-Rac1 using PAK-PBD beads (Cytoskeleton Inc.). Immunoprecipitates were eluted and 25 ug of protein was loaded onto SDS-PAGE gradient gels and then probed with monoclonal Rac-1 primary antibody (Cytoskeleton Inc.) overnight at 4° C., washed, and hybridized with anti-mouse HRP (Jackson Labs). Prior to immunoprecipitation, some sample was retained for protein estimation and total Rac1 estimation. Basal samples indicate CER-expressing cell lines cultured without target cells. FIG. 85B: Gel bands were quantified using ImageJ and the proportion of activated Rac1 quantified. FIG. 85C: Representative FACs profiles for pHrodo+ cells in Ba/f3 cell lines harboring CER21 after 6 hour co-culture. The addition of a specific Rac1 small molecule inhibitor abolishes phagocytosis (right). The numbers indicates the percentage (phagocytosis) of pHrodo+ cells in CER21 Ba/f3 cells. FIG. 85D: Phagocytic indices were calculated from fluorescent imaging (FIG. 85E). FIG. 85E: Representative visualization of phagocytosis assays of CER-harboring Ba/f3 cell lines in the presence or absence of Rac1 inhibition. FIG. 85F: Ba/f3 cell lines were co-cultured with pHrodo-red labeled-target cells (prey) overnight and subsequently purified by FACS. Target cell destruction was visualized by time-lapse imaging and quantified over time. The addition of a TRAF6 signaling to CER116 domain enhances CER116 luminal content degradation over time, with near complete resolution of luminal contents by 36 hours. FIG. 85G: Time lapse imaging demonstrates destruction of CER116-expressing Ba/F3 cells luminal contents. pHrodo-red labeled contents are broken down over-time; CER116-harboring Ba/f3 cells (top panels) catabolize target cells, allowing cells to return to homeostasis and resume immune responsiveness.

DETAILED DESCRIPTION

Figure 1:
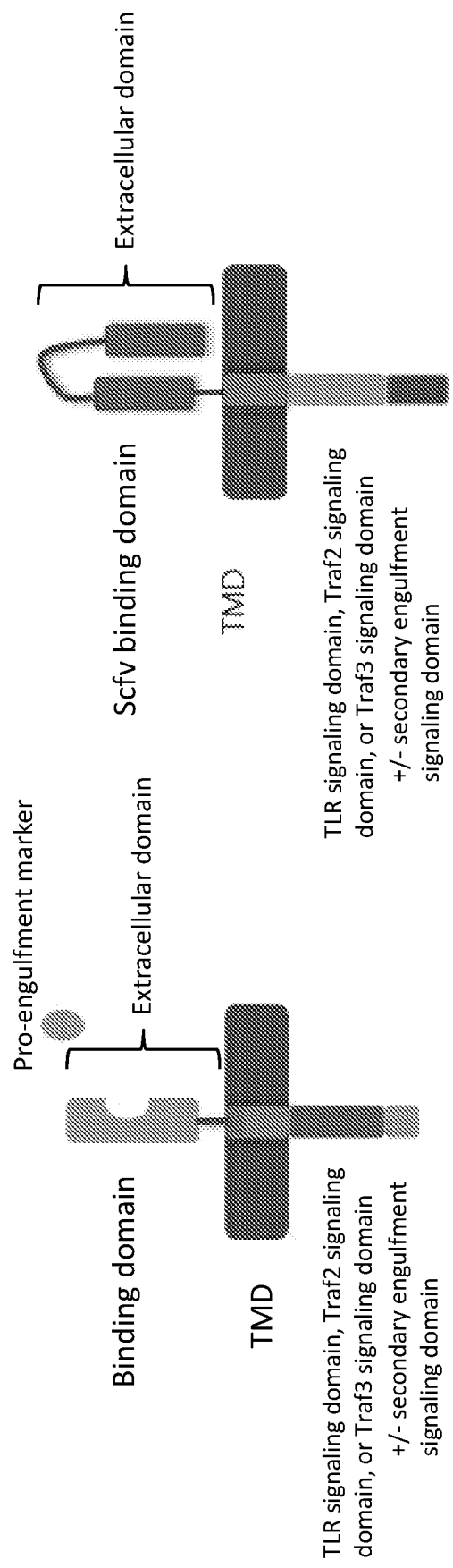
FIGS. 1A-1B show illustrative schematics of chimeric engulfment receptors (CERs).

Chimeric proteins including (a) an extracellular domain comprising an extracellular binding domain and, optionally, an extracellular spacer domain, (b) a transmembrane domain, and (c) an engulfment signaling domain comprising a toll-like receptor (TLR) signaling domain, a Traf6 signaling domain, a Traf2 signaling domain, or a Traf3 signaling domain, and nucleic acid molecules encoding said chimeric proteins are described herein. Additionally, cells modified to express these chimeric proteins and methods and compositions for delivery of such modified cells to a subject in need thereof are provided. The chimeric proteins are referred to herein as a "chimeric engulfment receptor" or "chimeric engulfment receptors" ("CER" in the singular and "CERs" in the plural). Chimeric engulfment receptors described herein are capable of conferring an engulfment phenotype to a host cell that is genetically modified to express said chimeric engulfment receptor. In such certain embodiments, expression of a CER as described herein confers an engulfment phenotype to a host cell that does not naturally exhibit an engulfment phenotype. In other such embodiments, expression of a CER as described herein by a host cell confers an engulfment phenotype specific to a pro-engulfment marker or antigenic marker not naturally targeted by the host cell. In still other such embodiments, expression of a CER as described herein by a host cell confers an engulfment phenotype specific to a pro-engulfment marker or antigenic marker naturally targeted by the host cell and expression of the CER by the host cell enhances engulfment by the host cell of cells, microbes, or particles exhibiting the targeted pro-engulfment or antigenic marker.

In certain embodiments, the CER targets an engulfment marker associated with apoptotic, dead, dying, damaged, infected, or necrotic cells. In other embodiments, the CER targets an antibody bound cell associated with an infectious microbe or particle. In still other embodiments, the CER targets an antigenic marker displayed by aberrant cells or misfolded proteins associated with a disease, disorder, or other undesired condition.

One or more CERs according to the present description can be transduced into and expressed in cells, such as T cells, Natural Killer Cells, Natural Killer T cells, B cells, lymphoid precursor cells, dendritic cells, Langerhans cells, and myeloid cells. In certain embodiments, in addition to engineering the CER to bind to a specified target molecule (e.g., an engulfment marker or an antigenic marker), the engulfment signaling domain of the CER is selected to provide desired engulfment activity. In another embodiment, the CER comprises a primary engulfment signaling domain and a secondary engulfment signaling domain.

Host cells that are genetically modified to express one or more CERs according to the present description can be used for specific engulfment of a target cell or particle expressing a target molecule to which the extracellular domain of the CER binds. In certain embodiments, the target cell or particle may be a tumor cell, a cancer cell, a microbe (e.g., bacteria, fungus, virus), a protozoan parasite, an aberrant cell, or a misfolded protein associated with an infection, disease, disorder, or other undesired condition. In further embodiments, host cells that are genetically modified to express one or more CERs according to the present description are used to treat cancer, an infectious disease (viral, bacterial, fungal, protozoan), an inflammatory disease, an immune disease (e.g., autoimmune disease) in a subject either as a primary therapy or as an adjunct or combination therapy. The CER of the present disclosure may confer pro-inflammatory (immunogenic) phenotype to a host cell expressing the CER via the TLR, Traf6, Traf2, or Traf3 engulfment signaling domain. In certain embodiments, the CER modified host cell further exhibits enhanced proliferative activity, expansion activity, activation, memory formation, cytolytic activity, antigen presentation activity, phagocytic signaling activity, luminal degradation, or any combination thereof that may otherwise not be present in a host cell that does not express the CER.

Definitions

Prior to setting forth this disclosure in more detail, it may be helpful to an understanding thereof to provide definitions of certain terms to be used herein.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

Terms understood by those in the art of antibody technology are each given the meaning acquired in the art, unless expressly defined differently herein. The term "antibody" is used in the broadest sense and includes polyclonal and monoclonal antibodies. An "antibody" may refer to an intact antibody comprising at least two heavy (H) chains and two light (L) chains inter-connected by disulfide bonds, as well as an antigen-binding portion (or antigen-binding domain) of an intact antibody that has or retains the capacity to bind a target molecule. An antibody may be naturally occurring, recombinantly produced, genetically engineered, or modified forms of immunoglobulins, for example intrabodies, peptibodies, nanobodies, single domain antibodies, SMIPs, multispecific antibodies (e.g., bispecific antibodies, diabodies, triabodies, tetrabodies, tandem di-scFV, tandem tri-scFv, ADAPTIR). A monoclonal antibody or antigen-binding portion thereof may be non-human, chimeric, humanized, or human, preferably humanized or human. Immunoglobulin structure and function are reviewed, for example, in Harlow et al., Eds., Antibodies: A Laboratory Manual, Chapter 14 (Cold Spring Harbor Laboratory, Cold Spring Harbor, 1988). "Antigen-binding portion" or "antigen-binding domain" of an intact antibody is meant to encompass an "antibody fragment," which indicates a portion of an intact antibody and refers to the antigenic determining variable regions or complementary determining regions of an intact antibody. Examples of antibody fragments include, but are not limited to, Fab, Fab', F(ab')2, and Fv fragments, Fab'-SH, F(ab')2, diabodies, linear antibodies, scFv antibodies, VH, and multispecific antibodies formed from antibody fragments. A "Fab" (fragment antigen binding) is a portion of an antibody that binds to antigens and includes the variable region and CH1 of the heavy chain linked to the light chain via an inter-chain disulfide bond. An antibody may be of any class or subclass, including IgG and subclasses thereof ($IgG_1$, $IgG_2$, $IgG_3$, $IgG_4$), IgM, IgE, IgA, and IgD.

The term "variable region" or "variable domain" refers to the domain of an antibody heavy or light chain that is involved in binding of the antibody to antigen. The variable domains of the heavy chain and light chain (VH and VL, respectively) of a native antibody generally have similar structures, with each domain comprising four conserved framework regions (FRs) and three CDRs. (See, e.g., Kindt et al. Kuby Immunology, 6th ed., W. H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150: 880-887 (1993); Clarkson et al., Nature 352:624-628 (1991).

The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (HCDR1, HCDR2, HCDR3) and three CDRs in each light chain variable region (LCDR1, LCDR2, LCDR3).

The terms "antigen" and "Ag" refer to a molecule that provokes an immune response. The immune response provoked may involve antibody production, the activation of specific immunologically-competent cells, or both. Macromolecules, including proteins, glycoproteins, and glycolipids, can serve as an antigen. Antigens can be derived from recombinant or genomic DNA. As contemplated herein, an antigen need not be encoded (i) solely by a full length nucleotide sequence of a gene or (ii) by a "gene" at all. An antigen can be generated or synthesized, or an antigen can be derived from a biological sample. Such a biological sample can include, but is not limited, to a tissue sample, a tumor sample, a cell, or a biological fluid.

The term "epitope" or "antigenic epitope" includes any molecule, structure, amino acid sequence or protein determinant within an antigen that is specifically bound by a cognate immune binding molecule, such as an antibody or fragment thereof (e.g., scFv), T cell receptor (TCR), chimeric engulfment receptor, or other binding molecule, domain or protein. Epitopic determinants generally contain chemically active surface groupings of molecules, such as amino acids or sugar side chains, and can have specific three dimensional structural characteristics, as well as specific charge characteristics. An epitope may be a linear epitope or a conformational epitope. The term "anti-tumor effect" refers to a biological effect which can be manifested by a decrease in tumor volume, a decrease in the number of tumor cells, a decrease in the number of metastases, an increase in life expectancy, or amelioration of various physiological symptoms associated with a cancerous condition. An "anti-tumor effect" can also be manifested by prevention of a hematological malignancy or tumor formation.

"Autoimmune disease" refers to a disorder that results from an autoimmune response. An autoimmune disease is the result of an inappropriately excessive response to a self-antigen. An autoimmune response may involve self-reactive B-cells that produce autoantibodies, self-reactive T-cells, or both. An "autoantibody" as used herein is an antibody produced by a subject that binds to a self-antigen also produced by the subject.

"Autologous" refers to any material derived from the same subject to which it is later to be re-introduced.

"Allogeneic" refers to a graft derived from a different subject of the same species.

As used herein, the terms "binding domain," "binding region," and "binding moiety" refer to a molecule, such as a peptide, oligopeptide, polypeptide, or protein that possesses the ability to specifically and non-covalently bind, associate, unite, recognize, or combine with a target molecule (e.g., PtdSer, an IgG antibody, an IgE antibody, an IgA antibody, CD138, CD38, CD33, CD123, CD79b, mesothelin, PSMA, BCMA, ROR1, MUC-16, L1CAM, CD22, CD19, EGFRviii, VEGFR-2, or GD2). A binding domain includes any naturally occurring, synthetic, semi-synthetic, or recombinantly produced binding partner for a biological molecule or other target of interest. In some embodiments, the binding domain is an antigen-binding domain, such as an antibody or functional binding domain or antigen-binding portion thereof. Exemplary binding domains include single chain antibody variable regions (e.g., domain antibodies, sFv, scFv, Fab), receptor ectodomains (e.g., TNF-α), ligands (e.g., cytokines, chemokines), or synthetic polypeptides selected for the specific ability to bind to a biological molecule.

A variety of assays are known for identifying binding domains of the present disclosure that specifically bind a particular target, as well as determining binding domain affinities, such as Western blot, ELISA, and BIACORE® analysis (see also, e.g., Scatchard et al., Ann. N.Y. Acad. Sci. 51:660, 1949; and U.S. Pat. Nos. 5,283,173, 5,468,614, or the equivalent). As used herein, "specifically binds" refers to an association or union of a binding domain, or a fusion protein thereof, to a target molecule with an affinity or $K_a$ (i.e., an equilibrium association constant of a particular binding interaction with units of 1/M) equal to or greater than $10^5$ $M^{-1}$, while not significantly associating or uniting with any other molecules or components in a sample.

The term "cancer" as used herein is defined as disease characterized by the rapid and uncontrolled growth of aberrant cells. The aberrant cells may form solid tumors or constitute a hematological malignancy. Cancer cells can spread locally or through the bloodstream and lymphatic system to other parts of the body. Examples of various cancers include, but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

A "disease" is a state of health of a subject wherein the subject cannot maintain homeostasis, and wherein, if the disease is not ameliorated, then the subject's health continues to deteriorate. In contrast, a "disorder" or "undesirable condition" in a subject is a state of health in which the subject is able to maintain homeostasis, but in which the subject's state of health is less favorable than it would be in the absence of the disorder or undesirable condition. Left untreated, a disorder or undesirable condition does not necessarily result in a further decrease in the subject's state of health.

A "microbe" or "microorganism" refers to any species of bacteria, virus, archaea, or fungi.

A "particle" refers to a fragment of a cell or a small object of at least 100 nm and up to 6 μm in diameter and that is derived from a living cell or organism. A particle can be a viral particle, small mineral particle, cellular debris, or a synthetic particle.

"Encoding" refers to the inherent property of specific polynucleotide sequences, such as DNA, cDNA, and mRNA sequences, to serve as templates for synthesis of other polymers and macromolecules in biological processes having either a defined sequence of nucleotides (i.e., rRNA, tRNA and mRNA) or a defined sequence of amino acids and the biological properties resulting therefrom.

Thus, a polynucleotide encodes a protein if transcription and translation of mRNA corresponding to that polynucleotide produces the protein in a cell or other biological system. Both a coding strand and a non-coding strand can be referred to as encoding a protein or other product of the polynucleotide.

Unless otherwise specified, a "nucleotide sequence encoding an amino acid sequence" includes all nucleotide sequences that are degenerate versions of each other and that encode the same amino acid sequence.

As used herein, the term "endogenous" or "native" refers to a gene, protein, compound, molecule or activity that is normally present in a host or host cell.

As used herein, the term "engulfment" refers to a receptor-mediated process wherein endogenous or exogenous cells or particles greater than 100 nm in diameter are internalized by a phagocyte or host cell of the present disclosure. Engulfment is typically composed of multiple steps: (1) tethering of the target cell or particle via binding of an engulfment receptor to a pro-engulfment marker or antigenic marker directly or indirectly (via a bridging molecule) on a target cell or particle; and (2) internalization or engulfment of the whole target cell or particle, or a portion thereof. In certain embodiments, internalization may occur via cytoskeletal rearrangement of a phagocyte or host cell to form a phagosome, a membrane-bound compartment containing the internalized target. Engulfment may further include maturation of the phagosome, wherein the phagosome becomes increasingly acidic and fuses with lysosomes (to form a phagolysosome), whereupon the engulfed target is degraded (e.g. "phagocytosis"). Alternatively, phagosome-lysosome fusion may not be observed in engulfment. In yet another embodiment, a phagosome may regurgitate or discharge its contents to the extracellular environment before complete degradation. In some embodiments, engulfment refers to phagocytosis. In some embodiments, engulfment includes tethering of the target cell or particle by the phagocyte of host cell of the present disclosure, but not internalization. In some embodiments, engulfment includes tethering of the target cell or particle by the phagocyte of host cell of the present disclosure and internalization of part of the target cell or particle.

As used herein, the term "phagocytosis" refers to an engulfment process of cells or large particles (>100 nm) wherein tethering of a target cell or particle, engulfment of the target cell or particle, and degradation of the internalized target cell or particle occurs. In certain embodiments, phagocytosis comprises formation of a phagosome that encompasses the internalized target cell or particle and phagosome fusion with a lysosome to form a phagolysosome, wherein the contents therein are degraded. In certain embodiments, during phagocytosis, following binding of a CER expressed on a phagocyte or a host cell of the present disclosure to an engulfment marker expressed by a target cell or particle, a phagocytic synapse is formed; an actin-rich phagocytic cup is generated at the phagocytic synapse; phagocytic arms are extended around the target cell or particle through cytoskeletal rearrangements; and ultimately, the target cell or particle is pulled into the phagocyte or host cell through force generated by motor proteins. As used herein, "phagocytosis" includes the process of "efferocytosis", which specifically refers to the phagocytosis of apoptotic or necrotic cells in a non-inflammatory manner.

As used herein, the term "pro-engulfment marker" refers to a moiety (e.g., protein, lipid, or polysaccharide) that an apoptotic, necrotic, pyroptotic, or infected cell exhibits on its surface that distinguishes it from a non-apoptotic, non-necrotic, non-pyroptotic, oncotic, or uninfected cell, respectively. A pro-engulfment marker can be an intracellular moiety that is surface exposed on an apoptotic or necrotic cell, a moiety that has altered glycosylation or altered surface charge on an apoptotic or necrotic cell, or a serum moiety that is bound to an apoptotic, necrotic, pyroptotic, or oncotic cell. Examples of pro-engulfment markers for apoptotic cells include phosphatidylserine (PtdSer), ICAM-3, oxidized low density lipoprotein, calreticulin, annexin I, complement C1q, and thrombospondin. Necrotic, oncotic, and pyroptotic cells also expose PtdSer pro-engulfment markers on the cell surface. Engulfment receptors can detect (or bind) a pro-engulfment marker on a target cell (e.g., a damaged, infected, apoptotic, necrotic, pyroptotic, or oncotic cell) directly or indirectly using soluble bridging molecules as intermediaries that bind to the pro-engulfment marker.

A "toll-like receptor" refers to a member of a family of conserved immune receptors that are pattern recognition receptors (PRR) that recognize molecules that are conserved in pathogens but distinguishable from host molecules (e.g., pathogen-associated molecular patterns (PAMPs)) as well as endogenous molecules released from necrotic or dying cells (danger-associated molecular patterns (DAMPs)). Examples of TLR PAMP ligands include bacterial lipoprotein, bacterial peptidoglycans, double-stranded RNA, lipopolysaccharides, bacterial flagella, single-stranded RNA, and CpG DNA. DAMPs include heat shock proteins and protein fragments from the extracellular matrix. TLRs are type I transmembrane proteins characterized by an extracellular domain containing leucine-rich repeats (LRRs), a juxtamembrane domain comprising acidic amino acids lying between the LRRs and the transmembrane domain, and a cytoplasmic signaling domain that contains a conserved region called the Toll/IL-1 receptor (TIR) domain. TLRs are expressed on the membranes of leukocytes including dendritic cells, macrophages, natural killer cells, cells of the adaptive immunity (T and B cells) and non-immune cells (epithelial and endothelial cells, and fibroblasts). Ligand binding by TLRs initiates signaling cascades leading to the activation of transcription factors, such as AP-1, NF-kB and interferon regulatory factors (IRFs), resulting in production of interferons, pro-inflammatory cytokines, and effector cytokines that direct the adaptive immune response. A TLR may be from any mammal, e.g., humans, primates, cows, horses, sheep, dogs, cats, mice, rats, rabbits, guinea pigs, or pigs. A TLR may be any one of the ten TLRs (TLR1-TLR10) that have been identified in humans or any one of the thirteen TLRs have been identified in mice (TLR1-13). TLRs are located on the plasma membrane, except for TLR3, TLR7, TLR8, and TLR9, which are endosomal TLRs.

A "TLR signaling domain" refers to the cytoplasmic domain of a TLR molecule comprising a TIR domain or a functional fragment thereof. In certain embodiments, a TLR signaling domain may be a signaling domain or functional fragment thereof of any one of TLR1, TLR2, TLR3, TLR4, TLRS, TLR6, TLR7, TLR8, or TLR9.

An "engulfment signaling domain" refers to an intracellular effector domain, which upon binding of the target molecule (e.g., pro-engulfment marker or antigenic marker) targeted by the extracellular domain of a CER expressed by a host cell, activates one or more signaling pathways in the host cell resulting in engulfment, including, in specific embodiments, cytoskeletal rearrangement of the host cell and internalization of the target cell, microbe, or particle associated with the marker or antigen. In certain embodiments, an engulfment signaling domain activates one or more signaling pathways resulting in phagocytosis of the target cell, microbe, or particle. In certain embodiments, the engulfment signaling domain includes an engulfment signaling domain comprising a TLR signaling domain, Traf6 signaling domain, Traf2 signaling domain, or Traf3 signaling domain. In certain other embodiments, the engulfment signaling domain includes a primary engulfment signaling domain and a secondary engulfment signaling domain. An engulfment signaling domain may comprise the full length intracellular component of an engulfment signaling molecule or a functional fragment thereof.

A "pro-inflammatory engulfment signaling domain" refers to an effector domain that (i) stimulates engulfment of the targeted cell, microbe, or particle and (ii) is derived from an endogenous receptor or signaling molecule that typically stimulates one or more of (a) host cell secretion of inflammatory cytokines, such as, for example, TNFα, IL-1, IL-6, IL-12, and IL-23, (b) host cell secretion of inflammatory chemokines, such as, for example, CCLS (RANTES), CXCL9, and CXCL10, (c) upregulation of cell surface co-stimulatory markers, such as, for example, CD80, CD86, HLA-DR, CD40, HVEM, and 4-1BBL, and (d) activation of one or more signaling cascades, such as NF-KB, that induce, potentiate, or complement chemotherapies, antibody-based immune therapies, or cellular therapies, such as, for example, T cell targeted therapies. In certain embodiments, stimulation of pro-inflammatory engulfment signaling promotes inflammation in the local tissue milieu. A pro-inflammatory engulfment signaling domain can also be referred to as an "immunogenic" engulfment signaling domain or an "inflammatory" engulfment signaling domain.

As used herein, an "effector domain" is an intracellular portion of a fusion protein or receptor that can directly or indirectly promote a biological or physiological response in a cell expressing the effector domain when receiving the appropriate signal. In certain embodiments, an effector domain is part of a protein or protein complex that receives a signal when bound, or it binds directly to a target molecule, which triggers a signal from the effector domain. For example, in response to binding of the CER to a target molecule, the effector domain may transduce a signal to the interior of the host cell, eliciting an effector function, e.g., engulfment, phagolysosome maturation, secretion of inflammatory cytokines and/or chemokines. An effector domain may directly promote a cellular response when it contains one or more signaling domains or motifs. In other embodiments, an effector domain will indirectly promote a cellular response by associating with one or more other proteins that directly promote a cellular response.

As used herein, "heterologous" or "non-endogenous" or "exogenous" refers to any gene, protein, compound, molecule or activity that is not native to a host cell or a subject, or is any gene, protein, compound, molecule, or activity native to a host or host cell but has been altered or mutated such that the structure, activity or both is different as between the native and mutated molecules. In certain embodiments, heterologous, non-endogenous or exogenous molecules (e.g., receptors, ligands) may not be endogenous to a host cell or subject, but instead nucleic acids encoding such molecules may have been added to a host cell by conjugation, transformation, transfection, electroporation, or the like, wherein the added nucleic acid molecule may integrate into a host cell genome or can exist as extrachromosomal genetic material (e.g., as a plasmid or other self-replicating vector). The term "homologous" or "homolog" refers to a molecule or activity found in or derived from a host cell, species or strain. For example, a heterologous or exogenous molecule or gene encoding the molecule may be homologous to a native host or host cell molecule or gene that encodes the molecule, respectively, but may have an altered structure, sequence, expression level or combinations thereof. A non-endogenous molecule may be from the same species, a different species or a combination thereof.

"Junction amino acids" or "junction amino acid residues" refer to one or more (e.g., about 2-20) amino acid residues between two adjacent motifs, regions or domains of a polypeptide. Junction amino acids may result from the construct design of a chimeric protein (e.g., amino acid residues resulting from the use of a restriction enzyme site during the construction of a nucleic acid molecule encoding a fusion protein).

"Nucleic acid molecule" and "polynucleotide" can be in the form of RNA or DNA, which includes cDNA, genomic DNA, and synthetic DNA. A nucleic acid molecule may be double stranded or single stranded, and if single stranded, may be the coding strand or non-coding (anti-sense strand). A coding molecule may have a coding sequence identical to a coding sequence known in the art or may have a different coding sequence, which, as the result of the redundancy or degeneracy of the genetic code, or by splicing, can encode the same polypeptide.

The term "overexpressed" or "overexpression" of an antigen refers to an abnormally high level of antigen expression in a cell. Overexpressed antigen or overexpression of antigen is often associated with a disease state, such as in hematological malignancies and cells forming a solid tumor within a specific tissue or organ of a subject. Solid tumors or hematological malignancies characterized by overexpression of a tumor antigen can be determined by standard assays known in the art.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, the term "mature polypeptide" or "mature protein" refers to a protein or polypeptide that is secreted or localized in the cell membrane or inside certain cell organelles (e.g., the endoplasmic reticulum, golgi, or endosome) and does not include an N-terminal signal peptide.

A "signal peptide", also referred to as "signal sequence", "leader sequence", "leader peptide", "localization signal" or "localization sequence", is a short peptide (usually 15-30 amino acids in length) present at the N-terminus of newly synthesized proteins that are destined for the secretory pathway. A signal peptide typically comprises a short stretch of hydrophilic, positively charged amino acids at the N-terminus, a central hydrophobic domain of 5-15 residues, and a C-terminal region with a cleavage site for a signal peptidase. In eukaryotes, a signal peptide prompts translocation of the newly synthesized protein to the endoplasmic reticulum where it is cleaved by the signal peptidase, creating a mature protein that then proceeds to its appropriate destination.

The "percent identity" between two or more nucleic acid or amino acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., J. Mol. Biol. 215:403, 1990; see also BLASTN at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY:NY (1975), pp. 71-'7'7; Lewin, Genes IV, Oxford University Press, NY and Cell Press, Cambridge, Mass. (1990), p. 8).

The term "chimeric" refers to any nucleic acid molecule or protein that is not endogenous and comprises sequences joined or linked together that are not normally found joined or linked together in nature. For example, a chimeric nucleic acid molecule may comprise regulatory sequences and coding sequences that are derived from different sources, or regulatory sequences and coding sequences that are derived from the same source but arranged in a manner different than that found in nature.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "subject," "patient" and "individual" are used interchangeably herein and are intended to include living organisms in which an immune response can be elicited (e.g., mammals). Examples of subjects include humans, primates, cows, horses, sheep, dogs, cats, mice, rats, rabbits, guinea pigs, pigs, and transgenic species thereof.

The term "T cells" refers to cells of T cell lineage. "Cells of T cell lineage" refers to cells that show at least one phenotypic characteristic of a T cell or a precursor or progenitor thereof that distinguishes the cells from other lymphoid cells, and cells of the erythroid or myeloid lineages. Such phenotypic characteristics can include expression of one or more proteins specific for T cells (e.g., $CD3^+$, $CD4^+$, $CD8^+$), or a physiological, morphological, functional, or immunological feature specific for a T cell. For example, cells of the T cell lineage may be progenitor or precursor cells committed to the T cell lineage; $CD25^+$ immature and inactivated T cells; cells that have undergone CD4 or CD8 linage commitment; thymocyte progenitor cells that are $CD4^+CD8^+$ double positive; single positive $CD4^+$ or $CD8^+$; TCRαβ or TCR γδ; or mature and functional or activated T cells. The term "T cells" encompasses naïve T cells (CD45 RA+, CCR7+, CD62L+, CD27+, CD45RO−), central memory T cells ($CD45RO^+$, $CD62L^+$, $CD8^+$), effector memory T cells (CD45RA+, CD45RO−, CCR7−, CD62L−, CD27−), mucosal-associated invariant T cells, natural killer T cells, and tissue resident T cells.

The term "B cells" refers to cells of the B cell lineage. "Cells of T cell lineage" refers to cells that show at least one phenotypic characteristic of a B cell or a precursor or progenitor thereof that distinguishes the cells from other lymphoid cells, and cells of the erythroid or myeloid lineages. Such phenotypic characteristics can include expression of one or more proteins specific for B cells (e.g., $CD19^+$, CD72+, CD24+, $CD20^+$), or a physiological, morphological, functional, or immunological feature specific for a B cell. For example, cells of the B cell lineage may be progenitor or precursor cells committed to the B cell lineage (e.g., pre-pro-B cells, pro-B cells, and pre-B cells); immature and inactivated B cells or mature and functional or activated B cells. Thus, "B cells" encompass naïve B cells, plasma cells, regulatory B cells, marginal zone B cells, follicular B cells, lymphoplasmacytoid cells, plasmablast cells, and memory B cells (e.g., $CD27^+$,$IgD^-$).

A "therapeutically effective amount" or "effective amount" of a chimeric protein or cell expressing a chimeric protein of this disclosure (e.g., a CER or a cell expressing a CER) refers to that amount of protein or cells sufficient to result in amelioration of one or more symptoms of the disease, disorder, or undesired condition being treated. When referring to an individual active ingredient or a cell expressing a single active ingredient, administered alone, a therapeutically effective dose refers to the effects of that ingredient or cell expressing that ingredient alone. When referring to a combination, a therapeutically effective dose refers to the combined amounts of active ingredients or combined adjunctive active ingredient with a cell expressing an active ingredient that results in a therapeutic effect, whether administered serially or simultaneously.

"Treat" or "treatment" or "ameliorate" refers to medical management of a disease, disorder, or undesired condition of a subject. In general, an appropriate dose or treatment regimen comprising a host cell expressing a CER of this disclosure is administered in an amount sufficient to elicit a therapeutic or prophylactic benefit. Therapeutic or prophylactic/preventive benefit includes improved clinical outcome; lessening or alleviation of symptoms associated with a disease, disorder, or undesired condition; decreased occurrence of symptoms; improved quality of life; longer disease-free status; diminishment of extent of disease, disorder, or undesired condition; stabilization of disease state; delay of disease progression; remission; survival; prolonged survival; or any combination thereof.

The phrase "under transcriptional control" or "operatively linked" as used herein means that a promoter is in the correct location and orientation in relation to a polynucleotide to control the initiation of transcription by RNA polymerase and expression of the polynucleotide.

A "vector" is a nucleic acid molecule that is capable of transporting another nucleic acid. Vectors may be, for example, plasmids, cosmids, viruses, or phage. The term should also be construed to include non-plasmid and non-viral compounds which facilitate transfer of nucleic acid into cells. An "expression vector" is a vector that is capable of directing the expression of a protein encoded by one or more genes carried by the vector when it is present in the appropriate environment.

In certain embodiments, the vector is a viral vector. Examples of viral vectors include, but are not limited to, adenovirus vectors, adeno-associated virus vectors, retrovirus vectors, gammaretrovirus vectors, and lentivirus vectors.

"Retroviruses" are viruses having an RNA genome. "Gammaretrovirus" refers to a genus of the retroviridae family. Examples of gammaretroviruses include mouse stem cell virus, murine leukemia virus, feline leukemia virus, feline sarcoma virus, and avian reticuloendotheliosis viruses. "Lentivirus" refers to a genus of retroviruses that are capable of infecting dividing and non-dividing cells. Examples of lentiviruses include, but are not limited to HIV (human immunodeficiency virus, including HIV type 1 and HIV type 2, equine infectious anemia virus, feline immunodeficiency virus (Hy), bovine immune deficiency virus (BIV), and simian immunodeficiency virus (SIV).

In other embodiments, the vector is a non-viral vector. Examples of non-viral vectors include lipid-based DNA vectors, modified mRNA (modRNA), self-amplifying mRNA, closed-ended linear duplex (CELiD) DNA, and transposon-mediated gene transfer (PiggyBac, Sleeping Beauty). Where a non-viral delivery system is used, the delivery vehicle can be a liposome. Lipid formulations can be used to introduce nucleic acids into a host cell in vitro, ex vivo, or in vivo. The nucleic acid may be encapsulated in the interior of a liposome, interspersed within the lipid bilayer of a liposome, attached to a liposome via a linking molecule that is associated with both the liposome and the nucleic acid, contained or complexed with a micelle, or otherwise associated with a lipid.

Additional definitions are provided throughout the present disclosure.

Chimeric Engulfment Receptors (CERs)

Chimeric engulfment receptors (CERs) are described herein. In particular embodiments, the CER is a chimeric, single chain protein, which comprises an extracellular domain and an engulfment signaling domain comprising a TLR signaling domain, a Traf6 signaling domain, a Traf2 signaling domain, or a Traf3 signaling domain, which are connected by a transmembrane domain. The extracellular domain includes an extracellular binding domain and, optionally, an extracellular spacer domain. When expressed in a host cell, a CER confers an engulfment phenotype to the modified host cell (the host cell is "switched" to an engulfment phenotype), specific to a selected pro-engulfment marker or antigenic marker present on or expressed by target cells, microbes, particles, or other materials. In particular CER embodiments, the chimeric protein comprises, from amino-terminus to carboxy-terminus: an extracellular domain having a binding domain specific for a target molecule and an optional extracellular spacer domain; a transmembrane domain; and an engulfment signaling domain comprising a TLR signaling domain, Traf6 signaling domain, Traf2 signaling domain, or Traf3 signaling domain. In further embodiments, the engulfment signaling domain comprises a primary engulfment signaling domain and a secondary engulfment signaling domain (see, e.g., FIGS. 1A and 1B).

The component parts of a CER as disclosed herein can be selected and arranged to provide a desired engulfment phenotype. For example, in certain embodiments, the extracellular domain can include a binding domain specific to: (i) a pro-engulfment marker associated with apoptotic, dead, dying, damaged, or necrotic cells; or (ii) an antigenic marker displayed by foreign (e.g., a microbe), infected, or aberrant cells associated with an infection, disease, disorder, or other undesired condition.

The engulfment signaling domain can include one or more effector (also referred to as "signaling") domains that drive engulfment of the targeted cell. Signaling by the engulfment signaling domain is triggered by binding of the extracellular domain to the targeted pro-engulfment or antigenic marker. In certain embodiments, the engulfment signaling domain comprises an engulfment signaling domain comprising a TLR signaling domain, a Traf6 signaling domain, a Traf2 signaling domain, or a Traf3 signaling domain. In particular embodiments, a TLR signaling domain comprises a TLR1 signaling domain, a TLR 2 signaling domain, a TLR3 signaling domain, a TLR4 signaling domain, a TLR5 signaling domain, a TLR6 signaling domain, a TLR7 signaling domain, a TLR8 signaling domain, or a TLR9 signaling domain. In other embodiments, the engulfment signaling domain comprises a primary engulfment signaling domain comprising a TLR signaling domain, a Traf6 signaling domain, a Traf2 signaling domain, or a Traf3 signaling domain and a secondary engulfment signaling domain. In particular embodiments, the secondary engulfment signaling domain comprises a TLR1, TLR2, TLR3, TLR4, TLR5, TLR6, TLR7, TLR8, TLR9, TRAF6, TRAF2, TRAF3, FcγR1, FcγR2A, FcγR2B2, FcγR2C, FcγR3A, FcER1, FcaR1, BAFFR, NFAM1, Dap12, MERTK, or CD79b signaling domain. A CER according to the present disclosure can be engineered for application in a variety of therapeutic contexts (e.g., clearance of apoptotic, dead, dying, damaged, infected, or necrotic cells, clearance of microbes responsible for infectious disease, and clearance of aberrant cells associated with a disease, disorder or undesired condition), while providing engulfment signaling that complements the desired therapeutic outcome (e.g., pro-inflammatory engulfment signaling).

Figure 2:
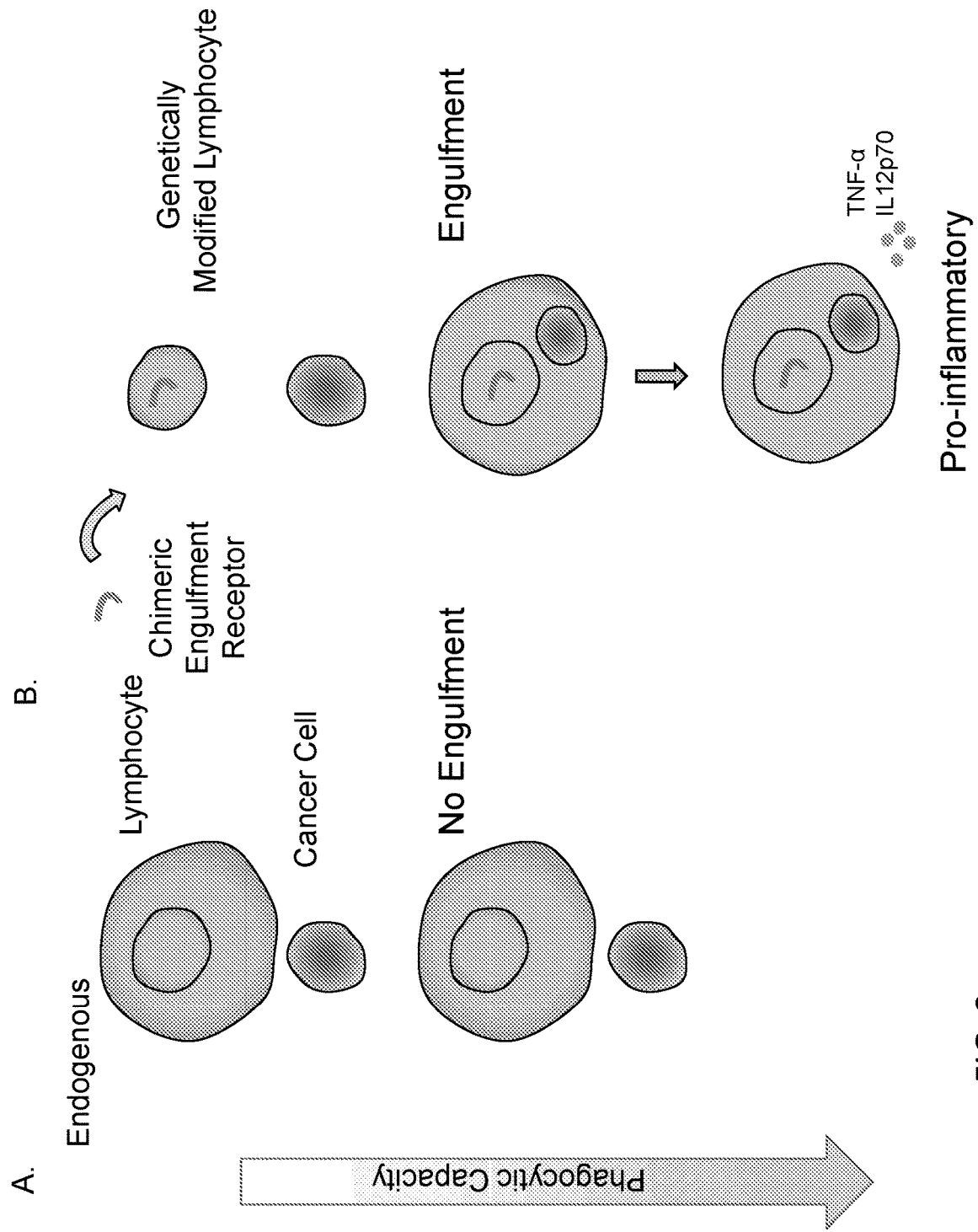
FIGS. 2A-2B show a comparison of a natural lymphocyte and a lymphocyte modified with a CER of the present disclosure.

FIGS. 2A and 2B provide a functional comparison of a natural lymphocyte with a lymphocyte modified with an embodiment of a CER of the present disclosure. FIG. 2A shows an endogenous lymphocyte, and as is represented in the figure, the natural lymphocyte does not exhibit an engulfment phenotype. However, as is illustrated in FIG. 2B, a lymphocyte modified to express a CER as described herein exhibits an engulfment phenotype specific to the targeted cancer cell, leading to engulfment (e.g., phagocytosis) and elimination of the targeted cancer cell. In particular embodiments, the engulfment signaling domains included in CERs according to the present description can drive pro-inflammatory engulfment signaling.

Component parts of the fusion proteins of the present disclosure are further described in detail herein.

I. Extracellular Domain

As described herein, a CER comprises an extracellular domain specific to a target molecule. In certain embodiments, the extracellular domain includes an extracellular binding domain that specifically binds a targeted pro-engulfment marker or antigen. Binding of a target molecule by the binding domain may block the interaction between the target molecule (e.g., a receptor or a ligand) and another molecule and, for example, interfere with, reduce or eliminate certain functions of the target molecule (e.g., signal transduction). In some embodiments, the binding of a target molecule may induce certain biological pathways or identify the target molecule or cell expressing the target molecule or cell expressing the target molecule for elimination.

A binding domain may be any polypeptide or peptide that specifically binds a target molecule of interest. Sources of binding domains include receptor binding domains, ligand binding domains, and antibodies or antigen binding portions, such as antibody variable regions from various species (which can be in the form of antibodies, sFvs, scFvs, Fabs, scFv-based grababody, or soluble VH domain or domain antibodies), including human, rodent, avian, or ovine. Additional sources of binding domains include variable regions of antibodies from other species, such as camelid (from camels, dromedaries, or llamas; Ghahroudi et al., FEBS Lett. 414:521, 1997; Vincke et al., J. Biol. Chem. 284:3273, 2009; Hamers-Casterman et al., Nature 363:446, 1993 and Nguyen et al., J. Mol. Biol. 275:413, 1998), nurse sharks (Roux et al., Proc. Nat'l. Acad. Sci. (USA) 95:11804, 1998), spotted ratfish (Nguyen et al., Immunogen. 54:39, 2002), or lamprey (Herrin et al., Proc. Nat'l. Acad. Sci. (USA) 105: 2040, 2008 and Alder et al. Nat. Immunol. 9:319, 2008). These antibodies can form antigen-binding regions using only a heavy chain variable region, i.e., these functional antibodies are homodimers of heavy chains only (referred to as "heavy chain antibodies") (Jespers et al., Nat. Biotechnol. 22:1161, 2004; Cortez-Retamozo et al., Cancer Res. 64:2853, 2004; Baral et al., Nature Med. 12:580, 2006; and Barthelemy et al., J. Biol. Chem. 283:3639, 2008).

In some embodiments, the extracellular domain binds to a pro-engulfment marker. In certain such embodiments, the pro-engulfment marker targeted by the extracellular domain is phosphatidylserine (PtdSer), ICAM-3, oxidized low density lipoprotein, calreticulin, annexin I, complement C1q, or thrombospondin. In further embodiments, the extracellular domain that binds to a pro-engulfment marker is derived from an endogenous engulfment receptor or a soluble bridging molecule for an engulfment receptor (e.g., GAS6, Protein S, MFG-E8). In some embodiments, the entire extracellular portion (for membrane spanning molecules), the entire bridging molecule, or a truncated portion of an engulfment receptor or bridging molecule is used, provided that the truncated portion retains sufficient binding activity to the pro-engulfment marker (i.e., is a functional variant). In further embodiments, the extracellular portion of an engulfment receptor or bridging molecule used for the extracellular domain is a variant of the entire extracellular portion (for membrane spanning molecules), the entire bridging molecule, or a truncated portion of the engulfment receptor or bridging molecule, provided that the variant retains sufficient binding activity to the pro-engulfment marker (i.e., is a functional variant). In some embodiments, the extracellular domain includes a T-cell immunoglobulin and mucin domain 1 (Tim1), T-cell immunoglobulin and mucin domain 4 (Tim4), T-cell immunoglobulin and mucin domain 3 (Tim3), stabilin-2, RAGE, or Fc receptor (FcR) extracellular domain. In specific embodiments, an FcR extracellular domain can include a binding domain from FcγR1, FcγR2A, FcγR2B2, FcγR2C, FcγR3A, FcER1, or FcaR1. In further embodiments, the extracellular domain can include a PtdSer binding domain from Tim1, Tim4, Tim3, stabilin-2, receptor for advanced glycation end products (RAGE), brain-specific angiogenesis inhibitor 1 (BAI1), Milk Fat Globule-EGF Factor 8 Protein (MFG-E8) (e.g., a FA58C2 domain that mediates high affinity binding to PtdSer), Growth Arrest Specific 6 (GAS6), protein S, protein C, Factor II, Factor VII, Factor IX, Factor X, Beta 2-glycoprotein I, α5p3 integrin and other integrins, CR3 complement receptor, CR4 complement receptor, CD14, CD93, annexin V, phosphatidylserine receptor (PSr), pro-thrombin, or scavenger receptors such as scavenger receptor B (SRB) (e.g., SRB1 (CD36)), scavenger receptor C (SRC) (e.g., LOX-1, SRCL), scavenger receptor D (SRD) (e.g., CD68, macrosialin), and PSOX.

In some embodiments, the extracellular domain comprises or is a sequence that is at least 90%, at least 91%, at least 92%, at least 93%, at least 94%, at least 95%, at least 96%, at least 97%, at least 98%, at least 99%, at least 99.5%, or 100% identical to a FcγRI binding domain comprising an amino acid sequence of SEQ ID NO:1 or amino acids 16-292 of SEQ ID NO:1, TIM1 binding domain comprising an amino acid sequence of SEQ ID NO:2 or amino acids 21-290 of SEQ ID NO:2, a TIM4 binding domain comprising an amino acid sequence of SEQ ID NO:3 or amino acids 25-314 of SEQ ID NO:3, a TIM3 binding domain comprising an amino acid sequence of SEQ ID NO:4 or amino acids 22-202 of SEQ ID NO:4, a FA58C2 binding domain comprising an amino acid sequence of SEQ ID NO:5, a GAS6 binding domain comprising an amino acid sequence of SEQ ID NO:6 or amino acids 31-94 of SEQ ID NO:6, a BAI1 binding domain comprising an amino acid sequence of SEQ ID NO:8 or a protein S binding domain comprising an amino acid sequence of SEQ ID NO:7 or amino acids 25-87 of SEQ ID NO:7. In certain other embodiments, the extracellular domain is encoded by a polynucleotide sequence that comprises or is a sequence that is at least 90%, at least 91%, at least 92%, at least 93%, at least 94%, at least 95%, at least 96%, at least 97%, at least 98%, at least 99%, at least 99.5%, or 100% identical to a polynucleotide encoding FcγRI binding domain according to SEQ ID NO:9, a polynucleotide encoding a TIM1 binding domain according to SEQ ID NO:10, a polynucleotide encoding a TIM4 binding domain according to SEQ ID NO:11, a polynucleotide encoding a TIM3 binding domain according to SEQ ID NO:12, a polynucleotide encoding FA58C2 binding domain according to SEQ ID NO:13, a polynucleotide encoding a GAS6 binding domain according to SEQ ID NO:14, a polynucleotide encoding a BAI1 binding domain according to SEQ ID NO:120, or a polynucleotide sequence encoding a protein S binding domain according to SEQ ID NO:15.

In other embodiments, the extracellular domain is derived from least one of the following: CD14, which binds to ICAM3; a scavenger receptor extracellular domain, which binds to oxidized LDL; a lectin, which binds to altered sugars; CD36, which binds to thrombospondin; or LRP1/CD91 or a lectin moiety, which binds to calreticulin.

In still other embodiments, the extracellular domain includes an antibody or antigen binding fragment thereof, such as a single chain Fv fragment (scFv) that comprises VH and VL regions, specific for a target molecule of interest. In certain embodiments, the antibody is chimeric, human, or humanized. In further embodiments, the VH and VL regions are human or humanized. In particular embodiments, the extracellular domain is an antibody or antigen binding portion thereof that is specific for a pro-engulfment marker. Antibodies specific for phosphatidylserine are known in the art (see, U.S. Pat. No. 7,247,303; Khogeer et al., 2015, Lupus 24:186-90; Gerber et al., 2015, Am. J. Nucl. Med. Mol. Imaging, 5:493-503, each of which is incorporated by reference in its entirety). In particular embodiments, a target molecule of interest is a tumor antigen, for example CD138, CD38, CD33, CD123, CD72, CD79a, CD79b, mesothelin, PSMA, BCMA, ROR1, MUC-16, L1CAM, CD22, CD19, CD20, CD23, CD24, CD37, CD30, CA125, CD56, c-Met, EGFR, GD-3, HPV E6, HPV E7, MUC-1, HER2, folate receptor α, CD97, CD171, CD179a, CD44v6, WT1, VEGF-α, VEGFR1, IL-13Rα1, IL-13Rα2, IL-11Rα, PSA, FcRH5, NKG2D ligand, NY-ESO-1, TAG-72, CEA, ephrin A2, ephrin B2, Lewis A antigen, Lewis Y antigen, MAGE, MAGE-Al, RAGE-1, folate receptor β, EGFRviii, VEGFR-2, LGRS, SSX2, AKAP-4, FLT3, fucosyl GM1, GM3, o-acetyl-GD2, and GD2, and exemplary $V_H$ and $V_L$ regions include the segments of anti-CD138, –CD38, –CD33, –CD123, –CD72, –CD79a –CD79b, –mesothelin, –PSMA, –BCMA, –ROR1, –MUC-16, –L1CAM, –CD22, –CD19, –CD20, –CD23, –CD24, –CD37, –CD30, –CA125, –CD56, –c-Met, –EGFR, –GD-3, –HPV E6, –HPV E7, −MUC-1, −HER2, −folate receptor α, −CD97, −CD171, −CD179a, −CD44v6, −WT1, −VEGF-α, −VEGFR1, −IL-13Rα1, −IL-13Rα2, −IL-11Rα, −PSA, −FcRH5, −NKG2D ligand, −NY-ESO-1, −TAG-72, −CEA, −ephrin A2, −ephrin B2, −Lewis A antigen, −Lewis Y antigen, −MAGE, −MAGE-Al, −RAGE-1, −folate receptor β, −EGFRviii, −VEGFR-2, −LGRS, −SSX2, −AKAP-4, −FLT3, −fucosyl GM1, −GM3, −o-acetyl-GD2, and −GD2 specific monoclonal antibodies, respectively.

In further embodiments, the extracellular domain includes a Fab specific for a target of interest. In such embodiments, targets of interest include CD138, CD38, CD33, CD123, CD72, CD79a, CD79b, mesothelin, PSMA, BCMA, ROR1, MUC-16, L1CAM, CD22, CD19, CD20, CD23, CD24, CD37, CD30, CA125, CD56, c-Met, EGFR, GD-3, HPV E6, HPV E7, MUC-1, HER2, folate receptor α, CD97, CD171, CD179a, CD44v6, WT1, VEGF-α, VEGFR1, IL-13Rα1, IL-13Rα2, IL-11Rα, PSA, FcRH5, NKG2D ligand, NY-ESO-1, TAG-72, CEA, ephrin A2, ephrin B2, Lewis A antigen, Lewis Y antigen, MAGE, MAGE-Al, RAGE-1, folate receptor β, EGFRviii, VEGFR-2, LGRS, SSX2, AKAP-4, FLT3, fucosyl GM1, GM3, o-acetyl-GD2, and GD2, and Fab regions include portions of anti-CD138, −CD38, −CD33, −CD123, −CD72, −CD79a, −CD79b, −mesothelin, −PSMA, −BCMA, −ROR1, −MUC-16, −L1CAM, −CD22, −CD19, −CD20, −CD23, −CD24, −CD37, −CD30, −CA125, −CD56, −c-Met, −EGFR, −GD-3, −HPV E6, −HPV E7, −MUC-1, −HER2, −folate receptor α, −CD97, −CD171, −CD179a, −CD44v6, −WT1, −VEGF-α, −VEGFR1, −IL-13Rα1, −IL-13Rα2, −IL-11Rα, −PSA, −FcRH5, −NKG2D ligand, −NY-ESO-1, −TAG-72, −CEA, −ephrin A2, −ephrin B2, −Lewis A antigen, −Lewis Y antigen, −MAGE, MAGE-Al, −RAGE-1, −folate receptor β, −EGFRviii, −VEGFR-2, −LGR5, −SSX2, AKAP-4, −FLT3, −fucosyl GM1, −GM3, −o-acetyl-GD2, and −GD2 specific monoclonal antibodies, respectively.

A target molecule, which is specifically bound by an extracellular domain of a CER of the present disclosure, may be found on or in association with a cell of interest ("target cell"). Exemplary target cells include a cancer cell, a cell associated with an autoimmune disease or disorder or with an inflammatory disease or disorder, and an infectious microbe (e.g., bacteria, virus, or fungi), or infected cell (e.g., virus-infected cell). A cell of an infectious organism, such as a mammalian parasite, is also contemplated as a target cell.

In some embodiments, the extracellular domain optionally comprises an extracellular, non-signaling spacer or linker domain. Where included, such a spacer or linker domain may position the binding domain away from the host cell surface to further enable proper cell/cell contact, binding, activation, and expansion. An extracellular spacer domain is generally located between the extracellular binding domain and the transmembrane domain. The length of the extracellular spacer may be varied to optimize target molecule binding based on the selected target molecule, selected binding epitope, binding domain size and affinity (see, e.g., Guest et al., J. Immunother. 28:203-11, 2005; Hudecek et al., Clin. Cancer Res. 19:3153-64, 2013; Hudecek et al., Cancer Immunol. Res. 3:125-35, 2015; PCT Publication No. WO 2014/031687; each of which is incorporated by reference in its entirety). In certain embodiments, an extracellular spacer domain comprises a TLR juxtamembrane domain (e.g., TLR1, TLR2, TLR3, TLR4, TLRS, TLR6, TLR7, TLR8, or TLR9 juxtamembrane domain). In a particular embodiment, an extracellular spacer domain comprises a TLR4 juxtamembrane domain comprising an amino acid sequence of SEQ ID NO:17. In certain embodiments, an extracellular spacer domain is an immunoglobulin hinge region (e.g., IgG1, IgG2, IgG3, IgG4, IgA, IgD). An immunoglobulin hinge region may be a wild type immunoglobulin hinge region or an altered wild type immunoglobulin hinge region. An altered IgG$_4$ hinge region is described in PCT Publication No. WO 2014/031687, which hinge region is incorporated herein by reference in its entirety. In a particular embodiment, an extracellular spacer domain comprises a modified IgG$_4$ hinge region having an amino acid sequence of ESKYGPPCPPCP (SEQ ID NO:16). Other examples of hinge regions that may be used in the CERs described herein include the hinge region present in the extracellular regions of type 1 membrane proteins, such as CD8a, CD4, CD28 and CD7, which may be wild-type or variants thereof. In further embodiments, an extracellular spacer domain comprises all or a portion of an immunoglobulin Fc domain selected from: a CH1 domain, a CH2 domain, a CH3 domain, or combinations thereof (see, e.g., PCT Publication WO2014/031687, which spacers are incorporated herein by reference in their entirety). In a particular embodiment, the Fc domain is modified to prevent in vivo interactions with cells expressing FcγRs that may result in off-target activation of CER-modified cells. In yet further embodiments, an extracellular spacer domain may comprise a stalk region of a type II C-lectin (the extracellular domain located between the C-type lectin domain and the transmembrane domain). Type II C-lectins include CD23, CD69, CD72, CD94, NKG2A, and NKG2D. In yet further embodiments, an extracellular spacer domain may be derived from MERTK.

II. Transmembrane Domains

The transmembrane domain connects and is positioned between the extracellular domain and the engulfment signaling domain. The transmembrane domain is a hydrophobic alpha helix that transverses the host cell membrane. The transmembrane domain may be directly fused to the binding domain or to the extracellular spacer domain if present. In certain embodiments, the transmembrane domain is derived from an integral membrane protein (e.g., receptor, cluster of differentiation (CD) molecule, enzyme, transporter, cell adhesion molecule, or the like). The transmembrane domain can be naturally associated with either the extracellular domain or the engulfment signaling domain included in the CER (e.g., a CER comprises a Tim4 binding domain and a Tim4 transmembrane domain). In certain embodiments, the transmembrane domain and the extracellular domain are derived from different molecules, the transmembrane domain and the engulfment signaling domain are derived from different molecules, or the transmembrane domain, extracellular domain, and engulfment signaling domain are all derived from different molecules.

In certain embodiments, the transmembrane domain is a TLR transmembrane domain (e.g., TLR1, TLR2, TLR3, TLR4, TLR5, TLR6, TLR7, TLR8, or TLR9 transmembrane domain), a Tim1 transmembrane domain, a Tim4 transmembrane domain, an FcR transmembrane domain (e.g., FcγR1, FcγR2A, FcγR2B2, FcγR2C, FcγR3A, FcER1, or FcaR1 transmembrane domain), a CD8a transmembrane domain, a MERTK transmembrane domain, an Axl transmembrane domain, a Tyro3 transmembrane domain, a BAI1 transmembrane domain, a CD4 transmembrane domain, a CD28 transmembrane domain a MRC1 transmembrane domain, or a DAP12 transmembrane domain.

In specific embodiments, the transmembrane domain comprises or is a sequence that is at least 90%, at least 91%, at least 92%, at least 93%, at least 94%, at least 95%, at least 96%, at least 97%, at least 98%, at least 99%, at least 99.5%, or 100% identical to a TLR1 transmembrane domain comprising an amino acid sequence of SEQ ID NO:31, a TLR2 transmembrane domain comprising an amino acid sequence of SEQ ID NO:32, a TLR3 transmembrane domain comprising an amino acid sequence of SEQ ID NO:33, a TLR4 transmembrane domain comprising an amino acid sequence of SEQ ID NO:34, a TLR5 transmembrane domain comprising an amino acid sequence of SEQ ID NO:35, a TLR6 transmembrane domain comprising an amino acid sequence of SEQ ID NO:36, a TLR7 transmembrane domain comprising an amino acid sequence of SEQ ID NO:37, a TLR8 transmembrane domain comprising an amino acid sequence of SEQ ID NO:38, a TLR9 transmembrane domain comprising an amino acid sequence of SEQ ID NO:39, a Tim1 transmembrane domain comprising an amino acid sequence of SEQ ID NO:18, a Tim4 transmembrane domain comprising an amino acid sequence of SEQ ID NO:19, an FcγRI transmembrane domain comprising an amino acid sequence of SEQ ID NO:20, a FcεRIγ transmembrane domain comprising an amino acid sequence of SEQ ID NO:21, a CD8a transmembrane domain comprising an amino acid sequence of SEQ ID NO:22, a MERTK transmembrane domain comprising an amino acid sequence of SEQ ID NO:23, an Axl transmembrane domain comprising an amino acid sequence of SEQ ID NO:24, a Tyro3 transmembrane domain comprising an amino acid sequence of SEQ ID NO:25, a BAI1 transmembrane domain comprising an amino acid sequence of SEQ ID NO:29, a CD28 transmembrane domain as set forth in an amino acid sequence of SEQ ID NO:26, a CD4 transmembrane domain comprising an amino acid sequence of SEQ ID NO:27, a MRC1 transmembrane domain comprising an amino acid sequence of SEQ ID NO:30, or a DAP12 transmembrane domain comprising an amino acid sequence of SEQ ID NO:28.

In other embodiments, the transmembrane domain is provided by a polynucleotide sequence that comprises or is a sequence that is at least 90%, at least 91%, at least 92%, at least 93%, at least 94%, at least 95%, at least 96%, at least 97%, at least 98%, at least 99%, at least 99.5%, or 100% identical to a polynucleotide sequence encoding a Tim1 transmembrane domain according to SEQ ID NO:40, a polynucleotide sequence encoding a Tim4 transmembrane domain according to SEQ ID NO:41, a polynucleotide sequence encoding a FcεRIγ transmembrane domain according to SEQ ID NO:121, a polynucleotide sequence encoding an FcγRI transmembrane domain according to SEQ ID NO:42, a polynucleotide sequence encoding a CD8a transmembrane domain according to SEQ ID NO:43, a polynucleotide sequence encoding MERTK transmembrane domain according to SEQ ID NO:44, a polynucleotide sequence encoding an Axl transmembrane domain according to SEQ ID NO:45, a polynucleotide sequence encoding a Tyro3 transmembrane domain according to SEQ ID NO:46, a polynucleotide sequence encoding a CD28 transmembrane domain according to SEQ ID NO:110, a polynucleotide sequence encoding a BAI1 transmembrane domain according to SEQ ID NO:113, a polynucleotide sequence encoding a CD4 transmembrane domain according to SEQ ID NO:47, a polynucleotide sequence encoding a DAP12 transmembrane domain according to SEQ ID NO:111, or a polynucleotide sequence encoding a TLR4 transmembrane domain according to SEQ ID NO:112.

It is understood that direct fusion of one domain to another domain of a CER described herein does not preclude the presence of intervening junction amino acids. Junction amino acids may be natural or non-natural (e.g., resulting from the construct design of a chimeric protein).

III. Engulfment Signaling Domains

The engulfment signaling domain of a CER is an intracellular effector domain and is capable of transmitting functional signals to a cell in response to binding of the extracellular domain of the CER to a target molecule. CERs of the present disclosure may include one or more engulfment signaling domains as described herein.

In certain embodiments, an engulfment signaling domain is an intracellular signaling domain of an endogenous toll-like (TLR) receptor or an intracellular signaling domain of an endogenous signal transduction protein that is involved in TLR signaling. Ten TLRs have been identified in humans. Examples of endogenous TLRs from which engulfment signaling domains can be derived include TLR1, TLR2, TLR3, TLR4, TLR5, TLR6, TLR7, TLR8, and TLR9. Examples of endogenous signal transduction proteins that are involved in TLR signaling that may be used to derive engulfment signaling domains include Traf6, Traf2, and Traf3.

In particular embodiments, the primary engulfment signaling domain comprises or is a sequence that is at least 90%, at least 91%, at least 92%, at least 93%, at least 94%, at least 95%, at least 96%, at least 97%, at least 98%, at least 99%, at least 99.5%, or 100% identical to a TLR1 signaling domain comprising an amino acid sequence of SEQ ID NO:48, a TLR2 signaling domain comprising an amino acid sequence of SEQ ID NO:49, a TLR3 signaling domain comprising an amino acid sequence of SEQ ID NO:50, a TLR4 signaling domain comprising an amino acid sequence of SEQ ID NO:51, a TLR5 signaling domain comprising an amino acid sequence of SEQ ID NO:52, a TLR6 signaling domain comprising an amino acid sequence of SEQ ID NO:53, a TLR7 signaling domain comprising an amino acid sequence of SEQ ID NO:54, a TLR8 signaling domain comprising an amino acid sequence of SEQ ID NO:55, a TLR9 signaling domain comprising an amino acid sequence of SEQ ID NO:56, a Traf6 signaling domain comprising an amino acid sequence of SEQ ID NO:57, a truncated Traf6 signaling domain comprising an amino acid sequence of SEQ ID NO:58, a Traf2 signaling domain comprising an amino acid sequence of SEQ ID NO:72, or a Traf3 signaling domain comprising an amino acid sequence of SEQ ID NO:73.

The engulfment signaling domain may be any portion of an engulfment signaling molecule that retains sufficient signaling activity. In some embodiments, a full length or full length intracellular component of an engulfment signaling molecule is used. In some embodiments, a truncated portion of an engulfment signaling molecule or intracellular component of an engulfment signaling molecule is used, provided that the truncated portion retains sufficient signal transduction activity. In further embodiments, an engulfment signaling domain is a variant of an entire or truncated portion of an engulfment signaling molecule, provided that the variant retains sufficient signal transduction activity (i.e., is a functional variant).

In certain embodiments, the engulfment signaling domain comprises: a primary engulfment signaling domain comprising a TLR signaling domain, a Traf6 signaling domain, a Traf2 signaling domain, or a Traf3 signaling domain; and a secondary engulfment signaling domain. A secondary engulfment signaling domain may comprise an FcR signaling domain (including an FcγR1 signaling domain, an FcγR2A signaling domain, an FcγR2C signaling domain, FcγR2B2 signaling domain, an FcγR3A signaling domain, FcγR2C signaling domain, FcγR3A signaling domain, FcεR1 signaling domain, and FcαR1 signaling domain), a B-cell activating factor receptor (BAFF-R) signaling domain, a DAP12 (also referred to as TYRO Protein Tyrosine Kinase Binding Protein (TYROBP)) signaling domain, an NFAT Activating Protein With ITAM Motif 1 (NFAM1) signaling domain, a MERTK signaling domain, a TLR1 signaling domain, a TLR2 signaling domain, a TLR3 signaling domain, a TLR4 signaling domain, a TLR5 signaling domain, a TLR6 signaling domain, a TLR7 signaling domain, a TLR8 signaling domain, a TLR9 signaling domain, a Traf6 signaling domain, a Traf2 signaling domain, or a Traf3 signaling domain, or a CD79b signaling domain. In particular embodiments, the secondary engulfment signaling domain comprises or is a sequence that is at least 90%, at least 91%, at least 92%, at least 93%, at least 94%, at least 95%, at least 96%, at least 97%, at least 98%, at least 99%, at least 99.5%, or 100% identical to a FcεRIγ signaling domain comprising an amino acid sequence of SEQ ID NO:62, an FcγR1 signaling domain comprising an amino acid sequence of SEQ ID NO:63, an FcγR2A signaling domain comprising an amino acid sequence of SEQ ID NO:64, an FcγR2C signaling domain comprising an amino acid sequence of SEQ ID NO:65, an FcγR3A signaling domain comprising an amino acid sequence of SEQ ID NO:66, a BAFF-R signaling domain comprising an amino acid sequence of SEQ ID NO:67, a DAP12 signaling domain comprising an amino acid sequence of SEQ ID NO:68, a NFAM1 signaling domain comprising an amino acid sequence of SEQ ID NO:69, a truncated NFAM1 signaling domain comprising an amino acid sequence of SEQ ID NO:70, a CD79b signaling domain comprising an amino acid sequence of SEQ ID NO:75, a truncated CD79b signaling domain comprising an amino acid sequence of SEQ ID NO:71, a MERTK signaling domain comprising an amino acid sequence of SEQ ID NO:59:, a TLR1 signaling domain comprising an amino acid sequence of SEQ ID NO:48, a TLR2 signaling domain comprising an amino acid sequence of SEQ ID NO:49, a TLR3 signaling domain comprising an amino acid sequence of SEQ ID NO:50, a TLR4 signaling domain comprising an amino acid sequence of SEQ ID NO:51, a TLR5 signaling domain comprising an amino acid sequence of SEQ ID NO:52, a TLR6 signaling domain comprising an amino acid sequence of SEQ ID NO:53, a TLR7 signaling domain comprising an amino acid sequence of SEQ ID NO:54, a TLR8 signaling domain comprising an amino acid sequence of SEQ ID NO:55, a TLR9 signaling domain comprising an amino acid sequence of SEQ ID NO:56, a Traf6 signaling domain comprising an amino acid sequence of SEQ ID NO:57, a truncated Traf6 signaling domain comprising an amino acid sequence of SEQ ID NO:58, a Traf2 signaling domain comprising an amino acid sequence of SEQ ID NO:72, or a Traf3 signaling domain comprising an amino acid sequence of SEQ ID NO:73.

In other embodiments, the secondary engulfment signaling domain is provided by a polynucleotide sequence that comprises or is a sequence that is at least 90%, at least 91%, at least 92%, at least 93%, at least 94%, at least 95%, at least 96%, at least 97%, at least 98%, at least 99%, at least 99.5%, or 100% identical to a polynucleotide encoding a FcεRIγ signaling domain according to SEQ ID NO:115, a polynucleotide encoding an FcγR1 signaling domain according to SEQ ID NO:77, a polynucleotide encoding an FcγR2A signaling domain according to SEQ ID NO:78, a polynucleotide encoding an FcγR2C signaling domain according to SEQ ID NO:79, a polynucleotide encoding an FcγR3A signaling domain according to SEQ ID NO:80, a polynucleotide encoding a BAFF-R signaling domain according to SEQ ID NO:117, a polynucleotide encoding a DAP12 signaling domain according to SEQ ID NO:116, a polynucleotide encoding a NFAM1 signaling domain according to SEQ ID NO:119, or a polynucleotide encoding a CD79b signaling domain according to SEQ ID NO:118.

In certain embodiments, signaling by the engulfment signaling domain results in expression of at least one of an inflammatory cytokine, an inflammatory chemokine, or a co-stimulatory cell surface marker. In yet further embodiments, the inflammatory cytokine is TNFα, IL-1, IL-6, IL-12, or IL-23; the inflammatory chemokine is CCL5 (RANTES), CXCL9, or CXCL10; and the co-stimulatory cell surface marker is CD80, CD86, HLA-DR, CD40, HVEM, or 4-1BBL; or any combination thereof.

In certain embodiments, the presence of a secondary engulfment signaling domain enhances engulfment activity of the CER, persistence of the CER modified host cell, expansion of the CER modified host cell, or a combination thereof. In a particular embodiment, inclusion of a secondary engulfment signaling domain with a primary engulfment signaling domain enhances engulfment activity of the CER, phagocytic signaling activity of the CER modified host cell, degradation of luminal contents by the CER modified host cell, activation of the CER modified host cell, persistence of the CER modified host cell, memory formation of the CER modified host cell, expansion of the CER modified host cell, antigen presenting activity by the CER modified host cell, or any combination thereof.

In certain embodiments, the presence of a TLR signaling domain with a Traf2, Traf3, or Traf6 signaling domain in a CER provides enhanced functionality to the CER and/or CER-modified host cell. In one embodiment, a primary engulfment signaling domain comprises a TLR1, TLR2, TLR3, TLR4, TLR5, TLR6, TLR7, TLR8, or TLR9 signaling domain and a secondary engulfment signaling domain comprises a Traf6, Traf2, or Traf3 signaling domain. In another embodiment, a primary engulfment signaling domain comprises a Traf6, Traf2, or Traf3 signaling domain, and a secondary engulfment signaling domain comprises a TLR1, TLR2, TLR3, TLR4, TLR5, TLR6, TLR7, TLR8, or TLR9 signaling domain. In certain embodiments, CERs comprising both a TLR signaling domain and a Traf2, Traf3, or Traf6 signaling domain exhibits enhanced activation, persistence, memory formation, antigen presentation, or any combination thereof.

It is understood that in embodiments where a CER comprises a primary engulfment signaling domain and a secondary engulfment signaling domain, the positions of the engulfment signaling domains may be exchanged. For example, in a CER comprising a primary engulfment signaling domain and a secondary engulfment signaling domain, the secondary engulfment signaling domain may comprise a TLR signaling domain (e.g., TLR1, TLR2, TLR3, TLR4, TLR5, TLR6, TLR7, TLR8 or TLR9), a Traf2 signaling domain, or a Traf3 signaling domain, and the primary signaling domain may comprise an FcR signaling domain (including an FcγR1 signaling domain, an FcγR2A signaling domain, an FcγR2C signaling domain, FcγR2B2 signaling domain, an FcγR3A signaling domain, FcγR2C signaling domain, FcγR3A signaling domain, FcER1 signaling domain, and FcaR1 signaling domain), a BAFF-R signaling domain, a DAP12 signaling domain, a NFAM1 signaling domain, MERTK signaling domain, a CD79b signaling domain, a TLR signaling domain, a Traf2 signaling domain, a Traf3 signaling domain, or a Traf6 signaling domain.

IV. Examples of CERs

The component parts of a CER as disclosed herein can be selected and arranged in various combinations to provide a desired engulfment phenotype to a host cell. In addition to inducing engulfment of a cell, microbe, or particle expressing or characterized by a molecule targeted by a CER-modified host cell, a CER as described herein may be designed to initiate a pro-inflammatory engulfment response, enhance engulfment activity, degradation of luminal contents, cytolytic activity, cell activation, cell expansion, cell memory, cell persistence, antigen presentation, or cell proliferation, depending upon the target cell or particle, disease state, and desired therapeutic outcome.

In one aspect, the present disclosure provides a chimeric engulfment receptor (CER) comprising a single chain chimeric protein, the single chain chimeric protein comprising: an extracellular domain comprising a binding domain that binds to phosphatidylserine (PtdSer); an engulfment signaling domain comprising a TLR signaling domain, a Traf6 signaling domain, a Traf2 signaling domain, or a Traf3 signaling domain; and a transmembrane domain positioned between and connecting the extracellular domain and the engulfment signaling domain.

In certain embodiments, the extracellular domain further comprises an extracellular spacer domain positioned between the binding domain and the transmembrane domain.

In certain embodiments, the CER further comprises a secondary engulfment signaling domain. A secondary engulfment signaling domain may comprise an FcR signaling domain (including an FcγR1 signaling domain, an FcγR2A signaling domain, an FcγR2C signaling domain, FcγR2B2 signaling domain, an FcγR3A signaling domain, FcγR2C signaling domain, FcγR3A signaling domain, FcER1 signaling domain, and FcaR1 signaling domain), a BAFF-R signaling domain, a DAP12 signaling domain, a NFAM1 signaling domain, a CD79b signaling domain, a MERTK signaling domain, a TLR signaling domain, a Traf6 signaling domain, a Traf2 signaling domain, or a Traf3 signaling domain.

Figure 6:
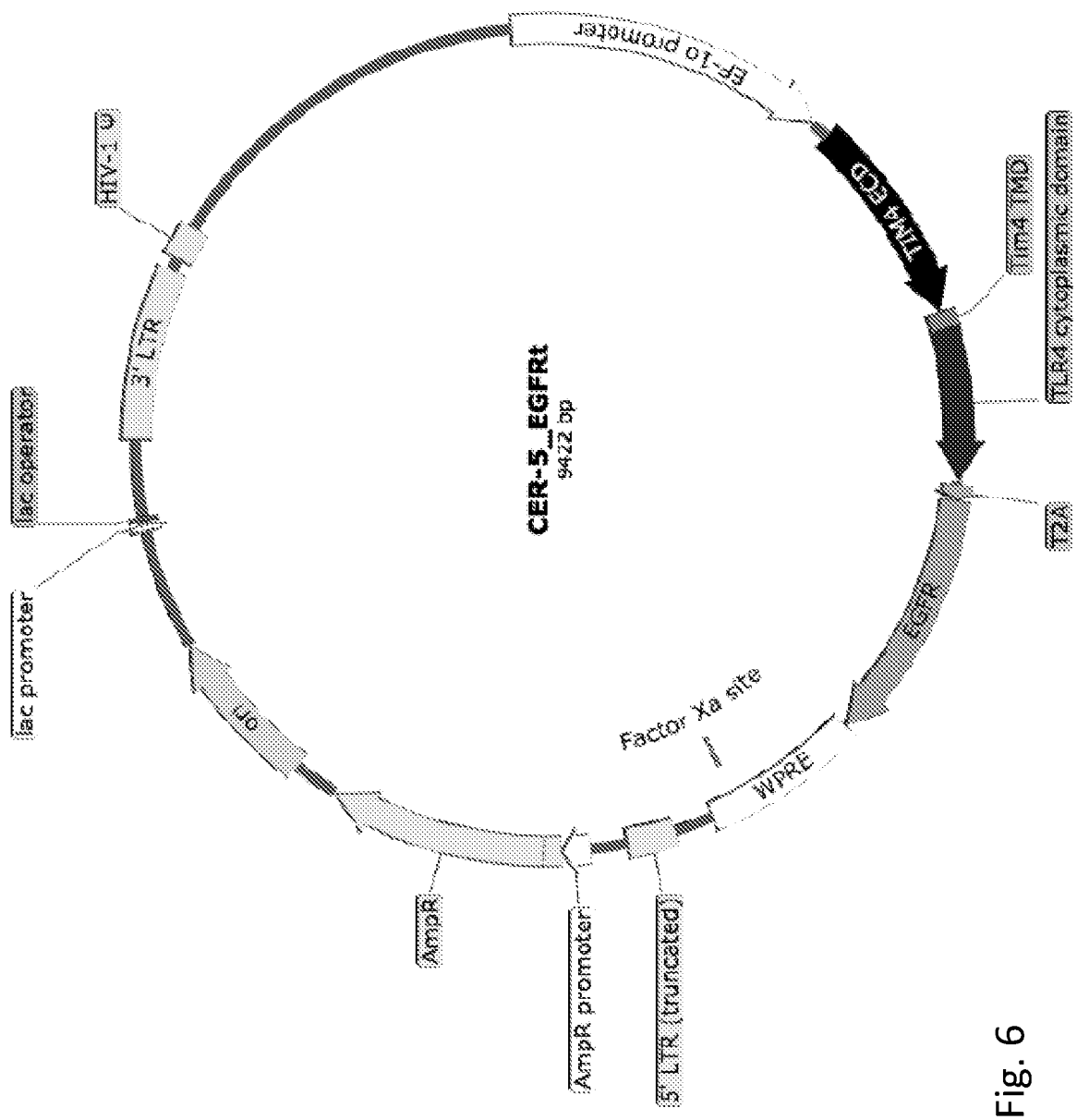
FIG. 6 shows a vector map for a lentiviral vector comprising "CER05" chimeric engulfment receptor having an amino acid sequence of SEQ ID NO:81. CER05 comprises a Tim4 binding domain, a Tim4 transmembrane domain, and a TLR4 signaling domain. The lentiviral vector also comprises a sequence encoding truncated EGFR (SEQ ID NO:105), which is separated from the CER05 sequence by a viral T2A sequence.

An embodiment of a CER including an extracellular domain comprising a binding domain that binds to PtdSer comprises: an extracellular domain comprising a TIM4 PtdSer binding domain; a transmembrane domain comprising a TIM4 transmembrane domain, and an engulfment signaling domain comprising a TLR4 signaling domain (also referred to herein as "CER05") (see, e.g., FIG. 6). In certain embodiments, such a CER comprises an amino acid sequence of SEQ ID NO:81. In some embodiments, the CER mature polypeptide sequence comprises an amino acid sequence of SEQ ID NO:81 without the signal peptide sequence (amino acids 1-22 of SEQ ID NO:81).

Another embodiment of a CER including an extracellular domain comprising a binding domain that binds to PtdSer comprises: an extracellular domain comprising a TIM4 PtdSer binding domain; a transmembrane domain comprising a TLR4 transmembrane domain, and an engulfment signaling domain comprising a TLR4 signaling domain (also referred to herein as "CER06"). In certain embodiments, such a CER comprises an amino acid sequence of SEQ ID NO:82. In some embodiments, the CER mature polypeptide sequence comprises an amino acid sequence of SEQ ID NO:82 without the signal peptide sequence (amino acids 1-22 of SEQ ID NO:82).

Another embodiment of a CER including an extracellular domain comprising a binding domain that binds to PtdSer comprises: an extracellular domain comprising a TIM4 PtdSer binding domain; an extracellular spacer domain comprising a TLR4 juxtamembrane domain, a transmembrane domain comprising a TLR4 transmembrane domain, and an engulfment signaling domain comprising a TLR4 signaling domain (also referred to herein as "CER07"). In certain embodiments, such a CER comprises an amino acid sequence of SEQ ID NO:83. In some embodiments, the CER mature polypeptide sequence comprises an amino acid sequence of SEQ ID NO:83 without the signal peptide sequence (amino acids 1-22 of SEQ ID NO:83).

Another embodiment of a CER including an extracellular domain comprising a binding domain that binds to PtdSer comprises: an extracellular domain comprising a TIM4 PtdSer binding domain; a transmembrane domain comprising a Tim4 transmembrane domain, and an engulfment signaling domain comprising a TLR3 signaling domain (also referred to herein as "CER17"). In certain embodiments, such a CER comprises an amino acid sequence of SEQ ID NO:84. In some embodiments, the CER mature polypeptide sequence comprises an amino acid sequence of SEQ ID NO:84 without the signal peptide sequence (amino acids 1-22 of SEQ ID NO:84).

Another embodiment of a CER including an extracellular domain comprising a binding domain that binds to PtdSer comprises: an extracellular domain comprising a TIM4 PtdSer binding domain; a transmembrane domain comprising a TLR3 transmembrane domain, and an engulfment signaling domain comprising a TLR3 signaling domain (also referred to herein as "CER18"). In certain embodiments, such a CER comprises an amino acid sequence of SEQ ID NO:85. In some embodiments, the CER mature polypeptide sequence comprises an amino acid sequence of SEQ ID NO:85 without the signal peptide sequence (amino acids 1-22 of SEQ ID NO:85).

Another embodiment of a CER including an extracellular domain comprising a binding domain that binds to PtdSer comprises: an extracellular domain comprising a TIM4 PtdSer binding domain; a transmembrane domain comprising a Tim4 transmembrane domain, and an engulfment signaling domain comprising a TLRS signaling domain (also referred to herein as "CER19"). In certain embodiments, such a CER comprises an amino acid sequence of SEQ ID NO:86. In some embodiments, the CER mature polypeptide comprises an amino acid sequence of SEQ ID NO:86 without the signal peptide sequence (amino acids 1-22 of SEQ ID NO:86).

Yet another embodiment of a CER including an extracellular domain comprising a binding domain that binds to PtdSer comprises: an extracellular domain comprising a TIM4 PtdSer binding domain; a transmembrane domain comprising a TLRS transmembrane domain, and an engulfment signaling domain comprising a TLRS signaling domain (also referred to herein as "CER20"). In certain embodiments, such a CER comprises an amino acid sequence of SEQ ID NO:87. In some embodiments, the CER mature polypeptide sequence comprises an amino acid sequence of SEQ ID NO:87 without the signal peptide sequence (amino acids 1-22 of SEQ ID NO:87).

Another embodiment of a CER including an extracellular domain comprising a binding domain that binds to PtdSer comprises: an extracellular domain comprising a TIM4 PtdSer binding domain; a transmembrane domain comprising a Tim4 transmembrane domain, and an engulfment signaling domain comprising a TLR8 signaling domain (also referred to herein as "CER21"). In certain embodiments, such a CER comprises an amino acid sequence of SEQ ID NO:88. In some embodiments, the CER mature polypeptide sequence comprises an amino acid sequence of SEQ ID NO:88 without the signal peptide sequence (amino acids 1-22 of SEQ ID NO:88).

Another embodiment of a CER including an extracellular domain comprising a binding domain that binds to PtdSer comprises: an extracellular domain comprising a TIM4 PtdSer binding domain; a transmembrane domain comprising a TLR8 transmembrane domain, and an engulfment signaling domain comprising a TLR8 signaling domain (also referred to herein as "CER22"). In certain embodiments, such a CER comprises an amino acid sequence of SEQ ID NO:89. In some embodiments, the CER mature polypeptide sequence comprises an amino acid sequence of SEQ ID NO:89 without the signal peptide sequence (amino acids 1-22 of SEQ ID NO:89).

Another embodiment of a CER including an extracellular domain comprising a binding domain that binds to PtdSer comprises: an extracellular domain comprising a TIM4 PtdSer binding domain; a transmembrane domain comprising a Tim4 transmembrane domain, and an engulfment signaling domain comprising a TLR9 signaling domain (also referred to herein as "CER23"). In certain embodiments, such a CER comprises an amino acid sequence of SEQ ID NO:90. In some embodiments, the CER mature polypeptide sequence comprises an amino acid sequence of SEQ ID NO:90 without the signal peptide sequence (amino acids 1-22 of SEQ ID NO:90).

Another embodiment of a CER including an extracellular domain comprising a binding domain that binds to PtdSer comprises: an extracellular domain comprising a TIM4 PtdSer binding domain; a transmembrane domain comprising a TLR9 transmembrane domain, and an engulfment signaling domain comprising a TLR9 signaling domain (also referred to herein as "CER24"). In certain embodiments, such a CER comprises an amino acid sequence of SEQ ID NO:91. In some embodiments, the CER mature polypeptide sequence comprises an amino acid sequence of SEQ ID NO:91 without the signal peptide sequence (amino acids 1-22 of SEQ ID NO:91).

Another embodiment of a CER including an extracellular domain comprising a binding domain that binds to PtdSer comprises: an extracellular domain comprising a TIM4 PtdSer binding domain; a transmembrane domain comprising a Tim4 transmembrane domain, and an engulfment signaling domain comprising a TLR1 signaling domain (also referred to herein as "CER26"). In certain embodiments, such a CER comprises an amino acid sequence of SEQ ID NO:92. In some embodiments, the CER comprises an amino acid sequence of SEQ ID NO:92 without the signal peptide sequence (amino acids 1-22 of SEQ ID NO:92).

Another embodiment of a CER including an extracellular domain comprising a binding domain that binds to PtdSer comprises: an extracellular domain comprising a TIM4 PtdSer binding domain; a transmembrane domain comprising a Tim4 transmembrane domain, and an engulfment signaling domain comprising a TLR2 signaling domain (also referred to herein as "CER27"). In certain embodiments, such a CER comprises an amino acid sequence of SEQ ID NO:93. In some embodiments, the CER comprises an amino acid sequence of SEQ ID NO:93 without the signal peptide sequence (amino acids 1-22 of SEQ ID NO:93).

Another embodiment of a CER including an extracellular domain comprising a binding domain that binds to PtdSer comprises: an extracellular domain comprising a TIM4 PtdSer binding domain; a transmembrane domain comprising a Tim4 transmembrane domain, and an engulfment signaling domain comprising a TLR7 signaling domain (also referred to herein as "CER28"). In certain embodiments, such a CER comprises an amino acid sequence of SEQ ID NO:94. In some embodiments, the CER comprises an amino acid sequence of SEQ ID NO:94 without the signal peptide sequence (amino acids 1-22 of SEQ ID NO:94).

Another embodiment of a CER including an extracellular domain comprising a binding domain that binds to PtdSer comprises: an extracellular domain comprising a TIM4 PtdSer binding domain; a transmembrane domain comprising a Tim4 transmembrane domain, and an engulfment signaling domain comprising a Traf2 signaling domain (also referred to herein as "CER30"). In certain embodiments, such a CER comprises an amino acid sequence of SEQ ID NO:96. In some embodiments, the CER comprises an amino acid sequence of SEQ ID NO:96 without the signal peptide sequence (amino acids 1-22 of SEQ ID NO:96).

Another embodiment of a CER including an extracellular domain comprising a binding domain that binds to PtdSer comprises: an extracellular domain comprising a TIM4 PtdSer binding domain; a transmembrane domain comprising a Tim4 transmembrane domain, and an engulfment signaling domain comprising a Traf3 signaling domain (also referred to herein as "CER31"). In certain embodiments, such a CER comprises an amino acid sequence of SEQ ID NO:97. In some embodiments, the CER comprises an amino acid sequence of SEQ ID NO:97 without the signal peptide sequence (amino acids 1-22 of SEQ ID NO:97).

Another embodiment of a CER including an extracellular domain comprising a binding domain that binds to PtdSer comprises: an extracellular domain comprising a CD22 specific scFv binding domain; an extracellular spacer domain comprising a mutated $IgG_4$ hinge region; a transmembrane domain comprising a TLR4 transmembrane domain, and an engulfment signaling domain comprising a TLR4 signaling domain (also referred to herein as "CER42"). In certain embodiments, such a CER comprises an amino acid sequence of SEQ ID NO:98. In some embodiments, the CER comprises an amino acid sequence of SEQ ID NO:98 without the signal peptide sequence (amino acids 1-22 of SEQ ID NO:98).

Another embodiment of a CER including an extracellular domain comprising a binding domain that binds to PtdSer comprises: an extracellular domain comprising a Tim4 binding domain, a transmembrane domain comprising a Tim4 transmembrane domain, an engulfment signaling domain comprising a truncated Traf6 signaling domain (also referred to herein as "CER29"). In certain embodiments, such a CER comprises an amino acid sequence of SEQ ID NO:124. In some embodiments, the CER mature polypeptide sequence comprises an amino acid sequence of SEQ ID NO:124 without the signal peptide sequence (amino acids 1-22 of SEQ ID NO:124).

Another embodiment of a CER including an extracellular domain comprising a binding domain that binds to PtdSer comprises: a Tim4 binding domain, a transmembrane domain comprising a Tim4 transmembrane domain, and an engulfment signaling domain comprising a primary engulfment signaling domain comprising a truncated Traf6 signaling domain and a secondary engulfment signaling domain comprising a NFAM1 signaling domain (also referred to herein as "CER112"). In certain embodiments, such a CER comprises an amino acid sequence of SEQ ID NO:128. In some embodiments, the CER mature polypeptide sequence comprises an amino acid sequence of SEQ ID NO:128 without the signal peptide sequence (amino acids 1-22 of SEQ ID NO:128).

Another embodiment of a CER including an extracellular domain comprising a binding domain that binds to PtdSer comprises: a Tim4 binding domain, a transmembrane domain comprising a Tim4 transmembrane domain, and an engulfment signaling domain comprising a primary engulfment signaling domain comprising a truncated Traf6 signaling domain and a secondary engulfment signaling domain comprising a DAP12 signaling domain (also referred to herein as "CER110"). In certain embodiments, such a CER comprises an amino acid sequence of SEQ ID NO:125. In some embodiments, the CER mature polypeptide sequence comprises an amino acid sequence of SEQ ID NO:125 without the signal peptide sequence (amino acids 1-22 of SEQ ID NO:125).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a truncated Traf6 signaling domain, and a secondary engulfment signaling domain comprising a BAFFR signaling domain (also referred to herein as "CER113"). In certain embodiments, such a CER comprises an amino acid sequence of SEQ ID NO:127 or 140. In some embodiments, the CER mature polypeptide sequence comprises an amino acid sequence of SEQ ID NO:127 without the signal peptide sequence (amino acids 1-22 of SEQ ID NO:127).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a truncated Traf6 signaling domain and a secondary engulfment signaling domain comprising a CD79b signaling domain (CD79b 185-213) (also referred to herein as "CER111B"). In certain embodiments, such a CER comprises an amino acid sequence of SEQ ID NO:126. In some embodiments, the CER mature polypeptide sequence comprises an amino acid sequence of SEQ ID NO:126 without the signal peptide sequence (amino acids 1-22 of SEQ ID NO:126).Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR8 signaling domain and a secondary engulfment signaling domain comprising a NFAM1 signaling domain (also referred to herein as "CER102"). In certain embodiments, such a CER comprises an amino acid sequence of SEQ ID NO:130. In some embodiments, the CER mature polypeptide sequence comprises an amino acid sequence of SEQ ID NO:130 without the signal peptide sequence (amino acids 1-22 of SEQ ID NO:130).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR8 signaling domain and a secondary engulfment signaling domain comprising a CD79b (185-229) signaling domain (also referred to herein as "CER103A"). In certain embodiments, such a CER comprises an amino acid sequence of SEQ ID NO:131. In some embodiments, the CER mature polypeptide comprises an amino acid sequence of SEQ ID NO:131 without the signal peptide sequence (amino acids 1-22 of SEQ ID NO:131)

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR8 signaling domain and a secondary engulfment signaling domain comprising a CD79b (185-213) signaling domain (also referred to herein as "CER103B"). In certain embodiments, such a CER comprises an amino acid sequence of SEQ ID NO:132. In some embodiments, the CER mature polypeptide comprises an amino acid sequence of SEQ ID NO:132 without the signal peptide sequence (amino acids 1-22 of SEQ ID NO:132).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR8 signaling domain and a secondary engulfment signaling domain comprising a DAP12 signaling domain (also referred to herein as "CER104"). In certain embodiments, such a CER comprises an amino acid sequence of SEQ ID NO:133. In some embodiments, the CER mature polypeptide comprises an amino acid sequence of SEQ ID NO:133 without the signal peptide sequence (amino acids 1-22 of SEQ ID NO:133).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR8 signaling domain and a secondary engulfment signaling domain comprising a BAFF-R signaling domain (also referred to herein as "CER105"). In certain embodiments, such a CER comprises an amino acid sequence of SEQ ID NO:134. In some embodiments, the CER mature polypeptide comprises an amino acid sequence of SEQ ID NO:134 without the signal peptide sequence (amino acids 1-22 of SEQ ID NO:134).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a NFAM1 signaling domain and a secondary engulfment signaling domain comprising a TLR8 signaling domain (also referred to herein as "CER106"). In certain embodiments, such a CER comprises an amino acid sequence of SEQ ID NO:135. In some embodiments, the CER mature polypeptide comprises an amino acid sequence of SEQ ID NO:135 without the signal peptide sequence (amino acids 1-22 of SEQ ID NO:135).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a CD79b (185-213) signaling domain and a secondary engulfment signaling domain comprising a TLR8 signaling domain (also referred to herein as "CER107"). In certain embodiments, such a CER comprises an amino acid sequence of SEQ ID NO:136. In some embodiments, the CER mature polypeptide comprises an amino acid sequence of SEQ ID NO:136 without the signal peptide sequence (amino acids 1-22 of SEQ ID NO:136).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a DAP12 signaling domain and a secondary engulfment signaling domain comprising a TLR8 signaling domain (also referred to herein as "CER108"). In certain embodiments, such a CER comprises an amino acid sequence of SEQ ID NO:137. In some embodiments, the CER mature polypeptide comprises an amino acid sequence of SEQ ID NO:137 without the signal peptide sequence (amino acids 1-22 of SEQ ID NO:137).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a BAFF-R signaling domain and a secondary engulfment signaling domain comprising a TLR8 signaling domain (also referred to herein as "CER109"). In certain embodiments, such a CER comprises an amino acid sequence of SEQ ID NO:138. In some embodiments, the CER mature polypeptide comprises an amino acid sequence of SEQ ID NO:138 without the signal peptide sequence (amino acids 1-22 of SEQ ID NO:138).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TRAF6 signaling domain and a secondary engulfment signaling domain comprising a CD79b (185-229) signaling domain (also referred to herein as "CER111A"). In certain embodiments, such a CER comprises an amino acid sequence of SEQ ID NO:139. In some embodiments, the CER mature polypeptide comprises an amino acid sequence of SEQ ID NO:139 without the signal peptide sequence (amino acids 1-22 of SEQ ID NO:139).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TRAF6 signaling domain and a secondary engulfment signaling domain comprising a MERTK signaling domain (also referred to herein as "CER114"). In certain embodiments, such a CER comprises an amino acid sequence of SEQ ID NO:141. In some embodiments, the CER mature polypeptide comprises an amino acid sequence of SEQ ID NO:141 without the signal peptide sequence (amino acids 1-22 of SEQ ID NO:141).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a MERTK signaling domain and a secondary engulfment signaling domain comprising TRAF6 signaling domain (also referred to herein as "CER115"). In certain embodiments, such a CER comprises an amino acid sequence of SEQ ID NO:142. In some embodiments, the CER mature polypeptide comprises an amino acid sequence of SEQ ID NO:142 without the signal peptide sequence (amino acids 1-22 of SEQ ID NO:142).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TRAF6 signaling domain and a secondary engulfment signaling domain comprising a TLR8 signaling domain (also referred to herein as "CER116"). In certain embodiments, such a CER comprises an amino acid sequence of SEQ ID NO:143. In some embodiments, the CER mature polypeptide comprises an amino acid sequence of SEQ ID NO:143 without the signal peptide sequence (amino acids 1-22 of SEQ ID NO:143).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR8 signaling domain and a secondary engulfment signaling domain comprising a TRAF6 signaling domain (also referred to herein as "CER117"). In certain embodiments, such a CER comprises an amino acid sequence of SEQ ID NO:144. In some embodiments, the CER mature polypeptide comprises an amino acid sequence of SEQ ID NO:144 without the signal peptide sequence (amino acids 1-22 of SEQ ID NO:144).

Another embodiment of a CER including an extracellular domain comprising a binding domain that binds to PtdSer comprises a Tim4 binding domain, a transmembrane domain comprising a Tim4 transmembrane domain, an engulfment signaling domain comprising a primary engulfment signaling domain comprising a TLR1 signaling domain and a secondary engulfment signaling domain comprising a NFAM1 signaling domain (also referred to herein as "CER118"). In certain embodiments, such a CER comprises an amino acid sequence of SEQ ID NO:145. In some embodiments, the CER mature polypeptide comprises an amino acid sequence of SEQ ID NO:145 without the signal peptide sequence (amino acids 1-22 of SEQ ID NO:145).

Yet another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR1 signaling domain and a secondary engulfment signaling domain comprising a CD79b (185-229) signaling domain (also referred to herein as "CER119A"). In certain embodiments, such a CER comprises an amino acid sequence of SEQ ID NO:173. In some embodiments, the CER mature polypeptide comprises an amino acid sequence of SEQ ID NO:173 without the signal peptide sequence (amino acids 1-22 of SEQ ID NO:173).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR1 signaling domain and a secondary engulfment signaling domain comprising a CD79b (185-213) signaling domain (also referred to herein as "CER119B"). In certain embodiments, such a CER comprises an amino acid sequence of SEQ ID NO:146. In some embodiments, the CER mature polypeptide comprises an amino acid sequence of SEQ ID NO:146 without the signal peptide sequence (amino acids 1-22 of SEQ ID NO:146).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR1 signaling domain and a secondary engulfment signaling domain comprising a DAP12 signaling domain (also referred to herein as "CER120"). In certain embodiments, such a CER comprises an amino acid sequence of SEQ ID NO:147. In some embodiments, the CER mature polypeptide comprises an amino acid sequence of SEQ ID NO:147 without the signal peptide sequence (amino acids 1-22 of SEQ ID NO:147).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR1 signaling domain and a secondary engulfment signaling domain comprising a TRAF6 signaling domain (also referred to herein as "CER121"). In certain embodiments, such a CER comprises an amino acid sequence of SEQ ID NO:148. In some embodiments, the CER mature polypeptide comprises an amino acid sequence of SEQ ID NO:148 without the signal peptide sequence (amino acids 1-22 of SEQ ID NO:148).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR2 signaling domain and a secondary engulfment signaling domain comprising a DAP12 signaling domain (also referred to herein as "CER122"). In certain embodiments, such a CER comprises an amino acid sequence of SEQ ID NO:149. In some embodiments, the CER mature polypeptide comprises an amino acid sequence of SEQ ID NO:149 without the signal peptide sequence (amino acids 1-22 of SEQ ID NO:149).

Yet another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR2 signaling domain and a secondary engulfment signaling domain comprising a TRAF6 signaling domain (also referred to herein as "CER123"). In certain embodiments, such a CER comprises an amino acid sequence of SEQ ID NO:150. In some embodiments, the CER mature polypeptide comprises an amino acid sequence of SEQ ID NO:150 without the signal peptide sequence (amino acids 1-22 of SEQ ID NO:150).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR2 signaling domain and a secondary engulfment signaling domain comprising a NFAM1 signaling domain (also referred to herein as "CER124"). In certain embodiments, such a CER comprises an amino acid sequence of SEQ ID NO:151. In some embodiments, the CER mature polypeptide comprises an amino acid sequence of SEQ ID NO:151 without the signal peptide sequence (amino acids 1-22 of SEQ ID NO:151).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR2 signaling domain and a secondary engulfment signaling domain comprising a CD79b (185-229) signaling domain (also referred to herein as "CER125A"). In certain embodiments, such a CER comprises an amino acid sequence of SEQ ID NO:152. In some embodiments, the CER mature polypeptide comprises an amino acid sequence of SEQ ID NO:152 without the signal peptide sequence (amino acids 1-22 of SEQ ID NO:152).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR2 signaling domain and a secondary engulfment signaling domain comprising CD79b (185-213) signaling domain (also referred to herein as "CER125B"). In certain embodiments, such a CER comprises an amino acid sequence of SEQ ID NO:153. In some embodiments, the CER mature polypeptide comprises an amino acid sequence of SEQ ID NO:153 without the signal peptide sequence (amino acids 1-22 of SEQ ID NO:153).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR2 signaling domain and a secondary engulfment signaling domain comprising a TRAF2 signaling domain (also referred to herein as "CER126"). In certain embodiments, such a CER comprises an amino acid sequence of SEQ ID NO:174. In some embodiments, the CER mature polypeptide comprises an amino acid sequence of SEQ ID NO:174 without the signal peptide sequence (amino acids 1-22 of SEQ ID NO:174).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TRAF2 signaling domain and a secondary engulfment signaling domain comprising a TLR2 signaling domain (also referred to herein as "CER127"). In certain embodiments, such a CER comprises an amino acid sequence of SEQ ID NO:175. In some embodiments, the CER mature polypeptide comprises an amino acid sequence of SEQ ID NO:175 without the signal peptide sequence (amino acids 1-22 of SEQ ID NO:175).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TRAF2 signaling domain and a secondary engulfment signaling domain comprising a TLR8 signaling domain (also referred to herein as "CER128"). In certain embodiments, such a CER comprises an amino acid sequence of SEQ ID NO:176. In some embodiments, the CER mature polypeptide comprises an amino acid sequence of SEQ ID NO:176 without the signal peptide sequence (amino acids 1-22 of SEQ ID NO:176).

Another embodiment of a CER including an extracellular domain comprising a binding domain that binds to PtdSer comprises: a Tim4 binding domain, a transmembrane domain comprising a Tim4 transmembrane domain, an engulfment signaling domain comprising a primary engulfment signaling domain comprising a TLR8 signaling domain and a secondary engulfment signaling domain comprising a TRAF2 signaling domain (also referred to herein as "CER129"). In certain embodiments, such a CER comprises an amino acid sequence of SEQ ID NO:177. In some embodiments, the CER mature polypeptide comprises an amino acid sequence of SEQ ID NO:177 without the signal peptide sequence (amino acids 1-22 of SEQ ID NO:177).

In another aspect, the present disclosure provides a CER comprising a single chain chimeric protein, the single chain chimeric protein comprising: an extracellular domain comprising a binding domain that binds to a pro-engulfment marker or target antigen; an engulfment signaling domain comprising a TLR signaling domain, a Traf2 signaling domain, or a Traf3 signaling domain; and a transmembrane domain positioned between and connecting the extracellular domain and the engulfment signaling domain. Such CERs may provide an inflammatory or immunogenic engulfment phenotype upon binding a target molecule (e.g., pro-engulfment marker or target antigen).

In certain embodiments of a CER including a TLR signaling domain, a Traf2 signaling domain, or a Traf3 signaling domain engulfment signaling domain, the extracellular domain further comprises an extracellular spacer domain positioned between the binding domain and the transmembrane domain.

In yet another aspect, the present disclosure provides a CER comprising a single chain chimeric protein, the single chain chimeric protein comprising: an extracellular domain comprising a binding domain that binds to a pro-engulfment marker or target antigen; an engulfment signaling domain comprising a primary engulfment signaling domain comprising a TLR signaling domain, a Traf6 signaling domain, a Traf2 signaling domain, or a Traf3 signaling domain and a secondary engulfment signaling domain; and a transmembrane domain positioned between and connecting the extracellular domain and the engulfment signaling domain. In some embodiments, the secondary engulfment signaling domain is proinflammatory engulfment signaling domain including an FcR signaling domain (including an FcγR1 signaling domain, an FcγR2A signaling domain, an FcγR2C signaling domain, FcγR2B2 signaling domain, an FcγR3A signaling domain, FcγR2C signaling domain, FcγR3A signaling domain, FcER1 signaling domain, and FcaR1 signaling domain), a BAFF-R signaling domain, a DAP12 signaling domain, a NFAM1 signaling domain, and a CD79b signaling domain.

In certain embodiments of a CER including an engulfment signaling domain comprising a primary engulfment signaling domain and a secondary engulfment signaling domain, the extracellular domain further comprises an extracellular spacer domain positioned between the binding domain and the transmembrane domain.

In yet another aspect, the present disclosure provides a CER comprising a single chain chimeric protein, the single chain chimeric protein comprising: an extracellular domain comprising an scFv that binds to a pro-engulfment marker or target antigen; an engulfment signaling domain comprising a TLR signaling domain, a Traf6 signaling domain, a Traf2 signaling domain, or a Traf3 signaling domain; and a transmembrane domain positioned between and connecting the extracellular domain and the engulfment signaling domain, wherein the transmembrane domain and engulfment signaling domain are each derived from a different molecule.

In certain embodiments of a CER that includes an extracellular domain comprising a scFv that binds to a pro-engulfment marker or target antigen, the extracellular domain further comprises an extracellular spacer domain positioned between the binding domain and the transmembrane domain.

An embodiment of a CER that includes an extracellular domain comprising an scFv that binds to a pro-engulfment marker or target antigen comprises an extracellular domain comprising a CD19 specific scFv binding domain; an extracellular spacer domain comprising a TLR4 juxtamembrane domain; a transmembrane domain comprising a TLR4 transmembrane domain, and an engulfment signaling domain comprising a TLR4 signaling domain (also referred to herein as "CER43"). In certain embodiments, such a CER comprises an amino acid sequence of SEQ ID NO:122. In some embodiments, the CER comprises an amino acid sequence of SEQ ID NO:122 without the signal peptide sequence (amino acids 1-22 of SEQ ID NO:122).

Another embodiment of a CER that includes an extracellular domain comprising an scFv that binds to a pro-engulfment marker or target antigen comprises an extracellular domain comprising a CD19 specific scFv binding domain; an extracellular spacer domain comprising a modified IgG$_4$ hinge region; a transmembrane domain comprising a TLR4 transmembrane domain, and an engulfment signaling domain comprising a TLR4 signaling domain (also referred to herein as "CER44"). In certain embodiments, such a CER comprises an amino acid sequence of SEQ ID NO:123. In some embodiments, the CER comprises an amino acid sequence of SEQ ID NO:123 without the signal peptide sequence (amino acids 1-22 of SEQ ID NO:123).

Another embodiment of a CER that includes an extracellular domain comprising an scFv that binds to a pro-engulfment marker or target antigen comprises an extracellular domain comprising a mesothelin specific scFv binding domain; an extracellular spacer domain comprising a TLR4 juxtamembrane domain; a transmembrane domain comprising a TLR4 transmembrane domain, and an engulfment signaling domain comprising a TLR4 signaling domain (also referred to herein as "CER51").

Another embodiment of a CER that includes an extracellular domain comprising an scFv that binds to a pro-engulfment marker or target antigen comprises an extracellular domain comprising a mesothelin specific scFv binding domain; an extracellular spacer domain comprising a modified IgG$_4$ hinge region; a transmembrane domain comprising a TLR4 transmembrane domain, and an engulfment signaling domain comprising a TLR4 signaling domain (also referred to herein as "CER52").

Another embodiment of a CER that includes an extracellular domain comprising an scFv that binds to a pro-engulfment marker or target antigen comprises an extracellular domain comprising a LGR5 specific scFv binding domain; an extracellular spacer domain comprising a TLR4 juxtamembrane domain; a transmembrane domain comprising a TLR4 transmembrane domain, and an engulfment signaling domain comprising a TLR4 signaling domain (also referred to herein as "CER53").

Another embodiment of a CER that includes an extracellular domain comprising an scFv that binds to a pro-engulfment marker or target antigen comprises an extracellular domain comprising a LGR5 specific scFv binding domain; an extracellular spacer domain comprising a modified IgG$_4$ hinge region; a transmembrane domain comprising a TLR4 transmembrane domain, and an engulfment signaling domain comprising a TLR4 signaling domain (also referred to herein as "CER54").

In certain embodiments, following binding of a CER expressed on the surface of a host cell to its cognate target molecule, lateral clustering of CERs occurs on the host cell surface, increasing the local CER concentration. Clustering is driven by the presence of multivalent ligands on the target cell or particle surface.

In certain embodiments, following binding of a CER expressed on the surface of a host cell to its cognate target molecule, dimerization or multimerization of the CERs occurs, bringing together intracellular engulfment signaling domains, which then become targets of intracellular kinases.

In certain embodiments, a CER of the present disclosure when expressed on the surface of a host cell is capable of tethering, internalizing, and processing (degrading) a target molecule or particle (e.g., phagocytosing a target). In other embodiments, a CER of the present disclosure is capable of tethering and internalizing a target molecule or particle (e.g., engulfing a target). In some embodiments, the target cell or particle may be discharged before or during phagosome maturation. Moreover, internalizing may comprise internalizing the whole cell or particle that is bound by the extracellular domain of the CER, or may comprise internalization of a piece or portion of the cell or particle that is bound by the extracellular domain of the CER.

In certain embodiments, a CER of the present disclosure tethers a target molecule or particle without internalization. A host cell expressing a CER may engulf or be tethered to multiple target cells or particles. Without wishing to be bound by theory, even in the absence of internalization and degradation of the target cell or particle, tethering of a target cell or particle by a host cell expressing a CER may result in degradation of the target cell or particle or promote an inflammatory environment, which is desirable in certain therapeutic contexts (e.g., cancer).

Figure 15:
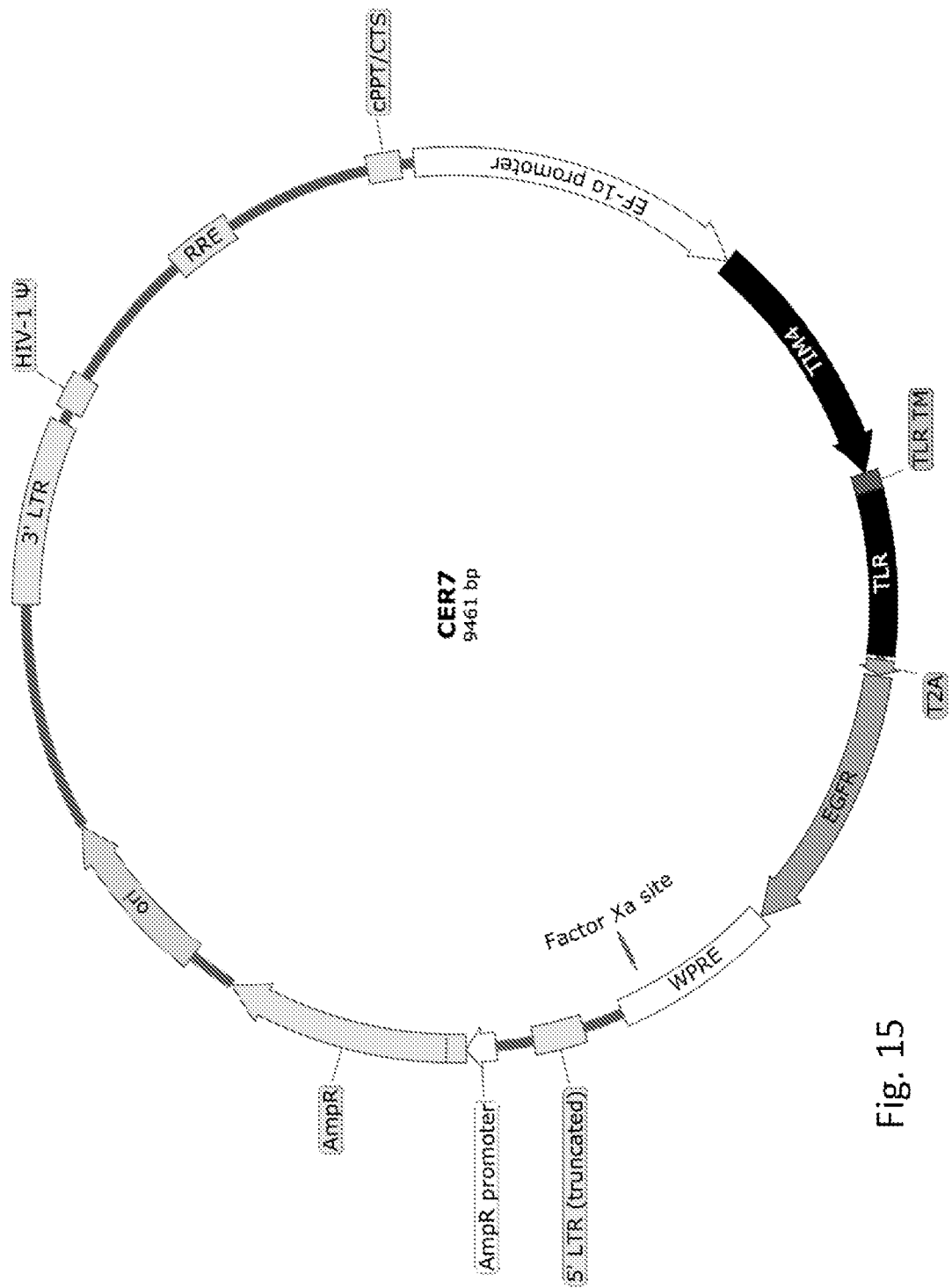
FIG. 15 shows a vector map for a lentiviral vector comprising "CER07" chimeric engulfment receptor having an amino acid sequence of SEQ ID NO:83. CER07 comprises a Tim4 binding domain, a TLR4 juxtamembrane domain, a TLR4 transmembrane domain, and a TLR4 signaling domain. The lentiviral vector also comprises a sequence encoding truncated EGFR (SEQ ID NO:105), which is separated from the CER07 sequence by a viral T2A sequence.
Figure 18:
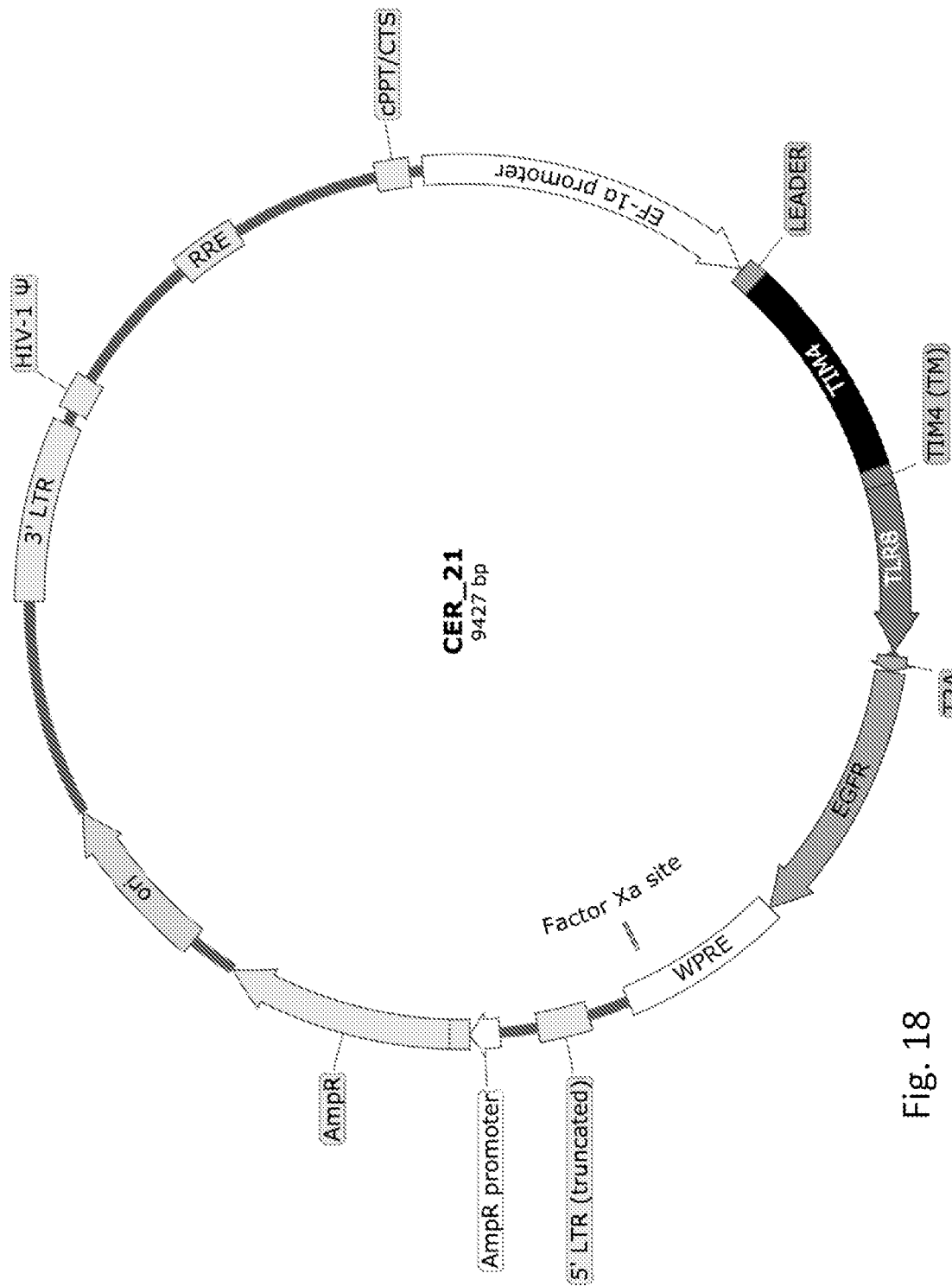
FIG. 18 shows a vector map for a lentiviral vector comprising "CER21" chimeric engulfment receptor having an amino acid sequence of SEQ ID NO:88. CER21 comprises a Tim4 binding domain, a Tim4 transmembrane domain, and a TLR8 signaling domain. The lentiviral vector also comprises a sequence encoding truncated EGFR (SEQ ID NO:105), which is separated from the CER21 sequence by a viral T2A sequence.

Embodiments of CERs according to the present description are illustrated in FIGS. 6, 15, 18, Sequence Listing, Table 1, and the examples.

TABLE 1

Exemplary Chimeric Engulfment Receptors

| CER Name | Binding Domain | Transmembrane Domain | First Engulfment Signaling Domain | Second Engulfment Signaling Domain | Exemplary Amino Acid Sequences |
|---|---|---|---|---|---|
| CER5 | Tim4 | Tim4 | TLR4 | | SEQ ID NO: 81 |
| CER6 | Tim4 | TLR4 | TLR4 | | SEQ ID NO: 82 |
| CER7 | Tim4 + TLR juxtamembrane domain | TLR4 | TLR4 | | SEQ ID NO: 83 |
| CER17 | Tim4 | Tim4 | TLR_3 | | SEQ ID NO: 84 |
| CER18 | Tim4 | TLR_3 | TLR_3 | | SEQ ID NO: 85 |
| CER19 | Tim4 | Tim4 | TLR_5 | | SEQ ID NO: 86 |
| CER20 | Tim4 | TLR_5 | TLR_5 | | SEQ ID NO: 87 |
| CER21 | Tim4 | Tim4 | TLR_8 | | SEQ ID NO: 88 |
| CER22 | Tim4 | TLR_8 | TLR_8 | | SEQ ID NO: 89 |
| CER23 | Tim4 | Tim4 | TLR_9 | | SEQ ID NO: 90 |
| CER24 | Tim4 | TLR_9 | TLR_9 | | SEQ ID NO: 91 |
| CER26 | Tim4 | Tim4 | TLR1 | | SEQ ID NO: 92 |
| CER27 | Tim4 | Tim4 | TLR_2 | | SEQ ID NO: 93 |
| CER28 | Tim4 | Tim4 | TLR_7 | | SEQ ID NO: 94 |
| CER29 | Tim4 | Tim4 | TRAF6 | | SEQ ID NO: 124 |
| CER30 | Tim4 | Tim4 | TRAF2 | | SEQ ID NO: 96 |
| CER31 | Tim4 | Tim4 | TRAF3 | | SEQ ID NO: 97 |
| CER102 | Tim4 | Tim4 | TLR8 | NFAM1 | SEQ ID NO: 130 |
| CER103A | Tim4 | Tim4 | TLR8 | CD79b (185-229) | SEQ ID NO: 131 |
| CER103B | Tim4 | Tim4 | TLR8 | CD79b (185-213) | SEQ ID NO: 132 |
| CER104 | Tim4 | Tim4 | TLR8 | DAP12 | SEQ ID NO: 133 |
| CER105 | Tim4 | Tim4 | TLR8 | Baff-R | SEQ ID NO: 134 |
| CER106 | Tim4 | Tim4 | NFAM1 | TLR8 | SEQ ID NO: 135 |
| CER107 | Tim4 | Tim4 | CD79b (185-213) | TLR8 | SEQ ID NO: 136 |
| CER108 | Tim4 | Tim4 | DAP12 | TLR8 | SEQ ID NO: 137 |
| CER109 | Tim4 | Tim4 | Baff-R | TLR8 | SEQ ID NO: 138 |
| CER110 | Tim4 | Tim4 | TRAF6 | DAP12 | SEQ ID NO: 125 |
| CER111A | Tim4 | Tim4 | TRAF6 | CD79b (185-229) | SEQ ID NO: 139 |
| CER111B | Tim4 | Tim4 | TRAF6 | CD79b (185-213) | SEQ ID NO: 126 |
| CER112 | Tim4 | Tim4 | TRAF6 | NFAM1 | SEQ ID NO: 128 |
| CER113 | Tim4 | Tim4 | TRAF6 | Baff-R | SEQ ID NO: 127 |
| CER114 | Tim4 | Tim4 | TRAF6 | MERTK | SEQ ID NO: 141 |
| CER115 | Tim4 | Tim4 | MERTK | TRAF6 | SEQ ID NO: 142 |
| CER116 | Tim4 | Tim4 | TRAF6 | TLR8 | SEQ ID NO: 143 |
| CER117 | Tim4 | Tim4 | TLR8 | TRAF6 | SEQ ID NO: 144 |
| CER118 | Tim4 | Tim4 | TLR1 | NFAM1 | SEQ ID NO: 145 |
| CER119B | Tim4 | Tim4 | TLR1 | CD79b (185-213) | SEQ ID NO: 146 |

TABLE 1-continued

Exemplary Chimeric Engulfment Receptors

| CER Name | Binding Domain | Transmembrane Domain | First Engulfment Signaling Domain | Second Engulfment Signaling Domain | Exemplary Amino Acid Sequences |
|---|---|---|---|---|---|
| CER119A | Tim4 | Tim4 | TLR1 | CD79b (185-229) | SEQ ID NO: 173 |
| CER120 | Tim4 | Tim4 | TLR1 | DAP12 | SEQ ID NO: 147 |
| CER121 | Tim4 | Tim4 | TLR1 | TRAF6 | SEQ ID NO: 148 |
| CER122 | Tim4 | Tim4 | TLR2 | DAP12 | SEQ ID NO: 149 |
| CER123 | Tim4 | Tim4 | TLR2 | TRAF6 | SEQ ID NO: 150 |
| CER124 | Tim4 | Tim4 | TLR2 | NFAM1 | SEQ ID NO: 151 |
| CER125A | Tim4 | Tim4 | TLR2 | CD79b (185-229) | SEQ ID NO: 152 |
| CER125B | Tim4 | Tim4 | TLR2 | CD79b (185-213_ | SEQ ID NO: 153 |
| CER126 | Tim4 | Tim4 | TLR2 | TRAF2 | SEQ ID NO: 174 |
| CER127 | Tim4 | Tim4 | TRAF2 | TLR2 | SEQ ID NO: 175 |
| CER128 | Tim4 | Tim4 | TRAF2 | TLR8 | SEQ ID NO: 176 |
| CER129 | Tim4 | Tim4 | TLR8 | TRAF2 | SEQ ID NO: 177 |

Nucleic Acids, Vectors, and Host Cells

In certain aspects, the present disclosure provides nucleic acid molecules that encode any one or more of the CERs described herein. The nucleic acid sequences encoding a desired CER can be obtained or produced using recombinant methods known in the art using standard techniques, such as by screening libraries from cells expressing the desired sequence or a portion thereof, by deriving the sequence from a vector known to include the same, or by isolating the sequence or a portion thereof directly from cells or tissues containing the same. Alternatively, the sequence of interest can be produced synthetically, rather than being cloned.

Polynucleotides encoding the CER compositions provided herein may be derived from any animal, such as humans, primates, cows, horses, sheep, dogs, cats, mice, rats, rabbits, guinea pigs, or pigs. In certain embodiments, a polynucleotide encoding the CER is from the same animal species as the host cell into which the polynucleotide is inserted.

Polynucleotides encoding the CER compositions provided herein may also include a sequence encoding a signal peptide (also referred to as leader peptide or signal sequence) at the amino terminal end of the CER for targeting of the precursor protein to the secretory pathway. The signal peptide is optionally cleaved from the N-terminus of the extracellular domain during cellular processing and localization of the CER to the cell membrane. A polypeptide from which a signal peptide sequence has been cleaved or removed may also be called a mature polypeptide. Examples of signal peptides that may be used in the CERs of the present disclosure include signal peptides derived from endogenous secreted proteins, including, e.g., GM-CSF (amino acid sequence of SEQ ID NO:99), Tim4 (amino acid sequence of SEQ ID NO:100 or amino acids 1-24 of SEQ ID NO:3). In certain embodiments, polynucleotide or polypeptide sequences of CERs of the present disclosure comprise sequences for mature polypeptides. It is understood by persons of skill in the art that for sequences disclosed herein that include a signal peptide sequence, the signal peptide sequence may be replaced with another signal peptide that is capable of trafficking the encoded protein to the extracellular membrane.

In certain embodiments, a nucleic acid molecule encoding a CER of the present disclosure is codon optimized for efficient expression in a target host cell.

Nucleic acid molecules encoding a desired CER can be inserted into an appropriate vector (e.g., viral vector, non-viral plasmid vector, and non-viral vectors, such as lipid-based DNA vectors, modified mRNA (modRNA), self-amplifying mRNA, CELiD, and transposon-mediated gene transfer (PiggyBac, Sleeping Beauty)) for introduction in a host cell of interest (e.g., a T cell, a natural killer cell, a B cell, a lymphocyte precursor cell, an antigen presenting cell, a Langerhans cell, or a myeloid cell). Nucleic acid molecules encoding a CER of the present disclosure can be cloned into any suitable vector, such as an expression vector, a replication vector, a probe generation vector, or a sequencing vector. In certain embodiments, a nucleic acid sequence encoding the extracellular domain, a nucleic acid sequence encoding the transmembrane domain, and a nucleic acid sequence encoding the engulfment signaling domain are joined together in a single polynucleotide and then inserted into a vector. In other embodiments, a nucleic acid sequence encoding the extracellular domain, a nucleic acid sequence encoding the transmembrane domain, and a nucleic acid sequence encoding the engulfment signaling domain may be inserted separately in a vector such that the resulting amino acid sequence produces a functional CER. A vector that encodes a CER is referred to herein as a "CER vector."

In certain embodiments, a vector comprises a nucleic acid molecule encoding one CER. In other embodiments, a vector comprises one or more nucleic acid molecules encoding two or more CERs. In one embodiment, two or more nucleic acid molecules each encoding a CER may be cloned sequentially into a vector at different multiple cloning sites, with each CER expressed under the regulation of different promoters. In another embodiment, a single nucleic acid molecule encoding multiple CERs is cloned into a cloning site and expressed from a single promoter, with each CER separated from each other by an IRES or viral 2A peptide sequence to allow for co-expression of multiple genes from a single open reading frame (e.g., a multicistronic vector). In certain embodiments, a viral 2A peptide is T2A (SEQ ID NOS:102, 154, 155, or 156), P2A (SEQ ID NO:101 or 157), E2A (SEQ ID NO:103), or F2A (SEQ ID NO:104).

In some embodiments, vectors that allow long-term integration of a transgene and propagation to daughter cells are utilized. Examples include viral vectors such as, adenovirus, adeno-associated virus, vaccinia virus, herpes viruses, Cytomegalovirus, pox virus, or retroviral vectors, such as lentiviral vectors. Vectors derived from lentivirus can be used to achieve long-term gene transfer and have added advantages over vectors including the ability to transduce non-proliferating cells, such as hepatocytes, and low immunogenicity.

In certain embodiments, a CER vector can be constructed to optimize spatial and temporal control. For example, CER vector can include promoter elements to optimize spatial and temporal control. In some embodiments, a CER vector includes tissue specific promoters or enhancers that enable specific induction of a CER to an organ or a pathologic microenvironment, such as tumor or infected tissue. An "enhancer" is an additional promoter element that can function either cooperatively or independently to activate transcription. In other embodiments, a CER vector includes a constitutive promoter. In still other embodiments, a CER vector includes an inducible promoter.

In further embodiments, a CER vector can include a homing receptor, such as CCR4 or CXCR4, to improve homing and antitumor activity in vivo.

Where temporal control is desired, a CER vector may include an element that allows for inducible depletion of transduced cells. For example, such a vector may include an inducible suicide gene. A suicide gene may be an apoptotic gene or a gene that confers sensitivity to an agent (e.g., drug), such as chemically inducible caspase 9 (iCASP9), chemically inducible Fas, or HSV-TK (confers sensitivity to ganciclovir). In further embodiments, a CER vector can be designed to express a known cell surface antigen that, upon infusion of an associated antibody, enables depletion of transduced cells. Examples of cell surface antigens and their associated antibodies that may be used for depletion of transduced cells include CD20 and Rituximab, RQR8 (combined CD34 and CD20 epitopes, allowing CD34 selection and anti-CD20 deletion) and Rituximab, and EGFR and Cetuximab.

Inducible vector systems, such as the tetracycline (Tet)-On vector system which activates transgene expression with doxycycline (Heinz et al., Hum. Gene Ther. 2011, 22:166-76) may also be used for inducible CER expression. Inducible CER expression may be also accomplished via retention using a selective hook (RUSH) system based on streptavidin anchored to the membrane of the endoplasmic reticulum through a hook and a streptavidin binding protein introduced into the CER structure where addition of biotin to the system leads to the release of the CER from the endoplasmic reticulum (Agaugue et al., 2015, Mol. Ther. 23(Suppl. 1):588).

As used herein, the term "recombinant" or "non-natural" refers to an organism, microorganism, cell, nucleic acid molecule, or vector that includes at least one genetic alteration or has been modified by introduction of an exogenous nucleic acid molecule, wherein such alterations or modifications are introduced by genetic engineering. Genetic alterations include, for example, modifications introducing expressible nucleic acid molecules encoding proteins, chimeric proteins or enzymes, or other nucleic acid molecule additions, deletions, substitutions or other functional disruption of a cell's genetic material. Additional modifications include, for example, non-coding regulatory regions in which the modifications alter expression of a gene or operon. In certain embodiments, a cell, such as a T cell, obtained from a subject may be genetically modified into a non-natural or recombinant cell (e.g., a non-natural or recombinant T cell) by introducing a nucleic acid that encodes a CER as described herein and whereby the cell expresses a cell surface located CER.

A vector that encodes a core virus is referred to herein as a "viral vector." There are a large number of available viral vectors suitable for use with the compositions of the instant disclosure, including those identified for human gene therapy applications (see Pfeifer and Verma, Ann. Rev. Genomics Hum. Genet. 2:177, 2001). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing chimeric receptor transgenes are known in the art and have been previous described, for example, in U.S. Pat. No. 8,119,772; Walchli et al., PLoS One 6:327930, 2011; Zhao et al., J. Immunol. 174:4415, 2005; Engels et al., Hum. Gene Ther. 14:1155, 2003; Frecha et al., Mol. Ther. 18:1748, 2010; Verhoeyen et al., Methods Mol. Biol. 506:97, 2009. Retroviral and lentiviral vector constructs and expression systems are also commercially available.

In certain embodiments, a viral vector is used to introduce a non-endogenous nucleic acid sequence encoding a CER specific for a target. A viral vector may be a retroviral vector or a lentiviral vector. A viral vector may also include nucleic acid sequences encoding a marker for transduction. Transduction markers for viral vectors are known in the art and include selection markers, which may confer drug resistance, or detectable markers, such as fluorescent markers or cell surface proteins that can be detected by methods such as flow cytometry. In particular embodiments, a viral vector further comprises a gene marker for transduction comprising fluorescent protein (e.g., green, yellow), an extracellular domain of human CD2, or a truncated human EGFR (encoding an amino acid sequence of SEQ ID NO:105) (huEGFRt; see Wang et al., Blood 118:1255, 2011). When a viral vector genome comprises a plurality of nucleic acid sequences to be expressed in a host cell as separate transcripts, the viral vector may also comprise additional sequences between the two (or more) transcripts allowing bicistronic or multicistronic expression. Examples of such sequences used in viral vectors include internal ribosome entry sites (IRES), furin cleavage sites, viral 2A peptides (e.g., T2A, P2A, E2A, F2A), or any combination thereof.

Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., Gene Ther. 5: 1517, 1998).

Other viral vectors recently developed for gene therapy uses can also be used with the compositions and methods of this disclosure. Such vectors include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as sleeping beauty or other transposon vectors). In some embodiments, a viral or plasmid vector further comprises a gene marker for transduction (e.g. green fluorescent protein, huEGFRt (encoding an amino acid sequence of SEQ ID NO:105).

In certain embodiments, gene editing methods are used to modify the host cell genome to comprise a polynucleotide encoding a CER of the present disclosure. Gene editing, or genome editing, is a method of genetic engineering wherein DNA is inserted, replaced, or removed from a host cell's genome using genetically engineered endonucleases. The nucleases create specific double-stranded breaks at targeted loci in the genome. The host cell's endogenous DNA repair pathways then repair the induced break(s), e.g., by non-homologous ending joining (NHEJ) and homologous recombination. Exemplary endonucleases useful in gene editing include a zinc finger nuclease (ZFN), a transcription activator-like effector (TALE) nuclease, a clustered regularly interspaced short palindromic repeats (CRISPR)/Cas nuclease system (e.g., CRISPR-Cas9), a meganuclease, or combinations thereof. Methods of disrupting or knocking out genes or gene expression in immune cells including B cells and T cells, using gene editing endonucleases are known in the art and described, for example, in PCT Publication Nos. WO 2015/066262; WO 2013/074916; WO 2014/059173; Cheong et al., Nat. Comm. 2016 7:10934; Chu et al., Proc. Natl. Acad. Sci. USA 2016 113:12514-12519; methods from each of which are incorporated herein by reference in their entirety.

In certain embodiments, B cells, lymphoid precursor cells, including common lymphocyte precursor cells, antigen presenting cells, including dendritic cells, Langerhans cells, a myeloid precursor cell, or mature myeloid cells are modified to comprise a non-endogenous nucleic acid molecule that encodes a CER of this disclosure.

In some embodiments, B cells are genetically modified to express one or more CERs. B cells possess certain properties that may be advantageous as host cells, including: trafficking to sites of inflammation (e.g., lymph nodes, tumors), capable of internalizing and presenting antigen, capable of costimulating T cells, highly proliferative, and self-renewing (persist for life). In certain embodiments, CER modified B cells are capable of digesting an engulfed target cell or engulfed target particle into smaller peptides and presenting them to T cells via an MEW molecule. Antigen presentation by CER modified B cells may contribute to antigen spreading of the immune response to non-targeted antigens. B cells include progenitor or precursor cells committed to the B cell lineage (e.g., pre-pro-B cells, pro-B cells, and pre-B cells); immature and inactivated B cells or mature and functional or activated B cells. In certain embodiments, B cells may be naïve B cells, plasma cells, regulatory B cells, marginal zone B cells, follicular B cells, lymphoplasmacytoid cell, plasmablast cell, memory B cells, or any combination thereof. Memory B cells may be distinguished from naïve B cells by expression of CD27, which is absent on naïve B cells. In certain embodiments, the B cells can be primary cells or cell lines derived from human, mouse, rat, or other mammals. B cell lines are well known in the art. If obtained from a mammal, a B cell can be obtained from numerous sources, including blood, bone marrow, spleen, lymph node, or other tissues or fluids. In certain embodiments, a B cell is isolated from a tumor site (tumor infiltrating B cell). A B cell composition may be enriched or purified.

In certain embodiments, expression of an endogenous gene of the host B cell is inhibited, knocked down, or knocked out. Examples of endogenous genes that may be inhibited, knocked down, or knocked out in a B cell include a B cell receptor (BCR) gene (e.g., CD79b, IGH, IGx, IGλ, or any combination thereof), an immune checkpoint molecule (e.g., PD-L1, PD-L2, CD80, CD86, B7-H3, B7-H4, HVEM, adenosine, GALS, VISTA, CEACAM-1, CEACAM-3, CEACAM-5, PVRL2, PD-1, CTLA-4, BTLA, KIR, LAG3, TIM3, A2aR, CD244/2B4, CD160, TIGIT, LAIR-1, PVRIG/CD112R, or any combination thereof), or any combination thereof. Expression of a BCR gene, an immune checkpoint molecule gene, or both may be inhibited, knocked down, or knocked out at the gene level, transcriptional level, or translational level, or a combination thereof. Methods of inhibiting, knocking down, or knocking out a BCR gene, immune checkpoint molecule gene, or both may be accomplished, for example, by RNA interference agents (e.g., siRNA, shRNA, miRNA, etc.) or engineered endonucleases (e.g., CRISPR/Cas nuclease system, a zinc finger nuclease (ZFN), a Transcription Activator Like Effector nuclease (TALEN), a meganuclease, or any combination thereof). In some embodiments, an endogenous gene (e.g., a BCR gene or an immune checkpoint molecule gene) is knocked out by insertion of a polynucleotide encoding a CER of the present disclosure into the locus of the endogenous B cell gene, such as via an engineered endonuclease.

In some embodiments, cells capable of expressing a CER of this disclosure on the cell surface are T cells, including CD4+, CD8+, naïve (CD45 RA+, CCR7+, CD62L+, CD27+, CD45RO−), central memory (CD45RO+, CD62L+, CD8+), effector memory (CD45RA+, CD45RO−, CCR7−, CD62L−, CD27−), virus-specific, mucosal-associated invariant, γδ(gd), tissue resident T cells, and natural killer T cells. In certain embodiments, the T cells can be primary cells or cell lines derived from human, mouse, rat, or other mammals. If obtained from a mammal, a T cell can be obtained from numerous sources, including blood, bone marrow, lymph node, thymus, or other tissues or fluids. In certain embodiments, a T cell is isolated from a tumor site (tumor infiltrating T cell). A T cell composition may be enriched or purified. T cell lines are well known in the art, some of which are described in Sandberg et al., Leukemia 21:230, 2000. In certain embodiments, T cells that lack endogenous expression of TCRα and β chains are used. Such T cells may naturally lack endogenous expression of TCRα and β chains or may have been modified to block expression (e.g., T cells from a transgenic mouse that does not express TCR α and β chains or cells that have been manipulated to inhibit expression of TCR α and β chains) or to knockout TCRα chain, TCRβ chain, or both genes. In certain embodiments, cells capable of expressing a chimeric protein of this disclosure on the cell surface are not T cells or cells of a T cell lineage, but cells that are progenitor cells, stem cells or cells that have been modified to express cell surface anti-CD3.

In certain embodiments, CER modified T cells are capable of digesting an engulfed target cell or engulfed target particle into smaller peptides and presenting them to T cells via an MHC molecule. Antigen presentation by CER modified T cells may contribute to antigen spreading of the immune response to non-targeted antigens.

In certain embodiments, a host T cell transfected to express a CER of this disclosure is a functional T cell, such as a virus-specific T cell, a tumor antigen specific cytotoxic T cell, a naïve T cell, a memory stem T cell, a central or effector memory T cell, or a CD4+CD25+ regulatory T cell.

In certain embodiments, expression of an endogenous gene of the host T cell is inhibited, knocked down, or knocked out. Examples of endogenous genes that may be inhibited, knocked down, or knocked out in a T cell include a TCR gene (TRA, TRB, or both), HLA gene (HLA class I gene, HLA class II gene, or both), an immune checkpoint molecule (PD-L1, PD-L2, CD80, CD86, B7-H3, B7-H4, HVEM, adenosine, GALS, VISTA, CEACAM-1, CEACAM-3, CEACAM-5, PVRL2, PD-1, CTLA-4, BTLA, KIR, LAG3, TIM3, A2aR, CD244/2B4, CD160, TIGIT, LAIR-1, PVRIG/CD112R, or any combination thereof), or any combination thereof. Expression of a TCR gene, an HLA gene, an immune checkpoint molecule gene, or any combination thereof may be inhibited, knocked down, or knocked out at the gene level, transcriptional level, or translational level, or any combination thereof. Methods of inhibited, knocked down, or knocked out a TCR gene, an HLA gene, immune checkpoint molecule gene, or any combination thereof may be accomplished, for example, by RNA interference agents (e.g., siRNA, shRNA, miRNA, etc.) or engineered endonucleases (e.g., CRISPR/Cas nuclease system, a zinc finger nuclease (ZFN), a Transcription Activator Like Effector nuclease (TALEN), a meganuclease, or any combination thereof). In some embodiments, an endogenous gene (e.g., a TCR gene, an HLA gene, or an immune checkpoint molecule gene) is knocked out by insertion of a polynucleotide encoding a CER of the present disclosure into the locus of the endogenous T cell gene, such as via an engineered endonuclease.

In certain embodiments, a host cell comprising a CER that comprises an extracellular domain comprising a binding domain that binds to phosphatidylserine (PtdSer) according to any of the embodiments described herein is a T cell, a natural killer cell, a B cell, a lymphoid precursor cell, including common lymphocyte precursor cells, an antigen presenting cell, including dendritic cells, a Langerhans cell, a myeloid precursor cell, or a mature myeloid cell.

In other embodiments, a host cell comprising a CER that comprises an extracellular domain comprising a binding domain (e.g., a scFv) that binds to a target antigen according to any of the embodiments described herein is a B cell.

In yet other embodiments a host cell comprising a CER that comprises an extracellular domain comprising a binding domain that binds to a pro-engulfment marker or target antigen according to any of the embodiments described herein is a cell that does not naturally exhibit an engulfment phenotype. In a particular embodiment, the host cell is a T cell, a natural killer cell, a B cell, or a lymphoid precursor cell, including common lymphocyte precursor cells. In a particular embodiment, the host cell is a cell that does not naturally exhibit an engulfment phenotype towards a mammalian cell.

In certain embodiments, a host cell may be genetically modified to express one type of CER. In other embodiments, a host cell may express at least two or more different CERs.

In certain embodiments, a population of host cells that are modified to express one or more CERs may be a population of B cells, a population of T cells, a population of natural killer cells, a population of lymphoid precursor cells, including common lymphocyte precursor cells, a population of antigen presenting cells, including dendritic cells, Langerhans cells, a population of myeloid precursor cells, a population of mature myeloid cells, or any combination thereof. In a particular embodiment, the population of host cells that are modified to express one or more CERs is a population of B cells, a population of T cells, or both.

In certain embodiments, each host cell within a population of host cells expresses the same CER or set of CERs. In other embodiments, a population of host cells comprises a mixture of two or more subpopulation of host cells, wherein each subpopulation expresses a different CER or set of CERs.

In certain embodiments, when preparing host cells, e.g., B cells or T cells, that express a CER as described herein, one or more growth factor cytokines that promote proliferation of the host cells, e.g., B cells or T cells, may be added to the cell culture. The cytokines may be human or non-human. Exemplary growth factor cytokines that may be used to promote T cell proliferation include IL-2, IL-15, or the like. Exemplary growth factor cytokines that may be used to promote B cell proliferation include CD40L, IL-2, IL-4, IL-15, IL-21, BAFF, or the like.

In further embodiments, selective gene transfer is used to localize the CER vector to a specific region or organ. In some embodiments, selective gene transfer is used to localize the CER vector to the liver or the lungs of a subject.

Prior to genetic modification of the host cells with a CER vector, a source of host cells (e.g., T cells, B cells, natural killer cells, etc.) is obtained from a subject (e.g., whole blood, peripheral blood mononuclear cells, bone marrow, lymph node tissue, cord blood, thymus tissue, tissue from a site of infection, ascites, pleural effusion, spleen tissue), from which host cells are isolated using methods known in the art. Specific host cell subsets can be collected in accordance with known techniques and enriched or depleted by known techniques, such as affinity binding to antibodies, flow cytometry and/or immunomagnetic selection. After enrichment and/or depletion steps and introduction of a CER, in vitro expansion of the desired modified host cells can be carried out in accordance with known techniques, or variations thereof that will be apparent those skilled in the art.

In certain embodiments, a host cell, including a T cell, a natural killer cell, a B cell, a lymphoid precursor cell, an antigen presenting cell, dendritic cell, a Langerhans cell, a myeloid precursor cell, and a mature myeloid cell, comprising a CER according to any of the embodiments described herein has a phagocytic index of about 20 to about 1,500 for a target cell. A "phagocytic index" is a measure of phagocytic activity of the transduced host cell as determined by counting the number of target cells ingested per CER modified host cell during a set period of incubation of a suspension of target cells and CER modified host cells in media. Phagocytic index may be calculated by multiplying [total number of engulfed target cells/total number of counted CER modified cells (e.g., phagocytic frequency)]x [average area of target cell staining per CER+Ba/F3 cell x 100 (e.g., hybrid capture)] or [total number of engulfed particles/total number of counted CER modified host cells]x [number of CER modified host cells containing engulfed particles/total number of counted CER cells]x 100. In certain embodiments, a CER modified cell has a phagocytic index of about 30 to about 1,500; about 40 to about 1,500; about 50 to about 1,500; about 75 to about 1,500; about 100 to about 1,500; about 200 to about 1,500; about 300 to about 1,500; about 400 to about 1,500; about 500 to about 1,500; about 20 to about 1,400; about 30 to about 1,400; about 40 to about 1,400; about 50 to about 1,400; about 100 to about 1,400; about 200 to about 1,400; about 300 to about 1,400; about 400 to about 1,400; about 500 to about 1,400; about 20 to about 1,300; about 30 to about 1,300; about 40 to about 1,300; about 50 to about 1,300; about 100 to about 1,300; about 200 to about 1,300; about 300 to about 1,300; about 400 to about 1,300; about 500 to about 1,300; about 20 to about 1,200; about 30 to about 1,200; about 40 to about 1,200; about 50 to about 1,200; about 100 to about 1,200; about 200 to about 1,200; about 300 to about 1,200; about 400 to about 1,200; about 500 to about 1,200; about 20 to about 1,100; about 30 to about 1,100; about 40 to about 1,100; about 50 to about 1,100; about 100 to about 1,100; about 200 to about 1,100; about 300 to about 1,100; about 400 to about 1,100; or about 500 to about 1,100; about 20 to about 1,000; about 30 to about 1,000; about 40 to about 1,000; about 50 to about 1,000; about 100 to about 1,000; about 200 to about 1,000; about 300 to about 1,000; about 400 to about 1,000; or about 500 to about 1,000; about 20 to about 750; about 30 to about 750; about 40 to about 750; about 50 to about 750; about 100 to about 750; about 200 to about 750; about 300 to about 750; about 400 to about 750; or about 500 to about 750; about 20 to about 500; about 30 to about 500; about 40 to about 500; about 50 to about 500; about 100 to about 500; about 200 to about 500; or about 300 to about 500. In further embodiments, the incubation time is from about 2 hours to about 4 hours, about 2 hours, about 3 hours, or about 4 hours. In yet further embodiments, a CER modified cell exhibits phagocytic index that is statistically significantly higher than a cell transduced with truncated EGFR control. Phagocytic index may be calculated using methods known in the art and as further described in the Examples, including quantification by flow cytometry or fluorescence microscopy.

In certain embodiments, a host cell that has been modified to express a CER according to one of the embodiments described herein exhibits: cytolytic activity towards a target cell, i.e., capable of lysing a target cell expressing a target antigen on its surface; exhibits enhanced activation (e.g., enhanced cytokine production, such as IFNγ); exhibits enhanced cell proliferation; exhibits enhanced cell expansion; exhibits enhanced persistence; exhibits enhanced memory formation; exhibits antigen presentation activity; exhibits induction of antigen-specific phagocytic signaling or enhanced antigen-specific phagocytic signaling; exhibits degradation of an engulfed target cell; or any combination thereof as compared to a host cell that does not express the CER. In certain embodiments, a CER modified host cell is capable of inducing antigenic spread via its antigen presenting activities.

Host cells may be from an animal, such as a primate, cow, horse, sheep, dog, cat, mouse, rat, rabbit, guinea pig, or pig. In a preferred embodiment, the animal is a human. Host cells may be obtained from a healthy subject or a subject having a disease associated with expression of an antigen.

Uses of CERs and Cells Modified to Express CERs

The present disclosure provides methods for altering the engulfment phenotype of a host cell. In one aspect, the present disclosure provides methods for producing a population of cells exhibiting an engulfment phenotype comprising introducing into a population of host cells that do not naturally exhibit an engulfment phenotype a nucleic acid molecule encoding at least one CER or a vector comprising at least one CER according to any of the embodiments described herein; and expressing the at least one CER in the population of host cells. In certain embodiments, the engulfment phenotype is phagocytosis. In certain embodiments, the population of host cells expressing the at least one CER is capable of antigen-specific phagocytic signaling activity. Induction of an antigen-specific phagocytic signaling cascade may comprise activation of CDC42, Rac1, or both. In certain embodiments, the population of host cells expressing the at least one CER is capable of degrading engulfed target cells.

In another aspect, the present disclosure provides methods for altering the engulfment phenotype of a population of cells comprising introducing into a population of host cells a nucleic acid molecule encoding at least one CER or a vector comprising at least one CER according to any of the embodiments described herein; and expressing the at least one CER in the population of host cells, wherein the at least one CER confers an engulfment phenotype specific to a pro-engulfment marker or antigenic marker (target antigen) that is not naturally targeted by the host cells. In certain embodiments, the engulfment phenotype is phagocytosis.

In yet another aspect, the present disclosure provides methods for enhancing the engulfment phenotype of a population of cells comprising introducing into a population of host cells a nucleic acid molecule encoding at least one CER or a vector comprising at least one CER according to any of the embodiments described herein; and expressing the at least one CER in the population of host cells, wherein the at least one CER is specific to a pro-engulfment marker or antigenic marker (target antigen) that is naturally targeted by the host cells and expression of the at least one CER by the host cells enhances the engulfment by the host cells of cells, microbes, or particles exhibiting the targeted pro-engulfment or antigenic marker.

In further embodiments of the methods of producing a population of host cells exhibiting an engulfment phenotype, altering the engulfment phenotype in a population of cells, or enhancing the engulfment phenotype in a population of cells, expression of at least one CER by the population of host cells enhances proliferative capacity of the population of cells, enhances activation of the population of cells (e.g., enhanced cytokine production, such as IFNγ), enhances expansion of the population of host cells, enhances persistence of the population of host cells, enhances memory formation of the population of cells, confers antigen presenting activity to the population of host cells, confers or enhances cytolytic activity of the population of host cells, or any combination thereof. In certain embodiments, a population of CER modified host cell is capable of inducing antigenic spread via the antigen presenting activities.

CERs, nucleic acid molecules encoding CERs, vectors comprising CERs, and host cells that express CERs according to any of the embodiments described herein may also be used in a method of treating a subject suffering from a disease, disorder or undesired condition. Embodiments of these methods include administering to a subject a therapeutically effective amount of a pharmaceutical composition including one or more CERs, nucleic acid molecules encoding one or more CERs, vectors comprising one or more CERs, or a population of host cells genetically modified to express one or more CERs according to the present description.

Diseases that may be treated with cells expressing a CER as described in the present disclosure include cancer, infectious diseases (viral, bacterial, fungal, protozoan infections), inflammatory, or immune diseases (e.g., autoimmune diseases, inflammatory bowel diseases, multiple sclerosis), degenerative disease (e.g., joint and cartilage), and neurodegenerative diseases (e.g., Alzheimer's disease). Adoptive immune and gene therapies are promising treatments for various types of cancer (Morgan et al., Science 314:126, 2006; Schmitt et al., Hum. Gene Ther. 20:1240, 2009; June, 1 Clin. Invest. 117:1466, 2007) and infectious disease (Kitchen et al., PLoS One 4:38208, 2009; Rossi et al., Nat. Biotechnol. 25:1444, 2007; Zhang et al., PLoS Pathog. 6:e1001018, 2010; Luo et al., J. Mol. Med. 89:903, 2011).

Subjects that can be treated by the compositions and methods of the present disclosure include animals, such as humans, primates, cows, horses, sheep, dogs, cats, mice, rats, rabbits, guinea pigs, or pigs. The subject may be male or female, and can be any suitable age, including infant, juvenile, adolescent, adult, and geriatric subjects.

A wide variety of cancers, including solid tumors and leukemias are amenable to the compositions and methods disclosed herein. Exemplary types of cancer that may be treated include adenocarcinoma of the breast, prostate, and colon; all forms of bronchogenic carcinoma of the lung; myeloid leukemia; melanoma; hepatoma; neuroblastoma;

papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated include histiocytic disorders; malignant histiocytosis; leukemia; Hodgkin's disease; immunoproliferative small; non-Hodgkin's lymphoma; plasmacytoma; multiple myeloma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Exemplifying hyperproliferative disorders amenable to CER therapy are B-cell cancers, including B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), Hairy cell leukemia, B cell blast transformation of chronic myeloid leukemia) and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder.

Inflammatory and autoimmune diseases include arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, Alzheimer's disease, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjörgen's syndrome, Stevens-Johnson syndrome, solid organ transplant rejection, graft versus host disease (GVHD), bullous pemphigoid, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant), non-specific interstitial pneumonia (NSIP), Guillain-BarreSyndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans. In certain embodiments, in the context of treating an inflammatory disease, it may be preferable to design a CER with a homeostatic (non-inflammatory) engulfment signaling domain.

Infectious diseases include those associated with infectious agents and include any of a variety of bacteria (e.g., pathogenic *E. coli, S. typhimurium, P. aeruginosa, B. anthracis, C. botulinum, C. difficile, C. perfringens, H.*

*pylori, V. cholerae, Listeria* spp., *Rickettsia* spp., *Chlamydia* spp., and the like), mycobacteria, and parasites (including any known parasitic member of the Protozoa). Infectious viruses include eukaryotic viruses, such as adenovirus, bunyavirus, herpesvirus, papovavirus, papillomavirus (e.g., HPV), paramyxovirus, picornavirus, rhabdovirus (e.g., Rabies), orthomyxovirus (e.g., influenza), poxvirus (e.g., Vaccinia), reovirus, retrovirus, lentivirus (e.g., HIV), flavivirus (e.g., HCV, HBV) or the like. In certain embodiments, a composition comprising a CER according to the present disclosure is used for treating infection with a microbe capable of establishing a persistent infection in a subject.

Neurodegenerative diseases include Lewy body disease, postpoliomyelitis syndrome, Shy-Draeger syndrome, olivopontocerebellar atrophy, Parkinson's disease, multiple system atrophy, striatonigral degeneration, frontotemporal lobar degeneration with ubiquitinated inclusions (FLTD-U), tauopathies (including, but not limited to, Alzheimer disease and supranuclear palsy), prion diseases (also known as transmissible spongiform encephalopathies, including, but not limited to, bovine spongiform encephalopathy, scrapie, Creutz-feldt-Jakob syndrome, kuru, Gerstmann-Straussler-Scheinker disease, chronic wasting disease, and fatal familial insomnia), bulbar palsy, motor neuron disease (including Amyotrophic lateral sclerosis (Lou Gehrig's disease)), and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia), cancer (e.g., of the CNS and/or brain, including brain metastases resulting from cancer elsewhere in the body). Many neurodegenerative diseases, including Alzheimer's disease, Parkinson's disease, Huntington's disease, Amyotrophic lateral sclerosis (Lou Gehrig's disease) and prion diseases, share a neuropathological signature, the aberrant accumulation of proteins, such as amyloid-β or tau in Alzheimer's disease; α-synuclein in Parkinson's disease (PD), dementia with Lewy bodies, multiple system atrophy, or Alzheimer's disease; huntingtin in Huntington's disease, SOD1 in Amyotrophic lateral sclerosis, proteins with polyglutamine (polyQ) repeats in Huntington's disease or Amyotrophic lateral sclerosis; TDP-43 in Amyotrophic lateral sclerosis or FLTD-U; or prion protein (e.g., $PrP^{Sc}$) in prion diseases. Thus, in certain embodiments, CER therapy may be designed to target the disease-associated protein in order to reduce or prevent aberrant protein accumulation, thereby slowing or preventing progression of the neurodegenerative disease.

A CER of this disclosure may be administered to a subject in cell-bound form (e.g., gene therapy of target cell population (mature T cells (e.g., CD8+ or CD4+ T cells) or other cells of T cell lineage)). Thus, for example, a CER of the present disclosure may be administered to a subject expressed on the surface of T cells, Natural Killer Cells, Natural Killer T cells, B cells, lymphoid precursor cells, antigen presenting cells, dendritic cells, Langerhans cells, myeloid precursor cells, mature myeloid cells, including subsets thereof, or any combination thereof. In certain embodiments, methods of treating a patient include administering an effective amount of CER modified cells (i.e., recombinant cells that express one or more CERs). In such embodiments, the CER modified cells are xenogeneic, syngeneic, allogeneic, or autologous cells of T cell lineage, Natural Killer cell lineage, Natural Killer T cell lineage, B cell lineage, lymphoid precursor cell lineage, dendritic cell lineage, Langerhans cell lineage, myeloid cell lineage, or any combination thereof.

Pharmaceutical compositions including a CER modified cells may be administered in a manner appropriate to the disease or condition to be treated (or prevented) as determined by persons skilled in the medical art. An appropriate dose, suitable duration, and frequency of administration of the compositions will be determined by such factors as the condition of the patient, size, weight, body surface area, age, sex, type and severity of the disease, particular therapy to be administered, particular form of the active ingredient, time and the method of administration, and other drugs being administered concurrently. The present disclosure provides pharmaceutical compositions comprising CER modified cells and a pharmaceutically acceptable carrier, diluent, or excipient. Suitable excipients include water, saline, dextrose, glycerol, or the like and combinations thereof. Other suitable infusion medium can be any isotonic medium formulation, including saline, Normosol R (Abbott), Plasma-Lyte A (Baxter), 5% dextrose in water, or Ringer's lactate.

A treatment effective amount of cells in a pharmaceutical composition is at least one cell (for example, one CER modified B cell) or is more typically greater than $10^2$ cells, for example, up to $10^6$, up to $10^7$, up to $10^8$ cells, up to $10^9$ cells, up to $10^{10}$ cells, or up to $10^{11}$ cells or more. In certain embodiments, the cells are administered in a range from about $10^6$ to about $10^{10}$ cells/m$^2$, preferably in a range of about $10^7$ to about $10^9$ cells/m$^2$. The number of cells will depend upon the ultimate use for which the composition is intended as well the type of cells included therein. For example, a composition comprising cells modified to contain a CER specific for a particular antigen will comprise a cell population containing from about 5% to about 95% or more of such cells. In certain embodiments, a composition comprising CER modified cells comprises a cell population comprising at least 5%, 10%, 15%, 20%, 25%, 30%, 35%, 40%, 45%, 50%, 55%, 60%, 65%, 70%, 75%, 80%, 85%, 90%, 95% or more of such cells. For uses provided herein, the cells are generally in a volume of a liter or less, 500 mls or less, 250 mls or less, or 100 mls or less. Hence the density of the desired cells is typically greater than $10^4$ cells/ml and generally is greater than 10' cells/ml, generally $10^8$ cells/ml or greater. The cells may be administered as a single infusion or in multiple infusions over a range of time. Repeated infusions of CER modified cells may be separated by days, weeks, months, or even years if relapses of disease or disease activity are present. A clinically relevant number of immune cells can be apportioned into multiple infusions that cumulatively equal or exceed $10^6$, 10',$10^8$, $10^9$, $10^{10}$, or $10^{11}$ cells. A preferred dose for administration of a host cell comprising a recombinant expression vector as described herein is about 10' cells/m$^2$, about 5×10' cells/m$^2$, about $10^8$ cells/m$^2$, about 5×$10^8$ cells/m$^2$, about $10^9$ cells/m$^2$, about 5×$10^9$ cells/m$^2$, about $10^{10}$ cells/m$^2$, about 5×$10^{10}$ cells/m$^2$, or about $10^{11}$ cells/m$^2$. In certain embodiments, a composition of CER modified B cells and a composition of CER modified T cells are both administered, which administration may be simultaneous, concurrent or sequential.

In some embodiments, a composition as described herein is administered intravenously, intraperitoneally, intratumoraly, into the bone marrow, into the lymph node, and/or into cerebrospinal fluid. In some embodiments, chimeric engulfment receptor engineered compositions are delivered to the site of the tumor.

In some embodiments, CER modified cells are administered to a subject in conjunction or combination with one or more additional therapies. In such embodiments, the one or more additional therapies may be one or more of radiation therapy, genetically engineered cellular immunotherapy (e.g., T cell, dendritic cell, natural killer cell, macrophage, chimeric antigen receptor (CAR) therapy), antibody therapy, immune checkpoint molecule inhibitor therapy, or a pharmaceutical therapy, such as a chemotherapeutic, a therapeutic peptide, a hormonal therapy, antibiotic, anti-viral agent, anti-fungal agent, anti-inflammatory agent, UV light therapy, electric pulse therapy, high intensity focused ultrasound therapy, oncolytic virus therapy, or a small molecule therapy. In such embodiments, the CER modified cells may clear apoptotic, dead, dying, damaged, infected, or necrotic cells displaying pro-apoptotic markers induced in the setting of the one or more additional therapies. In certain embodiments where CER modified cells are administered in combination with one or more additional therapies, the one or more additional therapies may be administered at a subtherapeutic dose due to an additive or synergistic effect of the combination with CER therapy. Combination therapy includes administration of a CER before an additional therapy (e.g., 1 day to 30 days or more before the additional therapy), concurrently with an additional therapy (on the same day), or after an additional therapy (e.g., 1 day-30 days or more after the additional therapy). In certain embodiments, the CER modified cells are administered after administration of the one or more additional therapies. In further embodiments, the CER modified cells are administered 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days after administration of the one or more additional therapies. In still further embodiments, the CER modified cells are administered within 4 weeks, within 3 weeks, within 2 weeks, or within 1 week after administration of the one or more additional therapies. Where the one or more additional therapies involves multiple doses, the CER modified cells may be administered after the initial dose of the one or more additional therapies, after the final dose of the one or more additional therapies, or in between multiple doses of the one or more additional therapies.

Figure 5:
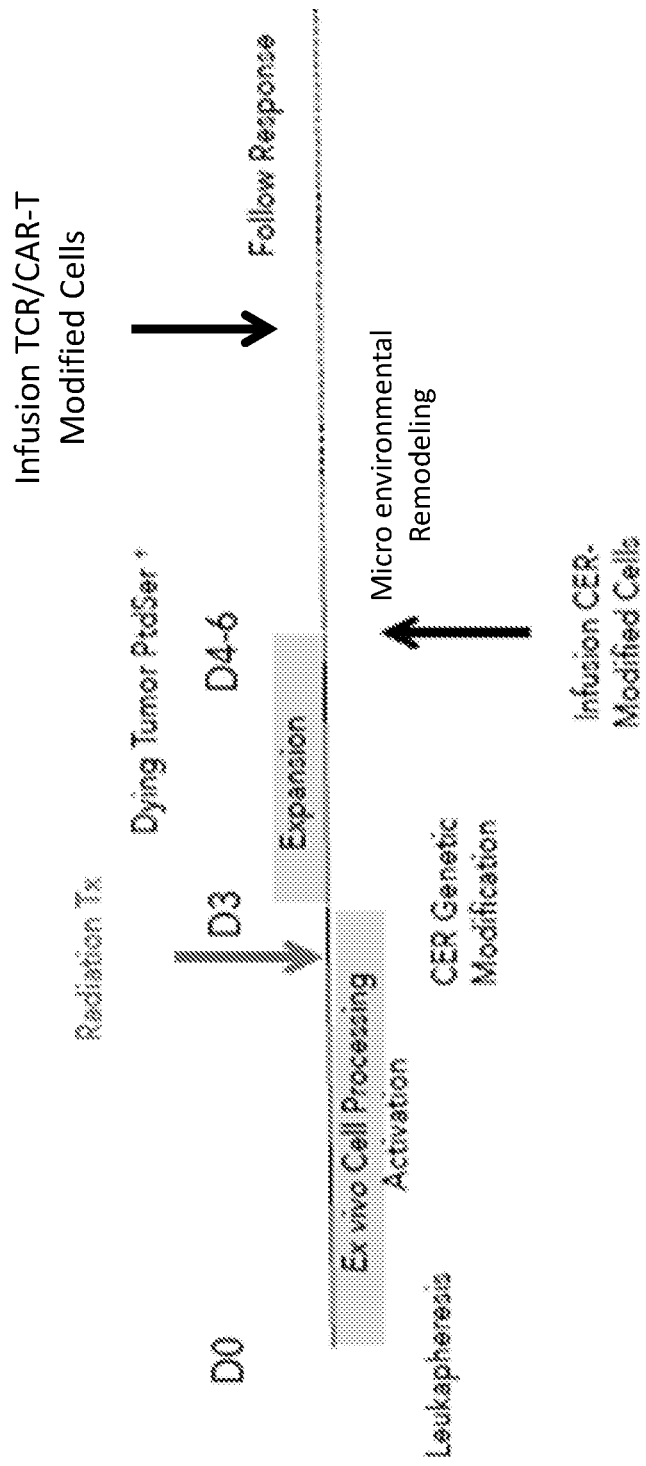
FIG. 5 shows an illustrative triple combination treatment timeline comprising radiation therapy, CER immunotherapy (e.g., targeting phosphatidylserine expressing cells), followed by TCR or CAR immunotherapy.

An example of a triple combination therapy (radiation+CER+CAR/or TCR) regimen is shown in FIG. 5. Following radiation therapy, tumor antigen specific, CER modified host cells (e.g., comprising a binding domain that binds to a tumor antigen) according to the present disclosure are administered to a subject to promote an anti-tumor immune response and recruit immune activating cells into the tumor microenvironment. In certain embodiments, CERs traffic to local, irradiated tumors and render the tumor tissue permissive for immune infiltration and destruction (e.g., via expression of inflammatory cytokines, activation of effector T cells, activation of dendritic cells, inhibition of regulatory T cells), thereby sensitizing the tumor microenvironment for subsequent adoptive T cell immunotherapy (e.g., CAR or TCR immunotherapy). In certain embodiments, the CER modified cells are administered 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days after administration of the radiation therapy. In further embodiments, the CER modified cells are administered within 4 weeks, within 3 weeks, within 2 weeks, or within 1 week after administration of the radiation therapy. In certain embodiments, the CAR or TCR immunotherapy is administered 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days after administration of the CER therapy or within 4 weeks, within 3 weeks, within 2 weeks, or within 1 week after administration of the CER therapy. In certain embodiments, the radiation therapy, the CAR or TCR immunotherapy, or both are administered at subtherapeutic levels.

Examples of radiation therapy that may be used in combination with CER therapy include external beam radiation therapy (e.g., conventional external beam radiation therapy, stereotactic radiation, 3-dimensional conformal radiation therapy, intensity-modulated radiation therapy, volumetric modulated arc therapy, particle therapy, proton therapy, auger therapy), brachytherapy, systemic radioisotope therapy, intraoperative radiotherapy, or any combination thereof. In certain embodiments, a lower or dose of radiation therapy than the typical dose or a subtherapeutic dose is used in combination with CER therapy. Low or subtherapeutic dose radiation therapy may be sufficient to cause sub-lytic membrane damage to the cells but not necessarily be cytolytic. The sub-lytic membrane damage is sufficient to expose pro-engulfment markers (e.g., phosphatidylserine) that can be targeted by CER therapy.

Examples of immune checkpoint molecules that may be targeted in combination with CER therapy include PD-L1, PD-L2, CD80, CD86, B7-H3, B7-H4, HVEM, adenosine, GALS, VISTA, CEACAM-1, CEACAM-3, CEACAM-5, PVRL2, PD-1, CTLA-4, BTLA, KIR, LAG3, TIM3, A2aR, CD244/2B4, CD160, TIGIT, LAIR-1, PVRIG/CD112R, or any combination thereof. In certain embodiments, an immune checkpoint molecule inhibitor is an antibody, a peptide, an RNAi agent, or a small molecule. An antibody specific for CTLA-4 may be ipilimumab or tremelimumab. An antibody specific for PD-1 may be pidilizumab, nivolumab, or pembrolizumab. An antibody specific for PD-L1 may be durvalumab, atezolizumab, or avelumab.

A chemotherapeutic includes non-specific cytotoxic agents that inhibit mitosis or cell division, as well as molecularly targeted therapy that blocks the growth and spread of cancer cells by targeting specific molecules that are involved in tumor growth, progression, and metastasis (e.g., oncogenes). Exemplary non-specific chemotherapeutics include an alkylating agent, a platinum based agent, a cytotoxic agent, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Examples of chemotherapeutic agents considered for use in combination therapies include vemurafenib, dabrafenib, trametinib, cobimetinib, anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

Exemplary alkylating agents include nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexalen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), and Dacarbazine (DTIC-Dome®). Additional exemplary alkylating agents include, without limitation, Oxaliplatin (Eloxatin®); Temozolomide (Temodar® and Temodal®); Dactinomycin (also known as actinomycin-D, Cosmegen®); Melphalan (also known as L-PAM, L-sarcolysin, and phenylalanine mustard, Alkeran®); Altretamine (also known as hexamethylmelamine (HMM), Hexalen®); Carmustine (BiCNU®); Bendamustine (Treanda®); Busulfan (Busulfex® and Myleran®); Carboplatin (Paraplatin®); Lomustine (also known as CCNU, CeeNU®); Cisplatin (also known as CDDP, Platinol® and Platinol®-AQ); Chlorambucil (Leukeran®); Cyclophosphamide (Cytoxan® and Neosar®); Dacarbazine (also known as DTIC, DIC and imidazole carboxamide, DTIC-Dome®); Altretamine (also known as hexamethylmelamine (HMM), Hexalen®); Ifosfamide (Ifex®); Prednumustine; Procarbazine (Matulane®); Mechlorethamine (also known as nitrogen mustard, mustine and mechloroethamine hydrochloride, Mustargen®); Streptozocin (Zanosar®); Thiotepa (also known as thiophosphoamide, TESPA and TSPA, Thioplex®); Cyclophosphamide (Endoxan®, Cytoxan®, Neosar®, Procytox®, Revimmune®); and Bendamustine HCl (Treanda®).

Exemplary platinum based agents include carboplatin, cisplatin, oxaliplatin, nedaplatin, picoplatin, satraplatin, phenanthriplatin, and triplatin tetranitrate.

Exemplary angiogenesis inhibitors include, without limitation A6 (Angstrom Pharmaceuticals), ABT-510 (Abbott Laboratories), ABT-627 (Atrasentan) (Abbott Laboratories/Xinlay), ABT-869 (Abbott Laboratories), Actimid (CC4047, Pomalidomide) (Celgene Corporation), AdGVPEDF.11D (GenVec), ADH-1 (Exherin) (Adherex Technologies), AEE788 (Novartis), AG-013736 (Axitinib) (Pfizer), AG3340 (Prinomastat) (Agouron Pharmaceuticals), AGX1053 (AngioGenex), AGX51 (AngioGenex), ALN-VSP (ALN-VSP 02) (Alnylam Pharmaceuticals), AMG 386 (Amgen), AMG706 (Amgen), Apatinib (YN968D1) (Jiangsu Hengrui Medicine), AP23573 (Ridaforolimus/MK8669) (Ariad Pharmaceuticals), AQ4N (Novavea), ARQ 197 (ArQule), ASA404 (Novartis/Antisoma), Atiprimod (Callisto Pharmaceuticals), ATN-161 (Attenuon), AV-412 (Aveo Pharmaceuticals), AV-951 (Aveo Pharmaceuticals), Avastin (Bevacizumab) (Genentech), AZD2171 (Cediranib/Recentin) (AstraZeneca), BAY 57-9352 (Telatinib) (Bayer), BEZ235 (Novartis), BIBF1120 (Boehringer Ingelheim Pharmaceuticals), BIBW 2992 (Boehringer Ingelheim Pharmaceuticals), BMS-275291 (Bristol-Myers Squibb), BMS-582664 (Brivanib) (Bristol-Myers Squibb), BMS-690514 (Bristol-Myers Squibb), Calcitriol, CCI-779 (Torisel) (Wyeth), CDP-791 (ImClone Systems), Ceflatonin (Homoharringtonine/HHT) (ChemGenex Therapeutics), Celebrex (Celecoxib) (Pfizer), CEP-7055 (Cephalon/Sanofi), CHIR-265 (Chiron Corporation), NGR-TNF, COL-3 (Metastat) (Collagenex Pharmaceuticals), Combretastatin (Oxigene), CP-751,871(Figitumumab) (Pfizer), CP-547,632 (Pfizer), CS-7017 (Daiichi Sankyo Pharma), CT-322 (Angiocept) (Adnexus), Curcumin, Dalteparin (Fragmin) (Pfizer), Disulfiram (Antabuse), E7820 (Eisai Limited), E7080 (Eisai Limited), EMD 121974 (Cilengitide) (EMD Pharmaceuticals), ENMD-1198 (EntreMed), ENMD-2076 (EntreMed), Endostar (Simcere), Erbitux (ImClone/Bristol-Myers Squibb), EZN-2208 (Enzon Pharmaceuticals), EZN-2968 (Enzon Pharmaceuticals), GC1008 (Genzyme), Genistein, GSK1363089 (Foretinib) (GlaxoSmithKline), GW786034 (Pazopanib) (GlaxoSmithKline), GT-111 (Vascular Biogenics Ltd.), IMC-1121B (Ramucirumab) (ImClone Systems), IMC-18F1 (ImClone Systems), IMC-3G3 (ImClone LLC), INCB007839 (Incyte Corporation), INGN 241 (Introgen Therapeutics), Iressa (ZD1839/Gefitinib), LBH589 (Faridak/Panobinostst) (Novartis), Lucentis (Ranibizumab) (Genentech/Novartis), LY317615 (Enzastaurin) (Eli Lilly and Company), Macugen (Pegaptanib) (Pfizer), MEDI522 (Abegrin) (MedImmune), MLN518 (Tandutinib) (Millennium), Neovastat (AE941/Benefin) (Aeterna Zentaris), Nexavar (Bayer/Onyx), NM-3 (Genzyme Corporation), Noscapine (Cougar Biotechnology), NPI-2358 (Nereus Pharmaceuticals), OSI-930 (OSI), Palomid 529 (Paloma Pharmaceuticals, Inc.), Panzem Capsules (2ME2) (EntreMed), Panzem NCD (2ME2) (EntreMed), PF-02341066 (Pfizer), PF-04554878 (Pfizer), PI-88 (Progen Industries/Medigen Biotechnology), PKC412 (Novartis), Polyphenon E (Green Tea Extract) (Polypheno E International, Inc.), PPI-2458 (Praecis Pharmaceuticals), PTC299 (PTC Therapeutics), PTK787 (Vatalanib) (Novartis), PXD101 (Belinostat) (CuraGen Corporation), RAD001 (Everolimus) (Novartis), RAF265 (Novartis), Regorafenib (BAY73-4506) (Bayer), Revlimid (Celgene), Retaane (Alcon Research), SN38 (Liposomal) (Neopharm), SNS-032 (BMS-387032) (Sunesis), SOM230 (Pasireotide) (Novartis), Squalamine (Genaera), Suramin, Sutent (Pfizer), Tarceva (Genentech), TB-403 (Thrombogenics), Tempostatin (Collard Biopharmaceuticals), Tetrathiomolybdate (Sigma-Aldrich), TG100801 (TargeGen), Thalidomide (Celgene Corporation), Tinzaparin Sodium, TKI258 (Novartis), TRC093 (Tracon Pharmaceuticals Inc.), VEGF Trap (Aflibercept) (Regeneron Pharmaceuticals), VEGF Trap-Eye (Regeneron Pharmaceuticals), Veglin (VasGene Therapeutics), Bortezomib (Millennium), XL184 (Exelixis), XL647 (Exelixis), XL784 (Exelixis), XL820 (Exelixis), XL999 (Exelixis), ZD6474 (AstraZeneca), Vorinostat (Merck), and Z STK474.

Exemplary molecularly targeted inhibitors include angiogenesis inhibitors (e.g., a VEGF pathway inhibitors), tyrosine kinase inhibitors (e.g., an EGF pathway inhibitors), receptor tyrosine kinase inhibitors, growth factor inhibitors, GTPase inhibitors, serine/threonine kinase inhibitors, transcription factor inhibitors, BRaf inhibitors, MEK inhibitors, mTOR inhibitors, EGFR inhibitors, ALK inhibitors, ROS1 inhibitors, BCL-2 inhibitors, PI3K inhibitors, VEGFR inhibitors, BCR-ABL inhibitors, MET inhibitors, MYC inhibitors, ABL inhibitors, HER2 inhibitors, BTK inhibitors, H-RAS inhibitors, K-RAS inhibitors, and PDGFR inhibitors. In certain embodiments, use of molecularly targeted therapy comprises administering a molecularly targeted therapy specific for the molecular target to a subject identified as having a tumor that possesses the molecular target (e.g., driver oncogene). In certain embodiments, the molecular target has an activating mutation. In certain embodiments, use of CER modified cells in combination with a molecularly targeted inhibitor increases the magnitude of anti-tumor response, the durability of anti-tumor response, or both. In certain embodiments, a lower than typical dose or a subtherapeutic dose of molecularly targeted therapy is used in combination with CER modified cells.

Exemplary Vascular Endothelial Growth Factor (VEGF) receptor inhibitors include, but are not limited to, Bevacizumab (Avastin®), axitinib (Inlyta®); Brivanib alaninate (BMS-582664, (S)—((R)-1-(4-(4-Fluoro-2-methyl-1H-indol-5-yloxy)-5-methylpyrrolo[2,14][1,2,4]triazin-6-yloxy) propan-2-yl)2-aminopropanoate); Sorafenib (Nexavar®); Pazopanib (Votrient®); Sunitinib malate (Sutent®); Cediranib (AZD2171, CAS 288383-20-1); Vargatef (BIBF1120, CAS 928326-83-4); Foretinib (GSK1363089); Telatinib (BAY57-9352, CAS 332012-40-5); Apatinib (YN968D1, CAS 811803-05-1); Imatinib (Gleevec®); Ponatinib (AP24534, CAS 943319-70-8); Tivozanib (AV951, CAS 475108-18-0); Regorafenib (BAY73-4506, CAS 755037-03-7); Vatalanib dihydrochloride (PTK787, CAS 212141-51-0); Brivanib (BMS-540215, CAS 649735-46-6); Vandetanib (Caprelsa® or AZD6474); Motesanib diphosphate (AMG706, CAS 857876-30-3, N-(2,3-dihydro-3,3-dimethyl-1H-indol-6-yl)-2-[(4-pyridinylmethyl)amino]-3-pyridinecarboxamide, described in PCT Publication No. WO 02/066470); Dovitinib dilactic acid (TKI258, CAS 852433-84-2); Linfanib (ABT869, CAS 796967-16-3); Cabozantinib (XL184, CAS 849217-68-1); Lestaurtinib (CAS 111358-88-4); N[5-[[[5-(1,1-Dimethylethyl)-2-oxazolyl] methyl]thio]-2-thiazolyl]-4-piperidinecarboxamide (BMS38703, CAS 345627-80-7); (3R,4R)-4-Amino-1-((4-((3-methoxyphenyl)amino)pyrrolo[2,1-f][1,2,4]triazin-5-yl) methyl)piperidin-3-ol (BMS690514); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); 4-Methyl-3-[[1-methyl-6-(3-pyridinyl)-1H-pyrazolo[3,4-d]pyrimidin-4-yl]amino]-N-[3-(trifluoromethyl)phenyl]-benzamide (BHG712, CAS 940310-85-0); and Aflibercept (Eylea®).

Exemplary EGF pathway inhibitors include, without limitation tyrphostin 46, EKB-569, erlotinib (Tarceva®), gefitinib (Iressa®), erbitux, nimotuzumab, lapatinib (Tykerb®), cetuximab (anti-EGFR mAb), $^{188}$Re-labeled nimotuzumab (anti-EGFR mAb), and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980. Exemplary EGFR antibodies include, but are not limited to, Cetuximab (Erbitux®); Panitumumab (Vectibix®); Matuzumab (EMD-72000); Trastuzumab (Herceptin®); Nimotuzumab (hR3); Zalutumumab; TheraCIM h-R3; MDX0447 (CAS 339151-96-1); and ch806 (mAb-806, CAS 946414-09-1). Exemplary Epidermal growth factor receptor (EGFR) inhibitors include, but are not limited to, Erlotinib hydrochloride (Tarceva®); brigatinib; osimeritinib; icotinib; Gefitnib (Iressa®); N-[4-[(3-Chloro-4-fluorophenyl)amino]-7-[[(3"S")-tetrahydro-3-furanyl]oxy]-6-quinazolinyl]-4(dimethylamino)-2-butenamide, Tovok®); Vandetanib (Caprelsa®); Lapatinib (Tykerb®); (3R,4R)-4-Amino-1-((4-((3-methoxyphenyl)amino)pyrrolo[2,1-f][1,2,4]triazin-5-yl)methyl)piperidin-3-ol (BMS690514); Canertinib dihydrochloride (CI-1033); 644-[(4-Ethyl-I-piperazinyl)methyl]phenyl]-N-[(1R)-1-phenylethyl]-7H-Pyrrolo[2,3-d]pyrimidin-4-amine (AEE788, CAS 497839-62-0); Mubritinib (TAK165); Pelitinib (EKB569); Afatinib (BIBW2992); Neratinib (HKI-272); N-[44[1-[(3-Fluorophenyl)methyl]-1H-indazol-5-yl]amino]-5-methylpyrrolo[2,1-f][1,2,4]triazin-6-yl]-carbamic acid, (3S)-3-morpholinylmethyl ester (BMS599626); N-(3,4-Dichloro-2-fluorophenyl)-6-methoxy-7-[[(3aα,5β,6aα)-octahydro-2-methylcyclopenta[c]pyrrol-5-yl]methoxy]-4-quinazolinamine (XL647, CAS 781613-23-8); and 4-[4-[[(1R)-1-Phenylethyl]amino]-7H-pyrrolo[2,3-d]pyrimidin-6-yl]-phenol (PKI166, CAS 187724-61-4).

Exemplary mTOR inhibitors include, without limitation, rapamycin (Rapamune®), and analogs and derivatives thereof; SDZ-RAD; Temsirolimus (Torisel®; also known as CCI-779); Ridaforolimus (formally known as deferolimus, (1R,2R,4S)-4-[(2R)-2 [(1R,9S,12 S,15R,16E,18R,19R,21R, 23 S,24E,26E,28Z,30S,32 S,35R)-1,18-dihydroxy-19,30-dimethoxy-15,17,21,23,29,35-hexamethyl-2,3,10,14,20-pentaoxo-11,36-dioxa azatricyclo[30.3.1.04'9]hexatriaconta-16, 24,26,28-tetraen-12-yl]propyl]methoxycyclohexyl dimethylphosphinate, also known as AP23573 and MK8669, and described in PCT Publication No. WO03/064383); Everolimus (Afinitor® or RAD001); Rapamycin (AY22989, Sirolimus®); Simapimod (CAS 164301-51-3); (5-{2,4-Bi s[(3 S)-3-methylmorpholin-4-yl]pyrido[2,3-d] pyrimidin-7-yl}-2-methoxyphenyl)methanol (AZD8055); 2-Amino-8-[trans-4-(2-hydroxyethoxy)cyclohexyl]-6-(6-methoxy-3-pyridinyl)-4-methyl-pyrido[2,3-d]pyrimidin-7 (8H)-one (PF04691502, CAS 1013101-36-4); and N$^2$41,4-dioxo-[[4-(4-oxo-8-phenyl-4H-1-benzopyran-2-yl) morpholinium-4-yl]methoxy]butylR-arginylglycyl-L-α-aspartylL-serine-, inner salt (SF1126, CAS 936487-67-1).

Exemplary Phosphoinositide 3-kinase (PI3K) inhibitors include, but are not limited to, 4[2-(1H-Indazol-4-yl)-64[4-(methylsulfonyl)piperazin-1-yl]methyl]thieno[3,2-d]pyrimidin-4-yl]morpholine (also known as GDC 0941 and described in PCT Publication Nos. WO09/036082 and WO09/055730); 2-Methyl-2-[4-[3-methyl-2-oxo-8-(quinolin-3-yl)-2,3-dihydroimidazo[4,5-c]quinolin-1-yl]phenyl] propionitrile (also known as BEZ 235 or NVP-BEZ 235, and described in PCT Publication No. WO06/122806); 4-(trifluoromethyl)-5-(2,6-dimorpholinopyrimidin-4-yl)pyridin-2-amine (also known as BKM120 or NVP-BKM120, and described in PCT Publication No. WO2007/084786); Tozasertib (VX680 or MK-0457, CAS 639089-54-6); (5Z)-5-[[4-(4-Pyridinyl)-6-quinolinyl]methylene]-2,4-thiazolidin-edione (GSK1059615, CAS 958852-01-2); (1E,4S,4aR,5R, 6aS,9aR)-5-(Acetyloxy)-1-[(di-2-propenylamino) methylene]-4,4a,5,6,6a,8,9,9a-octahydro-11-hydroxy-4-(methoxymethyl)-4a,6a-dimethyl-cyclopenta[5,6]naphtho [1,2-c]pyran-2,7,10(1H)-trione (PX866, CAS 502632-66-8); and 8-Phenyl-2-(morpholin-4-yl)-chromen-4-one (LY294002, CAS 154447-36-6). Exemplary Protein Kinase B (PKB) or AKT inhibitors include, but are not limited to. 8-[4-(1-Aminocyclobutyl)phenyl]phenyl-1,2,4-triazolo[3,4-f][1,6]naphthyridin-3(2H)-one (MK-2206, CAS 1032349 1); Perifosine (KRX0401); 4-Dodecyl-N-1,3,4-thiadiazol-2-yl-benzenesulfonamide (PHT-427, CAS 1191951-57-1); 4-[2-(4-Amino-1,2,5-oxadiazol-3-yl)-1-ethyl-7-[(3S)-3-piperidinylmethoxy]-1H-imidazo[4,5-c]pyridin-4-yl]-2-methyl-3-butyn-2-ol (GSK690693, CAS 937174-76-0); 8-(1-Hydroxyethyl)-2-methoxy-3-[(4-methoxyphenyl) methoxy]-6H-dibenzo[b,d]pyran-6-one (palomid 529, P529, or SG-00529); Tricirbine (6-Amino-4-methyl-8-((3-D-ribofuranosyl)-4H,8H-pyrrolo[4,3,2-de]pyrimido[4,5-c]pyridazine); (αS)-α-[[[5-(3-Methyl-1H-indazol-5-yl)-3-pyridinyl]oxy]methyl]-benzeneethanamine (A674563, CAS 552325-73-2); 4-[(4-Chlorophenyl)methyl]-1-(7H-pyrrolo[2,3-d]pyrimidin-4-yl)-4-piperidinamine (CCT128930, CAS 885499-61-6); 4-(4-Chlorophenyl)-4-[4-(1H pyrazol-4-yl)phenyl]-piperidine (AT7867, CAS 857531-00-1); and Archexin (RX-0201, CAS 663232-27-7).

In certain embodiments, a tyrosine kinase inhibitor used in combination with CER modified cells is an anaplastic lymphoma kinase (ALK) inhibitor. Exemplary ALK inhibitors include crizotinib, ceritinib, alectinib, brigatinib, dalantercept, entrectinib, and lorlatinib.

Figure 3:
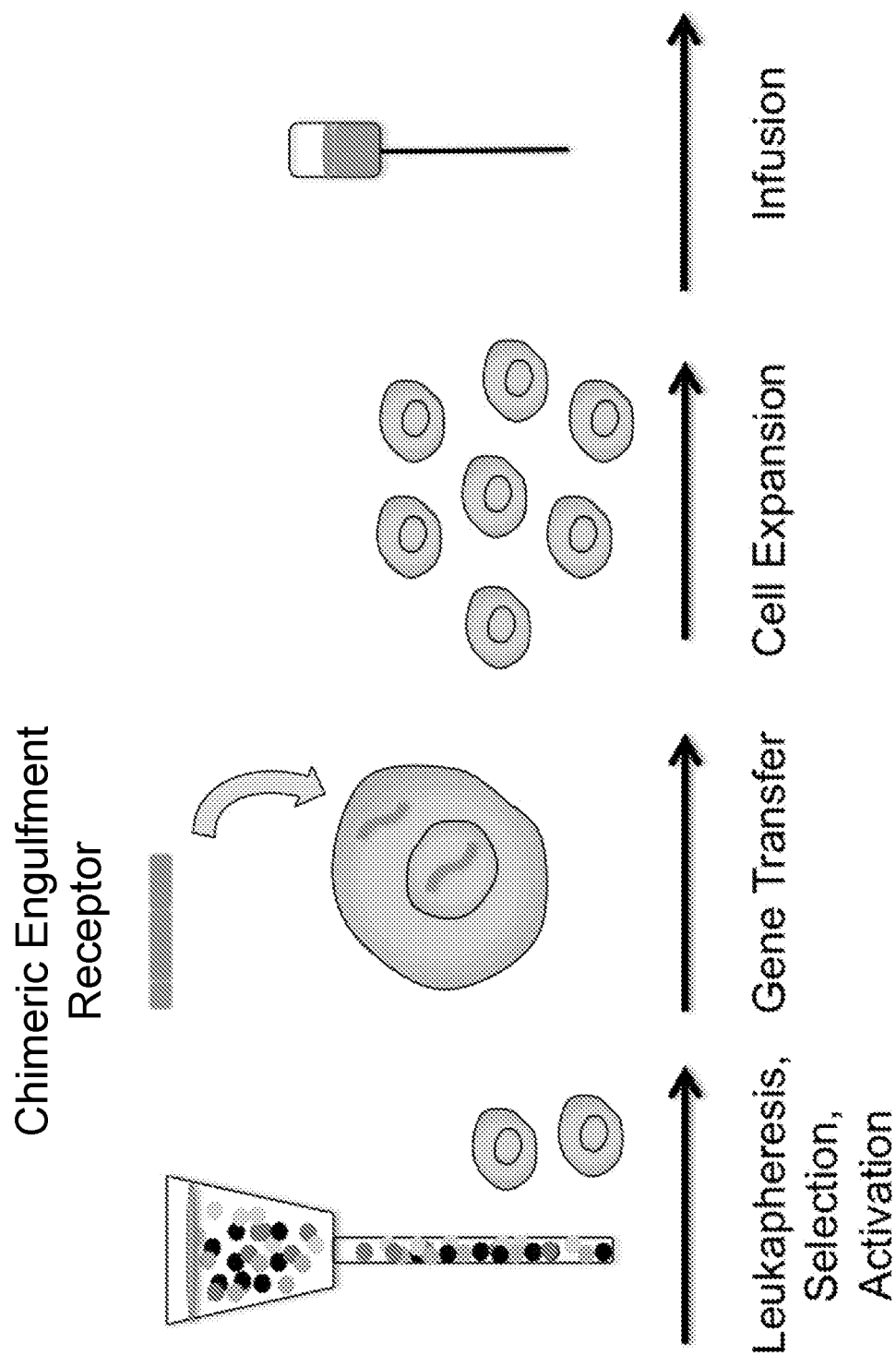
FIG. 3 shows an illustrative method of administration of the CERs of the present disclosure.

FIGS. 3-5 illustrate embodiments of regimens that utilize CER modified cells. As shown in FIGS. 3 and 4A, following leukapheresis, cells can be processed and activated ex vivo, undergoing genetic modification and expansion in preparation for infusion into a subject. FIG. 4B shows an illustrative treatment scheme for CER-modified cells used in combination with conventional T cell based therapies (e.g., CAR or TCR). An initial infusion of engineered T cells induces tumor cell apoptosis indicative of an anti-tumor effect. CER modified cells are then infused. The CER modified cells clear tumor cells displaying a pro-engulfment (e.g., PtdSer), which facilitates tumor regression while also bypassing the T cell suppressive tumor microenvironment. Alteration of the tumor microenvironment then re-sensitizes the tumor to T cell therapy, allowing a second infusion of T cells. Another embodiment of a therapeutic method is shown in FIG. 4C. The treatment scheme shown in FIG. 4C utilizes CER modified cells in combination with a monoclonal antibody therapy. Infusion of tumor-specific antibodies, such as Cetuximab targeting EGFR or Rituximab targeting CD20 may trigger cell death or induce a targeting moiety that is bound by CER modified cells. Subsequently, a subject receives CER modified cells that bind to and clear antibody bound cells. In such an embodiment, the CER extracellular domain may include an FcR binding domain, a PtdSer binding domain, or other antigen binding domain.

In another scenario, a CER modified cell can be combined with small molecule inhibitors such as a BTK inhibitor, a MEK inhibitor, an adenosine pathway inhibitor A2AR antagonist, an IDO1 inhibitor, IMiDs such as Lenalidomide, PI3K6 inhibitors, a BRAF inhibitor, or a BCR-ABL inhibitor.

In certain embodiments, methods of the present disclosure include a depletion step. A depletion step to remove CERs from the subject may occur after a sufficient amount of time for therapeutic benefit in order to mitigate toxicity to a subject. In such embodiments, the CER vector includes an inducible suicide gene, such as iCASP9, inducible Fas, or HSV-TK. Similarly, a CER vector may be designed for expression of a known cell surface antigen such as CD20 or truncated EGFR (SEQ ID NO:105) that facilitates depletion of transduced cells through infusion of an associated monoclonal antibody (mAb), for example, Rituximab for CD20 or Cetuximab for EGFR. Alemtuzumab, which targets CD52 present on the surface of mature lymphocytes, may also be used to deplete transduced B cells, T cells, or natural killer cells.

In further embodiments, cells expressing CER of the instant disclosure may be used in diagnostic methods or imaging methods, including methods used in relation to the indications or conditions identified herein.

Example 1

Construction of Tim4-Tlr4 Cer "Cer05"

The extracellular domain of the phosphatidylserine binding protein Tim4 (encoding amino acid sequence of SEQ ID NO:106), including the signal peptide (amino acids 1-22 of SEQ ID NO:106) and transmembrane domain (encoding amino acid sequence of SEQ ID NO:108), were fused to the intracellular signaling domain of the TLR4 (encoding amino acid sequence of SEQ ID NO:51) to create a chimeric engulfment receptor "CER05" (Tim4-TLR CER having an amino acid sequence of SEQ ID NO:81). The TLR4 signaling domain transduces a signal for engulfment, and Tim4 is a phosphatidylserine binding receptor. The Tim4-TLR4 (CER05) chimeric engulfment receptor nucleotide sequence was then inserted into the pLenti lentiviral vector along with truncated EGFR (EGFRt or tEGFR) (encoding amino acid sequence of SEQ ID NO:105) as a transduction marker, separated by T2A sequence (see, FIG. 6). Murine Ba/F3 B-cells were cultured in RMPI 1640 media supplemented with 10% fetal bovine serum, 1% penicillin-streptomycin, and 10 ng/mL murine IL-3 (Peprotech Catalog #213-13) in a 12 well plate at a density of 0.5 million cells/ml. Under normal conditions, the Ba/F3 murine B-cell line lacks the capacity to engulf target cells and was therefore selected to establish an assay system for engulfment. To transduce Ba/F3 cells, 100µl of viral vector expressing Tim4-TLR4 (CER05) and 5µl TRANSDUX™ transduction reagent were diluted in 0.5 ml Complete Cell Growth Media and added to the Ba/F3 cells. The Ba/F3 cells were then centrifuged at 270×g rpm for 1 hour in a 32° C. pre-warmed centrifuge. The Ba/F3 cells were incubated for 24 hours at 37° C. Ba/F3 cells were expanded for another 48 hours in Complete Cell Growth Media. Positive Ba/F3 cell transductants were sorted using fluorescence activated cell sorting (FACs) (Sony Sorter SH800) by either staining with a labeled EGFR-specific antibody (Cetuximab). Post sorting, purified, transduced Ba/F3 cells comprising the Tim4-TLR4-T2A-transduction marker containing viral vector were rested for 48 hours prior to being utilized for phagocytic assays.

Phagocytic Activity Against Primary Apoptotic Thymocytes

One day prior to phagocytic assay, primary thymocytes were isolated from a C3H mouse (Charles River Laboratories International, Inc.). Thymocytes were cultured in complete RPMI 1640 growth media supplemented with 10% fetal bovine serum and 1% penicillin-streptomycin in a 6-well plate. To induce apoptosis and phosphatidylserine expression on the cell surface, thymocytes were treated with 1 µM dexamethansone for 24 hours. Untreated thymocytes were used as a negative control. Thymocytes were collected from the 6-well plates, washed once with sterile 1X PBS, and then stained with 1 ng/µl pH sensitive pHrodo™ Red dye (ThermoFisher Scientific, Catalog #P36600) in PBS at room temperature for 15 minutes. Labeling target cells with pHrodo Red dye permits visualization of cells that are engulfed and transported into lysosomes due to their increased light emission in the acidic lysosomal environment (Miksa et al., 2009, Immunol. Methods 342:71-7). The cells were then supplemented with growth media and washed one more time to remove any excess pHrodo Red. pHrodo Red stained thymocytes were plated on a flat bottom 96 well plate at 250,000 cells/well in RMPI 1640 complete media.

Ba/F3 CER01$^+$tEGFR$^+$ cells made as described above were washed once with 1×PBS and stained with 1 µM CELLTRACE™ Violet dye (ThermoFisher Scientific, Catalog #C34557) in PBS for 10 minutes at 37° C. Stained, transduced Ba/F3 cells were supplemented with growth media, washed once with 1×PBS to remove excess CELL-TRACE™ Violet, and plated on the same flat bottom 96 well plate at approximately 25,000 cells/well in RPMI 1640 complete media.

Figure 7:
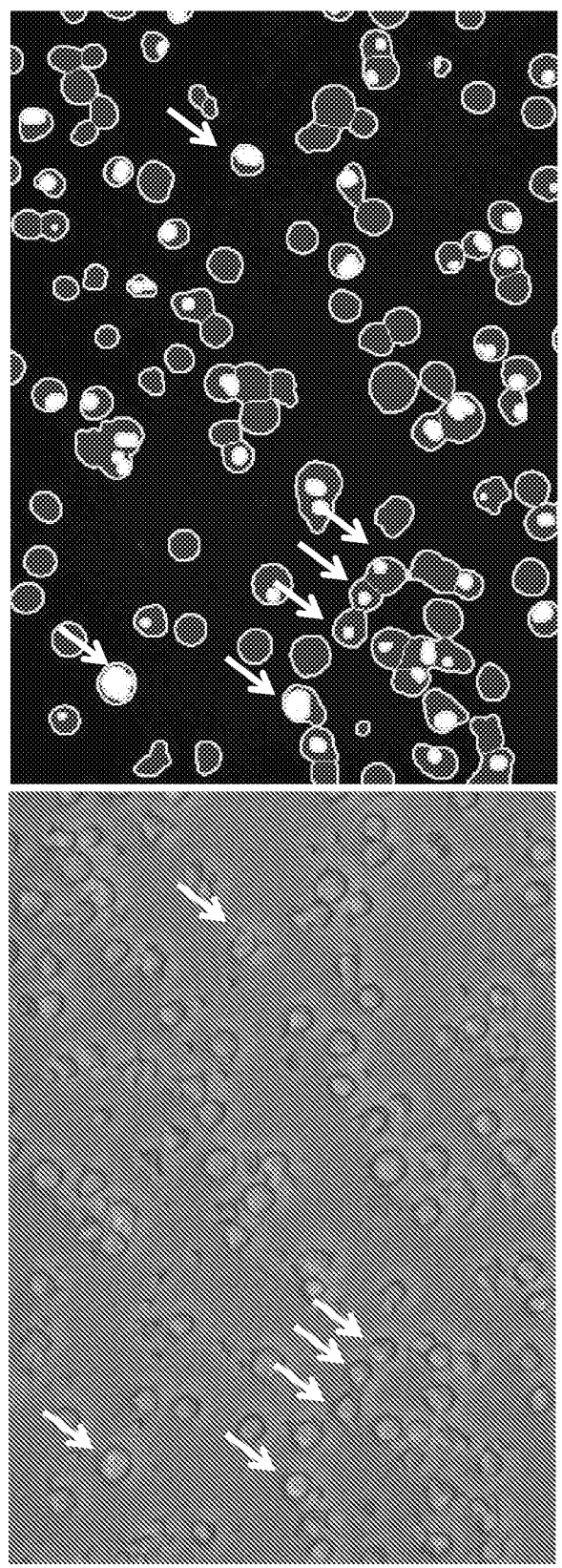
FIG. 7 show fluorescence microscope images of in vitro engulfment of dexamethasone treated thymocytes by CER05+Ba/F3 cells. White arrows indicate phagocytosis events. The image on the right is was created by automated software using the image on the left, with the CER05+Ba/F3 cells outlined in blue and the engulfed target cells shown in white.

Target thymocytes were co-cultured with stained, Ba/F3 CER05+ cells at a ratio of 10:1 (target cell: effector cell) for 3 hours or overnight (~14 hours) at 37° C. After incubation, the plate was centrifuged and the media replaced with PBS supplemented with 2% fetal bovine serum, pH 9. The 96 well plate was then viewed using KEYENCE BZ-X710 fluorescence microscope, 20X objective. Ba/F3 cells transduced with pLenti vector expressing truncated EGFR were used as a negative control. Fluorescent microscopy showed that CER05+Ba/F3 cells engulf dexamethasone-treated thymocytes (white arrows indicate engulfment events) (see, FIG. 7).

Figure 8:
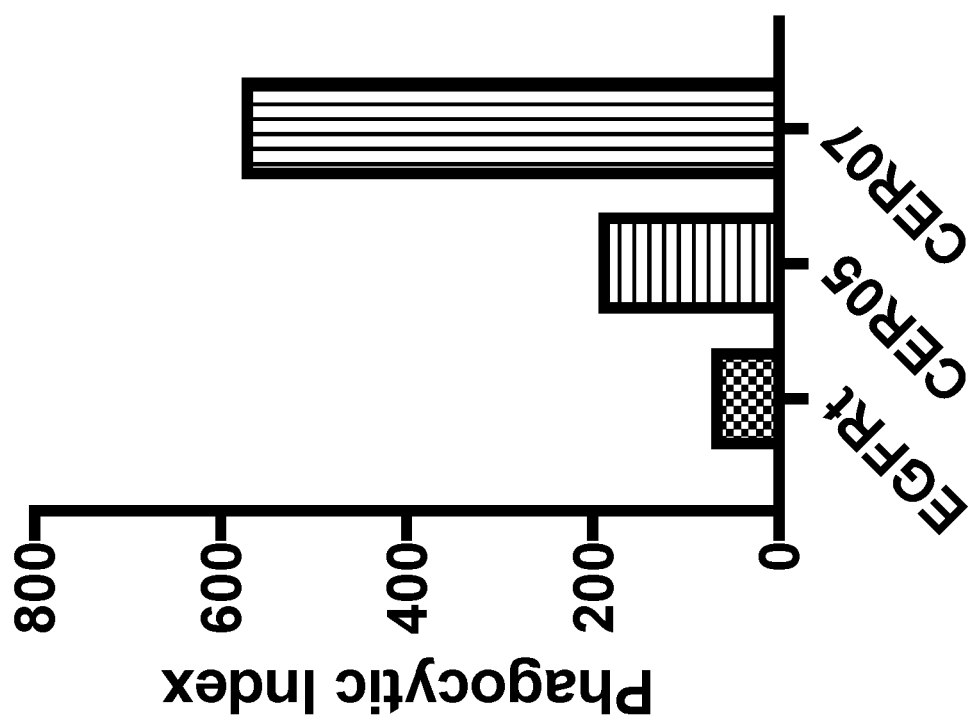
FIG. 8 shows a bar graph of phagocytic index of CER05+, CER07+, or control EGFRt+Ba/F3 cells that were co-cultured with dexamethasone treated thymocytes.

A phagocytic index was calculated by multiplying [mean of total number of engulfed target cells/total number of counted CER modified cells (e.g., phagocytic frequency)] by [average area of target cell staining per CER+Ba/F3 cell x 100 (e.g., hybrid capture)] as compared to control EGFRt+ Ba/F3 cells (see, FIG. 8).

Figure 9:
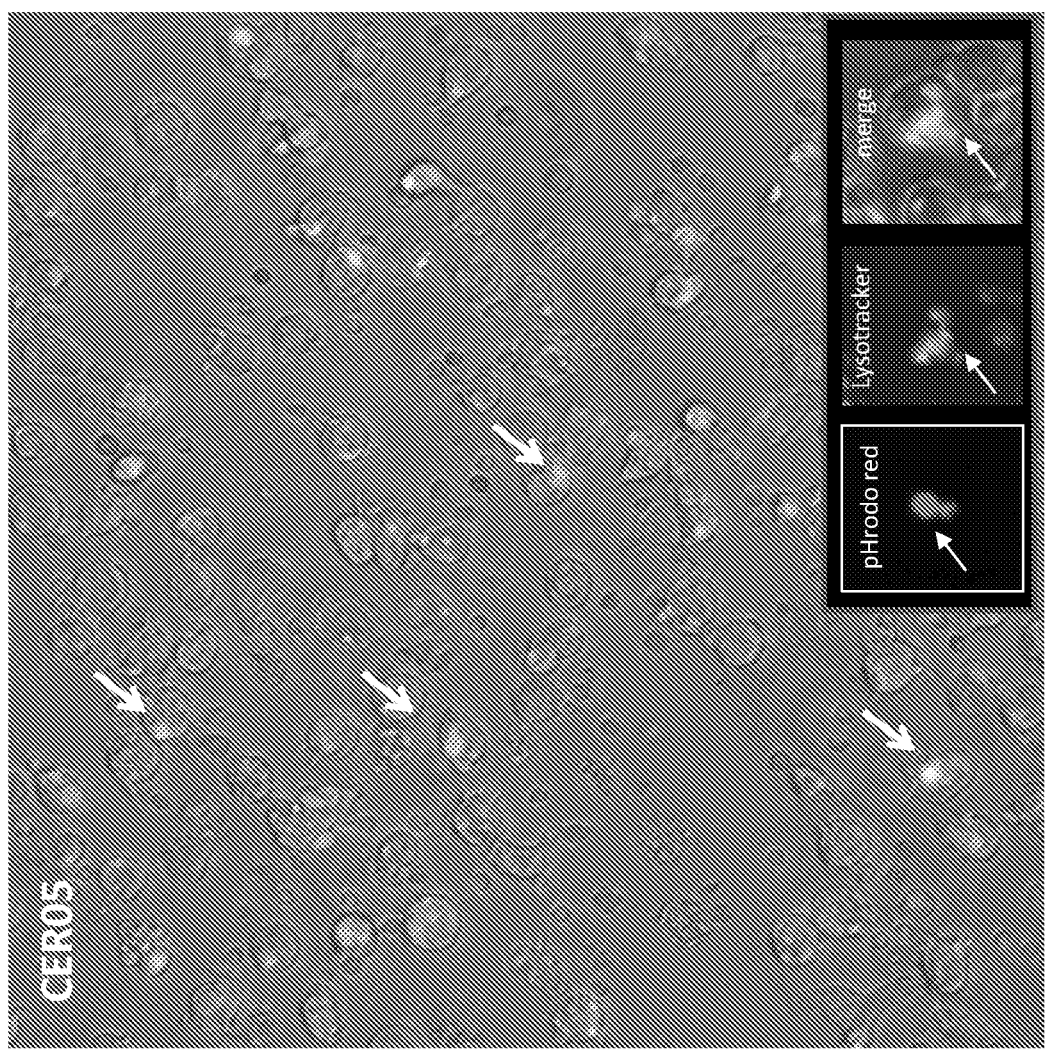
FIG. 9 shows fluorescence microscope image of co-localization of engulfed thymocytes and Lysotracker green signal in CER05+Ba/F3 cells. White arrows indicate co-localization of pHrodo red labeled thymocytes and acidic compartments stained with LysoTracker green.
Figure 10:
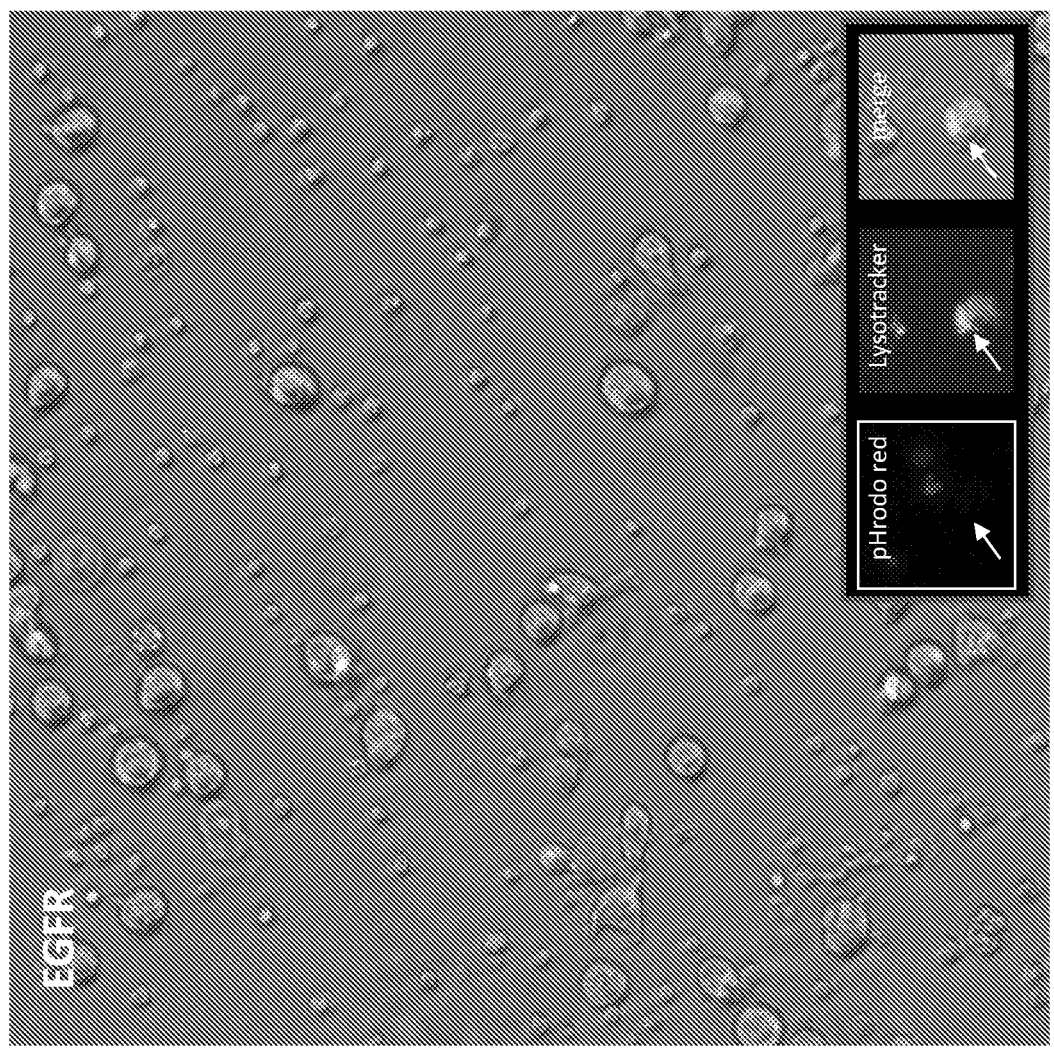
FIG. 10 shows fluorescence microscope image of co-localization of engulfed pHrodo red labeled thymocytes and acidic compartments stained with Lysotracker green signal in control tEGFR+Ba/F3 cells. No co-localization is observed in this image.

A duplicate plate of co-cultured Ba/F3 CER05+ cells and dexamethasone treated thymocytes was incubated for 6 hours in media containing IL-3. 50 nM LysoTracker green, which stains acidic compartments in live cells green (e.g., lysosomes) was added 5 minutes prior to the end of incubation period. Co-localization of internalized pHrodo red labeled thymocytes with LysoTracker green vesicles can be visualized by the overlay of these 2 images. Co-localization of red and green fluorescence gives rise to yellow/orange fluorescence in the merged images, indicating pHrodo-labeled target cells have been internalized into lysosomes, leading to rapid acidification and killing of the ingested cell (see, FIG. 9; white arrows indicate co-localization of pHrodo red labeled thymocytes with LysoTracker green vesicles). Fluorescent microscope image of co-cultured control Ba/F3 cells transduced with truncated EGFR and dexamethasone treated thymocytes is shown in FIG. 10.

Phagocytic Activity Against Murine Cell Lines

One day prior to the phagocytosis assay, CT26 murine colon carcinoma cells were cultured in complete RPMI 1640 growth media supplemented with 10% fetal bovine serum and 1% penicillin-streptomycin in a 6-well plate and treated with 1 mM staurosporine (STS) for 12 hours to induce apoptosis. Untreated CT26 cells were used as a negative control.

On the day of the phagocytosis assay, CT26 cells were collected, washed twice with 1×PBS to remove excess staurosporine and then stained with 1 ng/µl pHrodo Red in PBS at room temperature for 15 minutes. The CT26 cells were supplemented with growth media, washed once to remove excess pHrodo Red, and plated onto a flat bottom, 96 well plate at 250,000 cells/well in RPMI 1640 complete media.

Ba/F3 CER05+EGFR+ cells made as described above were washed once with 1×PBS and stained with 1 µM CELLTRACE™ Violet dye (ThermoFisher Scientific, Catalog #C34557) in PBS for 10 minutes at 37° C. Stained, transduced Ba/F3 cells were supplemented with growth media, washed once with 1×PBS to remove excess CELL-TRACE™ Violet, and plated on the same flat bottom 96 well plate at approximately 50,000 cells/well in RPMI 1640 complete media.

Figure 11:
FIG. 11 shows fluorescence microscope image of in vitro engulfment of staurosporine treated, pHrodo red stained CT26 colon cancer cells by CELLTRACE Violet stained CER05+Ba/F3 cells. White arrows indicate phagocytosis events.

Target CT26 cells were co-cultured with stained, CER05+ tEGFR+ cells at a ratio of 5:1 (target cell:effector cell) for 3 hours at 37° C. After incubation, the plate was centrifuged and the media replaced with PBS supplemented with 2% fetal bovine serum, pH 9. The 96 well plate was then viewed using KEYENCE BZ-X710 fluorescence microscope, 20X objective. Ba/F3 cells transduced with pLenti vector expressing truncated EGFR were used as negative control. Fluorescent micrograph showing in vitro phagocytosis is shown in FIG. 11 (white arrows show phagocytosis events). CT26 cells labeled with pHrodo Red fluoresced inside the low pH compartments of lysosomes when engulfed (outlined in pink).

Figure 12:
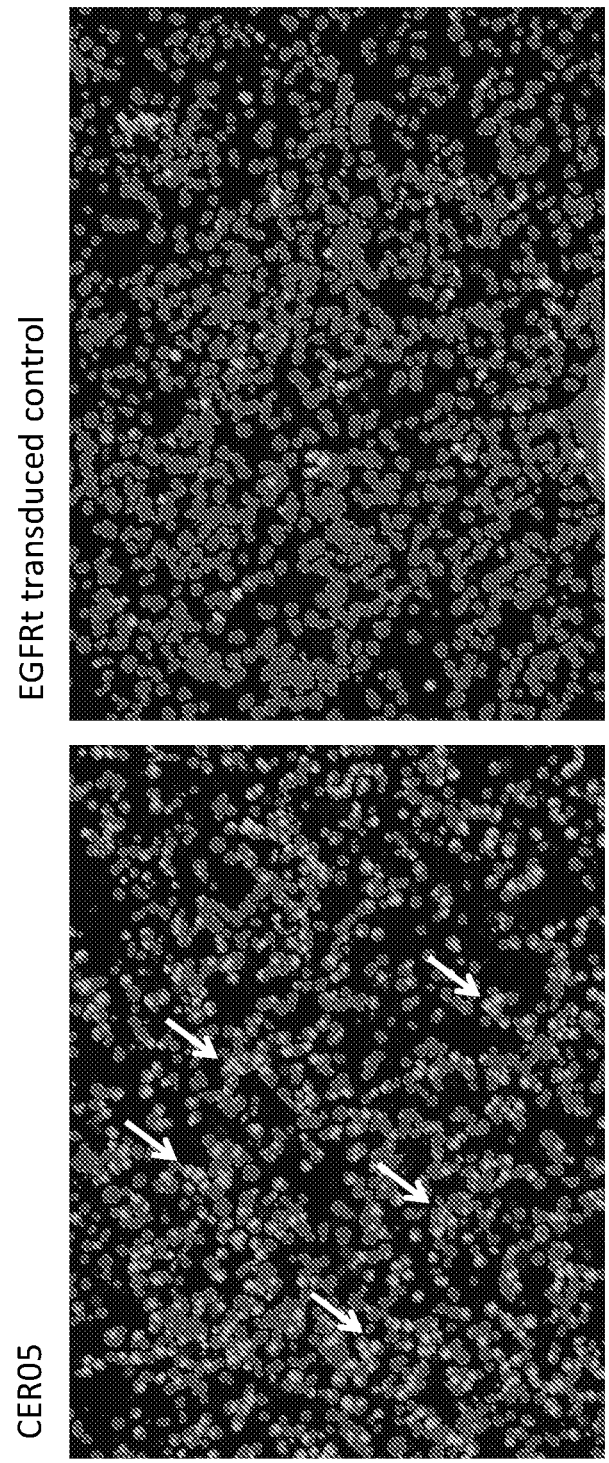
FIG. 12 shows fluorescence microscope images of in vitro engulfment of staurosporine treated, pHrodo red stained CT26 colon cancer cells by CELLTRACE Violet stained CER05+Ba/F3 cells (left) compared to control tEGFR+Ba/F3 cells (right). White arrows indicate phagocytosis events.
Figure 13:
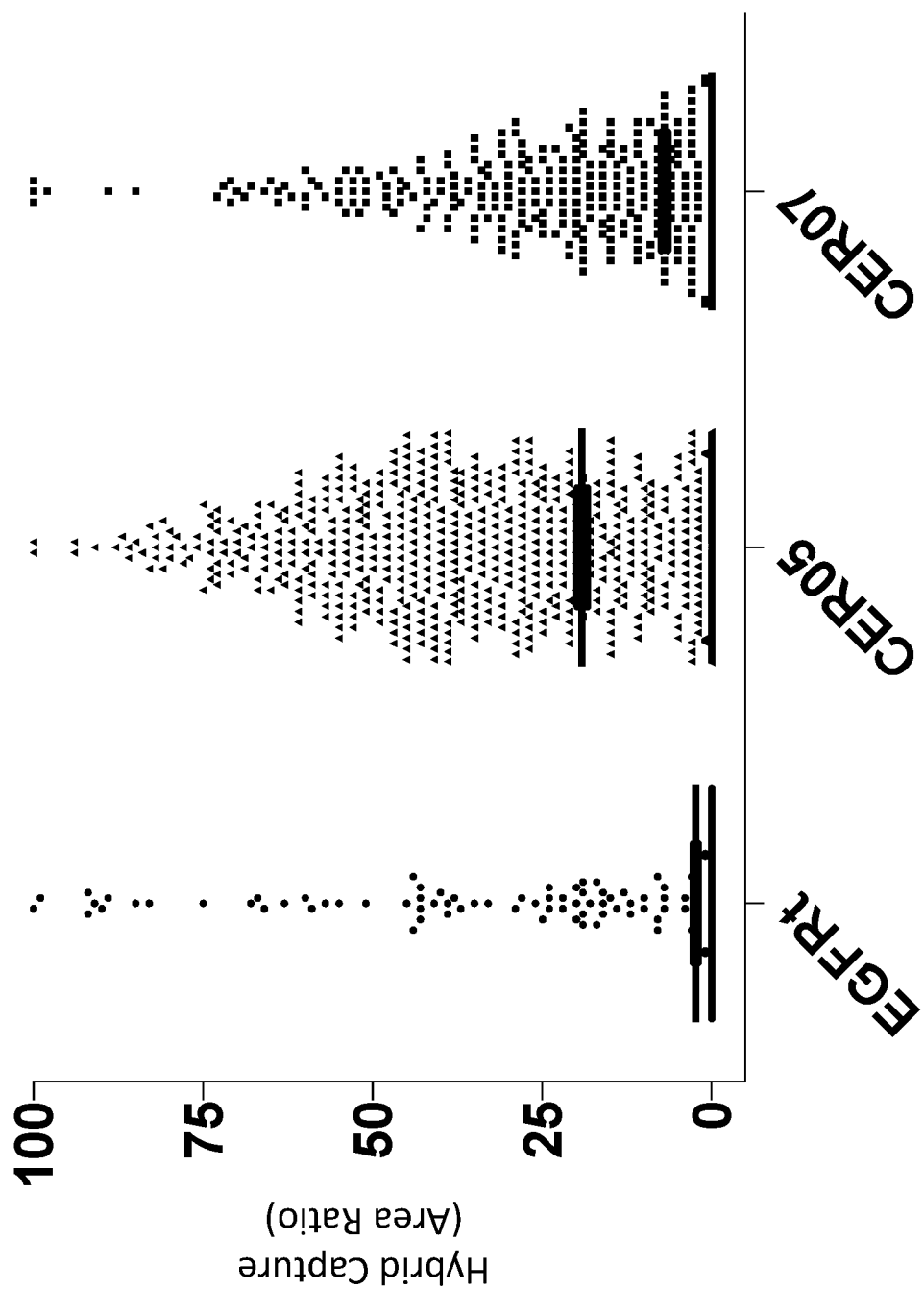
FIG. 13 shows a scatterplot of hybrid cell counts extracting CT26 target cell area from CER05+Ba/F3 cells, CER07+Ba/F3 cells, or EGFRt+ control Ba/F3 cells. The area ratio represents the overlay area of CT26 cells within Ba/F3 cells.
Figure 14:
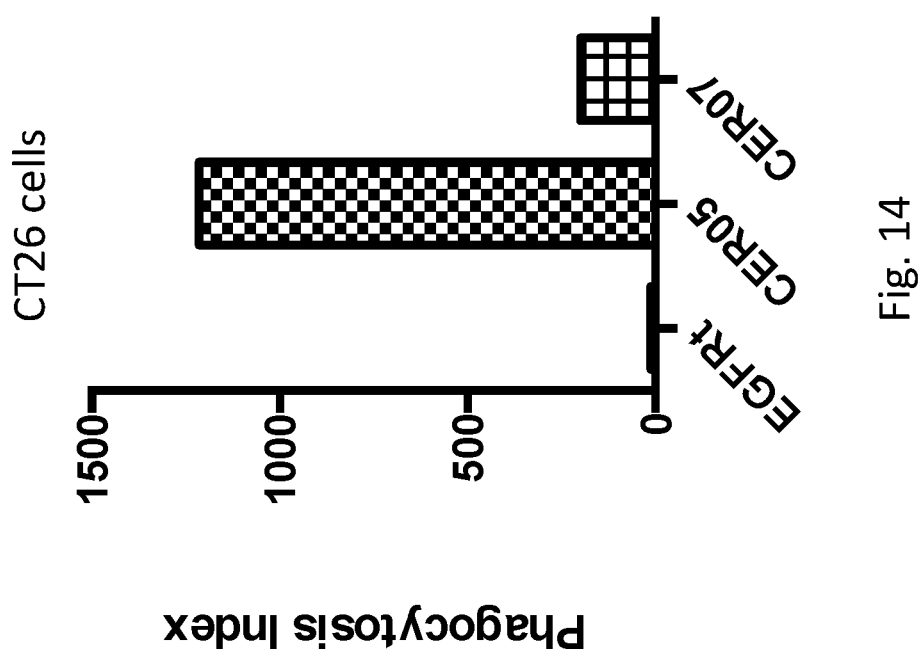
FIG. 14 a bar graph of phagocytic index of CER05+, CER07+, or control EGFRt+Ba/F3 cells that were co-cultured with staurosporine treated CT26 colon cancer cells.

A hybrid capture algorithm that detects fluorescence of pHrodo Red within CELLTRACE Violet staining area was applied to fluorescent images to quantify the area of engulfed target cells/area of CER+ B cells or control tEGFR+ B cells (see, FIG. 12). FIG. 13 shows a scatterplot of hybrid cell counts extracting CT26 target cell area within Ba/F3 cells transduced with CER05+EGFR+ or EGFR+ control. The area ratio represents the co-localization area of CT26 cells within Ba/F3 cells. A phagocytic index for CER05+Ba/F3 cells as compared to EGFRt transduced Ba/F3 control cells is shown in FIG. 14.

Example 2

Construction of Tim4-Tlr4 (Tlr4 Tmd) Cer "Cer07"

The extracellular domain of the phosphatidylserine binding protein Tim4 (amino acid sequence of SEQ ID NO:106), including the signal peptide (amino acids 1-22 of SEQ ID NO:106), was fused to a TLR4 transmembrane domain (amino acid sequence of SEQ ID NO:34) and an intracellular signaling domain of TLR4 (SEQ ID NO:51) to create a chimeric engulfment receptor "CER07" (Tim4-Tyro3 CER having an amino acid sequence of SEQ ID NO:83). The TLR4 signaling domain transduces a signal for engulfment, and Tim4 is a phosphatidylserine binding receptor. The Tim4-TLR4-TLR4 (CER07) chimeric engulfment receptor nucleotide sequence was then inserted into the pLenti lentiviral vector along with truncated EGFR as a transduction marker, separated by T2A sequence (see, FIG. 15). Murine Ba/F3 B-cells were transduced with pLenti vector expressing Tim4-TLR4-TLR4 (CER07) and EGFRt, expanded, sorted by FACs, and used for in vitro studies as described in Example 1.

Phagocytic Activity Against Primary Apoptotic Thymocytes

Primary C3H mouse thymocytes were isolated, treated with dexamethasone, and stained with pHrodo Red as described in Example 1. Ba/F3 CER07+tEGFR+ cells were labeled with CELLTRACE™ Violet dye as described in Example 1. Co-culture experiments were carried out at a 10:1 target cell to effector cell ratio, and Ba/F3 CER07+ tEGFR+ cells were quantified for phagocytosis by fluorescence microscopy and FACs as described in Example 1. Ba/F3 cells transduced with pLenti vector expressing truncated EGFR were used as a negative control.

Fluorescent microscopy showed that CER07+Ba/F3 cells engulfed dexamethasone-treated thymocytes as compared to EGFRt transduced Ba/F3 control cells.

A phagocytic index was calculated by multiplying [mean of total number of engulfed target cells/total number of counted CER modified cells (e.g., phagocytic frequency)] by [average area of target cell staining per CER+Ba/F3 cell x 100 (e.g., hybrid capture)] as compared to EGFRt transduced Ba/F3 control cells (see, FIG. 8).

Phagocytic Activity Against Murine Cell Lines

Figure 16:
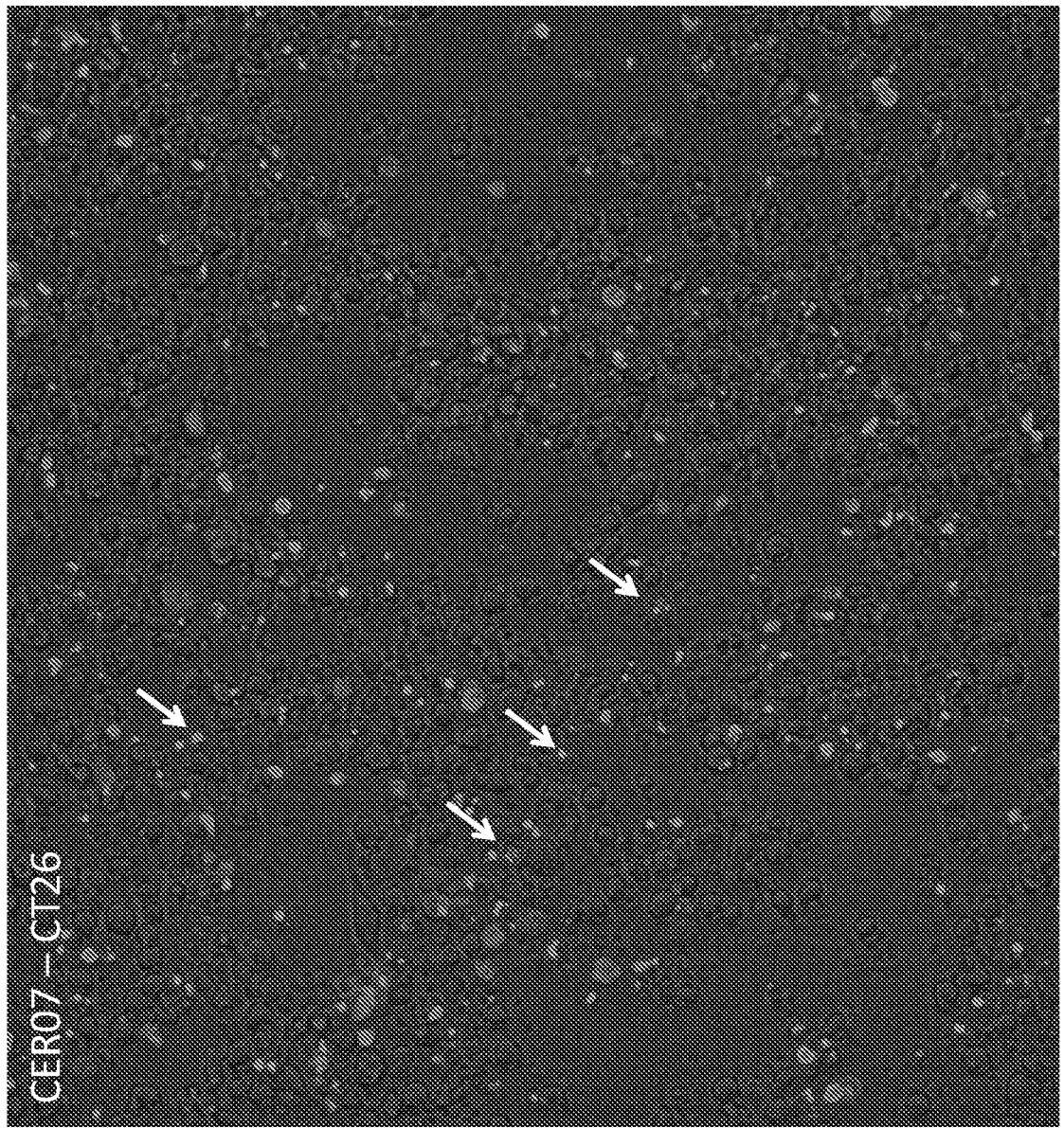
FIG. 16 shows fluorescence microscope image of in vitro engulfment of staurosporine treated CT26 colon cancer cells by CER07+Ba/F3 cells. White arrows indicate phagocytosis events.

CER07+Ba/F3 cells were co-cultured with CT26 murine colon carcinoma cells as described in Example 1. Fluorescent microscopy showed that CER07+Ba/F3 cells engulfed staurosporine treated CT26 cells (see, FIG. 16, white arrows indicate phagocytosis). Ba/F3 cells transduced with EGFRt was used as a control.

Figure 17:
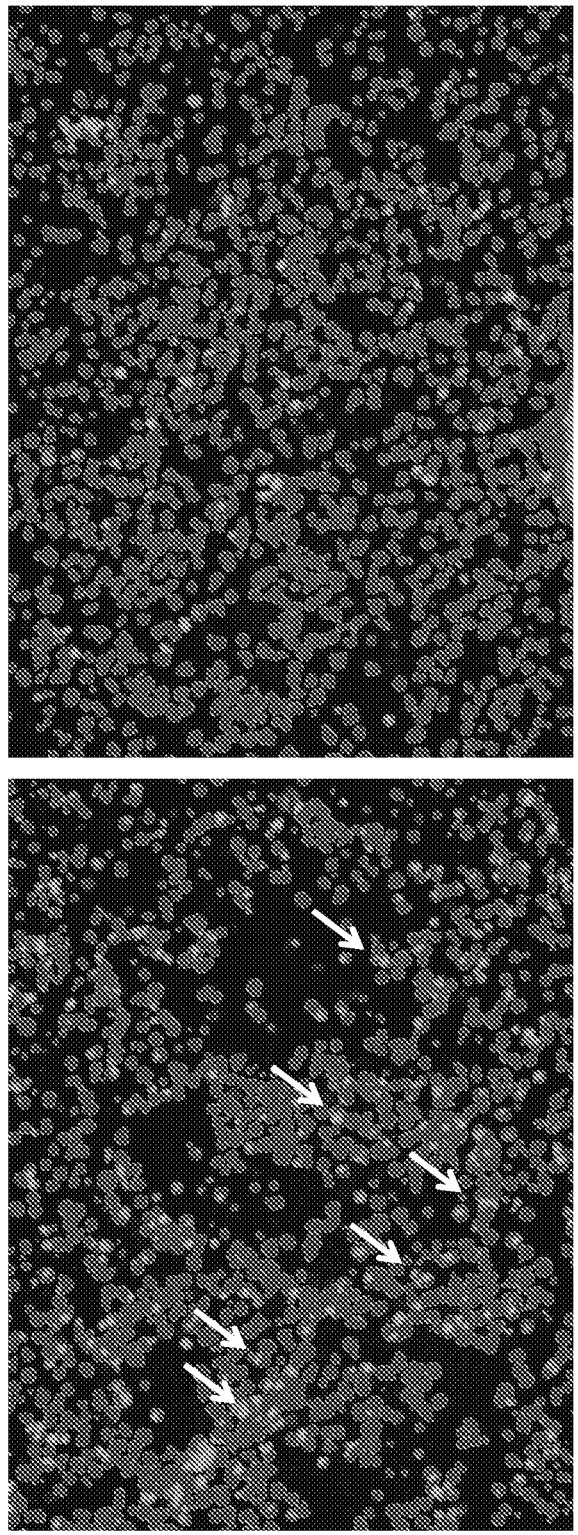
FIG. 17 shows fluorescence microscope images of in vitro engulfment of staurosporine treated, pHrodo red stained CT26 colon cancer cells by CELLTRACE Violet stained CER07+Ba/F3 cells (left) compared to control tEGFR+Ba/F3 cells (right). White arrows indicate phagocytosis events.

A hybrid capture algorithm that detects fluorescence of pHrodo Red within CELLTRACE Violet staining area was applied to fluorescent images to quantify the area of engulfed target cells/area of CER+ B cells (see, FIG. 17). FIG. 13 shows a scatterplot of hybrid cell counts extracting CT26 target cell area within Ba/F3 cells transduced with CER07+EGFR+ or EGFR+ control. The area ratio represents the co-localization area of CT26 cells within Ba/F3 cells. A phagocytic index for CER07+Ba/F3 cells as compared to EGFRt transduced Ba/F3 control cells is shown in FIG. 14.

Example 3

CONSTRUCTION OF TIM4-TLR8 (TLR4 TMD and Spacer) CER "CER21" and TIM4-TLR5) CER "CER19"

The extracellular domain of the phosphatidylserine binding protein Tim4 (amino acid sequence of SEQ ID NO:106), including the signal peptide (amino acids 1-22 of SEQ ID NO:106), and Tim4 transmembrane domain (amino acid sequence of SEQ ID NO:108), were fused to the intracellular signaling domain of TLR8 (SEQ ID NO:55) to create a chimeric engulfment receptor "CER21" (Tim4-TLR8 CER having an amino acid sequence of SEQ ID NO:88). The TLR8 signaling domain transduces a signal for engulfment, and Tim4 is a phosphatidylserine binding receptor. The Tim4-TLR8 (CER21) chimeric engulfment receptor nucleotide sequence was then inserted into the pLenti lentiviral vector along with truncated EGFR as a transduction marker, separated by T2A sequence (see, FIG. 18). Human primary B cells were transduced with pLenti vector expressing Tim4-TLR8 (CER21) and EGFRt, expanded, sorted by FACS, and used for in vitro studies as described in Example 1.

The extracellular domain of the phosphatidylserine binding protein Tim4 (amino acid sequence of SEQ ID NO:106), including the signal peptide (amino acids 1-22 of SEQ ID NO:106), and Tim4 transmembrane domain (amino acid sequence of SEQ ID NO:108), were fused to the intracellular signaling domain of TLR5 (SEQ ID NO:52) to create a chimeric engulfment receptor "CER19" (Tim4-TLR5 CER having an amino acid sequence of SEQ ID NO:86). The TLR5 signaling domain transduces a signal for engulfment, and Tim4 is a phosphatidylserine binding receptor. The Tim4-TLR5 (CER19) chimeric engulfment receptor nucleotide sequence was then inserted into the pLenti lentiviral vector along with truncated EGFR as a transduction marker, separated by T2A sequence. Human primary B cells were transduced with pLenti vector expressing Tim4-TLR8 (CER19) and EGFRt, expanded, sorted by FACS, and used for in vitro studies as described in Example 1.

Phagocytic Activity of Human Cer21+B Cells Against Human Cell LINE

One day prior to setting up the phagocytosis assay, Jurkat human B lymphocytes were cultured in complete RPMI 1640 growth media supplemented with 10% fetal bovine serum and 1% penicillin-streptomycin in a 6 well plate and treated with 1 mM staurosporine for three hours to induce apoptosis. Jurkat cells were washed twice in 1x PBS to remove excess staurosporine and then stained with pHrodo Red (1 ng/µ.1 in PBS) for 15 minutes at room temperature. The Jurkat cells were supplemented with growth media, washed once to remove excess pHrodo Red, and plated on flat bottom 96 well plates at approximately 250,000 cells/well in RPMI 1640 complete media.

Figure 19:
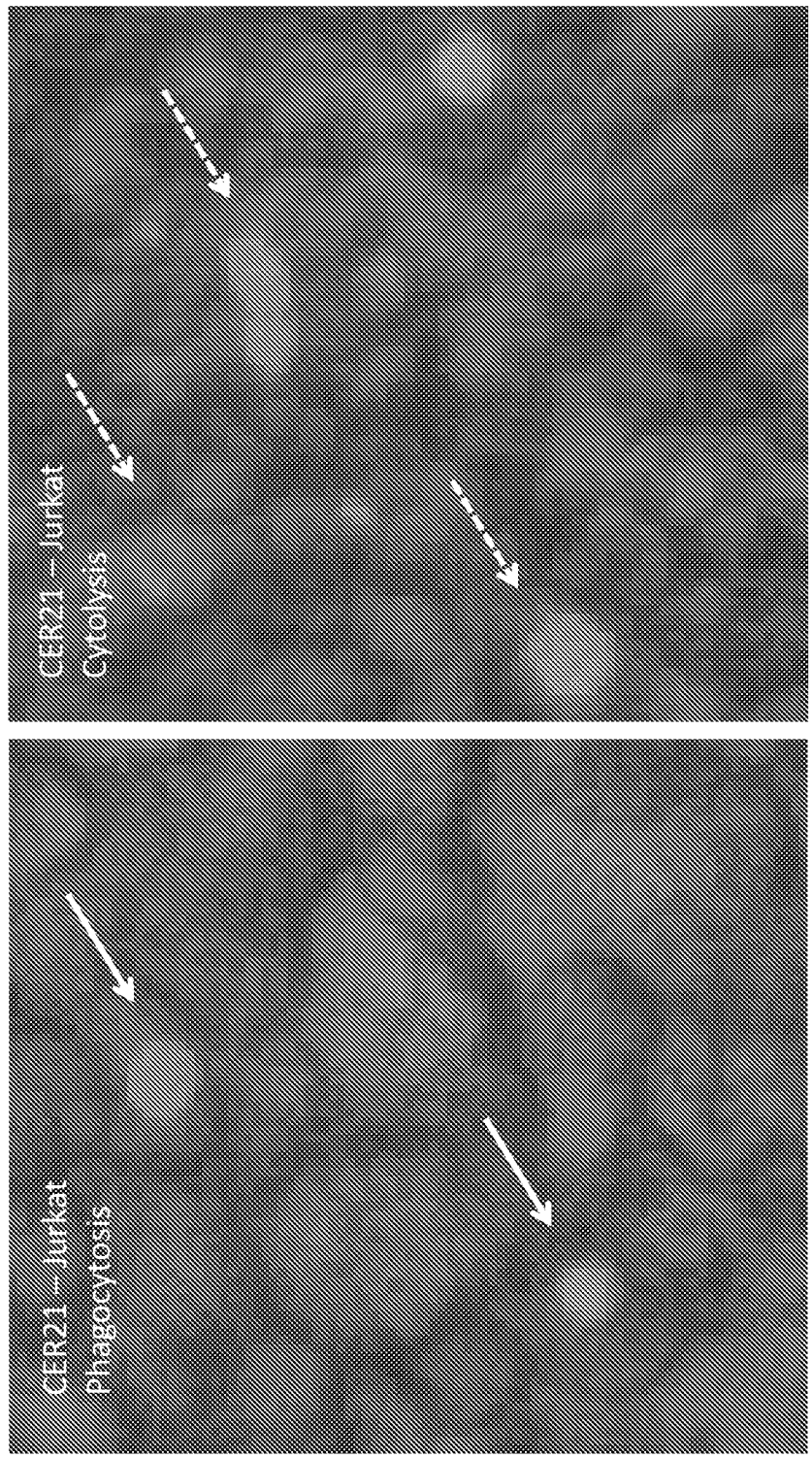
FIG. 19 shows fluorescence microscope images of in vitro phagocytosis (FIG. 19A) and cytolysis (FIG. 19B) of staurosporine treated Jurkat cells by CER21+ human primary B cells.

Transduced CER21+ human primary B cells were washed once with 1×PBS and stained with 1 µM CELLTRACE Violet in PBS for 10 minutes at 37° C. The CER21+ human primary B cells were supplemented with growth media, washed once with 1×PBS to remove excess CELLTRACE Violet, and plated onto 96 well plate at approximately 50,000 cells/well in RPMI 1640 complete media. Human CER21+primary B cells and Jurkat cells were co-cultured at a target cell to effector cell ratio of 5:1 at 37° C. for 3 hours. After incubation, the co-culture plate was then centrifuged, and the media replaced with PBS supplemented with 2% fetal bovine serum, pH 9. Phagocytic events were quantified by fluorescent microscopy (KEYENCE BZ-X710 fluorescence microscope, 20X objective). Fluorescent microscope image showing in vitro phagocytosis is shown in FIG. 19A for CER021+ B cells co-cultured with Jurkat cells. Solid arrows show engulfment activity. Fluorescent microscope image showing in vitro cytolysis of Jurkat cells engulfed by CER21+ B cells is shown in FIG. 19B. Dashed arrows show cytolytic activity.

Figure 20:
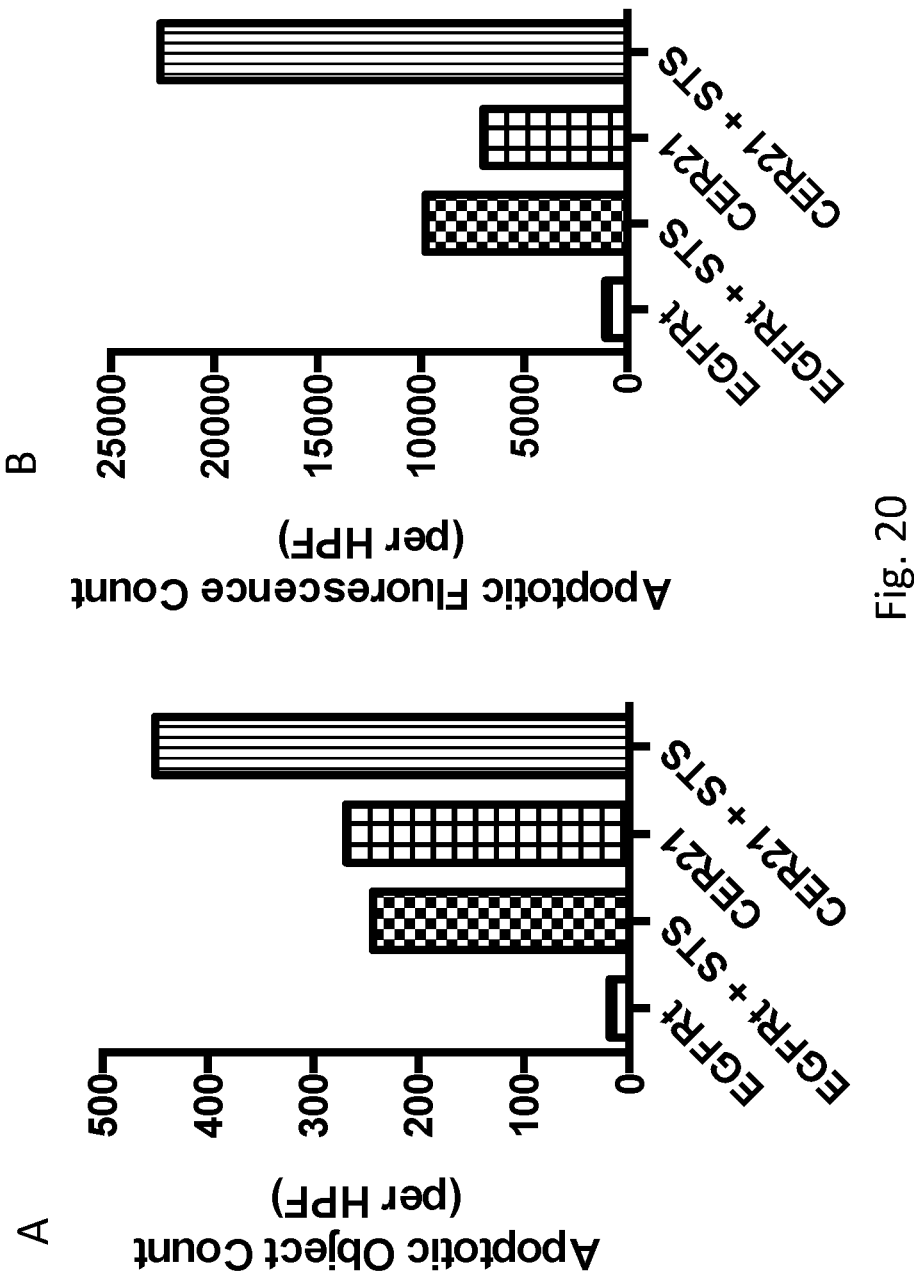
FIGS. 20A-20B show graphs measuring apoptotic object count (FIG. 20A) and apoptotic fluorescent count (FIG. 20B) for CER21+ human primary B cells co-cultured with Jurkat cells (+ and − staurosporine (STS)) as a measure of cytolytic activity. Human primary B cells transduced with truncated EGFR was used as controls (+ and − STS).

Apoptotic cells were quantified from fluorescent images using automated software, and the number of apoptotic cells per high power view (FIG. 20A) and total fluorescence emission per high power view (FIG. 20B) were calculated using pH indicator dye. CER21+ B cells co-cultured with staurosporine treated (subtherapeutic dose) Jurkat cells exhibited enhanced killing of target cells.

Figure 21:
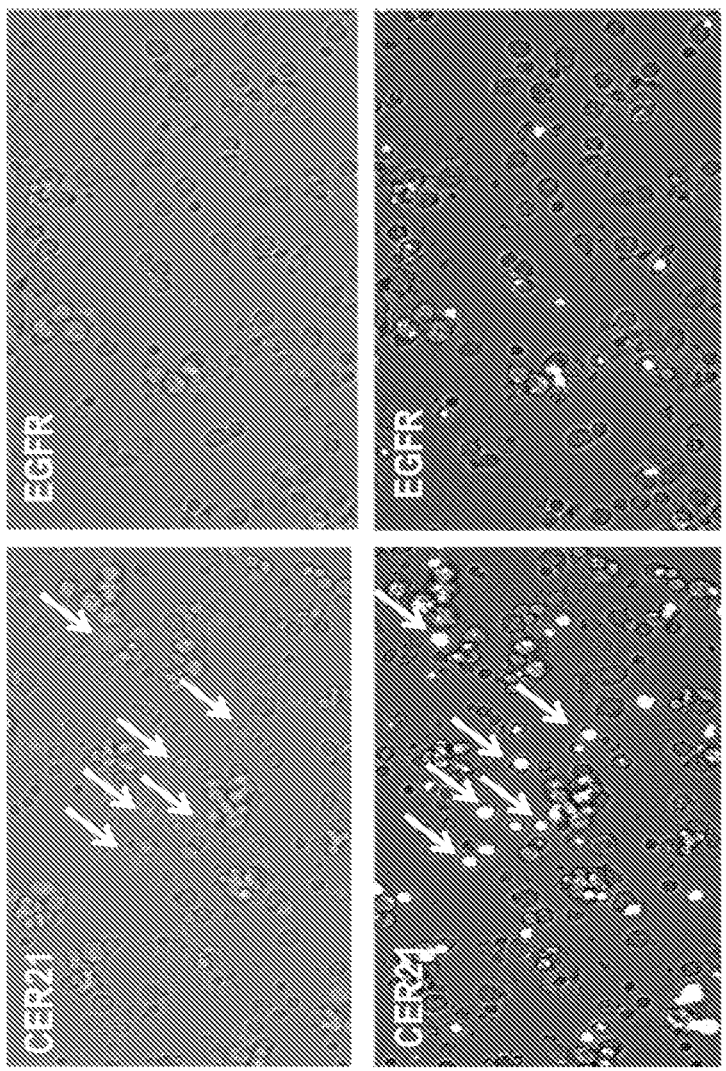
FIG. 21 shows fluorescence microscope images of in vitro apoptosis in co-culture of CER21+ human primary B cells or control EGFRt+ human primary B cells with paclitaxel treated H1703 non-small cell lung cancer cells. Cells undergoing apoptosis fluoresce red (top row). Automated software outlined the red fluorescent objects (bottom row).
Figure 22:
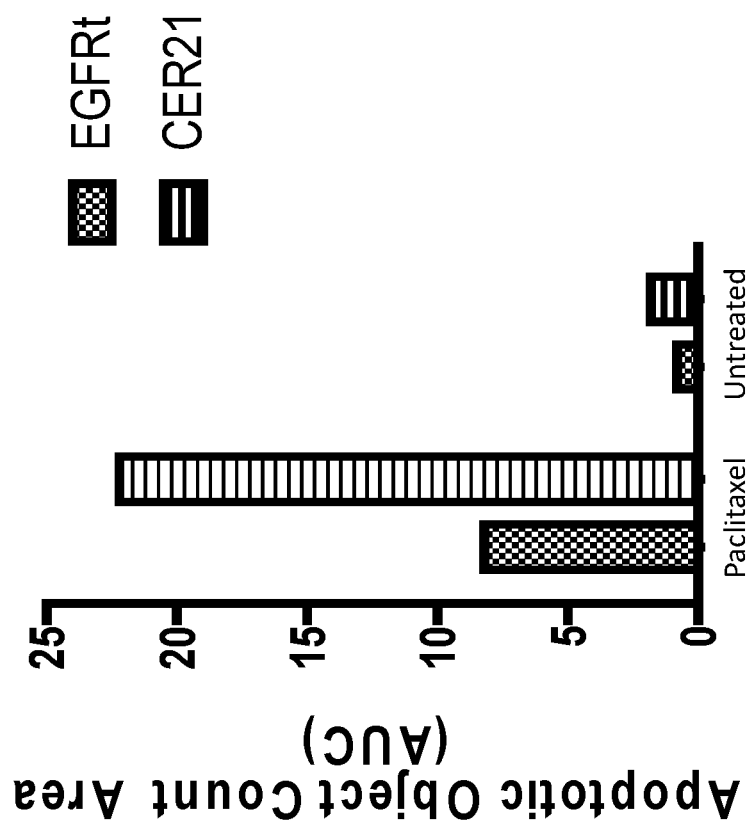
FIG. 22 shows a graph of apoptotic object count area for CER21+ human primary B cells or control EGFRt+ human primary B cells co-cultured with paclitaxel treated H1703 cells.

Enhanced Killing by Human Cer21+B Cells Against Chemotherapy-Treated HUMAN CELL LINE Human primary B cells were transduced with pLenti Tim4-TLR8 (CER21) lentivirus expressing truncated EGFR as a transduction marker and stained with CELLTRACE Violet as described in Example 1. One day prior to setting up a co-culture assay, H1703 non-small cell lung cancer cells were incubated with phosphatidylserine inducing chemotherapy Paclitaxel (30 µM) in serum-free media for 24 hours. Floating and adherent H1703 cells were collected, centrifuged, incubated with pHrodo red (1 ng/µL) for 15 minutes at room temperature in PBS, washed, and then plated in a non-adherent 96 well plate. Human CER21+ B cells and H1703 cells were co-cultured at a target cell to effector cell ratio of 5:1 at 37° C. for 3 hours. B cells transduced with truncated EGFR were used as control. The plate was then imaged using a 20X objective, Keyence BZ-X710 microscope (FIG. 21). Cells undergoing apoptosis show increasing Red fluorescence as the intracellular pH drops in the earliest stages of apoptosis (FIG. 21, top row). Adjacent cells not induced by Paclitaxel treatment remain only dimly fluorescent. Apoptotic measurements in the presence of CER21+ B cells were quantified as the Area under the Curve of red fluorescent objects and outlined in blue using automated software (FIG. 21, bottom row; FIG. 22), for each high powered field. White arrows show apoptosis events. CER21+ B cells were found to enhance killing of target cells at sub-therapeutic dose of chemotherapy.

Enhanced Proliferation Capacity of Cer19+ and Cer21+B Cells

Figure 23:
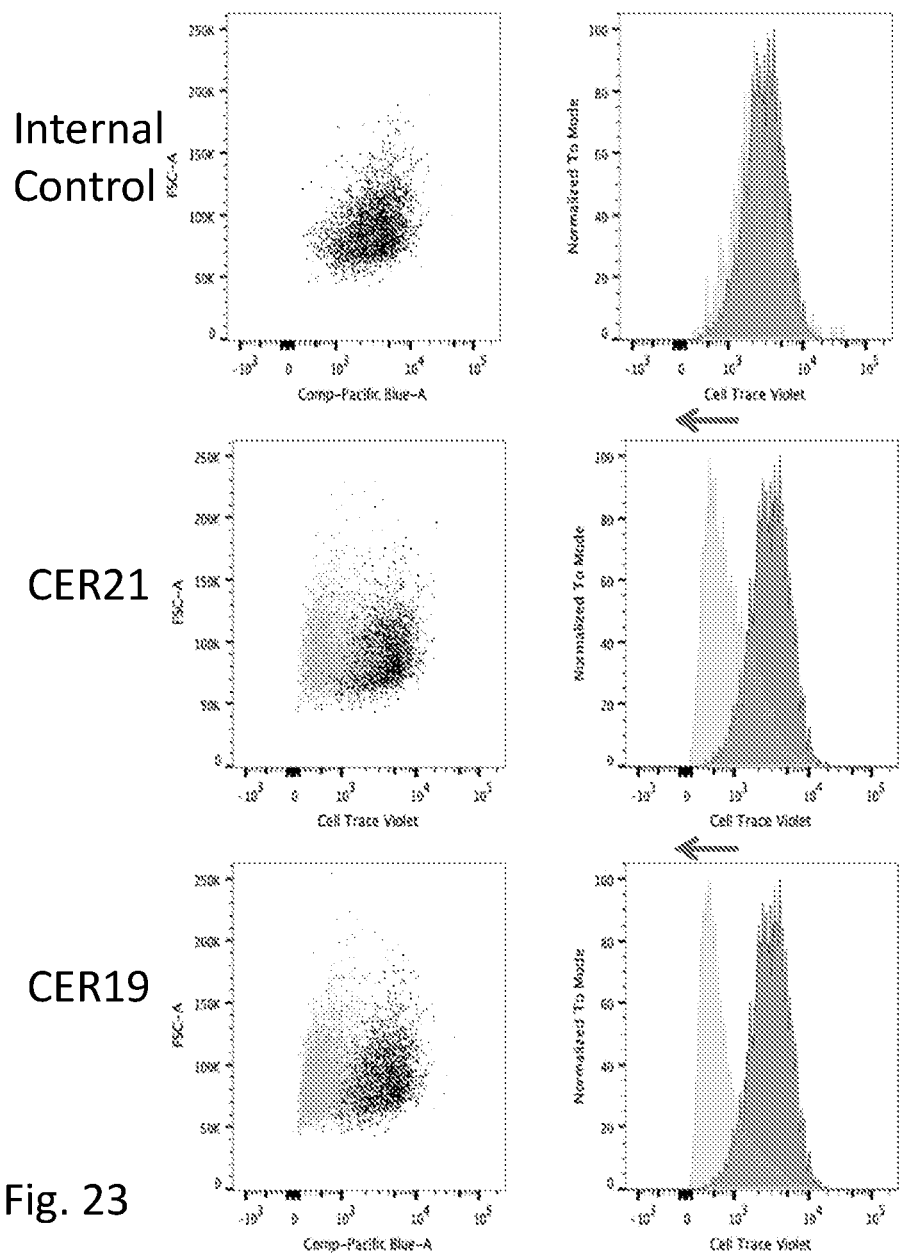
FIG. 23 shows FACS plots (left) and histograms (right) of CER19+, CER21+, or control human primary B cell proliferation following co-culture with paclitaxel treated Jurkat lymphoma cells in the absence of exogenous cytokines.

The proliferation capacity of CER19+ and CER21+ human primary B cells was evaluated by co-culture with paclitaxel (30 µM) treated Jurkat lymphoma cells. CER-transduced B cells were labeled with CELLTRACE Violet and then co-cultured with paclitaxel treated Jurkat cells a target cell to effector cell ratio of 5:1 at 37° C. in the absence of exogenous cytokines for 5 days. Proliferation of CER19+ or CER21+B cells was assessed by flow cytometry by measuring dilution of CELLTRACE Violet (FIG. 23). Both CER19+ and CER21+ B cells increased approximately 10-fold after 5 days of co-culture in the absence of exogenous cytokines. In contrast, cells transduced with a control vector displayed no increase in cell numbers.

Enhanced Activation State of Cer21+B Cells

Figure 24:
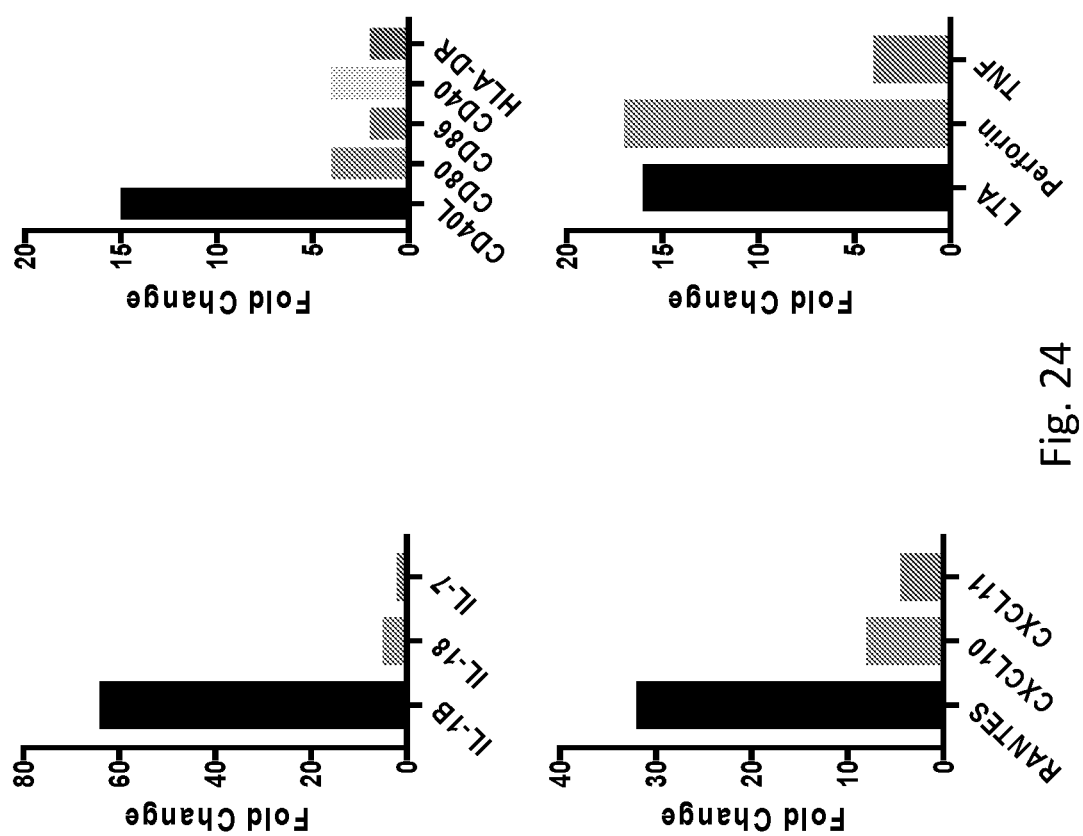
FIG. 24 shows enhanced activation state of CER21+ human primary B cells as measured by increased expression of pro-inflammatory IL-1 cytokines (graph on upper left), costimulatory molecules (graph on upper right), B cell activation and survival molecules (graph on upper right), lymphocyte chemoattractants (graph on lower left) and molecules involved in lymph node tissue remodeling (graph on lower right). Expression levels were compared to control vector transduced B cells.

To evaluate the activation state of CER21+ human primary B cells, gene expression profiles were examined from transduced B cell populations. In agreement with previous reports linking activation of the TLR family to expression of pro-inflammatory IL-1 cytokines (e.g., IL-1B and IL-18) and elevation in co-stimulatory molecules (e.g., CD80, CD86), CER21 also promoted B cell activation molecules and survival factors (e.g., CD40, CD40L), lymphocyte chemo-attractants (RANTES, CXCL10, and CXCL11), and expresses molecules involved in lymph node tissue remodeling that facilitate the development of tumor-specific, adaptive immune responses, such as LTα and TNFa (see, FIG. 24; bar graphs show fold change in B cell mRNA levels compared to transduced control B cells).

Example 4

CONSTRUCTION OF FMC63 scFv-TLR4 CER "CER43" and FMC 63 scFv-IgG$_4$-TLR4 CER "CER44"

An anti-CD19 single chain fragment variable (scFv) (encoding amino acid sequence of SEQ ID NO:109) derived from the FMC63 mouse IgG2a mouse monoclonal antibody and comprising a GM-CSF derived signal peptide (amino acids 1-22 of SEQ ID NO:109) was fused to a TLR4 juxtamembrane domain (SEQ ID NO:17), a TLR4 transmembrane domain (amino acid sequence of SEQ ID NO:34) and to an intracellular signaling domain of TLR4 (SEQ ID NO:51) to create a chimeric engulfment receptor "CER43" (FMC63 scFv-TLR4 CER having an amino acid sequence of SEQ ID NO:122). The TLR4 signaling domain transduces a signal for engulfment, and FMC63 scFv binds to CD19. The FMC63 scFv-TLR4 (CER43) chimeric engulfment receptor nucleotide sequence was then inserted into the pLenti lentiviral vector along with truncated EGFR (EGFRt) as a transduction marker, separated by T2A sequence. Murine Ba/F3 B-cells were transduced with pLenti vector expressing FMC63 scFv-TLR4 (CER43) and EGFRt, expanded, sorted by FACs, and used for in vitro studies as described in Example 1.

An anti-CD19 single chain fragment variable (scFv) (encoding amino acid sequence of SEQ ID NO:109) derived from the FMC63 mouse IgG2a mouse monoclonal antibody and comprising a GM-CSF derived signal peptide (amino acids 1-22 of SEQ ID NO:109) was fused to a modified IgG4 hinge extracellular spacer domain comprising (SEQ ID NO:16), a TLR4 transmembrane domain (amino acid sequence of SEQ ID NO:34), and an intracellular signaling domain of TLR4 (SEQ ID NO:51) to create a chimeric engulfment receptor "CER44" (FMC63 scFv-IgG$_4$-TLR4 CER having an amino acid sequence of SEQ ID NO:123). The TLR4 signaling domain transduces a signal for engulfment, and FMC63 scFv binds to CD19. The FMC63 scFv-IgG$_4$-TLR4 (CER44) chimeric engulfment receptor nucleotide sequence was then inserted into the pLenti lentiviral vector along with truncated EGFR as a transduction marker, separated by T2A sequence. Murine Ba/F3 B-cells were transduced with pLenti vector expressing FMC63 scFv-IgG$_4$-TLR4 (CER44) and EGFRt, expanded, sorted by FACs, and used for in vitro studies as described in Example 1.

Phagocytic Activity Against Human Lymphoma Cell Line

Figure 25:
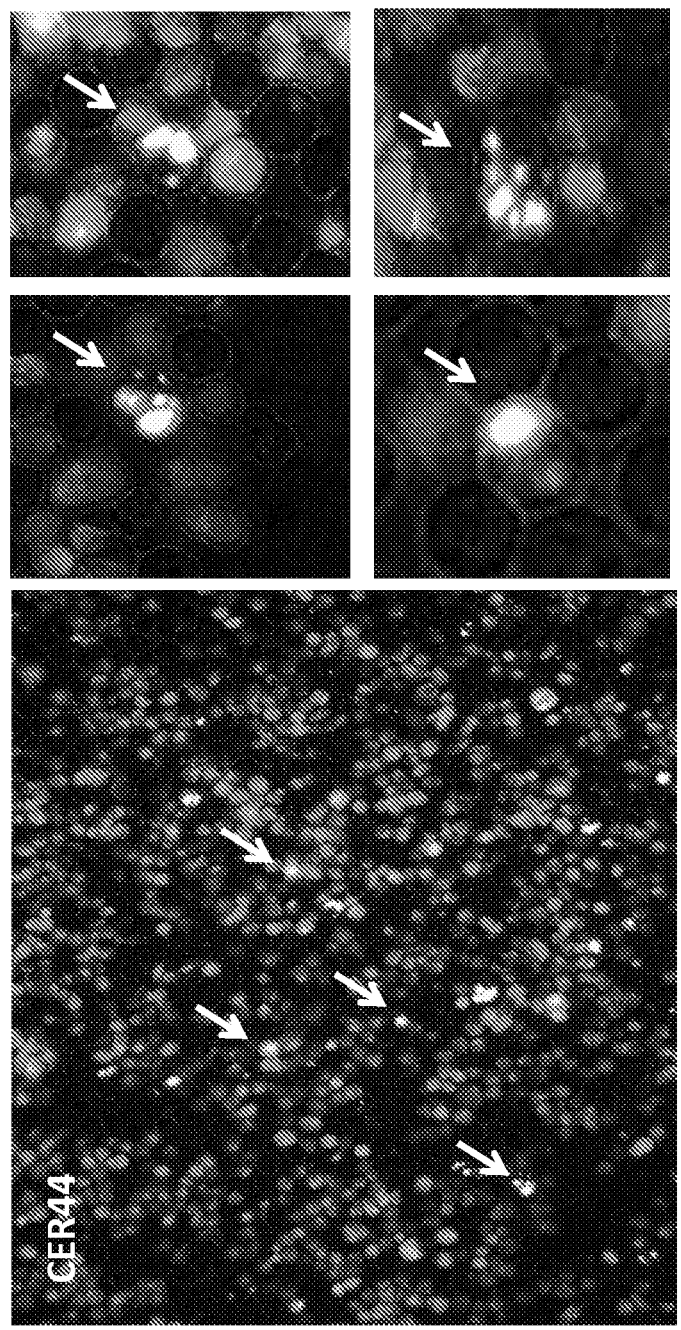
FIG. 25 shows fluorescence microscope images of in vitro phagocytosis of CD19+Raji cells by CD19 specific CER44+Ba/F3 cells. White arrows indicate engulfment events. Four enlargements of the fluorescent microscope images showing phagocytosis are shown on the right.
Figure 26:
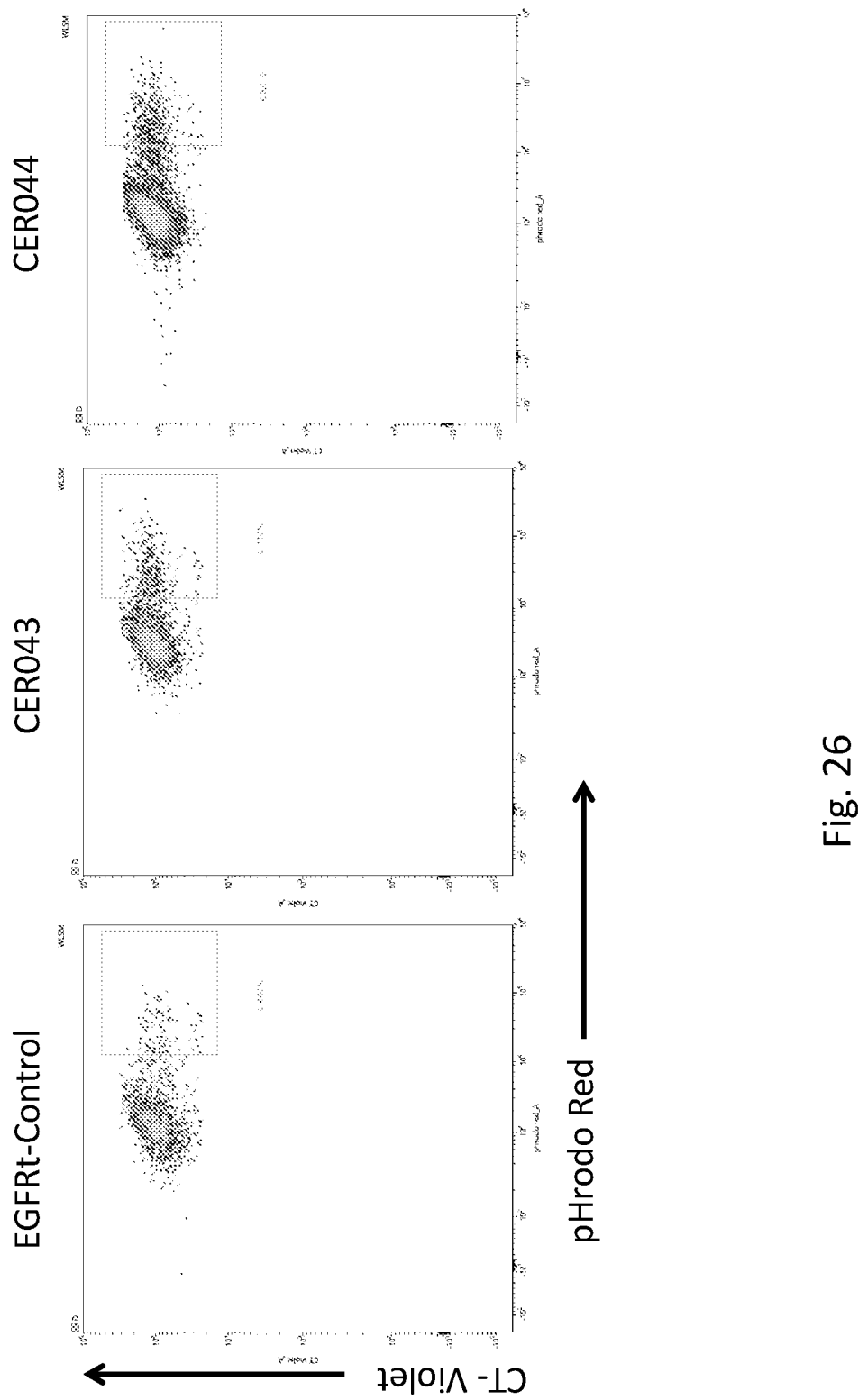
FIG. 26 shows FACS analysis of CER43+Ba/F3 cells, CER44+Ba/F3 cells, or control EGFRt Ba/F3 cells that were co-cultured with CD19+Raji lymphoma cells. Engulfment of Raji cells by CER43+, CER44+, or EGFRt+Ba/F3 cells was measured by cell population that stained double positive for pHrodo Red and CELLTRACE Violet.
Figure 27:
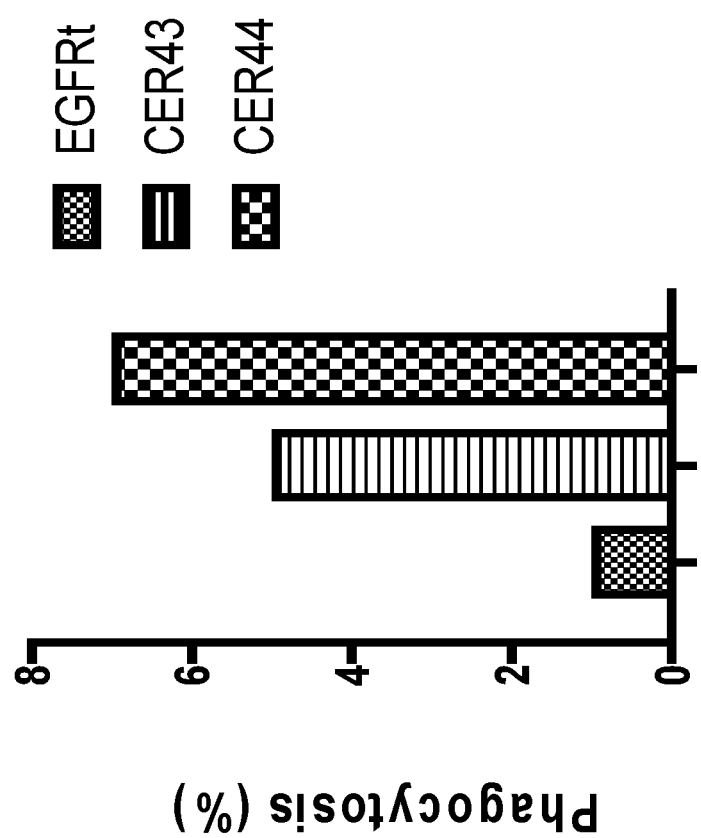
FIG. 27 shows a graph of frequency of phagocytosis for CER43+, CER44+, or control EGFRt+Ba/F3 cells co-cultured with Raji cells.
Figure 28:
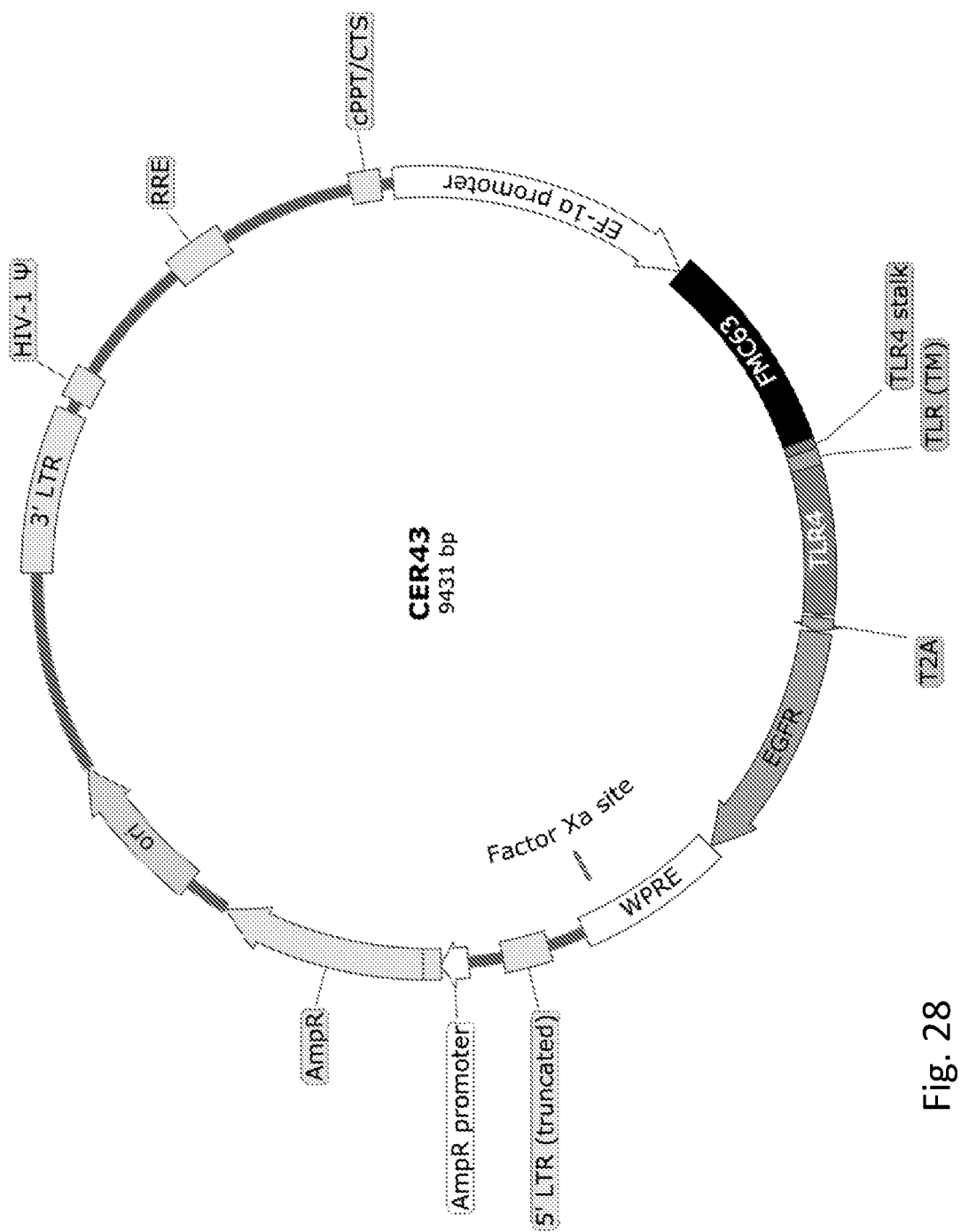
FIG. 28 shows a vector map for a lentiviral vector comprising "CER43" chimeric engulfment receptor having an amino acid sequence of SEQ ID NO:122. CER43 comprises an extracellular domain comprising a CD19 specific FMC63 scFv, an extracellular spacer region comprising a TLR4 juxtamembrane domain, a TLR4 transmembrane domain, and an engulfment signaling domain comprising a TLR4 signaling domain. The lentiviral vector also comprises a sequence encoding truncated EGFR (SEQ ID NO:105), which is separated from the CER43 sequence by a viral T2A sequence.
Figure 29:
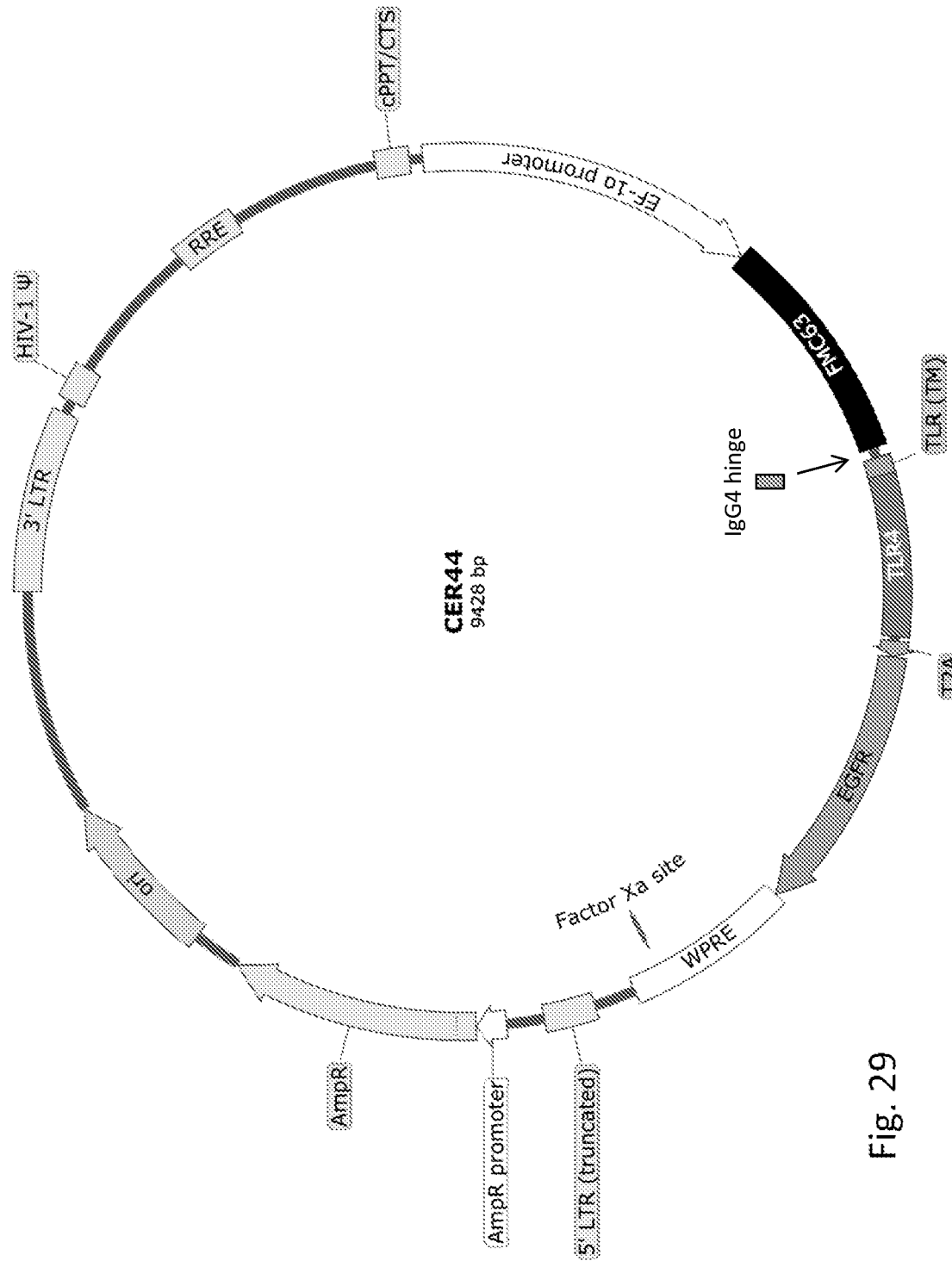
FIG. 29 shows a vector map for a lentiviral vector comprising "CER44" chimeric engulfment receptor having an amino acid sequence of SEQ ID NO:123. CER44 comprises an extracellular domain comprising a CD19 specific FMC63 scFv, an extracellular spacer region comprising a modified IgG4 hinge region, a TLR4 transmembrane domain, and an engulfment signaling domain comprising a TLR4 signaling domain. The lentiviral vector also comprises a sequence encoding truncated EGFR (SEQ ID NO:105), which is separated from the CER44 sequence by a viral T2A sequence.

Raji human Burkitt B-cell lymphoma cells were labeled with 1 μM of pHrodo Red dye and used as target cells for phagocytosis assays. CER43+ or CER44+ modified Ba/F3 cells were stained with CELLTRACE Violet as described in Example 1. Co-culture experiments with genetically modified CD19-targeted CER43+ or CER44+Ba/F3 cells and CD19+Raji cells were carried out as described in Example 1. Ba/F3 cells transduced with truncated EGFR were used as control. CER43+ or CER44+Ba/F3 cells and Raji cells were co-cultured at a target cell to effector cell ratio of 5:1 at 37° C. for 3 hours. Phagocytic events were quantified by fluorescent microscopy (KEYENCE BZ-X710 fluorescence microscope, 20X objective). FIG. 25 shows engulfment of Raji cells by CD19 specific CER44 expressing Ba/F3 cells (white arrows indicate engulfment events). The frequency of phagocytosis was quantified as the cell population staining double positive for pHrodo Red and CELLTRACE Violet as detected by FACS. FIG. 26 shows FACS plots showing the double positive cell population for CER43+Ba/F3 cells (9.10%), CER44+Ba/F3 cells (6.92%), or control EGFRt+ Ba/F3 cells (4.49%) co-cultured with Raji cells. Frequency of phagocytosis for CER43+, CER44+, or control EGFRt+ Ba/F3 cells co-cultured with Raji cells is also shown in the bar graph of FIG. 27. Ba/F3 cells transduced with lentivirus vector expressing CD19 specific CER43 or CER44 exhibited enhanced phagocytic uptake of Raji lymphoma cells.

Example 5

Construction of Cers, Tcrs, and Modified T Cells for Cellular IMMUNOTHERAPY COMBINATIONS A polynucleotide comprising the extracellular domain of the phosphatidylserine binding protein Tim4 and Tim4 transmembrane domain was fused to the intracellular signaling domain of TLR4 to create chimeric engulfment receptor "CER5" encoding an amino acid sequence of SEQ ID NO:81.

A polynucleotide comprising the extracellular domain of the phosphatidylserine binding protein Tim4 and Tim4 transmembrane domain was fused to the intracellular signaling domain of TLR3 to create chimeric engulfment receptor "CER17" encoding an amino acid sequence of SEQ ID NO:84.

A polynucleotide comprising the extracellular domain of the phosphatidylserine binding protein Tim4 and Tim4 transmembrane domain was fused to the intracellular signaling domain of TLR5 to create chimeric engulfment receptor "CER19" encoding an amino acid sequence of SEQ ID NO:86.

A polynucleotide comprising the extracellular domain of the phosphatidylserine binding protein Tim4 was Tim4 transmembrane domain and TLR8 intracellular signaling domain to create chimeric engulfment receptor "CER21" encoding an amino acid sequence of SEQ ID NO:88.

A polynucleotide comprising the extracellular domain of the phosphatidylserine binding protein Tim4 and Tim4 transmembrane domain was fused to the intracellular signaling domain of TLR9 to create chimeric engulfment receptor "CER23" encoding an amino acid sequence of SEQ ID NO:90.

A polynucleotide comprising the extracellular domain of the phosphatidylserine binding protein Tim4 and Tim4 transmembrane domain was fused to the intracellular signaling domain of TLR1 to create chimeric engulfment receptor "CER26" encoding an amino acid sequence of SEQ ID NO:92.

A polynucleotide comprising the extracellular domain of the phosphatidylserine binding protein Tim4 and Tim4 transmembrane domain was fused to the intracellular signaling domain of TLR2 to create chimeric engulfment receptor "CER27" encoding an amino acid sequence of SEQ ID NO:93.

A polynucleotide comprising the extracellular domain of the phosphatidylserine binding protein Tim4 and Tim4 transmembrane domain was fused to the intracellular signaling domain of TLR8 and a truncated intracellular signaling domain of CD79b to create chimeric engulfment receptor "CER103B" encoding an amino acid sequence of SEQ ID NO:132.

A polynucleotide comprising the extracellular domain of the phosphatidylserine binding protein Tim4 and Tim4 transmembrane domain was fused to the intracellular signaling domain of TLR8 and the intracellular signaling domain of DAP12 to create chimeric engulfment receptor "CER104" encoding an amino acid sequence of SEQ ID NO:133.

A polynucleotide comprising the extracellular domain of the phosphatidylserine binding protein Tim4 and Tim4 transmembrane domain was fused to the intracellular signaling domain of TLR8 and the intracellular signaling domain of BAFF-R to create chimeric engulfment receptor "CER105" encoding an amino acid sequence of SEQ ID NO:134.

A polynucleotide comprising the extracellular domain of the phosphatidylserine binding protein Tim4 and Tim4 transmembrane domain was fused to the intracellular signaling domain of NFAM1 and the intracellular signaling domain of TLR8 to create chimeric engulfment receptor "CER106" encoding an amino acid sequence of SEQ ID NO:135.

A polynucleotide comprising the extracellular domain of the phosphatidylserine binding protein Tim4 and Tim4 transmembrane domain was fused to the intracellular signaling domain of Traf6 and the intracellular signaling domain of TLR8 to create chimeric engulfment receptor "CER116" encoding an amino acid sequence of SEQ ID NO:143.

A polynucleotide encoding a TCRβ chain and a polynucleotide encoding a TCRα of a HPV16 E7 specific TCR (see, PCT Publication No. WO2015/184228) were fused using a sequence encoding a P2A self-cleaving peptide there between. The TCR Vα domain comprises an amino acid sequence of SEQ ID NO:162, and the TCR Vβ region comprises an amino acid sequence of SEQ ID NO:160. The Ca domain comprises a cysteine substitution and LVL substitutions at positions 12, 14, and 15 and comprises an amino acid sequence of SEQ ID NO:163. The Cβ also comprises a cysteine substitution and comprises an amino acid sequence of SEQ ID NO:161. The encoded HPV16 E7 specific TCR comprises an amino acid sequence of SEQ ID NO:158.

A selected CER polynucleotide and the HPV16 E7 TCR polynucleotide were each inserted into a pLenti lentiviral vector. Peripheral blood was collected by venipuncture from a human donor, and human peripheral blood mononuclear cells (PBMCs) were isolated by density gradient centrifugation using lymphocyte separation media. CD8+ or CD4+ T cells were enriched from PBMCs using a commercially available isolation kit and activated with anti-CD3 and anti-CD28 in Complete Cell Growth Media. 50 µl of viral vector expressing the HPV16 E7 TCR were diluted in 0.5 ml Complete Cell Growth Media and added to the CD8+ T cells. 50 µl of viral vector expressing the a selected CER were diluted in 0.5 ml Complete Cell Growth Media and added to the CD4+ T cells. The transduced T cells were then centrifuged at 270×g rpm for 1 hour in a 32° C. pre-warmed centrifuge. The T cells were incubated for 24 hours at 37° C. T cells were expanded for another 72 hours in Complete Cell Growth Media, de-beaded, and allowed to expand x 5 days prior to being utilized for functional assays. Transduced CD4 and CD8 T cells were combined at a 1:1 ratio for functional assays.

Figure 30B:
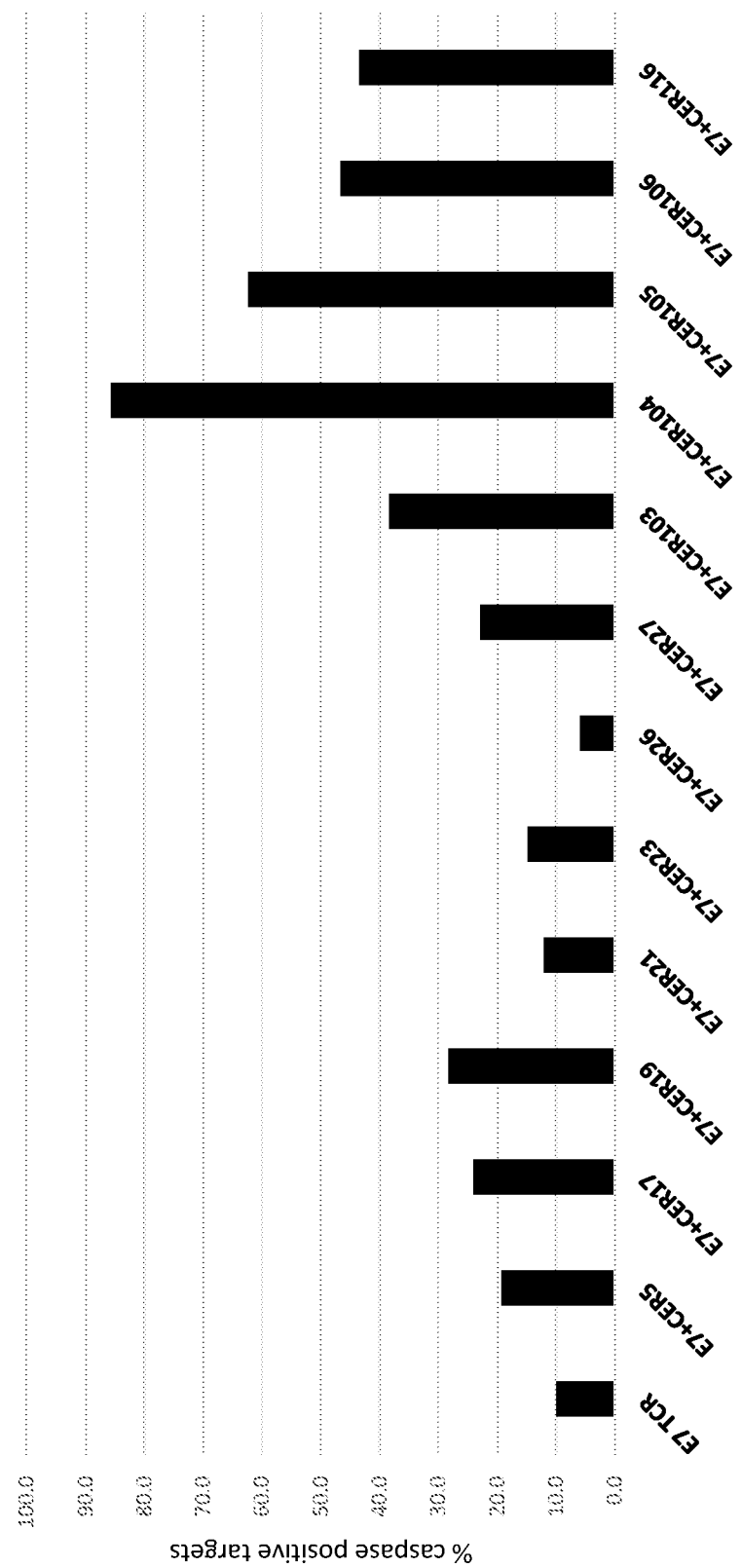
Figure 31:
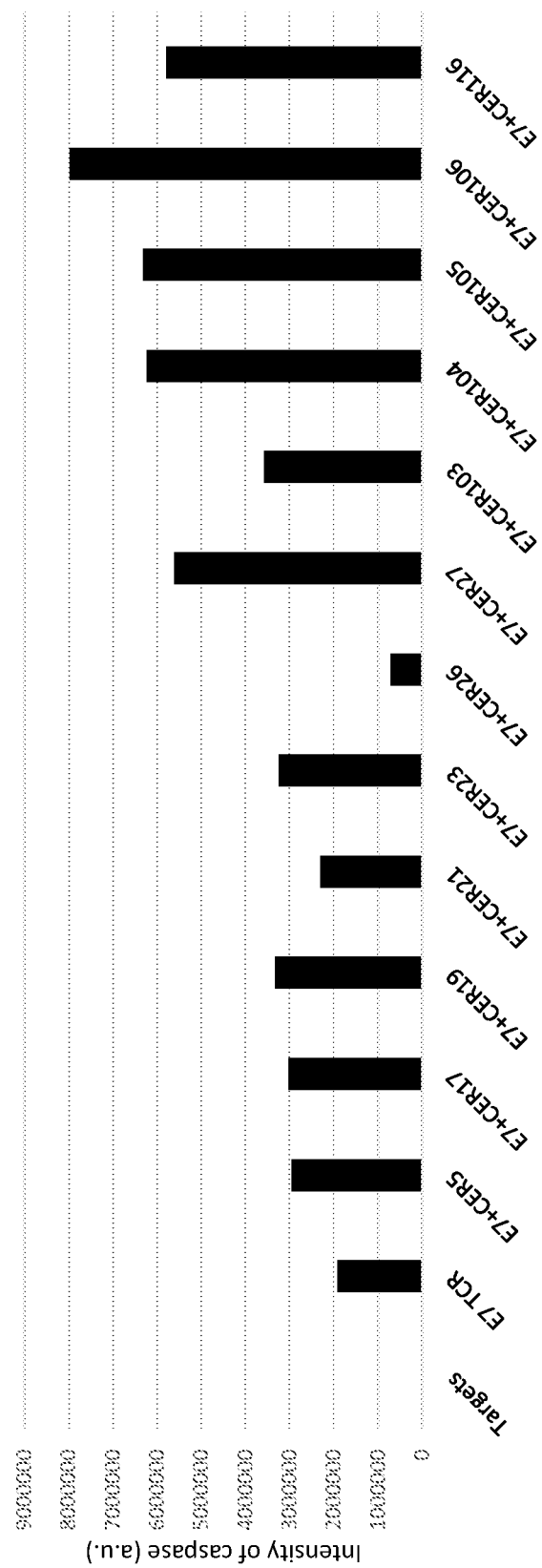
FIG. 31 is bar graph showing that combination of CD4 T cell/CER of the present disclosure with a CD8+/HPV16 E7 TCR enhances cytolysis of target cells as measured by caspase induction compared to administration of the HPV16 E7 TCR alone. Human primary CD8+ cells transduced with a HPV16 E7 TCR were co-cultured alone with SCC152 cells or in combination with CD4+ T cells transduced with various CERs of the present disclosure (CERS, CER17, CER19, CER21, CER23, CER26, CER27, CER103B, CER104, CER105, CER106, or CER116) at a 1:1 ratio. The number of caspase positive SCC152 target cells in the co-culture assay was measured by quantifying the intensity of red fluorescence from a caspase 3/7 apoptosis reagent that couples the activated caspase 3/7 recognition motif with a red reagent that fluoresces upon cleavage. The caspase 3/7 apoptosis reagent was added to the co-culture assay after 6 hours, and fluorescence was detected using BZ-X710 Keyence microscope and using hybrid capture software. The Y-axis represent the intensity of caspase reagent in arbitrary units (a.u.)
Figure 34:
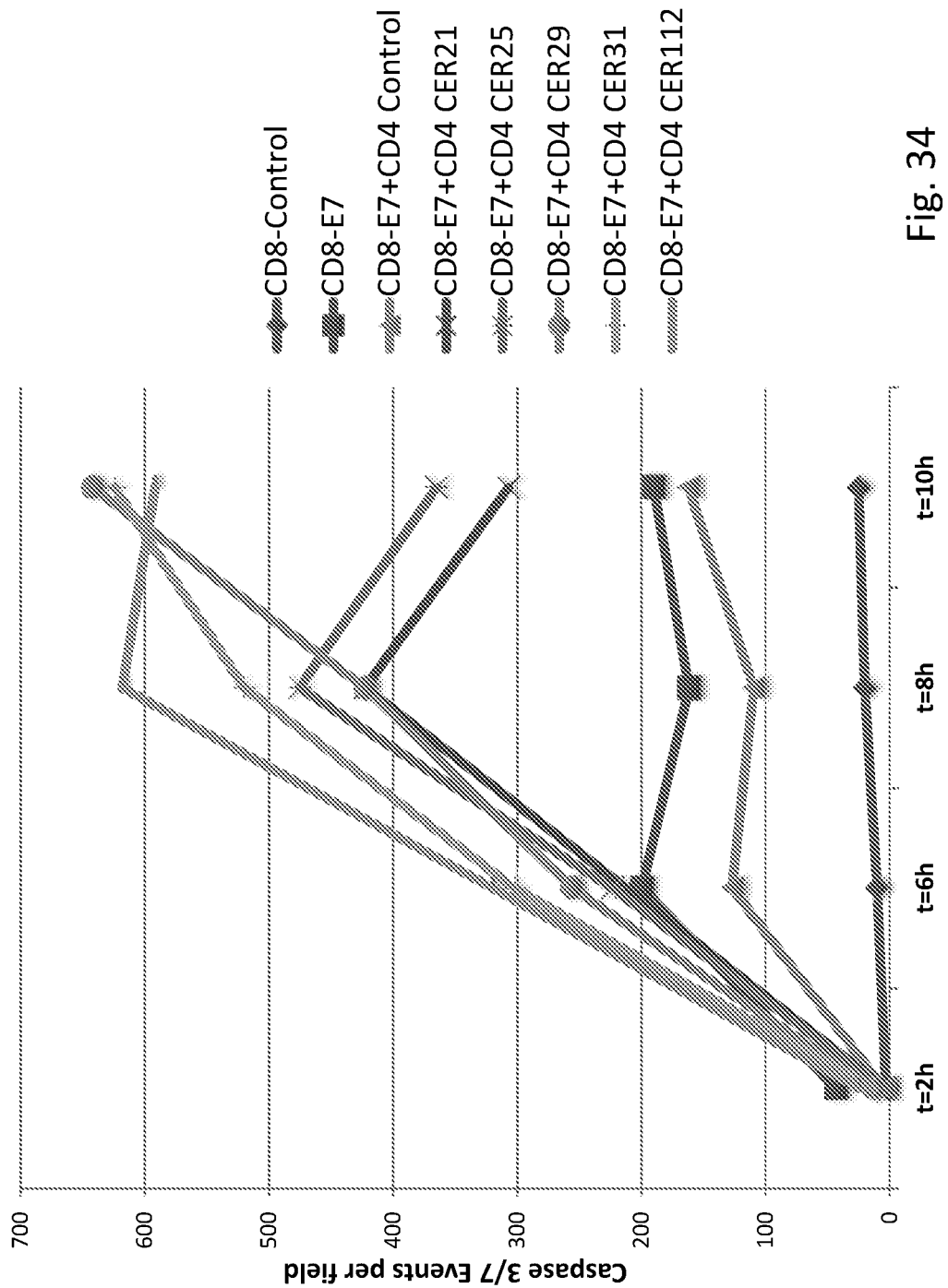
FIG. 34 is a line graph showing caspase 3/7 induction over time in co-culture experiments. The graph shows the number of caspase positive SCC152 target cells in a co-culture assay containing CD8 T cells transduced with HPV16 E7 TCR and CD4 T cells transduced with either control or a selected CER. The intensity of caspase was measured by quantifying the intensity of red fluorescence from a caspase 3/7 apoptosis reagent that couples the activated caspase 3/7 recognition motif with a red reagent that fluoresces upon cleavage. Measurements were taken at 2, 6, 8, and 10 hours of the co-culture assay.

Combinations of Cd8 T Cell-Tcr+Cd4 T Cell-Cer Exhibit Enhanced Antigen SPECIFIC CYTOLYTIC ACTIVITY AND PHAGOCYTIC ACTIVITY Dual HPV16 E7 TCR and CER-mediated elimination of target SCC152 cells was detected using cytotoxicity and phagocytosis assays (see, FIG. 30A). SCC152 cells are HPV+ cells from a squamous cell carcinoma of the hypopharynx. Cytotoxic activity of CD8+ T cells transduced with HPV16 E7 specific TCR was detected using a caspase 3/7 apoptosis reagent (IncuCyte®) that couples the activated caspase 3/7 recognition motif with a red reagent that fluoresces upon cleavage. The fluorescent signal was measured using fluorescent microscopy. HPV16 E7 TCR transduced CD8+ T cells and selected CER transduced CD4+ T cells were mixed at a 1:1 ratio and co-cultured with HPV16 E7+ head and neck squamous cell carcinoma cells (SCC152) at a 1:1 ratio, and caspase 3/7 apoptosis reagent was added to the co-culture. Cytotoxic activity was measured over time by measuring fluorescence. Control samples were CD8 T cells transduced with HPV16 E7 TCR alone. As shown in the graphs of FIGS. 30B, 31, and 34, and fluorescent micrographs (data not shown), addition of CD4+ T cells transduced with most of the CERs tested to CD8 T cells transduced with the HPV16 E7 TCR enhanced cytolytic activity over mono-treatment with CD8 T cells transduced with HPV16 E7 TCR.

Figure 32:
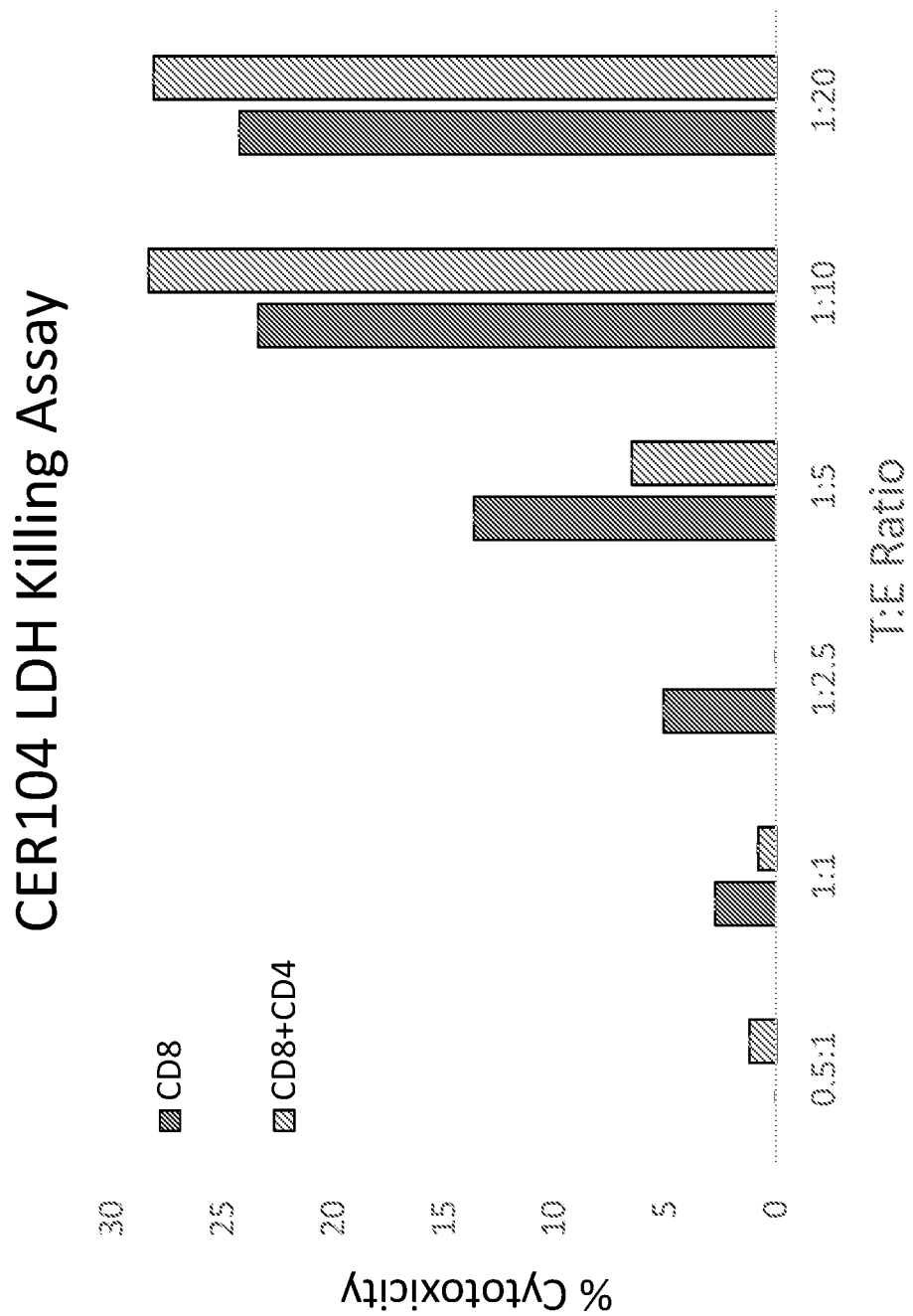
FIG. 32 is a bar graph showing that addition of CD4+ T cell/CER104 (Tim4-TLR8) to co-culture experiments with CD8+ T cell/HPV16 E7 TCR and SCC152 target cells enhances cytotoxicity as measured by lactate dehydrogenase (LDH) cytotoxicity assay. Presence of LDH was assayed 4 hours after co-culture of CD8 T cells transduced with HPV16 E7 TCR and CD4 T cells transduced with CER104 at a 1:1 ratio with SCC152 target cells at varying target cell:effector cell ratios (0.5:1, 1:1, 1:2.5, 1:5, 1:10, 1:20).

The enhanced cytolytic activity of CD4 T cell transduced with CER104 +CD8 T cells transduced with HPV16 E7 TCR was observed when measured using a lactate dehydrogenase (LDH) cytoxicity assay (see, FIG. 32). LDH is a cytosolic enzyme that is released by a cell into cell culture media when the plasma membrane is damaged. Thus, LDH's presence in culture medium is a marker for cell death. LDH assays are capable of detecting low level damage to cell membrane which cannot be detected using other methods. LDH may be detected using colorimetric or fluorometric methods.

Figure 33:
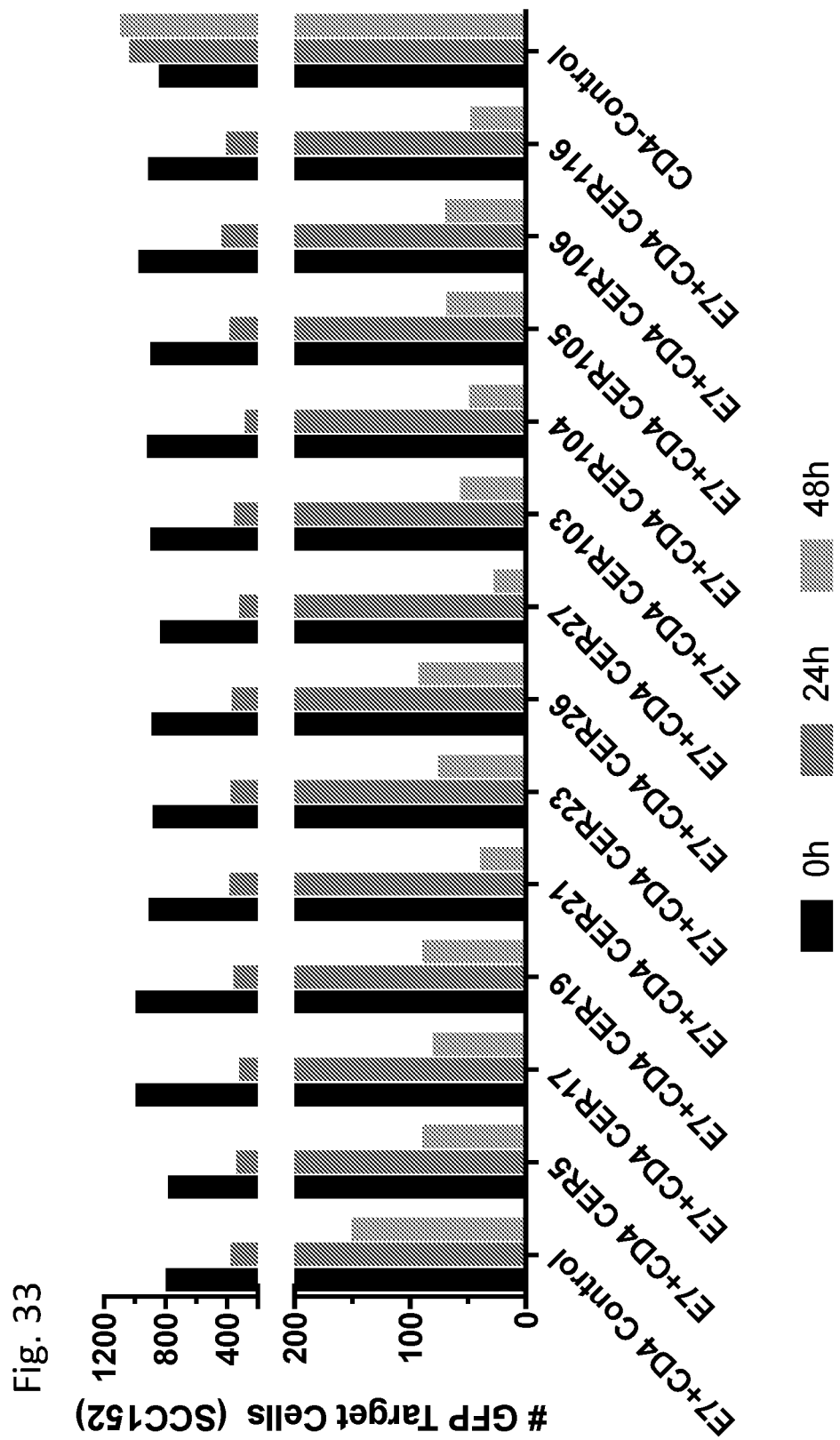
FIG. 33 is a bar graph of the quantification of SCC152 HPV+ head and neck squamous carcinoma cells over time. Target cells were co-cultured with CD8 T cells transduced with HPV16 E7 TCR+CD4 T cells transduced with a selected CER, or controls (CD8 T cell transduced with HPV16 E7 TCR+CD4 transduced control) at a 1:1:1 ratio. The number of target cells were quantified using imaging software. Addition of CD4+ T cells transduced with various CERs of the present disclosure to CD8+ T cell/HPV16 E7 TCRs enhanced clearance of SCC152 target cells.

Elimination of target SCC152 cells was also detected by quantifying green fluorescent protein expression by SCC152 cells over time (0 hr, 24 hr, 48 hr) during co-incubation with CD8+ T cells transduced with HPV16 E7 specific TCR+ CD4 T cells transduced with selected CER (see, FIG. 33). By 48 hrs, all of the CD4 T cell/CER+CD8 T cell/HPV16 E7 TCR combination co-cultures showed enhanced elimination of SCC152 cells compared to controls. Time lapse imaging of co-culture experiments similarly showed enhanced elimination of SCC152 cells by CD4 T cell/CER+CD8 T cell/HPV16 E7 TCR combination co-cultures compared to controls (data not shown).

Figure 35:
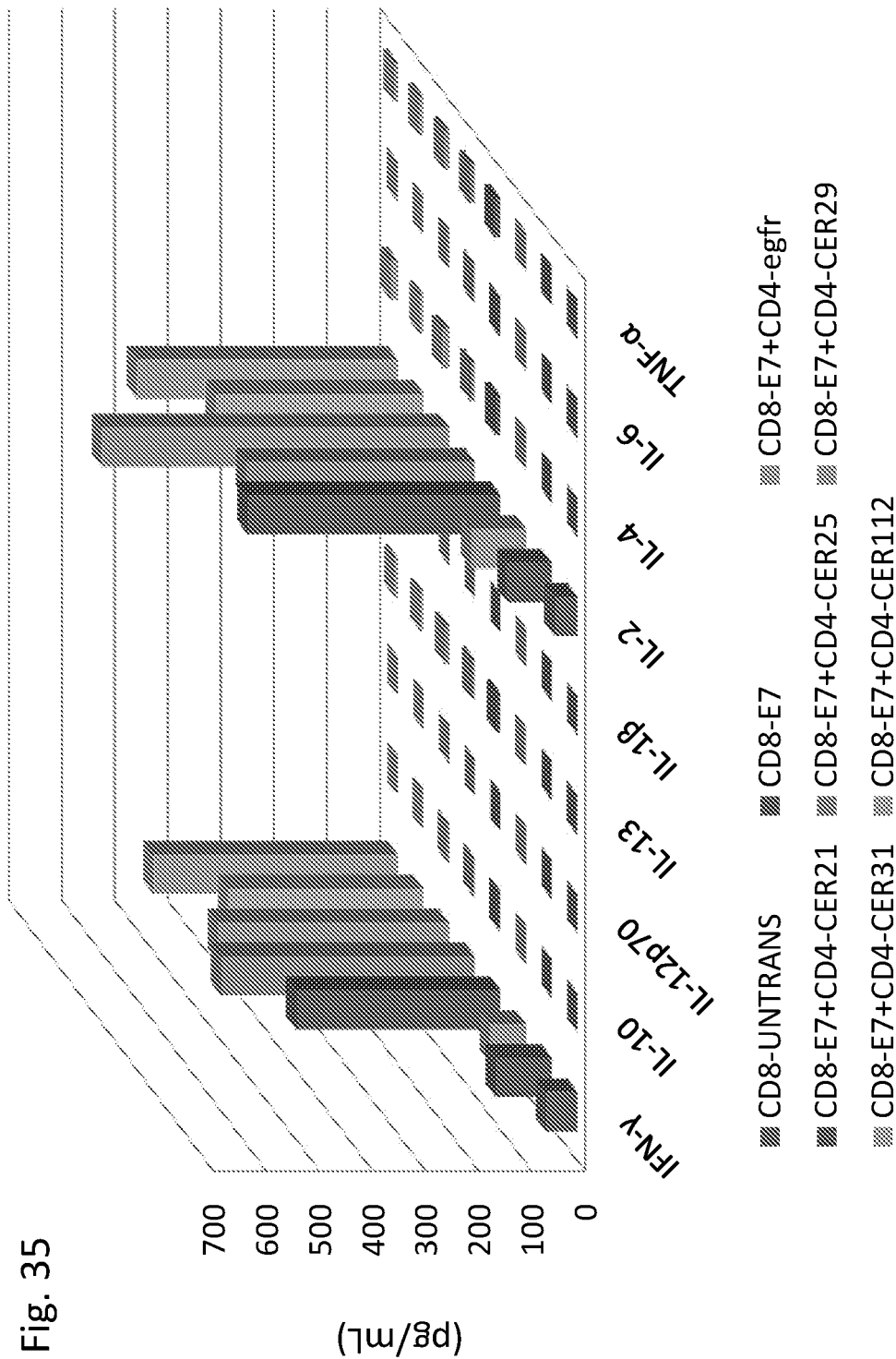
FIG. 35 is a bar graph showing enhanced effector cytokine profile elicited upon co-culture of SCC152 cells with CD8 T cells transduced with HPV16 E7 TCR+CD4 T cells transduced with selected CERs of the present disclosure. CD8 T cells transduced with HPV16 E7 TCRs were co-administered with CD4 T cells transduced selected CERs at a 1:1 ratio to SCC152 target cells for an effector:target cell ratio of 1:1. Antigen-specific cytokine secretion was determined by measuring cytokine concentrations in the cell supernatants from each co-culture experiment using a mesoscale multi-array cytokine plate. The addition of a CD4 T cell/CER to CD8 T cell/HPV16 E7 TCR enhances IFN-γ, IL-2, TNFa, and IL-13 responses over CD8 T cell/HPV16 E7 TCR alone or combined with CD4 T cell transduced with truncated EGFR. The following cytokines were measured in the assay: IFN-γ, IL-2, TNFα, IL-4, IL-6, IL-12b, IL-13, IL-1b, and IL-10.

Cytokine response of co-culture experiments was measured by sampling the cellular supernatants using a mesoscale multi-array cytokine plate. The following cytokines were measured: IFNγ, IL-2, TNFα, IL-4, IL-6, IL-12b, IL-13, IL-1b, and IL-10. Enhanced cytokine production indicative of activated profile (e.g., IFNγ, IL-2) were elicited in co-cultures with CD4 T cell/CER+CD8 T cell/HPV16 E7 TCR combinations compared to controls (see, FIG. 35).

Figure 36:
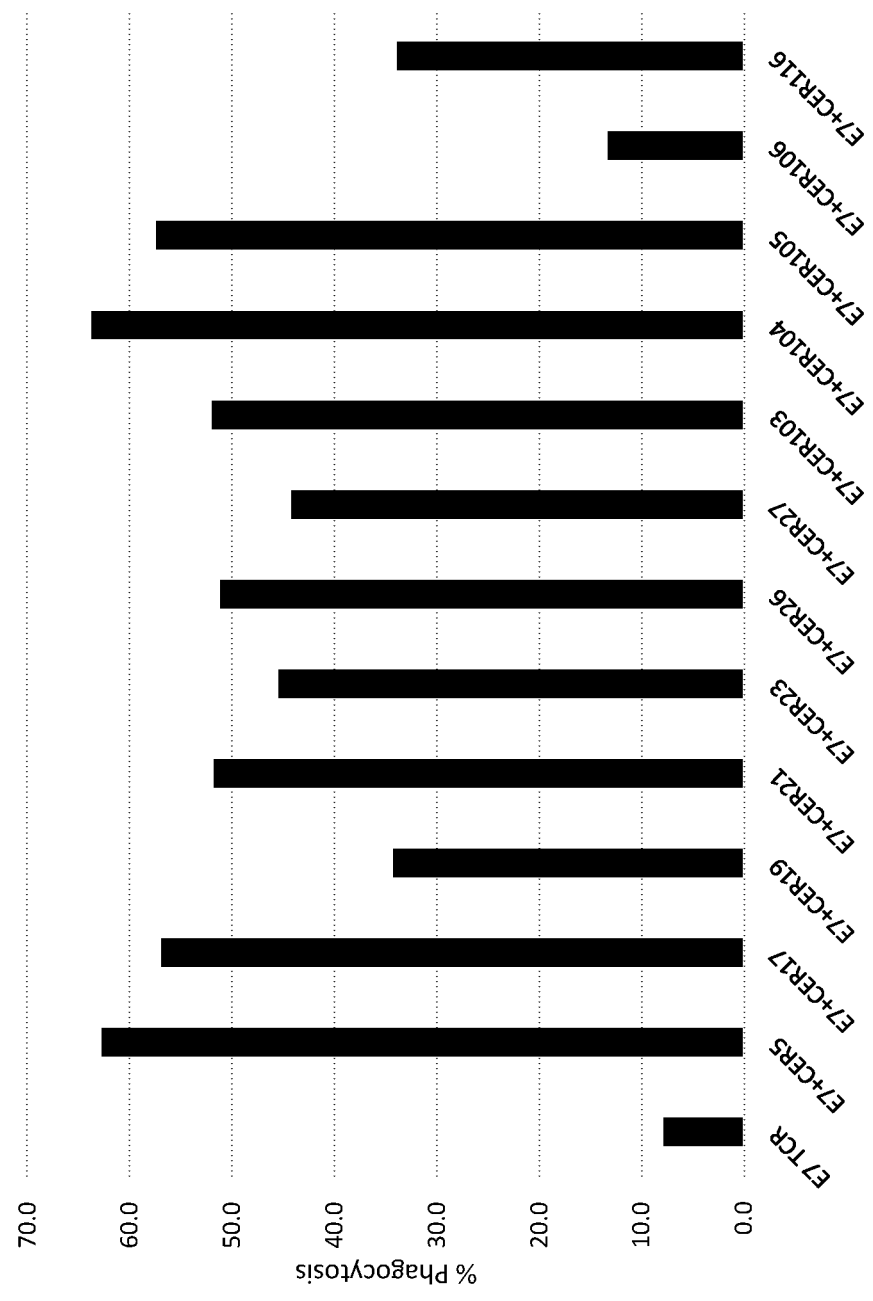
FIG. 36 is a bar graph representing quantification of CD4 T cell-CER mediated phagocytosis of SCC152 target cells. Results calculated as ((number of phagocytic target events)/ (total number of effectors))*100 from 3×3 40×images, 4 hours after initiation of co-culture assay. CD8 T cells transduced with HPV16 E7 TCR and CD4 T cells transduced with selected CERs (CER5, CER17, CER19, CER21, CER23, CER26, CER27, CER103B, CER104, CER105, CER106, or CER116) were co-cultured with SCC152 squamous head and neck carcinoma target cells at a 1:1:0.5 ratio for 4 hours and imaged. CD8 T cell/HPV16 E7 TCR+CD4 T cell/CER displayed enhanced SCC152 engulfment activity as compared to CD8 T cell/HPV16 E7 TCR alone.
Figure 37:
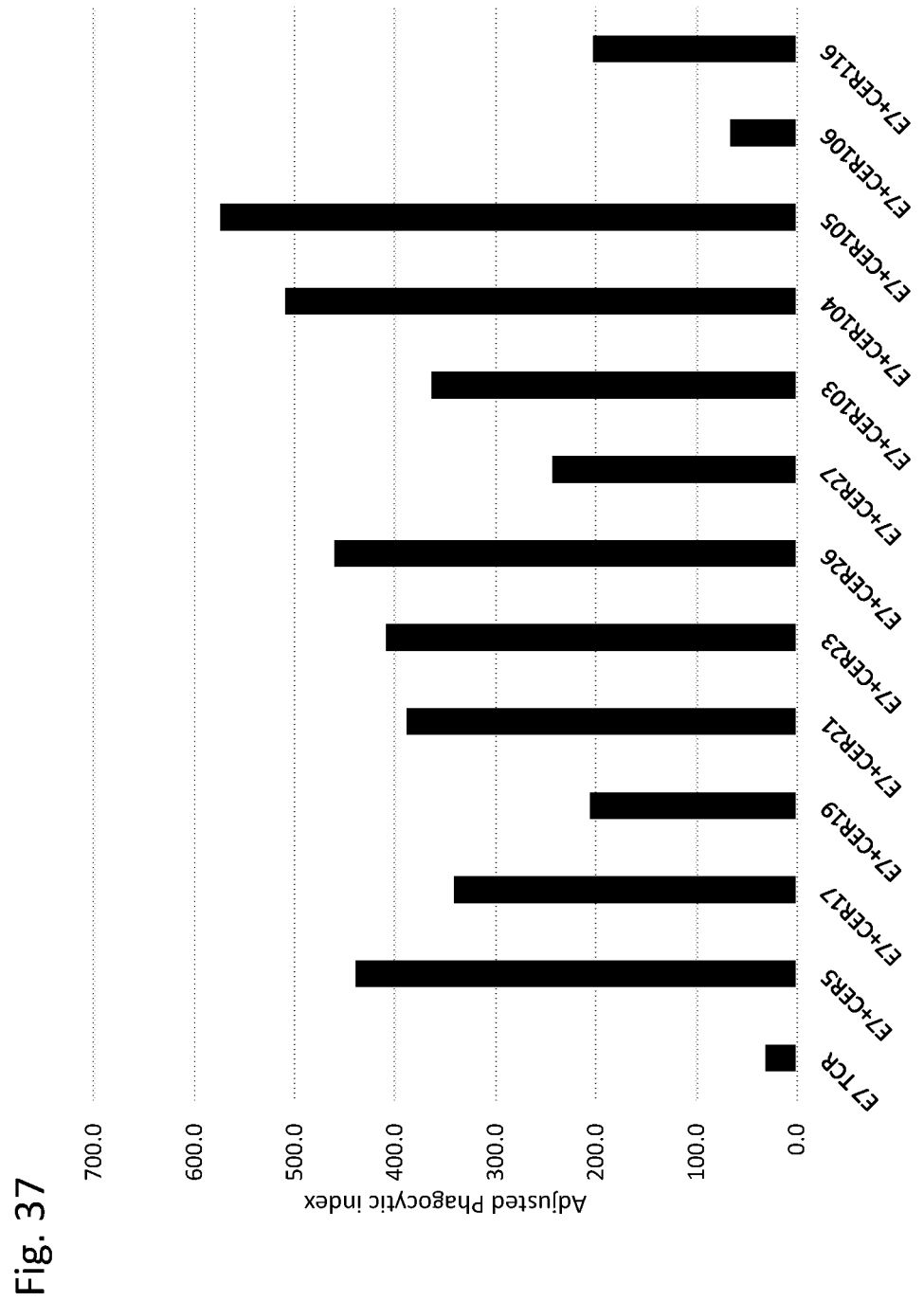
FIG. 37 is a bar graph representing quantification of CD4 T cell-CER mediated phagocytosis of SCC152 target cells. Results calculated as (median area ratio of target events in effector cells*% phagocytosis) from 3×3 40×images, 4 hours after initiation of co-culture assay. CD8 T cells transduced with HPV16 E7 TCR and CD4 T cells transduced with selected CERs (CER5, CER17, CER19, CER21, CER23, CER26, CER27, CER103B, CER104, CER105, CER106, or CER116) were co-cultured with SCC152 squamous head and neck carcinoma target cells at a 1:1:0.5 ratio for 4 hours and imaged. CD8 T cell/HPV16 E7 TCR+CD4 T cell/CER displayed enhanced SCC152 engulfment activity as compared to CD8 T cell/HPV16 E7 TCR alone.
Figure 38A:
FIGS. 38A-38F show vector maps for exemplary tandem expression cassettes. The tandem expression cassettes harbor both a HPV16 E7 specific TCR to induce a tumor (e.g., cervical) specific cytolytic response and a phosphatidylserine specific CER to elicit tumor specific phagocytic activity upon cytolysis-induced phosphatidylserine exposure.
Figure 38B:
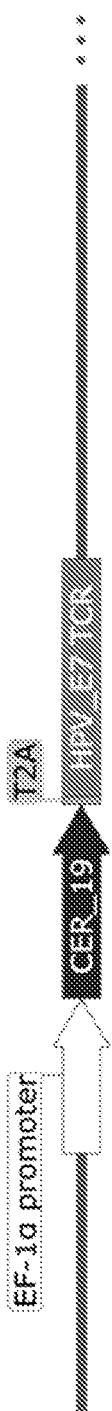
Figure 38C:
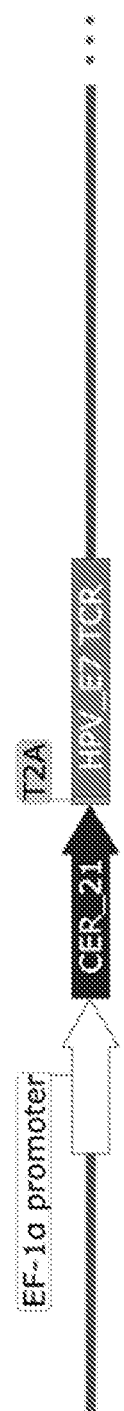
Figure 38D:
Figure 38E:
Figure 38F:

Phagocytic activity of CD4 T cell/CER+CD8 T cell/HPV16 E7 TCR combinations co-cultured with SCC152 cells was visualized and quantified using KEYENCE BZ-X710 fluorescence microscope, 20X objective and hybrid capture software. FIGS. 36-37 show that CD4+ T cells transduced with various CERs used in co-culture with CD8 T cells/HPV E7 TCR exhibited enhanced engulfment of SCC152 target cells over co-culture with control CD8 T cell/HPV16 E7 TCR alone.

Example 6

Construction of Tandem Expression Cassettes

A polynucleotide comprising the extracellular domain of the phosphatidylserine binding protein Tim4 and Tim4 transmembrane domain was fused to the intracellular signaling domain of TLR4 to create chimeric engulfment receptor "CER5" encoding an amino acid sequence of SEQ ID NO:81. A polynucleotide comprising the extracellular domain of the phosphatidylserine binding protein Tim4 and Tim4 transmembrane domain was fused to the intracellular signaling domain of TLR5 to create chimeric engulfment receptor "CER19" encoding an amino acid sequence of SEQ ID NO:98. A polynucleotide comprising the extracellular domain of the phosphatidylserine binding protein Tim4 was Tim4 transmembrane domain and TLR8 intracellular signaling domain to create chimeric engulfment receptor "CER21" encoding an amino acid sequence of SEQ ID NO:86. A polynucleotide comprising the extracellular domain of the phosphatidylserine binding protein Tim4 and Tim4 transmembrane domain was fused to the intracellular signaling domain of NFAM1 to create chimeric engulfment receptor "CER25" encoding an amino acid sequence of SEQ ID NO:159. A polynucleotide comprising the extracellular domain of the phosphatidylserine binding protein Tim4 and Tim4 transmembrane domain was fused to the intracellular signaling domain of TLR2 to create chimeric engulfment receptor "CER27" encoding an amino acid sequence of SEQ ID NO:93. A polynucleotide comprising the extracellular domain of the phosphatidylserine binding protein Tim4 and Tim4 transmembrane domain was fused to the intracellular signaling domain of Traf6 to create chimeric engulfment receptor "CER29" encoding an amino acid sequence of SEQ ID NO:102. A polynucleotide comprising the extracellular domain of the phosphatidylserine binding protein Tim4 and Tim4 transmembrane domain was fused to the intracellular signaling domain of Traf3 to create chimeric engulfment receptor "CER31" encoding an amino acid sequence of SEQ ID NO:124.

A polynucleotide encoding a TCRβ chain and a polynucleotide encoding a TCRα of an HPV16 E7 specific TCR (see, PCT Publication No. WO2015/184228) were fused using a sequence for P2A self-cleaving peptide there between. The TCR Vα domain comprises an amino acid sequence of SEQ ID NO:162, and the TCR Vβ region comprises an amino acid sequence of SEQ ID NO:160. The Cα domain comprises a cysteine substitution and LVL substitutions at positions 12, 14, and 15 and comprises an amino acid sequence of SEQ ID NO:163. The Cβ also comprises a cysteine substitution and comprises an amino acid sequence of SEQ ID NO:161. The encoded HPV16 E7 specific TCR comprises an amino acid sequence of SEQ ID NO:158. Amino acid sequences for the tandem expression constructs described in this example are provided in Table 2 (see, also FIGS. 38A-38F).

TABLE 2

Exemplary Tandem Expression Cassettes

| Name | Amino Acid Sequence | SEQ ID NO: # |
|---|---|---|
| CER5_T2A_HPV16 E7 TCR | MSKGLLLLWLVTELWWLYLTPAASEDTII GFLGQPVTLPCHYLSWSQSRNSMCWGKGS CPNSKCNAELLRTDGTRIISRKSTKYTLLG KVQFGEVSLTISNTNRGDSGVYCCRIEVPG WFNDVKKNVRLELRRATTTKKPTTTTRPT TTPYVTTTTPELLPTTVMTTSVLPTTTPPQT LATTAFSTAVTTCPSTTPGSFSQETTKGSAF TTESETLPASNHSQRSMMTISTDIAVLRPTG SNPGILPSTSQLTTQKTTLTTSESLQKTTKS HQINSRQTILIIACCVGFVLMVLLFLAFLKF YFHLMLLAGCIKYGRGENIYDAFVIYSSQD EDWVRNELVKNLEEGVPPFQLCLHYRDFIP GVAIAANIIHEGFHKSRKVIVVVSQHFIQSR WCIFEYEIAQTWQFLSSRAGIIFIVLQKVEK TLLRQQVELYRLLSRNTYLEWEDSVLGRHI FWRRLRKALLDGKSWNPEGTVGTGCNWQ EATSILEGGGEGRGSLLTCGDVEENPGPMA PGLLCWALLCLLGAGLVDAGVTQSPTHLI KTRGQQVTLRCSPKSGHDTVSWYQQALG QGPQFIFQYYEEEERQRGNFPDRFSGHQFP NYSSELNVNALLLGDSALYLCASSLGWRG GRYNEQFFGPGTRLTVLEDLRNVTPPKVSL FEPSKAEIANKQKATLVCLARGFFPDHVEL SWWVNGKEVHSGVCTDPQAYKESNYSYC LSSRLRVSATFWHNPRNHFRCQVQFHGLS EEDKWPEGSPKPVTQNISAEAWGRADCGI TSASYQQGVLSATILYEILLGKATLYAVLV STLVVMAMVKRKNSRAKRSGSGATNFSLL KQAGDVEENPGPMWGVFLLYVSMKGG TTGQNIDQPTEMTATEGAIVQINCTYQTSG FNGLFWYQQHAGEAPTFLSYNVLDGLEEK GRFSSFLSRSKGYSYLLLKELQMKDSASYL CASVDGNNRLAFGKGNQVVVIPNIQNPEP AVYQLKDPRSQDSTLCLFTDFDSQINVPKT MESGTFITDKCVLDMKAMDSKSNGAIAWS NQTSFTCQDIFKETNATYPSSDVPCDATLT EKSFETDMNLNFQNLLVIVLRILLLKVAGF NLLMTLRLWSS | SEQ ID NO: 164 |
| CER19_T2A_HPV16 E7 TCR | MSKGLLLLWLVTELWWLYLTPAASEDTII GFLGQPVTLPCHYLSWSQSRNSMCWGKGS CPNSKCNAELLRTDGTRIISRKSTKYTLLG KVQFGEVSLTISNTNRGDSGVYCCRIEVPG WFNDVKKNVRLELRRATTTKKPTTTTRPT TTPYVTTTTPELLPTTVMTTSVLPTTTPPQT LATTAFSTAVTTCPSTTPGSFSQETTKGSAF TTESETLPASNHSQRSMMTISTDIAVLRPTG SNPGILPSTSQLTTQKTTLTTSESLQKTTKS HQINSRQTILIIACCVGFVLMVLLFLAPLTK FRGFCFICYKTAQRLVFKDHPQGTEPDMY KYDAYLCFSSKDFTWVQNALLKHLDTQYS DQNRFNLCFEERDFVPGENRIANIQDAIWN SRKIVCLVSRHFLRDGWCLEAFSYAQGRC LSDLNSALIMVVVGSLSQYQLMKHQSIRGF VQKQQYLRWPEDFQDVGWFLHKLSQQIL KKEKEKKKDNNIPLQTVATISLEGGGEGRG SLLTCGDVEENPGPMAPGLLCWALLCLLG AGLVDAGVTQSPTHLIKTRGQQVTLRCSP KSGHDTVSWYQQALGQGPQFIFQYYEEEE RQRGNFPDRFSGHQFPNYSSELNVNALLLG DSALYLCASSLGWRGGRYNEQFFGPGTRL TVLEDLRNVTPPKVSLFEPSKAEIANKQKA TLVCLARGFFPDHVELSWWVNGKEVHSG VCTDPQAYKESNYSYCLSSRLRVSATFWH NPRNHFRCQVQFHGLSEEDKWPEGSPKPV TQNISAEAWGRADCGITSASYQQGVLSATI LYEILLGKATLYAVLVSTLVVMAMVKRK NSRAKRSGSGATNFSLLKQAGDVEENPGP MWGVFLLYVSMKGGTTGQNIDQPTEMT ATEGAIVQINCTYQTSGFNGLFWYQQHAG EAPTFLSYNVLDGLEEKGRFSSFLSRSKGY SYLLLKELQMKDSASYLCASVDGNNRLAF GKGNQVVVIPNIQNPEPAVYQLKDPRSQDS | SEQ ID NO: 165 |

TABLE 2-continued

Exemplary Tandem Expression Cassettes

| Name | Amino Acid Sequence | SEQ ID NO: # |
|---|---|---|
| | TLCLFTDFDSQINVPKTMESGTFITDKCVL DMKAMDSKSNGAIAWSNQTSFTCQDIFKE TNATYPSSDVPCDATLTEKSFETDMNLNFQ NLLVIVLRILLLKVAGFNLLMTLRLWSS | |
| CER21_ T2A_ HPV16 E7 TCR | MSKGLLLLWLVTELWWLYLTPAASEDTII GFLGQPVTLPCHYLSWSQSRNSMCWGKGS CPNSKCNAELLRTDGTRIISRKSTKYTLLG KVQFGEVSLTISNTNRGDSGVYCCRIEVPG WFNDVKKNVRLELRRATTTKKPTTTTRPT TTPYVTTTTPELLPTTVMTTSVLPTTTPPQT LATTAFSTAVTTCPSTTPGSFSQETTKGSAF TTESETLPASNHSQRSMMTISTDIAVLRPTG SNPGILPSTSQLTTQKTTLTTSESLQKTTKS HQINSRQTILIIACCVGFVLMVLLFLAFLHH LFYWDVWFIYNVCLAKVKGYRSLSTSQTF YDAYISYDTKDASVTDWVINELRYHLEES RDKNVLLCLEERDWDPGLAIIDNLMQSINQ SKKTVFVLTKKYAKSWNFKTAFYLALQRL MDENMDVIIFILLEPVLQHSQYLRLRQRIC KSSILQWPDNPKAEGLFWQTLRNVVLTEN DSRYNNMYVDSIKQYLEGGGEGRGSLLTC GDVEENPGPMAPGLLCWALLCLLGAGLV DAGVTQSPTHLIKTRGQQVTLRCSPKSGHD TVSWYQQALGQGPQFIFQYYEEEERQRGN FPDRFSGHQFPNYSSELNVNALLLGDSALY LCASSLGWRGGRYNEQFFGPGTRLTVLED LRNVTPPKVSLFEPSKAEIANKQKATLVCL ARGFFPDHVELSWWVNGKEVHSGVCTDP QAYKESNYSYCLSSRLRVSATFWHNPRNH FRCQVQFHGLSEEDKWPEGSPKPVTQNISA EAWGRADCGITSASYQQGVLSATILYEILL GKATLYAVLVSTLVVMAMVKRKNSRAKR SGSGATNFSLLKQAGDVEENPGPMWGVFL LYVSMKMGGTTGQNIDQPTEMTATEGAIV QINCTYQTSGFNGLFWYQQHAGEAPTFLS YNVLDGLEEKGRFSSFLSRSKGYSYLLLKE LQMKDSASYLCASVDGNNRLAFGKGNQV VVIPNIQNPEPAVYQLKDPRSQDSTLCLFT DFDSQINVPKTMESGTFITDKCVLDMKAM DSKSNGAIAWSNQTSFTCQDIFKETNATYP SSDVPCDATLTEKSFETDMNLNFQNLLVIV LRILLLKVAGFNLLMTLRLWSS | SEQ ID NO: 166 |
| CER25_ T2A_ HPV16 E7 TCR | MSKGLLLLWLVTELWWLYLTPAASEDTII GFLGQPVTLPCHYLSWSQSRNSMCWGKGS CPNSKCNAELLRTDGTRIISRKSTKYTLLG KVQFGEVSLTISNTNRGDSGVYCCRIEVPG WFNDVKKNVRLELRRATTTKKPTTTTRPT TTPYVTTTTPELLPTTVMTTSVLPTTTPPQT LATTAFSTAVTTCPSTTPGSFSQETTKGSAF TTESETLPASNHSQRSMMTISTDIAVLRPTG SNPGILPSTSQLTTQKTTLTTSESLQKTTKS HQINSRQTILIIACCVGFVLMVLLFLAFLLW NKKRMRGPGKDPTRKCPDPRSASSPKQHP SESVYTALQRRETEVYACIENEDGSSPTAK QSPLSQERPHRFEDDGELNLVYENLLEGGG EGRGSLLTCGDVEENPGPMAPGLLCWALL CLLGAGLVDAGVTQSPTHLIKTRGQQVTL RCSPKSGHDTVSWYQQALGQGPQFIFQYY EEEERQRGNFPDRFSGHQFPNYSSELNVNA LLLGDSALYLCASSLGWRGGRYNEQFFGP GTRLTVLEDLRNVTPPKVSLFEPSKAEIAN KQKATLVCLARGFFPDHVELSWWVNGKE VHSGVCTDPQAYKESNYSYCLSSRLRVSA TFWHNPRNHFRCQVQFHGLSEEDKWPEGS PKPVTQNISAEAWGRADCGITSASYQQGV LSATILYEILLGKATLYAVLVSTLVVMAM VKRKNSRAKRSGSGATNFSLLKQAGDVEE NPGPMWGVFLLYVSMKMGGTTGQNIDQP TEMTATEGAIVQINCTYQTSGFNGLFWYQ QHAGEAPTFLSYNVLDGLEEKGRFSSFLSR SKGYSYLLLKELQMKDSASYLCASVDGNN RLAFGKGNQVVVIPNIQNPEPAVYQLKDPR SQDSTLCLFTDFDSQINVPKTMESGTFITDK | SEQ ID NO: 167 |
| | CVLDMKAMDSKSNGAIAWSNQTSFTCQDI FKETNATYPSSDVPCDATLTEKSFETDMNL NFQNLLVIVLRILLLLKVAGFNLLMTLRLWS S | |
| CER27_ T2A_ HPV16 E7 TCR | MSKGLLLLWLVTELWWLYLTPAASEDTII GFLGQPVTLPCHYLSWSQSRNSMCWGKGS CPNSKCNAELLRTDGTRIISRKSTKYTLLG KVQFGEVSLTISNTNRGDSGVYCCRIEVPG WFNDVKKNVRLELRRATTTKKPTTTTRPT TTPYVTTTTPELLPTTVMTTSVLPTTTPPQT LATTAFSTAVTTCPSTTPGSFSQETTKGSAF TTESETLPASNHSQRSMMTISTDIAVLRPTG SNPGILPSTSQLTTQKTTLTTSESLQKTTKS HQINSRQTILIIACCVGFVLMVLLFLAFLHR FHGLWYMKMMWAWLQAKRKPRKAPSRN ICYDAFVSYSERDAYWVENLMVQELENFN PPPKLCLHKRDFIPGKWIIDNIIDSIEKSHKT VFVLSENFVKSEWCKYELDFSHFRLFDEN NDAAILILLEPIEKKAIPQRFCKLRHKIMNTK TYLEWPMDEAQREGFWVNLRAAIKSLEG GGEGRGSLLTCGDVEENPGPMAPGLLCWA LLCLLGAGLVDAGVTQSPTHLIKTRGQQV TLRCSPKSGHDTVSWYQQALGQGPQFIFQ YYEEEERQRGNFPDRFSGHQFPNYSSELNV NALLLGDSALYLCASSLGWRGGRYNEQFF GPGTRLTVLEDLRNVTPPKVSLFEPSKAEIA NKQKATLVCLARGFFPDHVELSWWVNGK EVHSGVCTDPQAYKESNYSYCLSSRLRVS ATFWHNPRNHFRCQVQFHGLSEEDKWPE GSPKPVTQNISAEAWGRADCGITSASYQQ GVLSATILYEILLGKATLYAVLVSTLVVMA MVKRKNSRAKRSGSGATNFSLLKQAGDV EENPGPMWGVFLLYVSMKMGGTTGQNID QPTEMTATEGAIVQINCTYQTSGFNGLFW YQQHAGEAPTFLSYNVLDGLEEKGRFSSFL SRSKGYSYLLLKELQMKDSASYLCASVDG NNRLAFGKGNQVVVIPNIQNPEPAVYQLK DPRSQDSTLCLFTDFDSQINVPKTMESGTFI TDKCVLDMKAMDSKSNGAIAWSNQTSFT CQDIFKETNATYPSSDVPCDATLTEKSFET DMNLNFQNLLVIVLRILLLKVAGFNLLMTL RLWSS | SEQ ID NO: 168 |
| CER29_ T2A_ HPV16 E7 TCR | MSKGLLLLWLVTELWWLYLTPAASEDTII GFLGQPVTLPCHYLSWSQSRNSMCWGKGS CPNSKCNAELLRTDGTRIISRKSTKYTLLG KVQFGEVSLTISNTNRGDSGVYCCRIEVPG WFNDVKKNVRLELRRATTTKKPTTTTRPT TTPYVTTTTPELLPTTVMTTSVLPTTTPPQT LATTAFSTAVTTCPSTTPGSFSQETTKGSAF TTESETLPASNHSQRSMMTISTDIAVLRPTG SNPGILPSTSQLTTQKTTLTTSESLQKTTKS HQINSRQTILIIACCVGFVLMVLLFLAFLMS LLNCENSCGSSQSESDCCVAMASSCSAVT KDDSVGGTASTGNLSSSFMEEIQGYDVEFD PPLESKYECPICLMALREAVQTPCGHRFCK ACIIKSIRDAGHKCPVDNEILLENQLFPDNF AKREILSLMVKCPNEGCLHKMELRHLEDH QAHCEFALMDCPQCQRPPQKFHININIHILKD CPRRQVSCDNCAASMAFEDKEIHDQNCPL ANVICEYCNTILIREQMPNHYDLDCPTAPIP CTFSTFGCHEKMQRNHLARHLQENTQSHM RMLALEGGGEGRGSLLTCGDVEENPGPMA PGLLCWALLCLLGAGLVDAGVTQSPTHLI KTRGQQVTLRCSPKSGHDTVSWYQQALG QGPQFIFQYYEEEERQRGNFPDRFSGHQFP NYSSELNVNALLLGDSALYLCASSLGWRG GRYNEQFFGPGTRLTVLEDLRNVTPPKVSL FEPSKAEIANKQKATLVCLARGFFPDHVEL SWWVNGKEVHSGVCTDPQAYKESNYSYC LSSRLRVSATFWHNPRNHFRCQVQFHGLS EEDKWPEGSPKPVTQNISAEAWGRADCGI TSASYQQGVLSATILYEILLGKATLYAVLV STLVVMAMVKRKNSRAKRSGSGATNFSLL | SEQ ID NO: 169 |

TABLE 2-continued

Exemplary Tandem Expression Cassettes

| Name | Amino Acid Sequence | SEQ ID NO: # |
|---|---|---|
| | KQAGDVEENPGPMWGVFLLYVSMKMGG TTGQNIDQPTEMTATEGAIVQINCTYQTSG FNGLFWYQQHAGEAPTFLSYNVLDGLEEK GRFSSFLSRSKGYSYLLLKELQMKDSASYL CASVDGNNRLAFGKGNQVVVIPNIQNPEP AVYQLKDPRSQDSTLCLFTDFDSQINVPKT MESGTFITDKCVLDMKAMDSKSNGAIAWS NQTSFTCQDIFKETNATYPSSDVPCDATLT EKSFETDMNLNFQNLLVIVLRILLLKVAGF NLLMTLRLWSS | |
| CER31_ T2A_ HPV16 E7 TCR | MSKGLLLLWLVTELWWLYLTPAASEDTII GFLGQPVTLPCHYLSWSQSRNSMCWGKGS CPNSKCNAELLRTDGTRIISRKSTKYTLLG KVQFGEVSLTISNTNRGDSGVYCCRIEVPG WFNDVKKNVRLELRRATTTKKPTTTTRPT TTPYVTTTTPELLPTTVMTTSVLPTTTPPQT LATTAFSTAVTTCPSTTPGSFSQETTKGSAF TTESETLPASNHSQRSMMTISTDIAVLRPTG SNPGILPSTSQLTTQKTTLTTSESLQKTTKS HQINSRQTILIIACCVGFVLMVLLFLAFLME SSKKMDSPGALQTNPPLKLHTDRSAGTPVF VPEQGGYKEKFVKTVEDKYKCEKCHLVL CSPKQTECGHRFCESCMAALLSSSSPKCTA CQESIVKDKVFKDNCCKREILALQIYCRNE SRGCAEQLMLGHLLVHLKNDCHFEELPCV RPDCKEKVLRKDLRDHVEKACKYREATCS HCKSQVPMIALQKHEDTDCPCVVVSCPHK CSVQTLLRSELSAHLSECVNAPSTCSFKRY GCVFQGTNQQIKAHEASSAVQHVNLLKE WSNSLEKKVLEGGGEGRGSLLTCGDVEEN PGPMAPGLLCWALLCLLGAGLVDAGVTQ SPTHLIKTRGQQVTLRCSPKSGHDTVSWY QQALGQGPQFIFQYYEEEERQRGNFPDRFS GHQFPNYSSELNVNALLLGDSALYLCASSL GWRGGRYNEQFFGPGTRLTVLEDLRNVTP PKVSLFEPSKAEIANKQKATLVCLARGFFP DHVELSWWVNGKEVHSGVCTDPQAYKES NYSYCLSSRLRVSATFWHNPRNHFRCQVQ FHGLSEEDKWPEGSPKPVTQNISAEAWGR ADCGITSASYQQGVLSATILYEILLGKATL YAVLVSTLVVMAMVKRKNSRAKRSGSGA TNFSLLKQAGDVEENPGPMWGVFLLYVS MKMGGTTGQNIDQPTEMTATEGAIVQINC TYQTSGFNGLFWYQQHAGEAPTFLSYNVL DGLEEKGRFSSFLSRSKGYSYLLLKELQMK DSASYLCASVDGNNRLAFGKGNQVVVIPN IQNPEPAVYQLKDPRSQDSTLCLFTDFDSQI NVPKTMESGTFITDKCVLDMKAMDSKSNG AIAWSNQTSFTCQDIFKETNATYPSSDVPC DATLTEKSFETDMNLNFQNLLVIVLRILLL KVAGFNLLMTLRLWSS | SEQ ID NO: 170 |

A selected CER polynucleotide and the HPV16 E7 TCR polynucleotide were inserted into the same pLenti lentiviral vector with a T2A sequence (encoding an amino acid sequence of SEQ ID NO:156) there between. (see, FIGS. 1A-1G). Peripheral blood was collected by venipuncture from a human donor, and human peripheral blood mononuclear cells (PBMCs) were isolated by density gradient centrifugation using lymphocyte separation media. CD8+ T cells were enriched from PBMCs using a commercially available isolation kit and activated with anti-CD3 and anti-CD28 in Complete Cell Growth Media. 50 μl of viral vector expressing the CER-HPV16 E7 TCR combination were diluted in 0.5 ml Complete Cell Growth Media and added to the CD8+ T cells. The transduced T cells were then centrifuged at 270×g rpm for 1 hour in a 32° C. pre-warmed centrifuge. The T cells were incubated for 24 hours at 37° C. T cells were expanded for another 72 hours in Complete Cell Growth Media, de-beaded, and allowed to expand x 5 days prior to being utilized for functional assays.

Figure 39:
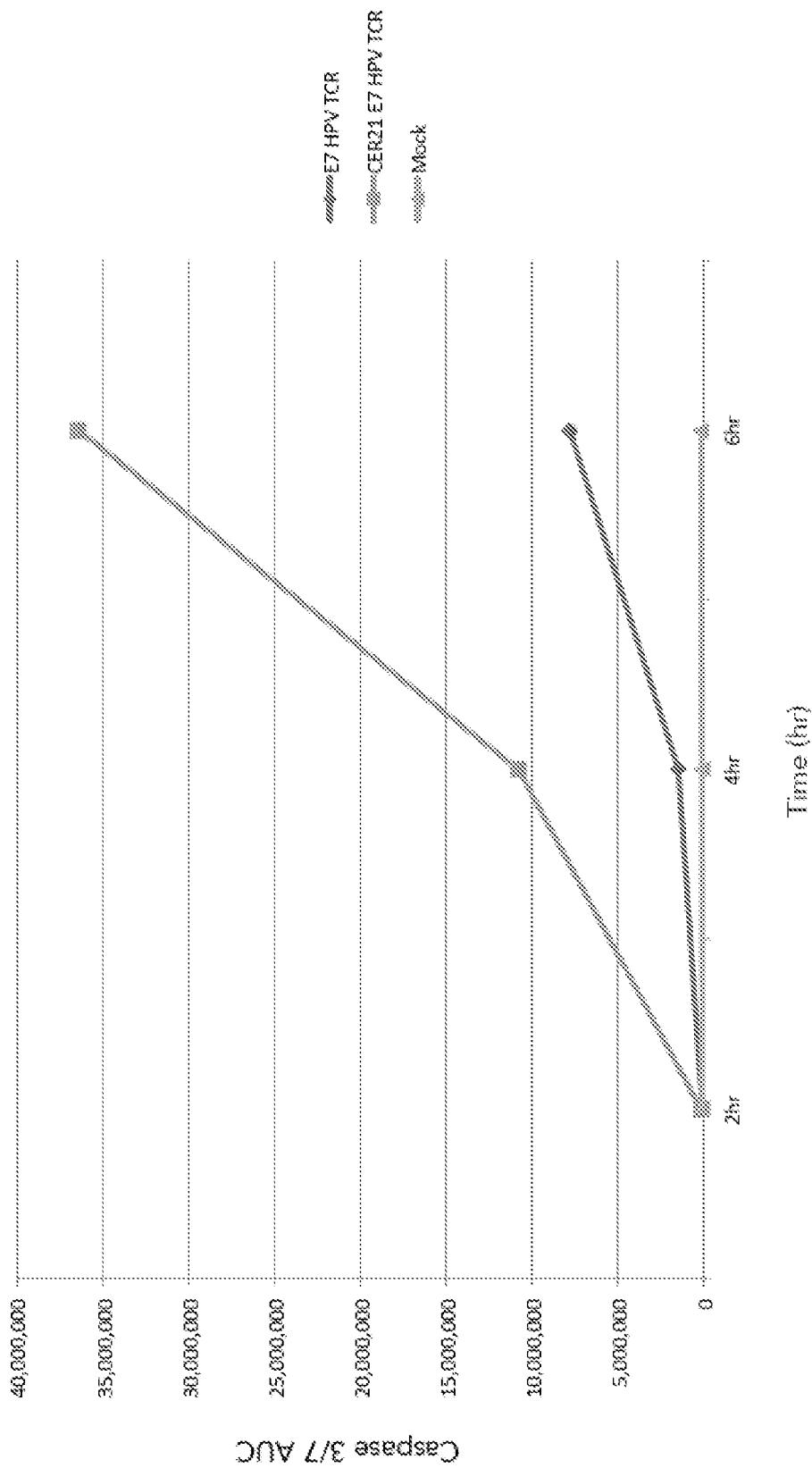
FIG. 39 is a line graph showing Caspase 3/7 induction over time in HPV16 E7+SCC152 cells following co-culture with human primary CD8 T cells transduced with a lentiviral vector comprising HPV16 E7 TCR and Chimeric Engulfment Receptor 21 (CER21) separated by a T2A sequence. The HPV16 E7 TCR and CER21 confers enhanced target cell killing capacity to host CD8 T cells as compared to host CD8 T cells comprising HPV16 E7 TCR alone. Effector CD8+ T cells were incubated with target SCC152 cells at a 1:1 ratio. Total caspase 3/7 fluorescence was quantified over time.
Figure 40:
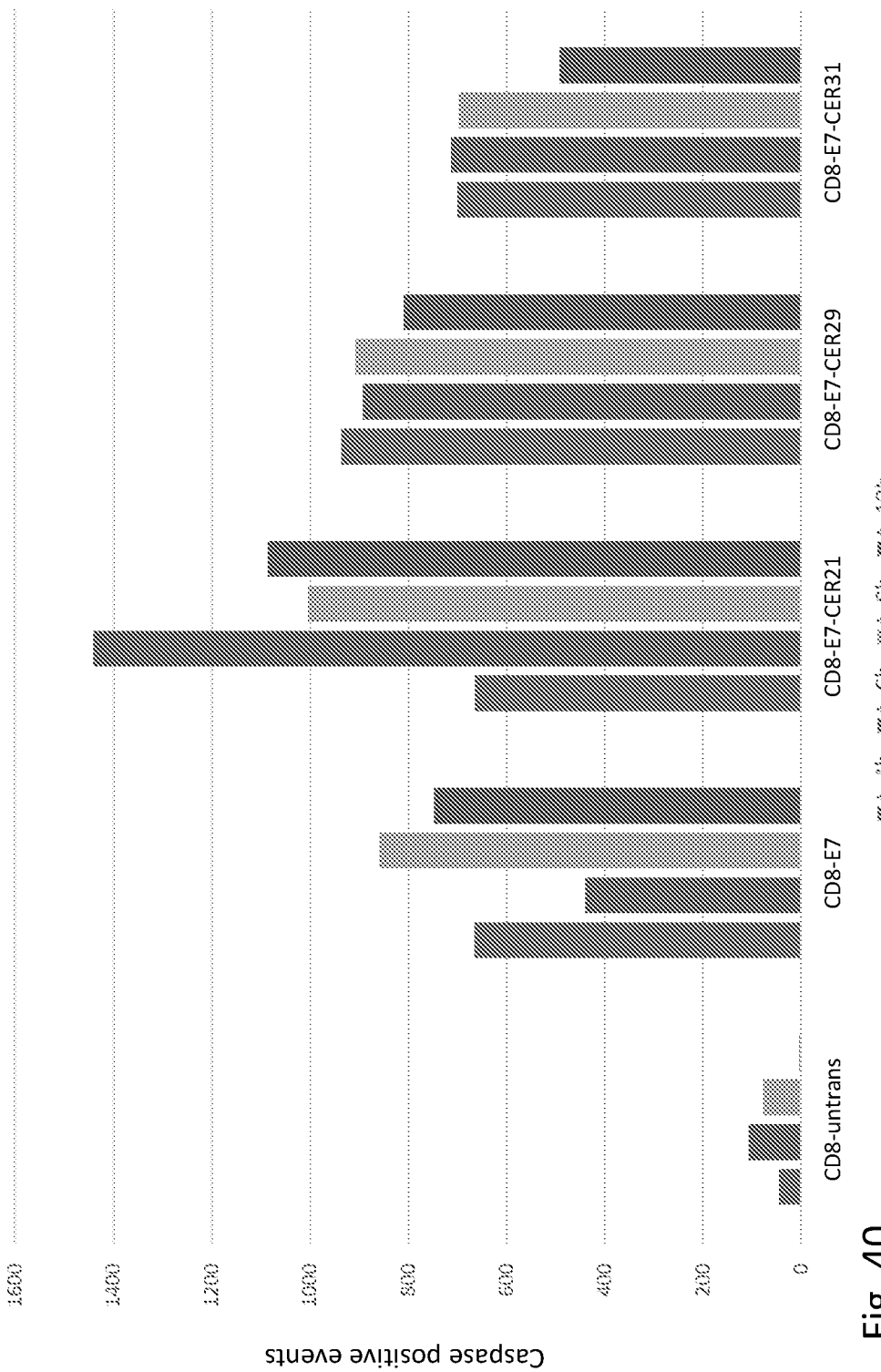
FIG. 40 is a bar graph showing caspase 3/7 induction in HPV16 E7+SCC152 cells upon co-culture with CD8 T cells transduced with a lentiviral vector comprising HPV16 E7 TCR and CER separated by a T2A sequence, Mock transduced cells were used as a negative control. Labeling of the IncuCyte® caspase 3/7 red apoptosis reagent enables detection of cells undergoing apoptosis (red fluorescence). Measurements were taken over time from co-culture experiments comparing CD8 transduced with a tandem CER- HPV16 E7 TCR cassette to HPV16 E7 TCR control.

Cd8 T Cells Transduced with Cer-Tcr Tandem Expression Cassette Exhibit ANTIGEN SPECIFIC CYTOLYTIC AND PHAGOCYTIC ACTIVITY Cytotoxic activity of tandem expression cassette transduced CD8+ T cells was detected using a caspase 3/7 apoptosis reagent (IncuCyte®) that couples the activated caspase 3/7 recognition motif with a red reagent that fluoresces upon cleavage. The fluorescent signal was measured using fluorescent microscopy. Transduced CD8+ T cells were co-cultured with HPV16 E7+ head and neck squamous cell carcinoma cells (SCC152) at a 1:1 ratio, and caspase 3/7 apoptosis reagent was added to the co-culture. CD8+ T cells comprising CER21-HPV16 E7 TCR tandem expression cassette exhibit cytotoxic activity toward SCC152 cells. The cytotoxic response by the CD8+ T cells transduced with CER21-HPV16 E7 TCR tandem expression cassette appears to be exponentially higher than the CD8+ T cells comprising HPV16 E7 TCR alone by 6 hours (see, FIG. 39). CD8+ T cells transduced with CER21-HPV16 E7 TCR tandem expression cassette, CER29-HPV16 E7 TCR tandem expression cassette, or CER31-HPV16 E7 TCR tandem expression cassette were co-cultured with SCC152 cells at a target:effector cell ratio of 1:1. The caspase 3/7 apoptosis reagent was added to the co-culture, and cytotoxic activity was measured over time by measuring fluorescence (see, FIG. 40). Control samples were CD8 T cells transduced with HPV16 E7 TCR alone or mock transduced T cells.

Figure 41:
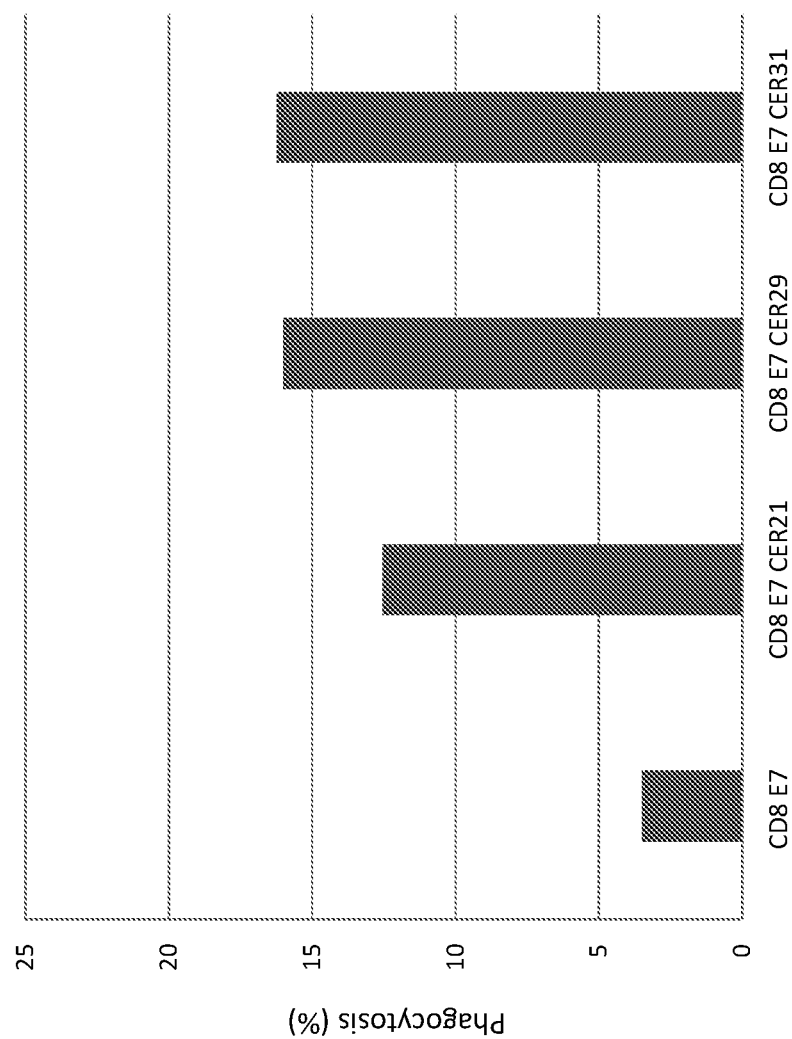
FIG. 41 is a bar graph showing quantification of phagocytosis after 6 hours of co-culture of CD8+ T cells transduced with HPV16 E7 TCR, CER21-HPV16 E7 TCR expression cassette, CER29-HPV16 E7 TCR expression cassette, or CER31-HPV16 E7 TCR expression cassette. Quantification of phagocytosis was performed by the hybrid capture software in Keyence BZ-X710 imaging system wherein % phagocytosis was determined by identifying the number of red fluorescent targets (SCC152 cells) inside blue stained effector cells (cell trace violet labeled CD8+ T cells transduced with CER-HPV16 E7 TCR expression cassette—# of red internalized/# of blue)×100.

Phagocytic activity of tandem expression cassette transduced CD8+ T cells was detected by co-culturing tandem expression cassette transduced CD8+ T cells with SCC152 cells for 6 hours at a 1:1 ratio. Phagocytic events were visualized and quantified using KEYENCE BZ-X710 fluorescence microscope, 20X objective and hybrid capture software. CD8+ T cells transduced with CER21-HPV16 E7 TCR, CER29-HPV16 E7 TCR, or CER31-HPV16 E7 TCR tandem cassettes were capable of phagocytosing SCC152 cells (see, FIG. 41). Rac1 inhibitor NSC23766 (50 μM) was also added to co-culture experiments and in vitro phagocytosis was measured. Treatment with Rac1 inhibitor revealed that the engulfment of SCC152 cells by the CER21-HPV16 E7 TCR, CER29-HPV16 E7 TCR, or CER31-HPV16 E7 TCR transduced T cells occurred in a Rac1-dependent manner (data not shown). CD8+ T cells transduced with CER21-HPV16 E7 TCR tandem expression cassette engulfed streptavidin coated latex beads, to which were coated with biotin-conjugated phosphatidylserine (data not shown). After about 30 minutes of incubation, the phosphatidylserine coated beads could be visualized inside the CER21-HPV16 E7 TCR+ T cells.

Figure 42:
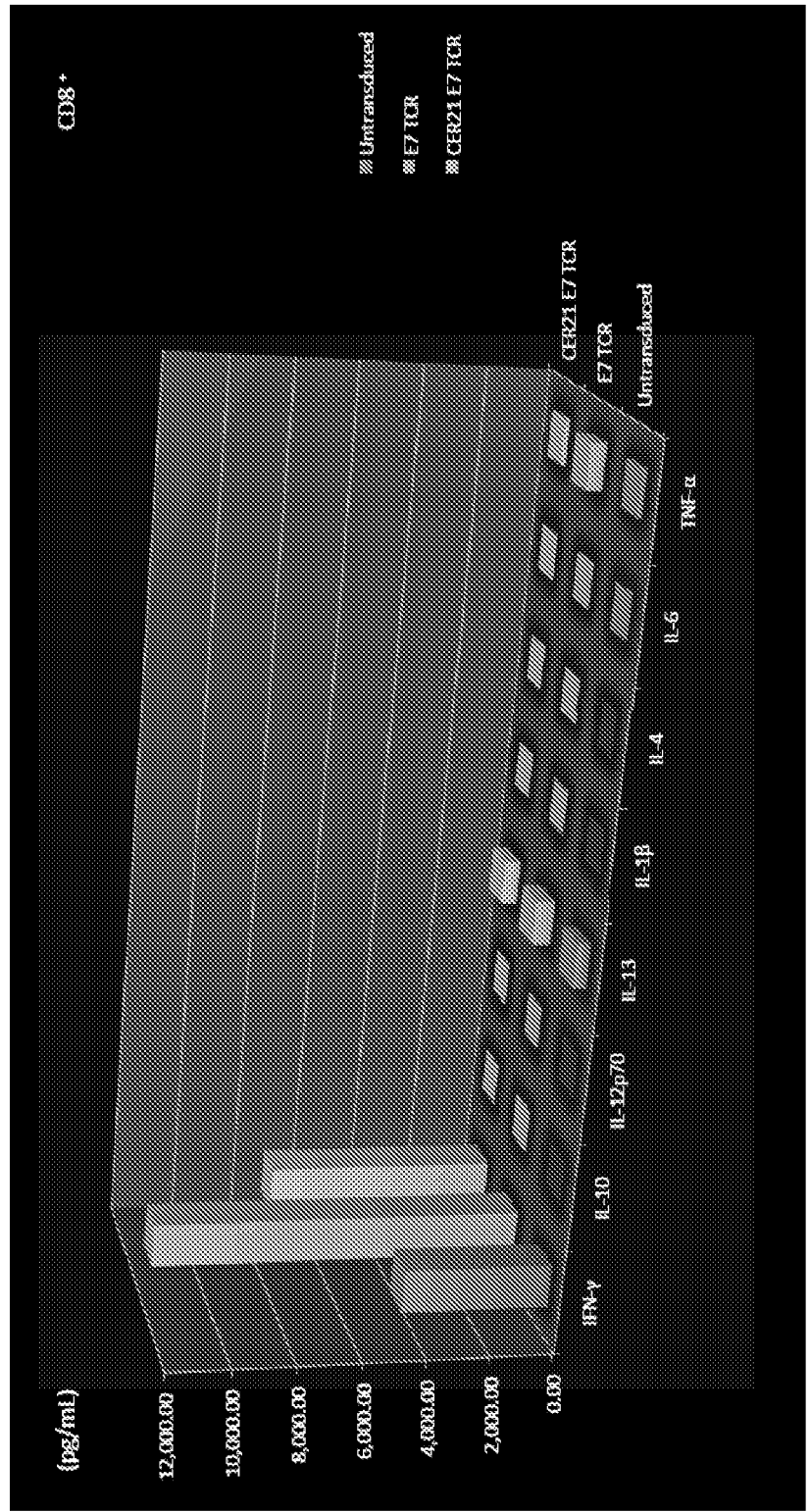
FIG. 42 is a 3D bar graph showing cytokine secretion patterns of CD8 T cells transduced with CER21-HPV16 E7 TCR expression cassette or HPV16 E7 TCR alone and co-cultured with SCC152 target cells. To determine cytokine secretion patterns, CER21-HPV16 E7 TCR modified CD8 T cells were co-cultured with SCC152 target cells. Antigen-specific cytokine secretion was determined by measuring cytokine concentrations in the cell supernatants from each co-culture using a mesoscale multi-array cytokine plate. The following cytokines were measured in the assay: IFNγ, IL-2, TNFα, IL-4, IL-6, IL-12b, IL-13, IL-1b, and IL-10. CD8 T cells transduced with CER21-HPV16 E7 TCR expression cassette exhibit antigen specific effector function as shown by cytokine secretion, e.g., IFNγ.

Cytokine response of CD8+ T cells transduced with CER21-HPV16 E7 TCR tandem expression cassette was measured during co-culture experiments with SCC152 cells by sampling the cellular supernatants and showed that CER21-HPV16 E7 TCR+ T cells exhibit antigen specific effector function as measured by IFNγ response (see, FIG. 42).

Example 7

Cer Enhancement of Molecularly Targeted Cancer Therapy

This example describes approaches to utilize molecularly targeted therapy in combination with CER-expressing cells, for the treatment of cancer. In this scenario, a small molecule inhibitor targeting a first molecule, e.g., a driver-oncogene, induces expression or membrane exposure of a second target molecule, which is recognized by a CER-expressing cell. This drug-inducible target may be a pro-engulfment marker (e.g., phosphatidylserine). Upon recognition and binding of the induced second target molecule, CER-expressing cells elicit anti-tumor activity via activation of phagocytic signal transduction cascades. This approach can be utilized to enhance molecular targeted therapy for hematologic and solid tumors.

Cer Enhancement of Egfr Inhibitors

~30-40% of non-small cell lung cancer (NSCLC) in Japanese patients and ~15% of harbor an epidermal growth factor (EGFR)-activating mutation. For the treatment of EGFR-mutated NSCLC, EGFR-tyrosine kinase inhibitors (EGFR-TKIs) have been developed that inhibit EGFR-induced downstream signaling pathways. Clinical studies show improved prognoses with EGFR inhibitors in patients with EGFR-mutated lung cancer, extending overall survival of advanced NSCLC from ~ 1 year to 2-3 years. EGFR inhibitors may be used in the treatment of other cancers possessing an activating EGFR mutation, including colorectal cancer, breast cancer, ovarian cancer, pancreatic cancer, and glioblastoma. Clinical oncology studies demonstrate that even with the most potent targeted therapeutics the vast majority of patients that receive drugs designed to interfere with a specific gene or protein eventually relapse, often with new tumors that no longer respond to therapy.

CER-modified cells that were engineered to recognize pro-engulfment marker phosphatidylserine were administered in conjunction with various EGFR inhibitors, Osimeritinib, Brigatinib, Erlotinib, and Gefitinib, to determine whether CER therapy could enhance EGFR targeted therapy.

Figure 43A:
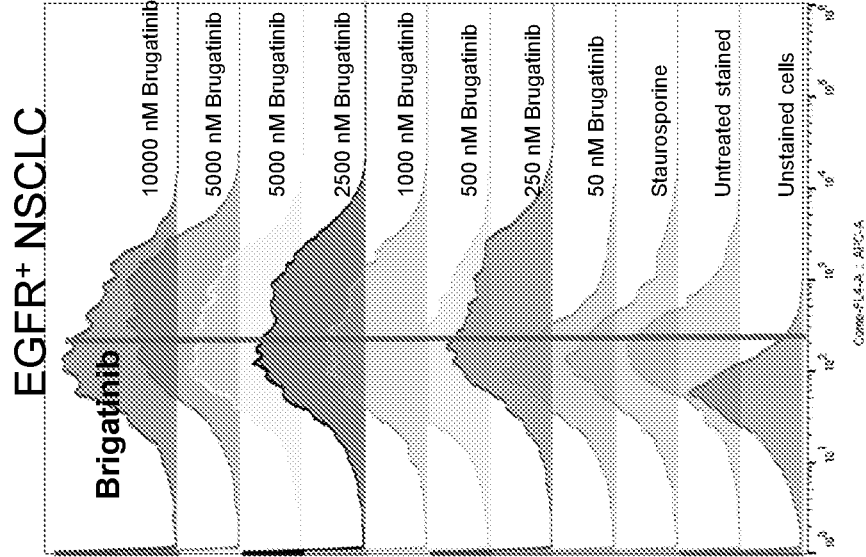
FIGS. 43A-43B show that EGFR-kinase inhibitors (FIG. 43A) Osimeritinib and (FIG. 43B) Brigatinib elicit a secondary, pro-engulfment marker on HCC159 cells upon drug exposure as detected by a Tim4-IgG1 Fc recombinant fusion protein.
Figure 43B:
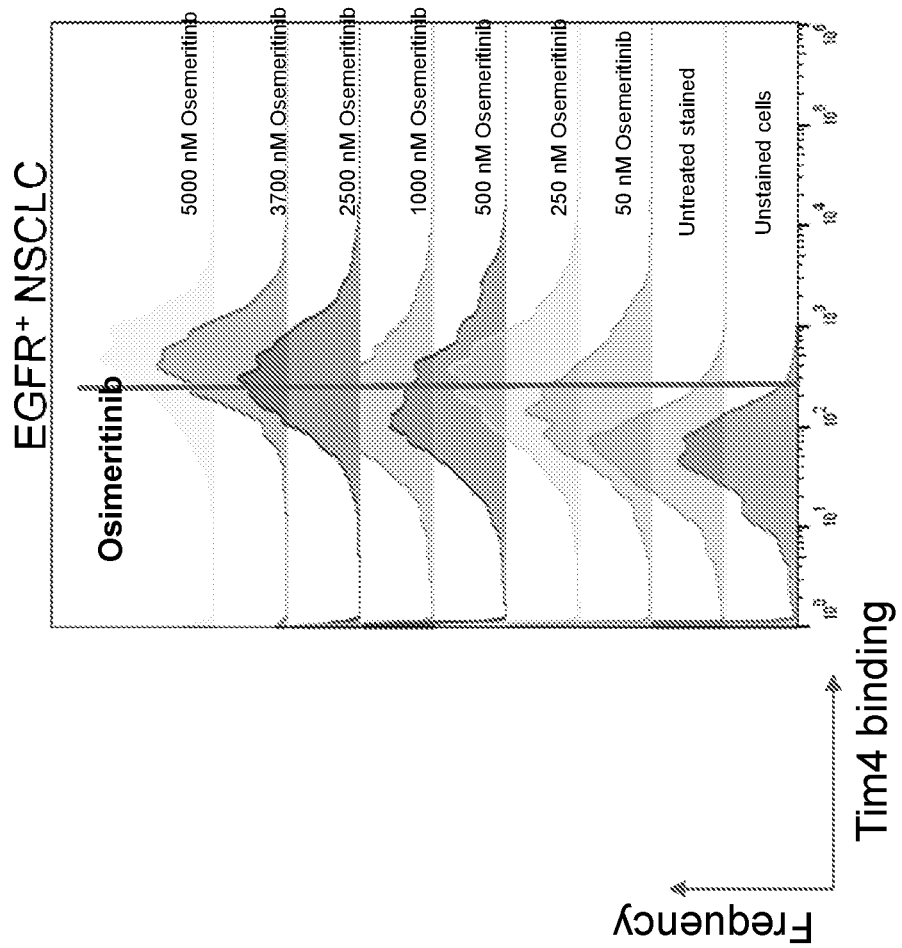
Figure 44B:
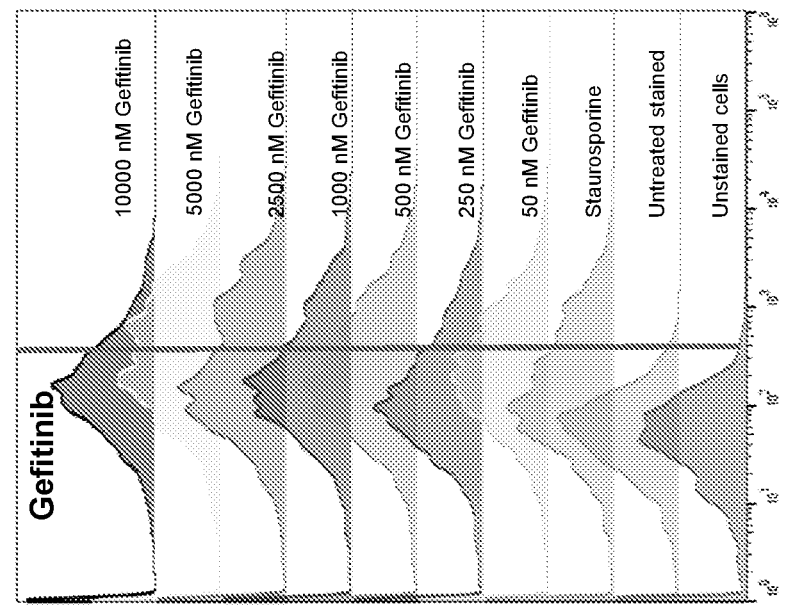
FIGS. 44A-44B show that EGFR-kinase inhibitors (FIG. 44A) Erlotinib and (FIG. 44B) Gefitinib elicit a secondary, pro-engulfment marker on HCC159 cells upon drug exposure as detected by a Tim4-IgG1 Fc recombinant fusion protein.
Figure 44A:
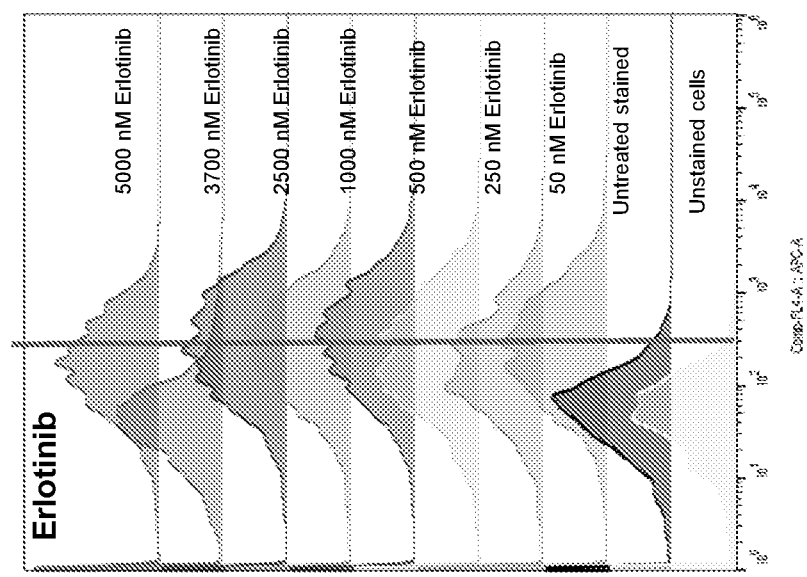

HCC159 lung adenocarcinoma cells harbor an EGFR mutation and are sensitive to EGFR inhibition. HCC159 cells were treated for 12 hours in the presence of EGFR kinase inhibitor Osimeritinib, Brigatinib, Erlotinib, or Gefitinib at increasing concentrations (50 nM, 250 nM, 500 nM, 1000 nM, 2500 nM, 3700 nM, or 5000 nM for Osimeritinib, Brigatinib, and Erlotinib; 50 nM, 250 nM, 500 nM, 1000 nM, 2500 nM, 5000 nM, 10000 nM for Brigatinib) and incubated with a Tim4-IgG$_1$ Fc recombinant fusion protein to evaluate for pro-engulfment marker (phosphatidylserine) exposure on target cells following EGFR inhibitor treatment. Increasing concentrations of Osimeritinib (FIG. 43A), Brigatinib (FIG. 43B), Erlotinib (FIG. 44A), and Gefitinib (FIG. 44B) enhanced surface staining with Tim4-IgG$_1$ Fc fusion protein, indicating that exposure of the phosphatidylserine target molecule is EGFR drug inducible.

H1975 lung adenocarcinoma cells harboring an EGFR mutation were co-cultured with CER123- or CER126-modified or Mock-transduced (vector only) CD4+ T cells with increasing concentrations of Osimeritinib. CER123 has a polypeptide sequence as set forth in SEQ ID NO:150 and comprises a Tim4 binding domain, Tim4 transmembrane domain, and an engulfment signaling domain comprising a primary engulfment signaling domain comprising a TLR2 signaling domain and a secondary engulfment signaling domain comprising a TRAF6 signaling domain. CER126 has a polypeptide sequence as set forth in SEQ ID NO:174 and comprises a Tim4 binding domain, Tim4 transmembrane domain, and an engulfment signaling domain comprising a primary engulfment signaling domain comprising a TLR2 signaling domain and a secondary engulfment signaling domain comprising a TRAF2 signaling domain. CD4 T cells were transduced with a lentiviral vector comprising CER123 or CER126 nucleic acid and truncated EGFR (transduction marker) nucleic acid. Assays were performed using CER modified T cells purified by FACS using an EGFR specific antibody 7 days after activation using CD3 & CD28 microbeads. CER modified T cells and H1975 cells were co-cultured at effector:target cell ratio (E:T) of 1:1, 2:1, or 5:1. After 48 hours of co-culture in the presence of Osimeritinib (0, 250 nM, 500 nM, or 1000 nM), T cells were washed away, and the number of viable H1975 cells were quantified using a calorimetric MTT assay. Cell viability experiments were performed in triplicate and presented as % of control (FIG. 45A). Bright field images of co-culture experiments demonstrate loss of H1975 cells in the presence of Osimeritinib (500 nM)+CER126-modified T cells (FIG. 45B, right panel) compared to control T cells (vector alone) (FIG. 45B, left panel). Thus, in the presence of an EGFR kinase inhibitor, CER-expressing T cells targeting a pro-engulfment marker demonstrate dose-dependent cell killing responses.

Figure 46:
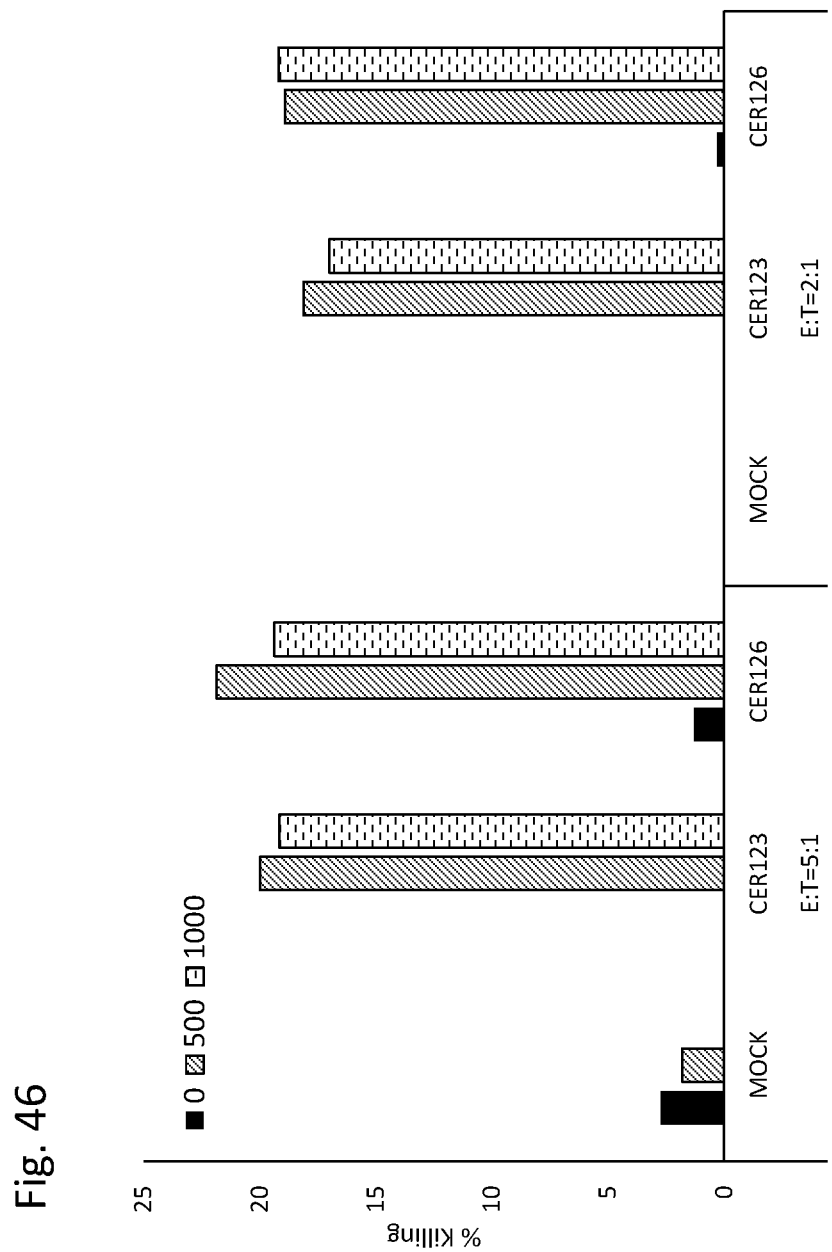
FIG. 46 shows that in the presence of osimeritinib (0, 500, or 1000 nM), CER123- or CER126-expressing cells demonstrate inducible, dose-dependent killing of NSCLC cells. The left bar graph shows data using an effector:target cell ratio of 5:1, and the right bar graph shows data using an effector:target ratio of 2:1.

H1975 NSCLC cells were co-cultured with CER123- or CER126-expressing CD4+ T cells with increasing concentrations of Osimeritnib (0, 500 nM, or 1000 nM). Mock-transduced (vector only) T cells were used as control. Assays were performed using CER modified T cells purified by FACS using an EGFR specific antibody 7 days after activation using CD3 & CD28 microbeads. CER modified T cells and H1975 cells were co-cultured at effector:target cell ratios of 2:1 or 5:1. After 18 hours of co-culture, bulk supernatants were evaluated using LDH-based cytotoxicity assay. In the presence of Osimeritinib, CER123- or CER126-expressing T cells demonstrate inducible cell killing responses (FIG. 46).

Figure 47:
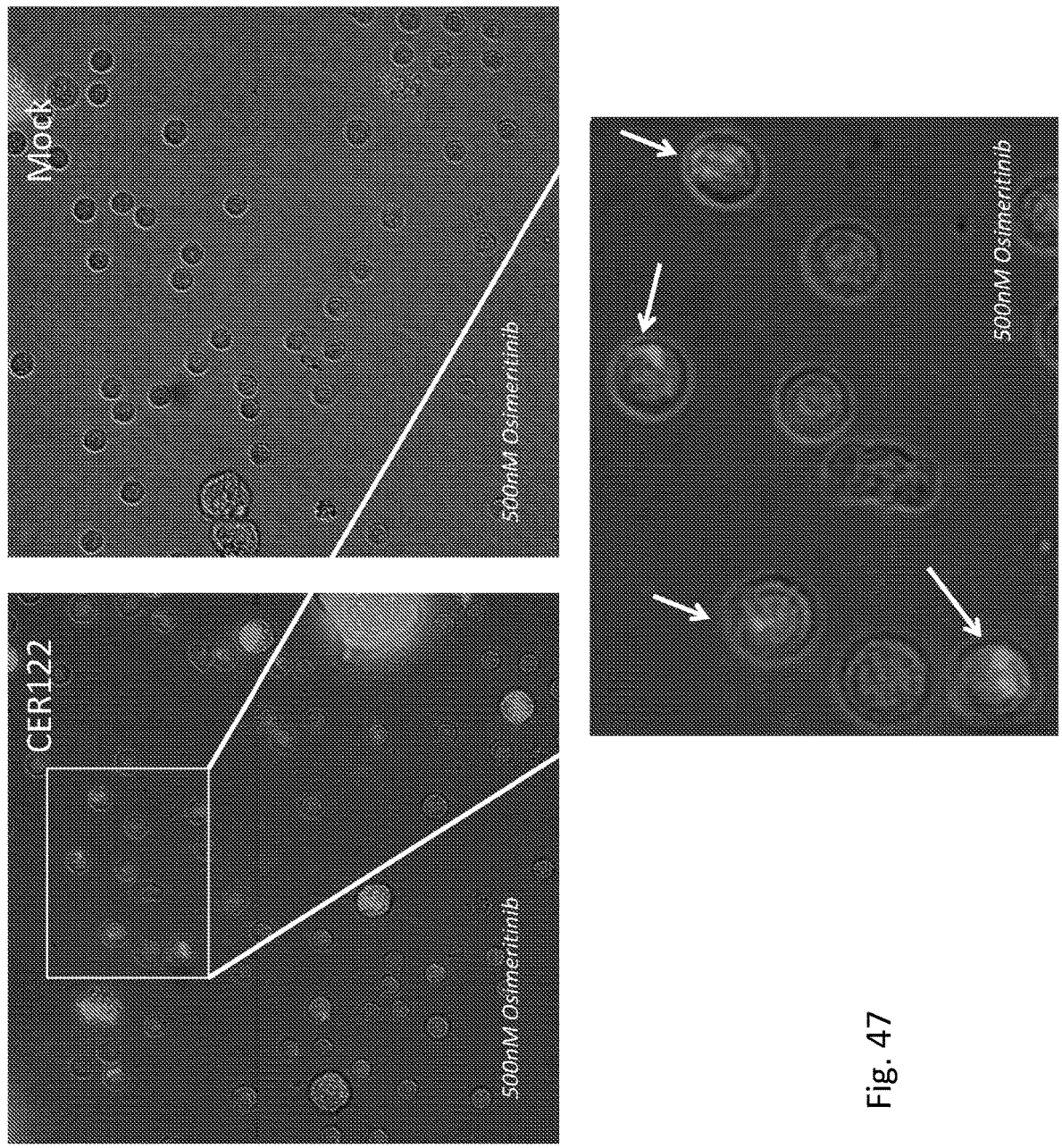
FIG. 47 shows fluorescent micrographs of phagocytic elimination of EGFR-mutated NSCLC cells by CER122-modified cells following treatment with 500 nM osimeritinib (left panel) and lack of phagocytosis of NSCLC cells by mock transduced cells following treatment with 500 nM osimeritinib (right panel). The lower panel shows an enlargement of phagocytosis of NSCLC cells by CER122-modified cells following osimeritinib treatment, with white arrows indicating phagocytic events (pHrodo red targets within CT-violet-labeled T cells).

H1975 NSCLC cells were treated with 500 nM Osimeritinib and then labeled with pH-rodo red, a pH sensing dye, to indicate localization to low-pH retaining endosomes. CD4+ T cells were transduced with a lentiviral vector comprising a CER122 nucleic acid and tEGFR nucleic acid (transduction marker). CER122 has a polypeptide sequence as set forth in SEQ ID NO:149 and comprises a Tim4 binding domain, Tim4 transmembrane domain, and an engulfment signaling domain comprising a primary engulfment signaling domain comprising a TLR2 signaling domain and a secondary engulfment signaling domain comprising a DAP12 signaling domain. CER122-transduced T cells labeled with CELLTRACE Violet were co-cultured with Osimeritinib-treated H1975 NSCLC cells. Fluorescent microscopy images (40X) were obtained 12 hours after co-culture of H1975 cells and CER-expressing T cells (FIG. 47, top left panel). Mock-transduced CD4+ T cells (vector alone) were used as control and exhibit no phagocytic activity (FIG. 47, top right panel). Phagocytic events can be visualized as pHrodo red targets within CELLTRACE Violet labeled T cells. An enlargement of phagocytosis of pHrodo red labeled H1975 cells by CELLTRACE Violet labeled CER122-modified T cells is shown in the bottom panel of FIG. 47, with white arrows indicating phagocytic events.

Figure 48A:
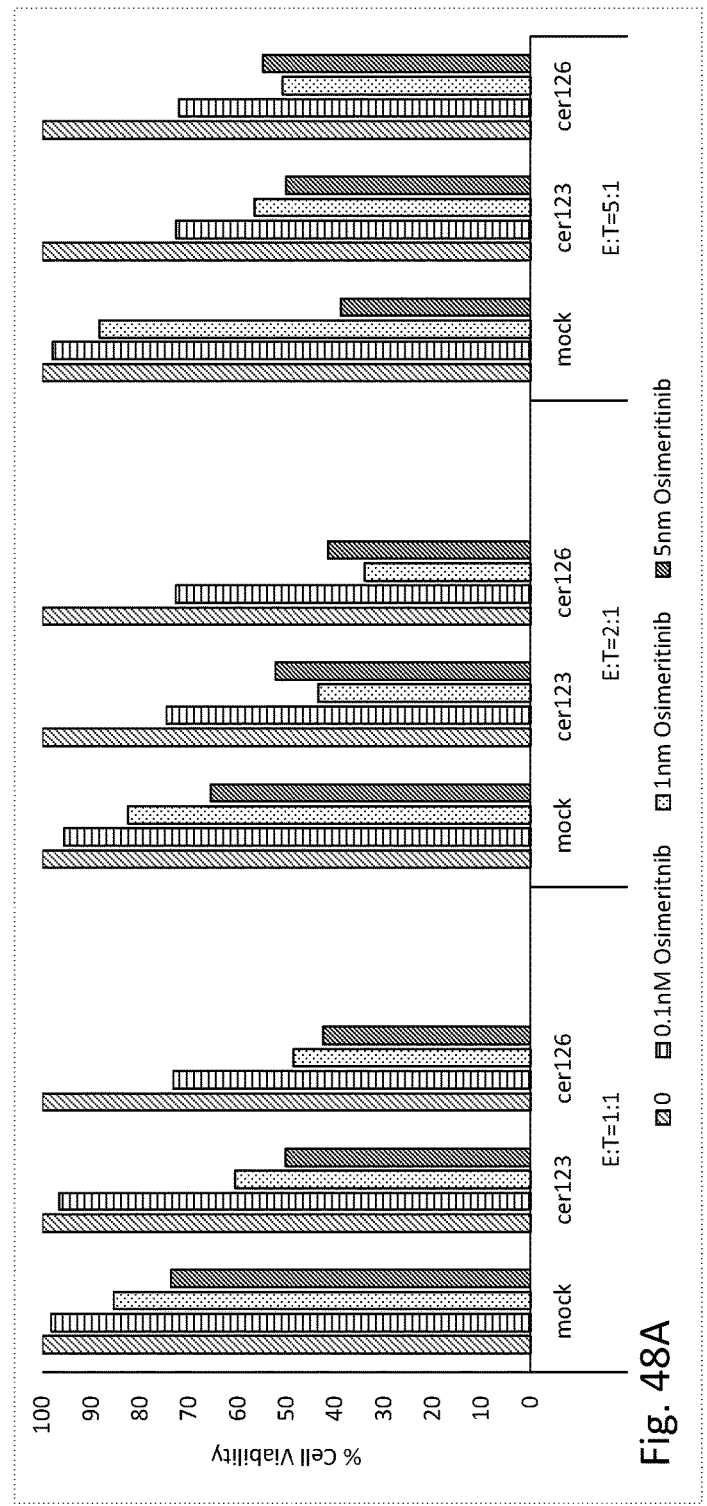
FIGS. 48A-48B show that when EGFR inhibitor Osimeritinib (0.1 nM, 1 nM, and 5 nM) was combined with phosphatidylserine-specific CER123- or CER126-expressing cells, growth of NSCLC cells harboring EGFR rearrangements was synergistically suppressed in vitro as measured by MTT assay (FIG. 48A) or microscopy (1 nM osimeritinib+CER123) (FIG. 48B).
Figure 48B:
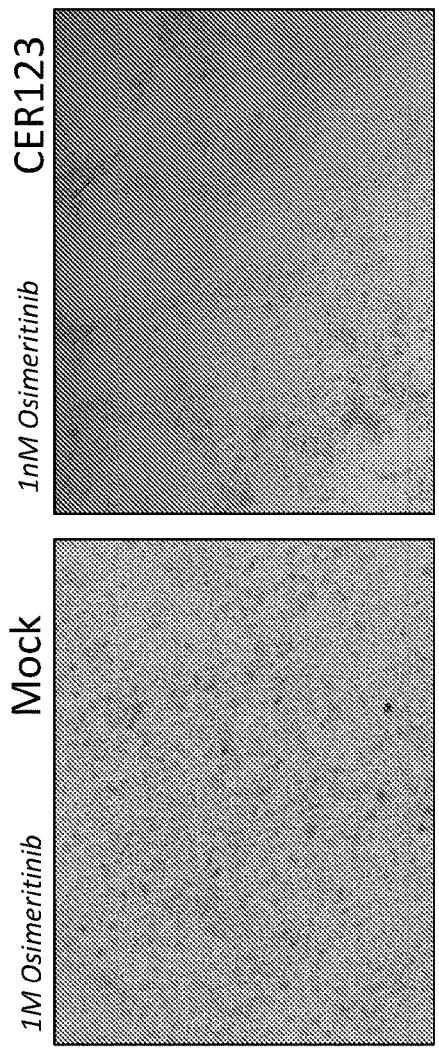

HCC159 lung adenocarcinoma cells harboring an EGFR mutation were co-cultured with CER123- or CER126-expressing CD4+ T cells with increasing concentrations of Osimeritinib (0.1 nM, 1 nM, or 5 nM). Mock transduced (vector only) T cells were used as control. After 48 hours of co-culture at effector: target cell ratios at 1:1, 2:1 or 5:1 in the presence of drug, T cells were washed away, and the number of viable HCC159 cells was quantified using a calorimetric MTT assay. Cell viability experiments were performed in triplicates and presented as % of control with (FIG. 48A). In the presence of an EGFR kinase inhibitor, CER123- and CER126-expressing cells demonstrate dose-dependent target cell killing responses. Bright field images demonstrate loss of HCC159 cells in the presence of 1 nM Osimeritinib and CER123-expressing T cells (FIG. 48B, right panel) compared to control T cells (vector alone) (FIG. 48B, left panel).

Figure 49:
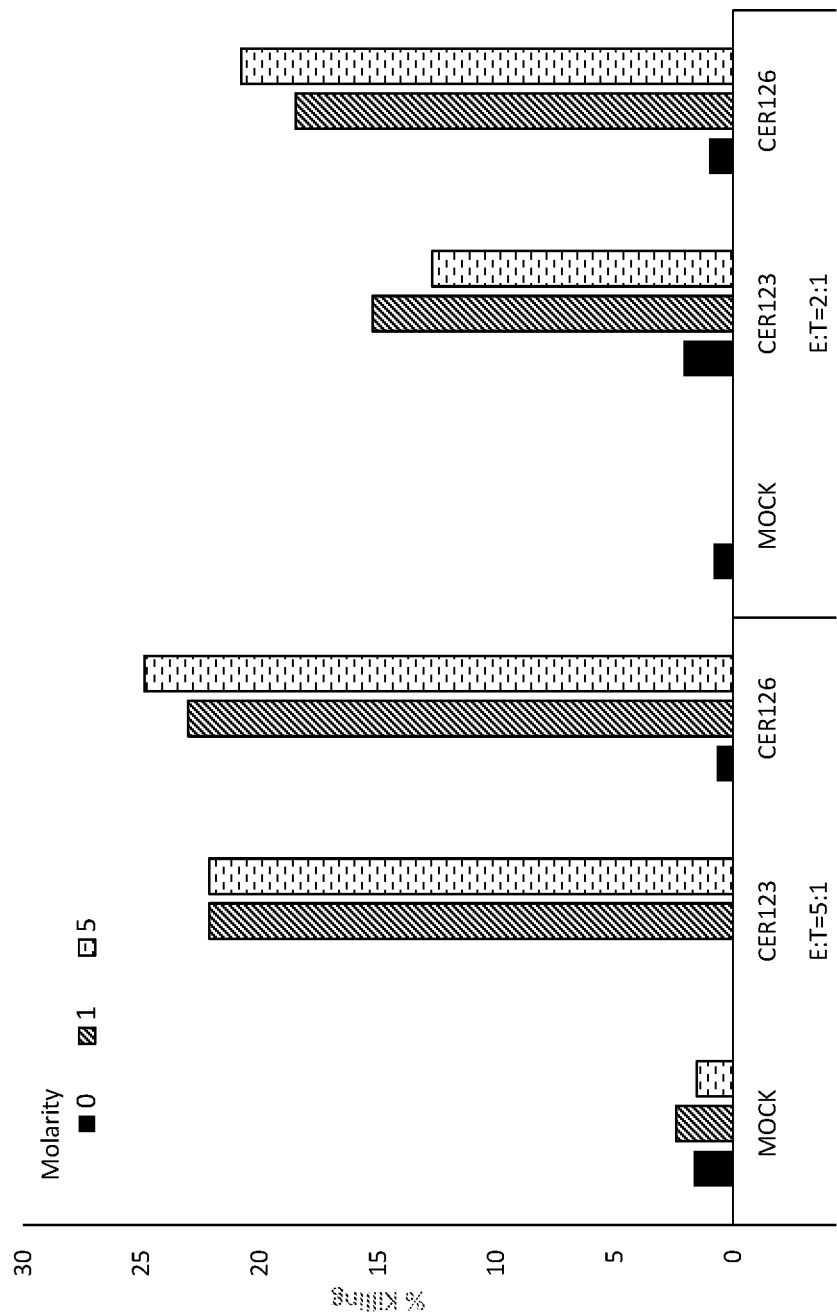
FIG. 49 shows that in the presence of osimeritinib (0, 1 nM, and 5 nM), CER123- or CER126-expressing cells demonstrate inducible, dose-dependent killing of NSCLC cells. The left bar graph shows data using an effector:target cell ratio of 5:1, and the right bar graph shows data using an effector:target ratio of 2:1.
Figure 50:
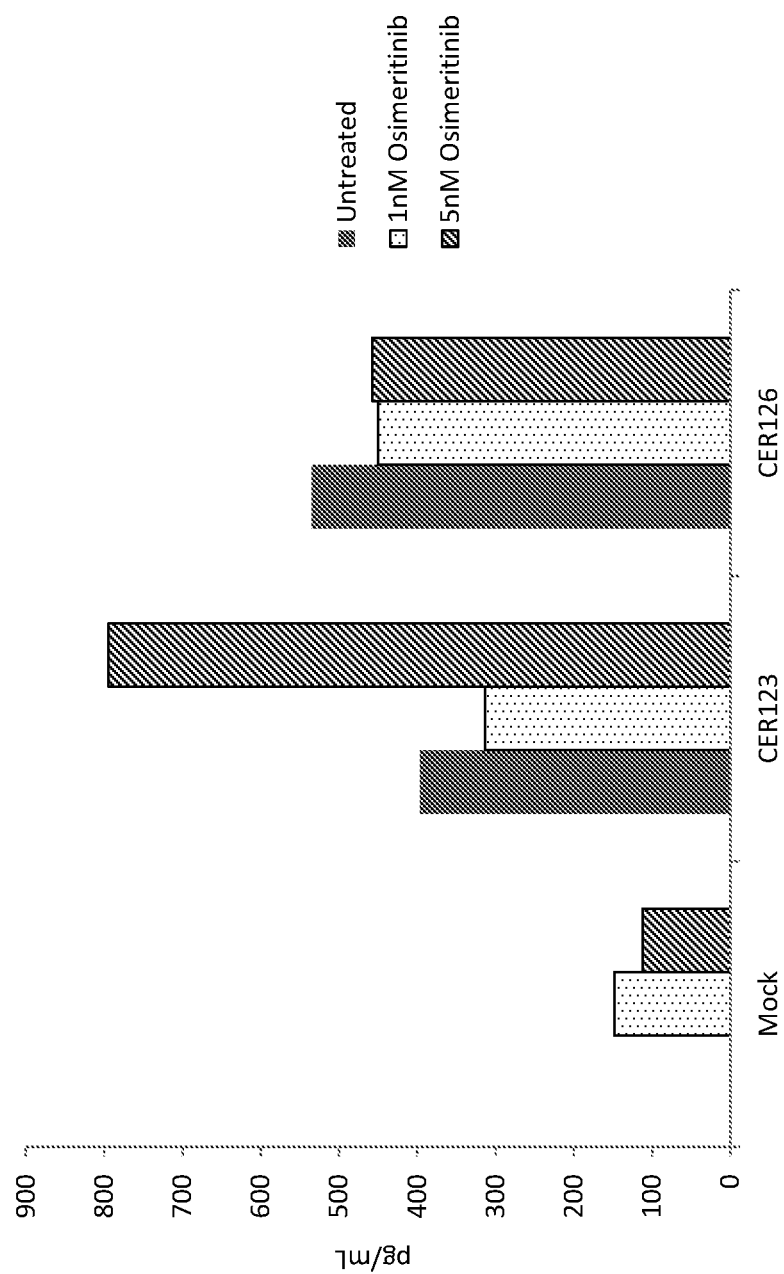
FIG. 50 shows IFN-γ secretion levels in CER123- and CER126-expressing cells co-cultured with HCC159 cells with varying levels of Osimeritinib (0, 1 nM and 5 nM).

HCC159 lung adenocarcinoma cells were co-cultured with CER123- or CER126-expressing CD4+ T cells with increasing concentrations of Osimeritnib (0, 1 nM, 5 nM). After 18 hours of co-culture, bulk supernatants were evaluated using a LDH-based cytotoxicity assay. T cells assays were performed using purified, EGFR+ (transduction marker), CER modified T cells 7 days after activation using CD3 & CD28 microbeads at effector:target cell ratios of 2:1 or 5:1. Control "Mock" T cells were transduced with vector alone. In the presence of Osimeritinib, CER123- and CER126-expressing cells demonstrate inducible cell killing responses (FIG. 49). Bulk supernatants were also analyzed after 18 hours of co-culture for Interferon Gamma (IFNγ) secretion (FIG. 50). Control "Mock" T cells were transduced with vector alone. In the presence of Osimeritinib, CER123– demonstrates inducible cytokine secretion.

Figures 51A, 51B:
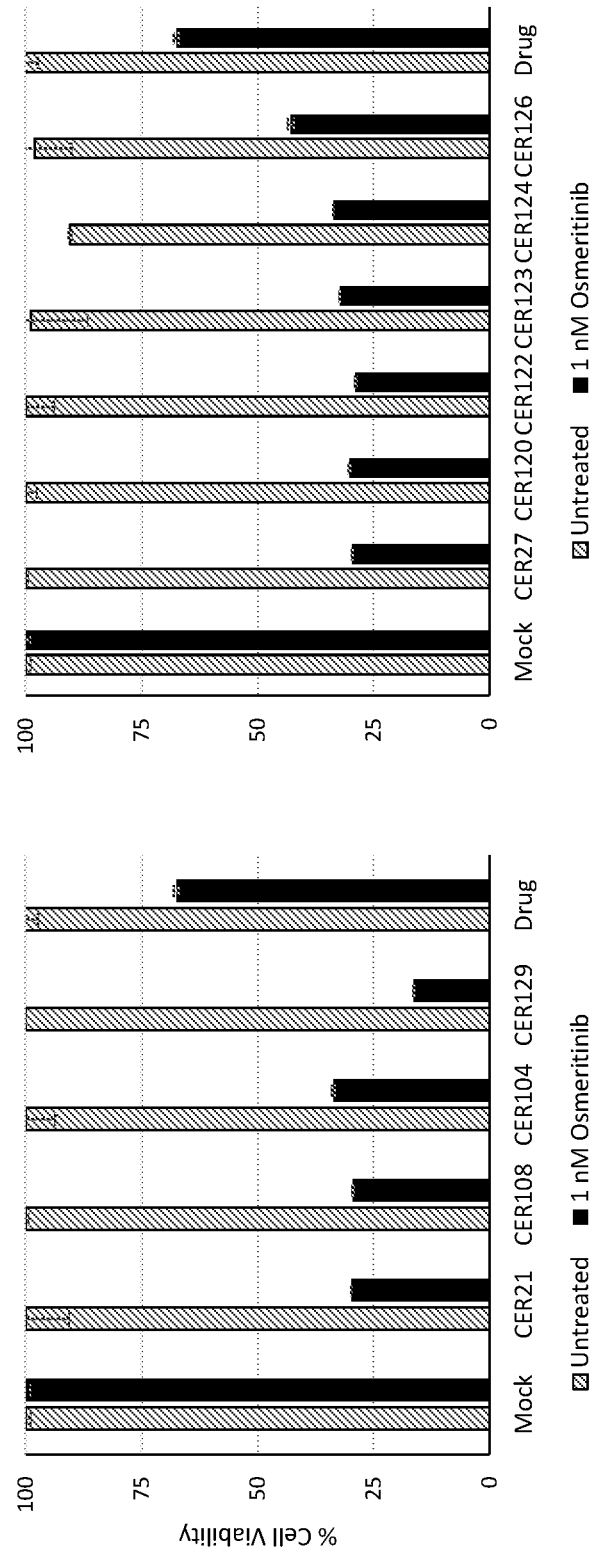
FIGS. 51A-51B: CER-expressing T cells in combination with Osimeritinib (1 nM) synergistically kill HCC827 NSCLC cells harboring EGFR mutations in vitro.
Figure 52:
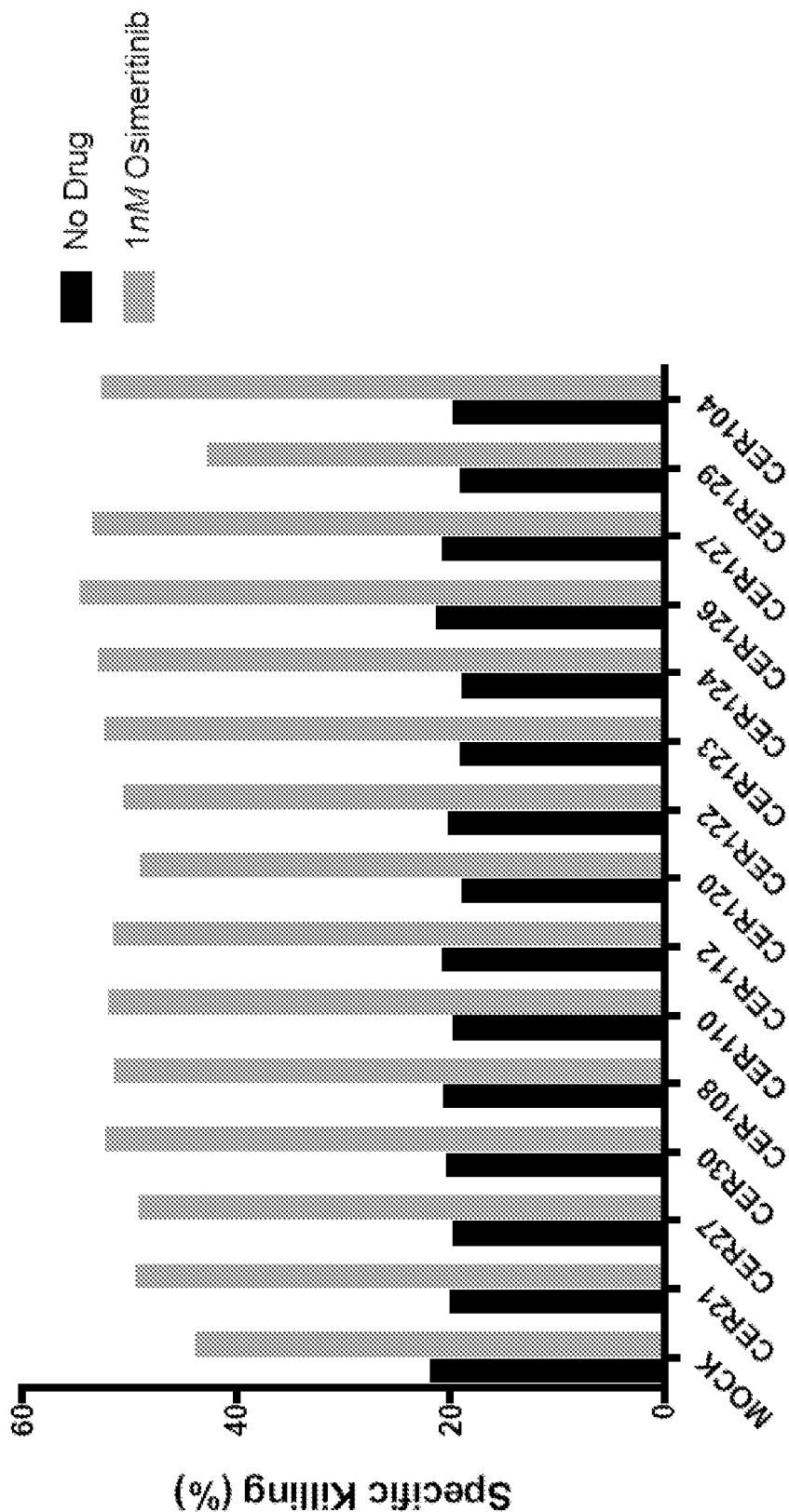
FIG. 52 shows % cell killing HCC159 NSCLC cells harboring EGFR mutation by CER-expressing CD4+ T cells in combination with +Osimeritinib (1 nM) as measured by LDH cytotoxicity assay.
Figure 53:
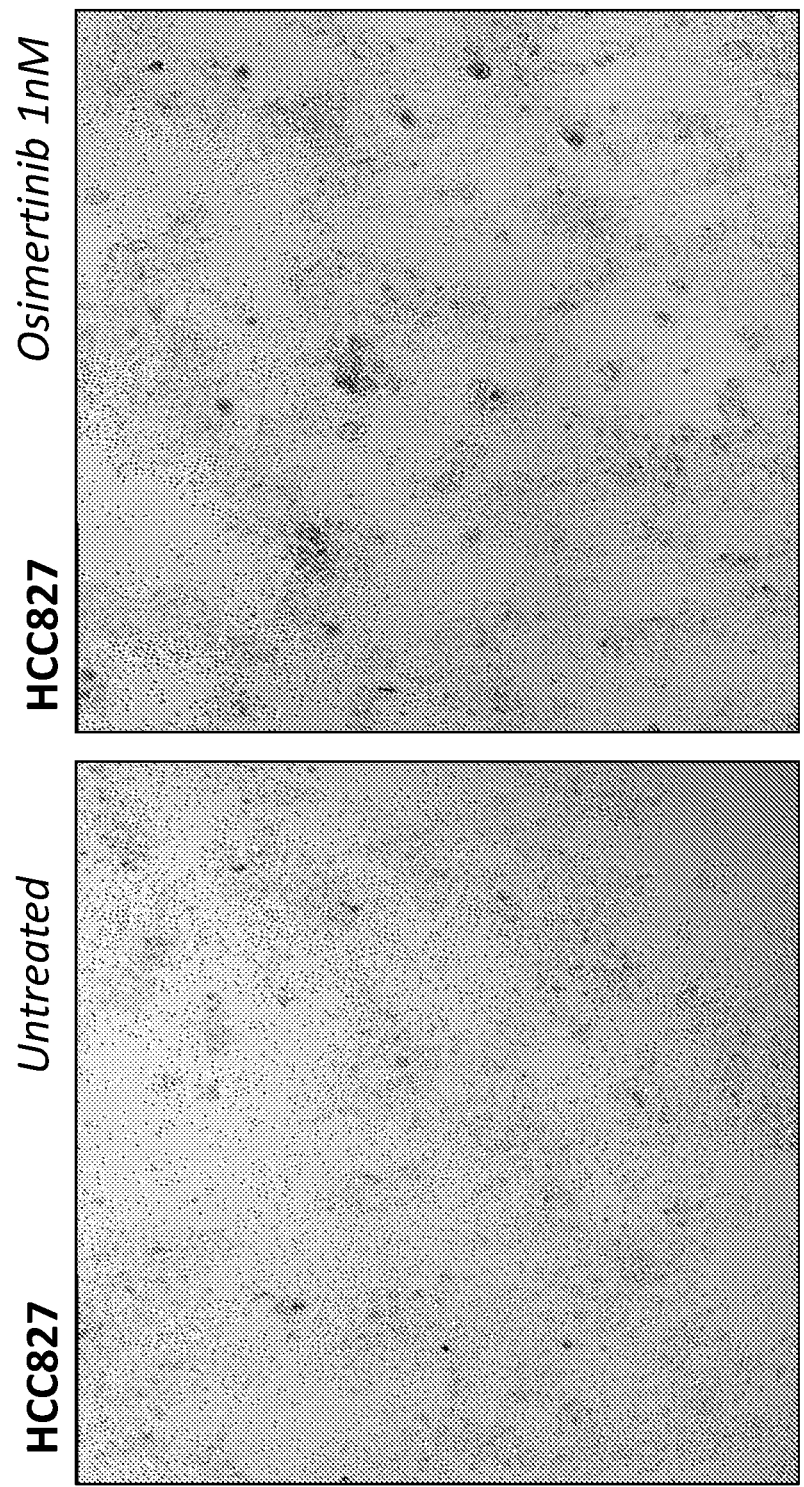
FIG. 53 shows bright field microscopy images from co-culture experiments of HCC827+ cells. Cells were treated with Osimeritinib (1 nM) for 48 hours (right image) or without (left image).

CD4+ T cells were transduced with lentiviral vectors encoding various CERs (CER21, CER108, CER104, CER129, CER27, CER120, CER122, CER123, CER124, or CER126). Mock transduced (vector only) CD4+ T cells were used as control. CER21 comprises a Tim4 binding domain, Tim4 transmembrane domain, and an engulfment signaling domain comprising a primary engulfment signaling domain comprising a TLR8 signaling domain. CER21 has a polypeptide sequence as set forth in SEQ ID NO:88. CER108 has a polypeptide sequence as set forth in SEQ ID NO:137 and comprises a Tim4 binding domain, Tim4 transmembrane domain, and an engulfment signaling domain comprising a primary engulfment signaling domain comprising a DAP12 signaling domain and a secondary engulfment signaling domain comprising a TLR8 signaling domain. CER104 has a polypeptide sequence as set forth in SEQ ID NO:133 and comprises a Tim4 binding domain, Tim4 transmembrane domain, and an engulfment signaling domain comprising a primary engulfment signaling domain comprising a TLR8 signaling domain and a secondary engulfment signaling domain comprising a DAP12 signaling domain. CER129 has a polypeptide sequence as set forth in SEQ ID NO:177 and comprises a Tim4 binding domain, Tim4 transmembrane domain, and an engulfment signaling domain comprising a primary engulfment signaling domain comprising a TLR8 signaling domain and a secondary engulfment signaling domain comprising a TRAF2 signaling domain. CER27 comprises a Tim4 binding domain, Tim4 transmembrane domain, and an engulfment signaling domain comprising a primary engulfment signaling domain comprising a TLR2 signaling domain. CER27 has a polypeptide sequence as set forth in SEQ ID NO:93. CER120 has a polypeptide sequence as set forth in SEQ ID NO:147 and comprises a Tim4 binding domain, Tim4 transmembrane domain, and an engulfment signaling domain comprising a primary engulfment signaling domain comprising a TLR1 signaling domain and a secondary engulfment signaling domain comprising a DAP12 signaling domain. CER122 has a polypeptide sequence as set forth in SEQ ID NO:149 and comprises a Tim4 binding domain, Tim4 transmembrane domain, and an engulfment signaling domain comprising a primary engulfment signaling domain comprising a TLR2 signaling domain and a secondary engulfment signaling domain comprising a DAP12 signaling domain. CER123 has a polypeptide sequence as set forth in SEQ ID NO:150 and comprises a Tim4 binding domain, Tim4 transmembrane domain, and an engulfment signaling domain comprising a primary engulfment signaling domain comprising a TLR2 signaling domain and a secondary engulfment signaling domain comprising a TRAF6 signaling domain. CER126 has a polypeptide sequence as set forth in SEQ ID NO:174 and comprises a Tim4 binding domain, Tim4 transmembrane domain, and an engulfment signaling domain comprising a primary engulfment signaling domain comprising a TLR2 signaling domain and a secondary engulfment signaling domain comprising a TRAF2 signaling domain. CER124 has a polypeptide sequence as set forth in SEQ ID NO:151 and comprises a Tim4 binding domain, Tim4 transmembrane domain, and an engulfment signaling domain comprising a primary engulfment signaling domain comprising a TLR2 signaling domain and a secondary engulfment signaling domain comprising a NFAM1 signaling domain. HCC827 lung adenocarcinoma cells harboring an EGFR mutation were co-cultured with CER-expressing T cells or mock-transduced T cells at a 1:1 effector:target cell ratio with 1 nM Osimeritinib for 48 hours. T cells were washed away, and the number of viable HCC827 cells was quantified using a calorimetric MTT assay. Cell viability experiments were performed in triplicate and presented as % of control. CER-expressing T cells demonstrate synergistic killing of HCC827 cells upon EGFR inhibition (FIGS. 51A-B). HCC827 cells harboring an EGFR mutation were co-cultured with CER-expressing or mock-transduced (vector only) CD4+ T cells with 1 nM of Osimeritinib. After 48 hours of co-culture at a 1:1 effector:target cell ratio, T cells were washed away, and the number of viable HCC827 cells was quantified using a calorimetric LDH assay (FIG. 52). Cell viability experiments were performed in triplicate and presented as % of control. Bright field microscopy images from CER+HCC827±1 nM Osimeritinib co-culture experiments were obtained at 48 hours (FIGS. 53-56).

Figure 57:
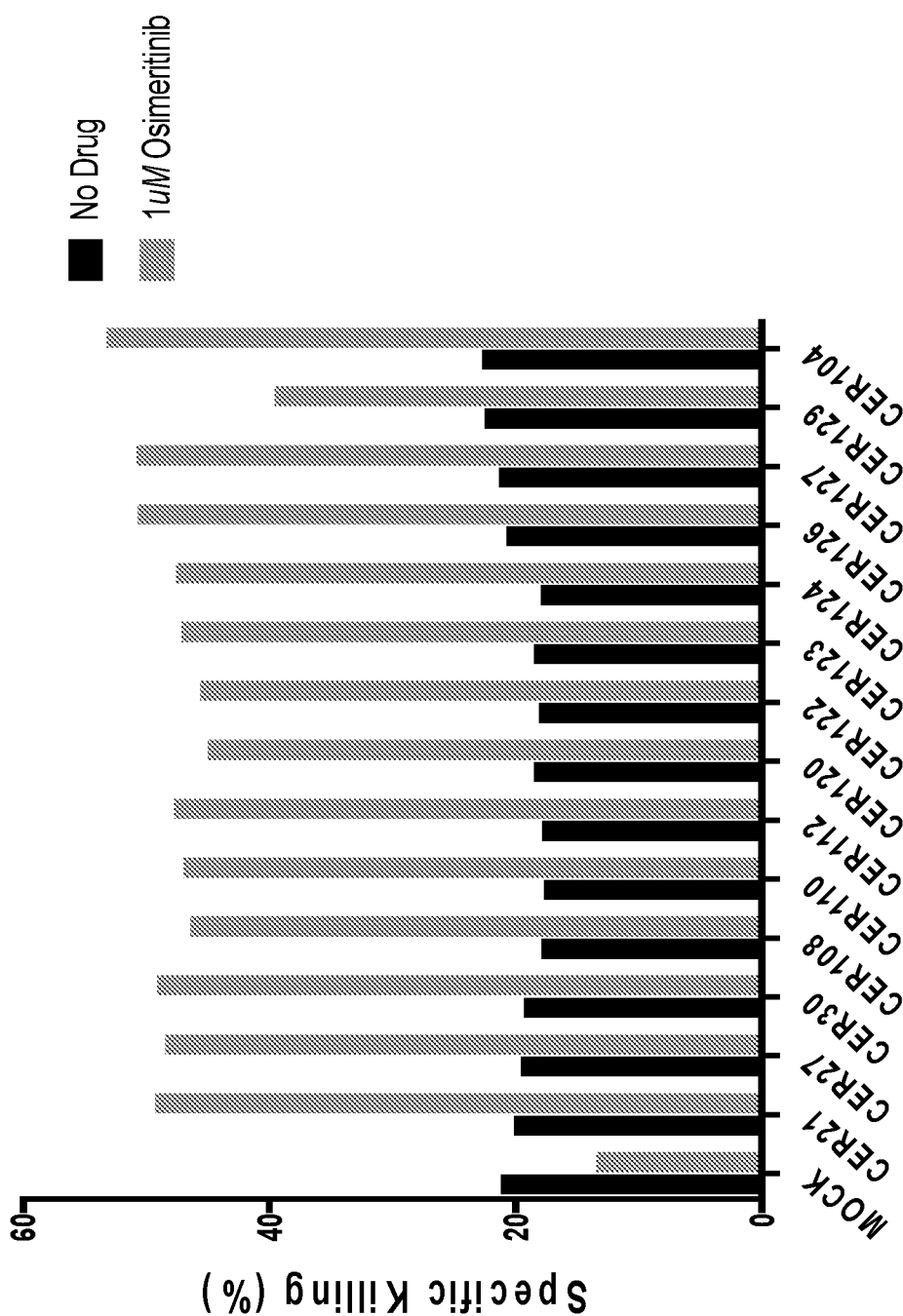
FIG. 57 shows % killing of H1975 NSCLC cells harboring EGFR mutations by CER-expressing T cells in combination with 1 µM Osimeritinib as measured by LDH cytotoxicity assay.

CER-expressing (CER21, CER27, CER30, CER108, CER110, CER112, CER120, CER122, CER123, CER124, CER126, CER127, CER129, or CER104) CD4+ T cells also demonstrated synergistic killing of H1975 lung adenocarcinoma cells upon EGFR inhibition (FIG. 57). CER30 comprises a Tim4 binding domain, Tim4 transmembrane domain, and an engulfment signaling domain comprising a primary engulfment signaling domain comprising a TRAF2 signaling domain. CER30 has a polypeptide sequence as set forth in SEQ ID NO:96. CER110 has a polypeptide sequence of SEQ ID NO:125 and comprises a Tim4 binding domain, Tim4 transmembrane domain, and an engulfment signaling domain comprising a primary engulfment signaling domain comprising a TRAF6 signaling domain and a secondary engulfment signaling domain comprising a DAP12 signaling domain. CER112 has a polypeptide sequence of SEQ ID NO:128 and comprises a Tim4 binding domain, Tim4 transmembrane domain, and an engulfment signaling domain comprising a primary engulfment signaling domain comprising a TRAF6 signaling domain and a secondary engulfment signaling domain comprising a NFAM1 signaling domain. CER127 has a polypeptide sequence of SEQ ID NO:175 and comprises a Tim4 binding domain, Tim4 transmembrane domain, and an engulfment signaling domain comprising a primary engulfment signaling domain comprising a TRAF2 signaling domain and a secondary engulfment signaling domain comprising a TLR2 signaling domain. H1975 cells are more resistant to EGFR inhibitors, so Osimeritinib was used at slightly higher concentration. H1975 lung adenocarcinoma cells harboring an EGFR mutation were co-cultured with CER-expressing or mock-transduced (vector only) CD4+ T cells with 1 μM of Osimeritinib. After 48 hours of co-culture at a 1:1 effector:target cell ratio, T cells were washed away, and the number of viable H1975 cells was quantified using a calorimetric LDH assay (FIG. 57). Cell viability experiments were performed in triplicate and presented as % of control. FIG. 58 shows bright field images from co-culture of H1975 cells with mock-transduced T cells (left image) or CER126+ T cells (right image) treated with Osimeritinib (500 nM) for 48 hours.

Cer Enhancement of Alk Inhibitors

Anaplastic Lymphoma Kinase (ALK) gene rearrangements account for ~7% of NSCLC patients. Selective inhibitors of ALK have been developed for the treatment of NSCLC. While clinical studies demonstrate superior efficacy and lower toxicity in the primary treatment of ALK-positive NSCLC with an ALK inhibitor, responses are typically incomplete and temporary.

CER-modified cells engineered to recognize pro-engulfment marker phosphatidylserine were administered in conjunction with various ALK inhibitors, Alectinib and Crizotinib, to determine whether CER therapy could enhance ALK targeted therapy.

Figure 59B:
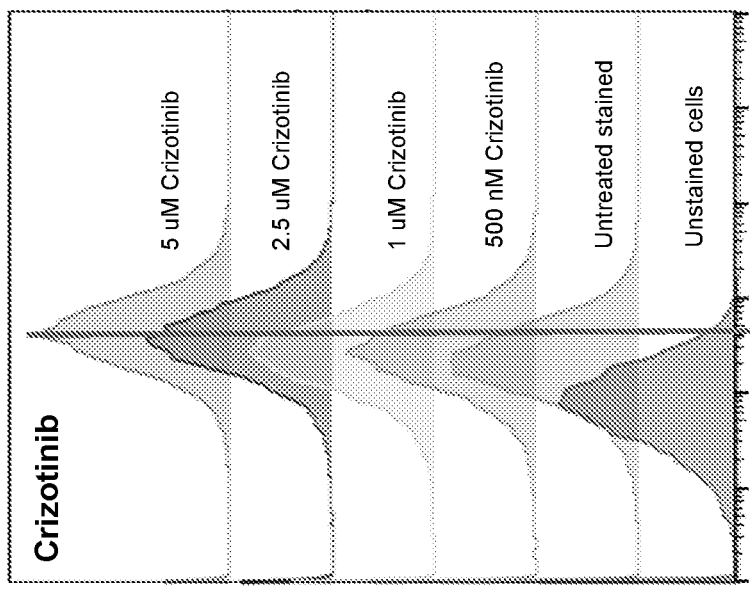
FIGS. 59A-59B show that ALK inhibitors (FIG. 59A) Alectinib and (FIG. 59B) Crizotinib elicit a secondary, pro-engulfment marker on A549 cells upon drug exposure as detected by a Tim4-IgG1 Fc recombinant fusion protein.
Figure 59A:
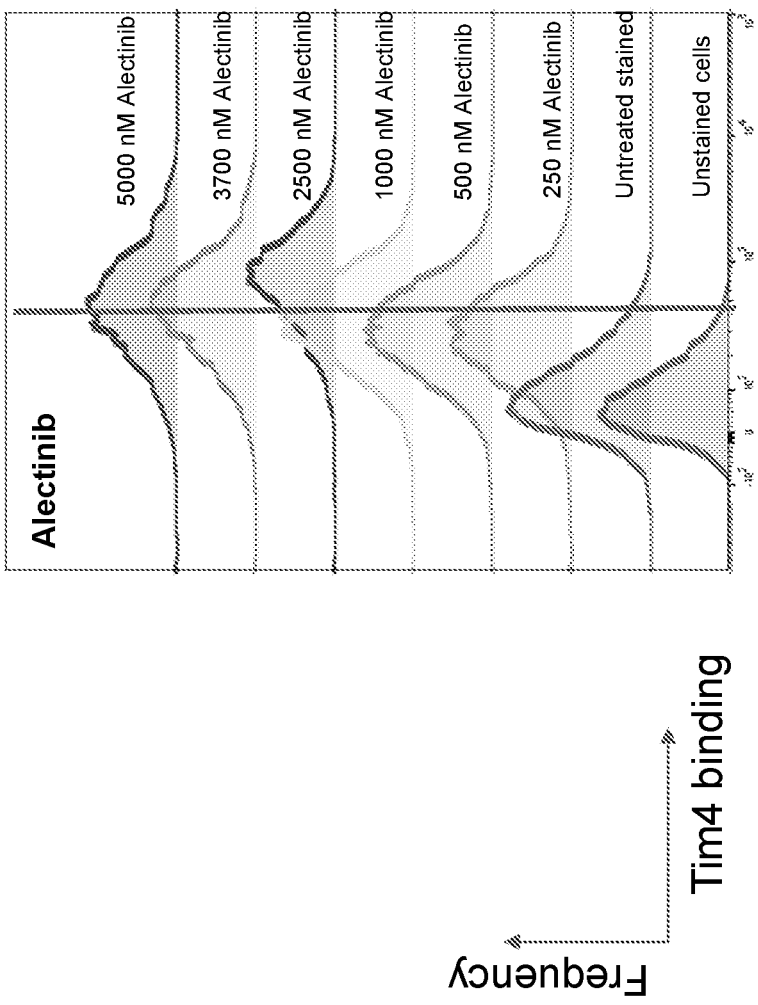

An ELM4-ALK fusion translocation was introduced into A549 lung adenocarcinoma cells. The A549 cells were then treated for 12 hours in the presence of increasing concentrations of ALK kinase inhibitors Alectinib (250 nM, 500 nM, 1000 nM, 2500 nM, 3700 nM, or 5000 nM) or Crizotinib (500 nM, 1 µM, 2.5 µM, or 5 µM) and stained with a Tim4-IgG$_1$ Fc recombinant fusion protein to evaluate for pro-engulfment marker (phosphatidylserine) exposure on target cells following ALK inhibitor treatment. Increasing concentrations of Alectinib (FIG. 59A) and Crizotinib (FIG. 59B) enhance surface staining with Tim4-IgG$_1$ Fc fusion protein, indicating that exposure of the phosphatidylserine target molecule is ALK inhibitor drug inducible.

Figure 60A:
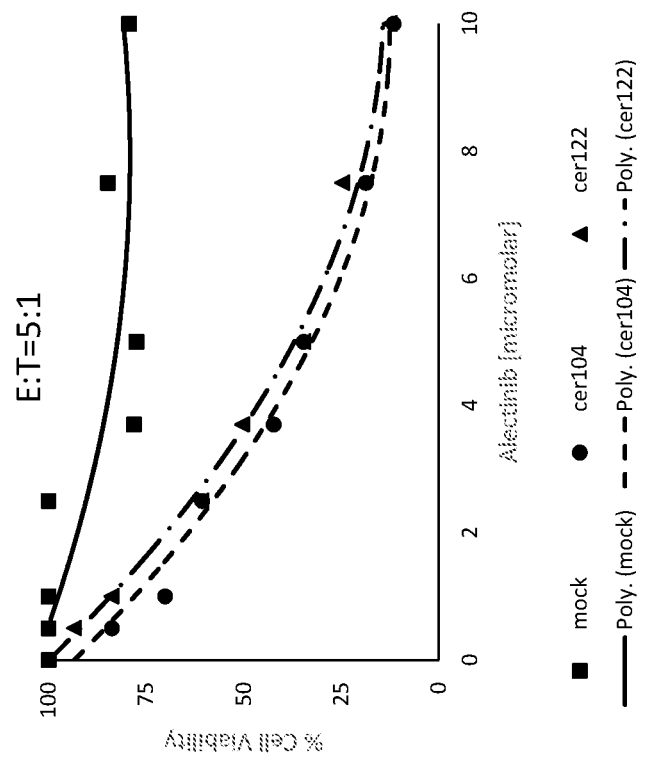
FIGS. 60A-60D show that ALK inhibitors Crizotinib or Alectinib combined with CER104- or CER122-expressing T cells synergistically suppress in vitro growth of NSCLC cells harboring ALK rearrangements.
Figure 60B:
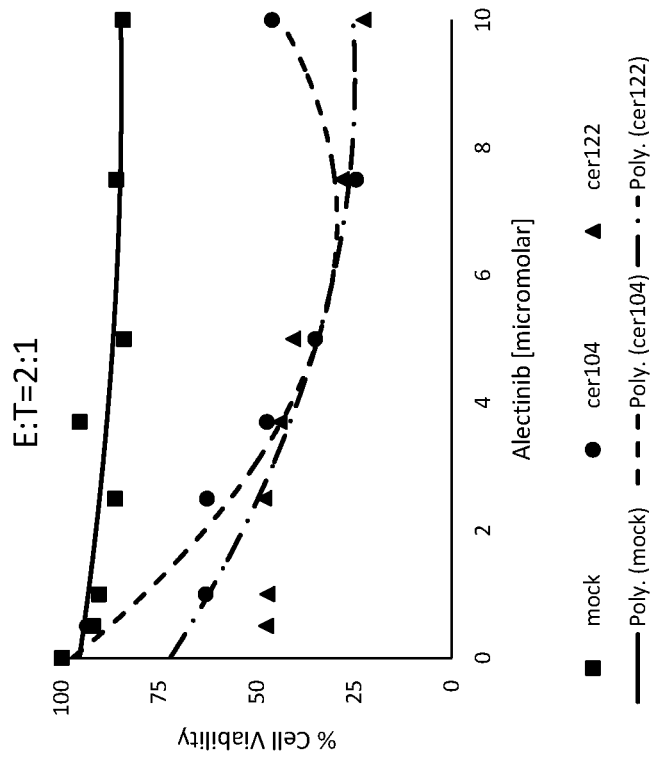
Figure 60D:
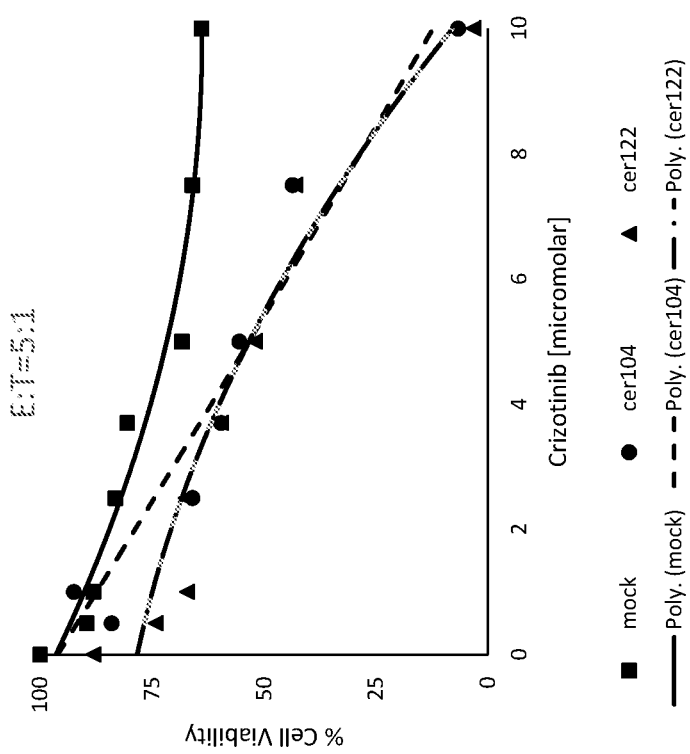
Figure 60C:
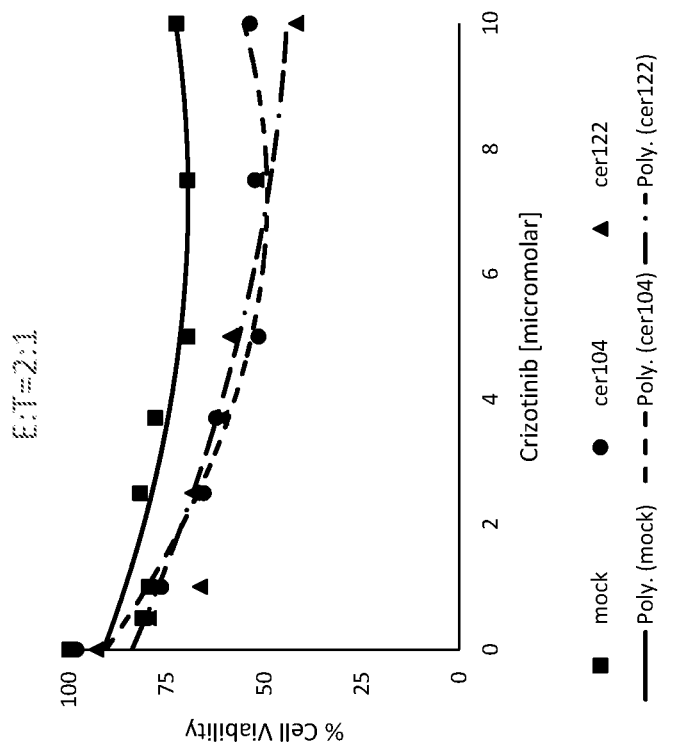
Figure 61A:
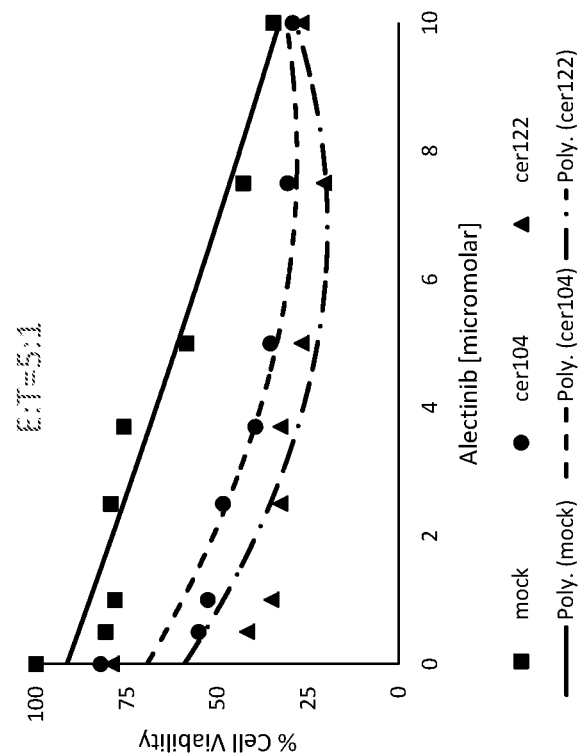
FIGS. 61A-61D show that ALK inhibitors Crizotinib or Alectinib combined with CER104- or CER122-expressing T cells synergistically suppress in vitro growth of NSCLC cells harboring ALK rearrangements.
Figure 61B:
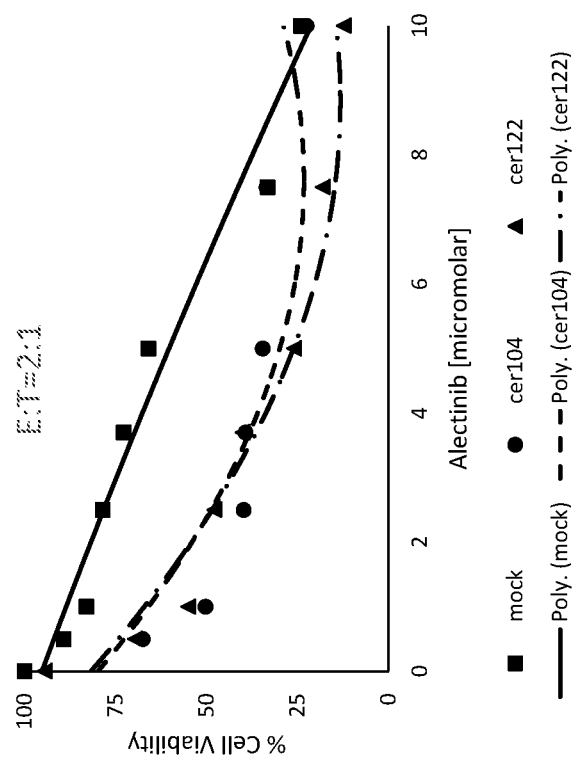
Figure 61D:
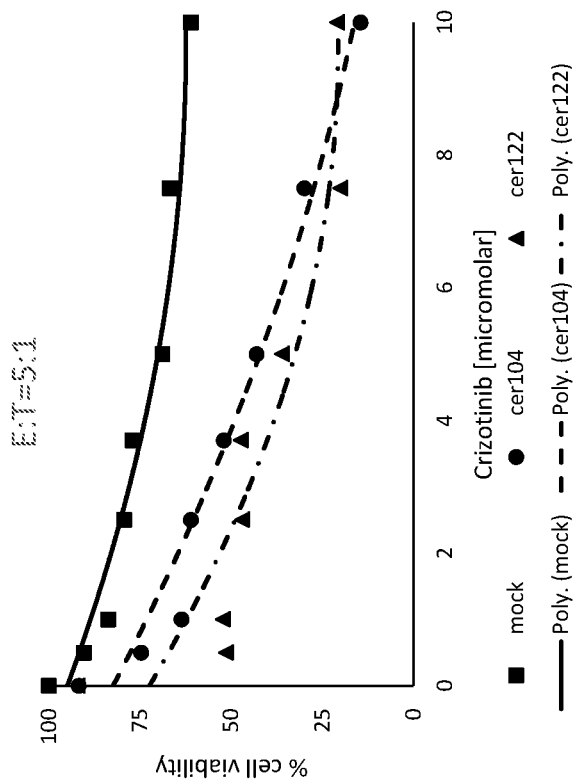
Figure 61C:
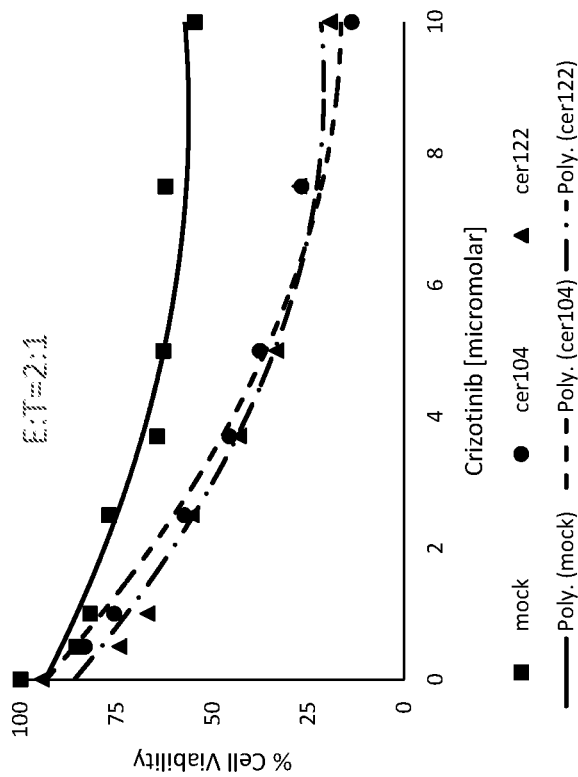

An ELM4-ALK translocation was introduced into A549 cells. The A549 cells were then co-cultured with CER104- or CER122-expressing T cells or Mock-transduced (vector only) T cells with increasing concentrations of ALK inhibitor drug Alectinib (250 nM, 500 nM, 1 µM, 2.5 µM, 3.7 µM, 7 µM, or 10 µM) or Crizotinib (250 nM, 500 nM, 1 µM, 2.5 µM, 3.7 µM, 7 µM, or 10 µM). CER104 has a polypeptide sequence set forth in SEQ ID NO:133 and comprises a Tim4 binding domain, Tim4 transmembrane domain, and an engulfment signaling domain comprising a primary engulfment signaling domain comprising a TLR8 signaling domain and a secondary engulfment signaling domain comprising a DAP12 signaling domain. CER122 has a polypeptide sequence set forth in SEQ ID NO:149 and comprises a Tim4 binding domain, Tim4 transmembrane domain, and an engulfment signaling domain comprising a primary engulfment signaling domain comprising a TLR2 signaling domain and a secondary engulfment signaling domain comprising a DAP12 signaling domain. Effector:target (E:T) cell ratio for co-culture was 2:1 or 5:1. After 48 hours and 72 hours of co-culture in the presence of ALK inhibitor drug, T cells were washed away, and the number of viable A549 cells were quantified using a calorimetric MTT assay. % cell viability for CER+Alectinib treated A549 cells at 48 hours post-treatment are shown in FIG. 60A (Effector:Target cell ratio of 2:1) and FIG. 60B (Effector:Target cell ratio of 5:1). % cell viability for CER+Crizotinib treated A549 cells at 48 hours post-treatment are shown in FIG. 60C (Effector:Target cell ratio of 2:1) and FIG. 60D (Effector:Target cell ratio of 5:1). % cell viability for CER+Alectinib treated A549 cells at 72 hours post-treatment are shown in FIG. 61A (Effector:Target cell ratio of 2:1) and FIG. 61B (Effector:Target cell ratio of 5:1). % cell viability for CER +Crizotinib treated A549 cells at 72 hours post-treatment are shown in FIG. 61C (Effector:Target cell ratio of 2:1) and FIG. 61D (Effector:Target cell ratio of 5:1). Cell viability experiments were performed in triplicates and presented as % of control. Best-fit curves were generated from raw data using linear regression models. In the presence of ALK kinase inhibitors, CER-expressing cells demonstrate dose-dependent cell killing responses.

Figure 62C:
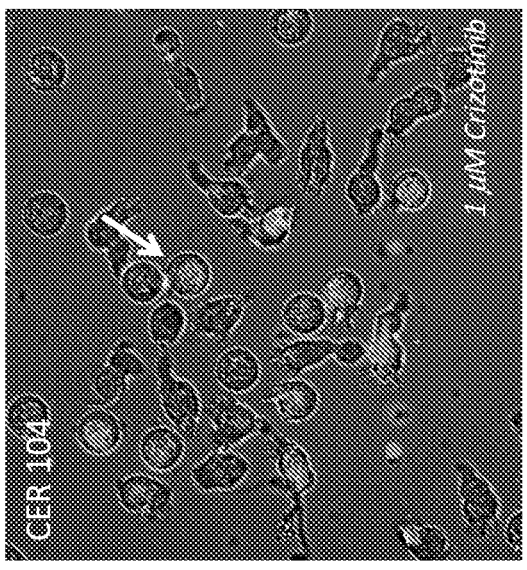
FIGS. 62A-62E show fluorescent micrographs (40× magnification) of phagocytic elimination of ALK-positive A549 NSCLC cells treated with ALK inhibitor (alectinib or crizotinib). A549 cells were labeled with pHrodo red dye, a pH sensing dye to indicate localization in low-PH retaining endosomes. CD4 T cells were labeled with CT-violet.
Figure 62E:
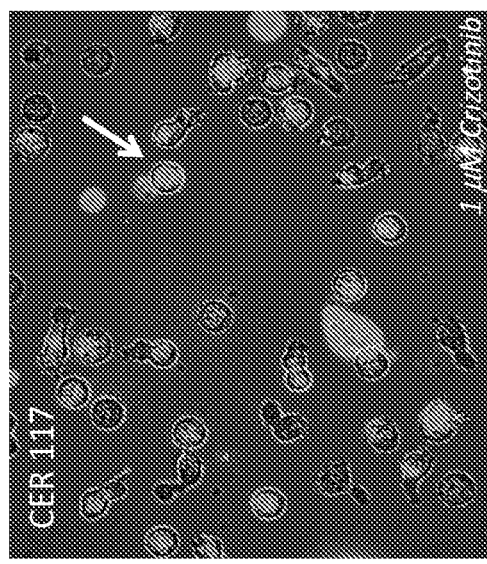
Figure 62B:
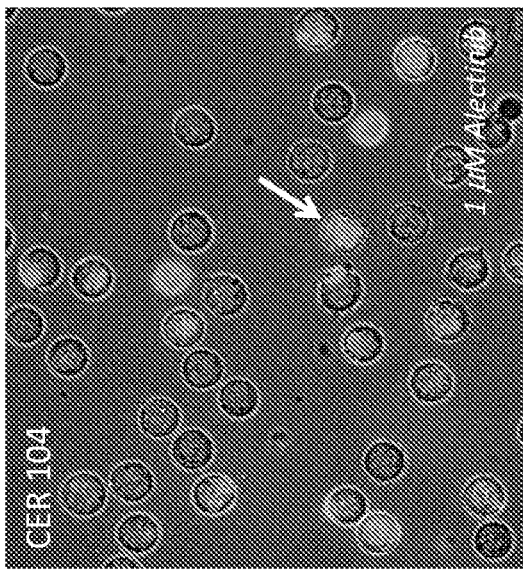
Figure 62D:
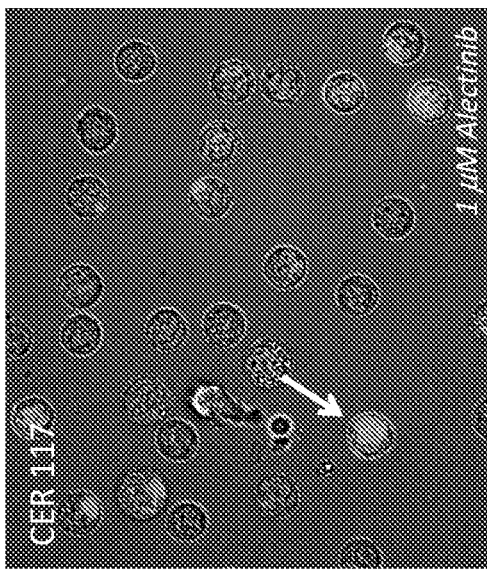
Figure 62A:
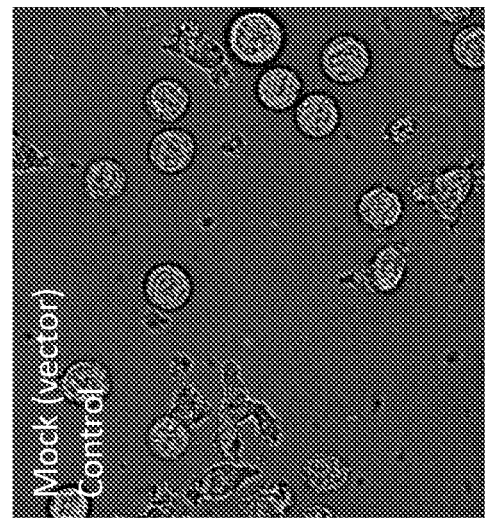

An ELM4-ALK translocation was introduced into A549 cells. ALK+A549 cells were treated with 1 µM Alectinib or 1 µM Crizotinib and labeled with pHrodo red, a pH sensitive dye, to indicate localization in low-pH retaining endosomes. CD4 T cells are modified to express CER104 or CER117 and labeled with CELLTRACE Violet. CER117 has a polypeptide sequence set forth in SEQ ID NO:144 and comprises a Tim4 binding domain, a Tim4 transmembrane domain, and an engulfment signaling domain comprising a primary engulfment signaling domain comprising a TLR8 signaling domain and a secondary engulfment signaling domain comprising a TRAF6 signaling domain. The ALK+A549 cells were then co-cultured with CER104- or CER117-expressing CD4+ T cells or Mock-transduced (vector only) T cells for 12 hours and images were obtained by fluorescent microscopy at 40× magnification (FIGS. 62A-E). White arrows indicate exemplary phagocytic events (pH rodo red cell targets within CELLTRACE Violet labeled CD4+ T cells). CER- expressing T cells phagocytosed ALK+A549 cells treated with Alectinib or Crizotinib (FIGS. 62B-E). Mock-transduced (vector only) controls exhibit no phagocytic activity (FIG. 62A).

Similarly, CER123- and CER126-expressing CD4+ T cells exhibited phagocytic elimination of ALK+A549 cells treated with 2.5 µM Alectinib (FIGS. 63B, 63C, 63E, 63F). ALK+A549 cells were treated with 2.5 µM Alectinib and then labeled with pH-rodo red, a pH sensing dye, to indicate localization to low-pH retaining endosomes. CER123- and CER126-transduced CD4+ and CD8+ T cells were labeled with CELLTRACE Violet and co-cultured with the A549 ALK-positive cells. Co-cultured cells were imaged by fluorescent microscopy at 63× magnification after 12 hours (FIGS. 63A-F). White arrows indicate exemplary phagocytic events (pHrodo red targets within CELLTRACE Violet-labeled CD4 T cells). CER- expressing T cells phagocytosed ALK+A549 cells treated with Alectinib (FIGS. 63B, 63C, 63E, and 63F). Mock-transduced (vector only) controls exhibit no phagocytic activity (FIGS. 63A, 63D).

Figure 64B:
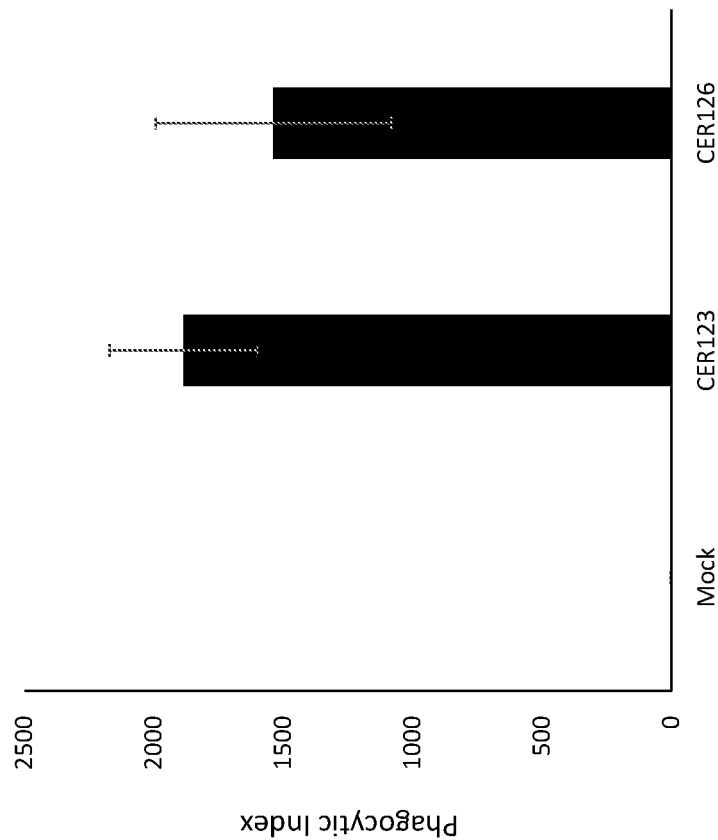
FIGS. 64A-64B are bar graphs representing % phagocytosis (FIG. 64A) and phagocytic index (FIG. 64B) of Alectinib (1 µM) treated A549 cells by CER123- or CER126-expressing T cells.
Figure 64A:
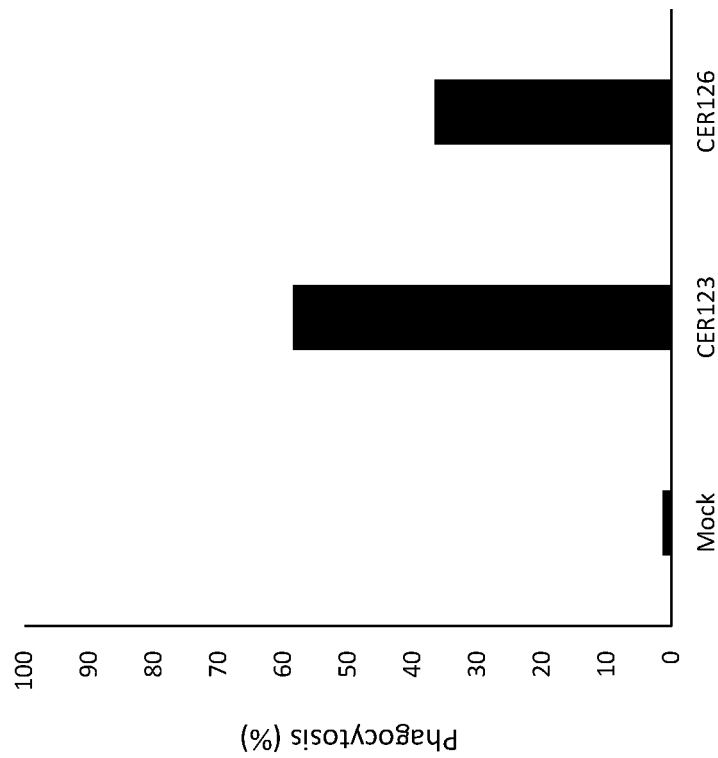

Phagocytosis of Alectinib-treated ALK+A549 cells by CER-expressing T cells was also quantified. A549 cells were treated with Alectinib at 1 µM for 12 hours and co-cultured with CER123- or CER126-expressing T cells at a 1:1 ratio for 12 hours. Bar graph in FIG. 64A represents quantification of percentage phagocytosis calculated as ((number of phagocytic target events)/(total number of effector cells))*100. Events were calculated from fluorescent 3×3 stitched images at 40×resolution after 12 hours of co-culture. Bar graph in FIG. 64B represents quantification of adjusted phagocytic index calculated as (median area ratio of target events in effector cells*phagocytosis). Events calculated from fluorescent 3×3 stitched images at 40×resolution after 12 hours of co-culture.

In the presence of ALK kinase inhibitors Crizotinib and Alectinib, CER123- or CER126-expressing T cells demonstrate dose-dependent inducible cytokine secretion and cell killing responses. An ELM4-ALK translocation was introduced into A549 cells. ALK+A549 cells were co-cultured with CER-expressing T cells with increasing concentrations of ALK inhibitor drugs Crizotinib or Alectinib (0, 2500 nM, or 3700 nM). Assays were performed with purified tEGFR+

Figure 65B:
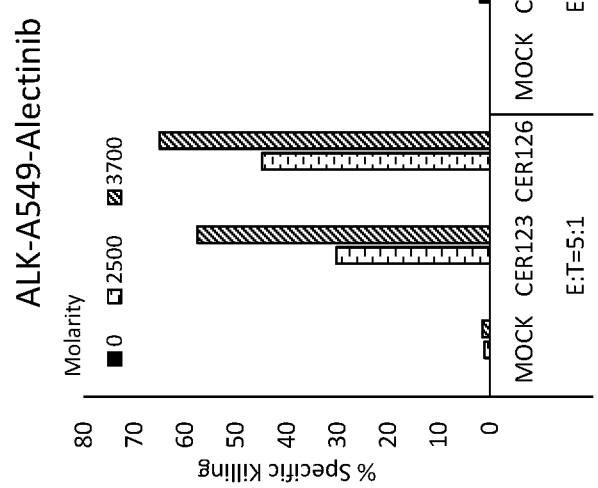
Figure 65A:
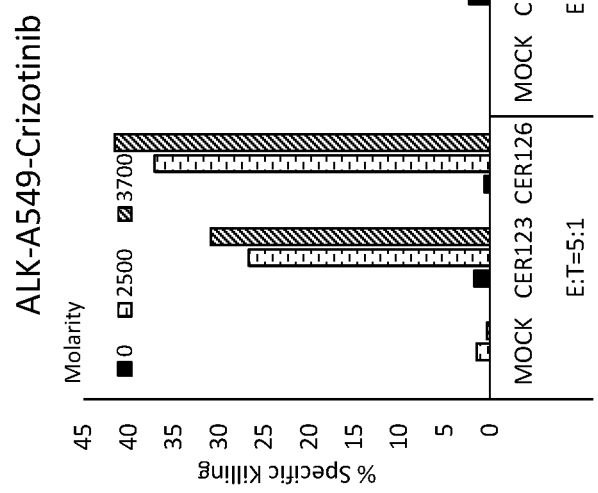

(transduction marker), CER-expressing T cells 7 days after activation using CD3 & CD28 microbeads at effector: target cell ratios of 2:1 or 5:1. Mock T cells were transduced with vector alone and used as control. After 18 hours of co-culture, bulk supernatants were evaluated using a LDH cytoxicity assay indicating cell killing (FIGS. 65A-B). Micrograph images from co-culture experiments demonstrate near complete loss of Crizotinib-treated A549 cells from wells in the presence of a CER126-transduced cell (FIG. 65C, left panel).

Figure 66B:
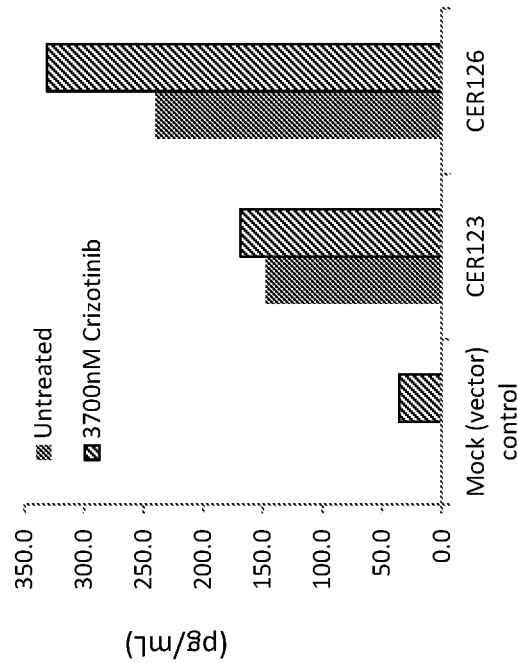
FIGS. 66A-66B show IFN-γ secretion levels in CER123- and CER126-expressing cells co-cultured with A549 cells with Alectinib (3,700 nM) (FIG. 66A) or Crizotinib (3,700 nM) (FIG. 66B).
Figure 66A:
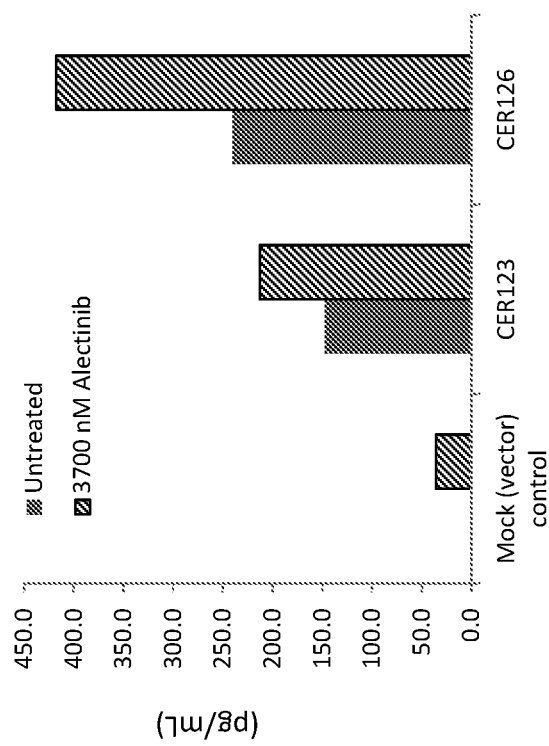

In the presence of ALK kinase inhibitors Crizotinib and Alectinib, CER123- or CER126-expressing T cells demonstrate dose-dependent inducible cytokine secretion (FIGS. 66A-B). A549 cells introduced with an ELM4-ALK translocation were co-cultured with CER123- or CER126-expressing T cells with ALK inhibitor Crizotinib (3700 nM) or Alectinib (3700 nM). After 18 hours of co-culture, bulk supernatants were evaluated for Interferon Gamma secretion (FIGS. 66A-B). Assays were performed using purified, tEGFR$^+$ (transduction marker), CER-expressing T cells 7 days after activation using CD3 & CD28 microbeads at effector: target ratios of (2:1 & 5:1). Control "Mock" T cells were transduced with vector alone.

Figure 67A:
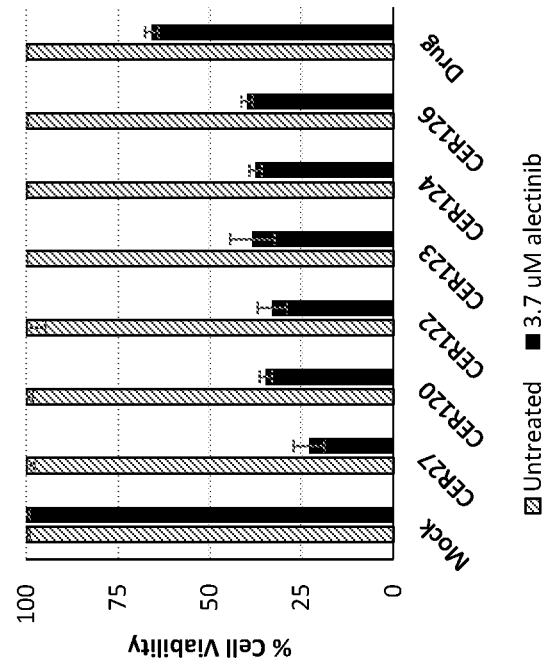
FIGS. 67A-67B show that various CER-expressing T cells in combination with Alectinib synergistically suppress growth of NSCLC cells harboring ALK rearrangements in vitro.
Figure 67B:
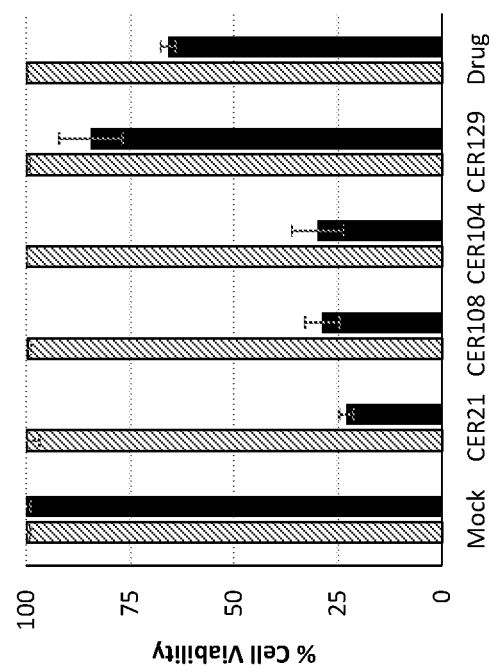
Figure 68:
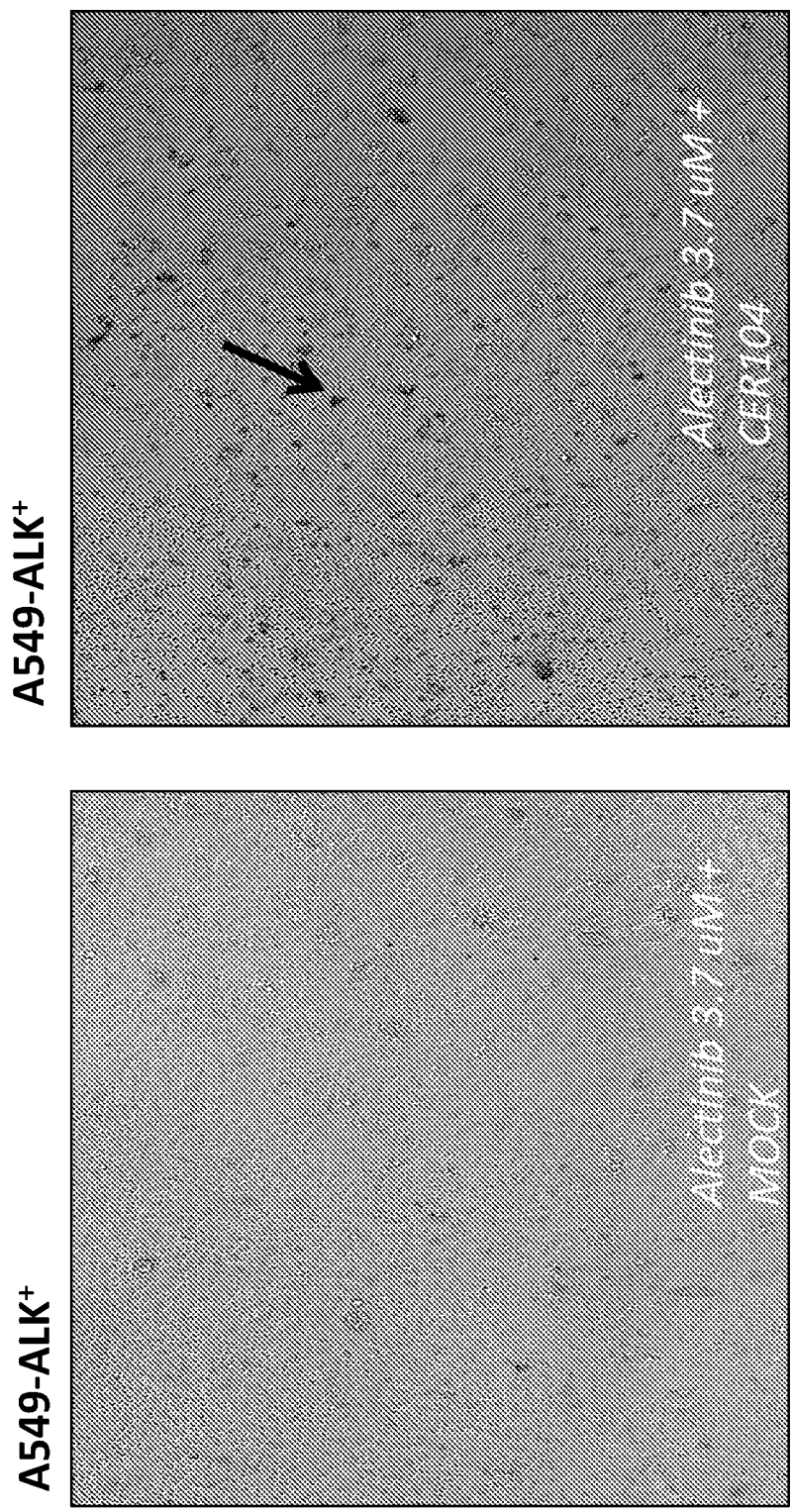
FIG. 68 shows bright field microscopy images from co-culture experiments of A549 ALK+ cells. A549 ALK+ cells were treated with CER104-transduced T cells+Alectinib (3.7 µM) for 48 hours (right image) or mock-transduced (vector only) T cells+Alectinib (3.7 µM) (left image). Arrow indicates cluster of dead A549 ALK+ cells surrounded by phagocytic CER104+ T cells.
Figure 69:
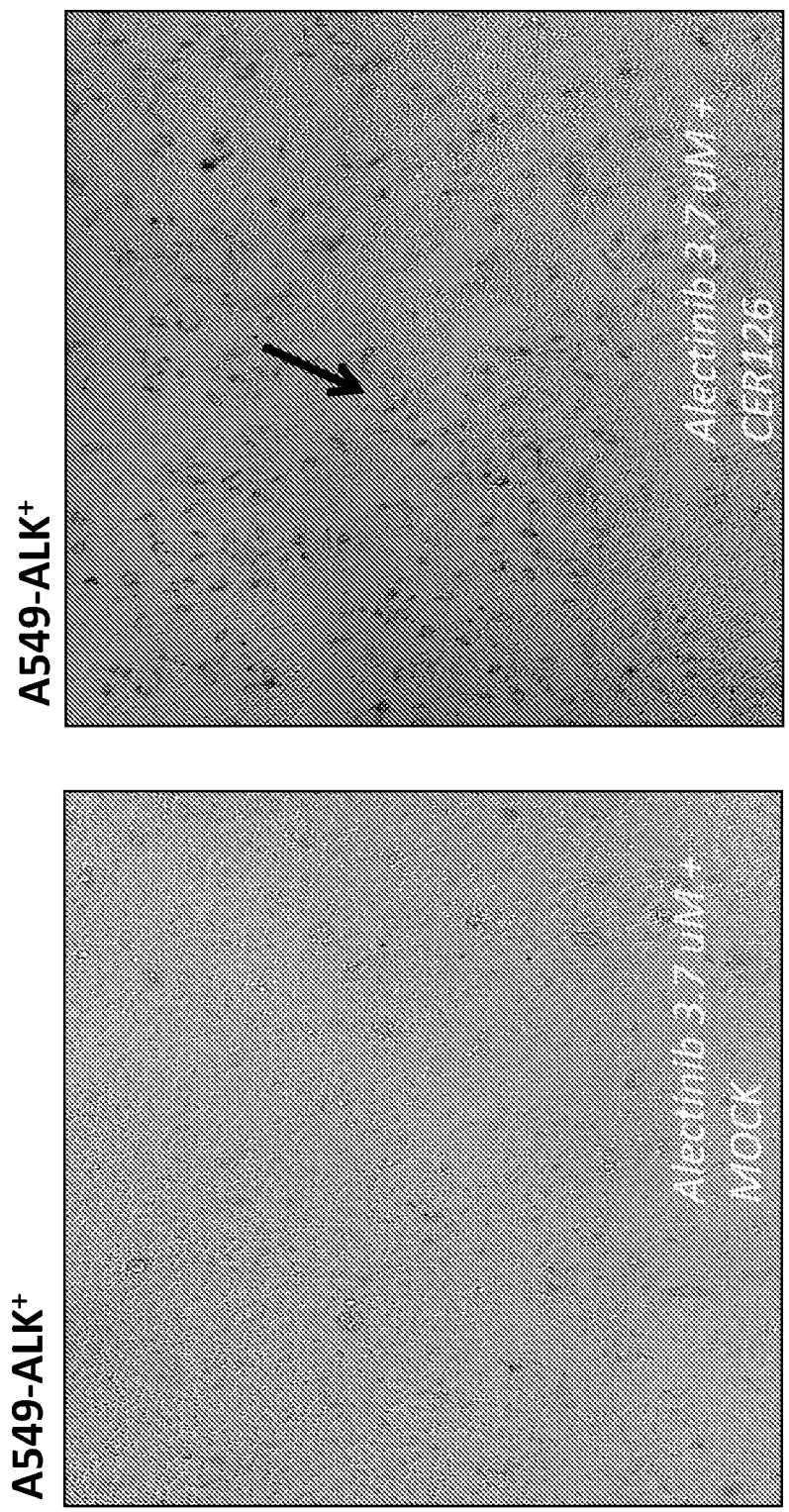
FIG. 69 shows bright field microscopy images from co-culture experiments of A549 ALK+ cells. A549 ALK+ cells were treated with CER126-transduced T cells+Alectinib (3.7 µM) for 48 hours (right image) or mock-transduced (vector only) T cells+Alectinib (3.7 µM) (left image). Arrow indicates cluster of dead A549 ALK+ cells surrounded by phagocytic CER126+ T cells.

CER21-, CER108-, CER104-, and CER129-transduced CD4+ T cells were tested for their ability to kill A549 ALK+ cells in the presence of ALK inhibitor. CD4+ T cells were transduced with a lentiviral vector comprising a CER21, CER108, CER104, CER129, CER27, CER120, CER122, CER123, CER124, or CER126 nucleic acid. A549 lung adenocarcinoma cells introduced with an ELM4-Alk translocation were co-cultured with CER-transduced or mock-transduced (vector only) CD4+ T cells at 1:1 effector:target cell ratio with 3.7 μM Alectinib for 48 hours. After 48 hours of co-culture, T cells were washed away and the number of viable A549 ALK+ cells was quantified using a calorimetric MTT assay (FIGS. 67A-B). Cell viability experiments were performed in triplicates and presented as % of control. Bright field microscopy images were also obtained from A549 ALK+co-culture experiments. FIG. 68 shows A549 ALK+ cells treated with Alectinib (3.7 μM) for 48 hours and co-cultured with mock-transduced T cells (left image) or CER104-transduced T cells (right image). Arrow indicates cluster of dead A549 ALK+ cells surrounded by phagocytic CER104+ T cells. FIG. 69 shows A549 ALK+ cells treated with Alectinib (3.7 μM) for 48 hours and co-cultured with mock-transduced T cells (left image) or CER126-transduced T cells (right image). Arrow indicates cluster of dead A549 ALK+ cells surrounded by phagocytic CER104+ T cells.

Figure 70:
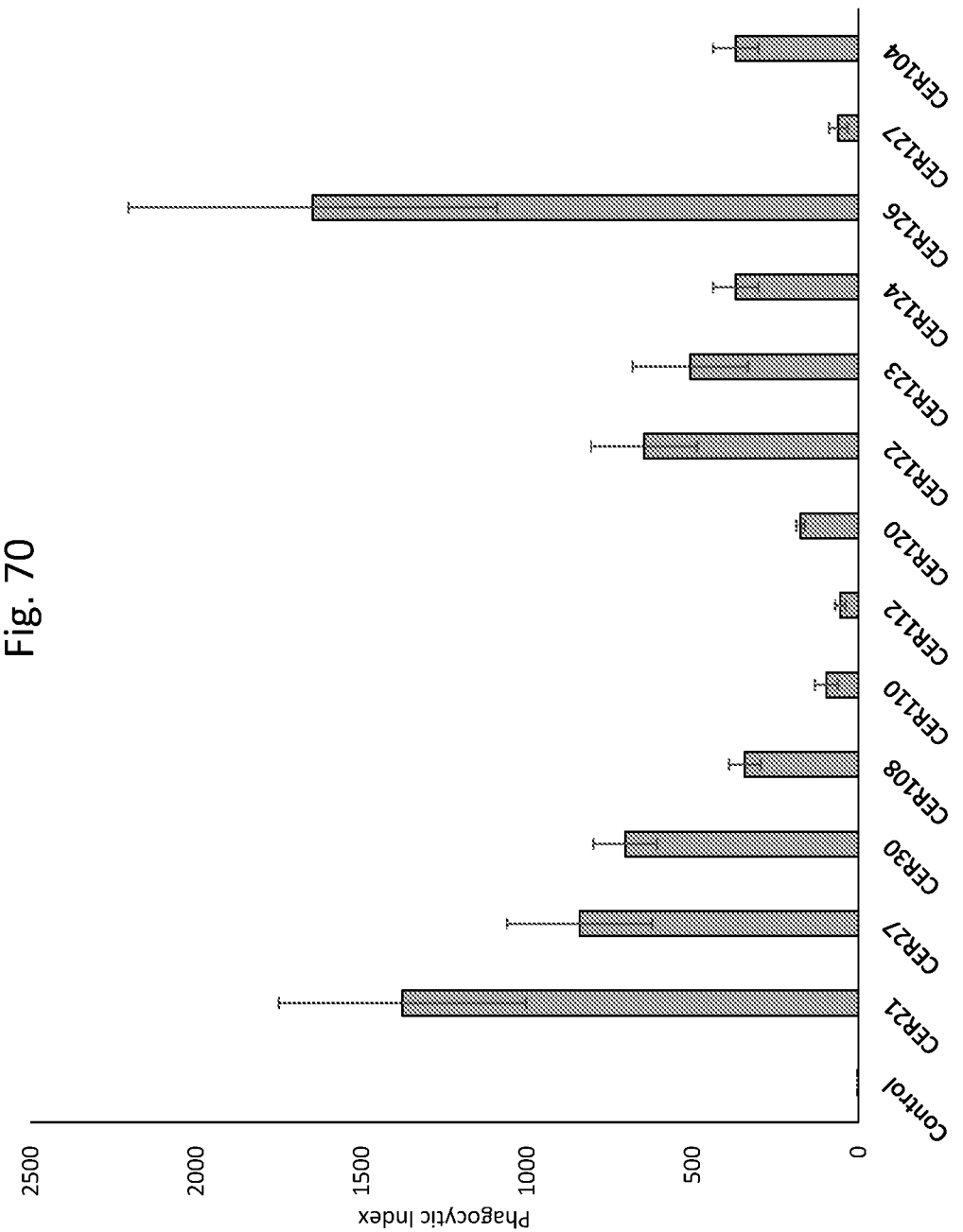
FIG. 70 shows a bar graph representing quantification of adjusted phagocytic index of Alectinib-treated A549 cells+ various CER-expressing T cells (CER21, CER27, CER30, CER108, CER110, CER112, CER120, CER122, CER123, CER124, CER126, CER127, or CER104).
Figure 71:
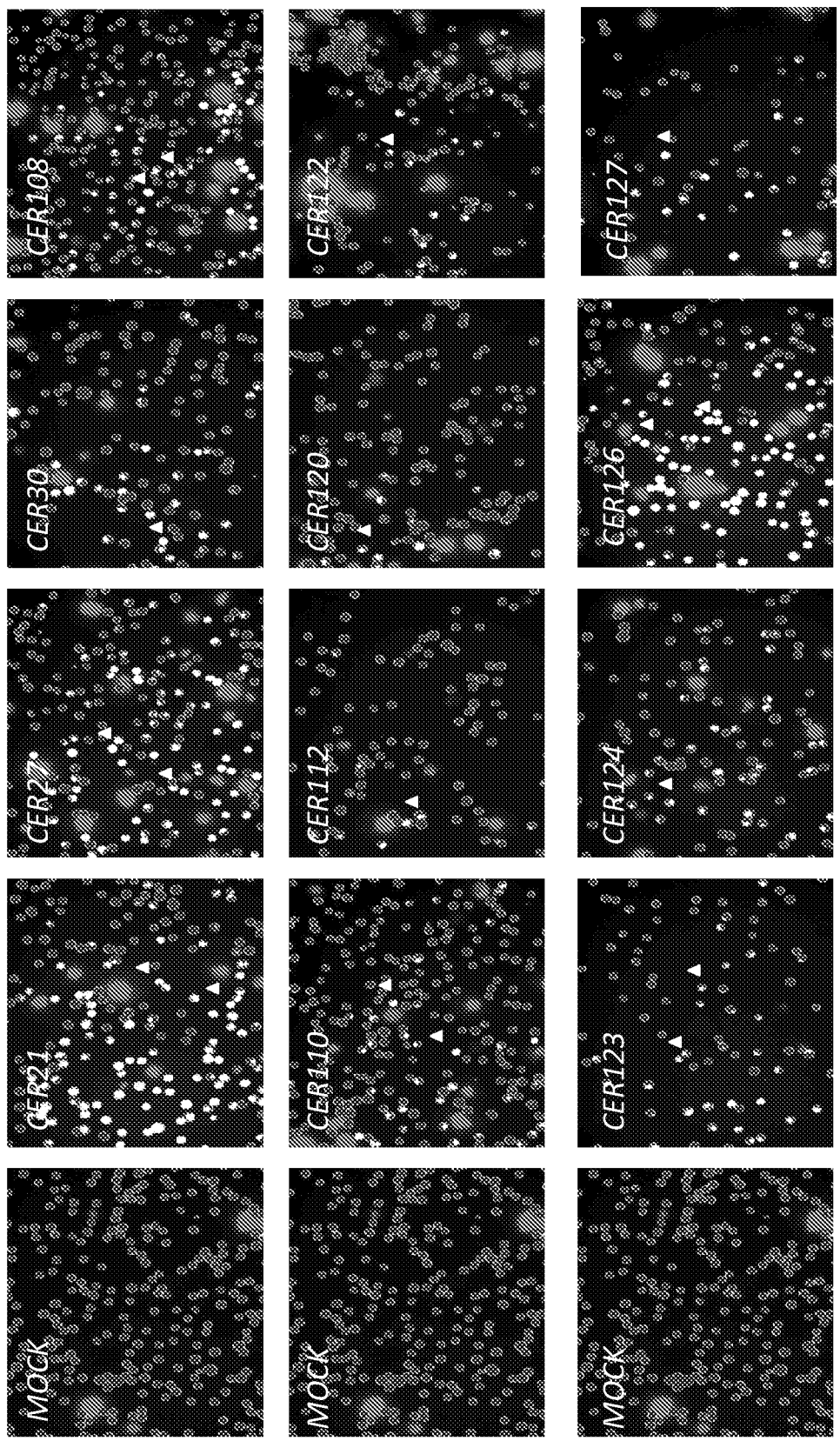
FIG. 71 shows fluorescent micrograph images (40×) of phagocytic elimination of ALK+NSCLC cells co-cultured with various CER-modified T-cells+Alectinib. Yellow triangles indicate phagocytic events (pH rodo red target cells within CT-violet-labeled CD4 T cells). Mock-transduced (vector only) T cells do not exhibit phagocytic activity.

Phagocytosis of alectinib treated A549 lung adenocarcinoma cells by various CER-transduced CD4+ T cells was also quantified. A549 cells were treated with Alectinib (1 μM) for 12 hours. CER21-, CER27-, CER30-, CER108-, CER110-, CER112-, CER120-, CER123-, CER124-, CER126-, CER127-, or CER104-transduced CD4+ T cells were co-cultured with Alectinib-treated A549 cells at a 1:1 ratio for 12 hours. Phagocytic events were calculated from 3×3 stitched fluorescent microscopy images at 40X resolution. FIG. 70 shows an adjusted phagocytic index calculated as (median area ratio of target events in effector cells*% phagocytosis). FIG. 71 shows fluorescent micrographs of Alectinib-treated A549 ALK+ cells that were labeled with pHrodo red and co-cultured with CER-transduced T cells labeled with CELL TRACE violet. Images were obtained after 12 hours of co-culture. Yellow triangles indicate exemplary phagocytic events (pHrodo red targets within CELL-TRACE violet labeled CD4+ T cells). Mock-transduced (vector only) T cells exhibit no phagocytic activity.

A time course study of phagocytic uptake of tumor cells by CER-transduced T cells was performed. CD4+ T cells were transduced with a lentiviral vector comprising CER122 nucleic acid. Mock-transduced (vector only) CD4+ T cells were used as control. CER122-transduced T cells were labeled with CELLTRACE violet and co-cultured with pHrodo red labeled A549 ALK+ lung adenocarcinoma cells. Fluorescent microscopy images were obtained at 4, 8, and 16 hours co-culture (FIG. 72C), and % phagocytosis (FIG. 72A) and phagocytic index (FIG. 72B) were calculated. Yellow triangles indicate exemplary phagocytic events by CER122-transduced T cells (pH rodo red targets within CELLTRACE violet labeled CD4+ T cells) (right image of FIG. 72C). Mock-transduced T cells exhibit no phagocytic activity (FIGS. 72C, left image).

Figure 73:
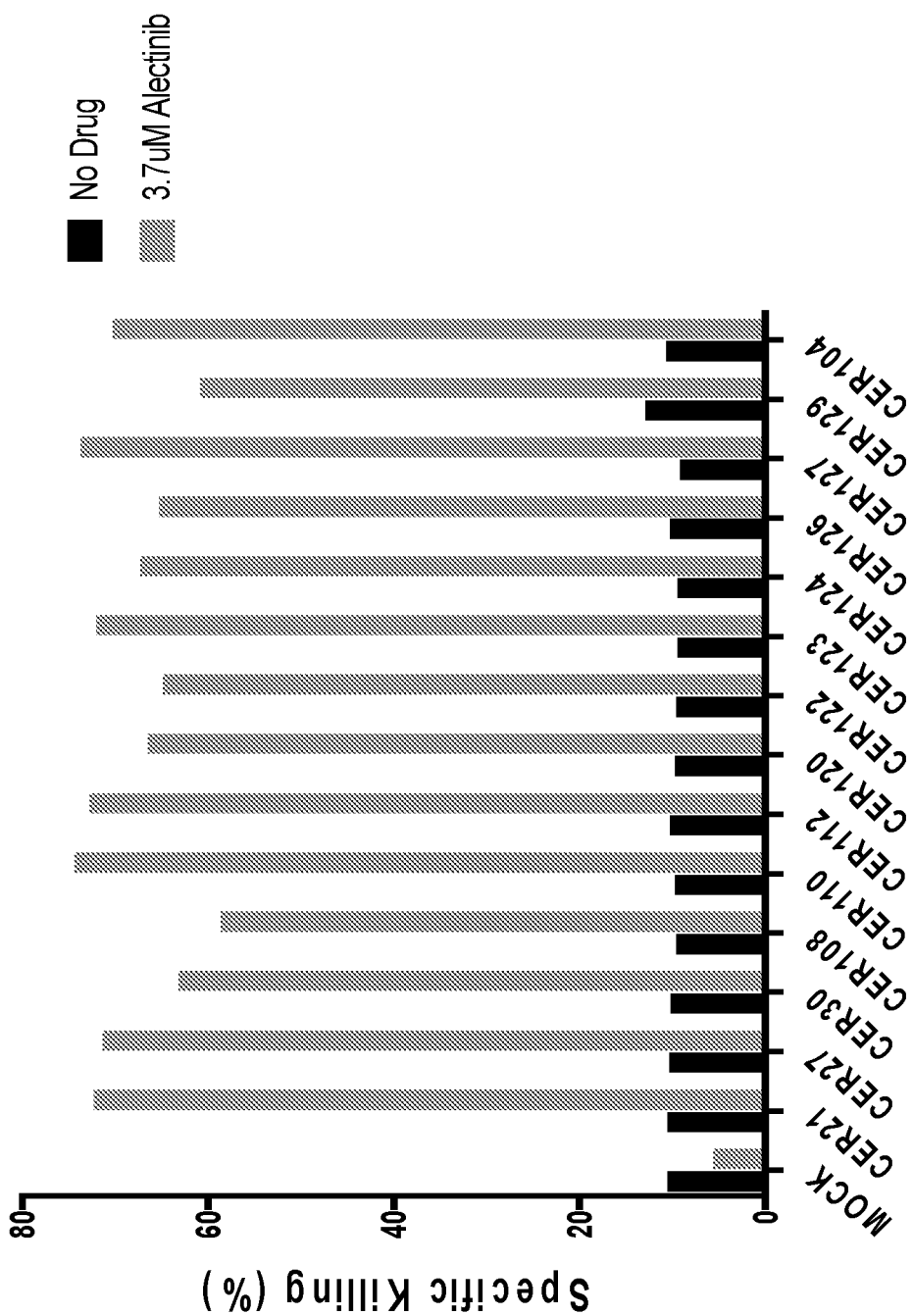
FIG. 73 shows a bar graph of % killing by CER-expressing T cells co-cultured with A549 ALK+ cells+Alectinib (3.704) as measured by LDH cytoxicity assay. Mock-transduced (vector only) T cells were used as a control.

Testing of additional CER types showed synergistic killing of A549 lung adenocarcinoma cells harboring ALK rearrangement upon ALK inhibition (FIG. 73). A549 cells introduced with an ELM4-ALK translocation were co-cultured with mock-transduced (vector only) CD4+ T cells or CER-transduced CD4+ T cells (CER21, CER27, CER30, CER108, CER110, CER112, CER120, CER122, CER123, CER124, CER126, CER127, CER129, or CER104) in combination with Alectinib (3.7 Effector:target cell ratio for co-culture was 1:1. After 18 hours of co-culture, bulk supernatants were evaluated by LDH cytotoxicity assay to measure cell killing (FIG. 73). CER-expressing T cells demonstrated synergistic killing responses upon ALK inhibition.

Cer Enhancement of Alk Inhibitor In Vivo

Figure 74:
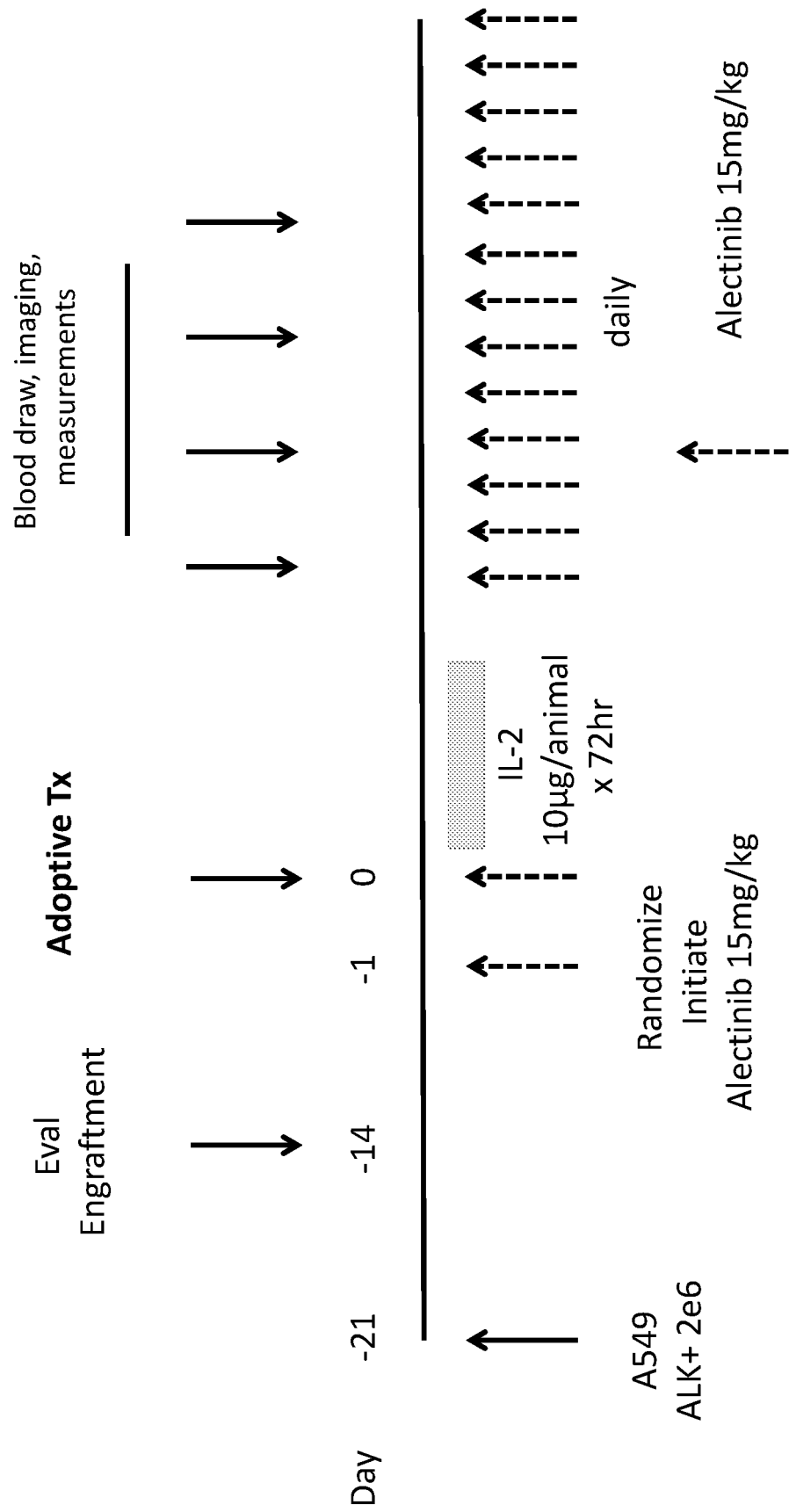
FIG. 74 is a schematic of an exemplary treatment regimen of adoptive transfer of CER-transduced T cells in combination with ALK inhibitor therapy.

The combination of CER therapy and ALK inhibitor therapy was also evaluated in vivo. FIG. 74 shows a schematic depicting details of adoptive cell therapy experiments using CER-expressing T cells in combination with ALK inhibitor therapy. A549 ALK+Luciferase$^+$ cells were engrafted into immunodeficient (NSG) mice 21 days prior to initiation of study and evaluated for engraftment by bioluminescent emission and tumor volume seven days later. The day prior to CER adoptive transfer (day-1), animals with established tumors were randomized into groups and treated with Alectinib 15 mg/kg (intraperitoneally) and then infused retro-orbitally with 10e6 CER-transduced human T cells. Animals received 10 μg of systemic IL-2 every 24 hours×3 days following cell infusion and then monitored for tumor progression and cell expansion and persistence thereafter.

Figure 75B:
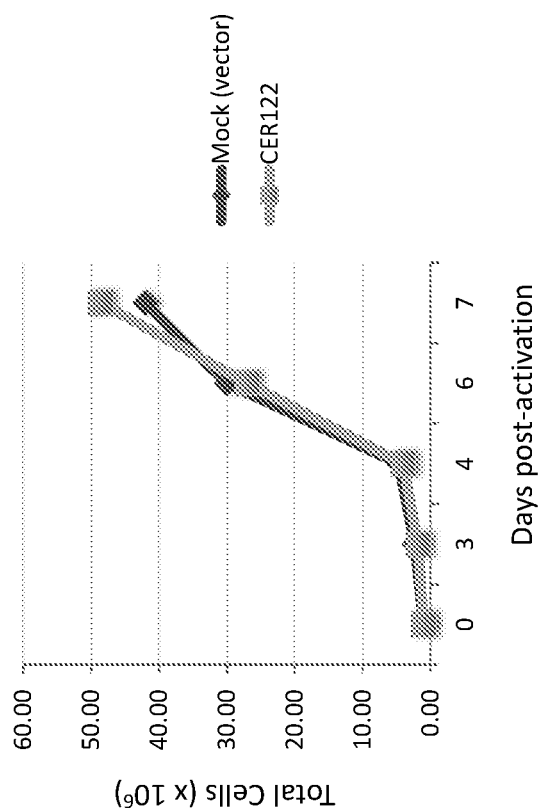
FIGS. 75A-75D show that generation of CER-expressing T cells can be expanded.
Figure 75A:
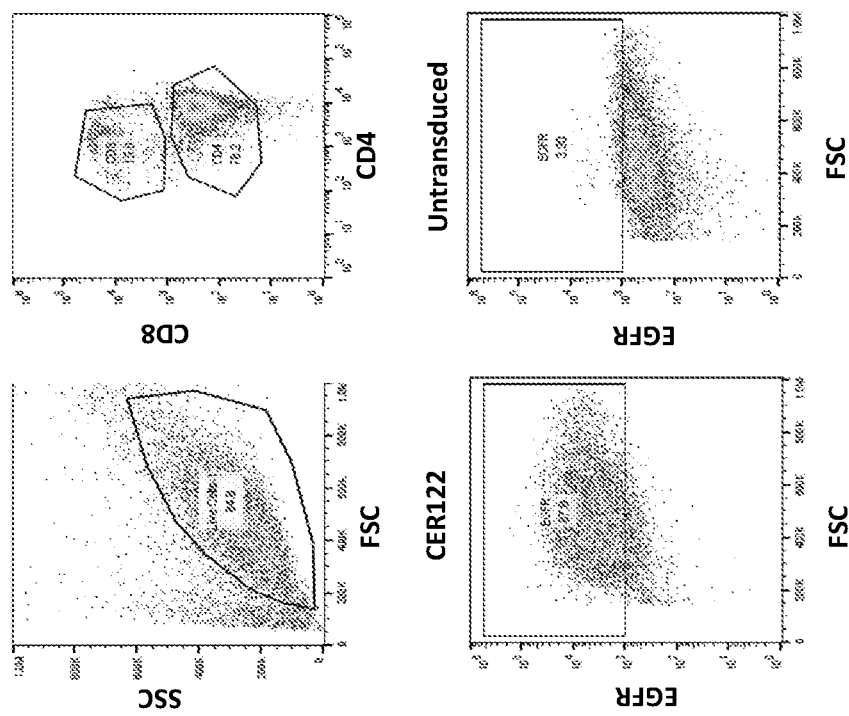
Figures 75C, 75D:
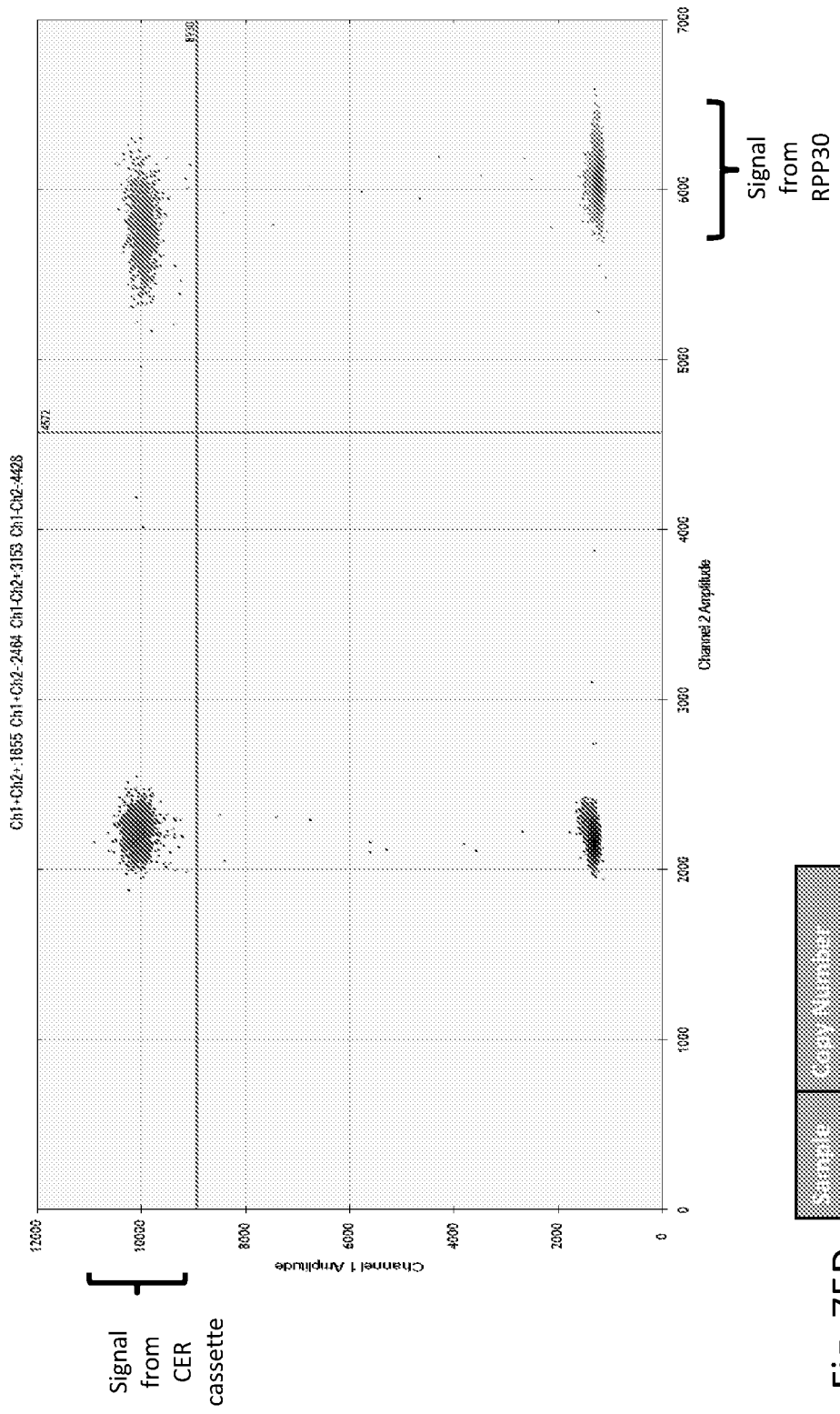

CER-expression T cells can be expanded ex vivo. T cells were enriched, activated, and transduced with a CER122-T2A-tEGFR lentiviral construct and phenotyped for surface EGFR and T-cell markers CD4, CD8 by FACS (FIG. 75A). The total number of transduced and control T cells (transduced with vector only) in unselected cultures was determined after CD3 and CD28 bead activation (FIG. 75B). 2-D fluorescence droplet digital PCR was performed on CER122-transduced T cell genomic DNA and demonstrates amplification of a region from the CER cassette (FIG. 75C). Copy number value for CER122-transduced T cells was determined from digital droplet PCR (FIG. 75D).

Figure 76B:
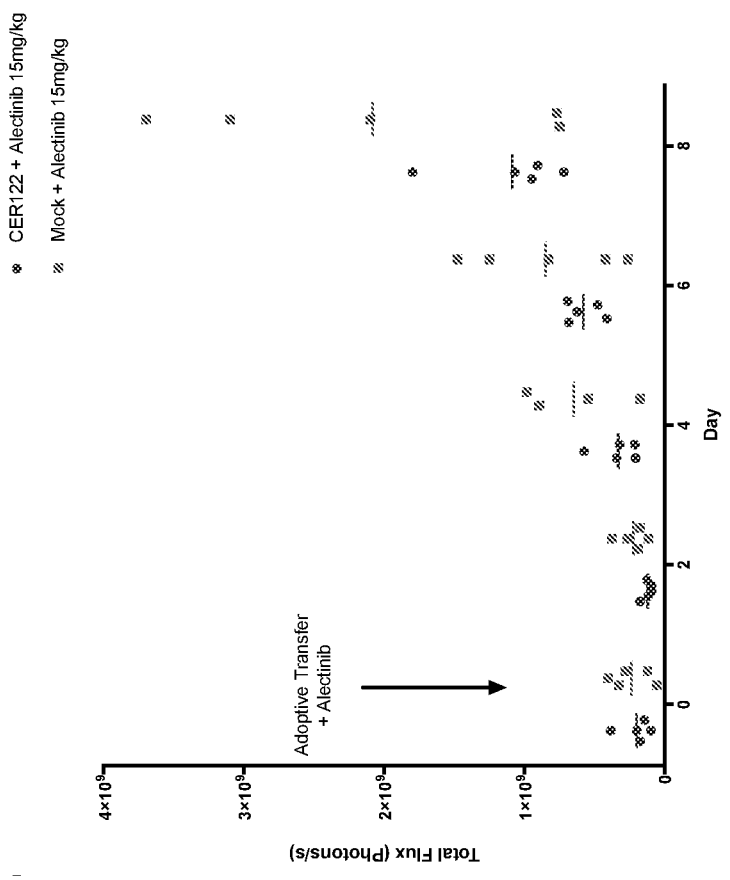
FIGS. 76A-76C show that CER122 expressing T cells enhance anti-tumor responses to ALK inhibitor (15 mg/kg Alectinib) in vivo.
Figure 76A:
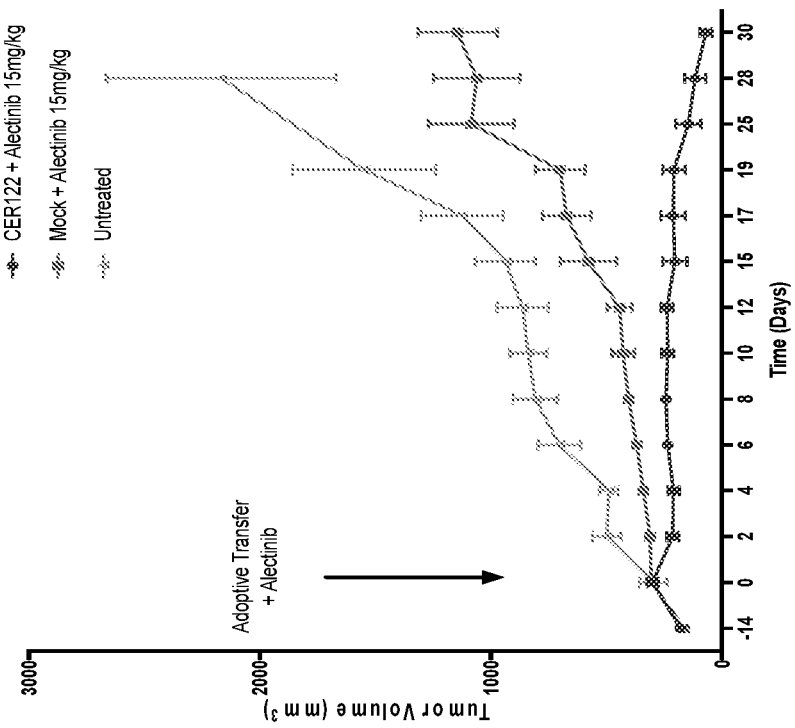
Figure 76C:
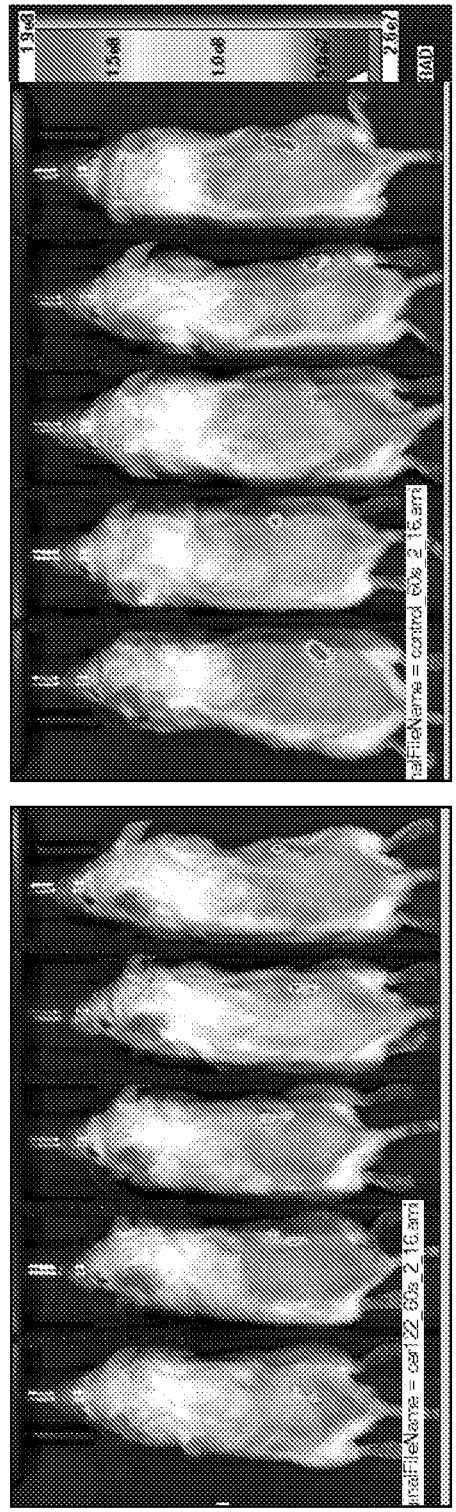
Figure 77A:
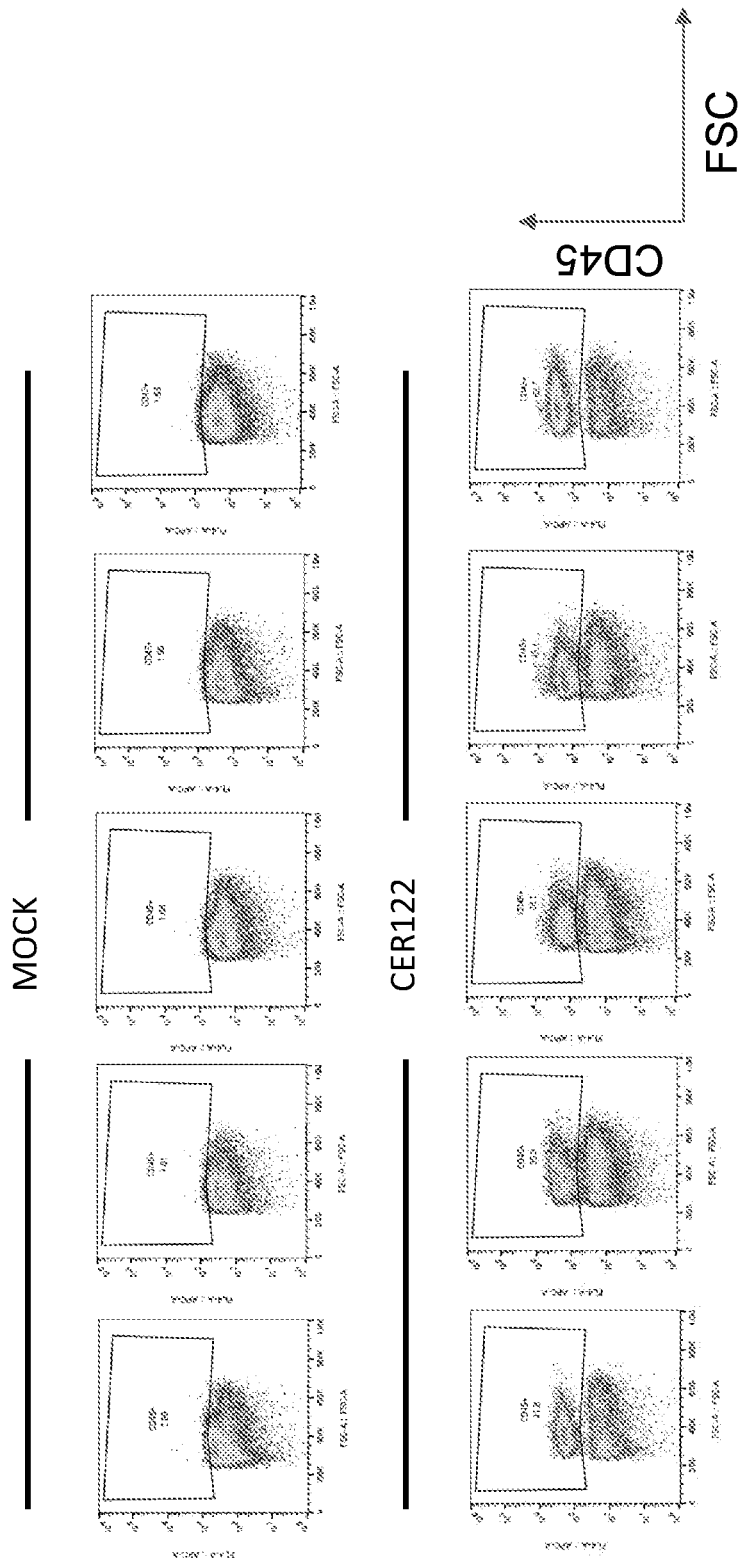
FIGS. 77A-77B show FACS plots (FIG. 77A) and bar graph (FIG. 77B) showing early expansion of CD45+/ CER122+ human T cells in peripheral blood post-adoptive cell treatment.
Figure 77B:
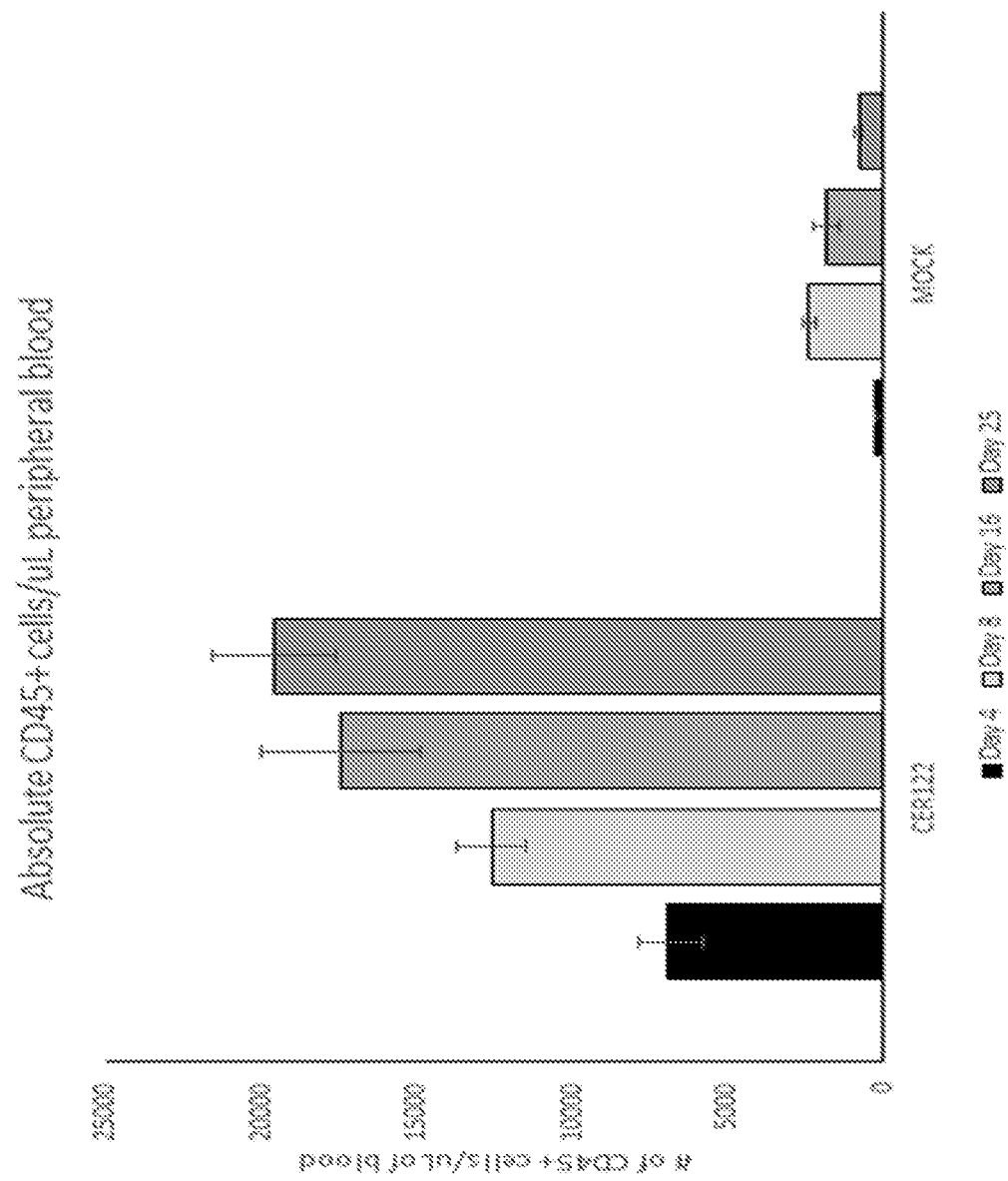

FIG. 76A shows tumor volume measurements from −14 to 30 days post-adoptive transfer in untreated, Alectinib only, and Alectinib+CER122-transduced T cells (n=5 per group). FIG. 76B shows growth of A549-luciferase+ALK-positive cells in NSG mice from 0 to 8 days post-adoptive transfer, as evaluated by bioluminescence imaging. FIG. 76C shows bioluminescence image of A549 ALK-positive tumor burden at day 8 post-adoptive transfer. Combination of CER122 therapy with alectinib treatment enhanced anti-tumor response to ALK+NSCLC in vivo. CER-transduced T cells exhibited early expansion post-adoptive transfer. FACS plots demonstrate early expansion of CD45+ human cells in peripheral blood of animals post-adoptive cell treatment (FIG. 77A). Peripheral blood sample was stained with anti-human CD45-APC-conjugated antibody 8 days following cell infusion. Each FACS plot indicates a single animal. A bar graph depicting frequency of human CD45+ cells/µL of peripheral blood at days 4, 8, 16, and 25 post-adoptive transfer of CER122+ T cells (FIG. 77B). Peripheral blood was obtained by retro-orbital bleeding and examined for evidence of T cell engraftment by FACS. The frequency of human-CD45 cells/µL of peripheral blood was determined by FACs using TRUCOUNT (BD Biosciences) beads.

Cer Enhancement of Egfr Inhibitor In Vivo

Figure 78:
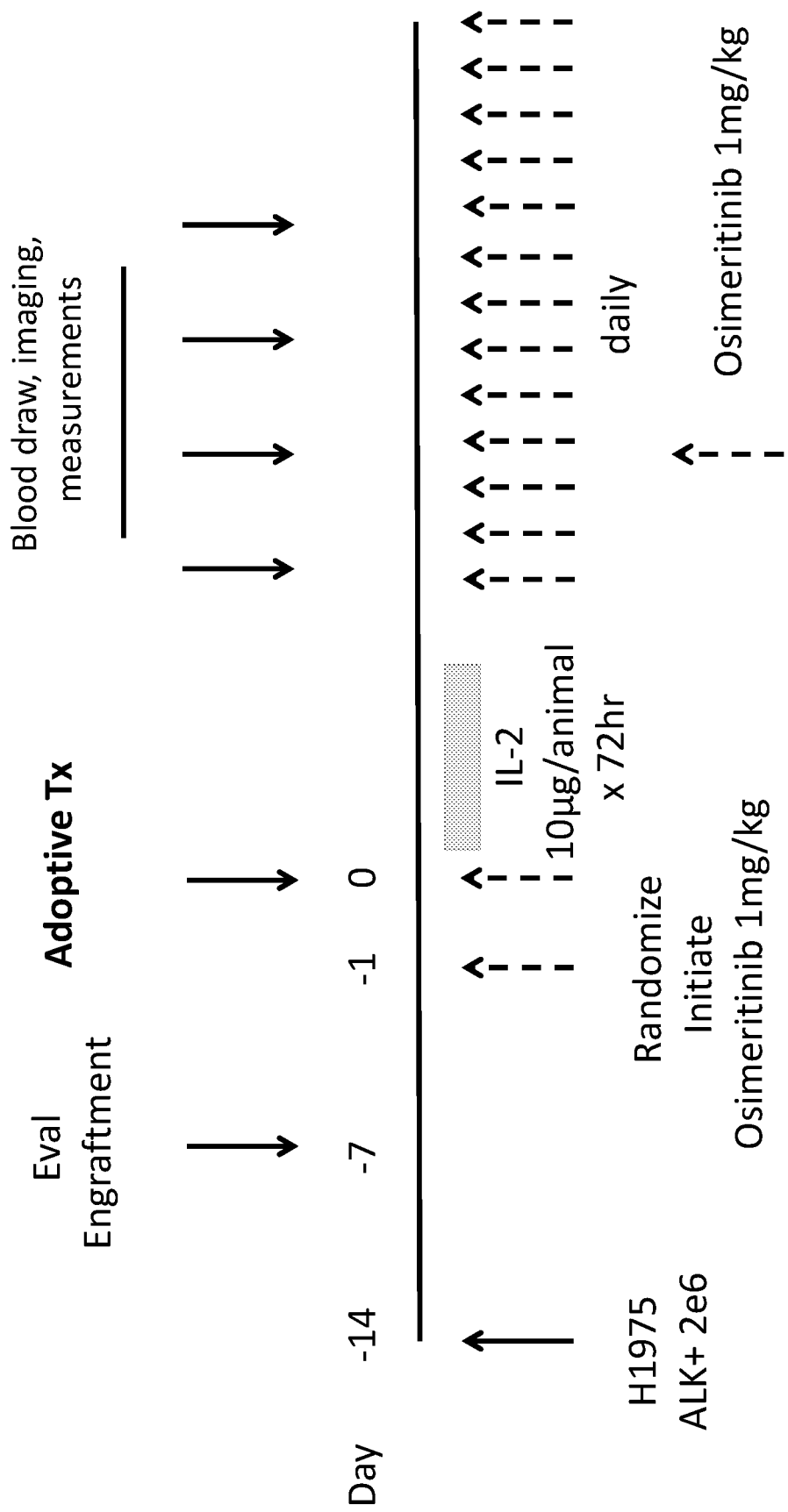
FIG. 78 is a schematic of an exemplary treatment regimen of adoptive transfer of CER-transduced T cells in combination with EGFR inhibitor therapy.
Figure 79:
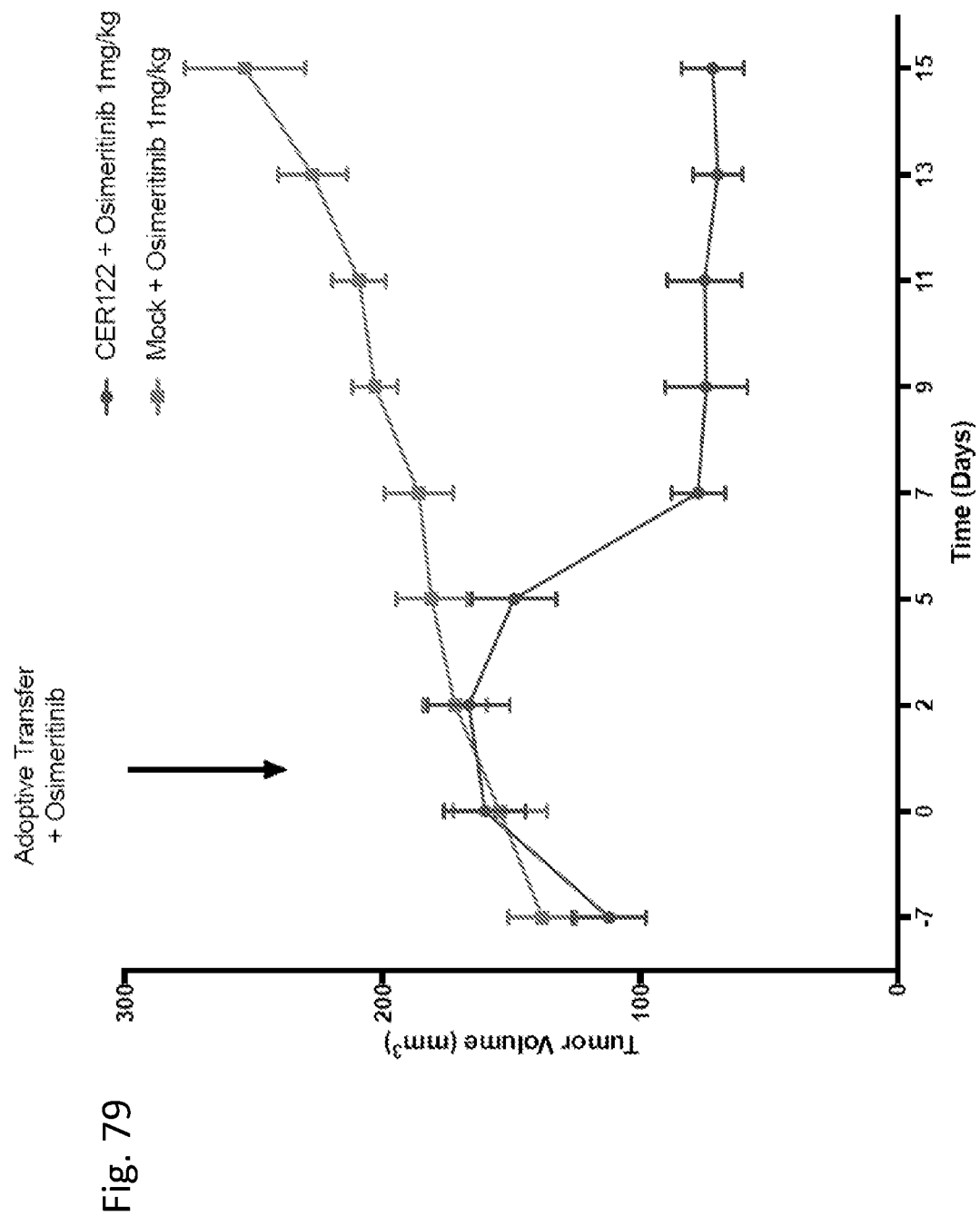
FIG. 79 is a line graph showing tumor volume measurements post-adoptive transfer in untreated, Osimeritinib only, and Osimeritinib+CER122-transduced cells (n=5 per group).

The combination of CER therapy and EGFR inhibitor therapy was also evaluated in vivo. FIG. 78 shows a schematic depicting details of adoptive cell therapy experiments using CER-expressing cells in combination with EGFR inhibitor therapy. H1975 EGFR+/Luciferase+ cells were engrafted into immunodeficient (NSG) mice 14 days prior to initiation of study and evaluated for engraftment by bioluminescent emission and tumor volume seven days later. The day prior to CER adoptive transfer (day-1), animals with established tumors were randomized into groups and treated with Osimeritinib 1 mg/kg (intraperitoneally) and then infused by tail vein with 10e6 CER-transduced human T cells. Animals received 10 µg of systemic IL-2 every 24 hours×3 days following cell infusion and then monitored for tumor progression and cell expansion and persistence thereafter. Tumor volume measurements were obtained post-adoptive transfer in untreated, Osimeritinib treated (1 mg/kg)+mock-transduced T cells (vector only), and Osimeritinib (1 mg/kg)+CER122-transduced T cells (n=5/group) (FIG. 79). CER122-expressing T cells combined with Osimeritinib enhanced anti-tumor responses in EGFR+NSCLC model in vivo.

Example 8

Characterization of Cer Modified Cd4 T Cells

Figure 80A:
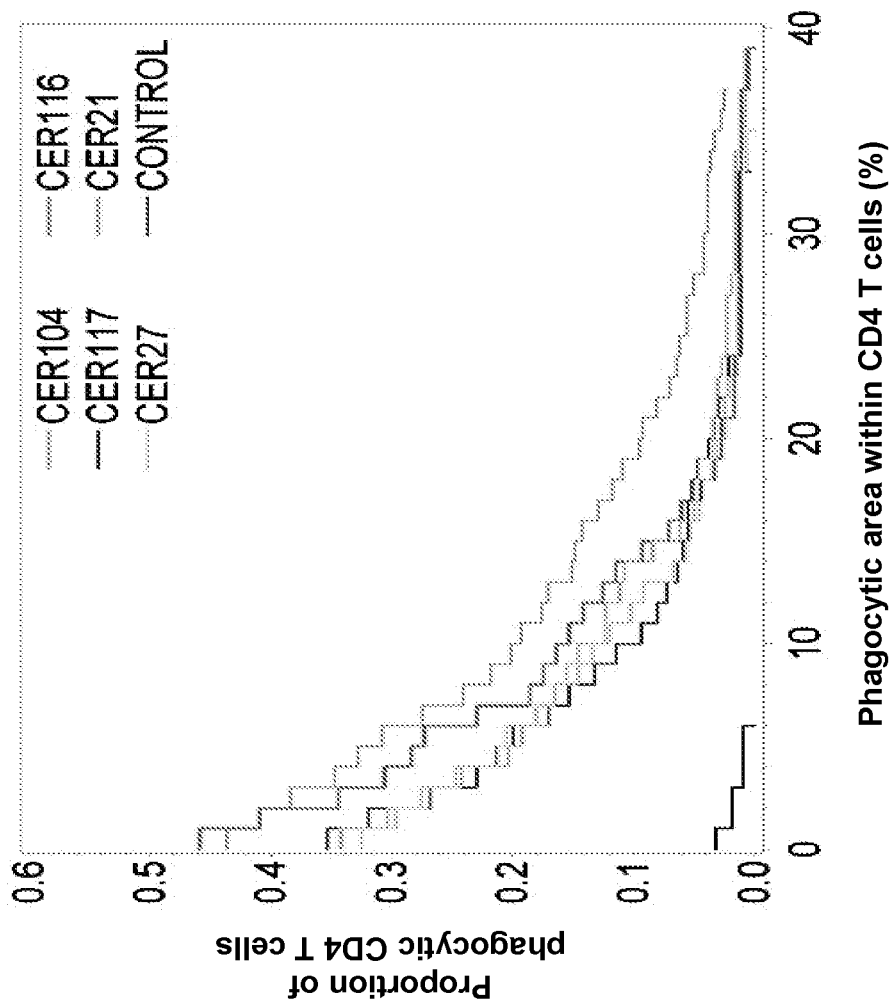

Various CER-modified CD4+ T cells were also evaluated for breadth of response to determine whether a particular CER confers a broad phagocytic response of low magnitude (e.g., 10% engulfment in 90% of cells) or a less frequent but strong phagocytic response (e.g., 90% engulfment in 10% of cells) in the host cells. CD8+ T cells were transduced with HPV16 E7 specific TCR as described in Example 5. CD4+ T cells were transduced with lentiviral vectors comprising a CER21, CER27, CER104, CER116, or CER117 nucleic acid. Mock-transduced (vector alone) CD4+ T cell were used as control. CD4+/CER+ and CD8+/E7 TCR+ T cells were stained with CELLTRACE violet. HPV16 E7+ head and neck squamous cell carcinoma cells (SCC152) were stained with pHrodo red. HPV16 E7 TCR transduced CD8+ T cells and selected CER transduced CD4+ T cells were mixed at a 1:1 ratio and co-cultured with SCC152 cells at a 1:1 ratio for 8 hours. Phagocytosis of target SCC152 cells by CER-transduced CD4+ T cells was analyzed by fluorescence microscopy. FIG. 80A shows a magnitude breadth curve for phagocytosis by CER type. The horizontal axis represents the % area of CER-transduced CD4+ T cells having engulfment or % area of the CER-transduced CD4+ T cells taken up by target SCC152 cells. This measure was rarely above 40% across CER types tested. The vertical axis represents the proportion of CER-transduced CD4+ T cells that were phagocytic. For CER104, about 20% of CER104-transduced CD4+ T cells have more than 10% engulfment. For CER117-transduced CD4+ T cells, less than 10% have more than 10% engulfment. FIG. 80B shows fluorescent micrograph images of SCC152 target cells engulfed by CER126-transduced CD4+ T cells.

Figure 81:
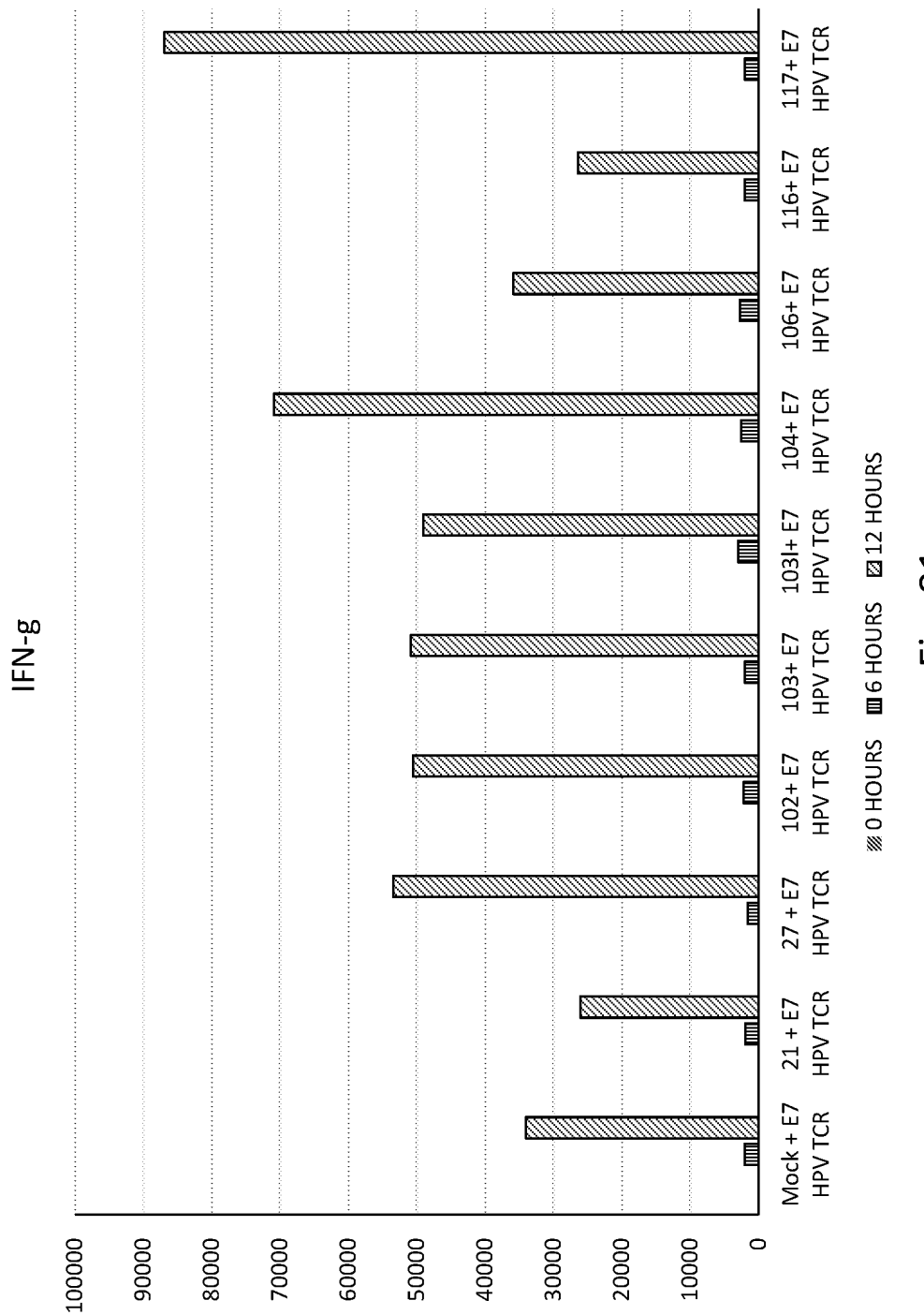
FIG. 81 shows cytokine secretion from CER-expressing CD4+ T cell +E7-specific TCR CD8+ T cell co-culture experiments. The addition of a CER-expressing CD4+ T cell to E7-specific TCR expressing CD8+ T cell enhanced levels of IFNγ secretion.

CD4+ T cells were transduced with lentiviral vectors comprising a CER21, CER27, CER102, CER103A, CER103B, CER104, CER106, CER116, or CER117 nucleic acid. Mock-transduced (vector alone) CD4+ T cell were used as control. CD8+ T cells were transduced with HPV16 E7 specific TCR. HPV16 E7 TCR transduced CD8+ T cells and selected CER transduced CD4+ T cells were mixed at a 1:1 ratio and co-cultured with SCC152 cells at a 1:1 ratio for 10 hours. Supernatants were then collected and analyzed for bulk cytokine secretion. As shown in FIG. 81, addition of a CER-expressing CD4+ T cell to E7 TCR-transduced CD8+ T cells enhanced levels of IFNγ secretion.

Example 9

Marker Analysis of Cer Modified Cd4 T Cells

Figures 83A, 83B:
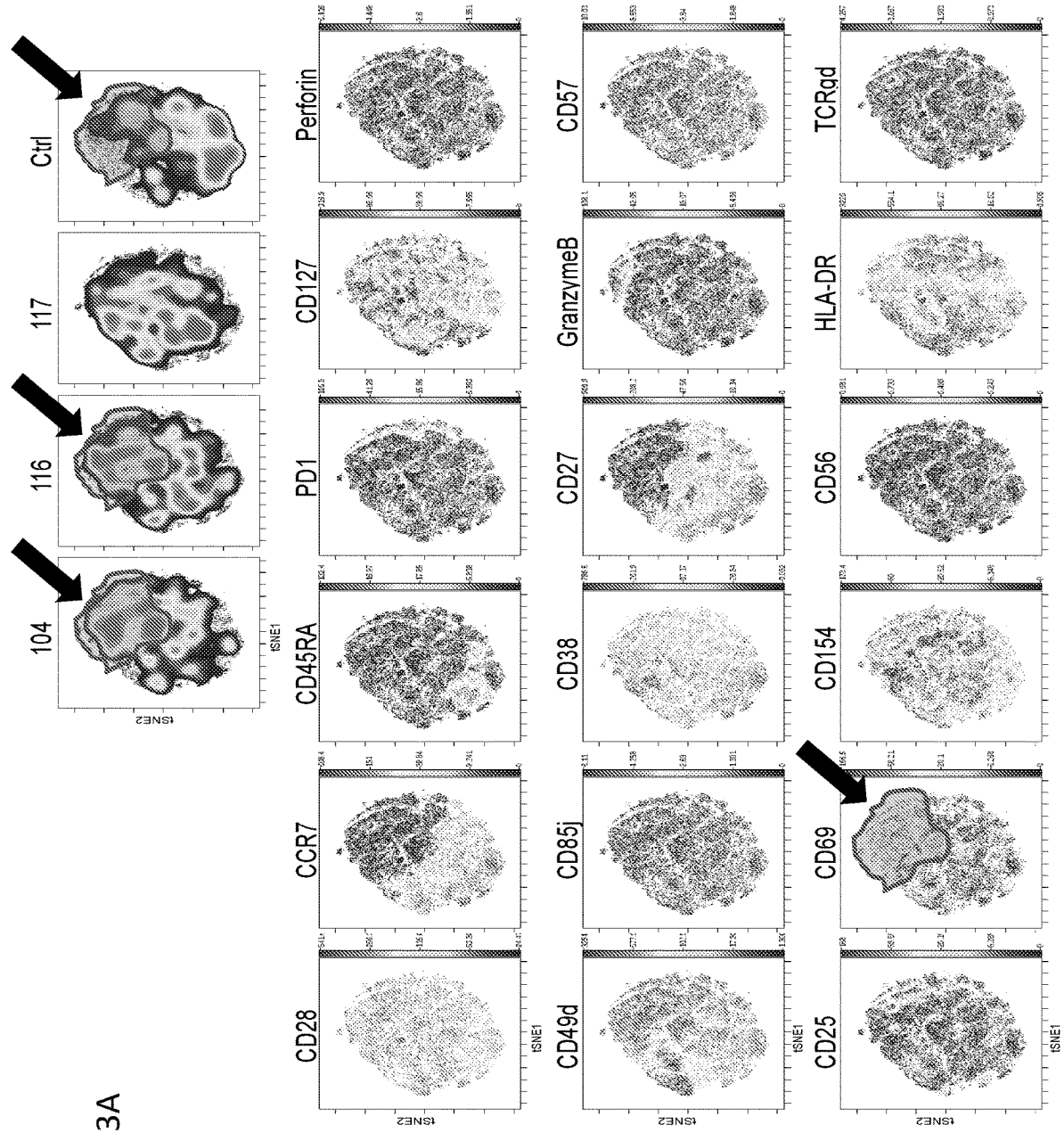
FIGS. 83A-83B show viSNE maps of mass cytometry data of CER-expressing CD4+ T cells upon antigen encounter. CER-transduced CD4+ T cells were co-cultured with E7-specific TCR-transduced CD8+ T cells and HPV+ SCC152 target cells and then interrogated by mass cytometry (CyTof). Intact CER-CD4+ T cells are shown in plots displaying tSNE1 and tSNE2 axes. Eighteen cell surface markers were used for the viSNE analysis. Each dot represents a single cell.
Figures 84A, 84B:
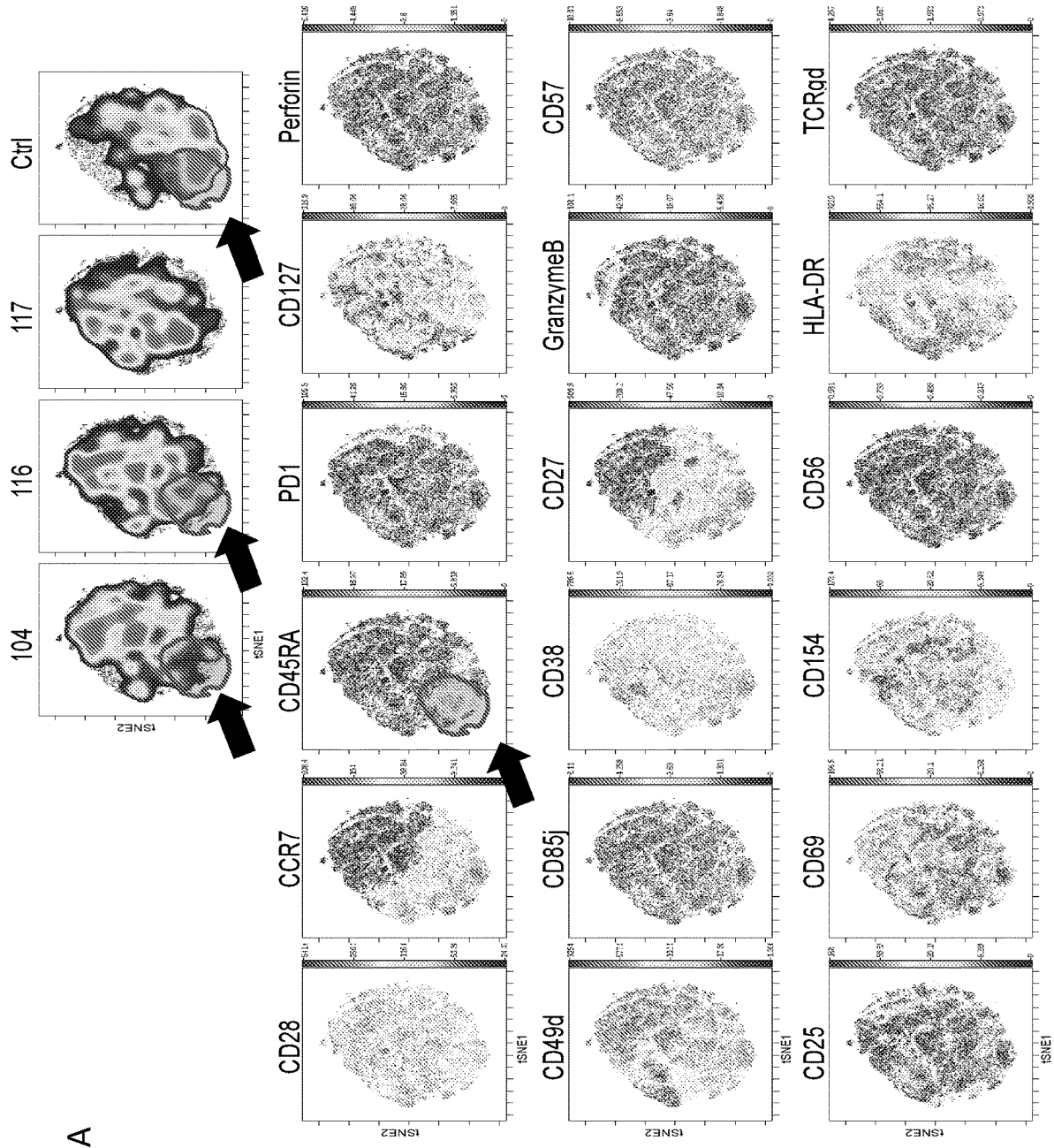
FIGS. 84A-84B show viSNE maps of mass cytometry data of CER-expressing CD4+ T cells upon antigen encounter. CER-transduced CD4+ T cells were co-cultured with E7-specific TCR-transduced CD8+ T cells and HPV+ SCC152 target cells and then interrogated by mass cytometry (CyTof). Intact CER-CD4+ T cells are shown in plots displaying tSNE1 and tSNE2 axes. Eighteen cell surface markers were used for the viSNE analysis. Each dot represents a single cell.

CD4+ T cells were transduced with lentiviral vector comprising CER104, CER116, or CER117 nucleic acid. CER104 (SEQ ID NO:133) comprises a Tim4 binding domain, Tim4 transmembrane domain, and an engulfment signaling domain comprising a primary engulfment signaling domain comprising a TLR8 signaling domain and a secondary engulfment signaling domain comprising a DAP12 signaling domain. CER116 (SEQ ID NO:143) comprises a Tim4 binding domain, Tim4 transmembrane domain, and an engulfment signaling domain comprising a primary engulfment signaling domain comprising a TRAF6 signaling domain and a secondary engulfment signaling domain comprising a TLR8 signaling domain. CER117 (SEQ ID NO:144) comprises a Tim4 binding domain, Tim4 transmembrane domain, and an engulfment signaling domain comprising a primary engulfment signaling domain comprising a TLR8 signaling domain and a secondary engulfment signaling domain comprising a TRAF6 signaling domain. CER-transduced CD4+ T cells were co-cultured with E7 TCR-transduced CD8+ T cells and HPV+SCC152 target cells and interrogated by mass cytometry (CyTOF) with viSNE for visualization of high dimensional single cell data (FIGS. 82-84). Intact CER-transduced CD4+ T cells are shown in plots displaying tSNE1 (horizontal) and tSNE2 (vertical) axes. 27 intracellular markers were used for the viSNE analysis. Each dot represents a single cell. Coloring the plots by a few of the measured markers (GM-CSF, MIP1b, Perforin, TNF, IL-17, Granzyme B, IL-4, IL-2, and IFNγ) shows the phenotype across viSNE 'islands' (FIG. 82A). Red represents high expression and blue represents low expression for each marker. Populations of CD4+ T cells were generated using a clustering algorithm from all 27 markers and overlaid onto the viSNE map. Arrows indicate enrichment of islands expressing the intracellular marker IFNγ in samples containing CER104, CER116, and CER117 (FIG. 82B). Populations of CD4+ T cells were generated using a clustering algorithm from all 18 markers and overlaid onto the viSNE map (FIG. 83A). Arrows indicate enrichment of islands expressing the T cell activation marker CD69 in samples containing CER104- and CER116-transduced CD4+ T cells. Color plots by 18 intracellular markers (CD28, CCR7, CD45RA, PD1, CD127, Perforin, CD49d, CD85j, CD38, CD27, Granzyme B, CD57, CD25, CD69, CD154, CD56, HLA-DR, and TCRγδ) show the phenotype across viSNE 'islands' (FIG. 83B). Red represents high expression and blue represents low expression for each marker. Highlighted region with arrow indicates cells expressing T cell activation marker CD69. Populations of CD4+ T cells were generated using a clustering algorithm from 18 intracellular markers (CD28, CCR7, CD45RA, PD1, CD127, Perforin, CD49d, CD85j, CD38, CD27, Granzyme B, CD57, CD25, CD69, CD154, CD56, HLA-DR, and TCRγ6) and overlaid onto the viSNE map. Arrows indicate loss of islands expressing the naïve T cell marker CD45RA within the CCR7+ population among CER104 and CER116 samples compared to controls (FIG. 84A). Color plots by the 18 intracellular markers show the phenotype across viSNE 'islands' (FIG. 84B). Red represents high expression and blue represents low expression for each marker. Highlighted region with arrow indicates cells expressing the naïve T cell marker CD45RA. Thus, this data show that CER104 and CER116-transduced CD4+ T cells are associated with memory formation after antigen encounter.

Example 10

Phagocytic Signaling Transduction in Cer Modified Cells

Figure 85B:
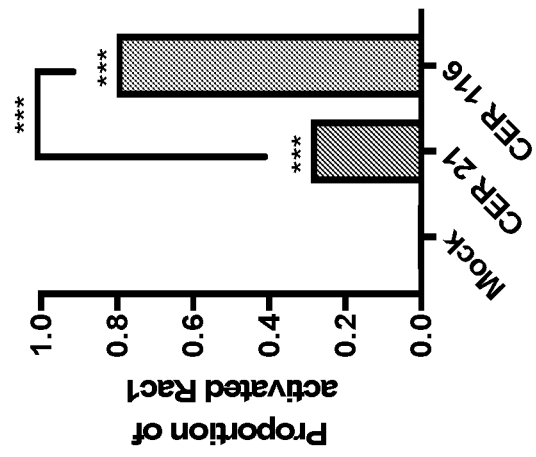
FIGS. 85A-85G show induction of phagocytic signal transduction cascades in CER-expressing cells and luminal content degradation.
Figure 85A:
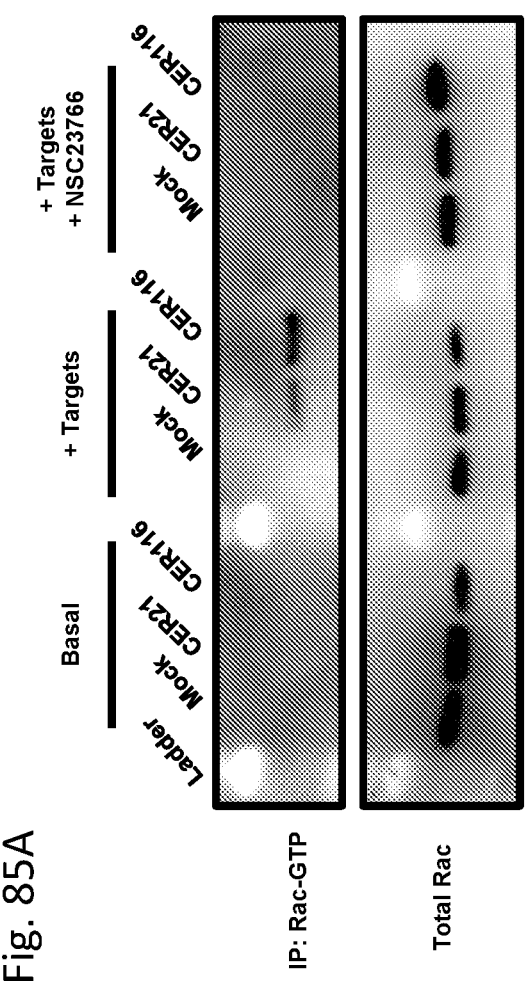
Figure 85C:
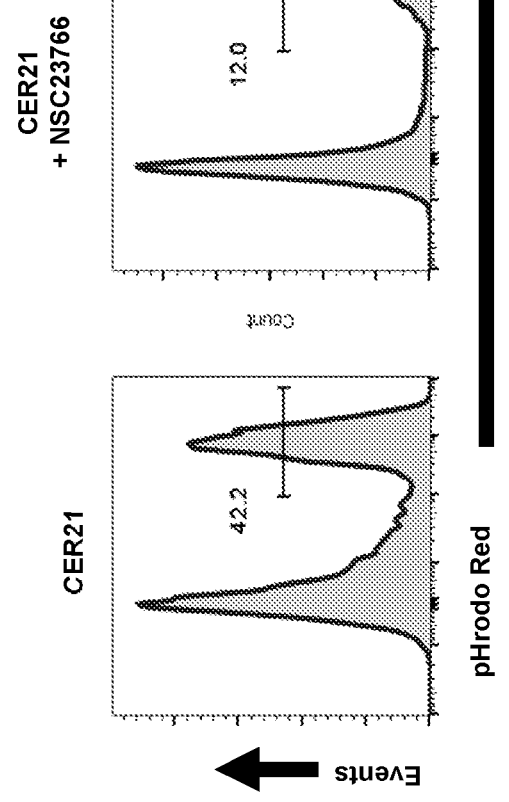
Figure 85D:
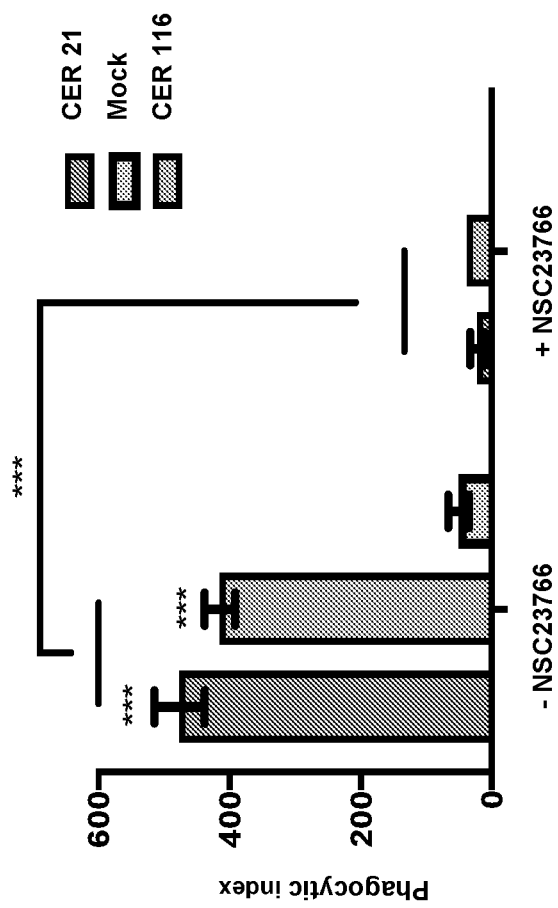
Figure 85E:
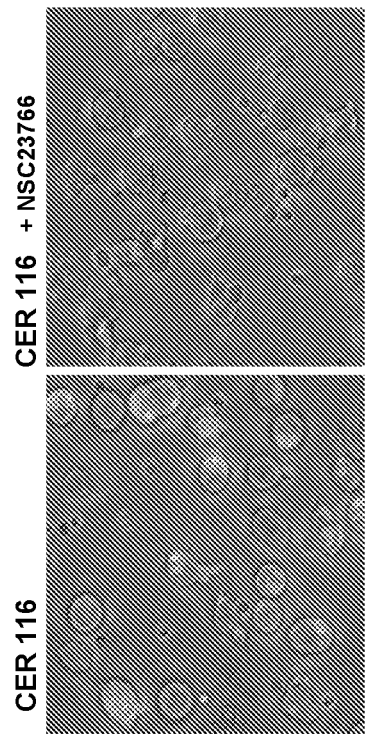

The Rho family of GTPases play essential roles in actin assembly during phagocytosis. Inhibition of either Rho GTPase Racl or CDC42 in macrophages results in a complete blockade of FcR-mediated phagocytosis due to defective actin assembly. To investigate induction of phagocytic signal transduction cascades, CER-expressing cells were interrogated for the activation of CDC42 and Racl. The activation of either Rho GTPase involves the transition from an inactive GDP-bound form to an active GTP-bound form, catalyzed by guanine nucleotide-exchange factors (GEFs). Ba/F3 cells were transduced with lentiviral vectors comprising CER21 nucleic acid, CER116 nucleic acid, or vector alone (mock). Target thymocyte cells were stained with pHrodo red. CER-transduced Ba/F3 cells were co-cultured with dexamethasone pre-treated thymocytes for 2 hours. The Racl inhibitor NSC23766 (Selleck Chem) was added during the co-culture in appropriate wells. Cells were then collected, solubilized in lysis buffer, and immunoprecipitation was performed on protein lysates to detect phospho-Racl using PAK-PBD agarose beads (Cytoskeleton, Inc.). Immunoprecipitates were eluted and 25 μg of protein was loaded onto SDS-PAGE gradient gels and then probed with monoclonal, mouse anti-Racl primary antibody (Cytoskeleton Inc.) overnight at 4° C., washed, and hybridized with secondary, anti-mouse antibody conjugated to horseradish peroxidase (Jackson Labs) (FIG. 85A). Prior to immunoprecipitation, Some protein lysate sample was reserved for total protein estimation and total Racl estimation. Basal samples comprise CER-expressing cells cultured without target cells. Protein gel bands were quantified using ImageJ image processing program, and the proportion of activated Racl was quantified (FIG. 85B). CER21 (SEQ ID NO:88) comprises a Tim4 binding domain, a Tim4 transmembrane domain, and a TLR8 signaling domain. CER116 (SEQ ID NO:143) comprises a Tim4 binding domain, a Tim4 transmembrane domain, and an engulfment signaling domain comprising a primary engulfment signaling domain comprising a TRAF6 signaling domain and a secondary engulfment signaling domain comprising a TLR8 signaling domain. The addition of a TRAF6 signaling domain enhanced Racl signaling in CER116-transduced Ba/F3 cells compared to CER21-transduced Ba/F3 cells. FIG. 85C shows representative FACs profiles of pHrodo+ in CER21-transduced Ba/F3 cells after 6 hour co-culture. CER21-transduced Ba/F3 cells shows considerable pHrodo+ signal indicating phagocytosis of target thymocytes (see, FIG. 85C left image). The addition of a specific Racl small molecule inhibitor abolishes phagocytosis (FIG. 85C, right image). The numbers associated with each peak indicates the percentage (phagocytosis) of pHrodo+ thymocytes in CER21+ Ba/F3 cells. Phagocytic indices (FIG. 85D) were calculated from fluorescent imaging shown in FIG. 85E. Representative fluorescent micrographs of phagocytosis assays of CER116-harboring Ba/F3 cells in presence or absence of Racl inhibitor NSC23766 (FIG. 85E). Engulfed thymocytes stained with pHrodo red are observed inside CELLTRACE violet stained CER116+Ba/F3 cells. Racl inhibition abolishes CER116 mediated phagocytosis of thymocytes.

Figure 85F:
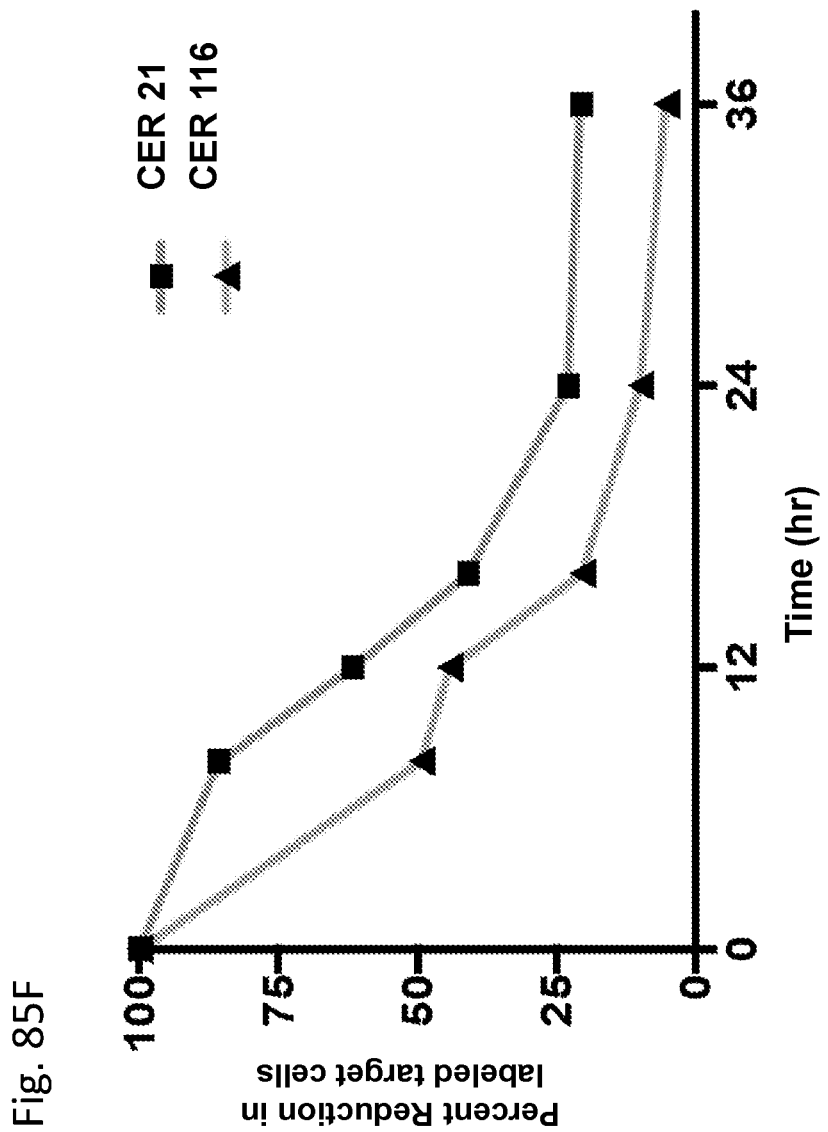
Figure 85G:
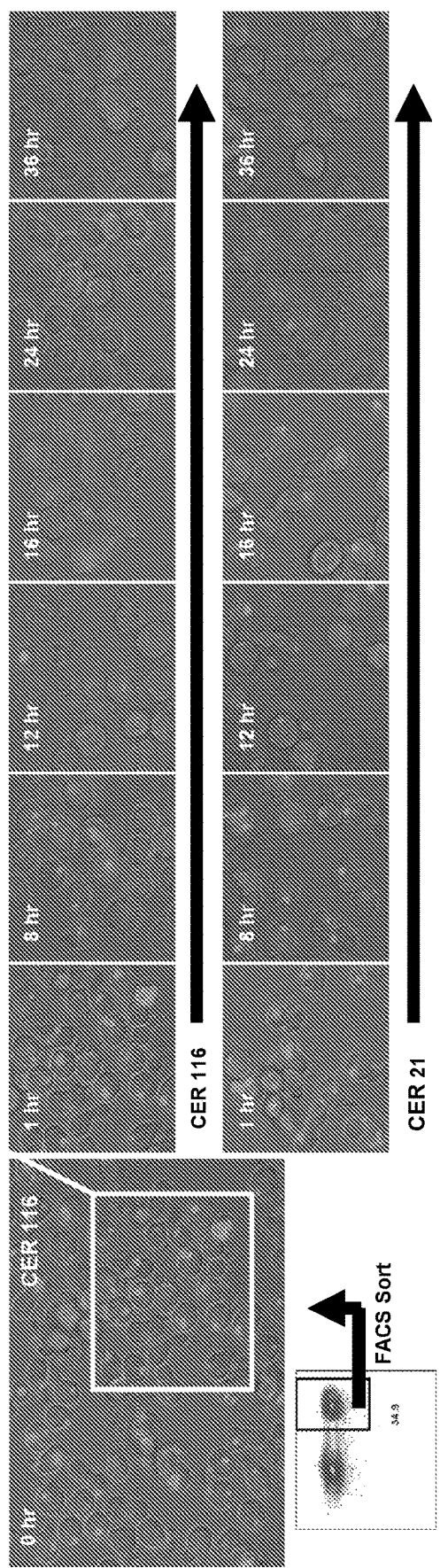

Luminal degradation in CER-transduced cells was also evaluated following engulfment. Ba/F3 cells transduced with CER21 or CER116 were co-cultured with pHrodo-red labeled, dexamethasone treated thymocytes overnight and subsequently purified by FACS. Target cell destruction was visualized by time-lapse imaging and quantified over time (FIG. 85F). The addition of a TRAF6 signaling domain enhanced CER116 luminal content degradation over time as compared to CER21, with near complete resolution of luminal contents by 36 hours (FIG. 85F). Time lapse imaging of CER116+Ba/F3 cells (FIG. 85G, top row images) and CER21+Ba/F3 cells (FIG. 85G, bottom row images) demonstrates destruction of luminal contents. pHrodo-red labeled contents are broken down over-time in both CER116- and CER21-modified cells, but appears to be more rapid in CER116-modified cells. CER116-harboring Ba/F3 cells (top) catabolize target cells, allowing cells to return to homeostasis and resume immune responsiveness. The addition of a TRAF6 signaling domain to the CER construct promotes rapid destruction of engulfed material.

Example 11

Antigen Presentation by Cer Modified T Cells

One strategy to enhance tumor cell killing by cytotoxic CD8+ T cells (CTLs) is to utilize antigen presenting cells (APCs), which have the unique capacity to "cross-present" exogenous antigen on MHC I molecules. Broadening tumor-specific CTL responses has the potential to induce effective immune responses against tumors. In this example the viral HPV E6 and E7 oncoproteins were used as model antigens to characterize the antigen processing and presenting capacity of chimeric engulfment receptor (CER)-expressing cells.

CD4+ and CD8+CER-expressing T cell lines were established from human PBMCs. Purified T cells were transduced with lentivirus encoding CER123 (SEQ ID NO:150) and truncated EGFR (transduction marker), after activation with CD3 & CD28 microbeads, and then expanded in medium containing IL-7, IL-15, and IL-2 for 5 days. The percentage of tEGFR+ T cells ranged between 40-60%.

A Jurkat cell line with a stable integration of an NFAT-inducible Luciferase reporter construct was utilized to study T cell responses. Human E6- and E7-specific engineered TCRs were transduced into Jurkat NFAT reporter cell lines to characterize NFAT activation upon co-culture with engineered CERs.

Figure 86:
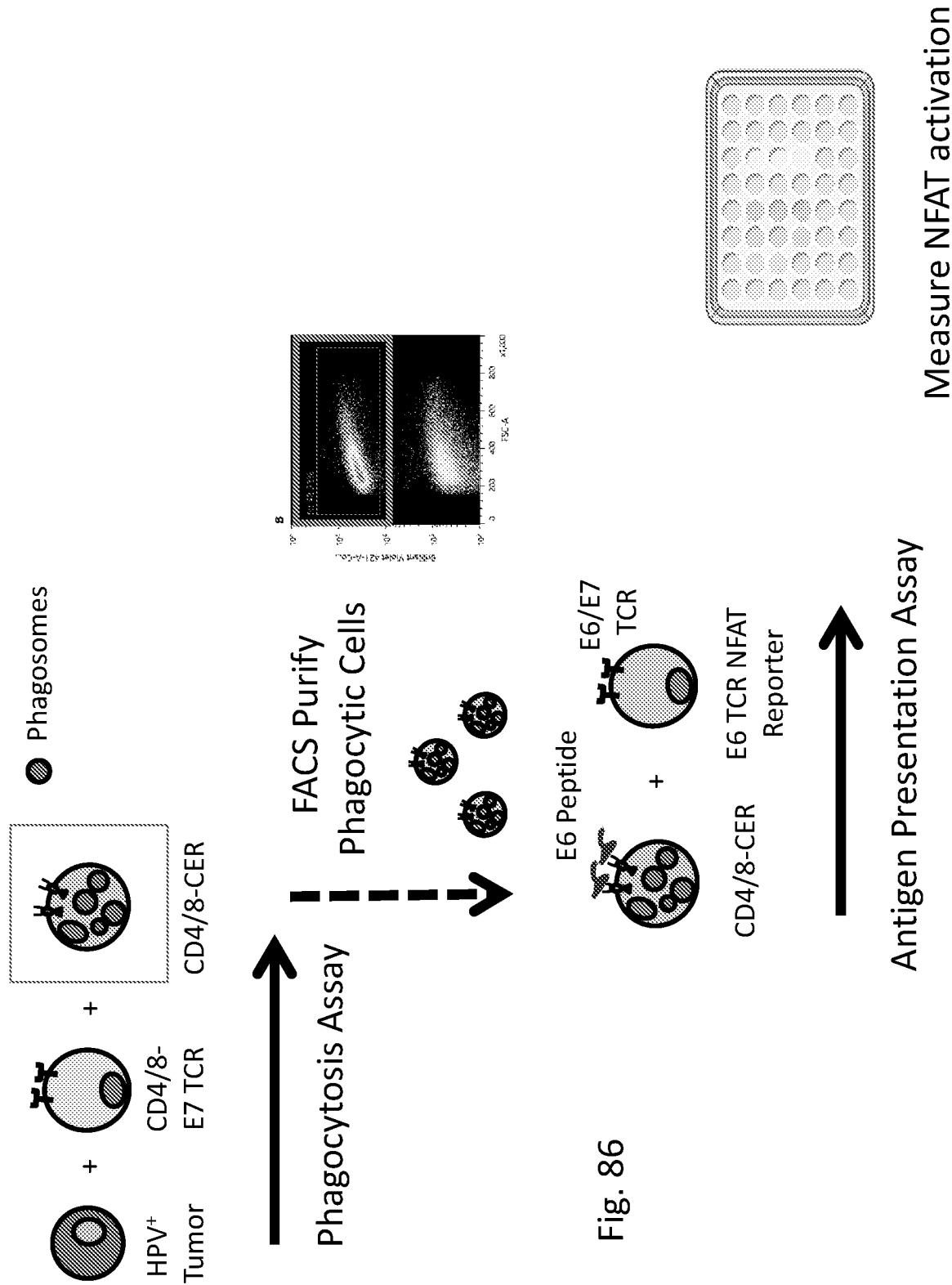
FIG. 86 shows a schematic of an exemplary antigen presentation assay. In a phagocytic assay step, CD4 and CD8+ T cell lines expressing CERs were co-cultured with the CD4 and CD8 T cells expressing HPV E7 specific TCR and SCC152 (HPV+) cells overnight. The following day CER+ T cells were subsequently FACS-sorted. FACS plot depicts CT violet+CERs. Following FACS purification, antigen presentation of HPV oncoproteins was evaluated. CER-expressing cells were co-cultured at a 1:2 ratio with E6 & E7-specific TCR/NFAT reporter cell lines, and NFAT activation measured over time using a plate reader.
Figure 87:
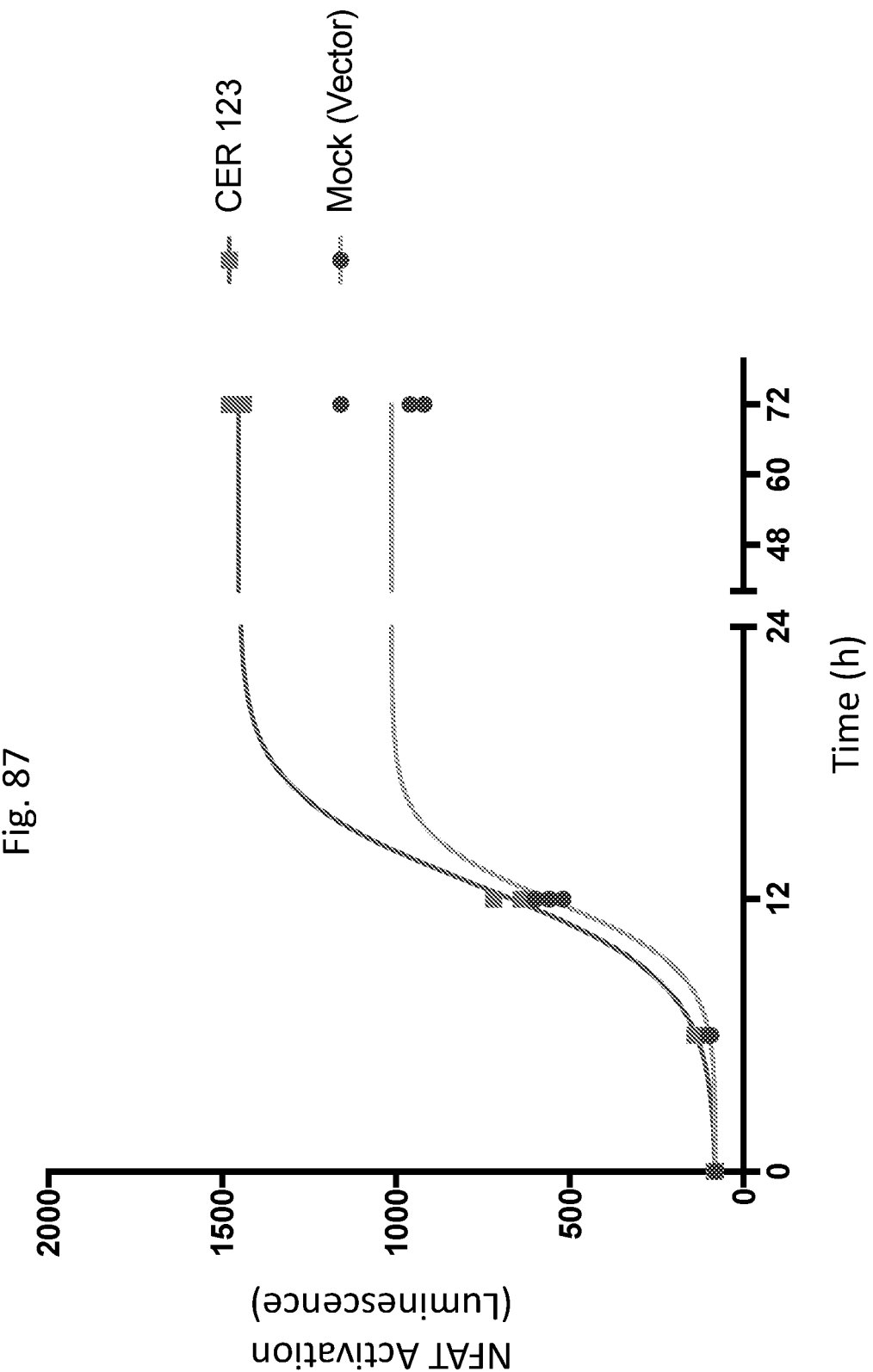
FIG. 87 shows a line graph of NFAT activation in E6/E7 TCR-transduced T cells comprising an NFAT reporter gene following co-culture with CD4+ and CD8+CER123-transduced T cells that have been co-cultured with HPV+tumor cells and CD4+/CD8+E7 TCR transduced T cells as shown in the schematic in FIG. 86. CER-expressing CD4+ and CD8+ T cell lines, after phagocytosing HPV+ tumor cells, are capable of cross-presentation of E7 HPV oncoproteins to E7 TCR/NFAT reporter-expressing T cells as measured by NFAT activation.

For assessing MHC-I cross-presentation, SCC152 HPV+ cells were co-cultured overnight with CER123-expressing CD4+ and CD8+ T cells or mock-transduced (vector only) T cells in the presence of T cells expressing an E7-specific TCR. Following overnight co-culture, CER123-expressing T cells or Mock-transduced T cells were purified using FACS, washed, and subsequently cultured with E6/E7-specific human TCR/NFAT reporter cell line at a 1:1 ratio. NFAT activation was assessed at serial time points (0, 6, 12, 24, and 72 hrs) by measuring luciferase activity in cell culture supernatants. A schematic of this assay is provided in FIG. 86. Cells were cultured in RPMI/10% FCS in 96-well round-bottom plates. CER123-expressing CD4+ and CD8+ T cell lines, after phagocytosing HPV+ tumors, were co-cultured overnight with Jurkat T cells expressing a $E7_{11-19}$—specific TCR and an NFAT reporter. Induction of $E7_{11-19}$—specific Jurkat T cells were quantified by luminescence of NFAT signaling at indicated time points and compared to Mock (vector-alone) transduced T cells (FIG. 87). CER123-expressing T cells demonstrated enhanced cross-presentation efficiency of HPV E7 oncoproteins following phagocytosis of HPV+ tumor cells.

Additional definitions are provided throughout the present disclosure.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheetincluding but not limited to U.S. Provisional Patent Application Nos. 62/563, 615, 62/649,529, and 62/652,822 are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING
>SEQ ID NO: 1 (Protein, Homo sapiens, FcγRI
binding domain, amino acids 1-15 signal peptide)
MWFLTTLLLWVPVDGQVDTTKAVITLQPPWVSVFQEETVTLHCEVLHLPG

SSSTQWFLNGTATQTSTPSYRITSASVNDSGEYRCQRGLSGRSDPIQLEI

HRGWLLLQVSSRVFTEGEPLALRCHAWKDKLVYNVLYYRNGKAFKFFHWN

SNLTILKTNISHNGTYHCSGMGKHRYTSAGISVTVKELFPAPVLNASVTS

PLLEGNLVTLSCETKLLLQRPGLQLYFSFYMGSKTLRGRNTSSEYQILTA

RREDSGLYWCEAATEDGNVLKRSPELELQVLGLQLPTPVWFH

>SEQ ID NO: 2 (Protein, Homo sapiens, Tim1
binding domain, amino acids 1-20 signal peptide)
MHPQVVILSLILHLADSVAGSVKVGGEAGPSVTLPCHYSGAVTSMCWNRG

SCSLFTCQNGIVWTNGTHVTYRKDTRYKLLGDLSRRDVSLTIENTAVSDS

GVYCCRVEHRGWFNDMKITVSLEIVPPKVTTTPIVTTVPTVTTVRTSTTV

PTTTTVPTTTVPTTMSIPTTTTVLTTMTVSTTTSVPTTTSIPTTTSVPVT

TTVSTFVPPMPLPRQNHEPVATSPSSPQPAETHPTTLQGAIRREPTSSPL

YSYTTDGNDTVTESSDGLWNNNQTQLFLEHSLLTANTTKG

>SEQ ID NO: 3 (Protein, Homo sapiens, Tim4
binding domain, amino acids 1-24 signal peptide)
MSKEPLILWLMIEFWWLYLTPVTSETVVTEVLGHRVTLPCLYSSWSHNSN

SMCWGKDQCPYSGCKEALIRTDGMRVTSRKSAKYRLQGTIPRGDVSLTIL

NPSESDSGVYCCRIEVPGWFNDVKINVRLNLQRASTTTHRTATTTTRRTT

TTSPTTTRQMTTTPAALPTTVVTTPDLTTGTPLQMTTIAVFTTANTCLSL

TPSTLPEEATGLLTPEPSKEGPILTAESETVLPSDSWSSVESTSADTVLL

TSKESKVWDLPSTSHVSMWKTSDSVSSPQPGASDTAVPEQNKTTKTGQMD

GIPMSMKNEMPISQ

>SEQ ID NO: 4 (Protein, Homo sapiens, Tim3
binding domain, amino acids 1-21 signal peptide)
MFSHLPFDCVLLLLLLLLTRSSEVEYRAEVGQNAYLPCFYTPAAPGNLVP

VCWGKGACPVFECGNVVLRTDERDVNYWTSRYWLNGDFRKGDVSLTIENV

TLADSGIYCCRIQIPGIMNDEKFNLKLVIKPAKVTPAPTRQRDFTAAFPR

MLTTRGHGPAETQTLGSLPDINLTQISTLANELRDSRLANDLRDSGATIR

IG

>SEQ ID NO: 5 (Protein, Homo sapiens, FA58C2
binding domain)
LNGCANPLGLKNNSIPDKQITASSSYKTWGLHLFSWNPSYARLDKQGNFN

AWVAGSYGNDQWLQVDLGSSKEVTGIITQGARNFGSVQFVASYKVAYSND

SANWTEYQDPRTGSSKIFPGNWDNHSHKKNLFETPILARYVRILPVAWHN

RIALRLELLGC

>SEQ ID NO: 6 (Protein, Homo sapiens, GAS6
binding domain, amino acids 1-30 signal peptide)
MAPSLSPGPAALRRAPQLLLLLLAAECALAALLPAREATQFLRPRQRRAF

QVFEEAKQGHLERECVEELCSREEAREVFENDPETDYFYPRYLD

>SEQ ID NO: 7 (Protein, Homo sapiens, protein S
binding domain, amino acids 1-24 signal peptide)
MRVLGGRCGALLACLLLVLPVSEANFLSKQQASQVLVRKRRANSLLEETK

QGNLERECIEELCNKEEAREVFENDPETDYFYPKYLV

>SEQ ID NO: 8 (Protein, Homo sapiens, BAI1
binding domain]
AAGADAGPGPEPCATLVQGKFFGYFSAAAVFPANASRCSWTLRNPDPRRY

TLYMKVAKAPVPCSGPGRVRTYQFDSFLESTRTYLGVESFDEVLRLCDPS

APLAFLQASKQFLQMRRQQPPQHDGLRPRAGPPGPTDDFSVEYLVVGNRN

PSRAACQMLCRWLDACLAGSRSSHPCGIMQTPCACLGGEAGGPAAGPLAP

RGDVCLRDAVAGGPENCLTSLTQDRGGHGATGGWKLWSLWGECTRDCGGG

LQTRTRTCLPAPGVEGGGCEGVLEEGRQCNREACGPAGRTSSRSQSLRST

DARRREELGDELQQFGFPAPQTGDPAAEEEWSPWSVCSSTCGEGWQTRTRF

CVSSSYSTQCSGPLREQRLCNNSAVCPVHGAWDEWSPWSLCSSTCGRGFR

DRTRTCRPPQFGGNPCEGPEKQTKFCNIALCPGRAVDGNWNEWSSWSACS

ASCSQGRQQRTRECNGPSYGGAECQGHWVETRDCFLQQCPVDGKWQAWAS

WGSCSVTCGAGSQRRERVCSGPFFGGAACQGPQDEYRQCGTQRCPEPHEI

CDEDNFGAVIWKETPAGEVAAVRCPRNATGLILRRCELDEEGIAYWEPPT

YIRCVSIDYRNIQMMTREHLAKAQRGLPGEGVSEVIQTLVEISQDGTSYS

GDLLSTIDVLRNMTEIFRRAYYSPTPGDVQNFVQILSNLLAEENRDKWEE

AQLAGPNAKELFRLVEDFVDVIGFRMKDLRDAYQVTDNLVLSIHKLPASG

ATDISFPMKGWRATGDWAKVPEDRVTVSKSVFSTGLTEADEASVFVVGTV

LYRNLGSFLALQRNTTVLNSKVISVTVKPPPRSLRTPLEIEFAHMYNGTT

NQTCILWDETDVPSSSAPPQLGPWSWRGCRTVPLDALRTRCLCDRLSTFA

ILAQLSADANMEKATLPS

>SEQ ID NO: 9 (DNA, Homo sapiens, FcγRI binding
domain)
ATGTGGTTCCTGACTACGTTGTTGCTGTGGGTCCCTGTAGACGGCCAAGT

AGACACAACGAAAGCAGTGATCACGCTCCAACCGCCTTGGGTGTCTGTGT

TCCAAGAAGAAACAGTTACACTGCACTGTGAGGTCCTCCACCTGCCTGGT

TCTTCATCTACTCAATGGTTTCTCAACGGAACAGCAACACAAACAAGTAC

CCCTTCCTACAGAATTACGAGTGCATCTGTTAACGATTCAGGAGAGTATA

GGTGCCAGCGAGGGCTTTCAGGCCGGTCCGACCCCATTCAACTCGAAATT

CACCGCGGTTGGCTTCTGCTGCAAGTATCCTCTCGGGTCTTCACGGAAGG

TGAACCACTTGCCTTGCGCTGTCACGCATGGAAAGATAAGCTCGTCTACA

ACGTTTTGTATTATCGGAATGGAAAGGCATTTAAGTTTTTTCATTGGAAC

TCAAACCTTACGATCCTCAAAACCAATATCAGTCATAACGGTACGTACCA

CTGCTCAGGCATGGGCAAGCATCGCTATACGTCCGCAGGGATTAGCGTGA

CAGTTAAGGAGCTCTTCCCCGCGCCTGTGCTGAATGCGAGCGTAACTTCA

CCCCTTCTGGAGGGCAACTTGGTGACCCTCTCTTGTGAGACGAAACTTCT

CCTTCAGAGGCCGGGCCTGCAACTCTATTTCAGCTTTTATATGGGTTCTA

AAACTCTTCGAGGCAGAAACGAGCAGCGAATATCAGATACTGACTGCC

CGGCGGGAAGACAGTGGCCTTTATTGGTGCGAGGCTGCAACAGAAGATGG

CAATGTCCTTAAAAGGTCTCCCGAATTGGAGCTCCAAGTGCTTGGCTTGC

AACTCCCTACACCCGTATGGTTCCAC

>SEQ ID NO: 10 (DNA, Homo sapiens, Tim1 binding
domain)
ATGCACCCCAGGTTGTTATACTTTCATTGATCCTGCATTTGGCCGACTC

CGTGGCGGGTTCCGTAAAAGTTGGAGGGGAAGCTGGACCAAGCGTCACCT

TGCCTTGCCACTACTCTGGAGCCGTGACGAGTATGTGCTGGAATCGAGGA

TCCTGTAGTCTTTTCACATGCCAAAATGGCATAGTTTGGACCAATGGGAC

GCACGTCACCTACCGAAAAGACACTAGATACAAACTCCTGGGTGACCTCA

GCAGGAGAGATGTGTCTCTGACTATTGAAAACACTGCTGTTTCTGACTCT

GGAGTCTACTGTTGCCGGGTCGAGCACCGAGGATGGTTCAATGACATGAA

GATCACGGTCAGCTTGGAAATCGTCCCGCCCAAGGTAACCACTACACCAA

TAGTTACTACGGTTCCCACGGTAACCACGGTTCGAACCAGCACCACAGTA

CCCACAACTACGACCGTTCCAACCACTACAGTCCCCACAACCATGAGTAT

CCCTACGACAACTACGGTCCTGACAACCATGACCGTCAGCACTACCACGA

GTGTGCCTACGACTACTAGCATACCGACGACTACTTCAGTTCCAGTCACC

ACCACGGTGAGTACATTCGTGCCTCCAATGCCATTGCCGAGGCAAAACCA

CGAACCCGTGGCGACATCTCCGTCTAGTCCGCAACCAGCAGAGACCCATC

CCACCACGCTTCAGGGGGCAATCAGGAGAGAACCTACAAGTTCACCCCTC

TACAGCTATACAACCGATGGAAACGACACAGTTACAGAAAGTAGTGACGG

TTTGTGGAATAACAACCAAACACAATTGTTCCTGGAGCACAGTCTGTTGA

CAGCCAACACTACAAAGGGA

>SEQ ID NO: 11 (DNA, Homo sapiens, Tim4 binding
domain)
ATGAGTAAAGAGCCGCTTATCCTGTGGCTTATGATAGAGTTTTGGTGGTT

GTATTTGACCCCGGTCACGAGCGAAACGGTAGTGACTGAAGTATTGGGTC

ATCGGGTAACCTTGCCTTGCTTGTATAGCTCCTGGTCTCATAATAGTAAT

AGCATGTGCTGGGGCAAGGACCAATGCCCCTATAGCGGATGCAAGGAGGC

GCTCATTCGCACAGACGGAATGCGGGTGACATCAAGGAAGAGTGCTAAGT

ACCGGCTTCAGGGCACAATCCCACGCGGCGACGTGTCACTGACTATCCTT

AATCCATCCGAGAGCGACTCTGGTGTCTATTGTTGCAGGATCGAGGTTCC

GGGATGGTTCAATGATGTAAAGATCAATGTAAGACTCAATCTGCAACGGG

CATCTACAACCACGCATCGGACAGCCACTACTACCACAAGGAGAACAACT

ACTACGTCACCCACGACTACTCGACAGATGACCACTACACCTGCGGCCCT

GCCAACTACGGTTGTAACTACTCCGGATCTGACAACCGGGACACCGTTGC

AAATGACAACCATTGCAGTATTTACCACGGCAAACACGTGTCTCTCTCTG

ACCCCATCTACTCTTCCGGAGGAGGCCACCGGGCTCCTTACACCGGAGCC

GTCTAAGGAAGGCCCAATCTTGACCGCAGAGAGTGAGACCGTACTTCCGA

GCGATTCATGGTCCAGTGTCGAGAGCACATCCGCTGACACCGTCCTTCTT

ACGTCCAAAGAAAGTAAAGTTTGGGACCTCCCGTCCACGAGCCACGTTTC

TATGTGGAAGACCTCAGATAGCGTTAGCTCCCCACAGCCAGGAGCAAGCG

ACACCGCAGTACCGGAGCAAAACAAGACGACTAAGACTGGCCAGATGGAT

GGTATCCCAATGTCAATGAAAATGAGATGCCCATATCACAA

>SEQ ID NO: 12 (DNA, Homo sapiens, Tim3 binding
domain)
ATGTTTAGCCATCTCCCTTTTGATTGCGTCTTGTTGCTTCTTCTTCTCCT

TCTGACGAGATCATCTGAAGTTGAATATCGCGCGGAAGTCGGCCAAAACG

CATATCTGCCGTGTTTTTACACCCCGGCTGCACCGGGGAACTTGGTTCCC

GTTTGTTGGGGTAAGGGGGCGTGTCCCGTTTTTGAGTGCGGTAACGTAGT

GCTCCGAACTGATGAAAGAGATGTAAATTACTGGACGAGCCGGTACTGGT

TGAATGGGATTTTAGGAAGGGCGACGTTTCCCTTACCATAGAAAACGTA

ACTCTTGCGGATTCTGGGATTTATTGTTGCAGGATACAAATCCCCGGAAT

AATGAACGATGAGAAATTCAATTTGAAGCTCGTAATAAAACCGGCAAAAG

TAACTCCAGCTCCCACCAGGCAGCGAGATTTTACGGCAGCATTTCCCAGG

ATGCTCACTACTCGCGGTCATGGCCCTGCCGAGACTCAGACCCTCGGTAG

TCTTCCTGATATCAATCTCACGCAAATTAGTACATTGGCGAATGAATTGA

GGGATTCAAGACTCGCCAATGATCTGCGCGACAGTGGAGCGACTATTAGG

ATAGGG

>SEQ ID NO: 13 (DNA, Homo sapiens, FA58C2
binding domain)
CTCAACGGGTGTGCTAATCCCCTTGGCCTGAAGAATAACAGCATACCTGA

CAAGCAAATAACAGCGTCAAGTTCTTATAAAACTTGGGGGCTGCATCTGT

TCTCCTGGAACCCCAGTTACGCTAGACTCGACAAACAAGGCAATTTTAAC

GCATGGGTGGCAGGCTCTTACGGGAACGATCAGTGGCTGCAAGTAGACTT

GGGAAGTAGTAAGGAGGTGACTGGGATCATTACCCAGGGGGCACGAAATT

TCGGTTCCGTTCAGTTCGTTGCATCTTATAAGGTAGCGTATTCAAATGAC

TCCGCGAATTGGACCGAATATCAGGACCCGCGAACCGGATCAAGCAAGAT

TTTTCCGGGGAATTGGGACAACCACTCTCACAAAAAAATTTGTTTGAAA

CACCTATACTGGCGCGGTACGTTAGAATCCTCCCAGTTGCCTGGCACAAC

CGGATAGCGCTTAGACTGGAATTGTTGGGGTGC

>SEQ ID NO: 14 (DNA, Homo sapiens, Gas6 binding domain)
ATGGCTCCCTCTTTGTCACCAGGACCTGCGGCTCTTAGGCGAGCCCCGCA

GCTGCTGCTTCTCCTGCTCGCTGCAGAATGCGCTCTCGCTGCACTCTTGC

CCGCGAGGGAGGCGACTCAGTTCTTGCGCCCCGGCAGAGACGAGCATTC

CAAGTCTTTGAGGAAGCGAAACAAGGTCATCTCGAGCGAGAATGCTGGA

GGAGCTGTGTTCTAGGGAGGAAGCACGCGAAGTCTTTGAGAATGACCCGG

AAACGGACTACTTTTACCCCCGGTATCTTGAT

>SEQ ID NO: 15 (DNA, Homo sapiens, Protein S binding domain)
ATGCGCGTGTTGGGGGGTCGCTGTGGTGCGCTCCTTGCTTGTCTCCTTTT

GGTTCTTCCCGTCTCCGAGGCTAATTTCCTGTCAAAACAACAGGCTAGTC

AAGTCTTGGTGCGCAAGAGGAGAGCTAACAGCCTTCTGGAAGAGACCAAG

CAAGGTAATCTGGAGAGAGTGTATCGAGGAACTTTGTAACAAAGAGGA

AGCACGCGAAGTATTTGAAAATGACCCGGAAACCGATTATTTTTACCCAA

AATATCTCGTA

>SEQ ID NO: 16 (Protein, Artificial Sequence, modified IgG4 hinge)
ESKYGPPCPPCP

>SEQ ID NO: 17 (Protein, Homo sapiens, TLR4 juxtamembrane domain)
PVLSLNITCQMNK

>SEQ ID NO: 18 (Protein, Homo sapiens, Tim1 transmembrane domain)
IYAGVCISVLVLLALLGVIIA >SEQ ID NO: 19 (Protein, Homo sapiens, Tim4 transmembrane domain)
LLMIIAPSLGFVLFALFVAFL >SEQ ID NO: 20 (Protein, Homo sapiens, FcγRI transmembrane domain)
VLFYLAVGIMFLVNTVLWVTI >SEQ ID NO: 21 (Protein, Homo sapiens, FcεRIγ transmembrane domain)
LCYILDAILFLYGIVLTLLYC >SEQ ID NO: 22 (Protein, Homo sapiens, CD8a transmembrane domain)
IYIWAPLAGTCGVLLLSLVIT >SEQ ID NO: 23 (Protein, Homo sapiens, MERTK transmembrane domain)
FGCFCGFILIGLILYISLAIR >SEQ ID NO: 24 (Protein, Homo sapiens, Axl transmembrane domain)
YVLLGAVVAAACVLILALFLV >SEQ ID NO: 25 (Protein, Homo sapiens, Tyro3 transmembrane domain)
VPVVLGVLTALVTAAALALIL >SEQ ID NO: 26 (Protein, Homo sapiens, CD28 transmembrane domain)
FWVLVVVGGVLACYSLLVTVAFIIFWV >SEQ ID NO: 27 (Protein, Homo sapiens, CD4 transmembrane domain)
MALIVLGGVAGLLLFIGLGIFF >SEQ ID NO: 28 (Protein, Homo sapiens, DAP12 transmembrane domain)
GVLAGIVMGDLVLTVLIALAV >SEQ ID NO: 29 (Protein, Homo sapiens, BAH transmembrane domain)
VTLIVGCGVSSLTLLMLVIIY >SEQ ID NO: 30 (Protein, Homo sapiens, MRC1 transmembrane domain)
GVVIIVILLILTGAGLAAYFF >SEQ ID NO: 31 (Protein, Homo sapiens, TLR1 transmembrane domain)
LLIVTIVATMLVLAVTVTSLC >SEQ ID NO: 32 (Protein, Homo sapiens, TLR2 transmembrane domain)
ALVSGMCCALFLLILLTGVLC >SEQ ID NO: 33 (Protein, Homo sapiens, TLR3 Transmembrane domain)
FFMINTSILLIFIFIVLLIHF >SEQ ID NO: 34 (Protein, Homo sapiens, TLR4 transmembrane domain)
TIIGVSVLSVLVVSVVAVLVY >SEQ ID NO: 35 (Protein, Homo sapiens, TLR5 transmembrane domain)
FSLFIVCTVTLTLFLMTILTV >SEQ ID NO: 36 (Protein, Homo sapiens, TLR6 transmembrane domain)
ALVSGMCCALFLLILLTGVLC >SEQ ID NO: 37 (Protein, Homo sapiens, TLR7 transmembrane domain)
LILFSLSISVSLFLMVMMTAS >SEQ ID NO: 38 (Protein, Homo sapiens, TLR8 transmembrane domain)
AVILFFFTFFITTMVMLAALA >SEQ ID NO: 39 (Protein, Homo sapiens, TLR9 transmembrane domain)
FALSLLAVALGLGVPMLHHLC >SEQ ID NO: 40 (DNA, Homo sapiens, Tim1 transmembrane domain)
ATATACGCTGGAGTCTGTATAAGTGTCCTTGTACTGTTGGCGTTGCTGGG

GGTCATTATTGCC

>SEQ ID NO: 41 (DNA, Homo sapiens, Tim4 transmembrane domain)
TTGCTTATGATTATTGCGCCAAGCCTTGGATTTGTGCTGTTCGCACTCTT

CGTAGCTTTTCTC

>SEQ ID NO: 42 (DNA, Homo sapiens, FcγRI transmembrane domain)
GTACTGTTTTATCTCGCCGTAGGGATAATGTTCCTCGTGAACACCGTACT

GTGGGTAACAATA

>SEQ ID NO: 43 (DNA, Homo sapiens, CD8a transmembrane domain)
ATATACATTTGGGCACCGCTGGCTGGAACTTGCGGCGTTCTCTTGTTGAG

TCTGGTGATTACT

>SEQ ID NO: 44 (DNA, Homo sapiens, MERTK
transmembrane domain)
TTTGGCTGTTTCTGTGGATTTATTCTGATTGGTCTTATCCTCTATATTC

CTTGGCGATCAGA

>SEQ ID NO: 45 (DNA, Homo sapiens, Axl
transmembrane domain)
TATGTCTTGCTTGGTGCCGTCGTTGCTGCCGCCTGTGTGTTGATACTCGC

ACTTTTCTTGGTG

>SEQ ID NO: 46 (DNA, Homo sapiens, Tyro3
transmembrane domain)
GTACCCGTCGTTTTGGGGGTCCTGACCGCGCTCGTTACTGCGGCAGCACT

CGCACTGATACTT

>SEQ ID NO: 47 (DNA, Homo sapiens, CD4
transmembrane domain)
ATGGCTCTGATCGTACTGGGCGGAGTGGCAGGATTGCTGCTCTTTATTGG

ACTGGGCATTTTCTTC

>SEQ ID NO: 48 (Protein, Homo sapiens, TLR1
signaling domain)
SYLDLPWYLRMVCQWTQTRRRARNIPLEELQRNLQFHAFISYSGHDSFWV

KNELLPNLEKEGMQICLHERNFVPGKSIVENIITCIEKSYKSIFVLSPNF

VQSEWCHYELYFAHHNLFHEGSNLILILLEPIPQYSIPSSYHKLKSLMA

RRTYLEWPKEKSKRGLFWANLRAAINIKLTEQAKK

>SEQ ID NO: 49 (Protein, Homo sapiens, TLR2
signaling domain)
HRFHGLWYMKMMWAWLQAKRKPRKAPSRNICYDAFVSYSERDAYWVENLM

VQELENFNPPFKLCLHKRDFIPGKWIIDNIIDSIEKSHKTVFVLSENFVK

SEWCKYELDFSHRFLFDENNDAAILILLEPIEKKAIPQRFCKLRKIMNTK

TYLEWPMDEAQREGFWVNLRAAIKS

>SEQ ID NO: 50 (Protein, Homo sapiens, TLR3
signaling domain)
EGWRISFYWNVSVHRVLGFKEIDRQTEQFEYAAYIIHAYKDKDWVWEHFS

SMEKEDQSLKFCLEERDFEAGVFELEAIVNSIKRSRKIIFVITHHLLKDP

LCKRFKVHHAVQQAIEQNLDSIILVFLEEIPDYKLNHALCLRRGMFKSHC

ILNWPVQKERIGAFRHKLQVALGSKNSVH

>SEQ ID NO: 51 (Protein, Homo sapiens, TLR4
signaling domain)
KFYFHLMLLAGCIKYGRGENIYDAFVIYSSQDEDWVRNELVKNLEEGVPP

FQLCLHYRDFIPGVAIAANIIHEGFHKSRKVIVVVSQHFIQSRWCIFEYE

IAQTWQFLSSRAGIIFIVLQKVEKTLLRQQVELYRLLSRNTYLEWEDSVL

GRHIFWRRLRKALLDGKSWNPEGTVGTGCNWQEATSI

>SEQ ID NO: 52 (Protein, Homo sapiens, TLR5
signaling domain)
TKFRGFCFICYKTAQRLVFKDHPQGTEPDMYKYDAYLCFSSKDFTWVQNA

LLKHLDTQYSDQNRFNLCFEERDFVPGENRIANIQDAIWNSRKIVCLVSR

HFLRDGWCLEAFSYAQGRCLSDLNSALIMVVVGSLSQYQLMKHQSIRGFV

QKQQYLRWPEDFQDVGWFLHKLSQQILKKEKEKKKDNNIPLQTVATIS

>SEQ ID NO: 53 (Protein, Homo sapiens, TLR6
signaling domain)
YLDLPWYLRMVCQWTQTRRRARNIPLEELQRNLQFHAFISYSEHDSAWVK

SELVPYLEKEDIQICLHERNFVPGKSIVENIINCIEKSYKSIFVLSPNFV

QSEWCHYELYFAHHNLFHEG

SNNLILILLEPIPQNSIPNKYHKLKALMTQRTYLQWPKEKSKRGLFWANI

RAAFNMKLTL

VTENNDVKS

>SEQ ID NO: 54 (Protein, Homo sapiens, TLR7
signaling domain)
HLYFWDVWYIYHFCKAKIKGYQRLISPDCCYDAFIVYDTKDPAVTEWVLA

ELVAKLEDPREKHFNLCLEERDWLPGQPVLENLSQSIQLSKKTVFVMTDK

YAKTENFKIAFYLSHQRLMDEKVDVIILIFLEKPFQKSKFLQLRKRLCGS

SVLEWPTNPQAHPYFWQCLKNALATDNHVAYSQVFKETV

>SEQ ID NO: 55 (Protein, Homo sapiens, TLR8
signaling domain)
HHLFYWDVWFIYNVCLAKVKGYRSLSTSQTFYDAYISYDTKDASVTDWVI

NELRYHLEESRDKNVLLCLEERDWDPGLAIIDNLMQSINQSKKTVFVLTK

KYAKSWNFKTAFYLALQRLMDENMDVIIFILLEPVLQHSQYLRLRQRICK

SSILQWPDNPKAEGLFWQTLRNVVLTENDSRYNNMYVDSIKQY

>SEQ ID NO: 56 (Protein, Homo sapiens, TLR9
signaling domain)
GWDLWYCFHLCLAWLPWRGRQSGRDEDALPYDAFVVFDKTQSAVADWVYN

ELRGQLEECRGRWALRLCLEERDWLPGKTLFENLWASVYGSRKTLFVLAH

TDRVSGLLRASFLLAQQRLLEDRKDVVVLVILSPDGRRSRYVRLRQRLCR

QSVLLWPHQPSGQRSFWAQLGMALTRDNHHFYNRNFCQGPTAE

>SEQ ID NO: 57 (Protein, Homo sapiens, Traf6
signaling domain - full length)
MSLLNCENSCGSSQSESDCCVAMASSCSAVTKDDSVGGTASTGNLSSSFM

EEIQGYDVEFDPPLESKYECPICLMALREAVQTPCGHRFCKACIIKSIRD

AGHKCPVDNEILLENQLFPDNFAKREILSLMVKCPNEGCLHKMELRHLED

HQAHCEFALMDCPQCQRPFQKFHINIHILKDCPRRQVSCDNCAASMAFED

KEIHDQNCPLANVICEYCNTILIREQMPNHYDLDCPTAPIPCTFSTFGCH

EKMQRNHLARHLQENTQSHMRMLAQAVHSLSVIPDSGYISEVRNFQETIH

QLEGRLVRQDHQIRELTAKMETQSMYVSELKRTIRTLEDKVAEIEAQQCN

GIYIWKIGNFGMHLKCQEEEKPVVIHSPGFYTGKPGYKLCMRLHLQLPTA

QRCANYISLFVHTMQGEYDSHLPWPFQGTIRLTILDQSEAPVRQNHEEIM

DAKPELLAFQRPTIPRNPKGFGYVTFMHLEALRQRTFIKDDTLLVRCEVS

TRFDMGSLRREGFQPRSTDAGV

>SEQ ID NO: 58 (Protein, Homo sapiens, truncated
TRAF6 signaling domain)
MSLLNCENSCGSSQSESDCCVAMASSCSAVTKDDSVGGTASTGNLSSSFM

EEIQGYDVEFDPPLESKYECPICLMALREAVQTPCGHRFCKACIIKSIRD

AGHKCPVDNEILLENQLFPDNFAKREILSLMVKCPNEGCLHKMELRHLED

HQAHCEFALMDCPQCQRPFQKFHINIHILKDCPRRQVSCDNCAASMAFED

KEIHDQNCPLANVICEYCNTILIREQMPNHYDLDCPTAPIPCTFSTFGCH

EKMQRNHLARHLQENTQSHMRMLA

>SEQ ID NO: 59 [Protein; Homo sapiens, MERTK
signaling domain]
KRVQETKFGNAFTEEDSELVVNYIAKKSFCRRAIELTLHSLGVSEELQNK

LEDVVIDRNL

-continued

LILGKILGEGEFGSVMEGNLKQEDGTSLKVAVKTMKLDNSSQREIEEFLS

EAACMKDFSHPNVIRLLGVCIEMSSQGIPKPMVILPFMKYGDLHTYLLYS

RLETGPKHIPLQTLLKFMVDIALGMEYLSNRNFLHRDLAARNCMLRDDMT

VCVADFGLSKKIYSGDYYRQGRIAKMPVKWIAIESLADRVYTSKSDVWAF

GVTMWEIATRGMTPYPGVQNHEMYDYLLHGHRLKQPEDCLDELYEIMYSC

WRTDPLDRPTFSVLRLQLEKLLESLPDVRNQADVIYVNTQLLESSEGLAQ

GSTLAPLDLNIDPDSIIASCTPRAAISVVTAEVHDSKPHEGRYILNGGSE

EWEDLTSAPSAAVTAEKNSVLPGERLVRNGVSWSHSSMLPLGSSLPDELL

FADDSSEGSEVLM

>SEQ ID NO: 60

>SEQ ID NO: 61

>SEQ ID NO: 62 (Protein, Homo sapiens, FcεRIγ
signaling domain)
RLKIQVRKAAITSYEKSDGVYTGLSTRNQETYETLKHEKPPQ >SEQ ID NO: 63 (Protein, Homo sapiens, FcγR1
signaling domain)
RKELKRKKKWDLEISLDSGHEKKVISSLQEDRHLEEELKCQEQKEEQLQE

GVHRKEPQGAT

>SEQ ID NO: 64 (Protein, Homo sapiens, FcγR2A
signaling domain)
CRKKRISANSTDPVKAAQFEPPGRQMIAIRKRQLEETNNDYETADGGYMT

LNPRAPTDDDKNIYLTLPPNDHVNSNN

>SEQ ID NO: 65 (Protein, Homo sapiens, FcγR2c
signaling domain)
CRKKRISANSTDPVKAAQFEPPGRQMIAIRKRQPEETNNDYETADGGYMT

LNPRAPTDDDKNIYLTLPPNDHVNSNN

>SEQ ID NO: 66 (Protein, Homo sapiens, FcγR3A
signaling domain)
KTNIRSSTRDWKDHKFKWRKDPQDK >SEQ ID NO: 67 (Protein, Homo sapiens, BAFF-R
signaling domain)
SWRRRQRRLRGASSAEAPDGDKDAPEPLDKVIILSPGISDATAPAWPPPG

EDPGTTPPGHSVPVPATELGSTELVTTKTAGPEQQ

>SEQ ID NO: 68 (Protein, Homo sapiens, DAP12
signaling domain)
YFLGRLVPRGRGAAEAATRKQRITETESPYQELQGQRSDVYSDLNTQRPY

YK

>SEQ ID NO: 69 (Protein, Homo sapiens, NFAM1
signaling domain)
LWNKKRMRGPGKDPTRKCPDPRSASSPKQHPSESVYTALQRRETEVYACI

ENEDGSSPTAKQSPLSQERPHRFEDDGELNLVYENL

>SEQ ID NO: 70 [Protein; Homo sapiens; truncated
NFAM1 signaling domain]
SSPKQHPSESVYTALQRRETEVYACIENE >SEQ ID NO: 71 (Protein, Homo sapiens, CD79b
truncated signaling domain (185-213))
DSKAGMEEDHTYEGLDIDQTATYEDIVTL >SEQ ID NO: 72 (Protein, Homo sapiens, TRAF2
signaling domain)
MAAASVTPPGSLELLQPGFSKTLLGTKLEAKYLCSACRNVLRRPFQAQCG

HRYCSFCLASILSSGPQNCAACVHEGIYEEGISILESSSAFPDNAARREV

ESLPAVCPSDGCTWKGTLKEYESCHEGRCPLMLTECPACKGLVRLGEKER

HLEHECPERSLSCRHCRAPCCGADVKAHHEVCPKFPLTCDGCGKKKIPRE

KFQDHVKTCGKCRVPCRFHAIGCLETVEGEKQQEHEVQWLREHLAMLLSS

VLEAKPLLGDQSHAGSELLQRCESLEKKTATFENIVCVLNREVERVAMTA

EAC

>SEQ ID NO: 73 (Protein, Homo sapiens, TRAF3
signaling domain)
MESSKKMDSPGALQTNPPLKLHTDRSAGTPVFVPEQGGYKEKFVKTVEDK

YKCEKCHLVLCSPKQTECGHRFCESCMAALLSSSSPKCTACQESIVKDKV

FKDNCCKREILALQIYCRNESRGCAEQLMLGHLLVHLKNDCHFEELPCVR

PDCKEKVLRKDLRDHVEKACKYREATCSHCKSQVPMIALQKHEDTCPCV

VVSCPHKCSVQTLLRSELSAHLSECVNAPSTCSFKRYGCVFQGTNQQIKA

HEASSAVQHVNLLKEWSNSLEKKV

>SEQ ID NO: 74 (DNA, Homo sapiens, Traf6
signaling domain - full length)
ATGTCACTCCTTAACTGCGAAAACAGTTGTGGGAGTTCACAATCCGAAAG

TGATTGTTGCGTGGCGATGGCGTCTTCATGCTCTGCGGTTACCAAGGATG

ACTCTGTGGGAGGCACCGCATCTACCGGAAATCTGAGCTCTTCTTTTATG

GAGGAAATTCAGGGCTACGACGTTGAGTTTGATCCTCCTCTCGAATCTAA

GTATGAGTGCCCCATATGTCTCATGGCGTTGAGAGAAGCAGTGCAGACTC

CGTGCGGACATCGCTTCTGCAAGGCGTGTATTATAAAGAGTATACGCGAT

GCGGGTCACAAATGTCCAGTGGACAACGAGATACTGCTTGAAAATCAACT

TTTCCCCGACAATTTTGCAAAGAGAGAGATACTGTCTTTGATGGTTAAGT

GTCCAAACGAGGGCTGCTTGCACAAAATGGAACTCCGACACCTTGAAGAC

CACCAGGCACACTGCGAGTTCGCCCTCATGGATTGCCCACAATGCCAGCG

CCCGTTCCAAAAGTTTCACATAAACATCCACATACTGAAGGACTGTCCTA

GGAGACAAGTAAGCTGTGACAATTGCGCAGCGTCAATGGCGTTCGAGGAC

AAGGAGATACACGATCAAAACTGTCCTCTGGCGAATGTGATCTGCGAATA

TTGCAATACGATCTTGATCCGCGAACAGATGCCTAATCATTACGACCTCG

ATTGTCCGACCGCGCCAATTCCTTGTACTTTTTCTACCTTCGGATGTCAT

GAGAAAATGCAACGAAATCACCTGGCTCGCCATCTTCAGGAGAATACTCA

GAGCCACATGCGCATGTTGGCTCAAGCCGTACATAGCCTTAGCGTAATAC

CGGACTCAGGTTATATATCCGAAGTACGGAATTTTCAAGAAACCATACAT

CAACTTGAAGGAAGGTTGGTACGACAGGATCATCAGATACGCGAATTGAC

GGCCAAGATGGAAACCCAGAGCATGTATGTCAGTGAGCTTAAGCGCACTA

TCCGAACCCTGGAGGATAAAGTTGCCGAAATCGAAGCTCAACAATGCAAC

GGGATATACATTTGGAAAATAGGTAACTTCGGAATGCACCTGAAGTGTCA

AGAAGAAGAAAAACCTGTCGTTATTCATTCCCCGGCTTTTATACAGGGA

AGCCTGGGTATAAGCTTTGCATGAGGCTCCACCTCCAATTGCCGACGGCG

CAAAGGTGCGCAAATTACATTTCTCTGTTTGTCCATACTATGCAGGGTGA

GTACGATAGTCACTTGCCGTGGCCCTTCCAGGGTACCATACGATTGACCA

TCCTGGATCAGAGCGAGGCCCCCGTGCGACAGAATCATGAAGAAATAATG

GATGCTAAGCCGGAACTGCTCGCTTTCCAGAGACCTACAATTCCGCGAAA

TCCTAAGGGTTTTGGCTATGTTACGTTCATGCATCTGGAAGCACTCAGAC

AAAGAACATTCATTAAAGATGACACCTTGCTTGTGCGGTGTGAGGTGTCA

ACCAGGTTCGACATGGGATCTCTCAGACGGGAGGGGTTCCAACCGCGCTC

TACAGACGCTGGAGTG

>SEQ ID NO: 75 (Protein, *Homo sapiens*, CD79b
signaling domain (185-229))
DSKAGMEEDHTYEGLDIDQTATYEDIVTLRTGEVKWSVGEHPGQE >SEQ ID NO: 76 (Protein, *Homo sapiens*, MyD88
TIR domain)
HMPERFDAFICYCPSDIQFVQEMIRQLEQTNYRLKLCVSDRDVLPGTCVW

SIASELIEKRCRRMVVVVSDDYLQSKECDFQTKFALSLSPGAHQKRLIPI

KYKAMKKEFPSILRFITVCDYTNPCTKSWFWTRLAKALSLP

>SEQ ID NO: 77 (DNA, *Homo sapiens*, FcγR1
signaling domain)
AGAAAGGAACTCAAGCGCAAGAAGAAGTGGGACCTGGAGATTTCTCTCGA

CTCCGGTCACGAAAAGAAGGTCATCAGTAGCTTGCAAGAGGACCGACACT

TGGAAGAAGAACTTAAATGCCAGGAACAGAAAGAGGAGCAGCTCCAGGAG

GGAGTCCACCGGAAAGAACCACAGGGAGCAACT

>SEQ ID NO: 78 (DNA, *Homo sapiens*, FcγR2A
signaling domain)
TGTCGAAAGAAGCGGATTTCAGCCAATAGTACAGACCCAGTGAAAGCCGC

TCAATTTGAGCCACCCGGTCGACAGATGATCGCAATTAGGAAACGCCAAC

TGGAGGAAACGAATAATGATTACGAAACGGCAGATGGGGGCTACATGACG

CTCAATCCTAGAGCTCCGACCGACGACGACAAGAATATATATCTGACTCT

CCCTCCCAACGACCACGTAAACAGTAATAAC

>SEQ ID NO: 79 (DNA, *Homo sapiens*, FcγR2C
signaling domain)
TGCAGAAAGAAGCGGATAAGTGCAAATAGTACTGATCCCGTTAAAGCAGC

ACAATTTGAGCCGCCAGGACGGCAAATGATTGCAATCAGAAAACGACAAC

CCGAGGAAACCAATAATGACTACGAGACCGCTGACGGAGGGTATATGACG

TTGAATCCCCGCGCACCAACGGATGACGATAAGAACATTTATCTTACGCT

GCCCCCTAACGATCATGTGAATAGCAATAAC

>SEQ ID NO: 80 (DNA, *Homo sapiens*, FcγR3A
signaling domain)
AAAACAAATATCCGGTCCTCTACGAGGGACTGGAAAGATCATAAATTCAA

GTGGAGAAAAGATCCTCAGGATAAA

>SEQ ID NO: 81 (Protein, Artificial Sequence,
CER05 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

KFYFHLMLLAGCIKYGRGENIYDAFVIYSSQDEDWVRNELVKNLEEGVPP

FQLCLHYRDFIPGVAIAANIIHEGFHKSRKVIVVVSQHFIQSRWCIFEYE

IAQTWQFLSSRAGIIFIVLQKVEKTLLRQQVELYRLLSRNTYLEWEDSVL

GRHIFWRRLRKALLDGKSWNPEGTVGTGCNWQEATSI

>SEQ ID NO: 82 (Protein, Artificial Sequence,
CER06 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTTIIGVSVLSVLVVSVVAVLVY

KFYFHLMLLAGCIKYGRGENIYDAFVIYSSQDEDWVRNELVKNLEEGVPP

FQLCLHYRDFIPGVAIAANIIHEGFHKSRKVIVVVSQHFIQSRWCIFEYE

IAQTWQFLSSRAGIIFIVLQKVEKTLLRQQVELYRLLSRNTYLEWEDSVL

GRHIFWRRLRKALLDGKSWNPEGTVGTGCNWQEATSI

>SEQ ID NO: 83 (Protein, Artificial Sequence,
CER07 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTPVLSLNITCQMNKTIIGVSVL

SVLVVSVVAVLVYKFYFHLMLLAGCIKYGRGENIYDAFVIYSSQDEDWVR

NELVKNLEEGVPPFQLCLHYRDFIPGVAIAANIIHEGFHKSRKVIVVVSQ

HFIQSRWCIFEYEIAQTWQFLSSRAGIIFIVLQKVEKTLLRQQVELYRLL

SRNTYLEWEDSVLGRHIFWRRLRKALLDGKSWNPEGTVGTGCNWQEATSI

>SEQ ID NO: 84 (Protein, Artificial Sequence,
CER17 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

EGWRISFYWNVSVHRVLGFKEIDRQTEQFEYAAYIIHAYKDKDWVWEHFS

SMEKEDQSLKFCLEERDFEAGVFELEAIVNSIKRSRKIIFVITHHLLKDP

LCKRFKVHHAVQQAIEQNLDSIILVFLEEIPDYKLNHALCLRRGMFKSHC

ILNWPVQKERIGAFRHKLQVALGSKNSVH

>SEQ ID NO: 85 (Protein, Artificial Sequence,
CER18 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

-continued
NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTFFMINTSILLIFIFIVLLIHF

EGWRISFYWNVSVHRVLGFKEIDRQTEQFEYAAYIIHAYKDKDWVWEHFS

SMEKEDQSLKFCLEERDFEAGVFELEAIVNSIKRSRKIIFVITHHLLKDP

LCKRFKVHHAVQQAIEQNLDSIILVFLEEIPDYKLNHALCLRRGMFKSHC

ILNWPVQKERIGAFRHKLQVALGSKNSVH

>SEQ ID NO: 86 (Protein, Artificial Sequence,
CER19 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

TKFRGFCFICYKTAQRLVFKDHPQGTEPDMYKYDAYLCFSSKDFTWVQNA

LLKHLDTQYSDQNRFNLCFEERDFVPGENRIANIQDAIWNSRKIVCLVSR

HFLRDGWCLEAFSYAQGRCLSDLNSALIMVVVGSLSQYQLMKHQSIRGFV

QKQQYLRWPEDFQDVGWFLHKLSQQILKKEKEKKKDNNIPLQTVATIS

>SEQ ID NO: 87 (Protein, Artificial Sequence,
CER20 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTFSLFIVCTVTLTLFLMTILTV

TKFRGFCFICYKTAQRLVFKDHPQGTEPDMYKYDAYLCFSSKDFTWVQNA

LLKHLDTQYSDQNRFNLCFEERDFVPGENRIANIQDAIWNSRKIVCLVSR

HFLRDGWCLEAFSYAQGRCLSDLNSALIMVVVGSLSQYQLMKHQSIRGFV

QKQQYLRWPEDFQDVGWFLHKLSQQILKKEKEKKKDNNIPLQTVATIS

>SEQ ID NO: 88 (Protein, Artificial Sequence,
CER21 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

HHLFYWDVWFIYNVCLAKVKGYRSLSTSQTFYDAYISYDTKDASVTDWVI

NELRYHLEESRDKNVLLCLEERDWDPGLAIIDNLMQSINQSKKTVFVLTK

KYAKSWNFKTAFYLALQRLMDENMDVIIFILLEPVLQHSQYLRLRQRICK

SSILQWPDNPKAEGLFWQTLRNVVLTENDSRYNNMYVDSIKQY

>SEQ ID NO: 89 (Protein, Artificial Sequence,
CER22 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTAVILFFFTFFITTMVMLAALA

HHLFYWDVWFIYNVCLAKVKGYRSLSTSQTFYDAYISYDTKDASVTDWVI

NELRYHLEESRDKNVLLCLEERDWDPGLAIIDNLMQSINQSKKTVFVLTK

KYAKSWNFKTAFYLALQRLMDENMDVIIFILLEPVLQHSQYLRLRQRICK

SSILQWPDNPKAEGLFWQTLRNVVLTENDSRYNNMYVDSIKQY

>SEQ ID NO: 90 (Protein, Artifical Sequence,
CER23 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

GWDLWYCFHLCLAWLPWRGRQSGRDEDALPYDAFVVFDKTQSAVADWVYN

ELRGQLEECRGRWALRLCLEERDWLPGKTLFENLWASVYGSRKTLFVLAH

TDRVSGLLRASFLLAQQRLLEDRKDVVVLVILSPDGRRSRYVRLRQRLCR

QSVLLWPHQPSGQRSFWAQLGMALTRDNHHFYNRNFCQGPTAE

>SEQ ID NO: 91 (Protein, Artificial Sequence,
CER24 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTFALSLLAVALGLGVPMLHELC

GWDLWYCFHLCLAWLPWRGRQSGRDEDALPYDAFVVFDKTQSAVADWVYN

ELRGQLEECRGRWALRLCLEERDWLPGKTLFENLWASVYGSRKTLFVLAH

TDRVSGLLRASFLLAQQRLLEDRKDVVVLVILSPDGRRSRYVRLRQRLCR

QSVLLWPHQPSGQRSFWAQLGMALTRDNHHFYNRNFCQGPTAE

>SEQ ID NO: 92 (Protein, Artificial Sequence,
CER26 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

SYLDLPWYLRMVCQWTQTRRRARNIPLEELQRNLQFHAFISYSGHDSFWV

KNELLPNLEKEGMQICLHERNFVPGKSIVENIITCIEKSYKSIFVLSPNF

VQSEWCHYELYFAHHNLFHEGSNSLILILLEPIPQYSIPSSYHKLKSLMA

RRTYLEWPKEKSKRGLFWANLRAAINIKLTEQAKK

>SEQ ID NO: 93 (Protein, Artificial Sequence,
CER27 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

HRFHGLWYMKMMWAWLQAKRKPRKAPSRNICYDAFVSYSERDAYWVENLM

VQELENFNPPFKLCLHKRDFIPGKWIIDNIIDSIEKSHKTVFVLSENFVK

SEWCKYELDFSHFRLFDENNDAAILILLEPIEKKAIPQRFCKLRKIMNTK

TYLEWPMDEAQREGFWVNLRAAIKS

>SEQ ID NO: 94 (Protein, Artificial Sequence,
CER28 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

HLYFWDVWYIYHFCKAKIKGYQRLISPDCCYDAFIVYDTKDPAVTEWVLA

ELVAKLEDPREKHFNLCLEERDWLPGQPVLENLSQSIQLSKKTVFVMTDK

YAKTENFKIAFYLSHQRLMDEKVDVIILIFLEKPFQKSKFLQLRKRLCGS

SVLEWPTNPQAHPYFWQCLKNALATDNHVAYSQVFKETV

>SEQ ID NO: 95 - intentionally blank

>SEQ ID NO: 96 (Protein, Artificial Sequence,
CER30 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

MAAASVTPPGSLELLQPGFSKTLLGTKLEAKYLCSACRNVLRRPFQAQCG

HRYCSFCLASILSSGPQNCAACVHEGIYEEGISILESSSAFPDNAARREV

ESLPAVCPSDGCTWKGTLKEYESCHEGRCPLMLTECPACKGLVRLGEKER

HLEHECPERSLSCRHCRAPCCGADVKAHHEVCPKFPLTCDGCGKKKIPRE

KFQDHVKTCGKCRVPCRFHAIGCLETVEGEKQQEHEVQWLREHLAMLLSS

VLEAKPLLGDQSHAGSELLQRCESLEKKTATFENIVCVLNREVERVAMTA

EAC

>SEQ ID NO: 97 (Protein, Artificial Sequence,
CER31 chimeric engulfment receptor, amino acids
1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

MESSKKMDSPGALQTNPPLKLHTDRSAGTPVFVPEQGGYKEKFVKTVEDK

YKCEKCHLVLCSPKQTECGHRFCESCMAALLSSSSPKCTACQESIVKDKV

FKDNCCKREILALQIYCRNESRGCAEQLMLGHLLVHLKNDCHFEELPCVR

PDCKEKVLRKDLRDHVEKACKYREATCSHCKSQVPMIALQKHEDTDCPCV

VVSCPHKCSVQTLLRSELSAHLSECVNAPSTCSFKRYGCVFQGTNQQIKA

HEASSAVQHVNLLKEWSNSLEKKV

>SEQ ID NO: 98 (Protein, Artificial Sequence,
CER42 chimeric engulfment receptor)
MLLLVTSLLLCELPHPAFLLIPQVQLQQSGPGLVKPSQTLSLTCAISGDS

VSSNSAAWNWIRQSPSRGLEWLGRTYYRSKWYNDYAVSVKSRITINPDTS

KNQFSLQLNSVTPEDTAVYYCAREVTGDLEDAFDIWGQGTMVTVSSGGGG

SDIQMTQSPSSLSASVGDRVTITCRASQTIWSYLNWYQQRPGKAPNLLIY

AASSLQSGVPSRFSGRGSGTDFTLTISSLQAEDFATYYCQQSYSIPQTFG

QGTKLEIKESKYGPPCPPCPTIIGVSVLSVLVVSVVAVLVYKFYFHLMLL

AGCIKYGRGENIYDAFVIYSSQDEDWVRNELVKNLEEGVPPFQLCLHYRD

FIPGVAIAANIIHEGFHKSRKVIVVVSQHFIQSRWCIFEYEIAQTWQFLS

SRAGIIFIVLQKVEKTLLRQQVELYRLLSRNTYLEWEDSVLGRHIFWRRL

RKALLDGKSWNPEGTVGTGCNWQEATSI

>SEQ ID NO: 99 (Protein, Homo sapiens, GM-CSF
signal peptide sequence)
MLLLVTSLLLCELPHPAFLLIP >SEQ ID NO: 100 (Protein, Mus musculus, Tim4
signal peptide sequence)
MSKGLLLLWLVTELWWLYLTPA >SEQ ID NO: 101 [Protein; Artificial Sequence;
P2A self-cleaving peptide]
ATNFSLLKQAGDVEENPGP >SEQ ID NO: 102 (Protein, Artificial Sequence,
T2A self-cleaving peptide)
EGRGSLLTCGDVEENPGP >SEQ ID NO: 103 (Protein, Artificial Sequence
E2A self-cleaving peptide)
QCTNYALLKLAGDVESNPGP >SEQ ID NO: 104 (Protein, Artificial Sequence F2A self-cleaving peptide)
VKQTLNFDLLKLAGDVESNPGP >SEQ ID NO: 105 (Protein, Homo sapiens, truncated EGFR)
RKVCNGIGIGEFKDSLSINATNIKHFKNCTSISGDLHILPVAFRGDSFTH

TPPLDPQELDILKTVKEITGFLLIQAWPENRTDLHAFENLEIIRGRTKQH

GQFSLAVVSLNITSLGLRSLKEISDGDVIISGNKNLCYANTINWKKLFGT

SGQKTKIISNRGENSCKATGQVCHALCSPEGCWGPEPRDCVSCRNVSRGR

ECVDKCNLLEGEPREFVENSECIQCHPECLPQAMNITCTGRGPDNCIQCA

HYIDGPHCVKTCPAGVMGENNTLVWKYADAGHVCH

>SEQ ID NO: 106 (Protein; Mus musculus; Tim4 binding domain; amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQT

>SEQ ID NO: 107 [Protein; Mus musculus, Tim4 binding domain without signal peptide]
ASEDTIIGFLGQPVTLPCHYLSWSQSRNSMCWGKGSCPNSKCNAELLRTD

GTRIISRKSTKYTLLGKVQFGEVSLTISNTNRGDSGVYCCRIEVPGWFND

VKKNVRLELRRATTTKKPTTTTRPTTTPYVTTTTPELLPTTVMTTSVLPT

TTPPQTLATTAFSTAVTTCPSTTPGSFSQETTKGSAFTTESETLPASNHS

QRSMMTISTDIAVLRPTGSNPGILPSTSQLTTQKTTLTTSESLQKTTKSH

QINSRQT

>SEQ ID NO: 108 [Protein; Mus musculus, Tim4 transmembrane domain]
ILIIACCVGFVLMVLLFLAFL >SEQ ID NO: 109 [Protein, Artificial Sequence, FMC63 scFv, amino acids 1-22 are signal peptide)
MLLLVTSLLLCELPHPAFLLIPDIQMTQTTSSLSASLGDRVTISCRASQD

ISKYLNWYQQKPDGTVKLLIYHTSRLHSGVPSRFSGSGSGTDYSLTISNL

EQEDIATYFCQQGNTLPYTFGGGTKLEITGSTSGSGKPGSGEGSTKGEVK

LQESGPGLVAPSQSLSVTCTVSGVSLPDYGVSWIRQPPRKGLEWLGVIWG

SETTYYNSALKSRLTIIKDNSKSQVFLKMNSLQTDDTAIYYCAKHYYYGG

SYAMDYWGQGTSVTVSS

>SEQ ID NO: 110 (DNA, Homo sapiens, CD28 transmembrane domain)
TTTTGGGTGCTGGTGGTGGTTGGTGGAGTCCTGG

CTTGCTATAGCTTGCTAGTAACAGTGGCCTTTATTATTTTCTGGGTG

>SEQ ID NO: 111 (DNA, Homo sapiens, DAP12 transmembrane domain)
GGCGTGCTGGCAGGGATCGTGATGGGAGACCTGGTGCTGACAGTGCTCAT

TGCCCTGGCCGTG

>SEQ ID NO: 112 (DNA, Homo sapiens, TLR4 transmembrane domain)
ACCATCATTGGTGTGTCGGTCCTCAGTGTGCTTGTAGTATCTGTTGTAGC

AGTTCTGGTCTAT

>SEQ ID NO: 113 (DNA, Homo sapiens, BAI1 transmembrane domain)
GTGACGCTCATCGTGGGCTGTGGCGTGTCCTCTCTCACCCTGCTCATGCT

GGTCATCATCTAC

>SEQ ID NO: 114 (Protein, Homo sapiens, Tim4 signal peptide)
MSKEPLILWLMIEFWWLYLTPVTS >SEQ ID NO: 115 (DNA, Homo sapiens, FcεRIγ signaling domain)
CGACTGAAGATCCAAGTGCGAAAGGCAGCTATAACCAGCTATGAGAAATC

AGATGGTGTTTACACGGGCCTGAGCACCAGGAACCAGGAGACTTACGAGA

CTCTGAAGCATGAGAAACCACCACAG

>SEQ ID NO: 116 (DNA, Homo sapiens, DAP12 signaling domain)
TATTTTCTGGGAAGGCTCGTTCCTAGAGGTAGAGGTGCTGCCGAAGCAGC

GACGCGCAAACAGAGGATTACTGAAACGGAGTCTCCCTACCAAGAGCTGC

AAGGCCAGAGGTCAGATGTCTATTCAGACTTGAACACACAAAGGCCATAC

TACAAA

>SEQ ID NO: 117 (DNA, Homo sapiens, BAFFR signaling domain)
TCCTGGAGACGGCGACAAAGGCGCTTGCGCGGCGCATCATCCGCAGAGGC

GCCCGACGGCGATAAGGACGCGCCCGAACCCCTTGATAAAGTTATTATCT

TGTCACCGGGAATTTCTGACGCTACGGCACCCGCGTGGCCTCCTCCGGGC

GAAGATCCTGGTACGACACCCCCTGGACACAGTGTTCCCGTGCCCGCGAC

AGAGCTCGGTAGCACAGAACTGGTGACCACAAAGACGGCGGGACCGGAAC

AGCAA

>SEQ ID NO: 118 (DNA, Homo sapiens, CD79b signaling domain)
GACAGTAAAGCCGGGATGGAAGAGGACCACACATACGAGGGGCTTGACAT

AGATCAAACAGCGACATACGAAGACATCGTAACCTTGCGGACTGGAGAGG

TTAAATGGTCAGTCGGAGAACACCCCGGCCAAGAA

>SEQ ID NO: 119 (DNA, Homo sapiens, NFAM1 signaling domain)
CTCTGGAATAAAAAGAGGATGCGCGGCCCGGGAAAAGACCCAACGAGAAA

GTGTCCCGATCCCCGCAGTGCGTCAAGCCCCAAGCAGCATCCTTCCGAAA

GCGTATATACGGCACTTCAACGCCGGGAAACGGAGGTATATGCGTGTATT

GAGAACGAGGACGGGTCATCCCCGACCGCCAAACAGTCCCCTCTCAGCCA

AGAGCGACCTCACAGGTTTGAGGACGATGGTGAACTCAATCTGGTCTACG

AAAACCTG

>SEQ ID NO: 120 (DNA, Homo sapiens, BAI1 binding domain)
GCCGCCGGAGCAGACGCGGGCCCGGGCCCGAGCCGTGCGCCACGCTGGT

GCAGGGAAAGTTCTTCGGCTACTTCTCCGCGGCCGCCGTGTTCCCGGCCA

ACGCCTCGCGCTGCTCCTGGACGCTACGCAACCCGGACCCGCGGCGCTAC

ACTCTCTACATGAAGGTGGCCAAGGCGCCCGTGCCCTGCAGCGGCCCCGG

```
CCGCGTGCGCACCTACCAGTTCGACTCCTTCCTCGAGTCCACGCGCACCT
ACCTGGGCGTGGAGAGCTTCGACGAGGTGCTGCGGCTCTGCGACCCCTCC
GCACCCCTGGCCTTCCTGCAGGCCAGCAAGCAGTTCCTGCAGATGCGGCG
CCAGCAGCCGCCCCAGCACGACGGGCTCCGGCCCCGGGCCGGGCCGCCGG
GCCCCACCGACGACTTCTCCGTGGAGTACCTGGTGGTGGGGAACCGCAAC
CCCAGCCGTGCCGCCTGCCAGATGCTGTGCCGCTGGCTGGACGCGTGTCT
GGCCGGTAGTCGCAGCTCGCACCCCTGCGGGATCATGCAGACCCCCTGCG
CCTGCCTGGGCGGCGAGGCGGGCGGCCCTGCCGCGGGACCCCTGGCCCCC
CGCGGGGATGTCTGCTTGAGAGATGCGGTGGCTGGTGGCCCTGAAAACTG
CCTCACCAGCCTGACCCAGGACCGGGGCGGGCACGGCGCACAGGCGGCT
GGAAGCTGTGGTCCCTGTGGGCGAATGCACGCGGGACTGCGGGGAGGC
CTCCAGACGCGGACGCGCACCTGCCTGCCCGCGCGGGCGTGGAGGGCGG
CGGCTGCGAGGGGGTGCTGGAGGAGGGTCGCCAGTGCAACCGCGAGGCCT
GCGGCCCCGCTGGGCGCACCAGCTCCCGGAGCCAGTCCCTGCGGTCCACA
GATGCCCGGCGGCGCGAGGAGCTGGGGGACGAGCTGCAGCAGTTTGGGTT
CCCAGCCCCCAGACCGGTGACCCAGCAGCCGAGGAGTGGTCCCCGTGGA
GCGTGTGCTCCAGCACCTGCGGCGAGGGCTGGCAGACCCGCACGCGCTTC
TGCGTGTCCTCCTCCTACAGCACGCAGTGCAGCGGACCCCTGCGCGAGCA
GCGGCTGTGCAACAACTCTGCCGTGTGCCCAGTGCATGGTGCCTGGGATG
AGTGGTCGCCCTGGAGCCTCTGCTCCAGCACCTGTGGCCGTGGCTTTCGG
GATCGCACGCGCACCTGCAGGCCCCCCCAGTTTGGGGGCA
ACCCCTGTGAGGGCCCTGAGAAGCAAACCAAGTTCTGCAACATTGCCCTG
TGCCCTGGCCGGGCAGTGGATGGAAACTGGAATGAGTGGTCGAGCTGGAG
CGCCTGCTCCGCCAGCTGCTCCCAGGGCCGACAGCAGCGCACGCGTGAAT
GCAACGGGCCTTCCTACGGGGTGCGGAGTGCCAGGGCCACTGGGTGGAG
ACCCGAGACTGCTTCCTGCAGCAGTGCCCAGTGGATGGCAAGTGGCAGGC
CTGGGCGTCATGGGGCAGTTGCAGCGTCAC
GTGTGGGCTGGCAGCCAGCGACGGGAGCGTGTCTGCTCTGGGCCCTTCT
TCGGGGAGCAGCCTGCCAGGGCCCCAGGATGAGTACCGGCAGTGCGGC
ACCCAGCGGTGTCCCGAGCCCATGAGATCTGTGATGAGGACAACTTTGG
TGCTGTGATCTGGAAGGAGACCCCAGCGGGAGAGGTGGCTGCTGTCCGGT
GTCCCCGCAACGCCACAGGACTCATCCTGCGACGGTGTGAGCTGGACGAG
GAAGGCATCGCCTACTGGGAGCCCCCACC
TACATCCGCTGTGTTTCCATTGACTACAGAAACATCCAGATGATGACCCG
GGAGCACCTGGCCAAGGCTCAGCGAGGGCTGCCTGGGGAGGGGGTCTCGG
AGGTCATCCAGACACTGGTGGAGATCTCTCAGGACGGGACCAGCTACAGT
GGGGACCTGCTGTCCACCATCGATGTCCTGAGGAACATGACAGAGATTTT
CCGGAGAGCGTACTACAGCCCCACCCCTGGGGACTACAGAACTTTGTCC
AGATCCTTAGCAACCTGTTGGCAGAGGAGA
ATCGGGACAAGTGGGAGGAGGCCCAGCTGGCGGGCCCCAACGCCAAGGAG
CTGTTCCGGCTGGTGGAGGACTTTGTGGACGTCATCGGCTTCCGCATGAA
GGACCTGAGGGATGCATACCAGGTGACAGACAACCTGGTTCTCAGCATCC
ATAAGCTCCCAGCCAGCGGAGCCACTGACATCAGCTTCCCCATGAAGGGC
TGGCGGGCCACGGGTGACTGGGCCAAGGTGCCAGAGGACAGGGTCACTGT
GTCCAAGAGTGTCTTCTCCACGGGGCTGAC
AGAGGCCGATGAAGCATCCGTGTTTGTGGTGGGCACCGTGCTCTACAGGA
ACCTGGGCAGCTTCCTGGCCCTGCAGAGGAACACGACCGTCCTGAATTCT
AAGGTGATCTCCGTGACTGTGAAACCCCCGCCTCGCTCCCTGCGCACACC
CTTGGAGATCGAGTTTGCCCACATGTATAATGGCACCACCAACCAGACCT
GTATCCTGTGGGATGAGACGGATGTACCCTCCTCCTCCGCCCCCCCGCAG
CTCGGGCCCTGGTCGTGGCGCGGCTGCCGCACGGTGCCCCTCGACGCCCT
CCGGACGCGCTGCCTCTGTGACCGGCTCTCCACCTTCGCCATCTTAGCCC
AGCTCAGCGCCGACGCGAACATGGAGAAGGCGACTCTGCCGTCG

>SEQ ID NO: 121 (DNA, Homo sapiens, FcεRIγ
transmembrane domain)
CTTTGTTACATTCTCGACGCGATATTGTTCCTTTATGGAATAGTTTTGAC
GCTCCTTTATTGC >SEQ ID NO: 122 (Protein, Artificial Sequence,
CER43 chimeric engulfment receptor, amino acids
1-22 are signal peptide)
MLLLVTSLLLCELPHPAFLLIPDIQMTQTTSSLSASLGDRVTISCRASQD
ISKYLNWYQQKPDGTVKLLIYHTSRLHSGVPSRFSGSGSGTDYSLTISNL
EQEDIATYFCQQGNTLPYTFGGGTKLEITGSTSGSGKPGSGEGSTKGEVK
LQESGPGLVAPSQSLSVTCTVSGVSLPDYGVSWIRQPPRKGLEWLGVIWG
SETTYYNSALKSRLTIIKDNSKSQVFLKMNSLQTDDTAIYYCAKHYYYGG
SYAMDYWGQGTSVTVSSPVLSLNITCQMNKTIIGVSVLSVLVVSVVAVLV
YKFYFHLMLLAGCIKYGRGENIYDAFVIYSSQDEDWVRNELVKNLEEGVP
PFQLCLHYRDFIPGVAIAANIIHEGFHKSRKVIVVVSQHFIQSRWCIFEY
EIAQTWQFLSSRAGIIFIVLQKVEKTLLRQQVELYRLLSRNTYLEWEDSV
LGRHIFWRRLRKALLDGKSWNPEGTVGTGCNWQEATSI >SEQ ID NO: 123 (Protein, Artificial Sequence,
CER44 chimeric engulfment receptor, amino acids
1-22 are signal peptide)
MLLLVTSLLLCELPHPAFLLIPDIQMTQTTSSLSASLGDRVTISCRASQD
ISKYLNWYQQKPDGTVKLLIYHTSRLHSGVPSRFSGSGSGTDYSLTISNL
EQEDIATYFCQQGNTLPYTFGGGTKLEITGSTSGSGKPGSGEGSTKGEVK
LQESGPGLVAPSQSLSVTCTVSGVSLPDYGVSWIRQPPRKGLEWLGVIWG
SETTYYNSALKSRLTIIKDNSKSQVFLKMNSLQTDDTAIYYCAKHYYYGG
SYAMDYWGQGTSVTVSSESKYGPPCPPCPTIIGVSVLSVLVVSVVAVLVY
KFYFHLMLLAGCIKYGRGENIYDAFVIYSSQDEDWVRNELVKNLEEGVPP
FQLCLHYRDFIPGVAIAANIIHEGFHKSRKVIVVVSQHFIQSRWCIFEYE
IAQTWQFLSSRAGIIFIVLQKVEKTLLRQQVELYRLLSRNTYLEWEDSVL
GRHIFWRRLRKALLDGKSWNPEGTVGTGCNWQEATSI
```

>SEQ ID NO: 124 (Protein, Artificial Sequence, CER29 chimeric engulfment receptor, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

MSLLNCENSCGSSQSESDCCVAMASSCSAVTKDDSVGGTASTGNLSSSFM

EEIQGYDVEFDPPLESKYECPICLMALREAVQTPCGHRFCKACIIKSIRD

AGHKCPVDNEILLENQLFPDNFAKREILSLMVKCPNEGCLHKMELRHLED

HQAHCEFALMDCPQCQRPFQKFHINIHILKDCPRRQVSCDNCAASMAFED

KEIHDQNCPLANVICEYCNTILIREQMPNHYDLDCPTAPIPCTFSTFGCH

EKMQRNHLARHLQENTQSHMRMLA

>SEQ ID NO: 125 (Protein, Artificial Sequence, CER110 chimeric engulfment receptor, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

MSLLNCENSCGSSQSESDCCVAMASSCSAVTKDDSVGGTASTGNLSSSFM

EEIQGYDVEFDPPLESKYECPICLMALREAVQTPCGHRFCKACIIKSIRD

AGHKCPVDNEILLENQLFPDNFAKREILSLMVKCPNEGCLHKMELRHLED

HQAHCEFALMDCPQCQRPFQKFHINIHILKDCPRRQVSCDNCAASMAFED

KEIHDQNCPLANVICEYCNTILIREQMPNHYDLDCPTAPIPCTFSTFGCH

EKMQRNHLARHLQENTQSHMRMLAYFLGRLVPRGRGAAEEAATRKQRITET

ESPYQELQGQRSDVYSDLNTQRPYYK

>SEQ ID NO: 126 (Protein, Artificial Sequence, CER111B chimeric engulfment receptor, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

MSLLNCENSCGSSQSESDCCVAMASSCSAVTKDDSVGGTASTGNLSSSFM

EEIQGYDVEFDPPLESKYECPICLMALREAVQTPCGHRFCKACIIKSIRD

AGHKCPVDNEILLENQLFPDNFAKREILSLMVKCPNEGCLHKMELRHLED

HQAHCEFALMDCPQCQRPFQKFHINIHILKDCPRRQVSCDNCAASMAFED

KEIHDQNCPLANVICEYCNTILIREQMPNHYDLDCPTAPIPCTFSTFGCH

EKMQRNHLARHLQENTQSHMRMLA

DSKAGMEEDHTYEGLDIDQTATYEDIVTL

>SEQ ID NO: 127 (Protein, Artificial Sequence, CER113 chimeric engulfment receptor, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQT

MSLLNCENSCGSSQSESDCCVAMASSCSAVTKDDSVGGTASTGNLSSSFM

EEIQGYDVEFDPPLESKYECPICLMALREAVQTPCGHRFCKACIIKSIRD

AGHKCPVDNEILLENQLFPDNFAKREILSLMVKCPNEGCLHKMELRHLED

HQAHCEFALMDCPQCQRPFQKFHINIHILKDCPRRQVSCDNCAASMAFED

KEIHDQNCPLANVICEYCNTILIREQMPNHYDLDCPTAPIPCTFSTFGCH

EKMQRNHLARHLQENTQSHMRMLASWRRRQRRLRGASSAEAPDGDKDAPE

PLDKVIILSPGISDATAPAWPPPGEDPGTTPPGHSVPVPATELGSTELVT

TKTAGPEQQ

>SEQ ID NO: 128 (Protein, Artificial Sequence, CER112 chimeric engulfment receptor, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

MSLLNCENSCGSSQSESDCCVAMASSCSAVTKDDSVGGTASTGNLSSSFM

EEIQGYDVEFDPPLESKYECPICLMALREAVQTPCGHRFCKACIIKSIRD

AGHKCPVDNEILLENQLFPDNFAKREILSLMVKCPNEGCLHKMELRHLED

HQAHCEFALMDCPQCQRPFQKFHINIHILKDCPRRQVSCDNCAASMAFED

KEIHDQNCPLANVICEYCNTILIREQMPNHYDLDCPTAPIPCTFSTFGCH

EKMQRNHLARHLQENTQSHMRMLALWNKKRMRGPGKDPTRKCPDPRSASS

PKQHPSESVYTALQRRETEVYACIENEDGSSPTAKQSPLSQERPHRFEDD

GELNLVYENL

>SEQ ID NO: 129

>SEQ ID NO: 130 (CER102, Protein, Artificial Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

-continued
QLTTQKTTLTTSESLQKTTKSHQINSRQTILIIACCVGFVLMVLLFLAFL

HHLFYWDVWFIYNVCLAKVKGYRSLSTSQTFYDAYISYDTKDASVTDWVI

NELRYHLEESRDKNVLLCLEERDWDPGLAIIDNLMQSINQSKKTVFVLTK

KYAKSWNFKTAFYLALQRLMDENMDVIIFILLEPVLQHSQYLRLRQRICK

SSILQWPDNPKAEGLFWQTLRNVVLTENDSRYNNMYVDSIKQYLWNKKRM

RGPGKDPTRKCPDPRSASSPKQHPSESVYTALQRRETEVYACIENEDGSS

PTAKQSPLSQERPHRFEDDGELNLVYENL

>SEQ ID NO: 131 (CER103A, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

HHLFYWDVWFIYNVCLAKVKGYRSLSTSQTFYDAYISYDTKDASVTDWVI

NELRYHLEESRDKNVLLCLEERDWDPGLAIIDNLMQSINQSKKTVFVLTK

KYAKSWNFKTAFYLALQRLMDENMDVIIFILLEPVLQHSQYLRLRQRICK

SSILQWPDNPKAEGLFWQTLRNVVLTENDSRYNNMYVDSIKQYDSKAGME

EDHTYEGLDIDQTATYEDIVTLRTGEVKWSVGEHPGQE

>SEQ ID NO: 132 (CER103B, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

HHLFYWDVWFIYNVCLAKVKGYRSLSTSQTFYDAYISYDTKDASVTDWVI

NELRYHLEESRDKNVLLCLEERDWDPGLAIIDNLMQSINQSKKTVFVLTK

KYAKSWNFKTAFYLALQRLMDENMDVIIFILLEPVLQHSQYLRLRQRICK

SSILQWPDNPKAEGLFWQTLRNVVLTENDSRYNNMYVDSIKQYDSKAGME

EDHTYEGLDIDQTATYEDIVTL

>SEQ ID NO: 133 (CER104, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

HHLFYWDVWFIYNVCLAKVKGYRSLSTSQTFYDAYISYDTKDASVTDWVI

NELRYHLEESRDKNVLLCLEERDWDPGLAIIDNLMQSINQSKKTVFVLTK

KYAKSWNFKTAFYLALQRLMDENMDVIIFILLEPVLQHSQYLRLRQRICK

SSILQWPDNPKAEGLFWQTLRNVVLTENDSRYNNMYVDSIKQYYFLGRLV

PRGRGAAEAATRKQRITETESPYQELQGQRSDVYSDLNTQRPYYK

>SEQ ID NO: 134 (CER105, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

HHLFYWDVWFIYNVCLAKVKGYRSLSTSQTFYDAYISYDTKDASVTDWVI

NELRYHLEESRDKNVLLCLEERDWDPGLAIIDNLMQSINQSKKTVFVLTK

KYAKSWNFKTAFYLALQRLMDENMDVIIFILLEPVLQHSQYLRLRQRICK

SSILQWPDNPKAEGLFWQTLRNVVLTENDSRYNNMYVDSIKQYSWRRRQR

RLRGASSAEAPDGDKDAPEPLDKVIILSPGISDATAPAWPPPGEDPGTTP

PGHSVPVPATELGSTELVTTKTAGPEQQ

>SEQ ID NO: 135 (CER106, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

LWNKKRMRGPGKDPTRKCPDPRSASSPKQHPSESVYTALQRRETEVYACI

ENEDGSSPTAKQSPLSQERPHRFEDDGELNLVYENLHEILFYWDVWFIYN

VCLAKVKGYRSLSTSQTFYDAYISYDTKDASVTDWVINELRYHLEESRDK

NVLLCLEERDWDPGLAIIDNLMQSINQSKKTVFVLTKKYAKSWNFKTAFY

LALQRLMDENMDVIIFILLEPVLQHSQYLRLRQRICKSSILQWPDNPKAE

GLFWQTLRNVVLTENDSRYNNMYVDSIKQY

>SEQ ID NO: 136 (CER107, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

DSKAGMEEDHTYEGLDIDQTATYEDIVTLHHLFYWDVWFIYNVCLAKVKG

YRSLSTSQTFYDAYISYDTKDASVTDWVINELRYHLEESRDKNVLLCLEE

RDWDPGLAIIDNLMQSINQSKKTVFVLTKKYAKSWNFKTAFYLALQRLMD

ENMDVIIFILLEPVLQHSQYLRLRQRICKSSILQWPDNPKAEGLFWQTLR

NVVLTENDSRYNNMYVDSIKQY

>SEQ ID NO: 137 (CER108, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

YFLGRLVPRGRGAAEAATRKQRITETESPYQELQGQRSDVYSDLNTQRPY

YKHEILFYWDVWFIYNVCLAKVKGYRSLSTSQTFYDAYISYDTKDASVTD

WVINELRYHLEESRDKNVLLCLEERDWDPGLAIIDNLMQSINQSKKTVFV

LTKKYAKSWNFKTAFYLALQRLMDENMDVIIFILLEPVLQHSQYLRLRQR

ICKSSILQWPDNPKAEGLFWQTLRNVVLTENDSRYNNMYVDSIKQY

>SEQ ID NO: 138 (CER109, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

SWRRRQRRLRGASSAEAPDGDKDAPEPLDKVIILSPGISDATAPAWPPPG

EDPGTTPPGHSVPVPATELGSTELVTTKTAGPEQQHHLFYWDVWFIYNVC

LAKVKGYRSLSTSQTFYDAYISYDTKDASVTDWVINELRYHLEESRDKNV

LLCLEERDWDPGLAIIDNLMQSINQSKKTVFVLTKKYAKSWNFKTAFYLA

LQRLMDENMDVIIFILLEPVLQHSQYLRLRQRICKSSILQWPDNPKAEGL

FWQTLRNVVLTENDSRYNNMYVDSIKQY

>SEQ ID NO: 139 (CER111A, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

MSLLNCENSCGSSQSESDCCVAMASSCSAVTKDDSVGGTASTGNLSSSFM

EEIQGYDVEFDPPLESKYECPICLMALREAVQTPCGHRFCKACIIKSIRD

AGHKCPVDNEILLENQLFPDNFAKREILSLMVKCPNEGCLHKMELRHLED

HQAHCEFALMDCPQCQRPFQKFHINIHILKDCPRRQVSCDNCAASMAFED

KEIHDQNCPLANVICEYCNTILIREQMPNHYDLDCPTAPIPCTFSTFGCH

EKMQRNHLARHLQENTQSHMRMLADSKAGMEEDHTYEGLDIDQTATYEDI

VTLRTGEVKWSVGEHPGQE

>SEQ ID NO: 140 (CER113, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

MSLLNCENSCGSSQSESDCCVAMASSCSAVTKDDSVGGTASTGNLSSSFM

EEIQGYDVEFDPPLESKYECPICLMALREAVQTPCGHRFCKACIIKSIRD

AGHKCPVDNEILLENQLFPDNFAKREILSLMVKCPNEGCLHKMELRHLED

HQAHCEFALMDCPQCQRPFQKFHINIHILKDCPRRQVSCDNCAASMAFED

KEIHDQNCPLANVICEYCNTILIREQMPNHYDLDCPTAPIPCTFSTFGCH

EKMQRNHLARHLQENTQSHMRMLASWRRRQRRLRGASSAEAPDGDKDAPE

PLDKVIILSPGISDATAPAWPPPGEDPGTTPPGHSVPVPATELGSTELVT

TKTAGPEQQ

>SEQ ID NO: 141 (CER114, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

MSLLNCENSCGSSQSESDCCVAMASSCSAVTKDDSVGGTASTGNLSSSFM

EEIQGYDVEFDPPLESKYECPICLMALREAVQTPCGHRFCKACIIKSIRD

AGHKCPVDNEILLENQLFPDNFAKREILSLMVKCPNEGCLHKMELRHLED

HQAHCEFALMDCPQCQRPFQKFHINIHILKDCPRRQVSCDNCAASMAFED

KEIHDQNCPLANVICEYCNTILIREQMPNHYDLDCPTAPIPCTFSTFGCH

EKMQRNHLARHLQENTQSHMRMLAALRRRVQETKFGGAFSEEDSQLVVNY

RAKKSFCRRAIELTLQSLGVSEELQNKLEDVVIDRNLLVLGKVLGEGEFG

SVMEGNLKQEDGTSQKVAVKTMKLDNFSQREIEEFLSEAACMKDFNHPNV

IRLLGVCIELSSQGIPKPMVILPFMKYGDLHTFLLYSRLNTGPKYIHLQT

LLKFMMDIAQGMEYLSNRNFLHRDLAARNCMLRDDMTVCVADFGLSKKIY

SGDYYRQGRIAKMPVKWIAIESLADRVYTSKSDVWAFGVTMWEITTRGMT

PYPGVQNHEMYDYLLHGHRLKQPEDCLDELYDIMYSCWSADPLDRPTFSV

LRLQLEKLSESLPDAQDKESIIYINTQLLESCEGIANGPSLTGLDMNIDP

DSIIASCTPGAAVSVVTAEVHENNLREERYILNGGNEEWEDVSSTPFAAV

TPEKDGVLPEDRLTKNGVSWSHHSTLPLGSPSPDELLFVDDSLEDSEVLM

>SEQ ID NO: 142 (CER115, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

```
-continued
NTNRGDSGVYCCRIEVPGWFNDVKKNVRLELRRATTTKKPTTTTRPTTTP
YVTTTTPELLPTTVMTTSVLPTTTPPQTLATTAFSTAVTTCPSTTPGSFS
QETTKGSAFTTESETLPASNHSQRSMMTISTDIAVLRPTGSNPGILPSTS
QLTTQKTTLTTSESLQKTTKSHQINSRQTILIIACCVGFVLMVLLFLAFL
ALRRRVQETKFGGAFSEEDSQLVVNYRAKKSFCRRAIELTLQSLGVSEEL
QNKLEDVVIDRNLLVLGKVLGEGEFGSVMEGNLKQEDGTSQKVAVKTMKL
DNFSQREIEEFLSEAACMKDFNHPNVIRLLGVCIELSSQGIPKPMVILPF
MKYGDLHTFLLYSRLNTGPKYIHLQTLLKFMMDIAQGMEYLSNRNFLHRD
LAARNCMLRDDMTVCVADFGLSKKIYSGDYYRQGRIAKMPVKWIAIESLA
DRVYTSKSDVWAFGVTMWEITTRGMTPYPGVQNHEMYDYLLHGHRLKQPE
DCLDELYDIMYSCWSADPLDRPTFSVLRLQLEKLSESLPDAQDKESIIYI
NTQLLESCEGIANGPSLTGLDMNIDPDSIIASCTPGAAVSVVTAEVHENN
LREERYILNGGNEEWEDVSSTPFAAVTPEKDGVLPEDRLTKNGVSWSHHS
TLPLGSPSPDELLFVDDSLEDSEVLMMSLLNCENSCGSSQSESDCCVAMA
SSCSAVTKDDSVGGTASTGNLSSSFMEEIQGYDVEFDPPLESKYECPICL
MALREAVQTPCGHRFCKACIIKSIRDAGHKCPVDNEILLENQLFPDNFAK
REILSLMVKCPNEGCLHKMELRHLEDHQAHCEFALMDCPQCQRPFQKFHI
NIHILKDCPRRQVSCDNCAASMAFEDKEIHDQNCPLANVICEYCNTILIR
EQMPNHYDLDCPTAPIPCTFSTFGCHEKMQRNHLARHLQENTQSHMRMLA >SEQ ID NO: 143 (CER116, Protein, Artificial
Sequence, amino acids 1-22 are signal peptide)
MSKGLLLLWLVTELWWLYLTPAASEDTIIGFLGQPVTLPCHYLSWSQSRN
SMCWGKGSCPNSKCNAELLRTDGTRIISRKSTKYTLLGKVQFGEVSLTIS
NTNRGDSGVYCCRIEVPGWFNDVKKNVRLELRRATTTKKPTTTTRPTTTP
YVTTTTPELLPTTVMTTSVLPTTTPPQTLATTAFSTAVTTCPSTTPGSFS
QETTKGSAFTTESETLPASNHSQRSMMTISTDIAVLRPTGSNPGILPSTS
QLTTQKTTLTTSESLQKTTKSHQINSRQTILIIACCVGFVLMVLLFLAFL
MSLLNCENSCGSSQSESDCCVAMASSCSAVTKDDSVGGTASTGNLSSSFM
EEIQGYDVEFDPPLESKYECPICLMALREAVQTPCGHRFCKACIIKSIRD
AGHKCPVDNEILLENQLFPDNFAKREILSLMVKCPNEGCLHKMELRHLED
HQAHCEFALMDCPQCQRPFQKFHINIHILKDCPRRQVSCDNCAASMAFED
KEIHDQNCPLANVICEYCNTILIREQMPNHYDLDCPTAPIPCTFSTFGCH
EKMQRNHLARHLQENTQSHMRMLAHHLFYWDVWFIYNVCLAKVKGYRSLS
TSQTFYDAYISYDTKDASVTDWVINELRYHLEESRDKNVLLCLEERDWDP
GLAIIDNLMQSINQSKKTVFVLTKKYAKSWNFKTAFYLALQRLMDENMDV
IIFILLEPVLQHSQYLRLRQRICKSSILQWPDNPKAEGLFWQTLRNVVLT
ENDSRYNNMYVDSIKQY >SEQ ID NO: 144 (CER117, Protein, Artificial
Sequence, amino acids 1-22 are signal peptide)
MSKGLLLLWLVTELWWLYLTPAASEDTIIGFLGQPVTLPCHYLSWSQSRN
SMCWGKGSCPNSKCNAELLRTDGTRIISRKSTKYTLLGKVQFGEVSLTIS
NTNRGDSGVYCCRIEVPGWFNDVKKNVRLELRRATTTKKPTTTTRPTTTP
YVTTTTPELLPTTVMTTSVLPTTTPPQTLATTAFSTAVTTCPSTTPGSFS -continued
QETTKGSAFTTESETLPASNHSQRSMMTISTDIAVLRPTGSNPGILPSTS
QLTTQKTTLTTSESLQKTTKSHQINSRQTILIIACCVGFVLMVLLFLAFL
HHLFYWDVWFIYNVCLAKVKGYRSLSTSQTFYDAYISYDTKDASVTDWVI
NELRYHLEESRDKNVLLCLEERDWDPGLAIIDNLMQSINQSKKTVFVLTK
KYAKSWNFKTAFYLALQRLMDENMDVIIFILLEPVLQHSQYLRLRQRICK
SSILQWPDNPKAEGLFWQTLRNVVLTENDSRYNNMYVDSIKQYMSLLNCE
NSCGSSQSESDCCVAMASSCSAVTKDDSVGGTASTGNLSSSFMEEIQGYD
VEFDPPLESKYECPICLMALREAVQTPCGHRFCKACIIKSIRDAGHKCPV
DNEILLENQLFPDNFAKREILSLMVKCPNEGCLHKMELRHLEDHQAHCEF
ALMDCPQCQRPFQKFHINIHILKDCPRRQVSCDNCAASMAFEDKEIHDQN
CPLANVICEYCNTILIREQMPNHYDLDCPTAPIPCTFSTFGCHEKMQRNH
LARHLQENTQSHMRMLA >SEQ ID NO: 145 (CER118, Protein, Artificial
Sequence, amino acids 1-22 are signal peptide)
MSKGLLLLWLVTELWWLYLTPAASEDTIIGFLGQPVTLPCHYLSWSQSRN
SMCWGKGSCPNSKCNAELLRTDGTRIISRKSTKYTLLGKVQFGEVSLTIS
NTNRGDSGVYCCRIEVPGWFNDVKKNVRLELRRATTTKKPTTTTRPTTTP
YVTTTTPELLPTTVMTTSVLPTTTPPQTLATTAFSTAVTTCPSTTPGSFS
QETTKGSAFTTESETLPASNHSQRSMMTISTDIAVLRPTGSNPGILPSTS
QLTTQKTTLTTSESLQKTTKSHQINSRQTILIIACCVGFVLMVLLFLAFL
SYLDLPWYLRMVCQWTQTRRRARNIPLEELQRNLQFHAFISYSGHDSFWV
KNELLPNLEKEGMQICLHERNFVPGKSIVENIITCIEKSYKSIFVLSPNF
VQSEWCHYELYFAHHNLFHEGSNSLILILLEPIPQYSIPSSYHKLKSLMA
RRTYLEWPKEKSKRGLFWANLRAAINIKLTEQAKKLWNKKRMRGPGKDPT
RKCPDPRSASSPKQHPSESVYTALQRRETEVYACIENEDGSSPTAKQSPL
SQERPHRFEDDGELNLVYENL >SEQ ID NO: 146 (CER119B, Protein, Artificial
Sequence, amino acids 1-22 are signal peptide)
MSKGLLLLWLVTELWWLYLTPAASEDTIIGFLGQPVTLPCHYLSWSQSRN
SMCWGKGSCPNSKCNAELLRTDGTRIISRKSTKYTLLGKVQFGEVSLTIS
NTNRGDSGVYCCRIEVPGWFNDVKKNVRLELRRATTTKKPTTTTRPTTTP
YVTTTTPELLPTTVMTTSVLPTTTPPQTLATTAFSTAVTTCPSTTPGSFS
QETTKGSAFTTESETLPASNHSQRSMMTISTDIAVLRPTGSNPGILPSTS
QLTTQKTTLTTSESLQKTTKSHQINSRQTILIIACCVGFVLMVLLFLAFL
SYLDLPWYLRMVCQWTQTRRRARNIPLEELQRNLQFHAFISYSGHDSFWV
KNELLPNLEKEGMQICLHERNFVPGKSIVENIITCIEKSYKSIFVLSPNF
VQSEWCHYELYFAHHNLFHEGSNSLILILLEPIPQYSIPSSYHKLKSLMA
RRTYLEWPKEKSKRGLFWANLRAAINIKLTEQAKKDSKAGMEEDHTYEGL
DIDQTATYEDIVTL >SEQ ID NO: 147 (CER120, Protein, Artificial
Sequence, amino acids 1-22 are signal peptide)
MSKGLLLLWLVTELWWLYLTPAASEDTIIGFLGQPVTLPCHYLSWSQSRN
SMCWGKGSCPNSKCNAELLRTDGTRIISRKSTKYTLLGKVQFGEVSLTIS
```

-continued
NTNRGDSGVYCCRIEVPGWFNDVKKNVRLELRRATTTKKPTTTTRPTTTP
YVTTTTPELLPTTVMTTSVLPTTTPPQTLATTAFSTAVTTCPSTTPGSFS
QETTKGSAFTTESETLPASNHSQRSMMTISTDIAVLRPTGSNPGILPSTS
QLTTQKTTLTTSESLQKTTKSHQINSRQTILIIACCVGFVLMVLLFLAFL
SYLDLPWYLRMVCQWTQTRRRARNIPLEELQRNLQFHAFISYSGHDSFWV
KNELLPNLEKEGMQICLHERNFVPGKSIVENIITCIEKSYKSIFVLSPNF
VQSEWCHYELYFAHHNLFHEGSNSLILILLEPIPQYSIPSSYHKLKSLMA
RRTYLEWPKEKSKRGLFWANLRAAINIKLTEQAKKYFLGRLVPRGRGAAE
AATRKQRITETESPYQELQGQRSDVYSDLNTQRPYYK >SEQ ID NO: 148 (CER121, Protein, Artificial
Sequence, amino acids 1-22 are signal peptide)
MSKGLLLLWLVTELWWLYLTPAASEDTIIGFLGQPVTLPCHYLSWSQSRN
SMCWGKGSCPNSKCNAELLRTDGTRIISRKSTKYTLLGKVQFGEVSLTIS
NTNRGDSGVYCCRIEVPGWFNDVKKNVRLELRRATTTKKPTTTTRPTTTP
YVTTTTPELLPTTVMTTSVLPTTTPPQTLATTAFSTAVTTCPSTTPGSFS
QETTKGSAFTTESETLPASNHSQRSMMTISTDIAVLRPTGSNPGILPSTS
QLTTQKTTLTTSESLQKTTKSHQINSRQTILIIACCVGFVLMVLLFLAFL
SYLDLPWYLRMVCQWTQTRRRARNIPLEELQRNLQFHAFISYSGHDSFWV
KNELLPNLEKEGMQICLHERNFVPGKSIVENIITCIEKSYKSIFVLSPNF
VQSEWCHYELYFAHHNLFHEGSNSLILILLEPIPQYSIPSSYHKLKSLMA
RRTYLEWPKEKSKRGLFWANLRAAINIKLTEQAKKMSLLNCENSCGSSQS
ESDCCVAMASSCSAVTKDDSVGGTASTGNLSSSFMEEIQGYDVEFDPPLE
SKYECPICLMALREAVQTPCGHRFCKACIIKSIRDAGHKCPVDNEILLEN
QLFPDNFAKREILSLMVKCPNEGCLHKMELRHLEDHQAHCEFALMDCPQC
QRPFQKFHINIHILKDCPRRQVSCDNCAASMAFEDKEIHDQNCPLANVIC
EYCNTILIREQMPNHYDLDCPTAPIPCTFSTFGCHEKMQRNHLARHLQEN
TQSHMRMLA >SEQ ID NO: 149 (CER122, Protein, Artificial
Sequence, amino acids 1-22 are signal peptide)
MSKGLLLLWLVTELWWLYLTPAASEDTIIGFLGQPVTLPCHYLSWSQSRN
SMCWGKGSCPNSKCNAELLRTDGTRIISRKSTKYTLLGKVQFGEVSLTIS
NTNRGDSGVYCCRIEVPGWFNDVKKNVRLELRRATTTKKPTTTTRPTTTP
YVTTTTPELLPTTVMTTSVLPTTTPPQTLATTAFSTAVTTCPSTTPGSFS
QETTKGSAFTTESETLPASNHSQRSMMTISTDIAVLRPTGSNPGILPSTS
QLTTQKTTLTTSESLQKTTKSHQINSRQTILIIACCVGFVLMVLLFLAFL
HRFHGLWYMKMMWAWLQAKRKPRKAPSRNICYDAFVSYSERDAYWVENLM
VQELENFNPPFKLCLHKRDFIPGKWIIDNIIDSIEKSHKTVFVLSENFVK
SEWCKYELDFSHFRLFDENNDAAILILLEPIEKKAIPQRFCKLRKIMNTK
TYLEWPMDEAQREGFWVNLRAAIKSYFLGRLVPRGRGAAEAATRKQRITE
TESPYQELQGQRSDVYSDLNTQRPYYK >SEQ ID NO: 150 (CER123, Protein, Artificial
Sequence, amino acids 1-22 are signal peptide)
MSKGLLLLWLVTELWWLYLTPAASEDTIIGFLGQPVTLPCHYLSWSQSRN
SMCWGKGSCPNSKCNAELLRTDGTRIISRKSTKYTLLGKVQFGEVSLTIS
NTNRGDSGVYCCRIEVPGWFNDVKKNVRLELRRATTTKKPTTTTRPTTTP
YVTTTTPELLPTTVMTTSVLPTTTPPQTLATTAFSTAVTTCPSTTPGSFS
QETTKGSAFTTESETLPASNHSQRSMMTISTDIAVLRPTGSNPGILPSTS
QLTTQKTTLTTSESLQKTTKSHQINSRQTILIIACCVGFVLMVLLFLAFL
HRFHGLWYMKMMWAWLQAKRKPRKAPSRNICYDAFVSYSERDAYWVENLM
VQELENFNPPFKLCLHKRDFIPGKWIIDNIIDSIEKSHKTVFVLSENFVK
SEWCKYELDFSHFRLFDENNDAAILILLEPIEKKAIPQRFCKLRKIMNTK
TYLEWPMDEAQREGFWVNLRAAIKSMSLLNCENSCGSSQSESDCCVAMAS
SCSAVTKDDSVGGTASTGNLSSSFMEEIQGYDVEFDPPLESKYECPICLM
ALREAVQTPCGHRFCKACIIKSIRDAGHKCPVDNEILLENQLFPDNFAKR
EILSLMVKCPNEGCLHKMELRHLEDHQAHCEFALMDCPQCQRPFQKFHIN
IHILKDCPRRQVSCDNCAASMAFEDKEIHDQNCPLANVICEYCNTILIRE
QMPNHYDLDCPTAPIPCTFSTFGCHEKMQRNHLARHLQENTQSHMRMLA >SEQ ID NO: 151 (CER124, Protein, Artificial
Sequence, amino acids 1-22 are signal peptide)
MSKGLLLLWLVTELWWLYLTPAASEDTIIGFLGQPVTLPCHYLSWSQSRN
SMCWGKGSCPNSKCNAELLRTDGTRIISRKSTKYTLLGKVQFGEVSLTIS
NTNRGDSGVYCCRIEVPGWFNDVKKNVRLELRRATTTKKPTTTTRPTTTP
YVTTTTPELLPTTVMTTSVLPTTTPPQTLATTAFSTAVTTCPSTTPGSFS
QETTKGSAFTTESETLPASNHSQRSMMTISTDIAVLRPTGSNPGILPSTS
QLTTQKTTLTTSESLQKTTKSHQINSRQTILIIACCVGFVLMVLLFLAFL
HRFHGLWYMKMMWAWLQAKRKPRKAPSRNICYDAFVSYSERDAYWVENLM
VQELENFNPPFKLCLHKRDFIPGKWIIDNIIDSIEKSHKTVFVLSENFVK
SEWCKYELDFSHFRLFDENNDAAILILLEPIEKKAIPQRFCKLRKIMNTK
TYLEWPMDEAQREGFWVNLRAAIKSLWNKKRMRGPGKDPTRKCPDPRSAS
SPKQHPSESVYTALQRRETEVYACIENEDGSSPTAKQSPLSQERPHRFED
DGELNLVYENL >SEQ ID NO: 152 (CER125A, Protein, Artificial
Sequence, amino acids 1-22 are signal peptide)
MSKGLLLLWLVTELWWLYLTPAASEDTIIGFLGQPVTLPCHYLSWSQSRN
SMCWGKGSCPNSKCNAELLRTDGTRIISRKSTKYTLLGKVQFGEVSLTIS
NTNRGDSGVYCCRIEVPGWFNDVKKNVRLELRRATTTKKPTTTTRPTTTP
YVTTTTPELLPTTVMTTSVLPTTTPPQTLATTAFSTAVTTCPSTTPGSFS
QETTKGSAFTTESETLPASNHSQRSMMTISTDIAVLRPTGSNPGILPSTS
QLTTQKTTLTTSESLQKTTKSHQINSRQTILIIACCVGFVLMVLLFLAFL
HRFHGLWYMKMMWAWLQAKRKPRKAPSRNICYDAFVSYSERDAYWVENLM
VQELENFNPPFKLCLHKRDFIPGKWIIDNIIDSIEKSHKTVFVLSENFVK
SEWCKYELDFSHFRLFDENNDAAILILLEPIEKKAIPQRFCKLRKIMNTK
TYLEWPMDEAQREGFWVNLRAAIKSDSKAGMEEDHTYEGLDIDQTATYED
IVTLRTGEVKWSVGEHPGQE >SEQ ID NO: 153 (CER125B, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

HRFHGLWYMKMMWAWLQAKRKPRKAPSRNICYDAFVSYSERDAYWVENLM

VQELENFNPPFKLCLHKRDFIPGKWIIDNIIDSIEKSHKTVFVLSENFVK

SEWCKYELDFSHFRLFDENNDAAILILLEPIEKKAIPQRFCKLRKIMNTK

TYLEWPMDEAQREGFWVNLRAAIKSDSKAGMEEDHTYEGLDIDQTATYED

IVTL

>SEQ ID NO: 154 (Protein, Artificial Sequence,
T2A self-cleaving peptide variant)
LEGGGEGRGSLLTCGDVEENPGPR >SEQ ID NO: 155 (Protein, Artificial Sequence,
T2A self-cleaving peptide variant)
EGRGSLLTCGDVEENPGPR >SEQ ID NO: 156 (Protein, Artificial Sequence,
T2A self-cleaving peptide variant)
LEGGGEGRGSLLTCGDVEENPGP >SEQ ID NO: 157 (Protein, Artificial Sequence,
P2A self-cleaving peptide variant)
RAKRSGSGATNFSLLKQAGDVEENPGP >SEQ ID NO: 158 (Artificial Sequence, HPV16 E7
TCRβ chain-P2A-TCRα chain)
MAPGLLCWALLCLLGAGLVDAGVTQSPTHLIKTRGQQVTLRCSPKSGHDT

VSWYQQALGQGPQFIFQYYEEEERQRGNFPDRFSGHQFPNYSSELNVNAL

LLGDSALYLCASSLGWRGGRYNEQFFGPGTRLTVLEDLRNVTPPKVSLFE

PSKAEIANKQKATLVCLARGFFPDHVELSWWVNGKEVHSGVCTDPQAYKE

SNYSYCLSSRLRVSATFWHNPRNHFRCQVQFHGLSEEDKWPEGSPKPVTQ

NISAEAWGRADCGITSASYQQGVLSATILYEILLGKATLYAVLVSTLVVM

AMVKRKNSRAKRSGSGATNFSLLKQAGDVEENPGPMWGVFLLYVSMKMGG

TTGQNIDQPTEMTATEGAIVQINCTYQTSGFNGLFWYQQHAGEAPTFLSY

NVLDGLEEKGRFSSFLSRSKGYSYLLLKELQMKDSASYLCASVDGNNRLA

FGKGNQVVVIPNIQNPEPAVYQLKDPRSQDSTLCLFTDFDSQINVPKTME

SGTFITDKCVLDMKAMDSKSNGAIAWSNQTSFTCQDIFKETNATYPSSDV

PCDATLTEKSFETDMNLNFQNLLVIVLRILLLKVAGFNLLMTRLWSS

>SEQ ID NO: 159 [Protein; Artificial Sequence;
CER25; amino acids 1-22 are signal peptide]
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

LWNKKRMRGPGKDPTRKCPDPRSASSPKQHPSESVYTALQRRETEVYACI

ENEDGSSPTAKQSPLSQERPHRFEDDGELNLVYENL

>SEQ ID NO: 160 (Protein, Artificial Sequence,
HPV16 E7 TCR Vβ region)
MAPGLLCWALLCLLGAGLVDAGVTQSPTHLIKTRGQQVTLRCSPKSGHDT

VSWYQQALGQGPQFIFQYYEEEERQRGNFPDRFSGHQFPNYSSELNVNAL

LLGDSALYLCASSLGWRGGRYNEQFFGPGTRLTVL

>SEQ ID NO: 161 (Protein, Artificial Sequence,
TCR Cβ region, Cys-substituted)
EDLRNVTPPKVSLFEPSKAEIANKQKATLVCLARGFFPDHVELSWWVNGK

EVHSGVCTDPQAYKESNYSYCLSSRLRVSATFWHNPRNHFRCQVQFHGLS

EEDKWPEGSPKPVTQNISAEAWGRADCGITSASYQQGVLSATILYEILLG

KATLYAVLVSTLVVMAMVKRKNS

>SEQ ID NO: 162 (Protein, Artificial Sequence,
HPV16 E7TCR Vα region)
MWGVFLLYVSMKMGGTTGQNIDQPTEMTATEGAIVQINCTYQTSGFNGLF

WYQQHAGEAPTFLSYNVLDGLEEKGRFSSFLSRSKGYSYLLLKELQMKDS

ASYLCASVDGNNRLAFGKGNQVVVIP

>SEQ ID NO: 163 (Protein, Artificial Sequence,
TCR Cα region, Cys-substituted, LVL substituted)
NIQNPEPAVYQLKDPRSQDSTLCLFTDFDSQINVPKTMESGTFITDKCVL

DMKAMDSKSNGAIAWSNQTSFTCQDIFKETNATYPSSDVPCDATLTEKSF

ETDMNLNFQNLLVIVLRILLLKVAGFNLLMTRLWSS

>SEQ ID NO: 164 (Protein, Artificial Sequence,
CER5_T2A_HPV16_E7_TCR tandem cassette)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

KFYFHLMLLAGCIKYGRGENIYDAFVIYSSQDEDWVRNELVKNLEEGVPP

FQLCLHYRDFIPGVAIAANIIHEGFHKSRKVIVVVSQHFIQSRWCIFEYE

IAQTWQFLSSRAGIIFIVLQKVEKTLLRQQVELYRLLSRNTYLEWEDSVL

GRHIFWRRLRKALLDGKSWNPEGTVGTGCNWQEATSILEGGGEGRGSLLT

CGDVEENPGPMAPGLLCWALLCLLGAGLVDAGVTQSPTHLIKTRGQQVTL

RCSPKSGHDTVSWYQQALGQGPQFIFQYYEEEERQRGNFPDRFSGHQFPN

YSSELNVNALLLGDSALYLCASSLGWRGGRYNEQFFGPGTRLTVLEDLRN

VTPPKVSLFEPSKAEIANKQKATLVCLARGFFPDHVELSWWVNGKEVHSG

VCTDPQAYKESNYSYCLSSRLRVSATFWHNPRNHFRCQVQFHGLSEEDKW

PEGSPKPVTQNISAEAWGRADCGITSASYQQGVLSATILYEILLGKATLY

AVLVSTLVVMAMVKRKNSRAKRSGSGATNFSLLKQAGDVEENPGPMWGVF

LLYVSMKMGGTTGQNIDQPTEMTATEGAIVQINCTYQTSGFNGLFWYQQH

AGEAPTFLSYNVLDGLEEKGRFSSFLSRSKGYSYLLLKELQMKDSASYLC

ASVDGNNRLAFGKGNQVVVIPNIQNPEPAVYQLKDPRSQDSTLCLFTDFD

-continued

SQINVPKTMESGTFITDKCVLDMKAMDSKSNGAIAWSNQTSFTCQDIFKE

TNATYPSSDVPCDATLTEKSFETDMNLNFQNLLVIVLRILLLKVAGFNLL

MTLRLWSS

>SEQ ID NO: 165 (Protein, Artificial Sequence,
CER19_T2A_HPV16_E7_TCR tandem cassette)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

TKFRGFCFICYKTAQRLVFKDHPQGTEPDMYKYDAYLCFSSKDFTWVQNA

LLKHLDTQYSDQNRFNLCFEERDFVPGENRIANIQDAIWNSRKIVCLVSR

HFLRDGWCLEAFSYAQGRCLSDLNSALIMVVGSLSQYQLMKHQSIRGFV

QKQQYLRWPEDFQDVGWFLHKLSQQILKKEKEKKKDNNIPLQTVATISLE

GGGEGRGSLLTCGDVEENPGPMAPGLLCWALLCLLGAGLVDAGVTQSPTH

LIKTRGQQVTLRCSPKSGHDTVSWYQQALGQGPQFIFQYYEEEERQRGNF

PDRFSGHQFPNYSSELNVNALLLGDSALYLCASSLGWRGGRYNEQFFGPG

TRLTVLEDLRNVTPPKVSLFEPSKAEIANKQKATLVCLARGFFPDHVELS

WWVNGKEVHSGVCTDPQAYKESNYSYCLSSRLVSATFWHNPRNHFRCQV

QFHGLSEEDKWPEGSPKPVTQNISAEAWGRADCGITSASYQQGVLSATIL

YEILLGKATLYAVLVSTLVVMAMVKRKNSRAKRSGSGATNFSLLKQAGDV

EENPGPMWGVFLLYVSMKMGGTTGQNIDQPTEMTATEGAIVQINCTYQTS

GFNGLFWYQQHAGEAPTFLSYNVLDGLEEKGRFSSFLSRSKGYSYLLLKE

LQMKDSASYLCASVDGNNRLAFGKGNQVVVIPNIQNPEPAVYQLKDPRSQ

DSTLCLFTDFDSQINVPKTMESGTFITDKCVLDMKAMDSKSNGAIAWSNQ

TSFTCQDIFKETNATYPSSDVPCDATLTEKSFETDMNLNFQNLLVIVLRI

LLLKVAGFNLLMTLRLWSS

>SEQ ID NO: 166 (Protein, Artificial Sequence,
CER21_T2A_HPV16_E7_TCR tandem cassette)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

HHLFYWDVWFIYNVCLAKVKGYRSLSTSQTFYDAYISYDTKDASVTDWVI

NELRYHLEESRDKNVLLCLEERDWDPGLAIIDNLMQSINQSKKTVFVLTK

KYAKSWNFKTAFYLALQRLMDENMDVIIFILLEPVLQHSQYLRLRQRICK

SSILQWPDNPKAEGLFWQTLRNVVLTENDSRYNNMYVDSIKQYLEGGGEG

RGSLLTCGDVEENPGPMAPGLLCWALLCLLGAGLVDAGVTQSPTHLIKTR

GQQVTLRCSPKSGHDTVSWYQQALGQGPQFIFQYYEEEERQRGNFPDRFS

-continued

GHQFPNYSSELNVNALLLGDSALYLCASSLGWRGGRYNEQFFGPGTRLTV

LEDLRNVTPPKVSLFEPSKAEIANKQKATLVCLARGFFPDHVELSWWVNG

KEVHSGVCTDPQAYKESNYSYCLSSRLVSATFWHNPRNHFRCQVQFHGL

SEEDKWPEGSPKPVTQNISAEAWGRADCGITSASYQQGVLSATILYEILL

GKATLYAVLVSTLVVMAMVKRKNSRAKRSGSGATNFSLLKQAGDVEENPG

PMWGVFLLYVSMKMGGTTGQNIDQPTEMTATEGAIVQINCTYQTSGFNGL

FWYQQHAGEAPTFLSYNVLDGLEEKGRFSSFLSRSKGYSYLLLKELQMKD

SASYLCASVDGNNRLAFGKGNQVVVIPNIQNPEPAVYQLKDPRSQDSTLC

LFTDFDSQINVPKTMESGTFITDKCVLDMKAMDSKSNGAIAWSNQTSFTC

QDIFKETNATYPSSDVPCDATLTEKSFETDMNLNFQNLLVIVLRILLLKV

AGFNLLMTLRLWSS

>SEQ ID NO: 167 (Protein, Artificial Sequence,
CER25_T2A_HPV16_E7_TCR tandem cassette)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

LWNKKRMRGPGKDPTRKCPDPRSASSPKQHPSESVYTALQRRETEVYACI

ENEDGSSPTAKQSPLSQERPHRFEDDGELNLVYENLLEGGGEGRGSLLTC

GDVEENPGPMAPGLLCWALLCLLGAGLVDAGVTQSPTHLIKTRGQQVTLR

CSPKSGHDTVSWYQQALGQGPQFIFQYYEEEERQRGNFPDRFSGHQFPNY

SSELNVNALLLGDSALYLCASSLGWRGGRYNEQFFGPGTRLTVLEDLRNV

TPPKVSLFEPSKAEIANKQKATLVCLARGFFPDHVELSWWVNGKEVHSGV

CTDPQAYKESNYSYCLSSRLVSATFWHNPRNHFRCQVQFHGLSEEDKWP

EGSPKPVTQNISAEAWGRADCGITSASYQQGVLSATILYEILLGKATLYA

VLVSTLVVMAMVKRKNSRAKRSGSGATNFSLLKQAGDVEENPGPMWGVFL

LYVSMKMGGTTGQNIDQPTEMTATEGAIVQINCTYQTSGFNGLFWYQQHA

GEAPTFLSYNVLDGLEEKGRFSSFLSRSKGYSYLLLKELQMKDSASYLCA

SVDGNNRLAFGKGNQVVVIPNIQNPEPAVYQLKDPRSQDSTLCLFTDFDS

QINVPKTMESGTFITDKCVLDMKAMDSKSNGAIAWSNQTSFTCQDIFKET

NATYPSSDVPCDATLTEKSFETDMNLNFQNLLVIVLRILLLKVAGFNLLM

TLRLWSS

>SEQ ID NO: 168 (Protein, Artificial Sequence,
CER27_T2A_HPV16_E7_TCR tandem cassette)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

HRFHGLWYMKMMWAWLQAKRKPRKAPSRNICYDAFVSYSERDAYWVENLM

-continued
VQELENFNPPPFKLCLHKRDFIPGKWIIDNIIDSIEKSHKTVFVLSENFVK

SEWCKYELDFSHFRLFDENNDAAILILLEPIEKKAIPQRFCKLRKIMNTK

TYLEWPMDEAQREGFWVNLRAAIKSLEGGGEGRGSLLTCGDVEENPGPMA

PGLLCWALLCLLGAGLVDAGVTQSPTHLIKTRGQQVTLRCSPKSGHDTVS

WYQQALGQGPQFIFQYYEEEERQRGNFPDRFSGHQFPNYSSELNVNALLL

GDSALYLCASSLGWRGGRYNEQFFGPGTRLTVLEDLRNVTPPKVSLFEPS

KAEIANKQKATLVCLARGFFPDHVELSWWVNGKEVHSGVCTDPQAYKESN

YSYCLSSRLRVSATFWHNPRNHFRCQVQFHGLSEEDKWPEGSPKPVTQNI

SAEAWGRADCGITSASYQQGVLSATILYEILLGKATLYAVLVSTLVVMAM

VKRKNSRAKRSGSGATNFSLLKQAGDVEENPGPMWGVFLLYVSMKMGGTT

GQNIDQPTEMTATEGAIVQINCTYQTSGFNGLFWYQQHAGEAPTFLSYNV

LDGLEEKGRFSSFLSRSKGYSYLLLKELQMKDSASYLCASVDGNNRLAFG

KGNQVVVIPNIQNPEPAVYQLKDPRSQDSTLCLFTDFDSQINVPKTMESG

TFITDKCVLDMKAMDSKSNGAIAWSNQTSFTCQDIFKETNATYPSSDVPC

DATLTEKSFETDMNLNFQNLLVIVLRILLLKVAGFNLLMTLRLWSS

>SEQ ID NO: 169 (Protein, Artificial Sequence,
CER29_T2A_HPV16_E7_TCR tandem cassette)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

MSLLNCENSCGSSQSESDCCVAMASSCSAVTKDDSVGGTASTGNLSSSFM

EEIQGYDVEFDPPLESKYECPICLMALREAVQTPCGHRFCKACIIKSIRD

AGHKCPVDNEILLENQLFPDNFAKREILSLMVKCPNEGCLHKMELRHLED

HQAHCEFALMDCPQCQRPFQKFHINIHILKDCPRRQVSCDNCAASMAFED

KEIHDQNCPLANVICEYCNTILIREQMPNHYDLDCPTAPIPCTFSTFGCH

EKMQRNHLARHLQENTQSHMRMLALEGGGEGRGSLLTCGDVEENPGPMAP

GLLCWALLCLLGAGLVDAGVTQSPTHLIKTRGQQVTLRCSPKSGHDTVSW

YQQALGQGPQFIFQYYEEEERQRGNFPDRFSGHQFPNYSSELNVNALLLG

DSALYLCASSLGWRGGRYNEQFFGPGTRLTVLEDLRNVTPPKVSLFEPSK

AEIANKQKATLVCLARGFFPDHVELSWWVNGKEVHSGVCTDPQAYKESNY

SYCLSSRLRVSATFWHNPRNHFRCQVQFHGLSEEDKWPEGSPKPVTQNIS

AEAWGRADCGITSASYQQGVLSATILYEILLGKATLYAVLVSTLVVMAMV

KRKNSRAKRSGSGATNFSLLKQAGDVEENPGPMWGVFLLYVSMKMGGTTG

QNIDQPTEMTATEGAIVQINCTYQTSGFNGLFWYQQHAGEAPTFLSYNVL

DGLEEKGRFSSFLSRSKGYSYLLLKELQMKDSASYLCASVDGNNRLAFGK

GNQVVVIPNIQNPEPAVYQLKDPRSQDSTLCLFTDFDSQINVPKTMESGT

FITDKCVLDMKAMDSKSNGAIAWSNQTSFTCQDIFKETNATYPSSDVPCD

ATLTEKSFETDMNLNFQNLLVIVLRILLLKVAGFNLLMTLRLWSS

>SEQ ID NO: 170 (Protein, Artificial Sequence,
CER31_T2A_HPV16_E7_TCR tandem cassette)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

MESSKKMDSPGALQTNPPLKLHTDRSAGTPVFVPEQGGYKEKFVKTVEDK

YKCEKCHLVLCSPKQTECGHRFCESCMAALLSSSSPKCTACQESIVKDKV

FKDNCCKREILALQIYCRNESRGCAEQLMLGHLLVHLKNDCHFEELPCVR

PDCKEKVLRKDLRDHVEKACKYREATCSHCKSQVPMIALQKHEDTDCPCV

VVSCPHKCSVQTLLRSELSAHLSECVNAPSTCSFKRYGCVFQGTNQQIKA

HEASSAVQHVNLLKEWSNSLEKKVLEGGGEGRGSLLTCGDVEENPGPMAP

GLLCWALLCLLGAGLVDAGVTQSPTHLIKTRGQQVTLRCSPKSGHDTVSW

YQQALGQGPQFIFQYYEEEERQRGNFPDRFSGHQFPNYSSELNVNALLLG

DSALYLCASSLGWRGGRYNEQFFGPGTRLTVLEDLRNVTPPKVSLFEPSK

AEIANKQKATLVCLARGFFPDHVELSWWVNGKEVHSGVCTDPQAYKESNY

SYCLSSRLRVSATFWHNPRNHFRCQVQFHGLSEEDKWPEGSPKPVTQNIS

AEAWGRADCGITSASYQQGVLSATILYEILLGKATLYAVLVSTLVVMAMV

KRKNSRAKRSGSGATNFSLLKQAGDVEENPGPMWGVFLLYVSMKMGGTTG

QNIDQPTEMTATEGAIVQINCTYQTSGFNGLFWYQQHAGEAPTFLSYNVL

DGLEEKGRFSSFLSRSKGYSYLLLKELQMKDSASYLCASVDGNNRLAFGK

GNQVVVIPNIQNPEPAVYQLKDPRSQDSTLCLFTDFDSQINVPKTMESGT

FITDKCVLDMKAMDSKSNGAIAWSNQTSFTCQDIFKETNATYPSSDVPCD

ATLTEKSFETDMNLNFQNLLVIVLRILLLKVAGFNLLMTLRLWSS

>SEQ ID NO: 171 (Protein, Homo sapiens, truncated
MyD88 signaling domain without TIR domain)
MAAGGPGAGSAAPVSSTSSLPLAALNMRVRRRLSLFLNVRTQVAADWTAL

AEEMDFEYLEIRQLETQADPTGRLLDAWQGRPGASVGRLLELLTKLGRDD

VLLELGPSIEEDCQKYILKQQQEEAEKPLQVAAVDSSVPRTAELAGITTL

DDPLG

>SEQ ID NO: 172 (Protein, Homo sapiens, MyD88
signaling domain)
MAAGGPGAGSAAPVSSTSSLPLAALNMRVRRRLSLFLNVRTQVAADWTAL

AEEMDFEYLEIRQLETQADPTGRLLDAWQGRPGASVGRLLELLTKLGRDD

VLLELGPSIEEDCQKYILKQQQEEAEKPLQVAAVDSSVPRTAELAGITTL

DDPLGHMPERFDAFICYCPSDIQFVQEMIRQLEQTNYRLKLCVSDRDVLP

GTCVWSIASELIEKRCRRMVVVVSDDYLQSKECDFQTKFALSLSPGAHQK

RLIPIKYKAMKKEFPSILRFITVCDYTNPCTKSWFWTRLAKALSLP

>SEQ ID NO: 173 (CER119A, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

SYLDLPWYLRMVCQWTQTRRRARNIPLEELQRNLQFHAFISYSGHDSFWV

KNELLPNLEKEGMQICLHERNFVPGKSIVENIITCIEKSYKSIFVLSPNF

VQSEWCHYELYFAHHNLFHEGSNSLILILLEPIPQYSIPSSYHKLKSLMA

RRTYLEWPKEKSKRGLFWANLRAAINIKLTEQAKKDSKAGMEEDHTYEGL

DIDQTATYEDIVTLRTGEVKWSVGEHPGQE

>SEQ ID NO: 174 (CER126, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

HRFHGLWYMKMMWAWLQAKRKPRKAPSRNICYDAFVSYSERDAYWVENLM

VQELENFNPPFKLCLHKRDFIPGKWIIDNIIDSIEKSHKTVFVLSENFVK

SEWCKYELDFSHFRLFDENNDAAILILLEPIEKKAIPQRFCKLRKIMNTK

TYLEWPMDEAQREGFWVNLRAAIKSMAAASVTPPGSLELLQPGFSKTLLG

TKLEAKYLCSACRNVLRRPFQAQCGHRYCSFCLASILSSGPQNCAACVHE

GIYEEGISILESSSAFPDNAARREVESLPAVCPSDGCTWKGTLKEYESCH

EGRCPLMLTECPACKGLVRLGEKERHLEHECPERSLSCRHCRAPCCGADV

KAHHEVCPKFPLTCDGCGKKKIPREKFQDHVKTCGKCRVPCRFHAIGCLE

TVEGEKQQEHEVQWLREHLAMLLSSVLEAKPLLGDQSHAGSELLQRCESL

EKKTATFENIVCVLNREVERVAMTAEAC

>SEQ ID NO: 175 (CER127, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

MAAASVTPPGSLELLQPGFSKTLLGTKLEAKYLCSACRNVLRRPFQAQCG

HRYCSFCLASILSSGPQNCAACVHEGIYEEGISILESSSAFPDNAARREV

ESLPAVCPSDGCTWKGTLKEYESCHEGRCPLMLTECPACKGLVRLGEKER

HLEHECPERSLSCRHCRAPCCGADVKAHHEVCPKFPLTCDGCGKKKIPRE

KFQDHVKTCGKCRVPCRFHAIGCLETVEGEKQQEHEVQWLREHLAMLLSS

VLEAKPLLGDQSHAGSELLQRCESLEKKTATFENIVCVLNREVERVAMTA

EACHRFHGLWYMKMMWAWLQAKRKPRKAPSRNICYDAFVSYSERDAYWVE

NLMVQELENFNPPFKLCLHKRDFIPGKWIIDNIIDSIEKSHKTVFVLSEN

FVKSEWCKYELDFSHFRLFDENNDAAILILLEPIEKKAIPQRFCKLRKIM

NTKTYLEWPMDEAQREGFWVNLRAAIKS

>SEQ ID NO: 176 (CER128, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

MAAASVTPPGSLELLQPGFSKTLLGTKLEAKYLCSACRNVLRRPFQAQCG

HRYCSFCLASILSSGPQNCAACVHEGIYEEGISILESSSAFPDNAARREV

ESLPAVCPSDGCTWKGTLKEYESCHEGRCPLMLTECPACKGLVRLGEKER

HLEHECPERSLSCRHCRAPCCGADVKAHHEVCPKFPLTCDGCGKKKIPRE

KFQDHVKTCGKCRVPCRFHAIGCLETVEGEKQQEHEVQWLREHLAMLLSS

VLEAKPLLGDQSHAGSELLQRCESLEKKTATFENIVCVLNREVERVAMTA

EACHHLFYWDVWFIYNVCLAKVKGYRSLSTSQTFYDAYISYDTKDASVTD

WVINELRYHLEESRDKNVLLCLEERDWDPGLAIIDNLMQSINQSKKTVFV

LTKKYAKSWNFKTAFYLALQRLMDENMDVIIFILLEPVLQHSQYLRLRQR

ICKSSILQWPDNPKAEGLFWQTLRNVVLTENDSRYNNMYVDSIKQY

>SEQ ID NO: 177 (CER129, Protein, Artificial
Sequence, amino acids 1-22 are signal peptide)
MSKGLLLLWLVTELWWLYLTPAASEDTIIGFLGQPVTLPCHYLSWSQSRN

SMCWGKGSCPNSKCNAELLRTDGTRIISRKSTKYTLLGKVQFGEVSLTIS

NTNRGDSGVYCCRIEVPGWFNDVKKNVRLELRRATTTKKPTTTTRPTTTP

YVTTTTPELLPTTVMTTSVLPTTTPPQTLATTAFSTAVTTCPSTTPGSFS

QETTKGSAFTTESETLPASNHSQRSMMTISTDIAVLRPTGSNPGILPSTS

QLTTQKTTLTTSESLQKTTKSHQINSRQTILIIACCVGFVLMVLLFLAFL

HHLFYWDVWFIYNVCLAKVKGYRSLSTSQTFYDAYISYDTKDASVTDWVI

NELRYHLEESRDKNVLLCLEERDWDPGLAIIDNLMQSINQSKKTVFVLTK

KYAKSWNFKTAFYLALQRLMDENMDVIIFILLEPVLQHSQYLRLRQRICK

SSILQWPDNPKAEGLFWQTLRNVVLTENDSRYNNMYVDSIKQYMAAASVT

PPGSLELLQPGFSKTLLGTKLEAKYLCSACRNVLRRPFQAQCGHRYCSFC

LASILSSGPQNCAACVHEGIYEEGISILESSSAFPDNAARREVESLPAVC

PSDGCTWKGTLKEYESCHEGRCPLMLTECPACKGLVRLGEKERHLEHECP

ERSLSCRHCRAPCCGADVKAHHEVCPKFPLTCDGCGKKKIPREKFQDHVK

TCGKCRVPCRFHAIGCLETVEGEKQQEHEVQWLREHLAMLLSSVLEAKPL

LGDQSHAGSELLQRCESLEKKTATFENIVCVLNREVERVAMTAEAC

The invention claimed is:

1. A chimeric engulfment receptor (CER) comprising a single chain chimeric protein, the single chain chimeric protein comprising:
   an extracellular domain comprising a binding domain that binds to phosphatidylserine (PtdSer);
   an engulfment signaling domain that comprises a toll-like receptor (TLR) signaling domain, a Traf2 signaling domain, or a Traf3 signaling domain; and
   a transmembrane domain positioned between and connecting the extracellular domain and the engulfment signaling domain.

2. The CER of claim 1, wherein the binding domain comprises an scFv specific to PtdSer, or a PtdSer binding domain from Tim1, Tim4, Tim3, stabilin-2, receptor for advanced glycation end products (RAGE), brain-specific angiogenesis inhibitor 1 (BAI1), Milk Fat Globule-EGF Factor 8 Protein (MFG-E8), Growth Arrest Specific 6 (GAS6), protein S, protein C, Factor II, Factor VII, Factor IX, Factor X, Beta 2-glycoprotein I, α5β3 integrin and other integrins, CR3 complement receptor, CR4 complement receptor, CD14, CD93, annexin V, phosphatidyl serine receptor (PSr), prothrombin, or a scavenger receptor.

3. The CER of claim 2, wherein the binding domain comprises a TIM1 domain comprising the amino acid sequence of SEQ ID NO:2 or amino acids 21-290 of SEQ ID NO:2, a TIM4 domain comprising the amino acid sequence of SEQ ID NO:3 or amino acids 25-314 of SEQ ID NO:3, a Tim3 domain comprising the amino acid sequence of SEQ ID NO:4 or amino acids 22-202 of SEQ ID NO:4, a FA58C2 domain comprising the amino acid sequence of SEQ ID NO:5, a GAS6 domain comprising the amino acid sequence of SEQ ID NO:6 or amino acids 31-94 of SEQ ID NO:6, a protein S binding domain comprising the amino acid sequence of SEQ ID NO:7 or amino acids 25-87 of SEQ ID:7, or a BAH domain comprising the amino acid sequence of SEQ ID NO:8.

4. The CER of claim 1, wherein the extracellular domain further comprises an extracellular spacer domain positioned between the binding domain and transmembrane domain.

5. The CER of claim 4, wherein the extracellular spacer domain comprises an immunoglobulin hinge region, a hinge region of a type 1 membrane protein, a stalk region of a type II C-lectin, an immunoglobulin constant domain, a juxtamembrane region of a toll-like receptor, or a fragment thereof.

6. The CER of claim 5, wherein the extracellular spacer domain comprises:
  (a) an IgG1 hinge region, IgG2 hinge region, IgG3 hinge region, IgG4 hinge region, IgA hinge region, or IgD hinge region;
  (b) a modified IgG4 hinge region comprising the amino acid sequence of SEQ ID NO:16;
  (c) a TLR1 juxtamembrane region, TLR2 juxtamembrane region, TLR3 juxtamembrane region, TLR4 juxtamembrane region, TLR5 juxtamembrane region, TLR6 juxtamembrane region, TLR7 juxtamembrane region, TLR8 juxtamembrane region, or TLR9 juxtamembrane region; or
  (d) a TLR4 juxtamembrane region comprising the amino acid sequence of SEQ ID NO:17.

7. The CER of claim 1, wherein the transmembrane domain comprises a Tim1 transmembrane domain, Tim4 transmembrane domain, Tim3 transmembrane domain, FcγR1 transmembrane domain, FcγR2A transmembrane domain, FcγR2B2 transmembrane domain, FcγR2C transmembrane domain, FcγR3A transmembrane domain, FcER1 transmembrane domain, FcaR1 transmembrane domain, CD8a transmembrane domain, CD28 transmembrane domain, MERTK transmembrane domain, Axl transmembrane domain, MRC1 transmembrane domain, Tyro3 transmembrane domain, BAH transmembrane domain, CD4 transmembrane domain, DAP12 transmembrane domain, TLR1 transmembrane domain, TLR2 transmembrane domain, TLR3 transmembrane domain, TLR4 transmembrane domain, TLR5 transmembrane domain, TLR6 transmembrane domain, TLR7 transmembrane domain, TLR8 transmembrane domain, or TLR9 transmembrane domain.

8. The CER of claim 7, wherein the transmembrane domain comprises a Tim1 transmembrane domain comprising the amino acid sequence of SEQ ID NO:18, a Tim4 transmembrane domain comprising the amino acid sequence of SEQ ID NO:19, an FcγRI transmembrane domain comprising the amino acid sequence of SEQ ID NO:20, a CD8a transmembrane domain comprising the amino acid sequence of SEQ ID NO:22, a MERTK transmembrane domain comprising the amino acid sequence of SEQ ID NO:23, an Axl transmembrane domain comprising the amino acid sequence of SEQ ID NO:24, a MRC1 transmembrane domain comprising the amino acid sequence of SEQ ID NO:30, a Tyro3 transmembrane domain comprising the amino acid sequence of SEQ ID NO:25, a CD28 transmembrane domain of SEQ ID NO:26, a BAI1 transmembrane domain of SEQ ID NO:29, a CD4 transmembrane domain comprising the amino acid sequence of SEQ ID NO:27, a FcεRIγ transmembrane domain comprising the amino acid sequence of SEQ ID NO:21, a DAP12 transmembrane domain comprising the amino acid sequence of SEQ ID NO:28, a TLR1 transmembrane domain comprising the amino acid sequence of SEQ ID NO:31, a TLR2 transmembrane domain comprising the amino acid sequence of SEQ ID NO:32, a TLR3 transmembrane domain comprising the amino acid sequence of SEQ ID NO:33, a TLR4 transmembrane domain comprising the amino acid sequence of SEQ ID NO:34, a TLR5 transmembrane domain comprising the amino acid sequence of SEQ ID NO:35, a TLR6 transmembrane domain comprising the amino acid sequence of SEQ ID NO:36, a TLR7 transmembrane domain comprising the amino acid sequence of SEQ ID NO:37, a TLR8 transmembrane domain comprising the amino acid sequence of SEQ ID NO:38, or a TLR9 transmembrane domain comprising the amino acid sequence of SEQ ID NO:39.

9. The CER of claim 1, wherein the TLR signaling domain is a TLR1 signaling domain, TLR2 signaling domain, TLR3 signaling domain, TLR4 signaling domain, TLR5 signaling domain, TLR6 signaling domain, TLR7 signaling domain, TLR8 signaling domain, or TLR9 signaling domain.

10. The CER of claim 1, wherein the engulfment signaling domain comprises a TLR1 signaling domain comprising the amino acid sequence of SEQ ID NO:48, a TLR2 signaling domain comprising the amino acid sequence of SEQ ID NO:49, a TLR3 signaling domain comprising the amino acid sequence of SEQ ID NO:50, a TLR4 signaling domain comprising the amino acid sequence of SEQ ID NO:51, a TLR5 signaling domain comprising the amino acid sequence of SEQ ID NO:52, a TLR6 signaling domain comprising the amino acid sequence of SEQ ID NO:53, a TLR7 signaling domain comprising the amino acid sequence of SEQ ID NO:54, a TLR8 signaling domain comprising the amino acid sequence of SEQ ID NO:55, a TLR9 signaling domain comprising the amino acid sequence of SEQ ID NO:56, a Traf2 signaling domain comprising the amino acid sequence of SEQ ID NO:72, or a Traf3 signaling domain comprising the amino acid sequence of SEQ ID NO:73.

11. The CER of claim 1, wherein signaling by the engulfment signaling domain results in expression of at least one of an inflammatory cytokine, an inflammatory chemokine, or a co-stimulatory cell surface marker.

12. The CER of claim 11, wherein the inflammatory cytokine is TNFα, IL-1, IL-6, IL-12, or IL-23; the inflammatory chemokine is CCL5 (RANTES), CXCL9, or CXCL10; and the co-stimulatory cell surface marker is CD80, CD86, HLA-DR, CD40, HVEM, or 4-1BBL; or any combination thereof.

13. The CER of claim 1, wherein the engulfment signaling domain comprises a primary engulfment signaling domain and a secondary engulfment signaling domain, wherein the primary engulfment signaling domain is a TLR signaling domain, a Traf2 signaling domain, or a Traf3 signaling domain.

14. The CER of claim 13, wherein the secondary engulfment signaling domain is a FcγR1 signaling domain, FcγR2A signaling domain, FcγR2B2 signaling domain, FcγR2C signaling domain, FcγR3A signaling domain, FcER1 signaling domain, FcaR1 signaling domain, BAFF-R signaling domain, DAP12 signaling domain, NFAM1 signaling domain, CD79b signaling domain, TLR1 signaling domain, TLR2 signaling domain, TLR3 signaling domain, TLR4 signaling domain, TLR5 signaling domain, TLR6 signaling domain, TLR7 signaling domain, TLR8 signaling domain, TLR9 signaling domain, Traf2 signaling domain, or Traf3 signaling domain.

15. The CER of claim 14, wherein the secondary engulfment signaling domain is a FcγR1 signaling domain comprising the amino acid sequence of SEQ ID NO:63, an FcγR2A signaling domain comprising the amino acid sequence of SEQ ID NO:64, an FcγR2C signaling domain comprising the amino acid sequence of SEQ ID NO:65, an FcγR3A signaling domain comprising the amino acid sequence of SEQ ID NO:66, a FcεRIγ signaling domain comprising the amino acid sequence of SEQ ID NO:62, a BAFF-R signaling domain comprising the amino acid sequence of SEQ ID NO:67, a DAP12 signaling domain comprising the amino acid sequence of SEQ ID NO:68, a NFAM1 signaling domain comprising the amino acid sequence of SEQ ID NO:69, a truncated NFAM1 signaling domain comprising the amino acid sequence of SEQ ID NO:70, a CD79b signaling domain comprising the amino acid sequence of SEQ ID NO:71, a TLR1 signaling domain comprising the amino acid sequence of SEQ ID NO:48, a TLR2 signaling domain comprising the amino acid sequence of SEQ ID NO:49, a TLR3 signaling domain comprising the amino acid sequence of SEQ ID NO:50, a TLR4 signaling domain comprising the amino acid sequence of SEQ ID NO:51, a TLR5 signaling domain comprising the amino acid sequence of SEQ ID NO:52, a TLR6 signaling domain comprising the amino acid sequence of SEQ ID NO:53, a TLR7 signaling domain comprising the amino acid sequence of SEQ ID NO:54, a TLR8 signaling domain comprising the amino acid sequence of SEQ ID NO:55, a TLR9 signaling domain comprising the amino acid sequence of SEQ ID NO:56, a Traf2 signaling domain comprising the amino acid sequence of SEQ ID NO:72, or a Traf3 signaling domain comprising the amino acid sequence of SEQ ID NO:73.

16. The CER of claim 14, wherein the primary engulfment signaling domain is a TLR1 signaling domain, TLR2 signaling domain, TLR3 signaling domain, TLR4 signaling domain, TLR5 signaling domain, TLR6 signaling domain, TLR7 signaling domain, TLR8 signaling domain, or TLR9 signaling domain and the secondary engulfment signaling domain is a Traf2 signaling domain, or a Traf3 signaling domain.

17. The CER of claim 1, wherein the CER comprises a TLR transmembrane domain and a TLR signaling domain, wherein the TLR transmembrane domain and TLR signaling domain are both derived from the same TLR.

18. The CER of claim 17, wherein the CER comprises an extracellular spacer domain positioned between the binding domain and TLR transmembrane domain, and the extracellular spacer domain comprises a TLR juxtamembrane region that is derived from the same TLR as the TLR transmembrane domain and TLR signaling domain.

19. A nucleic acid molecule encoding at least one CER according to claim 1.

20. A vector comprising a nucleic acid molecule according to claim 19.

21. A host cell comprising a vector according to claim 20.

22. The host cell according to claim 21, wherein the host cell is a T cell, a natural killer cell, a B cell, a lymphoid precursor cell, an antigen presenting cell, a myeloid precursor cell, or a mature myeloid cell.

23. A population cells comprising host cells according to claim 21.

24. A pharmaceutical composition comprising a host cell according to claim 21, and a pharmaceutically acceptable carrier.

25. The host cell of claim 22, wherein the host cell is a CD4$^+$ T cell, CD8$^+$ T cell, naïve T cell, central memory T cell, effector memory T cell, virus-specific T cell, mucosal-associated invariant T cell, γδ T cell, tissue resident T cell, or natural killer T cell.

26. The host cell of claim 22, wherein the host cell is a common lymphocyte precursor cell.

27. The host cell of claim 22, wherein the host cell is a dendritic cell or a Langerhans cell.

\* \* \* \* \*

SEQUENCE LISTING

<160> NUMBER OF SEQ ID NOS: 177

<210> SEQ ID NO 1
<211> LENGTH: 292
<212> TYPE: PRT
<213> ORGANISM: Homo sapiens
<220> FEATURE:
<223> OTHER INFORMATION: FcgammaRI binding domain
<220> FEATURE:
<221> NAME/KEY: sig_peptide
<222> LOCATION: 1...15

<400> SEQUENCE: 1

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His
    290

<210> SEQ ID NO 2
<211> LENGTH: 290
<212> TYPE: PRT
<213> ORGANISM: Homo sapiens
<220> FEATURE:
<223> OTHER INFORMATION: Tim1 binding domain -continued

```
<220> FEATURE:
<221> NAME/KEY: sig_peptide
<222> LOCATION: 1...20

<400> SEQUENCE: 2

Met His Pro Gln Val Val Ile Leu Ser Leu Ile Leu His Leu Ala Asp
1               5                   10                  15

Ser Val Ala Gly Ser Val Lys Val Gly Glu Ala Gly Pro Ser Val
            20                  25                  30

Thr Leu Pro Cys His Tyr Ser Gly Ala Val Thr Ser Met Cys Trp Asn
                35                  40                  45

Arg Gly Ser Cys Ser Leu Phe Thr Cys Gln Asn Gly Ile Val Trp Thr
            50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
                100                 105                 110

Phe Asn Asp Met Lys Ile Thr Val Ser Leu Glu Ile Val Pro Pro Lys
                115                 120                 125

Val Thr Thr Thr Pro Ile Val Thr Thr Val Pro Thr Val Thr Thr Val
130                 135                 140

Arg Thr Ser Thr Thr Val Pro Thr Thr Thr Thr Val Pro Thr Thr Thr
145                 150                 155                 160

Val Pro Thr Thr Met Ser Ile Pro Thr Thr Thr Val Leu Thr Thr
                165                 170                 175

Met Thr Val Ser Thr Thr Thr Ser Val Pro Thr Thr Thr Ser Ile Pro
                180                 185                 190

Thr Thr Thr Ser Val Pro Val Thr Thr Val Ser Thr Phe Val Pro
                195                 200                 205

Pro Met Pro Leu Pro Arg Gln Asn His Glu Pro Val Ala Thr Ser Pro
                210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
                260                 265                 270

Gln Thr Gln Leu Phe Leu Glu His Ser Leu Leu Thr Ala Asn Thr Thr
                275                 280                 285

Lys Gly
    290

<210> SEQ ID NO 3
<211> LENGTH: 314
<212> TYPE: PRT
<213> ORGANISM: Homo sapiens
<220> FEATURE:
<223> OTHER INFORMATION: Tim4 binding domain
<220> FEATURE:
<221> NAME/KEY: sig_peptide
<222> LOCATION: 1...24

<400> SEQUENCE: 3

Met Ser Lys Glu Pro Leu Ile Leu Trp Leu Met Ile Glu Phe Trp Trp
1               5                   10                  15
```

-continued

Leu Tyr Leu Thr Pro Val Thr Ser Glu Thr Val Val Thr Glu Val Leu
            20                  25                  30

Gly His Arg Val Thr Leu Pro Cys Leu Tyr Ser Ser Trp Ser His Asn
        35                  40                  45

Ser Asn Ser Met Cys Trp Gly Lys Asp Gln Cys Pro Tyr Ser Gly Cys
50                  55                  60

Lys Glu Ala Leu Ile Arg Thr Asp Gly Met Arg Val Thr Ser Arg Lys
65                  70                  75                  80

Ser Ala Lys Tyr Arg Leu Gln Gly Thr Ile Pro Arg Gly Asp Val Ser
                85                  90                  95

Leu Thr Ile Leu Asn Pro Ser Glu Ser Asp Ser Gly Val Tyr Cys Cys
            100                 105                 110

Arg Ile Glu Val Pro Gly Trp Phe Asn Asp Val Lys Ile Asn Val Arg
        115                 120                 125

Leu Asn Leu Gln Arg Ala Ser Thr Thr Thr His Arg Thr Ala Thr Thr
130                 135                 140

Thr Thr Arg Arg Thr Thr Thr Thr Ser Pro Thr Thr Thr Arg Gln Met
145                 150                 155                 160

Thr Thr Thr Pro Ala Ala Leu Pro Thr Thr Val Val Thr Thr Pro Asp
                165                 170                 175

Leu Thr Thr Gly Thr Pro Leu Gln Met Thr Thr Ile Ala Val Phe Thr
            180                 185                 190

Thr Ala Asn Thr Cys Leu Ser Leu Thr Pro Ser Thr Leu Pro Glu Glu
        195                 200                 205

Ala Thr Gly Leu Leu Thr Pro Glu Pro Ser Lys Glu Gly Pro Ile Leu
210                 215                 220

Thr Ala Glu Ser Glu Thr Val Leu Pro Ser Asp Ser Trp Ser Ser Val
225                 230                 235                 240

Glu Ser Thr Ser Ala Asp Thr Val Leu Leu Thr Ser Lys Glu Ser Lys
                245                 250                 255

Val Trp Asp Leu Pro Ser Thr Ser His Val Ser Met Trp Lys Thr Ser
            260                 265                 270

Asp Ser Val Ser Ser Pro Gln Pro Gly Ala Ser Asp Thr Ala Val Pro
        275                 280                 285

Glu Gln Asn Lys Thr Thr Lys Thr Gly Gln Met Asp Gly Ile Pro Met
290                 295                 300

Ser Met Lys Asn Glu Met Pro Ile Ser Gln
305                 310

<210> SEQ ID NO 4
<211> LENGTH: 202
<212> TYPE: PRT
<213> ORGANISM: Homo sapiens
<220> FEATURE:
<223> OTHER INFORMATION: Tim3 binding domain
<220> FEATURE:
<221> NAME/KEY: sig_peptide
<222> LOCATION: 1...21

<400> SEQUENCE: 4

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

-continued

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly
        195                 200

<210> SEQ ID NO 5
<211> LENGTH: 161
<212> TYPE: PRT
<213> ORGANISM: Homo sapiens
<220> FEATURE:
<223> OTHER INFORMATION: FA58C2 binding domain

<400> SEQUENCE: 5

Leu Asn Gly Cys Ala Asn Pro Leu Gly Leu Lys Asn Asn Ser Ile Pro
1               5                   10                  15

Asp Lys Gln Ile Thr Ala Ser Ser Ser Tyr Lys Thr Trp Gly Leu His
            20                  25                  30

Leu Phe Ser Trp Asn Pro Ser Tyr Ala Arg Leu Asp Lys Gln Gly Asn
        35                  40                  45

Phe Asn Ala Trp Val Ala Gly Ser Tyr Gly Asn Asp Gln Trp Leu Gln
    50                  55                  60

Val Asp Leu Gly Ser Ser Lys Glu Val Thr Gly Ile Ile Thr Gln Gly
65                  70                  75                  80

Ala Arg Asn Phe Gly Ser Val Gln Phe Val Ala Ser Tyr Lys Val Ala
                85                  90                  95

Tyr Ser Asn Asp Ser Ala Asn Trp Thr Glu Tyr Gln Asp Pro Arg Thr
            100                 105                 110

Gly Ser Ser Lys Ile Phe Pro Gly Asn Trp Asp Asn His Ser His Lys
        115                 120                 125

Lys Asn Leu Phe Glu Thr Pro Ile Leu Ala Arg Tyr Val Arg Ile Leu
130                 135                 140

Pro Val Ala Trp His Asn Arg Ile Ala Leu Arg Leu Glu Leu Leu Gly
145                 150                 155                 160

Cys

<210> SEQ ID NO 6
<211> LENGTH: 94
<212> TYPE: PRT
<213> ORGANISM: Homo sapeins
<220> FEATURE:
<223> OTHER INFORMATION: GAS6 binding domain

```
<220> FEATURE:
<221> NAME/KEY: sig_peptide
<222> LOCATION: 1...30

<400> SEQUENCE: 6

Met Ala Pro Ser Leu Ser Pro Gly Pro Ala Leu Arg Arg Ala Pro
1               5                   10                  15

Gln Leu Leu Leu Leu Leu Ala Ala Glu Cys Ala Leu Ala Ala Leu
            20                  25                  30

Leu Pro Ala Arg Glu Ala Thr Gln Phe Leu Arg Pro Gln Arg Arg
        35                  40                  45

Ala Phe Gln Val Phe Glu Glu Ala Lys Gln Gly His Leu Glu Arg Glu
    50                  55                  60

Cys Val Glu Glu Leu Cys Ser Arg Glu Glu Ala Arg Glu Val Phe Glu
65                  70                  75                  80

Asn Asp Pro Glu Thr Asp Tyr Phe Tyr Pro Arg Tyr Leu Asp
                85                  90

<210> SEQ ID NO 7
<211> LENGTH: 87
<212> TYPE: PRT
<213> ORGANISM: Homo sapiens
<220> FEATURE:
<223> OTHER INFORMATION: protein S binding domain
<220> FEATURE:
<221> NAME/KEY: sig_peptide
<222> LOCATION: 1...24

<400> SEQUENCE: 7

Met Arg Val Leu Gly Gly Arg Cys Gly Ala Leu Leu Ala Cys Leu Leu
1               5                   10                  15

Leu Val Leu Pro Val Ser Glu Ala Asn Phe Leu Ser Lys Gln Gln Ala
            20                  25                  30

Ser Gln Val Leu Val Arg Lys Arg Arg Ala Asn Ser Leu Leu Glu Glu
        35                  40                  45

Thr Lys Gln Gly Asn Leu Glu Arg Glu Cys Ile Glu Glu Leu Cys Asn
    50                  55                  60

Lys Glu Glu Ala Arg Glu Val Phe Glu Asn Asp Pro Glu Thr Asp Tyr
65                  70                  75                  80

Phe Tyr Pro Lys Tyr Leu Val
                85

<210> SEQ ID NO 8
<211> LENGTH: 918
<212> TYPE: PRT
<213> ORGANISM: Homo sapiens
<220> FEATURE:
<223> OTHER INFORMATION: BAI1 binding domain

<400> SEQUENCE: 8

Ala Ala Gly Ala Asp Gly Pro Gly Pro Glu Pro Cys Ala Thr Leu
1               5                   10                  15

Val Gln Gly Lys Phe Phe Gly Tyr Phe Ser Ala Ala Ala Val Phe Pro
            20                  25                  30

Ala Asn Ala Ser Arg Cys Ser Trp Thr Leu Arg Asn Pro Asp Pro Arg
        35                  40                  45

Arg Tyr Thr Leu Tyr Met Lys Val Ala Lys Ala Pro Val Pro Cys Ser
    50                  55                  60

Gly Pro Gly Arg Val Arg Thr Tyr Gln Phe Asp Ser Phe Leu Glu Ser
65                  70                  75                  80
```

```
Thr Arg Thr Tyr Leu Gly Val Glu Ser Phe Asp Val Leu Arg Leu
             85                  90                  95

Cys Asp Pro Ser Ala Pro Leu Ala Phe Leu Gln Ala Ser Lys Gln Phe
            100                 105                 110

Leu Gln Met Arg Arg Gln Gln Pro Pro Gln His Asp Gly Leu Arg Pro
            115                 120                 125

Arg Ala Gly Pro Pro Gly Pro Thr Asp Asp Phe Ser Val Glu Tyr Leu
        130                 135                 140

Val Val Gly Asn Arg Asn Pro Ser Arg Ala Ala Cys Gln Met Leu Cys
145                 150                 155                 160

Arg Trp Leu Asp Ala Cys Leu Ala Gly Ser Arg Ser His Pro Cys
                165                 170                 175

Gly Ile Met Gln Thr Pro Cys Ala Cys Leu Gly Gly Glu Ala Gly Gly
            180                 185                 190

Pro Ala Ala Gly Pro Leu Ala Pro Arg Gly Asp Val Cys Leu Arg Asp
            195                 200                 205

Ala Val Ala Gly Gly Pro Glu Asn Cys Leu Thr Ser Leu Thr Gln Asp
        210                 215                 220

Arg Gly Gly His Gly Ala Thr Gly Gly Trp Lys Leu Trp Ser Leu Trp
225                 230                 235                 240

Gly Glu Cys Thr Arg Asp Cys Gly Gly Gly Leu Gln Thr Arg Thr Arg
                245                 250                 255

Thr Cys Leu Pro Ala Pro Gly Val Glu Gly Gly Cys Glu Gly Val
            260                 265                 270

Leu Glu Glu Gly Arg Gln Cys Asn Arg Glu Ala Cys Gly Pro Ala Gly
        275                 280                 285

Arg Thr Ser Ser Arg Ser Gln Ser Leu Arg Ser Thr Asp Ala Arg Arg
        290                 295                 300

Arg Glu Glu Leu Gly Asp Glu Leu Gln Gln Phe Gly Phe Pro Ala Pro
305                 310                 315                 320

Gln Thr Gly Asp Pro Ala Ala Glu Glu Trp Ser Pro Trp Ser Val Cys
                325                 330                 335

Ser Ser Thr Cys Gly Glu Gly Trp Gln Thr Arg Thr Arg Phe Cys Val
            340                 345                 350

Ser Ser Ser Tyr Ser Thr Gln Cys Ser Gly Pro Leu Arg Glu Gln Arg
        355                 360                 365

Leu Cys Asn Asn Ser Ala Val Cys Pro Val His Gly Ala Trp Asp Glu
370                 375                 380

Trp Ser Pro Trp Ser Leu Cys Ser Ser Thr Cys Gly Arg Gly Phe Arg
385                 390                 395                 400

Asp Arg Thr Arg Thr Cys Arg Pro Pro Gln Phe Gly Gly Asn Pro Cys
                405                 410                 415

Glu Gly Pro Glu Lys Gln Thr Lys Phe Cys Asn Ile Ala Leu Cys Pro
            420                 425                 430

Gly Arg Ala Val Asp Gly Asn Trp Asn Glu Trp Ser Ser Trp Ser Ala
        435                 440                 445

Cys Ser Ala Ser Cys Ser Gln Gly Arg Gln Arg Thr Arg Glu Cys
        450                 455                 460

Asn Gly Pro Ser Tyr Gly Gly Ala Glu Cys Gln Gly His Trp Val Glu
465                 470                 475                 480

Thr Arg Asp Cys Phe Leu Gln Gln Cys Pro Val Asp Gly Lys Trp Gln
                485                 490                 495
```

```
Ala Trp Ala Ser Trp Gly Ser Cys Ser Val Thr Cys Gly Ala Gly Ser
            500                 505                 510

Gln Arg Arg Glu Arg Val Cys Ser Gly Pro Phe Phe Gly Gly Ala Ala
        515                 520                 525

Cys Gln Gly Pro Gln Asp Glu Tyr Arg Gln Cys Gly Thr Gln Arg Cys
    530                 535                 540

Pro Glu Pro His Glu Ile Cys Asp Glu Asp Asn Phe Gly Ala Val Ile
545                 550                 555                 560

Trp Lys Glu Thr Pro Ala Gly Glu Val Ala Ala Val Arg Cys Pro Arg
                565                 570                 575

Asn Ala Thr Gly Leu Ile Leu Arg Arg Cys Glu Leu Asp Glu Glu Gly
            580                 585                 590

Ile Ala Tyr Trp Glu Pro Pro Thr Tyr Ile Arg Cys Val Ser Ile Asp
        595                 600                 605

Tyr Arg Asn Ile Gln Met Met Thr Arg Glu His Leu Ala Lys Ala Gln
    610                 615                 620

Arg Gly Leu Pro Gly Glu Gly Val Ser Glu Val Ile Gln Thr Leu Val
625                 630                 635                 640

Glu Ile Ser Gln Asp Gly Thr Ser Tyr Ser Gly Asp Leu Leu Ser Thr
                645                 650                 655

Ile Asp Val Leu Arg Asn Met Thr Glu Ile Phe Arg Arg Ala Tyr Tyr
            660                 665                 670

Ser Pro Thr Pro Gly Asp Val Gln Asn Phe Val Gln Ile Leu Ser Asn
        675                 680                 685

Leu Leu Ala Glu Glu Asn Arg Asp Lys Trp Glu Glu Ala Gln Leu Ala
690                 695                 700

Gly Pro Asn Ala Lys Glu Leu Phe Arg Leu Val Glu Asp Phe Val Asp
705                 710                 715                 720

Val Ile Gly Phe Arg Met Lys Asp Leu Arg Asp Ala Tyr Gln Val Thr
                725                 730                 735

Asp Asn Leu Val Leu Ser Ile His Lys Leu Pro Ala Ser Gly Ala Thr
            740                 745                 750

Asp Ile Ser Phe Pro Met Lys Gly Trp Arg Ala Thr Gly Asp Trp Ala
        755                 760                 765

Lys Val Pro Glu Asp Arg Val Thr Val Ser Lys Ser Val Phe Ser Thr
770                 775                 780

Gly Leu Thr Glu Ala Asp Glu Ala Ser Val Phe Val Val Gly Thr Val
785                 790                 795                 800

Leu Tyr Arg Asn Leu Gly Ser Phe Leu Ala Leu Gln Arg Asn Thr Thr
                805                 810                 815

Val Leu Asn Ser Lys Val Ile Ser Val Thr Val Lys Pro Pro Pro Arg
            820                 825                 830

Ser Leu Arg Thr Pro Leu Glu Ile Glu Phe Ala His Met Tyr Asn Gly
        835                 840                 845

Thr Thr Asn Gln Thr Cys Ile Leu Trp Asp Glu Thr Asp Val Pro Ser
    850                 855                 860

Ser Ser Ala Pro Pro Gln Leu Gly Pro Trp Ser Trp Arg Gly Cys Arg
865                 870                 875                 880

Thr Val Pro Leu Asp Ala Leu Arg Thr Arg Cys Leu Cys Asp Arg Leu
                885                 890                 895

Ser Thr Phe Ala Ile Leu Ala Gln Leu Ser Ala Asp Ala Asn Met Glu
            900                 905                 910

Lys Ala Thr Leu Pro Ser
```

<210> SEQ ID NO 9
<211> LENGTH: 876
<212> TYPE: DNA
<213> ORGANISM: Homo sapiens
<220> FEATURE:
<221> NAME/KEY: misc_feature
<223> OTHER INFORMATION: FcgammaRI binding domain

<400> SEQUENCE: 9

```
atgtggttcc tgactacgtt gttgctgtgg gtccctgtag acggccaagt agacacaacg      60
aaagcagtga tcacgctcca accgccttgg gtgtctgtgt tccaagaaga aacagttaca     120
ctgcactgtg aggtcctcca cctgcctggt tcttcatcta ctcaatggtt tctcaacgga     180
acagcaacac aaacaagtac cccttcctac agaattacga gtgcatctgt taacgattca     240
ggagagtata ggtgccagcg agggctttca ggccggtccg accccattca actcgaaatt     300
caccgcggtt ggcttctgct gcaagtatcc tctcgggtct tcacgaaagg tgaaccactt     360
gccttgcgct gtcacgcatg aaagataag ctcgtctaca cgttttgta ttatcggaat      420
ggaaaggcat ttaagttttt tcattggaac tcaaacctta cgatcctcaa accaatatc     480
agtcataacg gtacgtacca ctgctcaggc atgggcaagc atcgctatac gtccgcaggg     540
attagcgtga cagttaagga gctcttcccc gcgcctgtgc tgaatgcgag cgtaacttca     600
cccttctgg agggcaactt ggtgaccctc tcttgtgaga cgaaacttct ccttcagagg      660
ccggcctgc aactctattt cagcttttat atgggttcta aaactcttcg aggcagaaac      720
acgagcagcg aatatcagat actgactgcc cggcgggaag acagtggcct ttattggtgc     780
gaggctgcaa cagaagatgg caatgtcctt aaaaggtctc ccgaattgga gctccaagtg     840
cttggcttgc aactccctac accgtatgg ttccac                                876
```

<210> SEQ ID NO 10
<211> LENGTH: 870
<212> TYPE: DNA
<213> ORGANISM: Homo sapiens
<220> FEATURE:
<221> NAME/KEY: misc_feature
<223> OTHER INFORMATION: Tim1 binding domain

<400> SEQUENCE: 10

```
atgcaccccc aggttgttat actttcattg atcctgcatt tggccgactc cgtggcgggt      60
tccgtaaaag ttggagggga agctggacca agcgtcacct tgccttgcca ctactctgga     120
gccgtgacga gtatgtgctg gaatcgagga tcctgtagtc tttttcacatg ccaaaatggc    180
atagtttgga ccaatgggac gcacgtcacc taccgaaaag acactagata caaactcctg     240
ggtgacctca gcaggagaga tgtgtctctg actattgaaa acactgctgt ttctgactct     300
ggagtctact gttgccgggt cgagcaccga ggatggttca atgacatgaa gatcacggtc     360
agcttggaaa tcgtcccgcc caaggtaacc actacaccaa tagttactac ggttcccacg     420
gtaaccacgg ttcgaaccag caccacagta cccacaacta cgaccgttcc aaccactaca     480
gtccccacaa ccatgagtat ccctacgaca actacggtcc tgacaaccat accgtcagc      540
actaccacga gtgtgcctac gactactagc ataccgacga ctacttcagt tccagtcacc     600
accacggtga gtacattcgt gcctccaatg ccattgccga ggcaaaacca cgaacccgtg     660
gcgacatctc cgtctagtcc gcaaccagca gagacccatc ccaccacgct tcaggggca     720
atcaggagag aacctacaag ttcacccctc tacagctata caaccgatgg aaacgacaca     780
```

```
gttacagaaa gtagtgacgg tttgtggaat aacaaccaaa cacaattgtt cctggagcac        840
agtctgttga cagccaacac tacaaaggga                                         870

<210> SEQ ID NO 11
<211> LENGTH: 942
<212> TYPE: DNA
<213> ORGANISM: Homo sapiens
<220> FEATURE:
<221> NAME/KEY: misc_feature
<223> OTHER INFORMATION: Tim4 binding domain

<400> SEQUENCE: 11
atgagtaaag agccgcttat cctgtggctt atgatagagt tttggtggtt gtatttgacc         60
ccggtcacga gcgaaacggt agtgactgaa gtattgggtc atcgggtaac cttgccttgc        120
ttgtatagct cctggtctca taatagtaat agcatgtgct ggggcaagga ccaatgcccc        180
tatagcggat gcaaggaggc gctcattcgc acagacggaa tgcgggtgac atcaaggaag        240
agtgctaagt accggcttca gggcacaatc ccacgcggcg acgtgtcact gactatcctt        300
aatccatccg agagcgactc tggtgtctat tgttgcagga tcgaggttcc gggatggttc        360
aatgatgtaa agatcaatgt aagactcaat ctgcaacggg catctacaac cacgcatcgg        420
acagccacta ctaccacaag gagaacaact actacgtcac ccacgactac tcgacagatg        480
accactacac ctgcggccct gccaactacg gttgtaacta ctccggatct gacaaccggg        540
acaccgttgc aaatgacaac cattgcagta tttaccacgg caaacacgtg tctctctctg        600
accccatcta ctcttccgga ggaggccacc gggctcctta ccggagcc gtctaaggaa         660 ggcccaatct tgaccgcaga gagtgagacc gtacttccga gcgattcatg gtccagtgtc        720
gagagcacat ccgctgacac cgtccttctt acgtccaaag aaagtaaagt ttgggacctc        780
ccgtccacga gccacgtttc tatgtggaag acctcagata gcgttagctc cccacagcca        840
ggagcaagcg acaccgcagt accggagcaa aacaagacga ctaagactgg ccagatggat        900
ggtatcccaa tgtcaatgaa aaatgagatg cccatatcac aa                          942

<210> SEQ ID NO 12
<211> LENGTH: 606
<212> TYPE: DNA
<213> ORGANISM: Homo sapiens
<220> FEATURE:
<221> NAME/KEY: misc_feature
<223> OTHER INFORMATION: Tim3 binding domain

<400> SEQUENCE: 12
atgtttagcc atctcccttt tgattgcgtc ttgttgcttc ttcttctcct tctgacgaga         60
tcatctgaag ttgaatatcg cgcggaagtc ggccaaaacg catatctgcc gtgttttttac       120 accccggctg caccggggaa cttggttccc gtttgttggg gtaaggggc gtgtcccgtt         180 tttgagtgcg gtaacgtagt gctccgaact gatgaaagag atgtaaatta ctggacgagc        240
cggtactggt tgaatgggga ttttaggaag ggcgacgttt cccttaccat agaaaacgta        300
actcttgcgg attctgggat ttattgttgc aggatacaaa tccccggaat aatgaacgat        360
gagaaattca atttgaagct cgtaataaaa ccggcaaaag taactccagc tcccaccagg        420
cagcgagatt ttacggcagc atttcccagg atgctcacta ctcgcggtca tggccctgcc        480
gagactcaga ccctcggtag tcttcctgat atcaatctca cgcaaattag tacattggcg        540
aatgaattga gggattcaag actcgccaat gatctgcgcg acagtggagc gactattagg        600
```

```
ataggg                                                            606

<210> SEQ ID NO 13
<211> LENGTH: 483
<212> TYPE: DNA
<213> ORGANISM: Homo sapiens
<220> FEATURE:
<221> NAME/KEY: misc_feature
<223> OTHER INFORMATION: FA58C2 binding domain

<400> SEQUENCE: 13
ctcaacgggt gtgctaatcc ccttggcctg aagaataaca gcatacctga caagcaaata    60
acagcgtcaa gttcttataa aacttggggg ctgcatctgt tctcctggaa ccccagttac   120
gctagactcg acaaacaagg caattttaac gcatgggtgg caggctctta cgggaacgat   180
cagtggctgc aagtagactt ggaagtagt aaggaggtga ctgggatcat tacccagggg    240
gcacgaaatt tcggttccgt tcagttcgtt gcatcttata aggtagcgta ttcaaatgac   300
tccgcgaatt ggaccgaata tcaggacccg cgaaccggat caagcaagat ttttccgggg   360
aattgggaca accactctca caaaaaaaat ttgtttgaaa cacctatact ggcgcggtac   420
gttagaatcc tcccagttgc ctggcacaac cggatagcgc ttagactgga attgttgggg   480
tgc                                                                 483

<210> SEQ ID NO 14
<211> LENGTH: 282
<212> TYPE: DNA
<213> ORGANISM: Homo sapiens
<220> FEATURE:
<221> NAME/KEY: misc_feature
<223> OTHER INFORMATION: Gas6 binding domain

<400> SEQUENCE: 14
atggctccct ctttgtcacc aggacctgcg gctcttaggc gagccccgca gctgctgctt    60
ctcctgctcg ctgcagaatg cgctctcgct gcactcttgc ccgcgaggga ggcgactcag   120
ttcttgcgcc cccggcagag acgagcattc caagtctttg aggaagcgaa acaaggtcat   180
ctcgagcgag aatgcgtgga ggagctgtgt tctagggagg aagcacgcga agtctttgag   240
aatgacccgg aaacggacta cttttacccc cggtatcttg at                      282

<210> SEQ ID NO 15
<211> LENGTH: 261
<212> TYPE: DNA
<213> ORGANISM: Homo sapiens
<220> FEATURE:
<221> NAME/KEY: misc_feature
<223> OTHER INFORMATION: Protein S binding domain

<400> SEQUENCE: 15
atgcgcgtgt tggggggtcg ctgtggtgcg ctccttgctt gtctcctttt ggttcttccc    60
gtctccgagg ctaatttcct gtcaaaacaa caggctagtc aagtcttggt gcgcaagagg   120
agagctaaca gccttctgga agagaccaag caaggtaatc tggagagaga gtgtatcgag   180
gaactttgta caaagagga agcacgcgaa gtatttgaaa atgacccgga aaccgattat    240
ttttacccaa aatatctcgt a                                             261

<210> SEQ ID NO 16
<211> LENGTH: 12
<212> TYPE: PRT
<213> ORGANISM: Artificial Sequence
<220> FEATURE:
```

<223> OTHER INFORMATION: modified IgG4 hinge

<400> SEQUENCE: 16

Glu Ser Lys Tyr Gly Pro Pro Cys Pro Pro Cys Pro
1               5                   10

<210> SEQ ID NO 17
<211> LENGTH: 13
<212> TYPE: PRT
<213> ORGANISM: Homo sapiens
<220> FEATURE:
<223> OTHER INFORMATION: TLR4 juxtamembrane domain

<400> SEQUENCE: 17

Pro Val Leu Ser Leu Asn Ile Thr Cys Gln Met Asn Lys
1               5                   10

<210> SEQ ID NO 18
<211> LENGTH: 21
<212> TYPE: PRT
<213> ORGANISM: Homo sapiens
<220> FEATURE:
<223> OTHER INFORMATION: Tim1 transmembrane domain

<400> SEQUENCE: 18

Ile Tyr Ala Gly Val Cys Ile Ser Val Leu Val Leu Leu Ala Leu Leu
1               5                   10                  15

Gly Val Ile Ile Ala
            20

<210> SEQ ID NO 19
<211> LENGTH: 21
<212> TYPE: PRT
<213> ORGANISM: Homo sapiens
<220> FEATURE:
<223> OTHER INFORMATION: Tim4 transmembrane domain

<400> SEQUENCE: 19

Leu Leu Met Ile Ile Ala Pro Ser Leu Gly Phe Val Leu Phe Ala Leu
1               5                   10                  15

Phe Val Ala Phe Leu
            20

<210> SEQ ID NO 20
<211> LENGTH: 21
<212> TYPE: PRT
<213> ORGANISM: Homo sapiens
<220> FEATURE:
<223> OTHER INFORMATION: FcgammaRI transmembrane domain

<400> SEQUENCE: 20

Val Leu Phe Tyr Leu Ala Val Gly Ile Met Phe Leu Val Asn Thr Val
1               5                   10                  15

Leu Trp Val Thr Ile
            20

<210> SEQ ID NO 21
<211> LENGTH: 21
<212> TYPE: PRT
<213> ORGANISM: Homo sapiens
<220> FEATURE:
<223> OTHER INFORMATION: FcepsilonRIgamma transmembrane domain

<400> SEQUENCE: 21

Leu Cys Tyr Ile Leu Asp Ala Ile Leu Phe Leu Tyr Gly Ile Val Leu

```
                1               5                  10                  15

Thr Leu Leu Tyr Cys
                20

<210> SEQ ID NO 22
<211> LENGTH: 21
<212> TYPE: PRT
<213> ORGANISM: Homo sapiens
<220> FEATURE:
<223> OTHER INFORMATION: CD8a transmembrane domain

<400> SEQUENCE: 22

Ile Tyr Ile Trp Ala Pro Leu Ala Gly Thr Cys Gly Val Leu Leu Leu
1               5                  10                  15

Ser Leu Val Ile Thr
                20

<210> SEQ ID NO 23
<211> LENGTH: 21
<212> TYPE: PRT
<213> ORGANISM: Homo sapiens
<220> FEATURE:
<223> OTHER INFORMATION: MERTK transmembrane domain

<400> SEQUENCE: 23

Phe Gly Cys Phe Cys Gly Phe Ile Leu Ile Gly Leu Ile Leu Tyr Ile
1               5                  10                  15

Ser Leu Ala Ile Arg
                20

<210> SEQ ID NO 24
<211> LENGTH: 21
<212> TYPE: PRT
<213> ORGANISM: Homo sapiens
<220> FEATURE:
<223> OTHER INFORMATION: Axl transmembrane domain

<400> SEQUENCE: 24

Tyr Val Leu Leu Gly Ala Val Val Ala Ala Ala Cys Val Leu Ile Leu
1               5                  10                  15

Ala Leu Phe Leu Val
                20

<210> SEQ ID NO 25
<211> LENGTH: 21
<212> TYPE: PRT
<213> ORGANISM: Homo sapiens
<220> FEATURE:
<223> OTHER INFORMATION: Tyro3 transmembrane domain

<400> SEQUENCE: 25

Val Pro Val Val Leu Gly Val Leu Thr Ala Leu Val Thr Ala Ala Ala
1               5                  10                  15

Leu Ala Leu Ile Leu
                20

<210> SEQ ID NO 26
<211> LENGTH: 27
<212> TYPE: PRT
<213> ORGANISM: Homo sapiens
<220> FEATURE:
<223> OTHER INFORMATION: CD28 transmembrane domain

<400> SEQUENCE: 26
```

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 27
<211> LENGTH: 22
<212> TYPE: PRT
<213> ORGANISM: Homo sapiens
<220> FEATURE:
<223> OTHER INFORMATION: CD4 transmembrane domain

<400> SEQUENCE: 27

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 28
<211> LENGTH: 21
<212> TYPE: PRT
<213> ORGANISM: Homo sapiens
<220> FEATURE:
<223> OTHER INFORMATION: DAP12 transmembrane domain

<400> SEQUENCE: 28

Gly Val Leu Ala Gly Ile Val Met Gly Asp Leu Val Leu Thr Val Leu
1               5                   10                  15

Ile Ala Leu Ala Val
            20

<210> SEQ ID NO 29
<211> LENGTH: 21
<212> TYPE: PRT
<213> ORGANISM: Homo sapiens
<220> FEATURE:
<223> OTHER INFORMATION: BAI1 transmembrane domain

<400> SEQUENCE: 29

Val Thr Leu Ile Val Gly Cys Gly Val Ser Ser Leu Thr Leu Leu Met
1               5                   10                  15

Leu Val Ile Ile Tyr
            20

<210> SEQ ID NO 30
<211> LENGTH: 21
<212> TYPE: PRT
<213> ORGANISM: Homo sapiens
<220> FEATURE:
<223> OTHER INFORMATION: MRC1 transmembrane domain

<400> SEQUENCE: 30

Gly Val Val Ile Ile Val Ile Leu Leu Ile Leu Thr Gly Ala Gly Leu
1               5                   10                  15

Ala Ala Tyr Phe Phe
            20

<210> SEQ ID NO 31
<211> LENGTH: 21
<212> TYPE: PRT
<213> ORGANISM: Homo sapiens
<220> FEATURE:
<223> OTHER INFORMATION: TLR1 transmembrane domain

<400> SEQUENCE: 31

```
Leu Leu Ile Val Thr Ile Val Ala Thr Met Leu Val Leu Ala Val Thr
1               5                   10                  15

Val Thr Ser Leu Cys
            20

<210> SEQ ID NO 32
<211> LENGTH: 21
<212> TYPE: PRT
<213> ORGANISM: Homo sapiens
<220> FEATURE:
<223> OTHER INFORMATION: TLR2 transmembrane domain

<400> SEQUENCE: 32

Ala Leu Val Ser Gly Met Cys Cys Ala Leu Phe Leu Leu Ile Leu Leu
1               5                   10                  15

Thr Gly Val Leu Cys
            20

<210> SEQ ID NO 33
<211> LENGTH: 21
<212> TYPE: PRT
<213> ORGANISM: Homo sapiens
<220> FEATURE:
<223> OTHER INFORMATION: TLR3 Transmembrane domain

<400> SEQUENCE: 33

Phe Phe Met Ile Asn Thr Ser Ile Leu Leu Ile Phe Ile Phe Ile Val
1               5                   10                  15

Leu Leu Ile His Phe
            20

<210> SEQ ID NO 34
<211> LENGTH: 21
<212> TYPE: PRT
<213> ORGANISM: Homo sapiens
<220> FEATURE:
<223> OTHER INFORMATION: TLR4 transmembrane domain

<400> SEQUENCE: 34

Thr Ile Ile Gly Val Ser Val Leu Ser Val Leu Val Val Ser Val Val
1               5                   10                  15

Ala Val Leu Val Tyr
            20

<210> SEQ ID NO 35
<211> LENGTH: 21
<212> TYPE: PRT
<213> ORGANISM: Homo sapiens
<220> FEATURE:
<223> OTHER INFORMATION: TLR5 transmembrane domain

<400> SEQUENCE: 35

Phe Ser Leu Phe Ile Val Cys Thr Val Thr Leu Thr Leu Phe Leu Met
1               5                   10                  15

Thr Ile Leu Thr Val
            20

<210> SEQ ID NO 36
<211> LENGTH: 21
<212> TYPE: PRT
<213> ORGANISM: Homo sapiens
<220> FEATURE:
<223> OTHER INFORMATION: TLR6 transmembrane domain
```

```
<400> SEQUENCE: 36

Ala Leu Val Ser Gly Met Cys Cys Ala Leu Phe Leu Leu Ile Leu Leu
1               5                   10                  15

Thr Gly Val Leu Cys
            20

<210> SEQ ID NO 37
<211> LENGTH: 21
<212> TYPE: PRT
<213> ORGANISM: Homo sapiens
<220> FEATURE:
<223> OTHER INFORMATION: TLR7 transmembrane domain

<400> SEQUENCE: 37

Leu Ile Leu Phe Ser Leu Ser Ile Ser Val Ser Leu Phe Leu Met Val
1               5                   10                  15

Met Met Thr Ala Ser
            20

<210> SEQ ID NO 38
<211> LENGTH: 21
<212> TYPE: PRT
<213> ORGANISM: Homo sapiens
<220> FEATURE:
<223> OTHER INFORMATION: TLR8 transmembrane domain

<400> SEQUENCE: 38

Ala Val Ile Leu Phe Phe Phe Thr Phe Phe Ile Thr Thr Met Val Met
1               5                   10                  15

Leu Ala Ala Leu Ala
            20

<210> SEQ ID NO 39
<211> LENGTH: 21
<212> TYPE: PRT
<213> ORGANISM: Homo sapiens
<220> FEATURE:
<223> OTHER INFORMATION: TLR9 transmembrane domain

<400> SEQUENCE: 39

Phe Ala Leu Ser Leu Leu Ala Val Ala Leu Gly Leu Gly Val Pro Met
1               5                   10                  15

Leu His His Leu Cys
            20

<210> SEQ ID NO 40
<211> LENGTH: 63
<212> TYPE: DNA
<213> ORGANISM: Homo sapiens
<220> FEATURE:
<221> NAME/KEY: misc_feature
<223> OTHER INFORMATION: Tim1 transmembrane domain

<400> SEQUENCE: 40
atatacgctg gagtctgtat aagtgtcctt gtactgttgg cgttgctggg ggtcattatt    60
gcc                                                                  63

<210> SEQ ID NO 41
<211> LENGTH: 63
<212> TYPE: DNA
<213> ORGANISM: Homo sapiens
<220> FEATURE:
<221> NAME/KEY: misc_feature
<223> OTHER INFORMATION: Tim4 transmembrane domain
```

```
<400> SEQUENCE: 41
ttgcttatga ttattgcgcc aagccttgga tttgtgctgt tcgcactctt cgtagctttt      60
ctc                                                                    63

<210> SEQ ID NO 42
<211> LENGTH: 63
<212> TYPE: DNA
<213> ORGANISM: Homo sapiens
<220> FEATURE:
<221> NAME/KEY: misc_feature
<223> OTHER INFORMATION: FcgammaRI transmembrane domain

<400> SEQUENCE: 42
gtactgtttt atctcgccgt agggataatg ttcctcgtga acaccgtact gtgggtaaca      60
ata                                                                    63

<210> SEQ ID NO 43
<211> LENGTH: 63
<212> TYPE: DNA
<213> ORGANISM: Homo sapiens
<220> FEATURE:
<221> NAME/KEY: misc_feature
<223> OTHER INFORMATION: CD8a transmembrane domain

<400> SEQUENCE: 43
atatacattt gggcaccgct ggctggaact tgcggcgttc tcttgttgag tctggtgatt      60
act                                                                    63

<210> SEQ ID NO 44
<211> LENGTH: 63
<212> TYPE: DNA
<213> ORGANISM: Homo sapiens
<220> FEATURE:
<221> NAME/KEY: misc_feature
<223> OTHER INFORMATION: MERTK transmembrane domain

<400> SEQUENCE: 44
tttggctgtt tctgtggatt tattctgatt ggtcttatcc tctatatttc cttggcgatc      60
aga                                                                    63

<210> SEQ ID NO 45
<211> LENGTH: 63
<212> TYPE: DNA
<213> ORGANISM: Homo sapiens
<220> FEATURE:
<221> NAME/KEY: misc_feature
<223> OTHER INFORMATION: Axl transmembrane domain

<400> SEQUENCE: 45
tatgtcttgc ttggtgccgt cgttgctgcc gcctgtgtgt tgatactcgc acttttcttg      60
gtg                                                                    63

<210> SEQ ID NO 46
<211> LENGTH: 63
<212> TYPE: DNA
<213> ORGANISM: Homo sapiens
<220> FEATURE:
<221> NAME/KEY: misc_feature
<223> OTHER INFORMATION: Tyro3 transmembrane domain

<400> SEQUENCE: 46
gtacccgtcg tttttggggt cctgaccgcg ctcgttactg cggcagcact cgcactgata      60
```

```
ctt                                                              63

<210> SEQ ID NO 47
<211> LENGTH: 66
<212> TYPE: DNA
<213> ORGANISM: Homo sapiens
<220> FEATURE:
<221> NAME/KEY: misc_feature
<223> OTHER INFORMATION: CD4 transmembrane domain

<400> SEQUENCE: 47
atggctctga tcgtactggg cggagtggca ggattgctgc tctttattgg actgggcatt    60
ttcttc                                                              66

<210> SEQ ID NO 48
<211> LENGTH: 185
<212> TYPE: PRT
<213> ORGANISM: Homo sapiens
<220> FEATURE:
<223> OTHER INFORMATION: TLR1 signaling domain

<400> SEQUENCE: 48
```

Ser Tyr Leu Asp Leu Pro Trp Tyr Leu Arg Met Val Cys Gln Trp Thr
1               5                   10                  15

Gln Thr Arg Arg Arg Ala Arg Asn Ile Pro Leu Glu Glu Leu Gln Arg
            20                  25                  30

Asn Leu Gln Phe His Ala Phe Ile Ser Tyr Ser Gly His Asp Ser Phe
        35                  40                  45

Trp Val Lys Asn Glu Leu Leu Pro Asn Leu Glu Lys Glu Gly Met Gln
    50                  55                  60

Ile Cys Leu His Glu Arg Asn Phe Val Pro Gly Lys Ser Ile Val Glu
65                  70                  75                  80

Asn Ile Ile Thr Cys Ile Glu Lys Ser Tyr Lys Ser Ile Phe Val Leu
                85                  90                  95

Ser Pro Asn Phe Val Gln Ser Glu Trp Cys His Tyr Glu Leu Tyr Phe
            100                 105                 110

Ala His His Asn Leu Phe His Glu Gly Ser Asn Ser Leu Ile Leu Ile
        115                 120                 125

Leu Leu Glu Pro Ile Pro Gln Tyr Ser Ile Pro Ser Ser Tyr His Lys
    130                 135                 140

Leu Lys Ser Leu Met Ala Arg Arg Thr Tyr Leu Glu Trp Pro Lys Glu
145                 150                 155                 160

Lys Ser Lys Arg Gly Leu Phe Trp Ala Asn Leu Arg Ala Ala Ile Asn
                165                 170                 175

Ile Lys Leu Thr Glu Gln Ala Lys Lys
            180                 185

```
<210> SEQ ID NO 49
<211> LENGTH: 175
<212> TYPE: PRT
<213> ORGANISM: Homo sapiens
<220> FEATURE:
<223> OTHER INFORMATION: TLR2 signaling domain

<400> SEQUENCE: 49
```

His Arg Phe His Gly Leu Trp Tyr Met Lys Met Met Trp Ala Trp Leu
1               5                   10                  15

Gln Ala Lys Arg Lys Pro Arg Lys Ala Pro Ser Arg Asn Ile Cys Tyr
            20                  25                  30

```
Asp Ala Phe Val Ser Tyr Ser Glu Arg Asp Ala Tyr Trp Val Glu Asn
        35                  40                  45

Leu Met Val Gln Glu Leu Glu Asn Phe Asn Pro Pro Phe Lys Leu Cys
 50                  55                  60

Leu His Lys Arg Asp Phe Ile Pro Gly Lys Trp Ile Ile Asp Asn Ile
 65                  70                  75                  80

Ile Asp Ser Ile Glu Lys Ser His Lys Thr Val Phe Val Leu Ser Glu
                 85                  90                  95

Asn Phe Val Lys Ser Glu Trp Cys Lys Tyr Glu Leu Asp Phe Ser His
                100                 105                 110

Phe Arg Leu Phe Asp Glu Asn Asn Asp Ala Ala Ile Leu Ile Leu Leu
            115                 120                 125

Glu Pro Ile Glu Lys Lys Ala Ile Pro Gln Arg Phe Cys Lys Leu Arg
            130                 135                 140

Lys Ile Met Asn Thr Lys Thr Tyr Leu Glu Trp Pro Met Asp Glu Ala
145                 150                 155                 160

Gln Arg Glu Gly Phe Trp Val Asn Leu Arg Ala Ala Ile Lys Ser
                165                 170                 175
```

<210> SEQ ID NO 50
<211> LENGTH: 179
<212> TYPE: PRT
<213> ORGANISM: Homo sapiens
<220> FEATURE:
<223> OTHER INFORMATION: TLR3 signaling domain

<400> SEQUENCE: 50

```
Glu Gly Trp Arg Ile Ser Phe Tyr Trp Asn Val Ser Val His Arg Val
 1               5                  10                  15

Leu Gly Phe Lys Glu Ile Asp Arg Gln Thr Glu Gln Phe Glu Tyr Ala
            20                  25                  30

Ala Tyr Ile Ile His Ala Tyr Lys Asp Lys Asp Trp Val Trp Glu His
        35                  40                  45

Phe Ser Ser Met Glu Lys Glu Asp Gln Ser Leu Lys Phe Cys Leu Glu
 50                  55                  60

Glu Arg Asp Phe Glu Ala Gly Val Phe Glu Leu Glu Ala Ile Val Asn
 65                  70                  75                  80

Ser Ile Lys Arg Ser Arg Lys Ile Ile Phe Val Ile Thr His His Leu
                 85                  90                  95

Leu Lys Asp Pro Leu Cys Lys Arg Phe Lys Val His His Ala Val Gln
                100                 105                 110

Gln Ala Ile Glu Gln Asn Leu Asp Ser Ile Ile Leu Val Phe Leu Glu
            115                 120                 125

Glu Ile Pro Asp Tyr Lys Leu Asn His Ala Leu Cys Leu Arg Arg Gly
            130                 135                 140

Met Phe Lys Ser His Cys Ile Leu Asn Trp Pro Val Gln Lys Glu Arg
145                 150                 155                 160

Ile Gly Ala Phe Arg His Lys Leu Gln Val Ala Leu Gly Ser Lys Asn
                165                 170                 175

Ser Val His
```

<210> SEQ ID NO 51
<211> LENGTH: 187
<212> TYPE: PRT
<213> ORGANISM: Homo sapiens
<220> FEATURE:

<223> OTHER INFORMATION: TLR4 signaling domain

<400> SEQUENCE: 51

Lys Phe Tyr Phe His Leu Met Leu Leu Ala Gly Cys Ile Lys Tyr Gly
1               5                   10                  15

Arg Gly Glu Asn Ile Tyr Asp Ala Phe Val Ile Tyr Ser Ser Gln Asp
            20                  25                  30

Glu Asp Trp Val Arg Asn Glu Leu Val Lys Asn Leu Glu Glu Gly Val
        35                  40                  45

Pro Pro Phe Gln Leu Cys Leu His Tyr Arg Asp Phe Ile Pro Gly Val
    50                  55                  60

Ala Ile Ala Ala Asn Ile Ile His Glu Gly Phe His Lys Ser Arg Lys
65                  70                  75                  80

Val Ile Val Val Ser Gln His Phe Ile Gln Ser Arg Trp Cys Ile
                85                  90                  95

Phe Glu Tyr Glu Ile Ala Gln Thr Trp Gln Phe Leu Ser Ser Arg Ala
            100                 105                 110

Gly Ile Ile Phe Ile Val Leu Gln Lys Val Glu Lys Thr Leu Leu Arg
        115                 120                 125

Gln Gln Val Glu Leu Tyr Arg Leu Leu Ser Arg Asn Thr Tyr Leu Glu
    130                 135                 140

Trp Glu Asp Ser Val Leu Gly Arg His Ile Phe Trp Arg Arg Leu Arg
145                 150                 155                 160

Lys Ala Leu Leu Asp Gly Lys Ser Trp Asn Pro Glu Gly Thr Val Gly
                165                 170                 175

Thr Gly Cys Asn Trp Gln Glu Ala Thr Ser Ile
            180                 185

<210> SEQ ID NO 52
<211> LENGTH: 198
<212> TYPE: PRT
<213> ORGANISM: Homo sapiens
<220> FEATURE:
<223> OTHER INFORMATION: TLR5 signaling domain

<400> SEQUENCE: 52

Thr Lys Phe Arg Gly Phe Cys Phe Ile Cys Tyr Lys Thr Ala Gln Arg
1               5                   10                  15

Leu Val Phe Lys Asp His Pro Gln Gly Thr Glu Pro Asp Met Tyr Lys
            20                  25                  30

Tyr Asp Ala Tyr Leu Cys Phe Ser Ser Lys Asp Phe Thr Trp Val Gln
        35                  40                  45

Asn Ala Leu Leu Lys His Leu Asp Thr Gln Tyr Ser Asp Gln Asn Arg
    50                  55                  60

Phe Asn Leu Cys Phe Glu Glu Arg Asp Phe Val Pro Gly Glu Asn Arg
65                  70                  75                  80

Ile Ala Asn Ile Gln Asp Ala Ile Trp Asn Ser Arg Lys Ile Val Cys
                85                  90                  95

Leu Val Ser Arg His Phe Leu Arg Asp Gly Trp Cys Leu Glu Ala Phe
            100                 105                 110

Ser Tyr Ala Gln Gly Arg Cys Leu Ser Asp Leu Asn Ser Ala Leu Ile
        115                 120                 125

Met Val Val Val Gly Ser Leu Ser Gln Tyr Gln Leu Met Lys His Gln
    130                 135                 140

Ser Ile Arg Gly Phe Val Gln Lys Gln Gln Tyr Leu Arg Trp Pro Glu
145                 150                 155                 160

```
Asp Phe Gln Asp Val Gly Trp Phe Leu His Lys Leu Ser Gln Gln Ile
                165                 170                 175

Leu Lys Lys Glu Lys Glu Lys Lys Asp Asn Asn Ile Pro Leu Gln
            180                 185                 190

Thr Val Ala Thr Ile Ser
            195

<210> SEQ ID NO 53
<211> LENGTH: 189
<212> TYPE: PRT
<213> ORGANISM: Homo sapiens
<220> FEATURE:
<223> OTHER INFORMATION: TLR6 signaling domain

<400> SEQUENCE: 53

Tyr Leu Asp Leu Pro Trp Tyr Leu Arg Met Val Cys Gln Trp Thr Gln
1               5                   10                  15

Thr Arg Arg Arg Ala Arg Asn Ile Pro Leu Glu Glu Leu Gln Arg Asn
                20                  25                  30

Leu Gln Phe His Ala Phe Ile Ser Tyr Ser Glu His Asp Ser Ala Trp
            35                  40                  45

Val Lys Ser Glu Leu Val Pro Tyr Leu Glu Lys Glu Asp Ile Gln Ile
50                  55                  60

Cys Leu His Glu Arg Asn Phe Val Pro Gly Lys Ser Ile Val Glu Asn
65                  70                  75                  80

Ile Ile Asn Cys Ile Glu Lys Ser Tyr Lys Ser Ile Phe Val Leu Ser
                85                  90                  95

Pro Asn Phe Val Gln Ser Glu Trp Cys His Tyr Glu Leu Tyr Phe Ala
            100                 105                 110

His His Asn Leu Phe His Glu Gly Ser Asn Asn Leu Ile Leu Ile Leu
        115                 120                 125

Leu Glu Pro Ile Pro Gln Asn Ser Ile Pro Asn Lys Tyr His Lys Leu
130                 135                 140

Lys Ala Leu Met Thr Gln Arg Thr Tyr Leu Gln Trp Pro Lys Glu Lys
145                 150                 155                 160

Ser Lys Arg Gly Leu Phe Trp Ala Asn Ile Arg Ala Ala Phe Asn Met
                165                 170                 175

Lys Leu Thr Leu Val Thr Glu Asn Asn Asp Val Lys Ser
            180                 185

<210> SEQ ID NO 54
<211> LENGTH: 189
<212> TYPE: PRT
<213> ORGANISM: Homo sapiens
<220> FEATURE:
<223> OTHER INFORMATION: TLR7 signaling domain

<400> SEQUENCE: 54

His Leu Tyr Phe Trp Asp Val Trp Tyr Ile Tyr His Phe Cys Lys Ala
1               5                   10                  15

Lys Ile Lys Gly Tyr Gln Arg Leu Ile Ser Pro Asp Cys Cys Tyr Asp
                20                  25                  30

Ala Phe Ile Val Tyr Asp Thr Lys Asp Pro Ala Val Thr Glu Trp Val
            35                  40                  45

Leu Ala Glu Leu Val Ala Lys Leu Glu Asp Pro Arg Glu Lys His Phe
50                  55                  60

Asn Leu Cys Leu Glu Glu Arg Asp Trp Leu Pro Gly Gln Pro Val Leu
```

```
                65                  70                  75                  80
Glu Asn Leu Ser Gln Ser Ile Gln Leu Ser Lys Lys Thr Val Phe Val
                    85                  90                  95

Met Thr Asp Lys Tyr Ala Lys Thr Glu Asn Phe Lys Ile Ala Phe Tyr
                    100                 105                 110

Leu Ser His Gln Arg Leu Met Asp Glu Lys Val Asp Val Ile Ile Leu
                    115                 120                 125

Ile Phe Leu Glu Lys Pro Phe Gln Lys Ser Lys Phe Leu Gln Leu Arg
                    130                 135                 140

Lys Arg Leu Cys Gly Ser Ser Val Leu Glu Trp Pro Thr Asn Pro Gln
145                 150                 155                 160

Ala His Pro Tyr Phe Trp Gln Cys Leu Lys Asn Ala Leu Ala Thr Asp
                    165                 170                 175

Asn His Val Ala Tyr Ser Gln Val Phe Lys Glu Thr Val
                    180                 185

<210> SEQ ID NO 55
<211> LENGTH: 193
<212> TYPE: PRT
<213> ORGANISM: Homo sapiens
<220> FEATURE:
<223> OTHER INFORMATION: TLR8 signaling domain

<400> SEQUENCE: 55

His His Leu Phe Tyr Trp Asp Val Trp Phe Ile Tyr Asn Val Cys Leu
1               5                   10                  15

Ala Lys Val Lys Gly Tyr Arg Ser Leu Ser Thr Ser Gln Thr Phe Tyr
                20                  25                  30

Asp Ala Tyr Ile Ser Tyr Asp Thr Lys Asp Ala Ser Val Thr Asp Trp
                35                  40                  45

Val Ile Asn Glu Leu Arg Tyr His Leu Glu Glu Ser Arg Asp Lys Asn
50                  55                  60

Val Leu Leu Cys Leu Glu Glu Arg Asp Trp Asp Pro Gly Leu Ala Ile
65                  70                  75                  80

Ile Asp Asn Leu Met Gln Ser Ile Asn Gln Ser Lys Lys Thr Val Phe
                85                  90                  95

Val Leu Thr Lys Lys Tyr Ala Lys Ser Trp Asn Phe Lys Thr Ala Phe
                100                 105                 110

Tyr Leu Ala Leu Gln Arg Leu Met Asp Glu Asn Met Asp Val Ile Ile
                115                 120                 125

Phe Ile Leu Leu Glu Pro Val Leu Gln His Ser Gln Tyr Leu Arg Leu
                130                 135                 140

Arg Gln Arg Ile Cys Lys Ser Ser Ile Leu Gln Trp Pro Asp Asn Pro
145                 150                 155                 160

Lys Ala Glu Gly Leu Phe Trp Gln Thr Leu Arg Asn Val Val Leu Thr
                    165                 170                 175

Glu Asn Asp Ser Arg Tyr Asn Asn Met Tyr Val Asp Ser Ile Lys Gln
                180                 185                 190

Tyr

<210> SEQ ID NO 56
<211> LENGTH: 193
<212> TYPE: PRT
<213> ORGANISM: Homo sapiens
<220> FEATURE:
<223> OTHER INFORMATION: TLR9 signaling domain
```

-continued

```
<400> SEQUENCE: 56

Gly Trp Asp Leu Trp Tyr Cys Phe His Leu Cys Leu Ala Trp Leu Pro
1               5                   10                  15

Trp Arg Gly Arg Gln Ser Gly Arg Asp Glu Asp Ala Leu Pro Tyr Asp
            20                  25                  30

Ala Phe Val Val Phe Asp Lys Thr Gln Ser Ala Val Ala Asp Trp Val
        35                  40                  45

Tyr Asn Glu Leu Arg Gly Gln Leu Glu Glu Cys Arg Gly Arg Trp Ala
    50                  55                  60

Leu Arg Leu Cys Leu Glu Glu Arg Asp Trp Leu Pro Gly Lys Thr Leu
65                  70                  75                  80

Phe Glu Asn Leu Trp Ala Ser Val Tyr Gly Ser Arg Lys Thr Leu Phe
                85                  90                  95

Val Leu Ala His Thr Asp Arg Val Ser Gly Leu Leu Arg Ala Ser Phe
            100                 105                 110

Leu Leu Ala Gln Gln Arg Leu Leu Glu Asp Arg Lys Asp Val Val Val
        115                 120                 125

Leu Val Ile Leu Ser Pro Asp Gly Arg Arg Ser Arg Tyr Val Arg Leu
    130                 135                 140

Arg Gln Arg Leu Cys Arg Gln Ser Val Leu Leu Trp Pro His Gln Pro
145                 150                 155                 160

Ser Gly Gln Arg Ser Phe Trp Ala Gln Leu Gly Met Ala Leu Thr Arg
                165                 170                 175

Asp Asn His His Phe Tyr Asn Arg Asn Phe Cys Gln Gly Pro Thr Ala
            180                 185                 190

Glu

<210> SEQ ID NO 57
<211> LENGTH: 522
<212> TYPE: PRT
<213> ORGANISM: Homo sapiens
<220> FEATURE:
<223> OTHER INFORMATION: Traf6 signaling domain - full length

<400> SEQUENCE: 57

Met Ser Leu Leu Asn Cys Glu Asn Ser Cys Gly Ser Ser Gln Ser Glu
1               5                   10                  15

Ser Asp Cys Cys Val Ala Met Ala Ser Ser Cys Ser Ala Val Thr Lys
            20                  25                  30

Asp Asp Ser Val Gly Gly Thr Ala Ser Thr Gly Asn Leu Ser Ser Ser
        35                  40                  45

Phe Met Glu Glu Ile Gln Gly Tyr Asp Val Glu Phe Asp Pro Pro Leu
    50                  55                  60

Glu Ser Lys Tyr Glu Cys Pro Ile Cys Leu Met Ala Leu Arg Glu Ala
65                  70                  75                  80

Val Gln Thr Pro Cys Gly His Arg Phe Cys Lys Ala Cys Ile Ile Lys
                85                  90                  95

Ser Ile Arg Asp Ala Gly His Lys Cys Pro Val Asp Asn Glu Ile Leu
            100                 105                 110

Leu Glu Asn Gln Leu Phe Pro Asp Asn Phe Ala Lys Arg Glu Ile Leu
        115                 120                 125

Ser Leu Met Val Lys Cys Pro Asn Glu Gly Cys Leu His Lys Met Glu
    130                 135                 140

Leu Arg His Leu Glu Asp His Gln Ala His Cys Glu Phe Ala Leu Met
145                 150                 155                 160
```

Asp Cys Pro Gln Cys Gln Arg Pro Phe Gln Lys Phe His Ile Asn Ile
              165                 170                 175

His Ile Leu Lys Asp Cys Pro Arg Arg Gln Val Ser Cys Asp Asn Cys
              180                 185                 190

Ala Ala Ser Met Ala Phe Glu Asp Lys Glu Ile His Asp Gln Asn Cys
              195                 200                 205

Pro Leu Ala Asn Val Ile Cys Glu Tyr Cys Asn Thr Ile Leu Ile Arg
              210                 215                 220

Glu Gln Met Pro Asn His Tyr Asp Leu Asp Cys Pro Thr Ala Pro Ile
225                 230                 235                 240

Pro Cys Thr Phe Ser Thr Phe Gly Cys His Glu Lys Met Gln Arg Asn
              245                 250                 255

His Leu Ala Arg His Leu Gln Glu Asn Thr Gln Ser His Met Arg Met
              260                 265                 270

Leu Ala Gln Ala Val His Ser Leu Ser Val Ile Pro Asp Ser Gly Tyr
              275                 280                 285

Ile Ser Glu Val Arg Asn Phe Gln Glu Thr Ile His Gln Leu Glu Gly
              290                 295                 300

Arg Leu Val Arg Gln Asp His Gln Ile Arg Glu Leu Thr Ala Lys Met
305                 310                 315                 320

Glu Thr Gln Ser Met Tyr Val Ser Glu Leu Lys Arg Thr Ile Arg Thr
              325                 330                 335

Leu Glu Asp Lys Val Ala Glu Ile Glu Ala Gln Gln Cys Asn Gly Ile
              340                 345                 350

Tyr Ile Trp Lys Ile Gly Asn Phe Gly Met His Leu Lys Cys Gln Glu
              355                 360                 365

Glu Glu Lys Pro Val Val Ile His Ser Pro Gly Phe Tyr Thr Gly Lys
              370                 375                 380

Pro Gly Tyr Lys Leu Cys Met Arg Leu His Leu Gln Leu Pro Thr Ala
385                 390                 395                 400

Gln Arg Cys Ala Asn Tyr Ile Ser Leu Phe Val His Thr Met Gln Gly
              405                 410                 415

Glu Tyr Asp Ser His Leu Pro Trp Pro Phe Gln Gly Thr Ile Arg Leu
              420                 425                 430

Thr Ile Leu Asp Gln Ser Glu Ala Pro Val Arg Gln Asn His Glu Glu
              435                 440                 445

Ile Met Asp Ala Lys Pro Glu Leu Leu Ala Phe Gln Arg Pro Thr Ile
450                 455                 460

Pro Arg Asn Pro Lys Gly Phe Gly Tyr Val Thr Phe Met His Leu Glu
465                 470                 475                 480

Ala Leu Arg Gln Arg Thr Phe Ile Lys Asp Asp Thr Leu Leu Val Arg
              485                 490                 495

Cys Glu Val Ser Thr Arg Phe Asp Met Gly Ser Leu Arg Arg Glu Gly
              500                 505                 510

Phe Gln Pro Arg Ser Thr Asp Ala Gly Val
              515                 520

<210> SEQ ID NO 58
<211> LENGTH: 274
<212> TYPE: PRT
<213> ORGANISM: Homo sapiens
<220> FEATURE:
<223> OTHER INFORMATION: truncated TRAF6 signaling domain

<400> SEQUENCE: 58

Met Ser Leu Leu Asn Cys Glu Asn Cys Gly Ser Ser Gln Ser Glu
1               5                   10                  15

Ser Asp Cys Cys Val Ala Met Ala Ser Ser Cys Ser Ala Val Thr Lys
            20                  25                  30

Asp Asp Ser Val Gly Gly Thr Ala Ser Thr Gly Asn Leu Ser Ser Ser
                35                  40                  45

Phe Met Glu Glu Ile Gln Gly Tyr Asp Val Glu Phe Asp Pro Pro Leu
    50                  55                  60

Glu Ser Lys Tyr Glu Cys Pro Ile Cys Leu Met Ala Leu Arg Glu Ala
65                  70                  75                  80

Val Gln Thr Pro Cys Gly His Arg Phe Cys Lys Ala Cys Ile Ile Lys
                85                  90                  95

Ser Ile Arg Asp Ala Gly His Lys Cys Pro Val Asp Asn Glu Ile Leu
                100                 105                 110

Leu Glu Asn Gln Leu Phe Pro Asp Asn Phe Ala Lys Arg Glu Ile Leu
            115                 120                 125

Ser Leu Met Val Lys Cys Pro Asn Glu Gly Cys Leu His Lys Met Glu
        130                 135                 140

Leu Arg His Leu Glu Asp His Gln Ala His Cys Glu Phe Ala Leu Met
145                 150                 155                 160

Asp Cys Pro Gln Cys Gln Arg Pro Phe Gln Lys Phe His Ile Asn Ile
                165                 170                 175

His Ile Leu Lys Asp Cys Pro Arg Arg Gln Val Ser Cys Asp Asn Cys
                180                 185                 190

Ala Ala Ser Met Ala Phe Glu Asp Lys Glu Ile His Asp Gln Asn Cys
            195                 200                 205

Pro Leu Ala Asn Val Ile Cys Glu Tyr Cys Asn Thr Ile Leu Ile Arg
        210                 215                 220

Glu Gln Met Pro Asn His Tyr Asp Leu Asp Cys Pro Thr Ala Pro Ile
225                 230                 235                 240

Pro Cys Thr Phe Ser Thr Phe Gly Cys His Glu Lys Met Gln Arg Asn
                245                 250                 255

His Leu Ala Arg His Leu Gln Glu Asn Thr Gln Ser His Met Arg Met
                260                 265                 270

Leu Ala

<210> SEQ ID NO 59
<211> LENGTH: 473
<212> TYPE: PRT
<213> ORGANISM: Homo sapiens
<220> FEATURE:
<223> OTHER INFORMATION: MERTK signaling domain

<400> SEQUENCE: 59

Lys Arg Val Gln Glu Thr Lys Phe Gly Asn Ala Phe Thr Glu Glu Asp
1               5                   10                  15

Ser Glu Leu Val Val Asn Tyr Ile Ala Lys Lys Ser Phe Cys Arg Arg
            20                  25                  30

Ala Ile Glu Leu Thr Leu His Ser Leu Gly Val Ser Glu Glu Leu Gln
            35                  40                  45

Asn Lys Leu Glu Asp Val Val Ile Asp Arg Asn Leu Leu Ile Leu Gly
        50                  55                  60

Lys Ile Leu Gly Glu Gly Glu Phe Gly Ser Val Met Glu Gly Asn Leu
65                  70                  75                  80

```
Lys Gln Glu Asp Gly Thr Ser Leu Lys Val Ala Lys Thr Met Lys
                85                  90                  95

Leu Asp Asn Ser Ser Gln Arg Glu Ile Glu Glu Phe Leu Ser Glu Ala
            100                 105                 110

Ala Cys Met Lys Asp Phe Ser His Pro Asn Val Ile Arg Leu Leu Gly
            115                 120                 125

Val Cys Ile Glu Met Ser Ser Gln Gly Ile Pro Lys Pro Met Val Ile
            130                 135                 140

Leu Pro Phe Met Lys Tyr Gly Asp Leu His Thr Tyr Leu Leu Tyr Ser
145                 150                 155                 160

Arg Leu Glu Thr Gly Pro Lys His Ile Pro Leu Gln Thr Leu Leu Lys
                165                 170                 175

Phe Met Val Asp Ile Ala Leu Gly Met Glu Tyr Leu Ser Asn Arg Asn
            180                 185                 190

Phe Leu His Arg Asp Leu Ala Ala Arg Asn Cys Met Leu Arg Asp Asp
            195                 200                 205

Met Thr Val Cys Val Ala Asp Phe Gly Leu Ser Lys Lys Ile Tyr Ser
        210                 215                 220

Gly Asp Tyr Tyr Arg Gln Gly Arg Ile Ala Lys Met Pro Val Lys Trp
225                 230                 235                 240

Ile Ala Ile Glu Ser Leu Ala Asp Arg Val Tyr Thr Ser Lys Ser Asp
                245                 250                 255

Val Trp Ala Phe Gly Val Thr Met Trp Glu Ile Ala Thr Arg Gly Met
            260                 265                 270

Thr Pro Tyr Pro Gly Val Gln Asn His Glu Met Tyr Asp Tyr Leu Leu
            275                 280                 285

His Gly His Arg Leu Lys Gln Pro Glu Asp Cys Leu Asp Glu Leu Tyr
        290                 295                 300

Glu Ile Met Tyr Ser Cys Trp Arg Thr Asp Pro Leu Asp Arg Pro Thr
305                 310                 315                 320

Phe Ser Val Leu Arg Leu Gln Leu Glu Lys Leu Leu Glu Ser Leu Pro
                325                 330                 335

Asp Val Arg Asn Gln Ala Asp Val Ile Tyr Val Asn Thr Gln Leu Leu
            340                 345                 350

Glu Ser Ser Glu Gly Leu Ala Gln Gly Ser Thr Leu Ala Pro Leu Asp
            355                 360                 365

Leu Asn Ile Asp Pro Asp Ser Ile Ile Ala Ser Cys Thr Pro Arg Ala
        370                 375                 380

Ala Ile Ser Val Val Thr Ala Glu Val His Asp Ser Lys Pro His Glu
385                 390                 395                 400

Gly Arg Tyr Ile Leu Asn Gly Gly Ser Glu Glu Trp Glu Asp Leu Thr
                405                 410                 415

Ser Ala Pro Ser Ala Ala Val Thr Ala Glu Lys Asn Ser Val Leu Pro
            420                 425                 430

Gly Glu Arg Leu Val Arg Asn Gly Val Ser Trp Ser His Ser Ser Met
            435                 440                 445

Leu Pro Leu Gly Ser Ser Leu Pro Asp Glu Leu Leu Phe Ala Asp Asp
        450                 455                 460

Ser Ser Glu Gly Ser Glu Val Leu Met
465                 470
```

<210> SEQ ID NO 60

<400> SEQUENCE: 60

000

<210> SEQ ID NO 61

<400> SEQUENCE: 61

000

<210> SEQ ID NO 62
<211> LENGTH: 42
<212> TYPE: PRT
<213> ORGANISM: Homo sapiens
<220> FEATURE:
<223> OTHER INFORMATION: FcepsilonRIgamma signaling domain

<400> SEQUENCE: 62

Arg Leu Lys Ile Gln Val Arg Lys Ala Ala Ile Thr Ser Tyr Glu Lys
1               5                   10                  15

Ser Asp Gly Val Tyr Thr Gly Leu Ser Thr Arg Asn Gln Glu Thr Tyr
            20                  25                  30

Glu Thr Leu Lys His Glu Lys Pro Pro Gln
        35                  40

<210> SEQ ID NO 63
<211> LENGTH: 61
<212> TYPE: PRT
<213> ORGANISM: Homo sapiens
<220> FEATURE:
<223> OTHER INFORMATION: FcgammaR1 signaling domain

<400> SEQUENCE: 63

Arg Lys Glu Leu Lys Arg Lys Lys Lys Trp Asp Leu Glu Ile Ser Leu
1               5                   10                  15

Asp Ser Gly His Glu Lys Lys Val Ile Ser Ser Leu Gln Glu Asp Arg
            20                  25                  30

His Leu Glu Glu Glu Leu Lys Cys Gln Glu Gln Lys Glu Glu Gln Leu
        35                  40                  45

Gln Glu Gly Val His Arg Lys Glu Pro Gln Gly Ala Thr
    50                  55                  60

<210> SEQ ID NO 64
<211> LENGTH: 77
<212> TYPE: PRT
<213> ORGANISM: Homo sapiens
<220> FEATURE:
<223> OTHER INFORMATION: FcgammaR2A signaling domain

<400> SEQUENCE: 64

Cys Arg Lys Lys Arg Ile Ser Ala Asn Ser Thr Asp Pro Val Lys Ala
1               5                   10                  15

Ala Gln Phe Glu Pro Pro Gly Arg Gln Met Ile Ala Ile Arg Lys Arg
            20                  25                  30

Gln Leu Glu Glu Thr Asn Asn Asp Tyr Glu Thr Ala Asp Gly Gly Tyr
        35                  40                  45

Met Thr Leu Asn Pro Arg Ala Pro Thr Asp Asp Asp Lys Asn Ile Tyr
    50                  55                  60

Leu Thr Leu Pro Pro Asn Asp His Val Asn Ser Asn Asn
65                  70                  75

<210> SEQ ID NO 65
<211> LENGTH: 77

```
<212> TYPE: PRT
<213> ORGANISM: Homo sapiens
<220> FEATURE:
<223> OTHER INFORMATION: FcgammaR2c signaling domain

<400> SEQUENCE: 65

Cys Arg Lys Lys Arg Ile Ser Ala Asn Ser Thr Asp Pro Val Lys Ala
1               5                   10                  15

Ala Gln Phe Glu Pro Pro Gly Arg Gln Met Ile Ala Ile Arg Lys Arg
            20                  25                  30

Gln Pro Glu Glu Thr Asn Asn Asp Tyr Glu Thr Ala Asp Gly Gly Tyr
        35                  40                  45

Met Thr Leu Asn Pro Arg Ala Pro Thr Asp Asp Asp Lys Asn Ile Tyr
    50                  55                  60

Leu Thr Leu Pro Pro Asn Asp His Val Asn Ser Asn Asn
65                  70                  75

<210> SEQ ID NO 66
<211> LENGTH: 25
<212> TYPE: PRT
<213> ORGANISM: Homo sapiens
<220> FEATURE:
<223> OTHER INFORMATION: FcgammaR3A signaling domain

<400> SEQUENCE: 66

Lys Thr Asn Ile Arg Ser Ser Thr Arg Asp Trp Lys Asp His Lys Phe
1               5                   10                  15

Lys Trp Arg Lys Asp Pro Gln Asp Lys
            20                  25

<210> SEQ ID NO 67
<211> LENGTH: 85
<212> TYPE: PRT
<213> ORGANISM: Homo sapiens
<220> FEATURE:
<223> OTHER INFORMATION: BAFF-R signaling domain

<400> SEQUENCE: 67

Ser Trp Arg Arg Arg Gln Arg Arg Leu Arg Gly Ala Ser Ser Ala Glu
1               5                   10                  15

Ala Pro Asp Gly Asp Lys Asp Ala Pro Glu Pro Leu Asp Lys Val Ile
            20                  25                  30

Ile Leu Ser Pro Gly Ile Ser Asp Ala Thr Ala Pro Ala Trp Pro Pro
        35                  40                  45

Pro Gly Glu Asp Pro Gly Thr Thr Pro Pro Gly His Ser Val Pro Val
    50                  55                  60

Pro Ala Thr Glu Leu Gly Ser Thr Glu Leu Val Thr Thr Lys Thr Ala
65                  70                  75                  80

Gly Pro Glu Gln Gln
                85

<210> SEQ ID NO 68
<211> LENGTH: 52
<212> TYPE: PRT
<213> ORGANISM: Homo sapiens
<220> FEATURE:
<223> OTHER INFORMATION: DAP12 signaling domain

<400> SEQUENCE: 68

Tyr Phe Leu Gly Arg Leu Val Pro Arg Gly Arg Gly Ala Ala Glu Ala
1               5                   10                  15
```

Ala Thr Arg Lys Gln Arg Ile Thr Glu Thr Ser Pro Tyr Gln Glu
            20                  25                  30

Leu Gln Gly Gln Arg Ser Asp Val Tyr Ser Asp Leu Asn Thr Gln Arg
         35                  40                  45

Pro Tyr Tyr Lys
    50

<210> SEQ ID NO 69
<211> LENGTH: 86
<212> TYPE: PRT
<213> ORGANISM: Homo sapiens
<220> FEATURE:
<223> OTHER INFORMATION: NFAM1 signaling domain

<400> SEQUENCE: 69

Leu Trp Asn Lys Lys Arg Met Arg Gly Pro Gly Lys Asp Pro Thr Arg
1               5                   10                  15

Lys Cys Pro Asp Pro Arg Ser Ala Ser Ser Pro Lys Gln His Pro Ser
            20                  25                  30

Glu Ser Val Tyr Thr Ala Leu Gln Arg Arg Glu Thr Glu Val Tyr Ala
         35                  40                  45

Cys Ile Glu Asn Glu Asp Gly Ser Ser Pro Thr Ala Lys Gln Ser Pro
    50                  55                  60

Leu Ser Gln Glu Arg Pro His Arg Phe Glu Asp Asp Gly Glu Leu Asn
65                  70                  75                  80

Leu Val Tyr Glu Asn Leu
                85

<210> SEQ ID NO 70
<211> LENGTH: 29
<212> TYPE: PRT
<213> ORGANISM: Homo sapiens
<220> FEATURE:
<223> OTHER INFORMATION: truncated NFAM1 signaling domain

<400> SEQUENCE: 70

Ser Ser Pro Lys Gln His Pro Ser Glu Ser Val Tyr Thr Ala Leu Gln
1               5                   10                  15

Arg Arg Glu Thr Glu Val Tyr Ala Cys Ile Glu Asn Glu
            20                  25

<210> SEQ ID NO 71
<211> LENGTH: 29
<212> TYPE: PRT
<213> ORGANISM: Homo sapiens
<220> FEATURE:
<223> OTHER INFORMATION: CD79b truncated signaling domain (185-213)

<400> SEQUENCE: 71

Asp Ser Lys Ala Gly Met Glu Glu Asp His Thr Tyr Glu Gly Leu Asp
1               5                   10                  15

Ile Asp Gln Thr Ala Thr Tyr Glu Asp Ile Val Thr Leu
            20                  25

<210> SEQ ID NO 72
<211> LENGTH: 303
<212> TYPE: PRT
<213> ORGANISM: Homo sapiens
<220> FEATURE:
<223> OTHER INFORMATION: TRAF2 signaling domain

<400> SEQUENCE: 72

```
Met Ala Ala Ala Ser Val Thr Pro Pro Gly Ser Leu Glu Leu Leu Gln
  1               5                  10                  15

Pro Gly Phe Ser Lys Thr Leu Leu Gly Thr Lys Leu Glu Ala Lys Tyr
             20                  25                  30

Leu Cys Ser Ala Cys Arg Asn Val Leu Arg Arg Pro Phe Gln Ala Gln
             35                  40                  45

Cys Gly His Arg Tyr Cys Ser Phe Cys Leu Ala Ser Ile Leu Ser Ser
         50                  55                  60

Gly Pro Gln Asn Cys Ala Ala Cys Val His Glu Gly Ile Tyr Glu Glu
 65                  70                  75                  80

Gly Ile Ser Ile Leu Glu Ser Ser Ala Phe Pro Asp Asn Ala Ala
                 85                  90                  95

Arg Arg Glu Val Glu Ser Leu Pro Ala Val Cys Pro Ser Asp Gly Cys
                100                 105                 110

Thr Trp Lys Gly Thr Leu Lys Glu Tyr Glu Ser Cys His Glu Gly Arg
             115                 120                 125

Cys Pro Leu Met Leu Thr Glu Cys Pro Ala Cys Lys Gly Leu Val Arg
         130                 135                 140

Leu Gly Glu Lys Glu Arg His Leu Glu His Glu Cys Pro Glu Arg Ser
145                 150                 155                 160

Leu Ser Cys Arg His Cys Arg Ala Pro Cys Cys Gly Ala Asp Val Lys
                165                 170                 175

Ala His His Glu Val Cys Pro Lys Phe Pro Leu Thr Cys Asp Gly Cys
                180                 185                 190

Gly Lys Lys Lys Ile Pro Arg Glu Lys Phe Gln Asp His Val Lys Thr
             195                 200                 205

Cys Gly Lys Cys Arg Val Pro Cys Arg Phe His Ala Ile Gly Cys Leu
         210                 215                 220

Glu Thr Val Glu Gly Glu Lys Gln Gln Glu His Glu Val Gln Trp Leu
225                 230                 235                 240

Arg Glu His Leu Ala Met Leu Leu Ser Ser Val Leu Glu Ala Lys Pro
                245                 250                 255

Leu Leu Gly Asp Gln Ser His Ala Gly Ser Glu Leu Leu Gln Arg Cys
                260                 265                 270

Glu Ser Leu Glu Lys Lys Thr Ala Thr Phe Glu Asn Ile Val Cys Val
             275                 280                 285

Leu Asn Arg Glu Val Glu Arg Val Ala Met Thr Ala Glu Ala Cys
             290                 295                 300

<210> SEQ ID NO 73
<211> LENGTH: 274
<212> TYPE: PRT
<213> ORGANISM: Homo sapiens
<220> FEATURE:
<223> OTHER INFORMATION: TRAF3 signaling domain

<400> SEQUENCE: 73

Met Glu Ser Ser Lys Lys Met Asp Ser Pro Gly Ala Leu Gln Thr Asn
  1               5                  10                  15

Pro Pro Leu Lys Leu His Thr Asp Arg Ser Ala Gly Thr Pro Val Phe
             20                  25                  30

Val Pro Glu Gln Gly Gly Tyr Lys Glu Lys Phe Val Lys Thr Val Glu
             35                  40                  45

Asp Lys Tyr Lys Cys Glu Lys Cys His Leu Val Leu Cys Ser Pro Lys
         50                  55                  60
```

```
Gln Thr Glu Cys Gly His Arg Phe Cys Glu Ser Cys Met Ala Ala Leu
 65                  70                  75                  80

Leu Ser Ser Ser Pro Lys Cys Thr Ala Cys Gln Glu Ser Ile Val
                 85                  90                  95

Lys Asp Lys Val Phe Lys Asp Asn Cys Cys Lys Arg Glu Ile Leu Ala
            100                 105                 110

Leu Gln Ile Tyr Cys Arg Asn Glu Ser Arg Gly Cys Ala Glu Gln Leu
            115                 120                 125

Met Leu Gly His Leu Leu Val His Leu Lys Asn Asp Cys His Phe Glu
130                 135                 140

Glu Leu Pro Cys Val Arg Pro Asp Cys Lys Glu Lys Val Leu Arg Lys
145                 150                 155                 160

Asp Leu Arg Asp His Val Glu Lys Ala Cys Lys Tyr Arg Glu Ala Thr
                165                 170                 175

Cys Ser His Cys Lys Ser Gln Val Pro Met Ile Ala Leu Gln Lys His
            180                 185                 190

Glu Asp Thr Asp Cys Pro Cys Val Val Ser Cys Pro His Lys Cys
            195                 200                 205

Ser Val Gln Thr Leu Leu Arg Ser Glu Leu Ser Ala His Leu Ser Glu
210                 215                 220

Cys Val Asn Ala Pro Ser Thr Cys Ser Phe Lys Arg Tyr Gly Cys Val
225                 230                 235                 240

Phe Gln Gly Thr Asn Gln Ile Lys His Glu Ala Ser Ser Ala
                245                 250                 255

Val Gln His Val Asn Leu Leu Lys Glu Trp Ser Asn Ser Leu Glu Lys
            260                 265                 270

Lys Val
```

<210> SEQ ID NO 74
<211> LENGTH: 1566
<212> TYPE: DNA
<213> ORGANISM: Homo sapiens
<220> FEATURE:
<221> NAME/KEY: misc_feature
<223> OTHER INFORMATION: Traf6 signaling domain - full length

<400> SEQUENCE: 74

| | | | | | |
|---|---|---|---|---|---|
| atgtcactcc | ttaactgcga | aaacagttgt | gggagttcac | aatccgaaag | tgattgttgc | 60 |
| gtggcgatgg | cgtcttcatg | ctctgcggtt | accaaggatg | actctgtggg | aggcaccgca | 120 |
| tctaccggaa | atctgagctc | ttcttttatg | gaggaaattc | agggctacga | cgttgagttt | 180 |
| gatcctcctc | tcgaatctaa | gtatgagtgc | cccatatgtc | tcatggcgtt | gagagaagca | 240 |
| gtgcagactc | cgtgcggaca | tcgcttctgc | aaggcgtgta | ttataaagag | tatacgcgat | 300 |
| gcgggtcaca | aatgtccagt | ggacaacgag | atactgcttg | aaaatcaact | tttccccgac | 360 |
| aattttgcaa | agagagagat | actgtctttg | atggttaagt | gtccaaacga | gggctgcttg | 420 |
| cacaaaatgg | aactccgaca | ccttgaagac | caccaggcac | actgcgagtt | cgccctcatg | 480 |
| gattgcccac | aatgccagcg | cccgttccaa | agtttcaca | taaacatcca | catactgaag | 540 |
| gactgtccta | ggagacaagt | aagctgtgac | aattgcgcag | cgtcaatggc | gttcgaggac | 600 |
| aaggagatac | acgatcaaaa | ctgtcctctg | gcgaatgtga | tctgcgaata | ttgcaatacg | 660 |
| atcttgatcc | gcgaacagat | gcctaatcat | tacgacctcg | attgtccgac | cgcgccaatt | 720 |
| ccttgtactt | ttctacccnt | cggatgtcat | gagaaaatgc | aacgaaatca | cctggctcgc | 780 |
| catcttcagg | agaatactca | gagccacatg | cgcatgttgg | ctcaagccgt | acatagcctt | 840 |

-continued

```
agcgtaatac cggactcagg ttatatatcc gaagtacgga attttcaaga aaccatacat    900
caacttgaag gaaggttggt acgacaggat catcagatac gcgaattgac ggccaagatg    960
gaaacccaga gcatgtatgt cagtgagctt aagcgcacta tccgaaccct ggaggataaa    1020
gttgccgaaa tcgaagctca acaatgcaac gggatataca tttggaaaat aggtaacttc    1080
ggaatgcacc tgaagtgtca agaagaagaa aaacctgtcg ttattcattc ccccggcttt    1140
tatacaggga agcctgggta taagctttgc atgaggctcc acctccaatt gccgacggcg    1200
caaaggtgcg caaattacat ttctctgttt gtccatacta tgcagggtga gtacgatagt    1260
cacttgccgt ggcccttcca gggtaccata cgattgacca tcctggatca gagcgaggcc    1320
cccgtgcgac agaatcatga agaaataatg gatgctaagc cggaactgct cgctttccag    1380
agacctacaa ttccgcgaaa tcctaagggt tttggctatg ttacgttcat gcatctggaa    1440
gcactcagac aaagaacatt cattaaagat gacaccttgc ttgtgcggtg tgaggtgtca    1500
accaggttcg acatgggatc tctcagacgg gaggggttcc aaccgcgctc tacagacgct    1560
ggagtg                                                                1566
```

<210> SEQ ID NO 75
<211> LENGTH: 45
<212> TYPE: PRT
<213> ORGANISM: Homo sapiens
<220> FEATURE:
<223> OTHER INFORMATION: CD79b signaling domain (185-229)

<400> SEQUENCE: 75

```
Asp Ser Lys Ala Gly Met Glu Glu Asp His Thr Tyr Glu Gly Leu Asp
1               5                   10                  15

Ile Asp Gln Thr Ala Thr Tyr Glu Asp Ile Val Thr Leu Arg Thr Gly
            20                  25                  30

Glu Val Lys Trp Ser Val Gly Glu His Pro Gly Gln Glu
        35                  40                  45
```

<210> SEQ ID NO 76
<211> LENGTH: 141
<212> TYPE: PRT
<213> ORGANISM: Homo sapiens
<220> FEATURE:
<223> OTHER INFORMATION: MyD88 TIR domain

<400> SEQUENCE: 76

```
His Met Pro Glu Arg Phe Asp Ala Phe Ile Cys Tyr Cys Pro Ser Asp
1               5                   10                  15

Ile Gln Phe Val Gln Glu Met Ile Arg Gln Leu Glu Gln Thr Asn Tyr
            20                  25                  30

Arg Leu Lys Leu Cys Val Ser Asp Arg Asp Val Leu Pro Gly Thr Cys
        35                  40                  45

Val Trp Ser Ile Ala Ser Glu Leu Ile Glu Lys Arg Cys Arg Arg Met
    50                  55                  60

Val Val Val Val Ser Asp Asp Tyr Leu Gln Ser Lys Glu Cys Asp Phe
65                  70                  75                  80

Gln Thr Lys Phe Ala Leu Ser Leu Ser Pro Gly Ala His Gln Lys Arg
                85                  90                  95

Leu Ile Pro Ile Lys Tyr Lys Ala Met Lys Lys Glu Phe Pro Ser Ile
            100                 105                 110

Leu Arg Phe Ile Thr Val Cys Asp Tyr Thr Asn Pro Cys Thr Lys Ser
        115                 120                 125
```

```
Trp Phe Trp Thr Arg Leu Ala Lys Ala Leu Ser Leu Pro
    130                 135                 140
```

```
<210> SEQ ID NO 77
<211> LENGTH: 183
<212> TYPE: DNA
<213> ORGANISM: Homo sapiens
<220> FEATURE:
<221> NAME/KEY: misc_feature
<223> OTHER INFORMATION: FcgammaR1 signaling domain

<400> SEQUENCE: 77
agaaaggaac tcaagcgcaa gaagaagtgg gacctggaga tttctctcga ctccggtcac    60
gaaaagaagg tcatcagtag cttgcaagag gaccgacact tggaagaaga acttaaatgc   120
caggaacaga agaggagca gctccaggag ggagtccacc ggaaagaacc acagggagca    180
act                                                                 183

<210> SEQ ID NO 78
<211> LENGTH: 231
<212> TYPE: DNA
<213> ORGANISM: Homo sapiens
<220> FEATURE:
<221> NAME/KEY: misc_feature
<223> OTHER INFORMATION: FcgammaR2A signaling domain

<400> SEQUENCE: 78
tgtcgaaaga agcggatttc agccaatagt acagacccag tgaaagccgc tcaatttgag    60
ccacccggtc gacagatgat cgcaattagg aaacgccaac tggaggaaac gaataatgat   120
tacgaaacgg cagatggggg ctacatgacg ctcaatccta gagctccgac cgacgacgac   180
aagaatatat atctgactct ccctcccaac gaccacgtaa acagtaataa c             231

<210> SEQ ID NO 79
<211> LENGTH: 231
<212> TYPE: DNA
<213> ORGANISM: Homo sapiens
<220> FEATURE:
<221> NAME/KEY: misc_feature
<223> OTHER INFORMATION: FcgammaR2C signaling domain

<400> SEQUENCE: 79
tgcagaaaga agcggataag tgcaaatagt actgatcccg ttaaagcagc acaatttgag    60
ccgccaggac ggcaaatgat tgcaatcaga aaacgacaac ccgaggaaac caataatgac   120
tacgagaccg ctgacggagg gtatatgacg ttgaatcccc gcgcaccaac ggatgacgat   180
aagaacattt atcttacgct gcccctaac gatcatgtga atagcaataa c             231

<210> SEQ ID NO 80
<211> LENGTH: 75
<212> TYPE: DNA
<213> ORGANISM: Homo sapiens
<220> FEATURE:
<221> NAME/KEY: misc_feature
<223> OTHER INFORMATION: FcgammaR3A signaling domain

<400> SEQUENCE: 80
aaaacaaata tccggtcctc tacgagggac tggaaagatc ataaattcaa gtggagaaaa    60
gatcctcagg ataaa                                                    75

<210> SEQ ID NO 81
<211> LENGTH: 487
```

```
<212> TYPE: PRT
<213> ORGANISM: Artificial Sequence
<220> FEATURE:
<223> OTHER INFORMATION: CER05 chimeric engulfment receptor
<220> FEATURE:
<221> NAME/KEY: sig_peptide
<222> LOCATION: 1...22

<400> SEQUENCE: 81
```

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Lys Phe Tyr Phe
290                 295                 300

His Leu Met Leu Leu Ala Gly Cys Ile Lys Tyr Gly Arg Gly Glu Asn
305                 310                 315                 320

Ile Tyr Asp Ala Phe Val Ile Tyr Ser Ser Gln Asp Glu Asp Trp Val
                325                 330                 335

Arg Asn Glu Leu Val Lys Asn Leu Glu Glu Gly Val Pro Pro Phe Gln
            340                 345                 350

Leu Cys Leu His Tyr Arg Asp Phe Ile Pro Gly Val Ala Ile Ala Ala
        355                 360                 365

-continued

```
Asn Ile Ile His Glu Gly Phe His Lys Ser Arg Lys Val Ile Val Val
370                 375                 380

Val Ser Gln His Phe Ile Gln Ser Arg Trp Cys Ile Phe Glu Tyr Glu
385                 390                 395                 400

Ile Ala Gln Thr Trp Gln Phe Leu Ser Ser Arg Ala Gly Ile Ile Phe
            405                 410                 415

Ile Val Leu Gln Lys Val Glu Lys Thr Leu Arg Gln Gln Val Glu
            420                 425                 430

Leu Tyr Arg Leu Leu Ser Arg Asn Thr Tyr Leu Glu Trp Glu Asp Ser
            435                 440                 445

Val Leu Gly Arg His Ile Phe Trp Arg Leu Arg Lys Ala Leu Leu
450                 455                 460

Asp Gly Lys Ser Trp Asn Pro Glu Gly Thr Val Gly Thr Gly Cys Asn
465                 470                 475                 480

Trp Gln Glu Ala Thr Ser Ile
                485

<210> SEQ ID NO 82
<211> LENGTH: 487
<212> TYPE: PRT
<213> ORGANISM: Artificial Sequence
<220> FEATURE:
<223> OTHER INFORMATION: CER06 chimeric engulfment receptor
<220> FEATURE:
<221> NAME/KEY: sig_peptide
<222> LOCATION: 1...22

<400> SEQUENCE: 82

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Lys Pro Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220
```

```
Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
            260                 265                 270

Gln Ile Asn Ser Arg Gln Thr Thr Ile Ile Gly Val Ser Val Leu Ser
            275                 280                 285

Val Leu Val Val Ser Val Val Ala Val Leu Val Tyr Lys Phe Tyr Phe
            290                 295                 300

His Leu Met Leu Leu Ala Gly Cys Ile Lys Tyr Gly Arg Gly Glu Asn
305                 310                 315                 320

Ile Tyr Asp Ala Phe Val Ile Tyr Ser Ser Gln Asp Glu Asp Trp Val
            325                 330                 335

Arg Asn Glu Leu Val Lys Asn Leu Glu Glu Gly Val Pro Pro Phe Gln
            340                 345                 350

Leu Cys Leu His Tyr Arg Asp Phe Ile Pro Gly Val Ala Ile Ala Ala
            355                 360                 365

Asn Ile Ile His Glu Gly Phe His Lys Ser Arg Lys Val Ile Val Val
370                 375                 380

Val Ser Gln His Phe Ile Gln Ser Arg Trp Cys Ile Phe Glu Tyr Glu
385                 390                 395                 400

Ile Ala Gln Thr Trp Gln Phe Leu Ser Ser Arg Ala Gly Ile Ile Phe
            405                 410                 415

Ile Val Leu Gln Lys Val Glu Lys Thr Leu Leu Arg Gln Gln Val Glu
            420                 425                 430

Leu Tyr Arg Leu Leu Ser Arg Asn Thr Tyr Leu Glu Trp Glu Asp Ser
            435                 440                 445

Val Leu Gly Arg His Ile Phe Trp Arg Arg Leu Arg Lys Ala Leu Leu
            450                 455                 460

Asp Gly Lys Ser Trp Asn Pro Glu Gly Thr Val Gly Thr Gly Cys Asn
465                 470                 475                 480

Trp Gln Glu Ala Thr Ser Ile
                485

<210> SEQ ID NO 83
<211> LENGTH: 500
<212> TYPE: PRT
<213> ORGANISM: Artificial Sequence
<220> FEATURE:
<223> OTHER INFORMATION: CER07 chimeric engulfment receptor
<220> FEATURE:
<221> NAME/KEY: sig_peptide
<222> LOCATION: 1...22

<400> SEQUENCE: 83

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
            50                  55                  60

Asn Ala Glu Leu Leu Arg Thr Asp Gly Thr Arg Ile Ile Ser Arg Lys
65                  70                  75                  80
```

```
Ser Thr Lys Tyr Thr Leu Leu Gly Lys Val Gln Phe Gly Glu Val Ser
                85                  90                  95
Leu Thr Ile Ser Asn Thr Asn Arg Gly Asp Ser Gly Val Tyr Cys Cys
            100                 105                 110
Arg Ile Glu Val Pro Gly Trp Phe Asn Asp Val Lys Lys Asn Val Arg
        115                 120                 125
Leu Glu Leu Arg Arg Ala Thr Thr Lys Lys Pro Thr Thr Thr Thr Thr
    130                 135                 140
Arg Pro Thr Thr Thr Pro Tyr Val Thr Thr Thr Thr Pro Glu Leu Leu
145                 150                 155                 160
Pro Thr Thr Val Met Thr Thr Ser Val Leu Pro Thr Thr Thr Pro Pro
                165                 170                 175
Gln Thr Leu Ala Thr Thr Ala Phe Ser Thr Ala Val Thr Thr Cys Pro
            180                 185                 190
Ser Thr Thr Pro Gly Ser Phe Ser Gln Glu Thr Thr Lys Gly Ser Ala
        195                 200                 205
Phe Thr Thr Glu Ser Glu Thr Leu Pro Ala Ser Asn His Ser Gln Arg
    210                 215                 220
Ser Met Met Thr Ile Ser Thr Asp Ile Ala Val Leu Arg Pro Thr Gly
225                 230                 235                 240
Ser Asn Pro Gly Ile Leu Pro Ser Thr Ser Gln Leu Thr Thr Gln Lys
                245                 250                 255
Thr Thr Leu Thr Thr Ser Glu Ser Leu Gln Lys Thr Thr Lys Ser His
            260                 265                 270
Gln Ile Asn Ser Arg Gln Thr Pro Val Leu Ser Leu Asn Ile Thr Cys
        275                 280                 285
Gln Met Asn Lys Thr Ile Ile Gly Val Ser Val Leu Ser Val Leu Val
    290                 295                 300
Val Ser Val Val Ala Val Leu Val Tyr Lys Phe Tyr Phe His Leu Met
305                 310                 315                 320
Leu Leu Ala Gly Cys Ile Lys Tyr Gly Arg Gly Glu Asn Ile Tyr Asp
                325                 330                 335
Ala Phe Val Ile Tyr Ser Ser Gln Asp Glu Asp Trp Val Arg Asn Glu
            340                 345                 350
Leu Val Lys Asn Leu Glu Glu Gly Val Pro Pro Phe Gln Leu Cys Leu
        355                 360                 365
His Tyr Arg Asp Phe Ile Pro Gly Val Ala Ile Ala Ala Asn Ile Ile
    370                 375                 380
His Glu Gly Phe His Lys Ser Arg Lys Val Ile Val Val Val Ser Gln
385                 390                 395                 400
His Phe Ile Gln Ser Arg Trp Cys Ile Phe Glu Tyr Glu Ile Ala Gln
                405                 410                 415
Thr Trp Gln Phe Leu Ser Ser Arg Ala Gly Ile Ile Phe Ile Val Leu
            420                 425                 430
Gln Lys Val Glu Lys Thr Leu Leu Arg Gln Val Glu Leu Tyr Arg
        435                 440                 445
Leu Leu Ser Arg Asn Thr Tyr Leu Glu Trp Glu Asp Ser Val Leu Gly
    450                 455                 460
Arg His Ile Phe Trp Arg Arg Leu Arg Lys Ala Leu Leu Asp Gly Lys
465                 470                 475                 480
Ser Trp Asn Pro Glu Gly Thr Val Gly Thr Gly Cys Asn Trp Gln Glu
                485                 490                 495
Ala Thr Ser Ile
```

<210> SEQ ID NO 84
<211> LENGTH: 479
<212> TYPE: PRT
<213> ORGANISM: Artificial Sequence
<220> FEATURE:
<223> OTHER INFORMATION: CER17 chimeric engulfment receptor
<220> FEATURE:
<221> NAME/KEY: sig_peptide
<222> LOCATION: 1...22

<400> SEQUENCE: 84

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Glu Gly Trp Arg
    290                 295                 300

Ile Ser Phe Tyr Trp Asn Val Ser Val His Arg Val Leu Gly Phe Lys
305                 310                 315                 320

Glu Ile Asp Arg Gln Thr Glu Gln Phe Glu Tyr Ala Ala Tyr Ile Ile
                325                 330                 335

His Ala Tyr Lys Asp Lys Asp Trp Val Trp Glu His Phe Ser Ser Met
```

```
                340                 345                 350
Glu Lys Glu Asp Gln Ser Leu Lys Phe Cys Leu Glu Glu Arg Asp Phe
            355                 360                 365

Glu Ala Gly Val Phe Glu Leu Glu Ala Ile Val Asn Ser Ile Lys Arg
        370                 375                 380

Ser Arg Lys Ile Ile Phe Val Ile Thr His His Leu Leu Lys Asp Pro
385                 390                 395                 400

Leu Cys Lys Arg Phe Lys Val His His Ala Val Gln Gln Ala Ile Glu
            405                 410                 415

Gln Asn Leu Asp Ser Ile Ile Leu Val Phe Leu Glu Glu Ile Pro Asp
        420                 425                 430

Tyr Lys Leu Asn His Ala Leu Cys Leu Arg Arg Gly Met Phe Lys Ser
            435                 440                 445

His Cys Ile Leu Asn Trp Pro Val Gln Lys Glu Arg Ile Gly Ala Phe
        450                 455                 460

Arg His Lys Leu Gln Val Ala Leu Gly Ser Lys Asn Ser Val His
465                 470                 475

<210> SEQ ID NO 85
<211> LENGTH: 479
<212> TYPE: PRT
<213> ORGANISM: Artificial Sequence
<220> FEATURE:
<223> OTHER INFORMATION: CER18 chimeric engulfment receptor
<220> FEATURE:
<221> NAME/KEY: sig_peptide
<222> LOCATION: 1...22

<400> SEQUENCE: 85

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
            85                  90                  95

Leu Thr Ile Ser Asn Thr Asn Arg Gly Asp Ser Gly Val Tyr Cys Cys
        100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
        130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
            165                 170                 175

Gln Thr Leu Ala Thr Thr Ala Phe Ser Thr Ala Val Thr Thr Cys Pro
        180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
```

```
Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Phe Phe Met Ile Asn Thr Ser Ile Leu
        275                 280                 285

Leu Ile Phe Ile Phe Ile Val Leu Leu Ile His Phe Glu Gly Trp Arg
    290                 295                 300

Ile Ser Phe Tyr Trp Asn Val Ser Val His Arg Val Leu Gly Phe Lys
305                 310                 315                 320

Glu Ile Asp Arg Gln Thr Glu Gln Phe Glu Tyr Ala Ala Tyr Ile Ile
                325                 330                 335

His Ala Tyr Lys Asp Lys Asp Trp Val Trp Glu His Phe Ser Ser Met
                340                 345                 350

Glu Lys Glu Asp Gln Ser Leu Lys Phe Cys Leu Glu Glu Arg Asp Phe
            355                 360                 365

Glu Ala Gly Val Phe Glu Leu Glu Ala Ile Val Asn Ser Ile Lys Arg
        370                 375                 380

Ser Arg Lys Ile Ile Phe Val Ile Thr His His Leu Leu Lys Asp Pro
385                 390                 395                 400

Leu Cys Lys Arg Phe Lys Val His His Ala Val Gln Gln Ala Ile Glu
                405                 410                 415

Gln Asn Leu Asp Ser Ile Ile Leu Val Phe Leu Glu Glu Ile Pro Asp
                420                 425                 430

Tyr Lys Leu Asn His Ala Leu Cys Leu Arg Arg Gly Met Phe Lys Ser
            435                 440                 445

His Cys Ile Leu Asn Trp Pro Val Gln Lys Glu Arg Ile Gly Ala Phe
        450                 455                 460

Arg His Lys Leu Gln Val Ala Leu Gly Ser Lys Asn Ser Val His
465                 470                 475
```

<210> SEQ ID NO 86
<211> LENGTH: 498
<212> TYPE: PRT
<213> ORGANISM: Artificial Sequence
<220> FEATURE:
<223> OTHER INFORMATION: CER19 chimeric engulfment receptor
<220> FEATURE:
<221> NAME/KEY: sig_peptide
<222> LOCATION: 1...22

<400> SEQUENCE: 86

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
```

```
                     85                  90                  95
Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Lys Lys Pro Thr Thr Thr Thr Thr
                130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
                210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ala Cys Cys Val Gly
                275                 280                 285

Phe Val Leu Met Val Leu Leu Phe Leu Ala Phe Leu Thr Lys Phe Arg
                290                 295                 300

Gly Phe Cys Phe Ile Cys Tyr Lys Thr Ala Gln Arg Leu Val Phe Lys
305                 310                 315                 320

Asp His Pro Gln Gly Thr Glu Pro Asp Met Tyr Lys Tyr Asp Ala Tyr
                325                 330                 335

Leu Cys Phe Ser Ser Lys Asp Phe Thr Trp Val Gln Asn Ala Leu Leu
                340                 345                 350

Lys His Leu Asp Thr Gln Tyr Ser Asp Gln Asn Arg Phe Asn Leu Cys
                355                 360                 365

Phe Glu Glu Arg Asp Phe Val Pro Gly Glu Asn Arg Ile Ala Asn Ile
                370                 375                 380

Gln Asp Ala Ile Trp Asn Ser Arg Lys Ile Val Cys Leu Val Ser Arg
385                 390                 395                 400

His Phe Leu Arg Asp Gly Trp Cys Leu Glu Ala Phe Ser Tyr Ala Gln
                405                 410                 415

Gly Arg Cys Leu Ser Asp Leu Asn Ser Ala Leu Ile Met Val Val Val
                420                 425                 430

Gly Ser Leu Ser Gln Tyr Gln Leu Met Lys His Gln Ser Ile Arg Gly
                435                 440                 445

Phe Val Gln Lys Gln Gln Tyr Leu Arg Trp Pro Glu Asp Phe Gln Asp
                450                 455                 460

Val Gly Trp Phe Leu His Lys Leu Ser Gln Gln Ile Leu Lys Lys Glu
465                 470                 475                 480

Lys Glu Lys Lys Lys Asp Asn Asn Ile Pro Leu Gln Thr Val Ala Thr
                485                 490                 495

Ile Ser
```

<210> SEQ ID NO 87
<211> LENGTH: 498
<212> TYPE: PRT
<213> ORGANISM: Artificial Sequence
<220> FEATURE:
<223> OTHER INFORMATION: CER20 chimeric engulfment receptor
<220> FEATURE:
<221> NAME/KEY: sig_peptide
<222> LOCATION: 1...22

<400> SEQUENCE: 87

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Phe Ser Leu Phe Ile Val Cys Thr Val
        275                 280                 285

Thr Leu Thr Leu Phe Leu Met Thr Ile Leu Thr Val Thr Lys Phe Arg
    290                 295                 300

Gly Phe Cys Phe Ile Cys Tyr Lys Thr Ala Gln Arg Leu Val Phe Lys
305                 310                 315                 320

Asp His Pro Gln Gly Thr Glu Pro Asp Met Tyr Lys Tyr Asp Ala Tyr
                325                 330                 335

Leu Cys Phe Ser Ser Lys Asp Phe Thr Trp Val Gln Asn Ala Leu Leu
            340                 345                 350
```

```
Lys His Leu Asp Thr Gln Tyr Ser Asp Gln Asn Arg Phe Asn Leu Cys
            355                 360                 365

Phe Glu Glu Arg Asp Phe Val Pro Gly Glu Asn Arg Ile Ala Asn Ile
    370                 375                 380

Gln Asp Ala Ile Trp Asn Ser Arg Lys Ile Val Cys Leu Val Ser Arg
385                 390                 395                 400

His Phe Leu Arg Asp Gly Trp Cys Leu Glu Ala Phe Ser Tyr Ala Gln
                405                 410                 415

Gly Arg Cys Leu Ser Asp Leu Asn Ser Ala Leu Ile Met Val Val
            420                 425                 430

Gly Ser Leu Ser Gln Tyr Gln Leu Met Lys His Gln Ser Ile Arg Gly
            435                 440                 445

Phe Val Gln Lys Gln Gln Tyr Leu Arg Trp Pro Glu Asp Phe Gln Asp
    450                 455                 460

Val Gly Trp Phe Leu His Lys Leu Ser Gln Gln Ile Leu Lys Lys Glu
465                 470                 475                 480

Lys Glu Lys Lys Lys Asp Asn Asn Ile Pro Leu Gln Thr Val Ala Thr
                485                 490                 495

Ile Ser

<210> SEQ ID NO 88
<211> LENGTH: 493
<212> TYPE: PRT
<213> ORGANISM: Artificial Sequence
<220> FEATURE:
<223> OTHER INFORMATION: CER21 chimeric engulfment receptor
<220> FEATURE:
<221> NAME/KEY: sig_peptide
<222> LOCATION: 1...22

<400> SEQUENCE: 88

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
    115                 120                 125

Leu Glu Leu Arg Arg Ala Thr Thr Thr Lys Pro Thr Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
```

```
                195                 200                 205
Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu His His Leu Phe
290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                325                 330                 335

Ser Tyr Asp Thr Lys Asp Ala Ser Val Thr Asp Trp Val Ile Asn Glu
            340                 345                 350

Leu Arg Tyr His Leu Glu Glu Ser Arg Asp Lys Asn Val Leu Leu Cys
            355                 360                 365

Leu Glu Glu Arg Asp Trp Asp Pro Gly Leu Ala Ile Ile Asp Asn Leu
370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                405                 410                 415

Gln Arg Leu Met Asp Glu Asn Met Asp Val Ile Ile Phe Ile Leu Leu
            420                 425                 430

Glu Pro Val Leu Gln His Ser Gln Tyr Leu Arg Leu Arg Gln Arg Ile
            435                 440                 445

Cys Lys Ser Ser Ile Leu Gln Trp Pro Asp Asn Pro Lys Ala Glu Gly
450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr
                485                 490

<210> SEQ ID NO 89
<211> LENGTH: 493
<212> TYPE: PRT
<213> ORGANISM: Artificial Sequence
<220> FEATURE:
<223> OTHER INFORMATION: CER22 chimeric engulfment receptor
<220> FEATURE:
<221> NAME/KEY: sig_peptide
<222> LOCATION: 1...22

<400> SEQUENCE: 89

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
```

```
                50                  55                  60
Asn Ala Glu Leu Leu Arg Thr Asp Gly Thr Arg Ile Ile Ser Arg Lys
 65                  70                  75                  80

Ser Thr Lys Tyr Thr Leu Leu Gly Lys Val Gln Phe Gly Glu Val Ser
                 85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
            115                 120                 125

Leu Glu Leu Arg Arg Ala Thr Thr Lys Lys Pro Thr Thr Thr Thr Thr
        130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
        210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ala Val Ile Leu Phe Phe Phe Thr Phe
            275                 280                 285

Phe Ile Thr Thr Met Val Met Leu Ala Ala Leu Ala His His Leu Phe
        290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                325                 330                 335

Ser Tyr Asp Thr Lys Asp Ala Ser Val Thr Asp Trp Val Ile Asn Glu
                340                 345                 350

Leu Arg Tyr His Leu Glu Glu Ser Arg Asp Lys Asn Val Leu Leu Cys
            355                 360                 365

Leu Glu Glu Arg Asp Trp Asp Pro Gly Leu Ala Ile Ile Asp Asn Leu
        370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                405                 410                 415

Gln Arg Leu Met Asp Glu Asn Met Asp Val Ile Ile Phe Ile Leu Leu
                420                 425                 430

Glu Pro Val Leu Gln His Ser Gln Tyr Leu Arg Leu Arg Gln Arg Ile
            435                 440                 445

Cys Lys Ser Ser Ile Leu Gln Trp Pro Asp Asn Pro Lys Ala Glu Gly
        450                 455                 460

Leu Phe Trp Gln Thr Leu Arg Asn Val Val Leu Thr Glu Asn Asp Ser
465                 470                 475                 480
```

Arg Tyr Asn Asn Met Tyr Val Asp Ser Ile Lys Gln Tyr
                485                 490

<210> SEQ ID NO 90
<211> LENGTH: 493
<212> TYPE: PRT
<213> ORGANISM: Artificial Sequence
<220> FEATURE:
<223> OTHER INFORMATION: CER23 chimeric engulfment receptor
<220> FEATURE:
<221> NAME/KEY: sig_peptide
<222> LOCATION: 1...22

<400> SEQUENCE: 90

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
                35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ile Ala Cys Cys Val Gly
            275                 280                 285

Phe Val Leu Met Val Leu Leu Phe Leu Ala Phe Leu Gly Trp Asp Leu
290                 295                 300

Trp Tyr Cys Phe His Leu Cys Leu Ala Trp Leu Pro Trp Arg Gly Arg
305                 310                 315                 320

Gln Ser Gly Arg Asp Glu Asp Ala Leu Pro Tyr Asp Ala Phe Val Val
                325                 330                 335

```
Phe Asp Lys Thr Gln Ser Ala Val Ala Asp Trp Val Tyr Asn Glu Leu
            340                 345                 350

Arg Gly Gln Leu Glu Cys Arg Gly Arg Trp Ala Leu Arg Leu Cys
        355                 360                 365

Leu Glu Glu Arg Asp Trp Leu Pro Gly Lys Thr Leu Phe Glu Asn Leu
370                 375                 380

Trp Ala Ser Val Tyr Gly Ser Arg Lys Thr Leu Phe Val Leu Ala His
385                 390                 395                 400

Thr Asp Arg Val Ser Gly Leu Arg Ala Ser Phe Leu Leu Ala Gln
            405                 410                 415

Gln Arg Leu Leu Glu Asp Arg Lys Asp Val Val Leu Val Ile Leu
            420                 425                 430

Ser Pro Asp Gly Arg Arg Ser Arg Tyr Val Arg Leu Arg Gln Arg Leu
            435                 440                 445

Cys Arg Gln Ser Val Leu Leu Trp Pro His Gln Pro Ser Gly Gln Arg
450                 455                 460

Ser Phe Trp Ala Gln Leu Gly Met Ala Leu Thr Arg Asp Asn His His
465                 470                 475                 480

Phe Tyr Asn Arg Asn Phe Cys Gln Gly Pro Thr Ala Glu
            485                 490
```

<210> SEQ ID NO 91
<211> LENGTH: 493
<212> TYPE: PRT
<213> ORGANISM: Artificial Sequence
<220> FEATURE:
<223> OTHER INFORMATION: CER24 chimeric engulfment receptor
<220> FEATURE:
<221> NAME/KEY: sig_peptide
<222> LOCATION: 1...22

<400> SEQUENCE: 91

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Cys Pro
            180                 185                 190
```

```
Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Phe Ala Leu Ser Leu Leu Ala Val Ala
                275                 280                 285

Leu Gly Leu Gly Val Pro Met Leu His His Leu Cys Gly Trp Asp Leu
        290                 295                 300

Trp Tyr Cys Phe His Leu Cys Leu Ala Trp Leu Pro Trp Arg Gly Arg
305                 310                 315                 320

Gln Ser Gly Arg Asp Glu Asp Ala Leu Pro Tyr Asp Ala Phe Val Val
                325                 330                 335

Phe Asp Lys Thr Gln Ser Ala Val Ala Asp Trp Val Tyr Asn Glu Leu
            340                 345                 350

Arg Gly Gln Leu Glu Glu Cys Arg Gly Arg Trp Ala Leu Arg Leu Cys
                355                 360                 365

Leu Glu Glu Arg Asp Trp Leu Pro Gly Lys Thr Leu Phe Glu Asn Leu
        370                 375                 380

Trp Ala Ser Val Tyr Gly Ser Arg Lys Thr Leu Phe Val Leu Ala His
385                 390                 395                 400

Thr Asp Arg Val Ser Gly Leu Leu Arg Ala Ser Phe Leu Leu Ala Gln
                405                 410                 415

Gln Arg Leu Leu Glu Asp Arg Lys Asp Val Val Leu Val Ile Leu
            420                 425                 430

Ser Pro Asp Gly Arg Arg Ser Arg Tyr Val Arg Leu Arg Gln Arg Leu
        435                 440                 445

Cys Arg Gln Ser Val Leu Leu Trp Pro His Gln Pro Ser Gly Gln Arg
450                 455                 460

Ser Phe Trp Ala Gln Leu Gly Met Ala Leu Thr Arg Asp Asn His His
465                 470                 475                 480

Phe Tyr Asn Arg Asn Phe Cys Gln Gly Pro Thr Ala Glu
                485                 490
```

<210> SEQ ID NO 92
<211> LENGTH: 485
<212> TYPE: PRT
<213> ORGANISM: Artificial Sequence
<220> FEATURE:
<223> OTHER INFORMATION: CER26 chimeric engulfment receptor
<220> FEATURE:
<221> NAME/KEY: sig_peptide
<222> LOCATION: 1...22

<400> SEQUENCE: 92

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45
```

-continued

```
Arg Asn Ser Met Cys Trp Gly Lys Gly Ser Cys Pro Asn Ser Lys Cys
    50              55              60

Asn Ala Glu Leu Leu Arg Thr Asp Gly Thr Arg Ile Ile Ser Arg Lys
65              70              75              80

Ser Thr Lys Tyr Thr Leu Leu Gly Lys Val Gln Phe Gly Glu Val Ser
                85              90              95

Leu Thr Ile Ser Asn Thr Asn Arg Gly Asp Ser Gly Val Tyr Cys Cys
            100             105             110

Arg Ile Glu Val Pro Gly Trp Phe Asn Asp Val Lys Lys Asn Val Arg
        115             120             125

Leu Glu Leu Arg Arg Ala Thr Thr Thr Lys Lys Pro Thr Thr Thr Thr
    130             135             140

Arg Pro Thr Thr Thr Pro Tyr Val Thr Thr Thr Pro Glu Leu Leu
145             150             155             160

Pro Thr Thr Val Met Thr Thr Ser Val Leu Pro Thr Thr Pro Pro
                165             170             175

Gln Thr Leu Ala Thr Thr Ala Phe Ser Thr Ala Val Thr Thr Cys Pro
            180             185             190

Ser Thr Thr Pro Gly Ser Phe Ser Gln Glu Thr Lys Gly Ser Ala
        195             200             205

Phe Thr Thr Glu Ser Glu Thr Leu Pro Ala Ser Asn His Ser Gln Arg
    210             215             220

Ser Met Met Thr Ile Ser Thr Asp Ile Ala Val Leu Arg Pro Thr Gly
225             230             235             240

Ser Asn Pro Gly Ile Leu Pro Ser Thr Ser Gln Leu Thr Thr Gln Lys
                245             250             255

Thr Thr Leu Thr Thr Ser Glu Ser Leu Gln Lys Thr Thr Lys Ser His
            260             265             270

Gln Ile Asn Ser Arg Gln Thr Ile Leu Ile Ile Ala Cys Cys Val Gly
        275             280             285

Phe Val Leu Met Val Leu Leu Phe Leu Ala Phe Leu Ser Tyr Leu Asp
    290             295             300

Leu Pro Trp Tyr Leu Arg Met Val Cys Gln Trp Thr Gln Thr Arg Arg
305             310             315             320

Arg Ala Arg Asn Ile Pro Leu Glu Glu Leu Gln Arg Asn Leu Gln Phe
                325             330             335

His Ala Phe Ile Ser Tyr Ser Gly His Asp Ser Phe Trp Val Lys Asn
            340             345             350

Glu Leu Leu Pro Asn Leu Glu Lys Glu Gly Met Gln Ile Cys Leu His
        355             360             365

Glu Arg Asn Phe Val Pro Gly Lys Ser Ile Val Glu Asn Ile Ile Thr
    370             375             380

Cys Ile Glu Lys Ser Tyr Lys Ser Ile Phe Val Leu Ser Pro Asn Phe
385             390             395             400

Val Gln Ser Glu Trp Cys His Tyr Glu Leu Tyr Phe Ala His His Asn
                405             410             415

Leu Phe His Glu Gly Ser Asn Ser Leu Ile Leu Ile Leu Leu Glu Pro
            420             425             430

Ile Pro Gln Tyr Ser Ile Pro Ser Ser Tyr His Lys Leu Lys Ser Leu
        435             440             445

Met Ala Arg Arg Thr Tyr Leu Glu Trp Pro Lys Glu Lys Ser Lys Arg
    450             455             460
```

-continued

```
Gly Leu Phe Trp Ala Asn Leu Arg Ala Ala Ile Asn Ile Lys Leu Thr
465                 470                 475                 480

Glu Gln Ala Lys Lys
                485

<210> SEQ ID NO 93
<211> LENGTH: 475
<212> TYPE: PRT
<213> ORGANISM: Artificial Sequence
<220> FEATURE:
<223> OTHER INFORMATION: CER27 chimeric engulfment receptor
<220> FEATURE:
<221> NAME/KEY: sig_peptide
<222> LOCATION: 1...22

<400> SEQUENCE: 93

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
                35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu His Arg Phe His
    290                 295                 300

Gly Leu Trp Tyr Met Lys Met Met Trp Ala Trp Leu Gln Ala Lys Arg
305                 310                 315                 320
```

```
Lys Pro Arg Lys Ala Pro Ser Arg Asn Ile Cys Tyr Asp Ala Phe Val
                325                 330                 335

Ser Tyr Ser Glu Arg Asp Ala Tyr Trp Val Glu Asn Leu Met Val Gln
            340                 345                 350

Glu Leu Glu Asn Phe Asn Pro Phe Lys Leu Cys Leu His Lys Arg
        355                 360                 365

Asp Phe Ile Pro Gly Lys Trp Ile Ile Asp Asn Ile Asp Ser Ile
370                 375                 380

Glu Lys Ser His Lys Thr Val Phe Val Leu Ser Glu Asn Phe Val Lys
385                 390                 395                 400

Ser Glu Trp Cys Lys Tyr Glu Leu Asp Phe Ser His Phe Arg Leu Phe
                405                 410                 415

Asp Glu Asn Asn Asp Ala Ala Ile Leu Ile Leu Leu Glu Pro Ile Glu
                420                 425                 430

Lys Lys Ala Ile Pro Gln Arg Phe Cys Lys Leu Arg Lys Ile Met Asn
                435                 440                 445

Thr Lys Thr Tyr Leu Glu Trp Pro Met Asp Gly Ala Gln Arg Glu Gly
            450                 455                 460

Phe Trp Val Asn Leu Arg Ala Ala Ile Lys Ser
465                 470                 475

<210> SEQ ID NO 94
<211> LENGTH: 489
<212> TYPE: PRT
<213> ORGANISM: Artificial Sequence
<220> FEATURE:
<223> OTHER INFORMATION: CER28 chimeric engulfment receptor
<220> FEATURE:
<221> NAME/KEY: sig_peptide
<222> LOCATION: 1...22

<400> SEQUENCE: 94

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr
        130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190
```

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu His Leu Tyr Phe
    290                 295                 300

Trp Asp Val Trp Tyr Ile Tyr His Phe Cys Lys Ala Lys Ile Lys Gly
305                 310                 315                 320

Tyr Gln Arg Leu Ile Ser Pro Asp Cys Cys Tyr Asp Ala Phe Ile Val
                325                 330                 335

Tyr Asp Thr Lys Asp Pro Ala Val Thr Glu Trp Val Leu Ala Glu Leu
            340                 345                 350

Val Ala Lys Leu Glu Asp Pro Arg Glu Lys His Phe Asn Leu Cys Leu
        355                 360                 365

Glu Glu Arg Asp Trp Leu Pro Gly Gln Pro Val Leu Glu Asn Leu Ser
    370                 375                 380

Gln Ser Ile Gln Leu Ser Lys Lys Thr Val Phe Val Met Thr Asp Lys
385                 390                 395                 400

Tyr Ala Lys Thr Glu Asn Phe Lys Ile Ala Phe Tyr Leu Ser His Gln
                405                 410                 415

Arg Leu Met Asp Glu Lys Val Asp Val Ile Ile Leu Ile Phe Leu Glu
            420                 425                 430

Lys Pro Phe Gln Lys Ser Lys Phe Leu Gln Leu Arg Lys Arg Leu Cys
        435                 440                 445

Gly Ser Ser Val Leu Glu Trp Pro Thr Asn Pro Gln Ala His Pro Tyr
    450                 455                 460

Phe Trp Gln Cys Leu Lys Asn Ala Leu Ala Thr Asp Asn His Val Ala
465                 470                 475                 480

Tyr Ser Gln Val Phe Lys Glu Thr Val
                485

<210> SEQ ID NO 95

<400> SEQUENCE: 95

000

<210> SEQ ID NO 96
<211> LENGTH: 603
<212> TYPE: PRT
<213> ORGANISM: Artificial Sequence
<220> FEATURE:
<223> OTHER INFORMATION: CER30 chimeric engulfment receptor
<220> FEATURE:
<221> NAME/KEY: sig_peptide
<222> LOCATION: 1...22

<400> SEQUENCE: 96

Met Ser Lys Gly Leu Leu Leu Leu Trp Leu Val Thr Glu Leu Trp Trp
1               5                   10                  15

```
Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr Thr
130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
        210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Met Ala Ala Ala
        290                 295                 300

Ser Val Thr Pro Pro Gly Ser Leu Glu Leu Leu Gln Pro Gly Phe Ser
305                 310                 315                 320

Lys Thr Leu Leu Gly Thr Lys Leu Glu Ala Lys Tyr Leu Cys Ser Ala
                325                 330                 335

Cys Arg Asn Val Leu Arg Arg Pro Phe Gln Ala Gln Cys Gly His Arg
                340                 345                 350

Tyr Cys Ser Phe Cys Leu Ala Ser Ile Leu Ser Ser Gly Pro Gln Asn
                355                 360                 365

Cys Ala Ala Cys Val His Glu Gly Ile Tyr Glu Gly Ile Ser Ile
        370                 375                 380

Leu Glu Ser Ser Ser Ala Phe Pro Asp Asn Ala Ala Arg Arg Glu Val
385                 390                 395                 400

Glu Ser Leu Pro Ala Val Cys Pro Ser Asp Gly Cys Thr Trp Lys Gly
                405                 410                 415

Thr Leu Lys Glu Tyr Glu Ser Cys His Glu Gly Arg Cys Pro Leu Met
                420                 425                 430
```

```
Leu Thr Glu Cys Pro Ala Cys Lys Gly Leu Val Arg Leu Gly Glu Lys
            435                 440                 445

Glu Arg His Leu Glu His Glu Cys Pro Glu Arg Ser Leu Ser Cys Arg
        450                 455                 460

His Cys Arg Ala Pro Cys Cys Gly Ala Asp Val Lys Ala His His Glu
465                 470                 475                 480

Val Cys Pro Lys Phe Pro Leu Thr Cys Asp Gly Cys Gly Lys Lys Lys
                485                 490                 495

Ile Pro Arg Glu Lys Phe Gln Asp His Val Lys Thr Cys Gly Lys Cys
            500                 505                 510

Arg Val Pro Cys Arg Phe His Ala Ile Gly Cys Leu Glu Thr Val Glu
        515                 520                 525

Gly Glu Lys Gln Gln Glu His Glu Val Gln Trp Leu Arg Glu His Leu
    530                 535                 540

Ala Met Leu Leu Ser Ser Val Leu Glu Ala Lys Pro Leu Leu Gly Asp
545                 550                 555                 560

Gln Ser His Ala Gly Ser Glu Leu Leu Gln Arg Cys Glu Ser Leu Glu
                565                 570                 575

Lys Lys Thr Ala Thr Phe Glu Asn Ile Val Cys Val Leu Asn Arg Glu
            580                 585                 590

Val Glu Arg Val Ala Met Thr Ala Glu Ala Cys
        595                 600

<210> SEQ ID NO 97
<211> LENGTH: 574
<212> TYPE: PRT
<213> ORGANISM: Artificial Sequence
<220> FEATURE:
<223> OTHER INFORMATION: CER31 chimeric engulfment receptor
<220> FEATURE:
<221> NAME/KEY: sig_peptide
<222> LOCATION: 1...22

<400> SEQUENCE: 97

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175
```

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
        210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Met Glu Ser Ser
290                 295                 300

Lys Lys Met Asp Ser Pro Gly Ala Leu Gln Thr Asn Pro Pro Leu Lys
305                 310                 315                 320

Leu His Thr Asp Arg Ser Ala Gly Thr Pro Val Phe Val Pro Glu Gln
                325                 330                 335

Gly Gly Tyr Lys Glu Lys Phe Val Lys Thr Val Glu Asp Lys Tyr Lys
            340                 345                 350

Cys Glu Lys Cys His Leu Val Leu Cys Ser Pro Lys Gln Thr Glu Cys
        355                 360                 365

Gly His Arg Phe Cys Glu Ser Cys Met Ala Ala Leu Leu Ser Ser Ser
    370                 375                 380

Ser Pro Lys Cys Thr Ala Cys Gln Glu Ser Ile Val Lys Asp Lys Val
385                 390                 395                 400

Phe Lys Asp Asn Cys Cys Lys Arg Glu Ile Leu Ala Leu Gln Ile Tyr
                405                 410                 415

Cys Arg Asn Glu Ser Arg Gly Cys Ala Glu Gln Leu Met Leu Gly His
            420                 425                 430

Leu Leu Val His Leu Lys Asn Asp Cys His Phe Glu Glu Leu Pro Cys
        435                 440                 445

Val Arg Pro Asp Cys Lys Glu Lys Val Leu Arg Lys Asp Leu Arg Asp
    450                 455                 460

His Val Glu Lys Ala Cys Lys Tyr Arg Glu Ala Thr Cys Ser His Cys
465                 470                 475                 480

Lys Ser Gln Val Pro Met Ile Ala Leu Gln Lys His Glu Asp Thr Asp
                485                 490                 495

Cys Pro Cys Val Val Ser Cys Pro His Lys Cys Ser Val Gln Thr
            500                 505                 510

Leu Leu Arg Ser Glu Leu Ser Ala His Leu Ser Glu Cys Val Asn Ala
        515                 520                 525

Pro Ser Thr Cys Ser Phe Lys Arg Tyr Gly Cys Val Phe Gln Gly Thr
    530                 535                 540

Asn Gln Gln Ile Lys Ala His Glu Ala Ser Ser Ala Val Gln His Val
545                 550                 555                 560

Asn Leu Leu Lys Glu Trp Ser Asn Ser Leu Glu Lys Lys Val
                565                 570

<210> SEQ ID NO 98
<211> LENGTH: 478
<212> TYPE: PRT

```
<213> ORGANISM: Artificial Sequence
<220> FEATURE:
<223> OTHER INFORMATION: CER42 chimeric engulfment receptor
<220> FEATURE:
<221> NAME/KEY: sig_peptide
<222> LOCATION: 1...22

<400> SEQUENCE: 98

Met Leu Leu Leu Val Thr Ser Leu Leu Leu Cys Glu Leu Pro His Pro
1               5                   10                  15

Ala Phe Leu Leu Ile Pro Gln Val Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
        115                 120                 125

Leu Glu Asp Ala Phe Asp Ile Trp Gly Gln Gly Thr Met Val Thr Val
    130                 135                 140

Ser Ser Gly Gly Gly Gly Ser Asp Ile Gln Met Thr Gln Ser Pro Ser
145                 150                 155                 160

Ser Leu Ser Ala Ser Val Gly Asp Arg Val Thr Ile Thr Cys Arg Ala
                165                 170                 175

Ser Gln Thr Ile Trp Ser Tyr Leu Asn Trp Tyr Gln Gln Arg Pro Gly
            180                 185                 190

Lys Ala Pro Asn Leu Leu Ile Tyr Ala Ala Ser Ser Leu Gln Ser Gly
        195                 200                 205

Val Pro Ser Arg Phe Ser Gly Arg Gly Ser Gly Thr Asp Phe Thr Leu
    210                 215                 220

Thr Ile Ser Ser Leu Gln Ala Glu Asp Phe Ala Thr Tyr Tyr Cys Gln
225                 230                 235                 240

Gln Ser Tyr Ser Ile Pro Gln Thr Phe Gly Gln Gly Thr Lys Leu Glu
                245                 250                 255

Ile Lys Glu Ser Lys Tyr Gly Pro Pro Cys Pro Pro Cys Pro Thr Ile
            260                 265                 270

Ile Gly Val Ser Val Leu Ser Val Leu Val Ser Val Val Ala Val
        275                 280                 285

Leu Val Tyr Lys Phe Tyr Phe His Leu Met Leu Leu Ala Gly Cys Ile
    290                 295                 300

Lys Tyr Gly Arg Gly Glu Asn Ile Tyr Asp Ala Phe Val Ile Tyr Ser
305                 310                 315                 320

Ser Gln Asp Glu Asp Trp Val Arg Asn Glu Leu Val Lys Asn Leu Glu
                325                 330                 335

Glu Gly Val Pro Pro Phe Gln Leu Cys Leu His Tyr Arg Asp Phe Ile
            340                 345                 350

Pro Gly Val Ala Ile Ala Ala Asn Ile Ile His Glu Gly Phe His Lys
        355                 360                 365

Ser Arg Lys Val Ile Val Val Val Ser Gln His Phe Ile Gln Ser Arg
```

```
                370                 375                 380
Trp Cys Ile Phe Glu Tyr Glu Ile Ala Gln Thr Trp Gln Phe Leu Ser
385                 390                 395                 400

Ser Arg Ala Gly Ile Ile Phe Ile Val Leu Gln Lys Val Glu Lys Thr
                405                 410                 415

Leu Leu Arg Gln Gln Val Glu Leu Tyr Arg Leu Leu Ser Arg Asn Thr
                420                 425                 430

Tyr Leu Glu Trp Glu Asp Ser Val Leu Gly Arg His Ile Phe Trp Arg
                435                 440                 445

Arg Leu Arg Lys Ala Leu Leu Asp Gly Lys Ser Trp Asn Pro Glu Gly
            450                 455                 460

Thr Val Gly Thr Gly Cys Asn Trp Gln Glu Ala Thr Ser Ile
465                 470                 475
```

<210> SEQ ID NO 99
<211> LENGTH: 22
<212> TYPE: PRT
<213> ORGANISM: Homo sapiens
<220> FEATURE:
<223> OTHER INFORMATION: GM-CSF signal peptide sequence

<400> SEQUENCE: 99

```
Met Leu Leu Leu Val Thr Ser Leu Leu Leu Cys Glu Leu Pro His Pro
1               5                   10                  15

Ala Phe Leu Leu Ile Pro
            20
```

<210> SEQ ID NO 100
<211> LENGTH: 22
<212> TYPE: PRT
<213> ORGANISM: Mus musculus
<220> FEATURE:
<223> OTHER INFORMATION: Tim4 signal peptide sequence

<400> SEQUENCE: 100

```
Met Ser Lys Gly Leu Leu Leu Trp Leu Val Thr Glu Leu Trp Trp
1               5                   10                  15

Leu Tyr Leu Thr Pro Ala
            20
```

<210> SEQ ID NO 101
<211> LENGTH: 19
<212> TYPE: PRT
<213> ORGANISM: Artificial Sequence
<220> FEATURE:
<223> OTHER INFORMATION: P2A self-cleaving peptide

<400> SEQUENCE: 101

```
Ala Thr Asn Phe Ser Leu Leu Lys Gln Ala Gly Asp Val Glu Glu Asn
1               5                   10                  15

Pro Gly Pro
```

<210> SEQ ID NO 102
<211> LENGTH: 18
<212> TYPE: PRT
<213> ORGANISM: Artificial Sequence
<220> FEATURE:
<223> OTHER INFORMATION: T2A self-cleaving peptide

<400> SEQUENCE: 102

```
Glu Gly Arg Gly Ser Leu Leu Thr Cys Gly Asp Val Glu Glu Asn Pro
1               5                   10                  15
```

Gly Pro

<210> SEQ ID NO 103
<211> LENGTH: 20
<212> TYPE: PRT
<213> ORGANISM: Artificial Sequence
<220> FEATURE:
<223> OTHER INFORMATION: E2A self-cleaving peptide

<400> SEQUENCE: 103

Gln Cys Thr Asn Tyr Ala Leu Leu Lys Leu Ala Gly Asp Val Glu Ser
1               5                   10                  15

Asn Pro Gly Pro
            20

<210> SEQ ID NO 104
<211> LENGTH: 22
<212> TYPE: PRT
<213> ORGANISM: Artificial Sequence
<220> FEATURE:
<223> OTHER INFORMATION: F2A self-cleaving peptide

<400> SEQUENCE: 104

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 105
<211> LENGTH: 285
<212> TYPE: PRT
<213> ORGANISM: Homo sapiens
<220> FEATURE:
<223> OTHER INFORMATION: truncated EGFR

<400> SEQUENCE: 105

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser

```
              180                 185                 190
Cys Arg Asn Val Ser Arg Gly Arg Glu Cys Val Asp Lys Cys Asn Leu
            195                 200                 205

Leu Glu Gly Glu Pro Arg Glu Phe Val Glu Asn Ser Glu Cys Ile Gln
        210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His
        275                 280                 285

<210> SEQ ID NO 106
<211> LENGTH: 279
<212> TYPE: PRT
<213> ORGANISM: Mus musculus
<220> FEATURE:
<223> OTHER INFORMATION: Tim4 binding domain
<220> FEATURE:
<221> NAME/KEY: sig_peptide
<222> LOCATION: 1...22

<400> SEQUENCE: 106

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
```

245                 250                 255

Thr Thr Leu Thr Thr Ser Glu Ser Leu Gln Lys Thr Thr Lys Ser His
            260                 265                 270

Gln Ile Asn Ser Arg Gln Thr
        275

<210> SEQ ID NO 107
<211> LENGTH: 257
<212> TYPE: PRT
<213> ORGANISM: Mus musculus
<220> FEATURE:
<223> OTHER INFORMATION: Tim4 binding domain without signal peptide

<400> SEQUENCE: 107

Ala Ser Glu Asp Thr Ile Ile Gly Phe Leu Gly Gln Pro Val Thr Leu
1               5                   10                  15

Pro Cys His Tyr Leu Ser Trp Ser Gln Ser Arg Asn Ser Met Cys Trp
            20                  25                  30

Gly Lys Gly Ser Cys Pro Asn Ser Lys Cys Asn Ala Glu Leu Leu Arg
        35                  40                  45

Thr Asp Gly Thr Arg Ile Ile Ser Arg Lys Ser Thr Lys Tyr Thr Leu
    50                  55                  60

Leu Gly Lys Val Gln Phe Gly Glu Val Ser Leu Thr Ile Ser Asn Thr
65                  70                  75                  80

Asn Arg Gly Asp Ser Gly Val Tyr Cys Cys Arg Ile Glu Val Pro Gly
                85                  90                  95

Trp Phe Asn Asp Val Lys Lys Asn Val Arg Leu Glu Leu Arg Arg Ala
            100                 105                 110

Thr Thr Thr Lys Lys Pro Thr Thr Thr Thr Arg Pro Thr Thr Thr Pro
        115                 120                 125

Tyr Val Thr Thr Thr Pro Glu Leu Leu Pro Thr Thr Val Met Thr
    130                 135                 140

Thr Ser Val Leu Pro Thr Thr Thr Pro Pro Gln Thr Leu Ala Thr Thr
145                 150                 155                 160

Ala Phe Ser Thr Ala Val Thr Thr Cys Pro Ser Thr Thr Pro Gly Ser
                165                 170                 175

Phe Ser Gln Glu Thr Thr Lys Gly Ser Ala Phe Thr Thr Glu Ser Glu
            180                 185                 190

Thr Leu Pro Ala Ser Asn His Ser Gln Arg Ser Met Met Thr Ile Ser
        195                 200                 205

Thr Asp Ile Ala Val Leu Arg Pro Thr Gly Ser Asn Pro Gly Ile Leu
    210                 215                 220

Pro Ser Thr Ser Gln Leu Thr Thr Gln Lys Thr Thr Leu Thr Thr Ser
225                 230                 235                 240

Glu Ser Leu Gln Lys Thr Thr Lys Ser His Gln Ile Asn Ser Arg Gln
                245                 250                 255

Thr

<210> SEQ ID NO 108
<211> LENGTH: 21
<212> TYPE: PRT
<213> ORGANISM: Mus musculus
<220> FEATURE:
<223> OTHER INFORMATION: Tim4 transmembrane domain

<400> SEQUENCE: 108

Ile Leu Ile Ile Ala Cys Cys Val Gly Phe Val Leu Met Val Leu Leu

-continued

```
                1               5                    10                   15

Phe Leu Ala Phe Leu
            20

<210> SEQ ID NO 109
<211> LENGTH: 267
<212> TYPE: PRT
<213> ORGANISM: Artificial Sequence
<220> FEATURE:
<223> OTHER INFORMATION: FMC63 scFv
<220> FEATURE:
<221> NAME/KEY: sig_peptide
<222> LOCATION: 1...22

<400> SEQUENCE: 109

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser
            260                 265

<210> SEQ ID NO 110
<211> LENGTH: 81
<212> TYPE: DNA
<213> ORGANISM: Homo sapiens
<220> FEATURE:
<221> NAME/KEY: misc_feature
<223> OTHER INFORMATION: CD28 transmembrane domain

<400> SEQUENCE: 110
```

```
ttttgggtgc tggtggtggt tggtggagtc ctggcttgct atagcttgct agtaacagtg    60
gcctttatta ttttctgggt g                                              81

<210> SEQ ID NO 111
<211> LENGTH: 63
<212> TYPE: DNA
<213> ORGANISM: Homo sapiens
<220> FEATURE:
<221> NAME/KEY: misc_feature
<223> OTHER INFORMATION: DAP12 transmembrane domain

<400> SEQUENCE: 111
ggcgtgctgg cagggatcgt gatgggagac ctggtgctga cagtgctcat tgccctggcc    60
gtg                                                                  63

<210> SEQ ID NO 112
<211> LENGTH: 63
<212> TYPE: DNA
<213> ORGANISM: Homo sapiens
<220> FEATURE:
<221> NAME/KEY: misc_feature
<223> OTHER INFORMATION: TLR4 transmembrane domain

<400> SEQUENCE: 112
accatcattg gtgtgtcggt cctcagtgtg cttgtagtat ctgttgtagc agttctggtc    60
tat                                                                  63

<210> SEQ ID NO 113
<211> LENGTH: 63
<212> TYPE: DNA
<213> ORGANISM: Homo sapiens
<220> FEATURE:
<221> NAME/KEY: misc_feature
<223> OTHER INFORMATION: BAI1 transmembrane domain

<400> SEQUENCE: 113
gtgacgctca tcgtgggctg tggcgtgtcc tctctcaccc tgctcatgct ggtcatcatc    60
tac                                                                  63

<210> SEQ ID NO 114
<211> LENGTH: 24
<212> TYPE: PRT
<213> ORGANISM: Homo sapiens
<220> FEATURE:
<221> NAME/KEY: VARIANT
<223> OTHER INFORMATION: Tim4 signal peptide

<400> SEQUENCE: 114

Met Ser Lys Glu Pro Leu Ile Leu Trp Leu Met Ile Glu Phe Trp Trp
1               5                   10                  15

Leu Tyr Leu Thr Pro Val Thr Ser
            20

<210> SEQ ID NO 115
<211> LENGTH: 126
<212> TYPE: DNA
<213> ORGANISM: Homo sapiens
<220> FEATURE:
<221> NAME/KEY: misc_feature
<223> OTHER INFORMATION: FcepsilonRIgamma signaling domain

<400> SEQUENCE: 115
cgactgaaga tccaagtgcg aaaggcagct ataaccagct atgagaaatc agatggtgtt    60
```

```
tacacgggcc tgagcaccag gaaccaggag acttacgaga ctctgaagca tgagaaacca    120
ccacag                                                              126

<210> SEQ ID NO 116
<211> LENGTH: 156
<212> TYPE: DNA
<213> ORGANISM: Homo sapiens
<220> FEATURE:
<221> NAME/KEY: misc_feature
<223> OTHER INFORMATION: DAP12 signaling domain

<400> SEQUENCE: 116
tattttctgg gaaggctcgt tcctagaggt agaggtgctg ccgaagcagc gacgcgcaaa     60
cagaggatta ctgaaacgga gtctccctac caagagctgc aaggccagag gtcagatgtc    120
tattcagact tgaacacaca aaggccatac tacaaa                              156

<210> SEQ ID NO 117
<211> LENGTH: 255
<212> TYPE: DNA
<213> ORGANISM: Homo sapiens
<220> FEATURE:
<221> NAME/KEY: misc_feature
<223> OTHER INFORMATION: BAFFR signaling domain

<400> SEQUENCE: 117
tcctggagac ggcgacaaag gcgcttgcgc ggcgcatcat ccgcagaggc gcccgacggc     60
gataaggacg cgcccgaacc ccttgataaa gttattatct tgtcaccggg aatttctgac    120
gctacggcac ccgcgtggcc tcctccgggc gaagatcctg gtacgacacc cctggacac    180 agtgttcccg tgcccgcgac agagctcggt agcacagaac tggtgaccac aaagacggcg    240
ggaccggaac agcaa                                                     255

<210> SEQ ID NO 118
<211> LENGTH: 135
<212> TYPE: DNA
<213> ORGANISM: Homo sapiens
<220> FEATURE:
<221> NAME/KEY: misc_feature
<223> OTHER INFORMATION: CD79b signaling domain

<400> SEQUENCE: 118
gacagtaaag ccgggatgga agaggaccac acatacgagg ggcttgacat agatcaaaca     60
gcgacatacg aagacatcgt aaccttgcgg actggagagg ttaaatggtc agtcggagaa    120
caccccggcc aagaa                                                     135

<210> SEQ ID NO 119
<211> LENGTH: 258
<212> TYPE: DNA
<213> ORGANISM: Homo sapiens
<220> FEATURE:
<221> NAME/KEY: misc_feature
<223> OTHER INFORMATION: NFAM1 signaling domain

<400> SEQUENCE: 119
ctctggaata aaagaggat gcgcggcccg ggaaaagacc caacgagaaa gtgtcccgat      60
ccccgcagtg cgtcaagccc caagcagcat ccttccgaaa gcgtatatac ggcacttcaa    120
cgccgggaaa cggaggtata tgcgtgtatt gagaacgagg acgggtcatc cccgaccgcc    180
aaacagtccc ctctcagcca agagcgacct cacaggtttg aggacgatgg tgaactcaat    240
```
ctggtctacg aaaacctg          258

<210> SEQ ID NO 120
<211> LENGTH: 2754
<212> TYPE: DNA
<213> ORGANISM: Homo sapiens
<220> FEATURE:
<221> NAME/KEY: misc_feature
<223> OTHER INFORMATION: BAI1 binding domain

<400> SEQUENCE: 120

```
gccgccggag cagacgcggg gcccgggccc gagccgtgcg ccacgctggt gcagggaaag    60
ttcttcggct acttctccgc ggccgccgtg ttcccggcca acgcctcgcg ctgctcctgg   120
acgctacgca acccggaccc gcggcgctac actctctaca tgaaggtggc caaggcgccc   180
gtgccctgca gcggccccgg ccgcgtgcgc acctaccagt tcgactcctt cctcgagtcc   240
acgcgcacct acctgggcgt ggagagcttc gacgaggtgc tgcggctctg cgaccccctcc  300
gcaccctgg ccttcctgca ggccagcaag cagttcctgc agatgcggcg ccagcagccg    360
ccccagcacg acgggctccg ccccgggcc gggccgccgg ccccaccga cgacttctcc    420
gtggagtacc tggtggtggg gaaccgcaac cccagccgtg ccgcctgcca gatgctgtgc   480
cgctggctgg acgcgtgtct ggccggtagt cgcagctcgc accccctgcgg gatcatgcag  540
accccctgcg cctgcctggg cggcgaggcg ggcggccctg ccgcgggacc cctgccccc    600
cgcggggatg tctgcttgag agatgcggtg gctggtggcc ctgaaaactg cctcaccagc   660
ctgacccagg accggggcgg gcacggcgcc acaggcggct ggaagctgtg gtccctgtgg   720
ggcgaatgca cgcgggactg cggggaggc ctccagacgc ggacgcgcac ctgcctgccc   780
gcgccgggcg tggagggcgg cggctgcgag ggggtgctgg aggagggtcg ccagtgcaac   840
cgcgaggcct gcggccccgc tgggcgcacc agctcccgga gccagtccct gcggtccaca   900
gatgcccggc ggcgcgagga gctggggac gagctgcagc agtttgggtt cccagccccc   960
cagaccggtg acccagcagc cgaggagtgg tccccgtgga gcgtgtgctc cagcacctgc  1020
ggcgagggct ggcagacccg cacgcgcttc tgcgtgtcct cctcctacag cacgcagtgc  1080
agcggacccc tgcgcgagca gcggctgtgc aacaactctg ccgtgtgccc agtgcatggt  1140
gcctgggatg agtggtcgcc ctggagcctc tgctccagca cctgtggccg tggctttcgg  1200
gatcgcacgc gcacctgcag gccccccag tttgggggca acccctgtga gggccctgag  1260
aagcaaaacca agttctgcaa cattgccctg tgccctggcc gggcagtgga tggaaactgg  1320
aatgagtggt cgagctggag cgcctgctcc gccagctgct cccaggggcc gacagcagcgc  1380
acgcgtgaat gcaacgggcc ttcctacggg ggtgcggagt gccagggcca ctgggtggag  1440
acccgagact gcttcctgca gcagtgccca gtggatggca gtggcaggc ctgggcgtca  1500
tggggcagtt gcagcgtcac gtgtgggct ggcagccagc gacgggagcg tgtctgctct  1560
gggccccttct tcggggagc agcctgccag ggccccagg atgagtaccg gcagtgcggc  1620
acccagcggt gtcccgagcc ccatgagatc tgtgatgagg acaactttgg tgctgtgatc  1680
tggaaggaga cccagcgggg agaggtggct gctgtccggt gtcccgcaa cgccacagga  1740
ctcatcctgc gacggtgtga gctggacgag gaaggcatcg cctactggga gccccccacc  1800
tacatccgct gtgtttccat tgactacaga aacatccaga tgatgacccg ggagcacctg  1860
gccaaggctc agcgagggct gcctgggggag gggtctcgg aggtcatcca gacactggtg  1920
gagatctctc aggacgggac cagctacagt ggggacctgc tgtccaccat cgatgtcctg  1980
```

```
aggaacatga cagagatttt ccggagagcg tactacagcc ccacccctgg ggacgtacag    2040
aactttgtcc agatccttag caacctgttg gcagaggaga atcgggacaa gtgggaggag    2100
gcccagctgg cgggccccaa cgccaaggag ctgttccggc tggtggagga ctttgtggac    2160
gtcatcggct ccgcatgaa ggacctgagg gatgcatacc aggtgacaga caacctggtt    2220
ctcagcatcc ataagctccc agccagcgga gccactgaca tcagcttccc catgaagggc    2280
tggcgggcca cgggtgactg ggccaaggtg ccagaggaca gggtcactgt gtccaagagt    2340
gtcttctcca cggggctgac agaggccgat gaagcatccg tgtttgtggt gggcaccgtg    2400
ctctacagga acctgggcag cttcctggcc ctgcagagga acacgaccgt cctgaattct    2460
aaggtgatct ccgtgactgt gaaacccccg cctcgctccc tgcgcacacc cttggagatc    2520
gagtttgccc acatgtataa tggcaccacc aaccagacct gtatcctgtg ggatgagacg    2580
gatgtaccct cctcctccgc cccccgcag ctcgggccct ggtcgtggcg cggctgccgc    2640
acggtgcccc tcgacgccct ccggacgcgc tgcctctgtg accggctctc caccttcgcc    2700
atcttagccc agctcagcgc cgacgcgaac atggagaagg cgactctgcc gtcg         2754
```

<210> SEQ ID NO 121
<211> LENGTH: 63
<212> TYPE: DNA
<213> ORGANISM: Homo sapiens
<220> FEATURE:
<221> NAME/KEY: misc_feature
<223> OTHER INFORMATION: FcepsilonRIgamma transmembrane domain

<400> SEQUENCE: 121

```
ctttgttaca ttctcgacgc gatattgttc ctttatggaa tagttttgac gctcctttat    60
tgc                                                                  63
```

<210> SEQ ID NO 122
<211> LENGTH: 488
<212> TYPE: PRT
<213> ORGANISM: Artificial Sequence
<220> FEATURE:
<223> OTHER INFORMATION: CER43 chimeric engulfment receptor
<220> FEATURE:
<221> NAME/KEY: sig_peptide
<222> LOCATION: 1...22

<400> SEQUENCE: 122

```
Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
```

```
                130              135              140
Thr Lys Gly Glu Val Lys Leu Gln Glu Ser Gly Pro Gly Leu Val Ala
145              150              155              160
Pro Ser Gln Ser Leu Ser Val Thr Cys Thr Val Ser Gly Val Ser Leu
             165              170              175
Pro Asp Tyr Gly Val Ser Trp Ile Arg Gln Pro Pro Arg Lys Gly Leu
         180              185              190
Glu Trp Leu Gly Val Ile Trp Gly Ser Glu Thr Thr Tyr Tyr Asn Ser
             195              200              205
Ala Leu Lys Ser Arg Leu Thr Ile Ile Lys Asp Asn Ser Lys Ser Gln
         210              215              220
Val Phe Leu Lys Met Asn Ser Leu Gln Thr Asp Asp Thr Ala Ile Tyr
225              230              235              240
Tyr Cys Ala Lys His Tyr Tyr Tyr Gly Gly Ser Tyr Ala Met Asp Tyr
             245              250              255
Trp Gly Gln Gly Thr Ser Val Thr Val Ser Ser Pro Val Leu Ser Leu
             260              265              270
Asn Ile Thr Cys Gln Met Asn Lys Thr Ile Ile Gly Val Ser Val Leu
             275              280              285
Ser Val Leu Val Val Ser Val Val Ala Val Leu Val Tyr Lys Phe Tyr
290              295              300
Phe His Leu Met Leu Leu Ala Gly Cys Ile Lys Tyr Gly Arg Gly Glu
305              310              315              320
Asn Ile Tyr Asp Ala Phe Val Ile Tyr Ser Ser Gln Asp Glu Asp Trp
             325              330              335
Val Arg Asn Glu Leu Val Lys Asn Leu Glu Glu Gly Val Pro Pro Phe
             340              345              350
Gln Leu Cys Leu His Tyr Arg Asp Phe Ile Pro Gly Val Ala Ile Ala
             355              360              365
Ala Asn Ile Ile His Glu Gly Phe His Lys Ser Arg Lys Val Ile Val
             370              375              380
Val Val Ser Gln His Phe Ile Gln Ser Arg Trp Cys Ile Phe Glu Tyr
385              390              395              400
Glu Ile Ala Gln Thr Trp Gln Phe Leu Ser Ser Arg Ala Gly Ile Ile
             405              410              415
Phe Ile Val Leu Gln Lys Val Glu Lys Thr Leu Leu Arg Gln Gln Val
             420              425              430
Glu Leu Tyr Arg Leu Leu Ser Arg Asn Thr Tyr Leu Glu Trp Glu Asp
             435              440              445
Ser Val Leu Gly Arg His Ile Phe Trp Arg Arg Leu Arg Lys Ala Leu
450              455              460
Leu Asp Gly Lys Ser Trp Asn Pro Glu Gly Thr Val Gly Thr Gly Cys
465              470              475              480
Asn Trp Gln Glu Ala Thr Ser Ile
                 485

<210> SEQ ID NO 123
<211> LENGTH: 487
<212> TYPE: PRT
<213> ORGANISM: Artificial Sequence
<220> FEATURE:
<223> OTHER INFORMATION: CER44 chimeric engulfment receptor
<220> FEATURE:
<221> NAME/KEY: sig_peptide
<222> LOCATION: 1...22
```

<400> SEQUENCE: 123

```
Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
            115                 120                 125

Thr Gly Ser Thr Ser Gly Ser Gly Lys Pro Gly Ser Gly Glu Gly Ser
130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
            165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
            195                 200                 205

Ala Leu Lys Ser Arg Leu Thr Ile Ile Lys Asp Asn Ser Lys Ser Gln
            210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
            245                 250                 255

Trp Gly Gln Gly Thr Ser Val Thr Val Ser Ser Glu Ser Lys Tyr Gly
            260                 265                 270

Pro Pro Cys Pro Pro Cys Pro Thr Ile Ile Gly Val Ser Val Leu Ser
            275                 280                 285

Val Leu Val Val Ser Val Ala Val Leu Val Tyr Lys Phe Tyr Phe
290                 295                 300

His Leu Met Leu Leu Ala Gly Cys Ile Lys Tyr Gly Arg Gly Glu Asn
305                 310                 315                 320

Ile Tyr Asp Ala Phe Val Ile Tyr Ser Ser Gln Asp Glu Asp Trp Val
            325                 330                 335

Arg Asn Glu Leu Val Lys Asn Leu Glu Glu Gly Val Pro Pro Phe Gln
            340                 345                 350

Leu Cys Leu His Tyr Arg Asp Phe Ile Pro Gly Val Ala Ile Ala Ala
            355                 360                 365

Asn Ile Ile His Glu Gly Phe His Lys Ser Arg Lys Val Ile Val Val
            370                 375                 380

Val Ser Gln His Phe Ile Gln Ser Arg Trp Cys Ile Phe Glu Tyr Glu
385                 390                 395                 400

Ile Ala Gln Thr Trp Gln Phe Leu Ser Ser Arg Ala Gly Ile Ile Phe
            405                 410                 415
```

```
Ile Val Leu Gln Lys Val Glu Lys Thr Leu Arg Gln Gln Val Glu
                420             425                 430

Leu Tyr Arg Leu Leu Ser Arg Asn Thr Tyr Leu Glu Trp Glu Asp Ser
            435                 440                 445

Val Leu Gly Arg His Ile Phe Trp Arg Leu Arg Lys Ala Leu Leu
    450                 455                 460

Asp Gly Lys Ser Trp Asn Pro Glu Gly Thr Val Gly Thr Gly Cys Asn
465             470                 475                 480

Trp Gln Glu Ala Thr Ser Ile
                485

<210> SEQ ID NO 124
<211> LENGTH: 574
<212> TYPE: PRT
<213> ORGANISM: Artificial Sequence
<220> FEATURE:
<223> OTHER INFORMATION: CER29 chimeric engulfment receptor
<220> FEATURE:
<221> NAME/KEY: sig_peptide
<222> LOCATION: 1...22

<400> SEQUENCE: 124

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50              55                  60

Asn Ala Glu Leu Leu Arg Thr Asp Gly Thr Arg Ile Ile Ser Arg Lys
65              70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
            130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Ser Gln Leu Thr Thr Gln Lys
                245                 250                 255

Thr Thr Leu Thr Thr Ser Glu Ser Leu Gln Lys Thr Thr Lys Ser His
            260                 265                 270
```

```
Gln Ile Asn Ser Arg Gln Thr Ile Leu Ile Ala Cys Cys Val Gly
        275                 280                 285

Phe Val Leu Met Val Leu Leu Phe Leu Ala Phe Leu Met Ser Leu Leu
290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
                325                 330                 335

Gly Gly Thr Ala Ser Thr Gly Asn Leu Ser Ser Ser Phe Met Glu Glu
                340                 345                 350

Ile Gln Gly Tyr Asp Val Glu Phe Asp Pro Pro Leu Glu Ser Lys Tyr
        355                 360                 365

Glu Cys Pro Ile Cys Leu Met Ala Leu Arg Glu Ala Val Gln Thr Pro
        370                 375                 380

Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
                405                 410                 415

Leu Phe Pro Asp Asn Phe Ala Lys Arg Glu Ile Leu Ser Leu Met Val
                420                 425                 430

Lys Cys Pro Asn Glu Gly Cys Leu His Lys Met Glu Leu Arg His Leu
        435                 440                 445

Glu Asp His Gln Ala His Cys Glu Phe Ala Leu Met Asp Cys Pro Gln
        450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn
                500                 505                 510

Val Ile Cys Glu Tyr Cys Asn Thr Ile Leu Ile Arg Glu Gln Met Pro
        515                 520                 525

Asn His Tyr Asp Leu Asp Cys Pro Thr Ala Pro Ile Pro Cys Thr Phe
        530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala
                565                 570

<210> SEQ ID NO 125
<211> LENGTH: 626
<212> TYPE: PRT
<213> ORGANISM: Artificial Sequence
<220> FEATURE:
<223> OTHER INFORMATION: CER110 chimeric engulfment receptor
<220> FEATURE:
<221> NAME/KEY: sig_peptide
<222> LOCATION: 1...22

<400> SEQUENCE: 125

Met Ser Lys Gly Leu Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
        35                  40                  45
```

```
Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
                210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ile Ala Cys Cys Val Gly
                275                 280                 285

Phe Val Leu Met Val Leu Leu Phe Leu Ala Phe Leu Met Ser Leu Leu
                290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
                325                 330                 335

Gly Gly Thr Ala Ser Thr Gly Asn Leu Ser Ser Phe Met Glu Glu
                340                 345                 350

Ile Gln Gly Tyr Asp Val Glu Phe Asp Pro Pro Leu Glu Ser Lys Tyr
                355                 360                 365

Glu Cys Pro Ile Cys Leu Met Ala Leu Arg Glu Ala Val Gln Thr Pro
370                 375                 380

Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
                405                 410                 415

Leu Phe Pro Asp Asn Phe Ala Lys Arg Glu Ile Leu Ser Leu Met Val
                420                 425                 430

Lys Cys Pro Asn Glu Gly Cys Leu His Lys Met Glu Leu Arg His Leu
                435                 440                 445

Glu Asp His Gln Ala His Cys Glu Phe Ala Leu Met Asp Cys Pro Gln
450                 455                 460
```

-continued

```
Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
            485                 490                 495

Ala Phe Glu Asp Lys Glu Ile His Asp Gln Asn Cys Pro Leu Ala Asn
        500                 505                 510

Val Ile Cys Glu Tyr Cys Asn Thr Ile Leu Ile Arg Glu Gln Met Pro
    515                 520                 525

Asn His Tyr Asp Leu Asp Cys Pro Thr Ala Pro Ile Pro Cys Thr Phe
530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala Tyr Phe
                565                 570                 575

Leu Gly Arg Leu Val Pro Arg Gly Arg Gly Ala Ala Glu Ala Ala Thr
            580                 585                 590

Arg Lys Gln Arg Ile Thr Glu Thr Glu Ser Pro Tyr Gln Glu Leu Gln
            595                 600                 605

Gly Gln Arg Ser Asp Val Tyr Ser Asp Leu Asn Thr Gln Arg Pro Tyr
            610                 615                 620

Tyr Lys
625

<210> SEQ ID NO 126
<211> LENGTH: 574
<212> TYPE: PRT
<213> ORGANISM: Artificial Sequence
<220> FEATURE:
<223> OTHER INFORMATION: CER111B chimeric engulfment receptor
<220> FEATURE:
<221> NAME/KEY: sig_peptide
<222> LOCATION: 1...22

<400> SEQUENCE: 126

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175
```

-continued

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
        210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Met Ser Leu Leu
        290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
                325                 330                 335

Gly Gly Thr Ala Ser Thr Gly Asn Leu Ser Ser Ser Phe Met Glu Glu
            340                 345                 350

Ile Gln Gly Tyr Asp Val Glu Phe Asp Pro Pro Leu Glu Ser Lys Tyr
        355                 360                 365

Glu Cys Pro Ile Cys Leu Met Ala Leu Arg Glu Ala Val Gln Thr Pro
370                 375                 380

Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
                405                 410                 415

Leu Phe Pro Asp Asn Phe Ala Lys Arg Glu Ile Leu Ser Leu Met Val
            420                 425                 430

Lys Cys Pro Asn Glu Gly Cys Leu His Lys Met Glu Leu Arg His Leu
        435                 440                 445

Glu Asp His Gln Ala His Cys Glu Phe Ala Leu Met Asp Cys Pro Gln
        450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn
            500                 505                 510

Val Ile Cys Glu Tyr Cys Asn Thr Ile Leu Ile Arg Glu Gln Met Pro
        515                 520                 525

Asn His Tyr Asp Leu Asp Cys Pro Thr Ala Pro Ile Pro Cys Thr Phe
        530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala
                565                 570

<210> SEQ ID NO 127
<211> LENGTH: 638
<212> TYPE: PRT

<213> ORGANISM: Artificial Sequence
<220> FEATURE:
<223> OTHER INFORMATION: CER113 chimeric engulfment receptor
<220> FEATURE:
<221> NAME/KEY: sig_peptide
<222> LOCATION: 1...22

<400> SEQUENCE: 127

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
        180                 185                 190

Ser Thr Thr Pro Gly Ser Phe Ser Gln Glu Thr Lys Gly Ser Ala
            195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
                260                 265                 270

Gln Ile Asn Ser Arg Gln Thr Met Ser Leu Leu Asn Cys Glu Asn Ser
        275                 280                 285

Cys Gly Ser Ser Gln Ser Glu Ser Asp Cys Cys Val Ala Met Ala Ser
    290                 295                 300

Ser Cys Ser Ala Val Thr Lys Asp Asp Ser Val Gly Gly Thr Ala Ser
305                 310                 315                 320

Thr Gly Asn Leu Ser Ser Ser Phe Met Glu Glu Ile Gln Gly Tyr Asp
                325                 330                 335

Val Glu Phe Asp Pro Pro Leu Glu Ser Lys Tyr Glu Cys Pro Ile Cys
            340                 345                 350

Leu Met Ala Leu Arg Glu Ala Val Gln Thr Pro Cys Gly His Arg Phe
        355                 360                 365

Cys Lys Ala Cys Ile Ile Lys Ser Ile Arg Asp Ala Gly His Lys Cys
```

```
                370                 375                 380
Pro Val Asp Asn Glu Ile Leu Leu Glu Asn Gln Leu Phe Pro Asp Asn
385                 390                 395                 400

Phe Ala Lys Arg Glu Ile Leu Ser Leu Met Val Lys Cys Pro Asn Glu
                405                 410                 415

Gly Cys Leu His Lys Met Glu Leu Arg His Leu Glu Asp His Gln Ala
                420                 425                 430

His Cys Glu Phe Ala Leu Met Asp Cys Pro Gln Cys Gln Arg Pro Phe
            435                 440                 445

Gln Lys Phe His Ile Asn Ile His Ile Leu Lys Asp Cys Pro Arg Arg
        450                 455                 460

Gln Val Ser Cys Asp Asn Cys Ala Ala Ser Met Ala Phe Glu Asp Lys
465                 470                 475                 480

Glu Ile His Asp Gln Asn Cys Pro Leu Ala Asn Val Ile Cys Glu Tyr
                485                 490                 495

Cys Asn Thr Ile Leu Ile Arg Glu Gln Met Pro Asn His Tyr Asp Leu
                500                 505                 510

Asp Cys Pro Thr Ala Pro Ile Pro Cys Thr Phe Ser Thr Phe Gly Cys
            515                 520                 525

His Glu Lys Met Gln Arg Asn His Leu Ala Arg His Leu Gln Glu Asn
        530                 535                 540

Thr Gln Ser His Met Arg Met Leu Ala Ser Trp Arg Arg Arg Gln Arg
545                 550                 555                 560

Arg Leu Arg Gly Ala Ser Ser Ala Glu Ala Pro Asp Gly Asp Lys Asp
                565                 570                 575

Ala Pro Glu Pro Leu Asp Lys Val Ile Ile Leu Ser Pro Gly Ile Ser
                580                 585                 590

Asp Ala Thr Ala Pro Ala Trp Pro Pro Gly Glu Asp Pro Gly Thr
            595                 600                 605

Thr Pro Pro Gly His Ser Val Pro Val Pro Ala Thr Glu Leu Gly Ser
        610                 615                 620

Thr Glu Leu Val Thr Thr Lys Thr Ala Gly Pro Glu Gln Gln
625                 630                 635

<210> SEQ ID NO 128
<211> LENGTH: 660
<212> TYPE: PRT
<213> ORGANISM: Artificial Sequence
<220> FEATURE:
<223> OTHER INFORMATION: CER112 chimeric engulfment receptor
<220> FEATURE:
<221> NAME/KEY: sig_peptide
<222> LOCATION: 1...22

<400> SEQUENCE: 128

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
```

```
                    85                  90                  95
Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Lys Lys Pro Thr Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
                210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ala Cys Cys Val Gly
                275                 280                 285

Phe Val Leu Met Val Leu Leu Phe Leu Ala Phe Leu Met Ser Leu Leu
290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
                325                 330                 335

Gly Gly Thr Ala Ser Thr Gly Asn Leu Ser Ser Ser Phe Met Glu Glu
                340                 345                 350

Ile Gln Gly Tyr Asp Val Glu Phe Asp Pro Pro Leu Glu Ser Lys Tyr
                355                 360                 365

Glu Cys Pro Ile Cys Leu Met Ala Leu Arg Glu Ala Val Gln Thr Pro
                370                 375                 380

Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
                405                 410                 415

Leu Phe Pro Asp Asn Phe Ala Lys Arg Glu Ile Leu Ser Leu Met Val
                420                 425                 430

Lys Cys Pro Asn Glu Gly Cys Leu His Lys Met Glu Leu Arg His Leu
                435                 440                 445

Glu Asp His Gln Ala His Cys Glu Phe Ala Leu Met Asp Cys Pro Gln
                450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn
                500                 505                 510
```

Val Ile Cys Glu Tyr Cys Asn Thr Ile Leu Ile Arg Glu Gln Met Pro
            515                 520                 525

Asn His Tyr Asp Leu Asp Cys Pro Thr Ala Pro Ile Pro Cys Thr Phe
            530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala Leu Trp
            565                 570                 575

Asn Lys Lys Arg Met Arg Gly Pro Gly Lys Asp Pro Thr Arg Lys Cys
            580                 585                 590

Pro Asp Pro Arg Ser Ala Ser Ser Pro Lys Gln His Pro Ser Glu Ser
            595                 600                 605

Val Tyr Thr Ala Leu Gln Arg Arg Glu Thr Glu Val Tyr Ala Cys Ile
            610                 615                 620

Glu Asn Glu Asp Gly Ser Ser Pro Thr Ala Lys Gln Ser Pro Leu Ser
625                 630                 635                 640

Gln Glu Arg Pro His Arg Phe Glu Asp Asp Gly Glu Leu Asn Leu Val
            645                 650                 655

Tyr Glu Asn Leu
            660

<210> SEQ ID NO 129

<400> SEQUENCE: 129

000

<210> SEQ ID NO 130
<211> LENGTH: 579
<212> TYPE: PRT
<213> ORGANISM: Artificial Sequence
<220> FEATURE:
<223> OTHER INFORMATION: CER102 protein
<220> FEATURE:
<221> NAME/KEY: sig_peptide
<222> LOCATION: 1...22

<400> SEQUENCE: 130

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
            85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr
            130                 135                 140

Arg Pro Thr Thr Thr Pro Tyr Val Thr Thr Thr Pro Glu Leu Leu

-continued

```
            145                 150                 155                 160
        Pro Thr Thr Val Met Thr Thr Ser Val Leu Pro Thr Thr Pro Pro
                            165                 170                 175
        Gln Thr Leu Ala Thr Thr Ala Phe Ser Thr Ala Val Thr Thr Cys Pro
                            180                 185                 190
        Ser Thr Thr Pro Gly Ser Phe Ser Gln Glu Thr Thr Lys Gly Ser Ala
                            195                 200                 205
        Phe Thr Thr Glu Ser Glu Thr Leu Pro Ala Ser Asn His Ser Gln Arg
                            210                 215                 220
        Ser Met Met Thr Ile Ser Thr Asp Ile Ala Val Leu Arg Pro Thr Gly
        225                 230                 235                 240
        Ser Asn Pro Gly Ile Leu Pro Ser Thr Ser Gln Leu Thr Thr Gln Lys
                            245                 250                 255
        Thr Thr Leu Thr Thr Ser Glu Ser Leu Gln Lys Thr Thr Lys Ser His
                            260                 265                 270
        Gln Ile Asn Ser Arg Gln Thr Ile Leu Ile Ile Ala Cys Cys Val Gly
                            275                 280                 285
        Phe Val Leu Met Val Leu Leu Phe Leu Ala Phe Leu His His Leu Phe
                            290                 295                 300
        Tyr Trp Asp Val Trp Phe Ile Tyr Asn Val Cys Leu Ala Lys Val Lys
        305                 310                 315                 320
        Gly Tyr Arg Ser Leu Ser Thr Ser Gln Thr Phe Tyr Asp Ala Tyr Ile
                            325                 330                 335
        Ser Tyr Asp Thr Lys Asp Ala Ser Val Thr Asp Trp Val Ile Asn Glu
                            340                 345                 350
        Leu Arg Tyr His Leu Glu Glu Ser Arg Asp Lys Asn Val Leu Leu Cys
                            355                 360                 365
        Leu Glu Glu Arg Asp Trp Asp Pro Gly Leu Ala Ile Ile Asp Asn Leu
                            370                 375                 380
        Met Gln Ser Ile Asn Gln Ser Lys Lys Thr Val Phe Val Leu Thr Lys
        385                 390                 395                 400
        Lys Tyr Ala Lys Ser Trp Asn Phe Lys Thr Ala Phe Tyr Leu Ala Leu
                            405                 410                 415
        Gln Arg Leu Met Asp Glu Asn Met Asp Val Ile Ile Phe Ile Leu Leu
                            420                 425                 430
        Glu Pro Val Leu Gln His Ser Gln Tyr Leu Arg Leu Arg Gln Arg Ile
                            435                 440                 445
        Cys Lys Ser Ser Ile Leu Gln Trp Pro Asp Asn Pro Lys Ala Glu Gly
                            450                 455                 460
        Leu Phe Trp Gln Thr Leu Arg Asn Val Val Leu Thr Glu Asn Asp Ser
        465                 470                 475                 480
        Arg Tyr Asn Asn Met Tyr Val Asp Ser Ile Lys Gln Tyr Leu Trp Asn
                            485                 490                 495
        Lys Lys Arg Met Arg Gly Pro Gly Lys Asp Pro Thr Lys Cys Pro
                            500                 505                 510
        Asp Pro Arg Ser Ala Ser Ser Pro Lys Gln His Pro Ser Glu Ser Val
                            515                 520                 525
        Tyr Thr Ala Leu Gln Arg Arg Glu Thr Glu Val Tyr Ala Cys Ile Glu
                            530                 535                 540
        Asn Glu Asp Gly Ser Ser Pro Thr Ala Lys Gln Ser Pro Leu Ser Gln
        545                 550                 555                 560
        Glu Arg Pro His Arg Phe Glu Asp Asp Gly Glu Leu Asn Leu Val Tyr
                            565                 570                 575
```

Glu Asn Leu

<210> SEQ ID NO 131
<211> LENGTH: 538
<212> TYPE: PRT
<213> ORGANISM: Artificial Sequence
<220> FEATURE:
<223> OTHER INFORMATION: CER103A protein
<220> FEATURE:
<221> NAME/KEY: sig_peptide
<222> LOCATION: 1...22

<400> SEQUENCE: 131

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu His His Leu Phe
    290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                325                 330                 335

```
Ser Tyr Asp Thr Lys Asp Ala Ser Val Thr Asp Trp Val Ile Asn Glu
            340                 345                 350

Leu Arg Tyr His Leu Glu Glu Ser Arg Asp Lys Asn Val Leu Leu Cys
            355                 360                 365

Leu Glu Glu Arg Asp Trp Asp Pro Gly Leu Ala Ile Ile Asp Asn Leu
    370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                405                 410                 415

Gln Arg Leu Met Asp Glu Asn Met Asp Val Ile Ile Phe Ile Leu Leu
            420                 425                 430

Glu Pro Val Leu Gln His Ser Gln Tyr Leu Arg Leu Arg Gln Arg Ile
            435                 440                 445

Cys Lys Ser Ser Ile Leu Gln Trp Pro Asp Asn Pro Lys Ala Glu Gly
        450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr Asp Ser Lys
                485                 490                 495

Ala Gly Met Glu Glu Asp His Thr Tyr Glu Gly Leu Asp Ile Asp Gln
            500                 505                 510

Thr Ala Thr Tyr Glu Asp Ile Val Thr Leu Arg Thr Gly Glu Val Lys
            515                 520                 525

Trp Ser Val Gly Glu His Pro Gly Gln Glu
530                 535

<210> SEQ ID NO 132
<211> LENGTH: 522
<212> TYPE: PRT
<213> ORGANISM: Artificial Sequence
<220> FEATURE:
<223> OTHER INFORMATION: CER103B protein
<220> FEATURE:
<221> NAME/KEY: sig_peptide
<222> LOCATION: 1...22

<400> SEQUENCE: 132

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140
```

```
Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
            165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
    195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
                275                 280                 285

Phe Val Leu Met Val Leu Leu Phe Leu Ala Phe Leu His His Leu Phe
290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
            325                 330                 335

Ser Tyr Asp Thr Lys Asp Ala Ser Val Thr Asp Trp Val Ile Asn Glu
            340                 345                 350

Leu Arg Tyr His Leu Glu Glu Ser Arg Asp Lys Asn Val Leu Leu Cys
    355                 360                 365

Leu Glu Glu Arg Asp Trp Asp Pro Gly Leu Ala Ile Ile Asp Asn Leu
370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
            405                 410                 415

Gln Arg Leu Met Asp Glu Asn Met Asp Val Ile Ile Phe Ile Leu Leu
            420                 425                 430

Glu Pro Val Leu Gln His Ser Gln Tyr Leu Arg Leu Arg Gln Arg Ile
            435                 440                 445

Cys Lys Ser Ser Ile Leu Gln Trp Pro Asp Asn Pro Lys Ala Glu Gly
450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr Asp Ser Lys
            485                 490                 495

Ala Gly Met Glu Glu Asp His Thr Tyr Glu Gly Leu Asp Ile Asp Gln
            500                 505                 510

Thr Ala Thr Tyr Glu Asp Ile Val Thr Leu
            515                 520

<210> SEQ ID NO 133
<211> LENGTH: 545
<212> TYPE: PRT
<213> ORGANISM: Artificial Sequence
<220> FEATURE:
<223> OTHER INFORMATION: CER104 protein
```

```
<220> FEATURE:
<221> NAME/KEY: sig_peptide
<222> LOCATION: 1...22

<400> SEQUENCE: 133
```

| | | | | | | | | | | | | | | |
|---|---|---|---|---|---|---|---|---|---|---|---|---|---|---|
| Met | Ser | Lys | Gly | Leu | Leu | Leu | Trp | Leu | Val | Thr | Glu | Leu | Trp | Trp |
| 1 | | | | 5 | | | | | 10 | | | | | 15 |
| Leu | Tyr | Leu | Thr | Pro | Ala | Ala | Ser | Glu | Asp | Thr | Ile | Ile | Gly | Phe | Leu |
| | | | 20 | | | | | 25 | | | | | 30 | | |
| Gly | Gln | Pro | Val | Thr | Leu | Pro | Cys | His | Tyr | Leu | Ser | Trp | Ser | Gln | Ser |
| | | | 35 | | | | | 40 | | | | | 45 | | |
| Arg | Asn | Ser | Met | Cys | Trp | Gly | Lys | Gly | Ser | Cys | Pro | Asn | Ser | Lys | Cys |
| | | 50 | | | | | 55 | | | | | 60 | | | |
| Asn | Ala | Glu | Leu | Leu | Arg | Thr | Asp | Gly | Thr | Arg | Ile | Ile | Ser | Arg | Lys |
| 65 | | | | | 70 | | | | | 75 | | | | | 80 |
| Ser | Thr | Lys | Tyr | Thr | Leu | Leu | Gly | Lys | Val | Gln | Phe | Gly | Glu | Val | Ser |
| | | | | 85 | | | | | 90 | | | | | 95 | |
| Leu | Thr | Ile | Ser | Asn | Thr | Asn | Arg | Gly | Asp | Ser | Gly | Val | Tyr | Cys | Cys |
| | | | | 100 | | | | | 105 | | | | | 110 | |
| Arg | Ile | Glu | Val | Pro | Gly | Trp | Phe | Asn | Asp | Val | Lys | Lys | Asn | Val | Arg |
| | | | 115 | | | | | 120 | | | | | 125 | | |
| Leu | Glu | Leu | Arg | Arg | Ala | Thr | Thr | Thr | Lys | Lys | Pro | Thr | Thr | Thr | Thr |
| | | 130 | | | | | 135 | | | | | 140 | | | |
| Arg | Pro | Thr | Thr | Thr | Pro | Tyr | Val | Thr | Thr | Thr | Pro | Glu | Leu | Leu |
| 145 | | | | | 150 | | | | | 155 | | | | | 160 |
| Pro | Thr | Thr | Val | Met | Thr | Thr | Ser | Val | Leu | Pro | Thr | Thr | Thr | Pro | Pro |
| | | | | 165 | | | | | 170 | | | | | 175 | |
| Gln | Thr | Leu | Ala | Thr | Thr | Ala | Phe | Ser | Thr | Ala | Val | Thr | Thr | Cys | Pro |
| | | | 180 | | | | | 185 | | | | | 190 | | |
| Ser | Thr | Thr | Pro | Gly | Ser | Phe | Ser | Gln | Glu | Thr | Thr | Lys | Gly | Ser | Ala |
| | | | 195 | | | | | 200 | | | | | 205 | | |
| Phe | Thr | Thr | Glu | Ser | Glu | Thr | Leu | Pro | Ala | Ser | Asn | His | Ser | Gln | Arg |
| | | 210 | | | | | 215 | | | | | 220 | | | |
| Ser | Met | Met | Thr | Ile | Ser | Thr | Asp | Ile | Ala | Val | Leu | Arg | Pro | Thr | Gly |
| 225 | | | | | 230 | | | | | 235 | | | | | 240 |
| Ser | Asn | Pro | Gly | Ile | Leu | Pro | Ser | Thr | Ser | Gln | Leu | Thr | Thr | Gln | Lys |
| | | | | 245 | | | | | 250 | | | | | 255 | |
| Thr | Thr | Leu | Thr | Thr | Ser | Glu | Ser | Leu | Gln | Lys | Thr | Thr | Lys | Ser | His |
| | | | 260 | | | | | 265 | | | | | 270 | | |
| Gln | Ile | Asn | Ser | Arg | Gln | Thr | Ile | Leu | Ile | Ala | Cys | Cys | Val | Gly |
| | | | 275 | | | | | 280 | | | | | 285 | | |
| Phe | Val | Leu | Met | Val | Leu | Leu | Phe | Leu | Ala | Phe | Leu | His | His | Leu | Phe |
| | | 290 | | | | | 295 | | | | | 300 | | | |
| Tyr | Trp | Asp | Val | Trp | Phe | Ile | Tyr | Asn | Val | Cys | Leu | Ala | Lys | Val | Lys |
| 305 | | | | | 310 | | | | | 315 | | | | | 320 |
| Gly | Tyr | Arg | Ser | Leu | Ser | Thr | Ser | Gln | Thr | Phe | Tyr | Asp | Ala | Tyr | Ile |
| | | | | 325 | | | | | 330 | | | | | 335 | |
| Ser | Tyr | Asp | Thr | Lys | Asp | Ala | Ser | Val | Thr | Asp | Trp | Val | Ile | Asn | Glu |
| | | | 340 | | | | | 345 | | | | | 350 | | |
| Leu | Arg | Tyr | His | Leu | Glu | Glu | Ser | Arg | Asp | Lys | Asn | Val | Leu | Leu | Cys |
| | | | 355 | | | | | 360 | | | | | 365 | | |
| Leu | Glu | Glu | Arg | Asp | Trp | Asp | Pro | Gly | Leu | Ala | Ile | Ile | Asp | Asn | Leu |
| | | 370 | | | | | 375 | | | | | 380 | | | |
| Met | Gln | Ser | Ile | Asn | Gln | Ser | Lys | Lys | Thr | Val | Phe | Val | Leu | Thr | Lys |

```
                385                 390                 395                 400
Lys Tyr Ala Lys Ser Trp Asn Phe Lys Thr Ala Phe Tyr Leu Ala Leu
                    405                 410                 415

Gln Arg Leu Met Asp Glu Asn Met Asp Val Ile Ile Phe Ile Leu Leu
                420                 425                 430

Glu Pro Val Leu Gln His Ser Gln Tyr Leu Arg Leu Arg Gln Arg Ile
                435                 440                 445

Cys Lys Ser Ser Ile Leu Gln Trp Pro Asp Asn Pro Lys Ala Glu Gly
450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr Tyr Phe Leu
                    485                 490                 495

Gly Arg Leu Val Pro Arg Gly Arg Gly Ala Ala Glu Ala Ala Thr Arg
                500                 505                 510

Lys Gln Arg Ile Thr Glu Thr Glu Ser Pro Tyr Gln Glu Leu Gln Gly
                515                 520                 525

Gln Arg Ser Asp Val Tyr Ser Asp Leu Asn Thr Gln Arg Pro Tyr Tyr
530                 535                 540

Lys
545

<210> SEQ ID NO 134
<211> LENGTH: 578
<212> TYPE: PRT
<213> ORGANISM: Artificial Sequence
<220> FEATURE:
<223> OTHER INFORMATION: CER105 protein
<220> FEATURE:
<221> NAME/KEY: sig_peptide
<222> LOCATION: 1...22

<400> SEQUENCE: 134

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
                35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Thr Lys Lys Pro Thr Thr Thr Thr
                130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
```

```
            180                 185                 190
Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu His His Leu Phe
            290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                325                 330                 335

Ser Tyr Asp Thr Lys Asp Ala Ser Val Thr Asp Trp Val Ile Asn Glu
                340                 345                 350

Leu Arg Tyr His Leu Glu Glu Ser Arg Asp Lys Asn Val Leu Leu Cys
            355                 360                 365

Leu Glu Glu Arg Asp Trp Asp Pro Gly Leu Ala Ile Ile Asp Asn Leu
370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                405                 410                 415

Gln Arg Leu Met Asp Glu Asn Met Asp Val Ile Ile Phe Ile Leu Leu
            420                 425                 430

Glu Pro Val Leu Gln His Ser Gln Tyr Leu Arg Leu Arg Gln Arg Ile
            435                 440                 445

Cys Lys Ser Ser Ile Leu Gln Trp Pro Asp Asn Pro Lys Ala Glu Gly
            450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr Ser Trp Arg
                485                 490                 495

Arg Arg Gln Arg Arg Leu Arg Gly Ala Ser Ser Ala Glu Ala Pro Asp
            500                 505                 510

Gly Asp Lys Asp Ala Pro Glu Pro Leu Asp Lys Val Ile Ile Leu Ser
            515                 520                 525

Pro Gly Ile Ser Asp Ala Thr Ala Pro Ala Trp Pro Pro Gly Glu
            530                 535                 540

Asp Pro Gly Thr Thr Pro Pro Gly His Ser Val Pro Val Pro Ala Thr
545                 550                 555                 560

Glu Leu Gly Ser Thr Glu Leu Val Thr Thr Lys Thr Ala Gly Pro Glu
                565                 570                 575

Gln Gln

<210> SEQ ID NO 135
<211> LENGTH: 579
```

```
<212> TYPE: PRT
<213> ORGANISM: Artificial Sequence
<220> FEATURE:
<223> OTHER INFORMATION: CER106 protein
<220> FEATURE:
<221> NAME/KEY: sig_peptide
<222> LOCATION: 1...22

<400> SEQUENCE: 135

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Leu Trp Asn Lys
    290                 295                 300

Lys Arg Met Arg Gly Pro Gly Lys Asp Pro Thr Arg Lys Cys Pro Asp
305                 310                 315                 320

Pro Arg Ser Ala Ser Ser Pro Lys Gln His Pro Ser Glu Ser Val Tyr
                325                 330                 335

Thr Ala Leu Gln Arg Arg Glu Thr Glu Val Tyr Ala Cys Ile Glu Asn
            340                 345                 350

Glu Asp Gly Ser Ser Pro Thr Ala Lys Gln Ser Pro Leu Ser Gln Glu
        355                 360                 365
```

Arg Pro His Arg Phe Glu Asp Asp Gly Glu Leu Asn Leu Val Tyr Glu
    370                 375                 380

Asn Leu His His Leu Phe Tyr Trp Asp Val Trp Phe Ile Tyr Asn Val
385                 390                 395                 400

Cys Leu Ala Lys Val Lys Gly Tyr Arg Ser Leu Ser Thr Ser Gln Thr
                405                 410                 415

Phe Tyr Asp Ala Tyr Ile Ser Tyr Asp Thr Lys Asp Ala Ser Val Thr
            420                 425                 430

Asp Trp Val Ile Asn Glu Leu Arg Tyr His Leu Glu Glu Ser Arg Asp
        435                 440                 445

Lys Asn Val Leu Leu Cys Leu Glu Glu Arg Asp Trp Asp Pro Gly Leu
    450                 455                 460

Ala Ile Ile Asp Asn Leu Met Gln Ser Ile Asn Gln Ser Lys Lys Thr
465                 470                 475                 480

Val Phe Val Leu Thr Lys Lys Tyr Ala Lys Ser Trp Asn Phe Lys Thr
                485                 490                 495

Ala Phe Tyr Leu Ala Leu Gln Arg Leu Met Asp Glu Asn Met Asp Val
            500                 505                 510

Ile Ile Phe Ile Leu Leu Glu Pro Val Leu Gln His Ser Gln Tyr Leu
        515                 520                 525

Arg Leu Arg Gln Arg Ile Cys Lys Ser Ser Ile Leu Gln Trp Pro Asp
    530                 535                 540

Asn Pro Lys Ala Glu Gly Leu Phe Trp Gln Thr Leu Arg Asn Val Val
545                 550                 555                 560

Leu Thr Glu Asn Asp Ser Arg Tyr Asn Asn Met Tyr Val Asp Ser Ile
                565                 570                 575

Lys Gln Tyr

<210> SEQ ID NO 136
<211> LENGTH: 522
<212> TYPE: PRT
<213> ORGANISM: Artificial Sequence
<220> FEATURE:
<223> OTHER INFORMATION: CER107 protein
<220> FEATURE:
<221> NAME/KEY: sig_peptide
<222> LOCATION: 1...22

<400> SEQUENCE: 136

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr

```
            130                 135                 140
Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu Asp Ser Lys Ala
290                 295                 300

Gly Met Glu Glu Asp His Thr Tyr Glu Gly Leu Asp Ile Asp Gln Thr
305                 310                 315                 320

Ala Thr Tyr Glu Asp Ile Val Thr Leu His His Leu Phe Tyr Trp Asp
                325                 330                 335

Val Trp Phe Ile Tyr Asn Val Cys Leu Ala Lys Val Lys Gly Tyr Arg
                340                 345                 350

Ser Leu Ser Thr Ser Gln Thr Phe Tyr Asp Ala Tyr Ile Ser Tyr Asp
                355                 360                 365

Thr Lys Asp Ala Ser Val Thr Asp Trp Val Ile Asn Glu Leu Arg Tyr
            370                 375                 380

His Leu Glu Glu Ser Arg Asp Lys Asn Val Leu Leu Cys Leu Glu Glu
385                 390                 395                 400

Arg Asp Trp Asp Pro Gly Leu Ala Ile Ile Asp Asn Leu Met Gln Ser
                405                 410                 415

Ile Asn Gln Ser Lys Lys Thr Val Phe Val Leu Thr Lys Lys Tyr Ala
                420                 425                 430

Lys Ser Trp Asn Phe Lys Thr Ala Phe Tyr Leu Ala Leu Gln Arg Leu
                435                 440                 445

Met Asp Glu Asn Met Asp Val Ile Ile Phe Ile Leu Leu Glu Pro Val
450                 455                 460

Leu Gln His Ser Gln Tyr Leu Arg Leu Arg Gln Arg Ile Cys Lys Ser
465                 470                 475                 480

Ser Ile Leu Gln Trp Pro Asp Asn Pro Lys Ala Glu Gly Leu Phe Trp
                485                 490                 495

Gln Thr Leu Arg Asn Val Val Leu Thr Glu Asn Asp Ser Arg Tyr Asn
                500                 505                 510

Asn Met Tyr Val Asp Ser Ile Lys Gln Tyr
                515                 520

<210> SEQ ID NO 137
<211> LENGTH: 545
<212> TYPE: PRT
<213> ORGANISM: Artificial Sequence
```

```
<220> FEATURE:
<223> OTHER INFORMATION: CER108 protein
<220> FEATURE:
<221> NAME/KEY: sig_peptide
<222> LOCATION: 1...22

<400> SEQUENCE: 137

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
                35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ala Cys Cys Val Gly
                275                 280                 285

Phe Val Leu Met Val Leu Leu Phe Leu Ala Phe Leu Tyr Phe Leu Gly
                290                 295                 300

Arg Leu Val Pro Arg Gly Arg Gly Ala Ala Glu Ala Ala Thr Arg Lys
305                 310                 315                 320

Gln Arg Ile Thr Glu Thr Glu Ser Pro Tyr Gln Glu Leu Gln Gly Gln
                325                 330                 335

Arg Ser Asp Val Tyr Ser Asp Leu Asn Thr Gln Arg Pro Tyr Tyr Lys
                340                 345                 350

His His Leu Phe Tyr Trp Asp Val Trp Phe Ile Tyr Asn Val Cys Leu
                355                 360                 365

Ala Lys Val Lys Gly Tyr Arg Ser Leu Ser Thr Ser Gln Thr Phe Tyr
                370                 375                 380
```

-continued

```
Asp Ala Tyr Ile Ser Tyr Asp Thr Lys Asp Ala Ser Val Thr Asp Trp
385                 390                 395                 400

Val Ile Asn Glu Leu Arg Tyr His Leu Glu Ser Arg Asp Lys Asn
            405                 410                 415

Val Leu Leu Cys Leu Glu Glu Arg Asp Trp Asp Pro Gly Leu Ala Ile
            420                 425                 430

Ile Asp Asn Leu Met Gln Ser Ile Asn Gln Ser Lys Lys Thr Val Phe
            435                 440                 445

Val Leu Thr Lys Lys Tyr Ala Lys Ser Trp Asn Phe Lys Thr Ala Phe
            450                 455                 460

Tyr Leu Ala Leu Gln Arg Leu Met Asp Glu Asn Met Asp Val Ile Ile
465                 470                 475                 480

Phe Ile Leu Leu Glu Pro Val Leu Gln His Ser Gln Tyr Leu Arg Leu
                485                 490                 495

Arg Gln Arg Ile Cys Lys Ser Ser Ile Leu Gln Trp Pro Asp Asn Pro
            500                 505                 510

Lys Ala Glu Gly Leu Phe Trp Gln Thr Leu Arg Asn Val Val Leu Thr
            515                 520                 525

Glu Asn Asp Ser Arg Tyr Asn Asn Met Tyr Val Asp Ser Ile Lys Gln
            530                 535                 540

Tyr
545

<210> SEQ ID NO 138
<211> LENGTH: 578
<212> TYPE: PRT
<213> ORGANISM: Artificial Sequence
<220> FEATURE:
<223> OTHER INFORMATION: CER109 protein
<220> FEATURE:
<221> NAME/KEY: sig_peptide
<222> LOCATION: 1...22

<400> SEQUENCE: 138

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
            130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175
```

```
Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
195                 200                 205

Phe Thr Thr Glu Ser Glu Thr Leu Pro Ala Ser Asn His Ser Gln Arg
        210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Lys Ser His
        260                 265                 270

Gln Ile Asn Ser Arg Gln Thr Ile Leu Ile Ile Ala Cys Cys Val Gly
                275                 280                 285

Phe Val Leu Met Val Leu Leu Phe Leu Ala Phe Leu Ser Trp Arg Arg
        290                 295                 300

Arg Gln Arg Arg Leu Arg Gly Ala Ser Ser Ala Glu Ala Pro Asp Gly
305                 310                 315                 320

Asp Lys Asp Ala Pro Glu Pro Leu Asp Lys Val Ile Ile Leu Ser Pro
                325                 330                 335

Gly Ile Ser Asp Ala Thr Ala Pro Ala Trp Pro Pro Gly Glu Asp
                340                 345                 350

Pro Gly Thr Thr Pro Pro Gly His Ser Val Pro Val Pro Ala Thr Glu
        355                 360                 365

Leu Gly Ser Thr Glu Leu Val Thr Thr Lys Thr Ala Gly Pro Glu Gln
        370                 375                 380

Gln His His Leu Phe Tyr Trp Asp Val Trp Phe Ile Tyr Asn Val Cys
385                 390                 395                 400

Leu Ala Lys Val Lys Gly Tyr Arg Ser Leu Ser Thr Ser Gln Thr Phe
                405                 410                 415

Tyr Asp Ala Tyr Ile Ser Tyr Asp Thr Lys Asp Ala Ser Val Thr Asp
                420                 425                 430

Trp Val Ile Asn Glu Leu Arg Tyr His Leu Glu Glu Ser Arg Asp Lys
        435                 440                 445

Asn Val Leu Leu Cys Leu Glu Glu Arg Asp Trp Asp Pro Gly Leu Ala
450                 455                 460

Ile Ile Asp Asn Leu Met Gln Ser Ile Asn Gln Ser Lys Lys Thr Val
465                 470                 475                 480

Phe Val Leu Thr Lys Lys Tyr Ala Lys Ser Trp Asn Phe Lys Thr Ala
                485                 490                 495

Phe Tyr Leu Ala Leu Gln Arg Leu Met Asp Glu Asn Met Asp Val Ile
                500                 505                 510

Ile Phe Ile Leu Leu Glu Pro Val Leu Gln His Ser Gln Tyr Leu Arg
        515                 520                 525

Leu Arg Gln Arg Ile Cys Lys Ser Ser Ile Leu Gln Trp Pro Asp Asn
        530                 535                 540

Pro Lys Ala Glu Gly Leu Phe Trp Gln Thr Leu Arg Asn Val Val Leu
545                 550                 555                 560

Thr Glu Asn Asp Ser Arg Tyr Asn Asn Met Tyr Val Asp Ser Ile Lys
                565                 570                 575

Gln Tyr
```

-continued

```
<210> SEQ ID NO 139
<211> LENGTH: 619
<212> TYPE: PRT
<213> ORGANISM: Artificial Sequence
<220> FEATURE:
<223> OTHER INFORMATION: CER111A protein
<220> FEATURE:
<221> NAME/KEY: sig_peptide
<222> LOCATION: 1...22

<400> SEQUENCE: 139

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Met Ser Leu Leu
    290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
                325                 330                 335

Gly Gly Thr Ala Ser Thr Gly Asn Leu Ser Ser Phe Met Glu Glu
            340                 345                 350

Ile Gln Gly Tyr Asp Val Glu Phe Asp Pro Pro Leu Glu Ser Lys Tyr
```

```
                355                 360                 365
Glu Cys Pro Ile Cys Leu Met Ala Leu Arg Glu Ala Val Gln Thr Pro
            370                 375                 380

Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
            405                 410                 415

Leu Phe Pro Asp Asn Phe Ala Lys Arg Glu Ile Leu Ser Leu Met Val
            420                 425                 430

Lys Cys Pro Asn Glu Gly Cys Leu His Lys Met Glu Leu Arg His Leu
            435                 440                 445

Glu Asp His Gln Ala His Cys Glu Phe Ala Leu Met Asp Cys Pro Gln
            450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
            485                 490                 495

Ala Phe Glu Asp Lys Glu Ile His Asp Gln Asn Cys Pro Leu Ala Asn
            500                 505                 510

Val Ile Cys Glu Tyr Cys Asn Thr Ile Leu Ile Arg Glu Gln Met Pro
            515                 520                 525

Asn His Tyr Asp Leu Asp Cys Pro Thr Ala Pro Ile Pro Cys Thr Phe
            530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala Asp Ser
            565                 570                 575

Lys Ala Gly Met Glu Asp His Thr Tyr Glu Gly Leu Asp Ile Asp
            580                 585                 590

Gln Thr Ala Thr Tyr Glu Asp Ile Val Thr Leu Arg Thr Gly Glu Val
            595                 600                 605

Lys Trp Ser Val Gly Glu His Pro Gly Gln Glu
610                 615

<210> SEQ ID NO 140
<211> LENGTH: 659
<212> TYPE: PRT
<213> ORGANISM: Artificial Sequence
<220> FEATURE:
<223> OTHER INFORMATION: CER113 protein
<220> FEATURE:
<221> NAME/KEY: sig_peptide
<222> LOCATION: 1...22

<400> SEQUENCE: 140

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
            50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
```

```
                        85                  90                  95
Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
            115                 120                 125

Leu Glu Leu Arg Arg Ala Thr Thr Lys Lys Pro Thr Thr Thr Thr Thr
        130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Met Ser Leu Leu
290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
                325                 330                 335

Gly Gly Thr Ala Ser Thr Gly Asn Leu Ser Ser Ser Phe Met Glu Glu
            340                 345                 350

Ile Gln Gly Tyr Asp Val Glu Phe Asp Pro Pro Leu Glu Ser Lys Tyr
        355                 360                 365

Glu Cys Pro Ile Cys Leu Met Ala Leu Arg Glu Ala Val Gln Thr Pro
    370                 375                 380

Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
                405                 410                 415

Leu Phe Pro Asp Asn Phe Ala Lys Arg Glu Ile Leu Ser Leu Met Val
            420                 425                 430

Lys Cys Pro Asn Glu Gly Cys Leu His Lys Met Glu Leu Arg His Leu
        435                 440                 445

Glu Asp His Gln Ala His Cys Glu Phe Ala Leu Met Asp Cys Pro Gln
    450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn
            500                 505                 510
```

-continued

```
Val Ile Cys Glu Tyr Cys Asn Thr Ile Leu Ile Arg Glu Gln Met Pro
            515                 520                 525

Asn His Tyr Asp Leu Asp Cys Pro Thr Ala Pro Ile Pro Cys Thr Phe
530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala Ser Trp
            565                 570                 575

Arg Arg Arg Gln Arg Arg Leu Arg Gly Ala Ser Ser Ala Glu Ala Pro
            580                 585                 590

Asp Gly Asp Lys Asp Ala Pro Glu Pro Leu Asp Lys Val Ile Ile Leu
            595                 600                 605

Ser Pro Gly Ile Ser Asp Ala Thr Ala Pro Ala Trp Pro Pro Pro Gly
            610                 615                 620

Glu Asp Pro Gly Thr Thr Pro Pro Gly His Ser Val Pro Val Pro Ala
625                 630                 635                 640

Thr Glu Leu Gly Ser Thr Glu Leu Val Thr Thr Lys Thr Ala Gly Pro
            645                 650                 655

Glu Gln Gln

<210> SEQ ID NO 141
<211> LENGTH: 1050
<212> TYPE: PRT
<213> ORGANISM: Artificial Sequence
<220> FEATURE:
<223> OTHER INFORMATION: CER114 protein
<220> FEATURE:
<221> NAME/KEY: sig_peptide
<222> LOCATION: 1...22

<400> SEQUENCE: 141

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
        50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
            130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190
```

```
Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Met Ser Leu Leu
    290                 295                 300

Asn Cys Glu Asn Ser Cys Gly Ser Ser Gln Ser Glu Ser Asp Cys Cys
305                 310                 315                 320

Val Ala Met Ala Ser Ser Cys Ser Ala Val Thr Lys Asp Asp Ser Val
                325                 330                 335

Gly Gly Thr Ala Ser Thr Gly Asn Leu Ser Ser Ser Phe Met Glu Glu
            340                 345                 350

Ile Gln Gly Tyr Asp Val Glu Phe Asp Pro Pro Leu Glu Ser Lys Tyr
        355                 360                 365

Glu Cys Pro Ile Cys Leu Met Ala Leu Arg Glu Ala Val Gln Thr Pro
    370                 375                 380

Cys Gly His Arg Phe Cys Lys Ala Cys Ile Ile Lys Ser Ile Arg Asp
385                 390                 395                 400

Ala Gly His Lys Cys Pro Val Asp Asn Glu Ile Leu Leu Glu Asn Gln
                405                 410                 415

Leu Phe Pro Asp Asn Phe Ala Lys Arg Glu Ile Leu Ser Leu Met Val
            420                 425                 430

Lys Cys Pro Asn Glu Gly Cys Leu His Lys Met Glu Leu Arg His Leu
        435                 440                 445

Glu Asp His Gln Ala His Cys Glu Phe Ala Leu Met Asp Cys Pro Gln
    450                 455                 460

Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn
            500                 505                 510

Val Ile Cys Glu Tyr Cys Asn Thr Ile Leu Ile Arg Glu Gln Met Pro
        515                 520                 525

Asn His Tyr Asp Leu Asp Cys Pro Thr Ala Pro Ile Pro Cys Thr Phe
    530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala Ala Leu
                565                 570                 575

Arg Arg Arg Val Gln Glu Thr Lys Phe Gly Gly Ala Phe Ser Glu Glu
            580                 585                 590

Asp Ser Gln Leu Val Val Asn Tyr Arg Ala Lys Lys Ser Phe Cys Arg
        595                 600                 605

Arg Ala Ile Glu Leu Thr Leu Gln Ser Leu Gly Val Ser Glu Glu Leu
```

```
            610                 615                 620
Gln Asn Lys Leu Glu Asp Val Ile Asp Arg Asn Leu Leu Val Leu
625                 630                 635                 640

Gly Lys Val Leu Gly Glu Gly Glu Phe Gly Ser Val Met Glu Gly Asn
                645                 650                 655

Leu Lys Gln Glu Asp Gly Thr Ser Gln Lys Val Ala Val Lys Thr Met
                660                 665                 670

Lys Leu Asp Asn Phe Ser Gln Arg Glu Ile Glu Glu Phe Leu Ser Glu
                675                 680                 685

Ala Ala Cys Met Lys Asp Phe Asn His Pro Asn Val Ile Arg Leu Leu
690                 695                 700

Gly Val Cys Ile Glu Leu Ser Ser Gln Gly Ile Pro Lys Pro Met Val
705                 710                 715                 720

Ile Leu Pro Phe Met Lys Tyr Gly Asp Leu His Thr Phe Leu Leu Tyr
                725                 730                 735

Ser Arg Leu Asn Thr Gly Pro Lys Tyr Ile His Leu Gln Thr Leu Leu
                740                 745                 750

Lys Phe Met Met Asp Ile Ala Gln Gly Met Glu Tyr Leu Ser Asn Arg
                755                 760                 765

Asn Phe Leu His Arg Asp Leu Ala Ala Arg Asn Cys Met Leu Arg Asp
                770                 775                 780

Asp Met Thr Val Cys Val Ala Asp Phe Gly Leu Ser Lys Lys Ile Tyr
785                 790                 795                 800

Ser Gly Asp Tyr Tyr Arg Gln Gly Arg Ile Ala Lys Met Pro Val Lys
                805                 810                 815

Trp Ile Ala Ile Glu Ser Leu Ala Asp Arg Val Tyr Thr Ser Lys Ser
                820                 825                 830

Asp Val Trp Ala Phe Gly Val Thr Met Trp Glu Ile Thr Thr Arg Gly
                835                 840                 845

Met Thr Pro Tyr Pro Gly Val Gln Asn His Glu Met Tyr Asp Tyr Leu
850                 855                 860

Leu His Gly His Arg Leu Lys Gln Pro Glu Asp Cys Leu Asp Glu Leu
865                 870                 875                 880

Tyr Asp Ile Met Tyr Ser Cys Trp Ser Ala Asp Pro Leu Asp Arg Pro
                885                 890                 895

Thr Phe Ser Val Leu Arg Leu Gln Leu Glu Lys Leu Ser Glu Ser Leu
                900                 905                 910

Pro Asp Ala Gln Asp Lys Glu Ser Ile Ile Tyr Ile Asn Thr Gln Leu
                915                 920                 925

Leu Glu Ser Cys Glu Gly Ile Ala Asn Gly Pro Ser Leu Thr Gly Leu
930                 935                 940

Asp Met Asn Ile Asp Pro Asp Ser Ile Ile Ala Ser Cys Thr Pro Gly
945                 950                 955                 960

Ala Ala Val Ser Val Val Thr Ala Glu Val His Glu Asn Asn Leu Arg
                965                 970                 975

Glu Glu Arg Tyr Ile Leu Asn Gly Gly Asn Glu Glu Trp Glu Asp Val
                980                 985                 990

Ser Ser Thr Pro Phe Ala Ala Val Thr Pro Glu Lys Asp Gly Val Leu
                995                 1000                1005

Pro Glu Asp Arg Leu Thr Lys Asn Gly Val Ser Trp Ser His His Ser
        1010                1015                1020

Thr Leu Pro Leu Gly Ser Pro Ser Pro Asp Glu Leu Leu Phe Val Asp
1025                1030                1035                1040
```

```
Asp Ser Leu Glu Asp Ser Glu Val Leu Met
            1045                1050

<210> SEQ ID NO 142
<211> LENGTH: 1050
<212> TYPE: PRT
<213> ORGANISM: Artificial Sequence
<220> FEATURE:
<223> OTHER INFORMATION: CER115 protein
<220> FEATURE:
<221> NAME/KEY: sig_peptide
<222> LOCATION: 1...22

<400> SEQUENCE: 142

Met Ser Lys Gly Leu Leu Leu Trp Leu Val Thr Glu Leu Trp Trp
1                5              10                 15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Ala Leu Arg Arg
    290                 295                 300

Arg Val Gln Glu Thr Lys Phe Gly Gly Ala Phe Ser Glu Glu Asp Ser
305                 310                 315                 320

Gln Leu Val Val Asn Tyr Arg Ala Lys Lys Ser Phe Cys Arg Arg Ala
                325                 330                 335
```

```
Ile Glu Leu Thr Leu Gln Ser Leu Gly Val Ser Glu Leu Gln Asn
                340                 345                 350

Lys Leu Glu Asp Val Val Ile Asp Arg Asn Leu Leu Val Leu Gly Lys
            355                 360                 365

Val Leu Gly Glu Gly Gly Phe Gly Ser Val Met Glu Gly Asn Leu Lys
370                 375                 380

Gln Glu Asp Gly Thr Ser Gln Lys Val Ala Val Lys Thr Met Lys Leu
385                 390                 395                 400

Asp Asn Phe Ser Gln Arg Glu Ile Glu Phe Leu Ser Glu Ala Ala
                405                 410                 415

Cys Met Lys Asp Phe Asn His Pro Asn Val Ile Arg Leu Leu Gly Val
            420                 425                 430

Cys Ile Glu Leu Ser Ser Gln Gly Ile Pro Lys Pro Met Val Ile Leu
            435                 440                 445

Pro Phe Met Lys Tyr Gly Asp Leu His Thr Phe Leu Leu Tyr Ser Arg
            450                 455                 460

Leu Asn Thr Gly Pro Lys Tyr Ile His Leu Gln Thr Leu Leu Lys Phe
465                 470                 475                 480

Met Met Asp Ile Ala Gln Gly Met Glu Tyr Leu Ser Asn Arg Asn Phe
                485                 490                 495

Leu His Arg Asp Leu Ala Ala Arg Asn Cys Met Leu Arg Asp Asp Met
            500                 505                 510

Thr Val Cys Val Ala Asp Phe Gly Leu Ser Lys Lys Ile Tyr Ser Gly
            515                 520                 525

Asp Tyr Tyr Arg Gln Gly Arg Ile Ala Lys Met Pro Val Lys Trp Ile
            530                 535                 540

Ala Ile Glu Ser Leu Ala Asp Arg Val Tyr Thr Ser Lys Ser Asp Val
545                 550                 555                 560

Trp Ala Phe Gly Val Thr Met Trp Glu Ile Thr Thr Arg Gly Met Thr
                565                 570                 575

Pro Tyr Pro Gly Val Gln Asn His Glu Met Tyr Asp Tyr Leu Leu His
            580                 585                 590

Gly His Arg Leu Lys Gln Pro Glu Asp Cys Leu Asp Glu Leu Tyr Asp
            595                 600                 605

Ile Met Tyr Ser Cys Trp Ser Ala Asp Pro Leu Asp Arg Pro Thr Phe
            610                 615                 620

Ser Val Leu Arg Leu Gln Leu Glu Lys Leu Ser Glu Ser Leu Pro Asp
625                 630                 635                 640

Ala Gln Asp Lys Glu Ser Ile Ile Tyr Ile Asn Thr Gln Leu Leu Glu
                645                 650                 655

Ser Cys Glu Gly Ile Ala Asn Gly Pro Ser Leu Thr Gly Leu Asp Met
            660                 665                 670

Asn Ile Asp Pro Asp Ser Ile Ile Ala Ser Cys Thr Pro Gly Ala Ala
            675                 680                 685

Val Ser Val Val Thr Ala Glu Val His Glu Asn Asn Leu Arg Glu Glu
            690                 695                 700

Arg Tyr Ile Leu Asn Gly Gly Asn Glu Glu Trp Glu Asp Val Ser Ser
705                 710                 715                 720

Thr Pro Phe Ala Ala Val Thr Pro Glu Lys Asp Gly Val Leu Pro Glu
                725                 730                 735

Asp Arg Leu Thr Lys Asn Gly Val Ser Trp Ser His Ser Thr Leu
            740                 745                 750
```

```
Pro Leu Gly Ser Pro Ser Pro Asp Glu Leu Leu Phe Val Asp Asp Ser
        755                 760                 765

Leu Glu Asp Ser Glu Val Leu Met Met Ser Leu Leu Asn Cys Glu Asn
        770                 775                 780

Ser Cys Gly Ser Ser Gln Ser Glu Ser Asp Cys Cys Val Ala Met Ala
785                 790                 795                 800

Ser Ser Cys Ser Ala Val Thr Lys Asp Asp Ser Val Gly Gly Thr Ala
                805                 810                 815

Ser Thr Gly Asn Leu Ser Ser Ser Phe Met Glu Glu Ile Gln Gly Tyr
                820                 825                 830

Asp Val Glu Phe Asp Pro Pro Leu Glu Ser Lys Tyr Glu Cys Pro Ile
        835                 840                 845

Cys Leu Met Ala Leu Arg Glu Ala Val Gln Thr Pro Cys Gly His Arg
        850                 855                 860

Phe Cys Lys Ala Cys Ile Ile Lys Ser Ile Arg Asp Ala Gly His Lys
865                 870                 875                 880

Cys Pro Val Asp Asn Glu Ile Leu Leu Glu Asn Gln Leu Phe Pro Asp
                885                 890                 895

Asn Phe Ala Lys Arg Glu Ile Leu Ser Leu Met Val Lys Cys Pro Asn
                900                 905                 910

Glu Gly Cys Leu His Lys Met Glu Leu Arg His Leu Glu Asp His Gln
        915                 920                 925

Ala His Cys Glu Phe Ala Leu Met Asp Cys Pro Gln Cys Gln Arg Pro
        930                 935                 940

Phe Gln Lys Phe His Ile Asn Ile His Ile Leu Lys Asp Cys Pro Arg
945                 950                 955                 960

Arg Gln Val Ser Cys Asp Asn Cys Ala Ala Ser Met Ala Phe Glu Asp
                965                 970                 975

Lys Glu Ile His Asp Gln Asn Cys Pro Leu Ala Asn Val Ile Cys Glu
                980                 985                 990

Tyr Cys Asn Thr Ile Leu Ile Arg Glu Gln Met Pro Asn His Tyr Asp
        995                 1000                1005

Leu Asp Cys Pro Thr Ala Pro Ile Pro Cys Thr Phe Ser Thr Phe Gly
        1010                1015                1020

Cys His Glu Lys Met Gln Arg Asn His Leu Ala Arg His Leu Gln Glu
1025                1030                1035                1040

Asn Thr Gln Ser His Met Arg Met Leu Ala
                1045                1050

<210> SEQ ID NO 143
<211> LENGTH: 767
<212> TYPE: PRT
<213> ORGANISM: Artificial Sequence
<220> FEATURE:
<223> OTHER INFORMATION: CER116 protein
<220> FEATURE:
<221> NAME/KEY: sig_peptide
<222> LOCATION: 1...22

<400> SEQUENCE: 143

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45
```

```
Arg Asn Ser Met Cys Trp Gly Lys Gly Ser Cys Pro Asn Ser Lys Cys
 50                  55                  60
Asn Ala Glu Leu Leu Arg Thr Asp Gly Thr Arg Ile Ile Ser Arg Lys
 65                  70                  75                  80
Ser Thr Lys Tyr Thr Leu Leu Gly Lys Val Gln Phe Gly Glu Val Ser
                 85                  90                  95
Leu Thr Ile Ser Asn Thr Asn Arg Gly Asp Ser Gly Val Tyr Cys Cys
                100                 105                 110
Arg Ile Glu Val Pro Gly Trp Phe Asn Asp Val Lys Lys Asn Val Arg
                115                 120                 125
Leu Glu Leu Arg Arg Ala Thr Thr Thr Lys Lys Pro Thr Thr Thr Thr
130                 135                 140
Arg Pro Thr Thr Thr Pro Tyr Val Thr Thr Thr Thr Pro Glu Leu Leu
145                 150                 155                 160
Pro Thr Thr Val Met Thr Thr Ser Val Leu Pro Thr Thr Thr Pro Pro
                165                 170                 175
Gln Thr Leu Ala Thr Thr Ala Phe Ser Thr Ala Val Thr Thr Cys Pro
                180                 185                 190
Ser Thr Thr Pro Gly Ser Phe Ser Gln Glu Thr Thr Lys Gly Ser Ala
                195                 200                 205
Phe Thr Thr Glu Ser Glu Thr Leu Pro Ala Ser Asn His Ser Gln Arg
                210                 215                 220
Ser Met Met Thr Ile Ser Thr Asp Ile Ala Val Leu Arg Pro Thr Gly
225                 230                 235                 240
Ser Asn Pro Gly Ile Leu Pro Ser Thr Ser Gln Leu Thr Thr Gln Lys
                245                 250                 255
Thr Thr Leu Thr Thr Ser Glu Ser Leu Gln Lys Thr Thr Lys Ser His
                260                 265                 270
Gln Ile Asn Ser Arg Gln Thr Ile Leu Ile Ile Ala Cys Cys Val Gly
                275                 280                 285
Phe Val Leu Met Val Leu Leu Phe Leu Ala Phe Leu Met Ser Leu Leu
                290                 295                 300
Asn Cys Glu Asn Ser Cys Gly Ser Ser Gln Ser Glu Ser Asp Cys Cys
305                 310                 315                 320
Val Ala Met Ala Ser Ser Cys Ser Ala Val Thr Lys Asp Asp Ser Val
                325                 330                 335
Gly Gly Thr Ala Ser Thr Gly Asn Leu Ser Ser Ser Phe Met Glu Glu
                340                 345                 350
Ile Gln Gly Tyr Asp Val Glu Phe Asp Pro Pro Leu Glu Ser Lys Tyr
                355                 360                 365
Glu Cys Pro Ile Cys Leu Met Ala Leu Arg Glu Ala Val Gln Thr Pro
                370                 375                 380
Cys Gly His Arg Phe Cys Lys Ala Cys Ile Ile Lys Ser Ile Arg Asp
385                 390                 395                 400
Ala Gly His Lys Cys Pro Val Asp Asn Glu Ile Leu Leu Glu Asn Gln
                405                 410                 415
Leu Phe Pro Asp Asn Phe Ala Lys Arg Glu Ile Leu Ser Leu Met Val
                420                 425                 430
Lys Cys Pro Asn Glu Gly Cys Leu His Lys Met Glu Leu Arg His Leu
                435                 440                 445
Glu Asp His Gln Ala His Cys Glu Phe Ala Leu Met Asp Cys Pro Gln
450                 455                 460
Cys Gln Arg Pro Phe Gln Lys Phe His Ile Asn Ile His Ile Leu Lys
```

```
        465                 470                 475                 480
Asp Cys Pro Arg Arg Gln Val Ser Cys Asp Asn Cys Ala Ala Ser Met
                    485                 490                 495
Ala Phe Glu Asp Lys Glu Ile His Asp Gln Asn Cys Pro Leu Ala Asn
                500                 505                 510
Val Ile Cys Glu Tyr Cys Asn Thr Ile Leu Ile Arg Glu Gln Met Pro
            515                 520                 525
Asn His Tyr Asp Leu Asp Cys Pro Thr Ala Pro Ile Pro Cys Thr Phe
        530                 535                 540
Ser Thr Phe Gly Cys His Glu Lys Met Gln Arg Asn His Leu Ala Arg
545                 550                 555                 560
His Leu Gln Glu Asn Thr Gln Ser His Met Arg Met Leu Ala His His
                565                 570                 575
Leu Phe Tyr Trp Asp Val Trp Phe Ile Tyr Asn Val Cys Leu Ala Lys
                580                 585                 590
Val Lys Gly Tyr Arg Ser Leu Ser Thr Ser Gln Thr Phe Tyr Asp Ala
            595                 600                 605
Tyr Ile Ser Tyr Asp Thr Lys Asp Ala Ser Val Thr Asp Trp Val Ile
        610                 615                 620
Asn Glu Leu Arg Tyr His Leu Glu Glu Ser Arg Asp Lys Asn Val Leu
625                 630                 635                 640
Leu Cys Leu Glu Glu Arg Asp Trp Asp Pro Gly Leu Ala Ile Ile Asp
                645                 650                 655
Asn Leu Met Gln Ser Ile Asn Gln Ser Lys Lys Thr Val Phe Val Leu
                660                 665                 670
Thr Lys Lys Tyr Ala Lys Ser Trp Asn Phe Lys Thr Ala Phe Tyr Leu
            675                 680                 685
Ala Leu Gln Arg Leu Met Asp Glu Asn Met Asp Val Ile Ile Phe Ile
        690                 695                 700
Leu Leu Glu Pro Val Leu Gln His Ser Gln Tyr Leu Arg Leu Arg Gln
705                 710                 715                 720
Arg Ile Cys Lys Ser Ser Ile Leu Gln Trp Pro Asp Asn Pro Lys Ala
                725                 730                 735
Glu Gly Leu Phe Trp Gln Thr Leu Arg Asn Val Val Leu Thr Glu Asn
                740                 745                 750
Asp Ser Arg Tyr Asn Asn Met Tyr Val Asp Ser Ile Lys Gln Tyr
            755                 760                 765

<210> SEQ ID NO 144
<211> LENGTH: 767
<212> TYPE: PRT
<213> ORGANISM: Artificial Sequence
<220> FEATURE:
<223> OTHER INFORMATION: CER117 protein
<220> FEATURE:
<221> NAME/KEY: sig_peptide
<222> LOCATION: 1...22

<400> SEQUENCE: 144

Met Ser Lys Gly Leu Leu Leu Trp Leu Val Thr Glu Leu Trp Trp
1               5                   10                  15
Leu Tyr Leu Thr Pro Ala Ala Ser Glu Asp Thr Ile Ile Gly Phe Leu
                20                  25                  30
Gly Gln Pro Val Thr Leu Pro Cys His Tyr Leu Ser Trp Ser Gln Ser
            35                  40                  45
Arg Asn Ser Met Cys Trp Gly Lys Gly Ser Cys Pro Asn Ser Lys Cys
```

```
            50                  55                  60
Asn Ala Glu Leu Leu Arg Thr Asp Gly Thr Arg Ile Ile Ser Arg Lys
 65                  70                  75                  80

Ser Thr Lys Tyr Thr Leu Leu Gly Lys Val Gln Phe Gly Glu Val Ser
                 85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
                210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ile Ala Cys Cys Val Gly
                275                 280                 285

Phe Val Leu Met Val Leu Leu Phe Leu Ala Phe Leu His His Leu Phe
                290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                325                 330                 335

Ser Tyr Asp Thr Lys Asp Ala Ser Val Thr Asp Trp Val Ile Asn Glu
                340                 345                 350

Leu Arg Tyr His Leu Glu Glu Ser Arg Asp Lys Asn Val Leu Leu Cys
                355                 360                 365

Leu Glu Glu Arg Asp Trp Asp Pro Gly Leu Ala Ile Ile Asp Asn Leu
                370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                405                 410                 415

Gln Arg Leu Met Asp Glu Asn Met Asp Val Ile Ile Phe Ile Leu Leu
                420                 425                 430

Glu Pro Val Leu Gln His Ser Gln Tyr Leu Arg Leu Arg Gln Arg Ile
                435                 440                 445

Cys Lys Ser Ser Ile Leu Gln Trp Pro Asp Asn Pro Lys Ala Glu Gly
                450                 455                 460

Leu Phe Trp Gln Thr Leu Arg Asn Val Val Leu Thr Glu Asn Asp Ser
465                 470                 475                 480
```

```
Arg Tyr Asn Asn Met Tyr Val Asp Ser Ile Lys Gln Tyr Met Ser Leu
            485                 490                 495

Leu Asn Cys Glu Asn Ser Cys Gly Ser Ser Gln Ser Glu Ser Asp Cys
        500                 505                 510

Cys Val Ala Met Ala Ser Ser Cys Ser Ala Val Thr Lys Asp Asp Ser
        515                 520                 525

Val Gly Gly Thr Ala Ser Thr Gly Asn Leu Ser Ser Ser Phe Met Glu
        530                 535                 540

Glu Ile Gln Gly Tyr Asp Val Glu Phe Asp Pro Pro Leu Glu Ser Lys
545                 550                 555                 560

Tyr Glu Cys Pro Ile Cys Leu Met Ala Leu Arg Glu Ala Val Gln Thr
                565                 570                 575

Pro Cys Gly His Arg Phe Cys Lys Ala Cys Ile Ile Lys Ser Ile Arg
            580                 585                 590

Asp Ala Gly His Lys Cys Pro Val Asp Asn Glu Ile Leu Leu Glu Asn
        595                 600                 605

Gln Leu Phe Pro Asp Asn Phe Ala Lys Arg Glu Ile Leu Ser Leu Met
        610                 615                 620

Val Lys Cys Pro Asn Glu Gly Cys Leu His Lys Met Glu Leu Arg His
625                 630                 635                 640

Leu Glu Asp His Gln Ala His Cys Glu Phe Ala Leu Met Asp Cys Pro
                645                 650                 655

Gln Cys Gln Arg Pro Phe Gln Lys Phe His Ile Asn Ile His Ile Leu
            660                 665                 670

Lys Asp Cys Pro Arg Arg Gln Val Ser Cys Asp Asn Cys Ala Ala Ser
        675                 680                 685

Met Ala Phe Glu Asp Lys Glu Ile His Asp Gln Asn Cys Pro Leu Ala
        690                 695                 700

Asn Val Ile Cys Glu Tyr Cys Asn Thr Ile Leu Ile Arg Glu Gln Met
705                 710                 715                 720

Pro Asn His Tyr Asp Leu Asp Cys Pro Thr Ala Pro Ile Pro Cys Thr
                725                 730                 735

Phe Ser Thr Phe Gly Cys His Glu Lys Met Gln Arg Asn His Leu Ala
            740                 745                 750

Arg His Leu Gln Glu Asn Thr Gln Ser His Met Arg Met Leu Ala
        755                 760                 765

<210> SEQ ID NO 145
<211> LENGTH: 571
<212> TYPE: PRT
<213> ORGANISM: Artificial Sequence
<220> FEATURE:
<223> OTHER INFORMATION: CER118 protein
<220> FEATURE:
<221> NAME/KEY: sig_peptide
<222> LOCATION: 1...22

<400> SEQUENCE: 145

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60
```

```
Asn Ala Glu Leu Leu Arg Thr Asp Gly Thr Arg Ile Ile Ser Arg Lys
 65                  70                  75                  80

Ser Thr Lys Tyr Thr Leu Leu Gly Lys Val Gln Phe Gly Glu Val Ser
                 85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Ser Tyr Leu Asp
    290                 295                 300

Leu Pro Trp Tyr Leu Arg Met Val Cys Gln Trp Thr Gln Thr Arg Arg
305                 310                 315                 320

Arg Ala Arg Asn Ile Pro Leu Glu Glu Leu Gln Arg Asn Leu Gln Phe
                325                 330                 335

His Ala Phe Ile Ser Tyr Ser Gly His Asp Ser Phe Trp Val Lys Asn
            340                 345                 350

Glu Leu Leu Pro Asn Leu Glu Lys Glu Gly Met Gln Ile Cys Leu His
        355                 360                 365

Glu Arg Asn Phe Val Pro Gly Lys Ser Ile Val Glu Asn Ile Ile Thr
    370                 375                 380

Cys Ile Glu Lys Ser Tyr Lys Ser Ile Phe Val Leu Ser Pro Asn Phe
385                 390                 395                 400

Val Gln Ser Glu Trp Cys His Tyr Glu Leu Tyr Phe Ala His His Asn
                405                 410                 415

Leu Phe His Glu Gly Ser Asn Ser Leu Ile Leu Ile Leu Leu Glu Pro
            420                 425                 430

Ile Pro Gln Tyr Ser Ile Pro Ser Ser Tyr His Lys Leu Lys Ser Leu
        435                 440                 445

Met Ala Arg Arg Thr Tyr Leu Glu Trp Pro Lys Glu Lys Ser Lys Arg
    450                 455                 460

Gly Leu Phe Trp Ala Asn Leu Arg Ala Ala Ile Asn Ile Lys Leu Thr
465                 470                 475                 480
```

```
Glu Gln Ala Lys Lys Leu Trp Asn Lys Lys Arg Met Arg Gly Pro Gly
                485                 490                 495

Lys Asp Pro Thr Arg Lys Cys Pro Asp Pro Arg Ser Ala Ser Ser Pro
            500                 505                 510

Lys Gln His Pro Ser Glu Ser Val Tyr Thr Ala Leu Gln Arg Arg Glu
        515                 520                 525

Thr Glu Val Tyr Ala Cys Ile Glu Asn Glu Asp Gly Ser Ser Pro Thr
    530                 535                 540

Ala Lys Gln Ser Pro Leu Ser Gln Glu Arg Pro His Arg Phe Glu Asp
545                 550                 555                 560

Asp Gly Glu Leu Asn Leu Val Tyr Glu Asn Leu
                565                 570

<210> SEQ ID NO 146
<211> LENGTH: 514
<212> TYPE: PRT
<213> ORGANISM: Artificial Sequence
<220> FEATURE:
<223> OTHER INFORMATION: CER119B protein
<220> FEATURE:
<221> NAME/KEY: sig_peptide
<222> LOCATION: 1...22

<400> SEQUENCE: 146

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255
```

```
Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Ser Tyr Leu Asp
    290                 295                 300

Leu Pro Trp Tyr Leu Arg Met Val Cys Gln Trp Thr Gln Thr Arg Arg
305                 310                 315                 320

Arg Ala Arg Asn Ile Pro Leu Glu Glu Leu Gln Arg Asn Leu Gln Phe
                325                 330                 335

His Ala Phe Ile Ser Tyr Ser Gly His Asp Ser Phe Trp Val Lys Asn
            340                 345                 350

Glu Leu Leu Pro Asn Leu Glu Lys Glu Gly Met Gln Ile Cys Leu His
        355                 360                 365

Glu Arg Asn Phe Val Pro Gly Lys Ser Ile Val Glu Asn Ile Ile Thr
    370                 375                 380

Cys Ile Glu Lys Ser Tyr Lys Ser Ile Phe Val Leu Ser Pro Asn Phe
385                 390                 395                 400

Val Gln Ser Glu Trp Cys His Tyr Glu Leu Tyr Phe Ala His His Asn
                405                 410                 415

Leu Phe His Glu Gly Ser Asn Ser Leu Ile Leu Ile Leu Leu Glu Pro
            420                 425                 430

Ile Pro Gln Tyr Ser Ile Pro Ser Ser Tyr His Lys Leu Lys Ser Leu
        435                 440                 445

Met Ala Arg Arg Thr Tyr Leu Glu Trp Pro Lys Glu Lys Ser Lys Arg
    450                 455                 460

Gly Leu Phe Trp Ala Asn Leu Arg Ala Ala Ile Asn Ile Lys Leu Thr
465                 470                 475                 480

Glu Gln Ala Lys Lys Asp Ser Lys Ala Gly Met Glu Asp His Thr
                485                 490                 495

Tyr Glu Gly Leu Asp Ile Asp Gln Thr Ala Thr Tyr Glu Asp Ile Val
            500                 505                 510

Thr Leu

<210> SEQ ID NO 147
<211> LENGTH: 537
<212> TYPE: PRT
<213> ORGANISM: Artificial Sequence
<220> FEATURE:
<223> OTHER INFORMATION: CER120 protein
<220> FEATURE:
<221> NAME/KEY: sig_peptide
<222> LOCATION: 1...22

<400> SEQUENCE: 147

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
```

-continued

```
                    85                  90                  95
Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
                115                 120                 125

Leu Glu Leu Arg Arg Ala Thr Thr Lys Lys Pro Thr Thr Thr Thr Thr
            130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
                210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ala Cys Cys Val Gly
                275                 280                 285

Phe Val Leu Met Val Leu Leu Phe Leu Ala Phe Leu Ser Tyr Leu Asp
                290                 295                 300

Leu Pro Trp Tyr Leu Arg Met Val Cys Gln Trp Thr Gln Thr Arg Arg
305                 310                 315                 320

Arg Ala Arg Asn Ile Pro Leu Glu Glu Leu Gln Arg Asn Leu Gln Phe
                325                 330                 335

His Ala Phe Ile Ser Tyr Ser Gly His Asp Ser Phe Trp Val Lys Asn
                340                 345                 350

Glu Leu Leu Pro Asn Leu Glu Lys Glu Gly Met Gln Ile Cys Leu His
                355                 360                 365

Glu Arg Asn Phe Val Pro Gly Lys Ser Ile Val Glu Asn Ile Ile Thr
                370                 375                 380

Cys Ile Glu Lys Ser Tyr Lys Ser Ile Phe Val Leu Ser Pro Asn Phe
385                 390                 395                 400

Val Gln Ser Glu Trp Cys His Tyr Glu Leu Tyr Phe Ala His His Asn
                405                 410                 415

Leu Phe His Glu Gly Ser Asn Ser Leu Ile Leu Ile Leu Leu Glu Pro
                420                 425                 430

Ile Pro Gln Tyr Ser Ile Pro Ser Ser Tyr His Lys Leu Lys Ser Leu
                435                 440                 445

Met Ala Arg Arg Thr Tyr Leu Glu Trp Pro Lys Glu Lys Ser Lys Arg
                450                 455                 460

Gly Leu Phe Trp Ala Asn Leu Arg Ala Ala Ile Asn Ile Lys Leu Thr
465                 470                 475                 480

Glu Gln Ala Lys Lys Tyr Phe Leu Gly Arg Leu Val Pro Arg Gly Arg
                485                 490                 495

Gly Ala Ala Glu Ala Ala Thr Arg Lys Gln Arg Ile Thr Glu Thr Glu
                500                 505                 510
```

-continued

Ser Pro Tyr Gln Glu Leu Gln Gly Gln Arg Ser Asp Val Tyr Ser Asp
        515                 520                 525

Leu Asn Thr Gln Arg Pro Tyr Tyr Lys
    530                 535

<210> SEQ ID NO 148
<211> LENGTH: 759
<212> TYPE: PRT
<213> ORGANISM: Artificial Sequence
<220> FEATURE:
<223> OTHER INFORMATION: CER121 protein
<220> FEATURE:
<221> NAME/KEY: sig_peptide
<222> LOCATION: 1...22

<400> SEQUENCE: 148

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Ser Tyr Leu Asp
    290                 295                 300

Leu Pro Trp Tyr Leu Arg Met Val Cys Gln Trp Thr Gln Thr Arg Arg
305                 310                 315                 320

```
Arg Ala Arg Asn Ile Pro Leu Glu Glu Leu Gln Arg Asn Leu Gln Phe
                325                 330                 335
His Ala Phe Ile Ser Tyr Ser Gly His Asp Ser Phe Trp Val Lys Asn
                340                 345                 350
Glu Leu Leu Pro Asn Leu Glu Lys Gly Met Gln Ile Cys Leu His
                355                 360                 365
Glu Arg Asn Phe Val Pro Gly Lys Ser Ile Val Glu Asn Ile Ile Thr
            370                 375                 380
Cys Ile Glu Lys Ser Tyr Lys Ser Ile Phe Val Leu Ser Pro Asn Phe
385                 390                 395                 400
Val Gln Ser Glu Trp Cys His Tyr Glu Leu Tyr Phe Ala His His Asn
                405                 410                 415
Leu Phe His Glu Gly Ser Asn Ser Leu Ile Leu Ile Leu Leu Glu Pro
                420                 425                 430
Ile Pro Gln Tyr Ser Ile Pro Ser Ser Tyr His Lys Leu Lys Ser Leu
                435                 440                 445
Met Ala Arg Arg Thr Tyr Leu Glu Trp Pro Lys Glu Lys Ser Lys Arg
            450                 455                 460
Gly Leu Phe Trp Ala Asn Leu Arg Ala Ala Ile Asn Ile Lys Leu Thr
465                 470                 475                 480
Glu Gln Ala Lys Lys Met Ser Leu Leu Asn Cys Glu Asn Ser Cys Gly
                485                 490                 495
Ser Ser Gln Ser Glu Ser Asp Cys Cys Val Ala Met Ala Ser Ser Cys
                500                 505                 510
Ser Ala Val Thr Lys Asp Asp Ser Val Gly Gly Thr Ala Ser Thr Gly
                515                 520                 525
Asn Leu Ser Ser Ser Phe Met Glu Glu Ile Gln Gly Tyr Asp Val Glu
            530                 535                 540
Phe Asp Pro Pro Leu Glu Ser Lys Tyr Glu Cys Pro Ile Cys Leu Met
545                 550                 555                 560
Ala Leu Arg Glu Ala Val Gln Thr Pro Cys Gly His Arg Phe Cys Lys
                565                 570                 575
Ala Cys Ile Ile Lys Ser Ile Arg Asp Ala Gly His Lys Cys Pro Val
                580                 585                 590
Asp Asn Glu Ile Leu Leu Glu Asn Gln Leu Phe Pro Asp Asn Phe Ala
                595                 600                 605
Lys Arg Glu Ile Leu Ser Leu Met Val Lys Cys Pro Asn Glu Gly Cys
            610                 615                 620
Leu His Lys Met Glu Leu Arg His Leu Glu Asp His Gln Ala His Cys
625                 630                 635                 640
Glu Phe Ala Leu Met Asp Cys Pro Gln Cys Gln Arg Pro Phe Gln Lys
                645                 650                 655
Phe His Ile Asn Ile His Ile Leu Lys Asp Cys Pro Arg Arg Gln Val
                660                 665                 670
Ser Cys Asp Asn Cys Ala Ala Ser Met Ala Phe Glu Asp Lys Glu Ile
                675                 680                 685
His Asp Gln Asn Cys Pro Leu Ala Asn Val Ile Cys Glu Tyr Cys Asn
            690                 695                 700
Thr Ile Leu Ile Arg Glu Gln Met Pro Asn His Tyr Asp Leu Asp Cys
705                 710                 715                 720
Pro Thr Ala Pro Ile Pro Cys Thr Phe Ser Thr Phe Gly Cys His Glu
                725                 730                 735
```

Lys Met Gln Arg Asn His Leu Ala Arg His Leu Gln Glu Asn Thr Gln
                    740                 745                 750

Ser His Met Arg Met Leu Ala
        755

<210> SEQ ID NO 149
<211> LENGTH: 527
<212> TYPE: PRT
<213> ORGANISM: Artificial Sequence
<220> FEATURE:
<223> OTHER INFORMATION: CER122 protein
<220> FEATURE:
<221> NAME/KEY: sig_peptide
<222> LOCATION: 1...22

<400> SEQUENCE: 149

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
                20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
            115                 120                 125

Leu Glu Leu Arg Arg Ala Thr Thr Thr Lys Lys Pro Thr Thr Thr Thr
        130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu His Arg Phe His
    290                 295                 300

Gly Leu Trp Tyr Met Lys Met Met Trp Ala Trp Leu Gln Ala Lys Arg
305                 310                 315                 320

```
Lys Pro Arg Lys Ala Pro Ser Arg Asn Ile Cys Tyr Asp Ala Phe Val
                325                 330                 335

Ser Tyr Ser Glu Arg Asp Ala Tyr Trp Val Glu Asn Leu Met Val Gln
            340                 345                 350

Glu Leu Glu Asn Phe Asn Pro Phe Lys Leu Cys Leu His Lys Arg
        355                 360                 365

Asp Phe Ile Pro Gly Lys Trp Ile Ile Asp Asn Ile Asp Ser Ile
370                 375                 380

Glu Lys Ser His Lys Thr Val Phe Val Leu Ser Glu Asn Phe Val Lys
385                 390                 395                 400

Ser Glu Trp Cys Lys Tyr Glu Leu Asp Phe Ser His Phe Arg Leu Phe
                405                 410                 415

Asp Glu Asn Asn Asp Ala Ala Ile Leu Ile Leu Leu Glu Pro Ile Glu
            420                 425                 430

Lys Lys Ala Ile Pro Gln Arg Phe Cys Lys Leu Arg Lys Ile Met Asn
        435                 440                 445

Thr Lys Thr Tyr Leu Glu Trp Pro Met Asp Glu Ala Gln Arg Glu Gly
450                 455                 460

Phe Trp Val Asn Leu Arg Ala Ala Ile Lys Ser Tyr Phe Leu Gly Arg
465                 470                 475                 480

Leu Val Pro Arg Gly Arg Gly Ala Ala Glu Ala Ala Thr Arg Lys Gln
                485                 490                 495

Arg Ile Thr Glu Thr Glu Ser Pro Tyr Gln Glu Leu Gln Gly Gln Arg
            500                 505                 510

Ser Asp Val Tyr Ser Asp Leu Asn Thr Gln Arg Pro Tyr Tyr Lys
        515                 520                 525

<210> SEQ ID NO 150
<211> LENGTH: 749
<212> TYPE: PRT
<213> ORGANISM: Artificial Sequence
<220> FEATURE:
<223> OTHER INFORMATION: CER123 protein
<220> FEATURE:
<221> NAME/KEY: sig_peptide
<222> LOCATION: 1...22

<400> SEQUENCE: 150

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140
```

-continued

```
Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
            165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
            245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
            275                 280                 285

Phe Val Leu Met Val Leu Leu Phe Leu Ala Phe Leu His Arg Phe His
            290                 295                 300

Gly Leu Trp Tyr Met Lys Met Met Trp Ala Trp Leu Gln Ala Lys Arg
305                 310                 315                 320

Lys Pro Arg Lys Ala Pro Ser Arg Asn Ile Cys Tyr Asp Ala Phe Val
            325                 330                 335

Ser Tyr Ser Glu Arg Asp Ala Tyr Trp Val Glu Asn Leu Met Val Gln
            340                 345                 350

Glu Leu Glu Asn Phe Asn Pro Pro Phe Lys Leu Cys Leu His Lys Arg
            355                 360                 365

Asp Phe Ile Pro Gly Lys Trp Ile Ile Asp Asn Ile Ile Asp Ser Ile
            370                 375                 380

Glu Lys Ser His Lys Thr Val Phe Val Leu Ser Glu Asn Phe Val Lys
385                 390                 395                 400

Ser Glu Trp Cys Lys Tyr Glu Leu Asp Phe Ser His Phe Arg Leu Phe
            405                 410                 415

Asp Glu Asn Asn Asp Ala Ala Ile Leu Ile Leu Leu Glu Pro Ile Glu
            420                 425                 430

Lys Lys Ala Ile Pro Gln Arg Phe Cys Lys Leu Arg Lys Ile Met Asn
            435                 440                 445

Thr Lys Thr Tyr Leu Glu Trp Pro Met Asp Glu Ala Gln Arg Glu Gly
            450                 455                 460

Phe Trp Val Asn Leu Arg Ala Ala Ile Lys Ser Met Ser Leu Leu Asn
465                 470                 475                 480

Cys Glu Asn Ser Cys Gly Ser Ser Gln Ser Glu Ser Asp Cys Cys Val
            485                 490                 495

Ala Met Ala Ser Ser Cys Ser Ala Val Thr Lys Asp Asp Ser Val Gly
            500                 505                 510

Gly Thr Ala Ser Thr Gly Asn Leu Ser Ser Ser Phe Met Glu Glu Ile
            515                 520                 525

Gln Gly Tyr Asp Val Glu Phe Asp Pro Pro Leu Glu Ser Lys Tyr Glu
            530                 535                 540

Cys Pro Ile Cys Leu Met Ala Leu Arg Glu Ala Val Gln Thr Pro Cys
545                 550                 555                 560

Gly His Arg Phe Cys Lys Ala Cys Ile Ile Lys Ser Ile Arg Asp Ala
```

Gly His Lys Cys Pro Val Asp Asn Glu Ile Leu Leu Glu Asn Gln Leu
            565                 570                 575
                        580                 585                 590

Phe Pro Asp Asn Phe Ala Lys Arg Glu Ile Leu Ser Leu Met Val Lys
            595                 600                 605

Cys Pro Asn Glu Gly Cys Leu His Lys Met Glu Leu Arg His Leu Glu
        610                 615                 620

Asp His Gln Ala His Cys Glu Phe Ala Leu Met Asp Cys Pro Gln Cys
625                 630                 635                 640

Gln Arg Pro Phe Gln Lys Phe His Ile Asn Ile His Ile Leu Lys Asp
                    645                 650                 655

Cys Pro Arg Arg Gln Val Ser Cys Asp Asn Cys Ala Ala Ser Met Ala
            660                 665                 670

Phe Glu Asp Lys Glu Ile His Asp Gln Asn Cys Pro Leu Ala Asn Val
            675                 680                 685

Ile Cys Glu Tyr Cys Asn Thr Ile Leu Ile Arg Glu Gln Met Pro Asn
            690                 695                 700

His Tyr Asp Leu Asp Cys Pro Thr Ala Pro Ile Pro Cys Thr Phe Ser
705                 710                 715                 720

Thr Phe Gly Cys His Glu Lys Met Gln Arg Asn His Leu Ala Arg His
                    725                 730                 735

Leu Gln Glu Asn Thr Gln Ser His Met Arg Met Leu Ala
                740                 745

<210> SEQ ID NO 151
<211> LENGTH: 561
<212> TYPE: PRT
<213> ORGANISM: Artificial Sequence
<220> FEATURE:
<223> OTHER INFORMATION: CER124 protein
<220> FEATURE:
<221> NAME/KEY: sig_peptide
<222> LOCATION: 1...22

<400> SEQUENCE: 151

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro

```
                165                 170                 175
Gln Thr Leu Ala Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
            275                 280                 285

Phe Val Leu Met Val Leu Leu Phe Leu Ala Phe Leu His Arg Phe His
        290                 295                 300

Gly Leu Trp Tyr Met Lys Met Met Trp Ala Trp Leu Gln Ala Lys Arg
305                 310                 315                 320

Lys Pro Arg Lys Ala Pro Ser Arg Asn Ile Cys Tyr Asp Ala Phe Val
                325                 330                 335

Ser Tyr Ser Glu Arg Asp Ala Tyr Trp Val Glu Asn Leu Met Val Gln
            340                 345                 350

Glu Leu Glu Asn Phe Asn Pro Pro Phe Lys Leu Cys Leu His Lys Arg
            355                 360                 365

Asp Phe Ile Pro Gly Lys Trp Ile Ile Asp Asn Ile Ile Asp Ser Ile
            370                 375                 380

Glu Lys Ser His Lys Thr Val Phe Val Leu Ser Glu Asn Phe Val Lys
385                 390                 395                 400

Ser Glu Trp Cys Lys Tyr Glu Leu Asp Phe Ser His Phe Arg Leu Phe
                405                 410                 415

Asp Glu Asn Asn Asp Ala Ala Ile Leu Ile Leu Leu Glu Pro Ile Glu
            420                 425                 430

Lys Lys Ala Ile Pro Gln Arg Phe Cys Lys Leu Arg Lys Ile Met Asn
            435                 440                 445

Thr Lys Thr Tyr Leu Glu Trp Pro Met Asp Glu Ala Gln Arg Glu Gly
            450                 455                 460

Phe Trp Val Asn Leu Arg Ala Ala Ile Lys Ser Leu Trp Asn Lys Lys
465                 470                 475                 480

Arg Met Arg Gly Pro Gly Lys Asp Pro Thr Arg Lys Cys Pro Asp Pro
                485                 490                 495

Arg Ser Ala Ser Ser Pro Lys Gln His Pro Ser Glu Ser Val Tyr Thr
            500                 505                 510

Ala Leu Gln Arg Arg Glu Thr Glu Val Tyr Ala Cys Ile Glu Asn Glu
            515                 520                 525

Asp Gly Ser Ser Pro Thr Ala Lys Gln Ser Pro Leu Ser Gln Glu Arg
            530                 535                 540

Pro His Arg Phe Glu Asp Asp Gly Glu Leu Asn Leu Val Tyr Glu Asn
545                 550                 555                 560

Leu

<210> SEQ ID NO 152
<211> LENGTH: 520
```

```
<212> TYPE: PRT
<213> ORGANISM: Artificial Sequence
<220> FEATURE:
<223> OTHER INFORMATION: CER125A protein
<220> FEATURE:
<221> NAME/KEY: sig_peptide
<222> LOCATION: 1...22

<400> SEQUENCE: 152
```

| | | | | | | | | | | | | | | |
|---|---|---|---|---|---|---|---|---|---|---|---|---|---|---|
| Met | Ser | Lys | Gly | Leu | Leu | Leu | Trp | Leu | Val | Thr | Glu | Leu | Trp | Trp |
| 1 | | | | 5 | | | | | 10 | | | | | 15 |
| Leu | Tyr | Leu | Thr | Pro | Ala | Ala | Ser | Glu | Asp | Thr | Ile | Ile | Gly | Phe | Leu |
| | | | 20 | | | | | 25 | | | | | 30 | |
| Gly | Gln | Pro | Val | Thr | Leu | Pro | Cys | His | Tyr | Leu | Ser | Trp | Ser | Gln | Ser |
| | | | 35 | | | | | 40 | | | | | 45 | | |
| Arg | Asn | Ser | Met | Cys | Trp | Gly | Lys | Gly | Ser | Cys | Pro | Asn | Ser | Lys | Cys |
| | 50 | | | | | 55 | | | | | 60 | | | | |
| Asn | Ala | Glu | Leu | Leu | Arg | Thr | Asp | Gly | Thr | Arg | Ile | Ile | Ser | Arg | Lys |
| 65 | | | | | 70 | | | | | 75 | | | | | 80 |
| Ser | Thr | Lys | Tyr | Thr | Leu | Leu | Gly | Lys | Val | Gln | Phe | Gly | Glu | Val | Ser |
| | | | | 85 | | | | | 90 | | | | | 95 | |
| Leu | Thr | Ile | Ser | Asn | Thr | Asn | Arg | Gly | Asp | Ser | Gly | Val | Tyr | Cys | Cys |
| | | | 100 | | | | | 105 | | | | | 110 | | |
| Arg | Ile | Glu | Val | Pro | Gly | Trp | Phe | Asn | Asp | Val | Lys | Lys | Asn | Val | Arg |
| | | | 115 | | | | | 120 | | | | | 125 | | |
| Leu | Glu | Leu | Arg | Arg | Ala | Thr | Thr | Thr | Lys | Lys | Pro | Thr | Thr | Thr | Thr |
| | 130 | | | | | 135 | | | | | 140 | | | | |
| Arg | Pro | Thr | Thr | Thr | Pro | Tyr | Val | Thr | Thr | Thr | Thr | Pro | Glu | Leu | Leu |
| 145 | | | | | 150 | | | | | 155 | | | | | 160 |
| Pro | Thr | Thr | Val | Met | Thr | Thr | Ser | Val | Leu | Pro | Thr | Thr | Thr | Pro | Pro |
| | | | | 165 | | | | | 170 | | | | | 175 | |
| Gln | Thr | Leu | Ala | Thr | Thr | Ala | Phe | Ser | Thr | Ala | Val | Thr | Thr | Cys | Pro |
| | | | 180 | | | | | 185 | | | | | 190 | | |
| Ser | Thr | Thr | Pro | Gly | Ser | Phe | Ser | Gln | Glu | Thr | Thr | Lys | Gly | Ser | Ala |
| | | | 195 | | | | | 200 | | | | | 205 | | |
| Phe | Thr | Thr | Glu | Ser | Glu | Thr | Leu | Pro | Ala | Ser | Asn | His | Ser | Gln | Arg |
| | | 210 | | | | | 215 | | | | | 220 | | | |
| Ser | Met | Met | Thr | Ile | Ser | Thr | Asp | Ile | Ala | Val | Leu | Arg | Pro | Thr | Gly |
| 225 | | | | | 230 | | | | | 235 | | | | | 240 |
| Ser | Asn | Pro | Gly | Ile | Leu | Pro | Ser | Thr | Ser | Gln | Leu | Thr | Thr | Gln | Lys |
| | | | | 245 | | | | | 250 | | | | | 255 | |
| Thr | Thr | Leu | Thr | Thr | Ser | Glu | Ser | Leu | Gln | Lys | Thr | Thr | Lys | Ser | His |
| | | | 260 | | | | | 265 | | | | | 270 | | |
| Gln | Ile | Asn | Ser | Arg | Gln | Thr | Ile | Leu | Ile | Ala | Cys | Cys | Val | Gly |
| | | | 275 | | | | | 280 | | | | | 285 | | |
| Phe | Val | Leu | Met | Val | Leu | Leu | Phe | Leu | Ala | Phe | Leu | His | Arg | Phe | His |
| | | 290 | | | | | 295 | | | | | 300 | | | |
| Gly | Leu | Trp | Tyr | Met | Lys | Met | Met | Trp | Ala | Trp | Leu | Gln | Ala | Lys | Arg |
| 305 | | | | | 310 | | | | | 315 | | | | | 320 |
| Lys | Pro | Arg | Lys | Ala | Pro | Ser | Arg | Asn | Ile | Cys | Tyr | Asp | Ala | Phe | Val |
| | | | | 325 | | | | | 330 | | | | | 335 | |
| Ser | Tyr | Ser | Glu | Arg | Asp | Ala | Tyr | Trp | Val | Glu | Asn | Leu | Met | Val | Gln |
| | | | 340 | | | | | 345 | | | | | 350 | | |
| Glu | Leu | Glu | Asn | Phe | Asn | Pro | Pro | Phe | Lys | Leu | Cys | Leu | His | Lys | Arg |
| | | | 355 | | | | | 360 | | | | | 365 | | |

Asp Phe Ile Pro Gly Lys Trp Ile Ile Asp Asn Ile Ile Asp Ser Ile
        370                 375                 380

Glu Lys Ser His Lys Thr Val Phe Val Leu Ser Glu Asn Phe Val Lys
385                 390                 395                 400

Ser Glu Trp Cys Lys Tyr Glu Leu Asp Phe Ser His Phe Arg Leu Phe
                405                 410                 415

Asp Glu Asn Asn Asp Ala Ala Ile Leu Ile Leu Leu Glu Pro Ile Glu
            420                 425                 430

Lys Lys Ala Ile Pro Gln Arg Phe Cys Lys Leu Arg Lys Ile Met Asn
        435                 440                 445

Thr Lys Thr Tyr Leu Glu Trp Pro Met Asp Glu Ala Gln Arg Glu Gly
450                 455                 460

Phe Trp Val Asn Leu Arg Ala Ala Ile Lys Ser Asp Ser Lys Ala Gly
465                 470                 475                 480

Met Glu Glu Asp His Thr Tyr Glu Gly Leu Asp Ile Asp Gln Thr Ala
                485                 490                 495

Thr Tyr Glu Asp Ile Val Thr Leu Arg Thr Gly Glu Val Lys Trp Ser
            500                 505                 510

Val Gly Glu His Pro Gly Gln Glu
        515                 520

<210> SEQ ID NO 153
<211> LENGTH: 504
<212> TYPE: PRT
<213> ORGANISM: Artificial Sequence
<220> FEATURE:
<223> OTHER INFORMATION: CER125B protein
<220> FEATURE:
<221> NAME/KEY: sig_peptide
<222> LOCATION: 1...22

<400> SEQUENCE: 153

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr
        130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

```
Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu His Arg Phe His
    290                 295                 300

Gly Leu Trp Tyr Met Lys Met Met Trp Ala Trp Leu Gln Ala Lys Arg
305                 310                 315                 320

Lys Pro Arg Lys Ala Pro Ser Arg Asn Ile Cys Tyr Asp Ala Phe Val
                325                 330                 335

Ser Tyr Ser Glu Arg Asp Ala Tyr Trp Val Glu Asn Leu Met Val Gln
            340                 345                 350

Glu Leu Glu Asn Phe Asn Pro Pro Phe Lys Leu Cys Leu His Lys Arg
        355                 360                 365

Asp Phe Ile Pro Gly Lys Trp Ile Ile Asp Asn Ile Ile Asp Ser Ile
    370                 375                 380

Glu Lys Ser His Lys Thr Val Phe Val Leu Ser Glu Asn Phe Val Lys
385                 390                 395                 400

Ser Glu Trp Cys Lys Tyr Glu Leu Asp Phe Ser His Phe Arg Leu Phe
                405                 410                 415

Asp Glu Asn Asn Asp Ala Ala Ile Leu Ile Leu Leu Glu Pro Ile Glu
            420                 425                 430

Lys Lys Ala Ile Pro Gln Arg Phe Cys Lys Leu Arg Lys Ile Met Asn
        435                 440                 445

Thr Lys Thr Tyr Leu Glu Trp Pro Met Asp Glu Ala Gln Arg Glu Gly
    450                 455                 460

Phe Trp Val Asn Leu Arg Ala Ala Ile Lys Ser Asp Ser Lys Ala Gly
465                 470                 475                 480

Met Glu Glu Asp His Thr Tyr Glu Gly Leu Asp Ile Asp Gln Thr Ala
                485                 490                 495

Thr Tyr Glu Asp Ile Val Thr Leu
            500

<210> SEQ ID NO 154
<211> LENGTH: 24
<212> TYPE: PRT
<213> ORGANISM: Artificial Sequence
<220> FEATURE:
<223> OTHER INFORMATION: T2A self-cleaving peptide variant

<400> SEQUENCE: 154

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 155
<211> LENGTH: 19
```

<212> TYPE: PRT
<213> ORGANISM: Artificial Sequence
<220> FEATURE:
<223> OTHER INFORMATION: T2A self-cleaving peptide variant

<400> SEQUENCE: 155

Glu Gly Arg Gly Ser Leu Leu Thr Cys Gly Asp Val Glu Glu Asn Pro
1               5                   10                  15

Gly Pro Arg

<210> SEQ ID NO 156
<211> LENGTH: 23
<212> TYPE: PRT
<213> ORGANISM: Artificial Sequence
<220> FEATURE:
<223> OTHER INFORMATION: T2A self-cleaving peptide variant

<400> SEQUENCE: 156

Leu Glu Gly Gly Gly Glu Gly Arg Gly Ser Leu Leu Thr Cys Gly Asp
1               5                   10                  15

Val Glu Glu Asn Pro Gly Pro
            20

<210> SEQ ID NO 157
<211> LENGTH: 27
<212> TYPE: PRT
<213> ORGANISM: Artificial Sequence
<220> FEATURE:
<223> OTHER INFORMATION: P2A self-cleaving peptide variant

<400> SEQUENCE: 157

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 158
<211> LENGTH: 598
<212> TYPE: PRT
<213> ORGANISM: Artificial Sequence
<220> FEATURE:
<223> OTHER INFORMATION: HPV16 E7 TCRbeta chain-P2A-TCRalpha chain

<400> SEQUENCE: 158

Met Ala Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Gly Trp Arg Gly Gly Arg Tyr Asn Glu Gln Phe Phe Gly Pro
        115                 120                 125

Gly Thr Arg Leu Thr Val Leu Glu Asp Leu Arg Asn Val Thr Pro Pro

```
            130                 135                 140
Lys Val Ser Leu Phe Glu Pro Ser Lys Ala Glu Ile Ala Asn Lys Gln
145                 150                 155                 160

Lys Ala Thr Leu Val Cys Leu Ala Arg Gly Phe Phe Pro Asp His Val
                165                 170                 175

Glu Leu Ser Trp Trp Val Asn Gly Lys Glu Val His Ser Gly Val Cys
                180                 185                 190

Thr Asp Pro Gln Ala Tyr Lys Glu Ser Asn Tyr Ser Tyr Cys Leu Ser
                195                 200                 205

Ser Arg Leu Arg Val Ser Ala Thr Phe Trp His Asn Pro Arg Asn His
        210                 215                 220

Phe Arg Cys Gln Val Gln Phe His Gly Leu Ser Glu Glu Asp Lys Trp
225                 230                 235                 240

Pro Glu Gly Ser Pro Lys Pro Val Thr Gln Asn Ile Ser Ala Glu Ala
                245                 250                 255

Trp Gly Arg Ala Asp Cys Gly Ile Thr Ser Ala Ser Tyr Gln Gln Gly
                260                 265                 270

Val Leu Ser Ala Thr Ile Leu Tyr Glu Ile Leu Leu Gly Lys Ala Thr
        275                 280                 285

Leu Tyr Ala Val Leu Val Ser Thr Leu Val Val Met Ala Met Val Lys
        290                 295                 300

Arg Lys Asn Ser Arg Ala Lys Arg Ser Gly Ser Gly Ala Thr Asn Phe
305                 310                 315                 320

Ser Leu Leu Lys Gln Ala Gly Asp Val Glu Glu Asn Pro Gly Pro Met
                325                 330                 335

Trp Gly Val Phe Leu Leu Tyr Val Ser Met Lys Met Gly Gly Thr Thr
                340                 345                 350

Gly Gln Asn Ile Asp Gln Pro Thr Glu Met Thr Ala Thr Glu Gly Ala
        355                 360                 365

Ile Val Gln Ile Asn Cys Thr Tyr Gln Thr Ser Gly Phe Asn Gly Leu
        370                 375                 380

Phe Trp Tyr Gln Gln His Ala Gly Glu Ala Pro Thr Phe Leu Ser Tyr
385                 390                 395                 400

Asn Val Leu Asp Gly Leu Glu Glu Lys Gly Arg Phe Ser Ser Phe Leu
                405                 410                 415

Ser Arg Ser Lys Gly Tyr Ser Tyr Leu Leu Leu Lys Glu Leu Gln Met
                420                 425                 430

Lys Asp Ser Ala Ser Tyr Leu Cys Ala Ser Val Asp Gly Asn Asn Arg
        435                 440                 445

Leu Ala Phe Gly Lys Gly Asn Gln Val Val Val Ile Pro Asn Ile Gln
        450                 455                 460

Asn Pro Glu Pro Ala Val Tyr Gln Leu Lys Asp Pro Arg Ser Gln Asp
465                 470                 475                 480

Ser Thr Leu Cys Leu Phe Thr Asp Phe Asp Ser Gln Ile Asn Val Pro
                485                 490                 495

Lys Thr Met Glu Ser Gly Thr Phe Ile Thr Asp Lys Cys Val Leu Asp
                500                 505                 510

Met Lys Ala Met Asp Ser Lys Ser Asn Gly Ala Ile Ala Trp Ser Asn
        515                 520                 525

Gln Thr Ser Phe Thr Cys Gln Asp Ile Phe Lys Glu Thr Asn Ala Thr
        530                 535                 540

Tyr Pro Ser Ser Asp Val Pro Cys Asp Ala Thr Leu Thr Glu Lys Ser
545                 550                 555                 560
```

-continued

```
Phe Glu Thr Asp Met Asn Leu Asn Phe Gln Asn Leu Leu Val Ile Val
                565                 570                 575

Leu Arg Ile Leu Leu Leu Lys Val Ala Gly Phe Asn Leu Leu Met Thr
            580                 585                 590

Leu Arg Leu Trp Ser Ser
        595

<210> SEQ ID NO 159
<211> LENGTH: 386
<212> TYPE: PRT
<213> ORGANISM: Artificial Sequence
<220> FEATURE:
<223> OTHER INFORMATION: CER25 protein
<220> FEATURE:
<221> NAME/KEY: sig_peptide
<222> LOCATION: 1...22

<400> SEQUENCE: 159

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Leu Trp Asn Lys
    290                 295                 300
```

-continued

```
Lys Arg Met Arg Gly Pro Gly Lys Asp Pro Thr Arg Lys Cys Pro Asp
305                 310                 315                 320

Pro Arg Ser Ala Ser Ser Pro Lys Gln His Pro Ser Glu Ser Val Tyr
                325                 330                 335

Thr Ala Leu Gln Arg Arg Glu Thr Glu Val Tyr Ala Cys Ile Glu Asn
            340                 345                 350

Glu Asp Gly Ser Ser Pro Thr Ala Lys Gln Ser Pro Leu Ser Gln Glu
        355                 360                 365

Arg Pro His Arg Phe Glu Asp Asp Gly Glu Leu Asn Leu Val Tyr Glu
    370                 375                 380

Asn Leu
385

<210> SEQ ID NO 160
<211> LENGTH: 135
<212> TYPE: PRT
<213> ORGANISM: Artificial Sequence
<220> FEATURE:
<223> OTHER INFORMATION: HPV16 E7 TCR Vbeta region

<400> SEQUENCE: 160

Met Ala Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Leu Gly Trp Arg Gly Gly Arg Tyr Asn Glu Gln Phe Phe Gly Pro
        115                 120                 125

Gly Thr Arg Leu Thr Val Leu
    130                 135

<210> SEQ ID NO 161
<211> LENGTH: 173
<212> TYPE: PRT
<213> ORGANISM: Artificial Sequence
<220> FEATURE:
<223> OTHER INFORMATION: TCR Cbeta region, Cys-substituted

<400> SEQUENCE: 161

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Cys Thr Asp Pro Gln Ala Tyr Lys
    50                  55                  60

Glu Ser Asn Tyr Ser Tyr Cys Leu Ser Ser Arg Leu Arg Val Ser Ala
```

-continued

```
                65                  70                  75                  80
Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
            115                 120                 125

Ile Thr Ser Ala Ser Tyr Gln Gln Gly Val Leu Ser Ala Thr Ile Leu
        130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 162
<211> LENGTH: 126
<212> TYPE: PRT
<213> ORGANISM: Artificial Sequence
<220> FEATURE:
<223> OTHER INFORMATION: HPV16 E7TCR Valpha region

<400> SEQUENCE: 162

Met Trp Gly Val Phe Leu Leu Tyr Val Ser Met Lys Met Gly Gly Thr
1               5                   10                  15

Thr Gly Gln Asn Ile Asp Gln Pro Thr Glu Met Thr Ala Thr Glu Gly
            20                  25                  30

Ala Ile Val Gln Ile Asn Cys Thr Tyr Gln Thr Ser Gly Phe Asn Gly
        35                  40                  45

Leu Phe Trp Tyr Gln Gln His Ala Gly Glu Ala Pro Thr Phe Leu Ser
    50                  55                  60

Tyr Asn Val Leu Asp Gly Leu Glu Glu Lys Gly Arg Phe Ser Ser Phe
65                  70                  75                  80

Leu Ser Arg Ser Lys Gly Tyr Ser Tyr Leu Leu Leu Lys Glu Leu Gln
                85                  90                  95

Met Lys Asp Ser Ala Ser Tyr Leu Cys Ala Ser Val Asp Gly Asn Asn
            100                 105                 110

Arg Leu Ala Phe Gly Lys Gly Asn Gln Val Val Val Ile Pro
        115                 120                 125

<210> SEQ ID NO 163
<211> LENGTH: 137
<212> TYPE: PRT
<213> ORGANISM: Artificial Sequence
<220> FEATURE:
<223> OTHER INFORMATION: TCR Calpha region, Cys-substituted, LVL
      substituted

<400> SEQUENCE: 163

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80
```

-continued

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Lys Val Ala Gly Phe Asn Leu
        115                 120                 125

Leu Met Thr Leu Arg Leu Trp Ser Ser
    130                 135

<210> SEQ ID NO 164
<211> LENGTH: 1108
<212> TYPE: PRT
<213> ORGANISM: Artificial Sequence
<220> FEATURE:
<223> OTHER INFORMATION: CER5_T2A_HPV16_E7_TCR tandem cassette

<400> SEQUENCE: 164

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
    130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Lys Phe Tyr Phe
    290                 295                 300

-continued

His Leu Met Leu Leu Ala Gly Cys Ile Lys Tyr Gly Arg Gly Glu Asn
305                 310                 315                 320

Ile Tyr Asp Ala Phe Val Ile Tyr Ser Ser Gln Asp Glu Asp Trp Val
            325                 330                 335

Arg Asn Glu Leu Val Lys Asn Leu Glu Glu Gly Val Pro Pro Phe Gln
        340                 345                 350

Leu Cys Leu His Tyr Arg Asp Phe Ile Pro Gly Val Ala Ile Ala Ala
            355                 360                 365

Asn Ile Ile His Glu Gly Phe His Lys Ser Arg Lys Val Ile Val Val
        370                 375                 380

Val Ser Gln His Phe Ile Gln Ser Arg Trp Cys Ile Phe Glu Tyr Glu
385                 390                 395                 400

Ile Ala Gln Thr Trp Gln Phe Leu Ser Ser Arg Ala Gly Ile Ile Phe
            405                 410                 415

Ile Val Leu Gln Lys Val Glu Lys Thr Leu Arg Gln Gln Val Glu
        420                 425                 430

Leu Tyr Arg Leu Leu Ser Arg Asn Thr Tyr Leu Glu Trp Glu Asp Ser
            435                 440                 445

Val Leu Gly Arg His Ile Phe Trp Arg Arg Leu Arg Lys Ala Leu Leu
        450                 455                 460

Asp Gly Lys Ser Trp Asn Pro Glu Gly Thr Val Gly Thr Gly Cys Asn
465                 470                 475                 480

Trp Gln Glu Ala Thr Ser Ile Leu Glu Gly Gly Glu Gly Arg Gly
            485                 490                 495

Ser Leu Leu Thr Cys Gly Asp Val Glu Glu Asn Pro Gly Pro Met Ala
            500                 505                 510

Pro Gly Leu Leu Cys Trp Ala Leu Leu Cys Leu Leu Gly Ala Gly Leu
        515                 520                 525

Val Asp Ala Gly Val Thr Gln Ser Pro Thr His Leu Ile Lys Thr Arg
530                 535                 540

Gly Gln Gln Val Thr Leu Arg Cys Ser Pro Lys Ser Gly His Asp Thr
545                 550                 555                 560

Val Ser Trp Tyr Gln Gln Ala Leu Gly Gln Gly Pro Gln Phe Ile Phe
            565                 570                 575

Gln Tyr Tyr Glu Glu Glu Arg Gln Arg Gly Asn Phe Pro Asp Arg
        580                 585                 590

Phe Ser Gly His Gln Phe Pro Asn Tyr Ser Ser Glu Leu Asn Val Asn
            595                 600                 605

Ala Leu Leu Leu Gly Asp Ser Ala Leu Tyr Leu Cys Ala Ser Ser Leu
        610                 615                 620

Gly Trp Arg Gly Gly Arg Tyr Asn Glu Gln Phe Phe Gly Pro Gly Thr
625                 630                 635                 640

Arg Leu Thr Val Leu Glu Asp Leu Arg Asn Val Thr Pro Pro Lys Val
            645                 650                 655

Ser Leu Phe Glu Pro Ser Lys Ala Glu Ile Ala Asn Lys Gln Lys Ala
            660                 665                 670

Thr Leu Val Cys Leu Ala Arg Gly Phe Phe Pro Asp His Val Glu Leu
        675                 680                 685

Ser Trp Trp Val Asn Gly Lys Glu Val His Ser Gly Val Cys Thr Asp
        690                 695                 700

Pro Gln Ala Tyr Lys Glu Ser Asn Tyr Ser Tyr Cys Leu Ser Ser Arg
705                 710                 715                 720

-continued

```
Leu Arg Val Ser Ala Thr Phe Trp His Asn Pro Arg Asn His Phe Arg
                725                 730                 735
Cys Gln Val Gln Phe His Gly Leu Ser Glu Glu Asp Lys Trp Pro Glu
            740                 745                 750
Gly Ser Pro Lys Pro Val Thr Gln Asn Ile Ser Ala Glu Ala Trp Gly
        755                 760                 765
Arg Ala Asp Cys Gly Ile Thr Ser Ala Ser Tyr Gln Gln Gly Val Leu
    770                 775                 780
Ser Ala Thr Ile Leu Tyr Glu Ile Leu Leu Gly Lys Ala Thr Leu Tyr
785                 790                 795                 800
Ala Val Leu Val Ser Thr Leu Val Val Met Ala Met Val Lys Arg Lys
                805                 810                 815
Asn Ser Arg Ala Lys Arg Ser Gly Ser Gly Ala Thr Asn Phe Ser Leu
            820                 825                 830
Leu Lys Gln Ala Gly Asp Val Glu Glu Asn Pro Gly Pro Met Trp Gly
        835                 840                 845
Val Phe Leu Leu Tyr Val Ser Met Lys Met Gly Gly Thr Thr Gly Gln
    850                 855                 860
Asn Ile Asp Gln Pro Thr Glu Met Thr Ala Thr Glu Gly Ala Ile Val
865                 870                 875                 880
Gln Ile Asn Cys Thr Tyr Gln Thr Ser Gly Phe Asn Gly Leu Phe Trp
                885                 890                 895
Tyr Gln Gln His Ala Gly Glu Ala Pro Thr Phe Leu Ser Tyr Asn Val
            900                 905                 910
Leu Asp Gly Leu Glu Lys Gly Arg Phe Ser Ser Phe Leu Ser Arg
        915                 920                 925
Ser Lys Gly Tyr Ser Tyr Leu Leu Leu Lys Glu Leu Gln Met Lys Asp
    930                 935                 940
Ser Ala Ser Tyr Leu Cys Ala Ser Val Asp Gly Asn Asn Arg Leu Ala
945                 950                 955                 960
Phe Gly Lys Gly Asn Gln Val Val Val Ile Pro Asn Ile Gln Asn Pro
                965                 970                 975
Glu Pro Ala Val Tyr Gln Leu Lys Asp Pro Arg Ser Gln Asp Ser Thr
            980                 985                 990
Leu Cys Leu Phe Thr Asp Phe Asp Ser Gln Ile Asn Val Pro Lys Thr
        995                 1000                1005
Met Glu Ser Gly Thr Phe Ile Thr Asp Lys Cys Val Leu Asp Met Lys
    1010                1015                1020
Ala Met Asp Ser Lys Ser Asn Gly Ala Ile Ala Trp Ser Asn Gln Thr
1025                1030                1035                1040
Ser Phe Thr Cys Gln Asp Ile Phe Lys Glu Thr Asn Ala Thr Tyr Pro
                1045                1050                1055
Ser Ser Asp Val Pro Cys Asp Ala Thr Leu Thr Glu Lys Ser Phe Glu
            1060                1065                1070
Thr Asp Met Asn Leu Asn Phe Gln Asn Leu Leu Val Ile Val Leu Arg
        1075                1080                1085
Ile Leu Leu Leu Lys Val Ala Gly Phe Asn Leu Leu Met Thr Leu Arg
    1090                1095                1100
Leu Trp Ser Ser
1105

<210> SEQ ID NO 165
<211> LENGTH: 1119
<212> TYPE: PRT
```

<213> ORGANISM: Artificial Sequence
<220> FEATURE:
<223> OTHER INFORMATION: CER19_T2A_HPV16_E7_TCR tandem cassette

<400> SEQUENCE: 165

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Thr Lys Phe Arg
    290                 295                 300

Gly Phe Cys Phe Ile Cys Tyr Lys Thr Ala Gln Arg Leu Val Phe Lys
305                 310                 315                 320

Asp His Pro Gln Gly Thr Glu Pro Asp Met Tyr Lys Tyr Asp Ala Tyr
                325                 330                 335

Leu Cys Phe Ser Ser Lys Asp Phe Thr Trp Val Gln Asn Ala Leu Leu
            340                 345                 350

Lys His Leu Asp Thr Gln Tyr Ser Asp Gln Asn Arg Phe Asn Leu Cys
        355                 360                 365

Phe Glu Glu Arg Asp Phe Val Pro Gly Glu Asn Arg Ile Ala Asn Ile
    370                 375                 380

Gln Asp Ala Ile Trp Asn Ser Arg Lys Ile Val Cys Leu Val Ser Arg
```

```
                385                 390                 395                 400
His Phe Leu Arg Asp Gly Trp Cys Leu Glu Ala Phe Ser Tyr Ala Gln
                    405                 410                 415

Gly Arg Cys Leu Ser Asp Leu Asn Ser Ala Leu Ile Met Val Val Val
            420                 425                 430

Gly Ser Leu Ser Gln Tyr Gln Leu Met Lys His Gln Ser Ile Arg Gly
            435                 440                 445

Phe Val Gln Lys Gln Gln Tyr Leu Arg Trp Pro Glu Asp Phe Gln Asp
        450                 455                 460

Val Gly Trp Phe Leu His Lys Leu Ser Gln Gln Ile Leu Lys Lys Glu
465                 470                 475                 480

Lys Glu Lys Lys Lys Asp Asn Asn Ile Pro Leu Gln Thr Val Ala Thr
                485                 490                 495

Ile Ser Leu Glu Gly Gly Gly Glu Gly Arg Gly Ser Leu Leu Thr Cys
                500                 505                 510

Gly Asp Val Glu Glu Asn Pro Gly Pro Met Ala Pro Gly Leu Leu Cys
            515                 520                 525

Trp Ala Leu Leu Cys Leu Leu Gly Ala Gly Leu Val Asp Ala Gly Val
        530                 535                 540

Thr Gln Ser Pro Thr His Leu Ile Lys Thr Arg Gly Gln Gln Val Thr
545                 550                 555                 560

Leu Arg Cys Ser Pro Lys Ser Gly His Asp Thr Val Ser Trp Tyr Gln
                565                 570                 575

Gln Ala Leu Gly Gln Gly Pro Gln Phe Ile Phe Gln Tyr Tyr Glu Glu
            580                 585                 590

Glu Glu Arg Gln Arg Gly Asn Phe Pro Asp Arg Phe Ser Gly His Gln
            595                 600                 605

Phe Pro Asn Tyr Ser Ser Glu Leu Asn Val Asn Ala Leu Leu Leu Gly
        610                 615                 620

Asp Ser Ala Leu Tyr Leu Cys Ala Ser Ser Leu Gly Trp Arg Gly Gly
625                 630                 635                 640

Arg Tyr Asn Glu Gln Phe Phe Gly Pro Gly Thr Arg Leu Thr Val Leu
                645                 650                 655

Glu Asp Leu Arg Asn Val Thr Pro Pro Lys Val Ser Leu Phe Glu Pro
            660                 665                 670

Ser Lys Ala Glu Ile Ala Asn Lys Gln Lys Ala Thr Leu Val Cys Leu
        675                 680                 685

Ala Arg Gly Phe Phe Pro Asp His Val Glu Leu Ser Trp Trp Val Asn
690                 695                 700

Gly Lys Glu Val His Ser Gly Val Cys Thr Asp Pro Gln Ala Tyr Lys
705                 710                 715                 720

Glu Ser Asn Tyr Ser Tyr Cys Leu Ser Ser Arg Leu Arg Val Ser Ala
                725                 730                 735

Thr Phe Trp His Asn Pro Arg Asn His Phe Arg Cys Gln Val Gln Phe
            740                 745                 750

His Gly Leu Ser Glu Glu Asp Lys Trp Pro Glu Gly Ser Pro Lys Pro
        755                 760                 765

Val Thr Gln Asn Ile Ser Ala Glu Ala Trp Gly Arg Ala Asp Cys Gly
        770                 775                 780

Ile Thr Ser Ala Ser Tyr Gln Gln Gly Val Leu Ser Ala Thr Ile Leu
785                 790                 795                 800

Tyr Glu Ile Leu Leu Gly Lys Ala Thr Leu Tyr Ala Val Leu Val Ser
                805                 810                 815
```

Thr Leu Val Val Met Ala Met Val Lys Arg Lys Asn Ser Arg Ala Lys
                820                 825                 830

Arg Ser Gly Ser Gly Ala Thr Asn Phe Ser Leu Leu Lys Gln Ala Gly
            835                 840                 845

Asp Val Glu Asn Pro Gly Pro Met Trp Gly Val Phe Leu Leu Tyr
        850                 855                 860

Val Ser Met Lys Met Gly Gly Thr Gly Gln Asn Ile Asp Gln Pro
865                 870                 875                 880

Thr Glu Met Thr Ala Thr Glu Gly Ala Ile Val Gln Ile Asn Cys Thr
                885                 890                 895

Tyr Gln Thr Ser Gly Phe Asn Gly Leu Phe Trp Tyr Gln Gln His Ala
            900                 905                 910

Gly Glu Ala Pro Thr Phe Leu Ser Tyr Asn Val Leu Asp Gly Leu Glu
            915                 920                 925

Glu Lys Gly Arg Phe Ser Ser Phe Leu Ser Arg Ser Lys Gly Tyr Ser
        930                 935                 940

Tyr Leu Leu Leu Lys Glu Leu Gln Met Lys Asp Ser Ala Ser Tyr Leu
945                 950                 955                 960

Cys Ala Ser Val Asp Gly Asn Asn Arg Leu Ala Phe Gly Lys Gly Asn
                965                 970                 975

Gln Val Val Val Ile Pro Asn Ile Gln Asn Pro Glu Pro Ala Val Tyr
            980                 985                 990

Gln Leu Lys Asp Pro Arg Ser Gln Asp Ser Thr Leu Cys Leu Phe Thr
            995                 1000                1005

Asp Phe Asp Ser Gln Ile Asn Val Pro Lys Thr Met Glu Ser Gly Thr
            1010                1015                1020

Phe Ile Thr Asp Lys Cys Val Leu Asp Met Lys Ala Met Asp Ser Lys
1025                1030                1035                1040

Ser Asn Gly Ala Ile Ala Trp Ser Asn Gln Thr Ser Phe Thr Cys Gln
                1045                1050                1055

Asp Ile Phe Lys Glu Thr Asn Ala Thr Tyr Pro Ser Ser Asp Val Pro
            1060                1065                1070

Cys Asp Ala Thr Leu Thr Glu Lys Ser Phe Glu Thr Asp Met Asn Leu
            1075                1080                1085

Asn Phe Gln Asn Leu Leu Val Ile Val Leu Arg Ile Leu Leu Leu Lys
            1090                1095                1100

Val Ala Gly Phe Asn Leu Leu Met Thr Leu Arg Leu Trp Ser Ser
1105                1110                1115

<210> SEQ ID NO 166
<211> LENGTH: 1114
<212> TYPE: PRT
<213> ORGANISM: Artificial Sequence
<220> FEATURE:
<223> OTHER INFORMATION: CER21_T2A_HPV16_E7_TCR tandem cassette

<400> SEQUENCE: 166

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

```
Asn Ala Glu Leu Leu Arg Thr Asp Gly Thr Arg Ile Ile Ser Arg Lys
 65                  70                  75                  80

Ser Thr Lys Tyr Thr Leu Leu Gly Lys Val Gln Phe Gly Glu Val Ser
                 85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu His His Leu Phe
    290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                325                 330                 335

Ser Tyr Asp Thr Lys Asp Ala Ser Val Thr Asp Trp Val Ile Asn Glu
            340                 345                 350

Leu Arg Tyr His Leu Glu Glu Ser Arg Asp Lys Asn Val Leu Leu Cys
        355                 360                 365

Leu Glu Glu Arg Asp Trp Asp Pro Gly Leu Ala Ile Ile Asp Asn Leu
    370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                405                 410                 415

Gln Arg Leu Met Asp Glu Asn Met Asp Val Ile Ile Phe Ile Leu Leu
            420                 425                 430

Glu Pro Val Leu Gln His Ser Gln Tyr Leu Arg Leu Arg Gln Arg Ile
        435                 440                 445

Cys Lys Ser Ser Ile Leu Gln Trp Pro Asp Asn Pro Lys Ala Glu Gly
    450                 455                 460

Leu Phe Trp Gln Thr Leu Arg Asn Val Val Leu Thr Glu Asn Asp Ser
465                 470                 475                 480
```

```
Arg Tyr Asn Asn Met Tyr Val Asp Ser Ile Lys Gln Tyr Leu Glu Gly
                485                 490                 495

Gly Gly Glu Gly Arg Gly Ser Leu Leu Thr Cys Gly Asp Val Glu Glu
            500                 505                 510

Asn Pro Gly Pro Met Ala Pro Gly Leu Leu Cys Trp Ala Leu Leu Cys
            515                 520                 525

Leu Leu Gly Ala Gly Leu Val Asp Ala Gly Val Thr Gln Ser Pro Thr
            530                 535                 540

His Leu Ile Lys Thr Arg Gly Gln Gln Val Thr Leu Arg Cys Ser Pro
545                 550                 555                 560

Lys Ser Gly His Asp Thr Val Ser Trp Tyr Gln Gln Ala Leu Gly Gln
                565                 570                 575

Gly Pro Gln Phe Ile Phe Gln Tyr Tyr Glu Glu Glu Arg Gln Arg
                580                 585                 590

Gly Asn Phe Pro Asp Arg Phe Ser Gly His Gln Phe Pro Asn Tyr Ser
                595                 600                 605

Ser Glu Leu Asn Val Asn Ala Leu Leu Leu Gly Asp Ser Ala Leu Tyr
            610                 615                 620

Leu Cys Ala Ser Ser Leu Gly Trp Arg Gly Gly Arg Tyr Asn Glu Gln
625                 630                 635                 640

Phe Phe Gly Pro Gly Thr Arg Leu Thr Val Leu Glu Asp Leu Arg Asn
                645                 650                 655

Val Thr Pro Pro Lys Val Ser Leu Phe Glu Pro Ser Lys Ala Glu Ile
                660                 665                 670

Ala Asn Lys Gln Lys Ala Thr Leu Val Cys Leu Ala Arg Gly Phe Phe
                675                 680                 685

Pro Asp His Val Glu Leu Ser Trp Trp Val Asn Gly Lys Glu Val His
            690                 695                 700

Ser Gly Val Cys Thr Asp Pro Gln Ala Tyr Lys Glu Ser Asn Tyr Ser
705                 710                 715                 720

Tyr Cys Leu Ser Ser Arg Leu Arg Val Ser Ala Thr Phe Trp His Asn
                725                 730                 735

Pro Arg Asn His Phe Arg Cys Gln Val Gln Phe His Gly Leu Ser Glu
                740                 745                 750

Glu Asp Lys Trp Pro Glu Gly Ser Pro Lys Pro Val Thr Gln Asn Ile
            755                 760                 765

Ser Ala Glu Ala Trp Gly Arg Ala Asp Cys Gly Ile Thr Ser Ala Ser
            770                 775                 780

Tyr Gln Gln Gly Val Leu Ser Ala Thr Ile Leu Tyr Glu Ile Leu Leu
785                 790                 795                 800

Gly Lys Ala Thr Leu Tyr Ala Val Leu Val Ser Thr Leu Val Val Met
                805                 810                 815

Ala Met Val Lys Arg Lys Asn Ser Arg Ala Lys Arg Ser Gly Ser Gly
                820                 825                 830

Ala Thr Asn Phe Ser Leu Leu Lys Gln Ala Gly Asp Val Glu Glu Asn
            835                 840                 845

Pro Gly Pro Met Trp Gly Val Phe Leu Leu Tyr Val Ser Met Lys Met
            850                 855                 860

Gly Gly Thr Thr Gly Gln Asn Ile Asp Gln Pro Thr Glu Met Thr Ala
865                 870                 875                 880

Thr Glu Gly Ala Ile Val Gln Ile Asn Cys Thr Tyr Gln Thr Ser Gly
                885                 890                 895

Phe Asn Gly Leu Phe Trp Tyr Gln Gln His Ala Gly Glu Ala Pro Thr
```

```
                900             905             910
Phe Leu Ser Tyr Asn Val Leu Asp Gly Leu Glu Glu Lys Gly Arg Phe
            915             920             925

Ser Ser Phe Leu Ser Arg Ser Lys Gly Tyr Ser Tyr Leu Leu Leu Lys
        930             935             940

Glu Leu Gln Met Lys Asp Ser Ala Ser Tyr Leu Cys Ala Ser Val Asp
945             950             955             960

Gly Asn Asn Arg Leu Ala Phe Gly Lys Gly Asn Gln Val Val Val Ile
            965             970             975

Pro Asn Ile Gln Asn Pro Glu Pro Ala Val Tyr Gln Leu Lys Asp Pro
            980             985             990

Arg Ser Gln Asp Ser Thr Leu Cys Leu Phe Thr Asp Phe Asp Ser Gln
            995             1000            1005

Ile Asn Val Pro Lys Thr Met Glu Ser Gly Thr Phe Ile Thr Asp Lys
            1010            1015            1020

Cys Val Leu Asp Met Lys Ala Met Asp Ser Lys Ser Asn Gly Ala Ile
1025            1030            1035            1040

Ala Trp Ser Asn Gln Thr Ser Phe Thr Cys Gln Asp Ile Phe Lys Glu
            1045            1050            1055

Thr Asn Ala Thr Tyr Pro Ser Ser Asp Val Pro Cys Asp Ala Thr Leu
            1060            1065            1070

Thr Glu Lys Ser Phe Glu Thr Asp Met Asn Leu Asn Phe Gln Asn Leu
            1075            1080            1085

Leu Val Ile Val Leu Arg Ile Leu Leu Leu Lys Val Ala Gly Phe Asn
            1090            1095            1100

Leu Leu Met Thr Leu Arg Leu Trp Ser Ser
1105                1110

<210> SEQ ID NO 167
<211> LENGTH: 1007
<212> TYPE: PRT
<213> ORGANISM: Artificial Sequence
<220> FEATURE:
<223> OTHER INFORMATION: CER25_T2A_HPV16_E7_TCR tandem cassette

<400> SEQUENCE: 167

Met Ser Lys Gly Leu Leu Leu Trp Leu Val Thr Glu Leu Trp Trp
1               5               10              15

Leu Tyr Leu Thr Pro Ala Ala Ser Glu Asp Thr Ile Ile Gly Phe Leu
            20              25              30

Gly Gln Pro Val Thr Leu Pro Cys His Tyr Leu Ser Trp Ser Gln Ser
        35              40              45

Arg Asn Ser Met Cys Trp Gly Lys Gly Ser Cys Pro Asn Ser Lys Cys
    50              55              60

Asn Ala Glu Leu Leu Arg Thr Asp Gly Thr Arg Ile Ile Ser Arg Lys
65              70              75              80

Ser Thr Lys Tyr Thr Leu Leu Gly Lys Val Gln Phe Gly Glu Val Ser
            85              90              95

Leu Thr Ile Ser Asn Thr Asn Arg Gly Asp Ser Gly Val Tyr Cys Cys
            100             105             110

Arg Ile Glu Val Pro Gly Trp Phe Asn Asp Val Lys Lys Asn Val Arg
            115             120             125

Leu Glu Leu Arg Arg Ala Thr Thr Thr Lys Lys Pro Thr Thr Thr
        130             135             140

Arg Pro Thr Thr Thr Pro Tyr Val Thr Thr Thr Thr Pro Glu Leu Leu
```

```
            145                 150                 155                 160
Pro Thr Thr Val Met Thr Thr Ser Val Leu Pro Thr Thr Thr Pro Pro
                    165                 170                 175
Gln Thr Leu Ala Thr Thr Ala Phe Ser Thr Ala Val Thr Thr Cys Pro
                    180                 185                 190
Ser Thr Thr Pro Gly Ser Phe Ser Gln Glu Thr Thr Lys Gly Ser Ala
                    195                 200                 205
Phe Thr Thr Glu Ser Glu Thr Leu Pro Ala Ser Asn His Ser Gln Arg
            210                 215                 220
Ser Met Met Thr Ile Ser Thr Asp Ile Ala Val Leu Arg Pro Thr Gly
225                 230                 235                 240
Ser Asn Pro Gly Ile Leu Pro Ser Thr Ser Gln Leu Thr Thr Gln Lys
                    245                 250                 255
Thr Thr Leu Thr Thr Ser Glu Ser Leu Gln Lys Thr Thr Lys Ser His
                    260                 265                 270
Gln Ile Asn Ser Arg Gln Thr Ile Leu Ile Ala Cys Cys Val Gly
                    275                 280                 285
Phe Val Leu Met Val Leu Leu Phe Leu Ala Phe Leu Leu Trp Asn Lys
            290                 295                 300
Lys Arg Met Arg Gly Pro Gly Lys Asp Pro Thr Arg Lys Cys Pro Asp
305                 310                 315                 320
Pro Arg Ser Ala Ser Ser Pro Lys Gln His Pro Ser Glu Ser Val Tyr
                    325                 330                 335
Thr Ala Leu Gln Arg Arg Glu Thr Glu Val Tyr Ala Cys Ile Glu Asn
                    340                 345                 350
Glu Asp Gly Ser Ser Pro Thr Ala Lys Gln Ser Pro Leu Ser Gln Glu
            355                 360                 365
Arg Pro His Arg Phe Glu Asp Asp Gly Glu Leu Asn Leu Val Tyr Glu
            370                 375                 380
Asn Leu Leu Glu Gly Gly Gly Glu Gly Arg Gly Ser Leu Leu Thr Cys
385                 390                 395                 400
Gly Asp Val Glu Glu Asn Pro Gly Pro Met Ala Pro Gly Leu Leu Cys
                    405                 410                 415
Trp Ala Leu Leu Cys Leu Leu Gly Ala Gly Leu Val Asp Ala Gly Val
                    420                 425                 430
Thr Gln Ser Pro Thr His Leu Ile Lys Thr Arg Gly Gln Gln Val Thr
                    435                 440                 445
Leu Arg Cys Ser Pro Lys Ser Gly His Asp Thr Val Ser Trp Tyr Gln
            450                 455                 460
Gln Ala Leu Gly Gln Gly Pro Gln Phe Ile Phe Gln Tyr Tyr Glu Glu
465                 470                 475                 480
Glu Glu Arg Gln Arg Gly Asn Phe Pro Asp Arg Phe Ser Gly His Gln
                    485                 490                 495
Phe Pro Asn Tyr Ser Ser Glu Leu Asn Val Asn Ala Leu Leu Leu Gly
                    500                 505                 510
Asp Ser Ala Leu Tyr Leu Cys Ala Ser Ser Leu Gly Trp Arg Gly Gly
            515                 520                 525
Arg Tyr Asn Glu Gln Phe Phe Gly Pro Gly Thr Arg Leu Thr Val Leu
            530                 535                 540
Glu Asp Leu Arg Asn Val Thr Pro Pro Lys Val Ser Leu Phe Glu Pro
545                 550                 555                 560
Ser Lys Ala Glu Ile Ala Asn Lys Gln Lys Ala Thr Leu Val Cys Leu
                    565                 570                 575
```

```
Ala Arg Gly Phe Phe Pro Asp His Val Glu Leu Ser Trp Trp Val Asn
            580                 585                 590

Gly Lys Glu Val His Ser Gly Val Cys Thr Asp Pro Gln Ala Tyr Lys
        595                 600                 605

Glu Ser Asn Tyr Ser Tyr Cys Leu Ser Ser Arg Leu Arg Val Ser Ala
610                 615                 620

Thr Phe Trp His Asn Pro Arg Asn His Phe Arg Cys Gln Val Gln Phe
625                 630                 635                 640

His Gly Leu Ser Glu Glu Asp Lys Trp Pro Glu Gly Ser Pro Lys Pro
            645                 650                 655

Val Thr Gln Asn Ile Ser Ala Glu Ala Trp Gly Arg Ala Asp Cys Gly
            660                 665                 670

Ile Thr Ser Ala Ser Tyr Gln Gln Gly Val Leu Ser Ala Thr Ile Leu
        675                 680                 685

Tyr Glu Ile Leu Leu Gly Lys Ala Thr Leu Tyr Ala Val Leu Val Ser
        690                 695                 700

Thr Leu Val Val Met Ala Met Val Lys Arg Lys Asn Ser Arg Ala Lys
705                 710                 715                 720

Arg Ser Gly Ser Gly Ala Thr Asn Phe Ser Leu Leu Lys Gln Ala Gly
            725                 730                 735

Asp Val Glu Glu Asn Pro Gly Pro Met Trp Gly Val Phe Leu Leu Tyr
            740                 745                 750

Val Ser Met Lys Met Gly Gly Thr Thr Gly Gln Asn Ile Asp Gln Pro
        755                 760                 765

Thr Glu Met Thr Ala Thr Glu Gly Ala Ile Val Gln Ile Asn Cys Thr
        770                 775                 780

Tyr Gln Thr Ser Gly Phe Asn Gly Leu Phe Trp Tyr Gln Gln His Ala
785                 790                 795                 800

Gly Glu Ala Pro Thr Phe Leu Ser Tyr Asn Val Leu Asp Gly Leu Glu
            805                 810                 815

Glu Lys Gly Arg Phe Ser Ser Phe Leu Ser Arg Ser Lys Gly Tyr Ser
            820                 825                 830

Tyr Leu Leu Leu Lys Glu Leu Gln Met Lys Asp Ser Ala Ser Tyr Leu
        835                 840                 845

Cys Ala Ser Val Asp Gly Asn Asn Arg Leu Ala Phe Gly Lys Gly Asn
850                 855                 860

Gln Val Val Ile Pro Asn Ile Gln Asn Pro Glu Pro Ala Val Tyr
865                 870                 875                 880

Gln Leu Lys Asp Pro Arg Ser Gln Asp Ser Thr Leu Cys Leu Phe Thr
            885                 890                 895

Asp Phe Asp Ser Gln Ile Asn Val Pro Lys Thr Met Glu Ser Gly Thr
            900                 905                 910

Phe Ile Thr Asp Lys Cys Val Leu Asp Met Lys Ala Met Asp Ser Lys
        915                 920                 925

Ser Asn Gly Ala Ile Ala Trp Ser Asn Gln Thr Ser Phe Thr Cys Gln
        930                 935                 940

Asp Ile Phe Lys Glu Thr Asn Ala Thr Tyr Pro Ser Ser Asp Val Pro
945                 950                 955                 960

Cys Asp Ala Thr Leu Thr Glu Lys Ser Phe Glu Thr Asp Met Asn Leu
            965                 970                 975

Asn Phe Gln Asn Leu Leu Val Ile Val Leu Arg Ile Leu Leu Leu Lys
            980                 985                 990
```

```
Val Ala Gly Phe Asn Leu Leu Met Thr Leu Arg Leu Trp Ser Ser
            995                 1000                1005
```

<210> SEQ ID NO 168
<211> LENGTH: 1096
<212> TYPE: PRT
<213> ORGANISM: Artificial Sequence
<220> FEATURE:
<223> OTHER INFORMATION: CER27_T2A_HPV16_E7_TCR tandem cassette

<400> SEQUENCE: 168

```
Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
            35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
            195                 200                 205

Phe Thr Thr Glu Ser Glu Thr Leu Pro Ala Ser Asn His Ser Gln Arg
210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
            275                 280                 285

Phe Val Leu Met Val Leu Leu Phe Leu Ala Phe Leu His Arg Phe His
290                 295                 300

Gly Leu Trp Tyr Met Lys Met Met Trp Ala Trp Leu Gln Ala Lys Arg
305                 310                 315                 320

Lys Pro Arg Lys Ala Pro Ser Arg Asn Ile Cys Tyr Asp Ala Phe Val
                325                 330                 335

Ser Tyr Ser Glu Arg Asp Ala Tyr Trp Val Glu Asn Leu Met Val Gln
            340                 345                 350
```

-continued

```
Glu Leu Glu Asn Phe Asn Pro Pro Phe Lys Leu Cys Leu His Lys Arg
            355                 360                 365

Asp Phe Ile Pro Gly Lys Trp Ile Ile Asp Asn Ile Ile Asp Ser Ile
        370                 375                 380

Glu Lys Ser His Lys Thr Val Phe Val Leu Ser Glu Asn Phe Val Lys
385                 390                 395                 400

Ser Glu Trp Cys Lys Tyr Glu Leu Asp Phe Ser His Phe Arg Leu Phe
            405                 410                 415

Asp Glu Asn Asp Ala Ala Ile Leu Ile Leu Glu Pro Ile Glu
        420                 425                 430

Lys Lys Ala Ile Pro Gln Arg Phe Cys Lys Leu Arg Lys Ile Met Asn
            435                 440                 445

Thr Lys Thr Tyr Leu Glu Trp Pro Met Asp Glu Ala Gln Arg Glu Gly
        450                 455                 460

Phe Trp Val Asn Leu Arg Ala Ala Ile Lys Ser Leu Glu Gly Gly Gly
465                 470                 475                 480

Glu Gly Arg Gly Ser Leu Leu Thr Cys Gly Asp Val Glu Glu Asn Pro
            485                 490                 495

Gly Pro Met Ala Pro Gly Leu Leu Cys Trp Ala Leu Leu Cys Leu Leu
        500                 505                 510

Gly Ala Gly Leu Val Asp Ala Gly Val Thr Gln Ser Pro Thr His Leu
        515                 520                 525

Ile Lys Thr Arg Gly Gln Gln Val Thr Leu Arg Cys Ser Pro Lys Ser
        530                 535                 540

Gly His Asp Thr Val Ser Trp Tyr Gln Gln Ala Leu Gly Gln Gly Pro
545                 550                 555                 560

Gln Phe Ile Phe Gln Tyr Tyr Glu Glu Glu Arg Gln Arg Gly Asn
            565                 570                 575

Phe Pro Asp Arg Phe Ser Gly His Gln Phe Pro Asn Tyr Ser Ser Glu
        580                 585                 590

Leu Asn Val Asn Ala Leu Leu Leu Gly Asp Ser Ala Leu Tyr Leu Cys
        595                 600                 605

Ala Ser Ser Leu Gly Trp Arg Gly Gly Arg Tyr Asn Glu Gln Phe Phe
610                 615                 620

Gly Pro Gly Thr Arg Leu Thr Val Leu Glu Asp Leu Arg Asn Val Thr
625                 630                 635                 640

Pro Pro Lys Val Ser Leu Phe Glu Pro Ser Lys Ala Glu Ile Ala Asn
            645                 650                 655

Lys Gln Lys Ala Thr Leu Val Cys Leu Ala Arg Gly Phe Phe Pro Asp
            660                 665                 670

His Val Glu Leu Ser Trp Trp Val Asn Gly Lys Glu Val His Ser Gly
            675                 680                 685

Val Cys Thr Asp Pro Gln Ala Tyr Lys Glu Ser Asn Tyr Ser Tyr Cys
        690                 695                 700

Leu Ser Ser Arg Leu Arg Val Ser Ala Thr Phe Trp His Asn Pro Arg
705                 710                 715                 720

Asn His Phe Arg Cys Gln Val Gln Phe His Gly Leu Ser Glu Glu Asp
            725                 730                 735

Lys Trp Pro Glu Gly Ser Pro Lys Pro Val Thr Gln Asn Ile Ser Ala
            740                 745                 750

Glu Ala Trp Gly Arg Ala Asp Cys Gly Ile Thr Ser Ala Ser Tyr Gln
            755                 760                 765

Gln Gly Val Leu Ser Ala Thr Ile Leu Tyr Glu Ile Leu Leu Gly Lys
```

Ala Thr Leu Tyr Ala Val Leu Val Ser Thr Leu Val Val Met Ala Met
785             790             795             800

Val Lys Arg Lys Asn Ser Arg Ala Lys Arg Ser Gly Ser Gly Ala Thr
        805             810             815

Asn Phe Ser Leu Leu Lys Gln Ala Gly Asp Val Glu Glu Asn Pro Gly
        820             825             830

Pro Met Trp Gly Val Phe Leu Leu Tyr Val Ser Met Lys Met Gly Gly
        835             840             845

Thr Thr Gly Gln Asn Ile Asp Gln Pro Thr Glu Met Thr Ala Thr Glu
        850             855             860

Gly Ala Ile Val Gln Ile Asn Cys Thr Tyr Gln Thr Ser Gly Phe Asn
865             870             875             880

Gly Leu Phe Trp Tyr Gln Gln His Ala Gly Glu Ala Pro Thr Phe Leu
            885             890             895

Ser Tyr Asn Val Leu Asp Gly Leu Glu Glu Lys Gly Arg Phe Ser Ser
            900             905             910

Phe Leu Ser Arg Ser Lys Gly Tyr Ser Tyr Leu Leu Leu Lys Glu Leu
            915             920             925

Gln Met Lys Asp Ser Ala Ser Tyr Leu Cys Ala Ser Val Asp Gly Asn
        930             935             940

Asn Arg Leu Ala Phe Gly Lys Gly Asn Gln Val Val Val Ile Pro Asn
945             950             955             960

Ile Gln Asn Pro Glu Pro Ala Val Tyr Gln Leu Lys Asp Pro Arg Ser
            965             970             975

Gln Asp Ser Thr Leu Cys Leu Phe Thr Asp Phe Asp Ser Gln Ile Asn
            980             985             990

Val Pro Lys Thr Met Glu Ser Gly Thr Phe Ile Thr Asp Lys Cys Val
            995             1000            1005

Leu Asp Met Lys Ala Met Asp Ser Lys Ser Asn Gly Ala Ile Ala Trp
        1010            1015            1020

Ser Asn Gln Thr Ser Phe Thr Cys Gln Asp Ile Phe Lys Glu Thr Asn
1025            1030            1035            1040

Ala Thr Tyr Pro Ser Ser Asp Val Pro Cys Asp Ala Thr Leu Thr Glu
            1045            1050            1055

Lys Ser Phe Glu Thr Asp Met Asn Leu Asn Phe Gln Asn Leu Leu Val
            1060            1065            1070

Ile Val Leu Arg Ile Leu Leu Leu Lys Val Ala Gly Phe Asn Leu Leu
            1075            1080            1085

Met Thr Leu Arg Leu Trp Ser Ser
        1090            1095

<210> SEQ ID NO 169
<211> LENGTH: 1195
<212> TYPE: PRT
<213> ORGANISM: Artificial Sequence
<220> FEATURE:
<223> OTHER INFORMATION: CER29_T2A_HPV16_E7_TCR tandem cassette

<400> SEQUENCE: 169

Met Ser Lys Gly Leu Leu Leu Leu Trp Leu Val Thr Glu Leu Trp Trp
1               5               10              15

Leu Tyr Leu Thr Pro Ala Ala Ser Glu Asp Thr Ile Ile Gly Phe Leu
            20              25              30

Gly Gln Pro Val Thr Leu Pro Cys His Tyr Leu Ser Trp Ser Gln Ser

```
                35                  40                  45
Arg Asn Ser Met Cys Trp Gly Lys Gly Ser Cys Pro Asn Ser Lys Cys
 50                  55                  60
Asn Ala Glu Leu Leu Arg Thr Asp Gly Thr Arg Ile Ile Ser Arg Lys
 65                  70                  75                  80
Ser Thr Lys Tyr Thr Leu Leu Gly Lys Val Gln Phe Gly Glu Val Ser
                 85                  90                  95
Leu Thr Ile Ser Asn Thr Asn Arg Gly Asp Ser Gly Val Tyr Cys Cys
                100                 105                 110
Arg Ile Glu Val Pro Gly Trp Phe Asn Asp Val Lys Lys Asn Val Arg
                115                 120                 125
Leu Glu Leu Arg Arg Ala Thr Thr Lys Lys Pro Thr Thr Thr Thr Thr
                130                 135                 140
Arg Pro Thr Thr Thr Pro Tyr Val Thr Thr Thr Pro Glu Leu Leu
145                 150                 155                 160
Pro Thr Thr Val Met Thr Thr Ser Val Leu Pro Thr Thr Thr Pro Pro
                165                 170                 175
Gln Thr Leu Ala Thr Thr Ala Phe Ser Thr Ala Val Thr Thr Cys Pro
                180                 185                 190
Ser Thr Thr Pro Gly Ser Phe Ser Gln Glu Thr Thr Lys Gly Ser Ala
                195                 200                 205
Phe Thr Thr Glu Ser Glu Thr Leu Pro Ala Ser Asn His Ser Gln Arg
                210                 215                 220
Ser Met Met Thr Ile Ser Thr Asp Ile Ala Val Leu Arg Pro Thr Gly
225                 230                 235                 240
Ser Asn Pro Gly Ile Leu Pro Ser Thr Ser Gln Leu Thr Thr Gln Lys
                245                 250                 255
Thr Thr Leu Thr Thr Ser Glu Ser Leu Gln Lys Thr Thr Lys Ser His
                260                 265                 270
Gln Ile Asn Ser Arg Gln Thr Ile Leu Ile Ile Ala Cys Cys Val Gly
                275                 280                 285
Phe Val Leu Met Val Leu Leu Phe Leu Ala Phe Leu Met Ser Leu Leu
                290                 295                 300
Asn Cys Glu Asn Ser Cys Gly Ser Ser Gln Ser Glu Ser Asp Cys Cys
305                 310                 315                 320
Val Ala Met Ala Ser Ser Cys Ser Ala Val Thr Lys Asp Asp Ser Val
                325                 330                 335
Gly Gly Thr Ala Ser Thr Gly Asn Leu Ser Ser Ser Phe Met Glu Glu
                340                 345                 350
Ile Gln Gly Tyr Asp Val Glu Phe Asp Pro Pro Leu Glu Ser Lys Tyr
                355                 360                 365
Glu Cys Pro Ile Cys Leu Met Ala Leu Arg Glu Ala Val Gln Thr Pro
                370                 375                 380
Cys Gly His Arg Phe Cys Lys Ala Cys Ile Ile Lys Ser Ile Arg Asp
385                 390                 395                 400
Ala Gly His Lys Cys Pro Val Asp Asn Glu Ile Leu Leu Glu Asn Gln
                405                 410                 415
Leu Phe Pro Asp Asn Phe Ala Lys Arg Glu Ile Leu Ser Leu Met Val
                420                 425                 430
Lys Cys Pro Asn Glu Gly Cys Leu His Lys Met Glu Leu Arg His Leu
                435                 440                 445
Glu Asp His Gln Ala His Cys Glu Phe Ala Leu Met Asp Cys Pro Gln
                450                 455                 460
```

```
Cys Gln Arg Pro Phe Gln Lys Phe His Ile Asn Ile His Ile Leu Lys
465                 470                 475                 480

Asp Cys Pro Arg Arg Gln Val Ser Cys Asp Asn Cys Ala Ala Ser Met
                485                 490                 495

Ala Phe Glu Asp Lys Glu Ile His Asp Gln Asn Cys Pro Leu Ala Asn
            500                 505                 510

Val Ile Cys Glu Tyr Cys Asn Thr Ile Leu Ile Arg Glu Gln Met Pro
            515                 520                 525

Asn His Tyr Asp Leu Asp Cys Pro Thr Ala Pro Ile Pro Cys Thr Phe
            530                 535                 540

Ser Thr Phe Gly Cys His Glu Lys Met Gln Arg Asn His Leu Ala Arg
545                 550                 555                 560

His Leu Gln Glu Asn Thr Gln Ser His Met Arg Met Leu Ala Leu Glu
                565                 570                 575

Gly Gly Gly Glu Gly Arg Gly Ser Leu Leu Thr Cys Gly Asp Val Glu
            580                 585                 590

Glu Asn Pro Gly Pro Met Ala Pro Gly Leu Leu Cys Trp Ala Leu Leu
            595                 600                 605

Cys Leu Leu Gly Ala Gly Leu Val Asp Ala Gly Val Thr Gln Ser Pro
610                 615                 620

Thr His Leu Ile Lys Thr Arg Gly Gln Gln Val Thr Leu Arg Cys Ser
625                 630                 635                 640

Pro Lys Ser Gly His Asp Thr Val Ser Trp Tyr Gln Gln Ala Leu Gly
                645                 650                 655

Gln Gly Pro Gln Phe Ile Phe Gln Tyr Tyr Glu Glu Glu Arg Gln
            660                 665                 670

Arg Gly Asn Phe Pro Asp Arg Phe Ser Gly His Gln Phe Pro Asn Tyr
            675                 680                 685

Ser Ser Glu Leu Asn Val Asn Ala Leu Leu Leu Gly Asp Ser Ala Leu
            690                 695                 700

Tyr Leu Cys Ala Ser Ser Leu Gly Trp Arg Gly Gly Arg Tyr Asn Glu
705                 710                 715                 720

Gln Phe Phe Gly Pro Gly Thr Arg Leu Thr Val Leu Glu Asp Leu Arg
                725                 730                 735

Asn Val Thr Pro Pro Lys Val Ser Leu Phe Glu Pro Ser Lys Ala Glu
                740                 745                 750

Ile Ala Asn Lys Gln Lys Ala Thr Leu Val Cys Leu Ala Arg Gly Phe
                755                 760                 765

Phe Pro Asp His Val Glu Leu Ser Trp Trp Val Asn Gly Lys Glu Val
            770                 775                 780

His Ser Gly Val Cys Thr Asp Pro Gln Ala Tyr Lys Glu Ser Asn Tyr
785                 790                 795                 800

Ser Tyr Cys Leu Ser Ser Arg Leu Arg Val Ser Ala Thr Phe Trp His
                805                 810                 815

Asn Pro Arg Asn His Phe Arg Cys Gln Val Gln Phe His Gly Leu Ser
                820                 825                 830

Glu Glu Asp Lys Trp Pro Glu Gly Ser Pro Lys Pro Val Thr Gln Asn
            835                 840                 845

Ile Ser Ala Glu Ala Trp Gly Arg Ala Asp Cys Gly Ile Thr Ser Ala
            850                 855                 860

Ser Tyr Gln Gln Gly Val Leu Ser Ala Thr Ile Leu Tyr Glu Ile Leu
865                 870                 875                 880
```

Leu Gly Lys Ala Thr Leu Tyr Ala Val Leu Val Ser Thr Leu Val Val
            885                 890                 895

Met Ala Met Val Lys Arg Lys Asn Ser Arg Ala Lys Arg Ser Gly Ser
        900                 905                 910

Gly Ala Thr Asn Phe Ser Leu Leu Lys Gln Ala Gly Asp Val Glu Glu
        915                 920                 925

Asn Pro Gly Pro Met Trp Gly Val Phe Leu Leu Tyr Val Ser Met Lys
        930                 935                 940

Met Gly Gly Thr Thr Gly Gln Asn Ile Asp Gln Pro Thr Glu Met Thr
945                 950                 955                 960

Ala Thr Glu Gly Ala Ile Val Gln Ile Asn Cys Thr Tyr Gln Thr Ser
            965                 970                 975

Gly Phe Asn Gly Leu Phe Trp Tyr Gln Gln His Ala Gly Glu Ala Pro
            980                 985                 990

Thr Phe Leu Ser Tyr Asn Val Leu Asp Gly Leu Glu Glu Lys Gly Arg
            995                 1000                1005

Phe Ser Ser Phe Leu Ser Arg Ser Lys Gly Tyr Ser Tyr Leu Leu Leu
        1010                1015                1020

Lys Glu Leu Gln Met Lys Asp Ser Ala Ser Tyr Leu Cys Ala Ser Val
1025                1030                1035                1040

Asp Gly Asn Asn Arg Leu Ala Phe Gly Lys Gly Asn Gln Val Val Val
            1045                1050                1055

Ile Pro Asn Ile Gln Asn Pro Glu Pro Ala Val Tyr Gln Leu Lys Asp
            1060                1065                1070

Pro Arg Ser Gln Asp Ser Thr Leu Cys Leu Phe Thr Asp Phe Asp Ser
            1075                1080                1085

Gln Ile Asn Val Pro Lys Thr Met Glu Ser Gly Thr Phe Ile Thr Asp
        1090                1095                1100

Lys Cys Val Leu Asp Met Lys Ala Met Asp Ser Lys Ser Asn Gly Ala
1105                1110                1115                1120

Ile Ala Trp Ser Asn Gln Thr Ser Phe Thr Cys Gln Asp Ile Phe Lys
            1125                1130                1135

Glu Thr Asn Ala Thr Tyr Pro Ser Ser Asp Val Pro Cys Asp Ala Thr
            1140                1145                1150

Leu Thr Glu Lys Ser Phe Glu Thr Asp Met Asn Leu Asn Phe Gln Asn
            1155                1160                1165

Leu Leu Val Ile Val Leu Arg Ile Leu Leu Leu Lys Val Ala Gly Phe
            1170                1175                1180

Asn Leu Leu Met Thr Leu Arg Leu Trp Ser Ser
1185                1190                1195

<210> SEQ ID NO 170
<211> LENGTH: 1195
<212> TYPE: PRT
<213> ORGANISM: Artificial Sequence
<220> FEATURE:
<223> OTHER INFORMATION: CER31_T2A_HPV16_E7_TCR tandem cassette

<400> SEQUENCE: 170

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

```
Arg Asn Ser Met Cys Trp Gly Lys Gly Ser Cys Pro Asn Ser Lys Cys
 50                  55                  60

Asn Ala Glu Leu Leu Arg Thr Asp Gly Thr Arg Ile Ile Ser Arg Lys
 65                  70                  75                  80

Ser Thr Lys Tyr Thr Leu Leu Gly Lys Val Gln Phe Gly Glu Val Ser
                 85                  90                  95

Leu Thr Ile Ser Asn Thr Asn Arg Gly Asp Ser Gly Val Tyr Cys Cys
                100                 105                 110

Arg Ile Glu Val Pro Gly Trp Phe Asn Asp Val Lys Lys Asn Val Arg
            115                 120                 125

Leu Glu Leu Arg Arg Ala Thr Thr Lys Lys Pro Thr Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ile Ala Cys Cys Val Gly
                275                 280                 285

Phe Val Leu Met Val Leu Leu Phe Leu Ala Phe Leu Met Glu Ser Ser
            290                 295                 300

Lys Lys Met Asp Ser Pro Gly Ala Leu Gln Thr Asn Pro Pro Leu Lys
305                 310                 315                 320

Leu His Thr Asp Arg Ser Ala Gly Thr Pro Val Phe Val Pro Glu Gln
                325                 330                 335

Gly Gly Tyr Lys Glu Lys Phe Val Lys Thr Val Glu Asp Lys Tyr Lys
                340                 345                 350

Cys Glu Lys Cys His Leu Val Leu Cys Ser Pro Lys Gln Thr Glu Cys
            355                 360                 365

Gly His Arg Phe Cys Glu Ser Cys Met Ala Ala Leu Leu Ser Ser Ser
370                 375                 380

Ser Pro Lys Cys Thr Ala Cys Gln Glu Ser Ile Val Lys Asp Lys Val
385                 390                 395                 400

Phe Lys Asp Asn Cys Cys Lys Arg Glu Ile Leu Ala Leu Gln Ile Tyr
                405                 410                 415

Cys Arg Asn Glu Ser Arg Gly Cys Ala Glu Gln Leu Met Leu Gly His
            420                 425                 430

Leu Leu Val His Leu Lys Asn Asp Cys His Phe Glu Glu Leu Pro Cys
            435                 440                 445

Val Arg Pro Asp Cys Lys Glu Lys Val Leu Arg Lys Asp Leu Arg Asp
450                 455                 460

His Val Glu Lys Ala Cys Lys Tyr Arg Glu Ala Thr Cys Ser His Cys
```

-continued

```
            465                 470                 475                 480
Lys Ser Gln Val Pro Met Ile Ala Leu Gln Lys His Glu Asp Thr Asp
                    485                 490                 495
Cys Pro Cys Val Val Ser Cys Pro His Lys Cys Ser Val Gln Thr
                500                 505                 510
Leu Leu Arg Ser Glu Leu Ser Ala His Leu Ser Glu Cys Val Asn Ala
                515                 520                 525
Pro Ser Thr Cys Ser Phe Lys Arg Tyr Gly Cys Val Phe Gln Gly Thr
    530                 535                 540
Asn Gln Gln Ile Lys Ala His Glu Ala Ser Ser Ala Val Gln His Val
545                 550                 555                 560
Asn Leu Leu Lys Glu Trp Ser Asn Ser Leu Glu Lys Lys Val Leu Glu
                565                 570                 575
Gly Gly Gly Glu Gly Arg Gly Ser Leu Leu Thr Cys Gly Asp Val Glu
                580                 585                 590
Glu Asn Pro Gly Pro Met Ala Pro Gly Leu Leu Cys Trp Ala Leu Leu
            595                 600                 605
Cys Leu Leu Gly Ala Gly Leu Val Asp Ala Gly Val Thr Gln Ser Pro
    610                 615                 620
Thr His Leu Ile Lys Thr Arg Gly Gln Gln Val Thr Leu Arg Cys Ser
625                 630                 635                 640
Pro Lys Ser Gly His Asp Thr Val Ser Trp Tyr Gln Gln Ala Leu Gly
                645                 650                 655
Gln Gly Pro Gln Phe Ile Phe Gln Tyr Tyr Glu Glu Glu Arg Gln
                660                 665                 670
Arg Gly Asn Phe Pro Asp Arg Phe Ser Gly His Gln Phe Pro Asn Tyr
            675                 680                 685
Ser Ser Glu Leu Asn Val Asn Ala Leu Leu Leu Gly Asp Ser Ala Leu
    690                 695                 700
Tyr Leu Cys Ala Ser Ser Leu Gly Trp Arg Gly Gly Arg Tyr Asn Glu
705                 710                 715                 720
Gln Phe Phe Gly Pro Gly Thr Arg Leu Thr Val Leu Glu Asp Leu Arg
                725                 730                 735
Asn Val Thr Pro Pro Lys Val Ser Leu Phe Glu Pro Ser Lys Ala Glu
                740                 745                 750
Ile Ala Asn Lys Gln Lys Ala Thr Leu Val Cys Leu Ala Arg Gly Phe
            755                 760                 765
Phe Pro Asp His Val Glu Leu Ser Trp Trp Val Asn Gly Lys Glu Val
    770                 775                 780
His Ser Gly Val Cys Thr Asp Pro Gln Ala Tyr Lys Glu Ser Asn Tyr
785                 790                 795                 800
Ser Tyr Cys Leu Ser Ser Arg Leu Arg Val Ser Ala Thr Phe Trp His
                805                 810                 815
Asn Pro Arg Asn His Phe Arg Cys Gln Val Gln Phe His Gly Leu Ser
                820                 825                 830
Glu Glu Asp Lys Trp Pro Glu Gly Ser Pro Lys Pro Val Thr Gln Asn
            835                 840                 845
Ile Ser Ala Glu Ala Trp Gly Arg Ala Asp Cys Gly Ile Thr Ser Ala
    850                 855                 860
Ser Tyr Gln Gln Gly Val Leu Ser Ala Thr Ile Leu Tyr Glu Ile Leu
865                 870                 875                 880
Leu Gly Lys Ala Thr Leu Tyr Ala Val Leu Val Ser Thr Leu Val Val
                885                 890                 895
```

```
Met Ala Met Val Lys Arg Lys Asn Ser Arg Ala Lys Arg Ser Gly Ser
            900                 905                 910

Gly Ala Thr Asn Phe Ser Leu Leu Lys Gln Ala Gly Asp Val Glu Glu
            915                 920                 925

Asn Pro Gly Pro Met Trp Gly Val Phe Leu Leu Tyr Val Ser Met Lys
            930                 935                 940

Met Gly Gly Thr Thr Gly Gln Asn Ile Asp Gln Pro Thr Glu Met Thr
945                 950                 955                 960

Ala Thr Glu Gly Ala Ile Val Gln Ile Asn Cys Thr Tyr Gln Thr Ser
            965                 970                 975

Gly Phe Asn Gly Leu Phe Trp Tyr Gln Gln His Ala Gly Glu Ala Pro
            980                 985                 990

Thr Phe Leu Ser Tyr Asn Val Leu Asp Gly Leu Glu Glu Lys Gly Arg
            995                 1000                1005

Phe Ser Ser Phe Leu Ser Arg Ser Lys Gly Tyr Ser Tyr Leu Leu Leu
            1010                1015                1020

Lys Glu Leu Gln Met Lys Asp Ser Ala Ser Tyr Leu Cys Ala Ser Val
1025                1030                1035                1040

Asp Gly Asn Asn Arg Leu Ala Phe Gly Lys Gly Asn Gln Val Val Val
            1045                1050                1055

Ile Pro Asn Ile Gln Asn Pro Glu Pro Ala Val Tyr Gln Leu Lys Asp
            1060                1065                1070

Pro Arg Ser Gln Asp Ser Thr Leu Cys Leu Phe Thr Asp Phe Asp Ser
            1075                1080                1085

Gln Ile Asn Val Pro Lys Thr Met Glu Ser Gly Thr Phe Ile Thr Asp
            1090                1095                1100

Lys Cys Val Leu Asp Met Lys Ala Met Asp Ser Lys Ser Asn Gly Ala
1105                1110                1115                1120

Ile Ala Trp Ser Asn Gln Thr Ser Phe Thr Cys Gln Asp Ile Phe Lys
            1125                1130                1135

Glu Thr Asn Ala Thr Tyr Pro Ser Ser Asp Val Pro Cys Asp Ala Thr
            1140                1145                1150

Leu Thr Glu Lys Ser Phe Glu Thr Asp Met Asn Leu Asn Phe Gln Asn
            1155                1160                1165

Leu Leu Val Ile Val Leu Arg Ile Leu Leu Leu Lys Val Ala Gly Phe
            1170                1175                1180

Asn Leu Leu Met Thr Leu Arg Leu Trp Ser Ser
1185                1190                1195

<210> SEQ ID NO 171
<211> LENGTH: 155
<212> TYPE: PRT
<213> ORGANISM: Homo sapiens
<220> FEATURE:
<223> OTHER INFORMATION: truncated MyD88 signaling domain without TIR
      domain

<400> SEQUENCE: 171

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
            35                  40                  45

Ala Leu Ala Glu Glu Met Asp Phe Glu Tyr Leu Glu Ile Arg Gln Leu
```

```
                    50                  55                  60
Glu Thr Gln Ala Asp Pro Thr Gly Arg Leu Leu Asp Ala Trp Gln Gly
 65                  70                  75                  80

Arg Pro Gly Ala Ser Val Gly Arg Leu Leu Glu Leu Leu Thr Lys Leu
                 85                  90                  95

Gly Arg Asp Asp Val Leu Leu Glu Leu Gly Pro Ser Ile Glu Glu Asp
                100                 105                 110

Cys Gln Lys Tyr Ile Leu Lys Gln Gln Gln Glu Glu Ala Glu Lys Pro
                115                 120                 125

Leu Gln Val Ala Ala Val Asp Ser Ser Val Pro Arg Thr Ala Glu Leu
            130                 135                 140

Ala Gly Ile Thr Thr Leu Asp Asp Pro Leu Gly
145                 150                 155

<210> SEQ ID NO 172
<211> LENGTH: 296
<212> TYPE: PRT
<213> ORGANISM: Homo sapiens
<220> FEATURE:
<223> OTHER INFORMATION: MyD88 signaling domain

<400> SEQUENCE: 172

Met Ala Ala Gly Gly Pro Gly Ala Gly Ser Ala Ala Pro Val Ser Ser
  1               5                  10                  15

Thr Ser Ser Leu Pro Leu Ala Ala Leu Asn Met Arg Val Arg Arg Arg
                 20                  25                  30

Leu Ser Leu Phe Leu Asn Val Arg Thr Gln Val Ala Ala Asp Trp Thr
             35                  40                  45

Ala Leu Ala Glu Glu Met Asp Phe Glu Tyr Leu Glu Ile Arg Gln Leu
         50                  55                  60

Glu Thr Gln Ala Asp Pro Thr Gly Arg Leu Leu Asp Ala Trp Gln Gly
 65                  70                  75                  80

Arg Pro Gly Ala Ser Val Gly Arg Leu Leu Glu Leu Leu Thr Lys Leu
                 85                  90                  95

Gly Arg Asp Asp Val Leu Leu Glu Leu Gly Pro Ser Ile Glu Glu Asp
                100                 105                 110

Cys Gln Lys Tyr Ile Leu Lys Gln Gln Gln Glu Glu Ala Glu Lys Pro
                115                 120                 125

Leu Gln Val Ala Ala Val Asp Ser Ser Val Pro Arg Thr Ala Glu Leu
            130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Gln Phe Val Gln
                165                 170                 175

Glu Met Ile Arg Gln Leu Glu Gln Thr Asn Tyr Arg Leu Lys Leu Cys
                180                 185                 190

Val Ser Asp Arg Asp Val Leu Pro Gly Thr Cys Val Trp Ser Ile Ala
            195                 200                 205

Ser Glu Leu Ile Glu Lys Arg Cys Arg Arg Met Val Val Val Val Ser
210                 215                 220

Asp Asp Tyr Leu Gln Ser Lys Glu Cys Asp Phe Gln Thr Lys Phe Ala
                225                 230                 235                 240

Leu Ser Leu Ser Pro Gly Ala His Gln Lys Arg Leu Ile Pro Ile Lys
                245                 250                 255

Tyr Lys Ala Met Lys Lys Glu Phe Pro Ser Ile Leu Arg Phe Ile Thr
```

```
                260                 265                 270
Val Cys Asp Tyr Thr Asn Pro Cys Thr Lys Ser Trp Phe Trp Thr Arg
            275                 280                 285
Leu Ala Lys Ala Leu Ser Leu Pro
        290                 295

<210> SEQ ID NO 173
<211> LENGTH: 530
<212> TYPE: PRT
<213> ORGANISM: Artificial Sequence
<220> FEATURE:
<223> OTHER INFORMATION: CER119A protein
<220> FEATURE:
<221> NAME/KEY: sig_peptide
<222> LOCATION: 1...22

<400> SEQUENCE: 173

Met Ser Lys Gly Leu Leu Leu Trp Leu Val Thr Glu Leu Trp Trp
  1               5                  10                  15

Leu Tyr Leu Thr Pro Ala Ala Ser Glu Asp Thr Ile Ile Gly Phe Leu
                 20                  25                  30

Gly Gln Pro Val Thr Leu Pro Cys His Tyr Leu Ser Trp Ser Gln Ser
             35                  40                  45

Arg Asn Ser Met Cys Trp Gly Lys Gly Ser Cys Pro Asn Ser Lys Cys
 50                  55                  60

Asn Ala Glu Leu Leu Arg Thr Asp Gly Thr Arg Ile Ile Ser Arg Lys
 65                  70                  75                  80

Ser Thr Lys Tyr Thr Leu Leu Gly Lys Val Gln Phe Gly Glu Val Ser
                 85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Thr Lys Lys Pro Thr Thr Thr Thr
130                 135                 140

Arg Pro Thr Thr Thr Pro Tyr Val Thr Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
            180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
    210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
            260                 265                 270

Gln Ile Asn Ser Arg Gln Thr Ile Leu Ile Ile Ala Cys Cys Val Gly
        275                 280                 285

Phe Val Leu Met Val Leu Leu Phe Leu Ala Phe Leu Ser Tyr Leu Asp
    290                 295                 300

Leu Pro Trp Tyr Leu Arg Met Val Cys Gln Trp Thr Gln Thr Arg Arg
```

```
305                 310                 315                 320
Arg Ala Arg Asn Ile Pro Leu Glu Glu Leu Gln Arg Asn Leu Gln Phe
                325                 330                 335
His Ala Phe Ile Ser Tyr Ser Gly His Asp Ser Phe Trp Val Lys Asn
                340                 345                 350
Glu Leu Leu Pro Asn Leu Glu Lys Glu Gly Met Gln Ile Cys Leu His
                355                 360                 365
Glu Arg Asn Phe Val Pro Gly Lys Ser Ile Val Glu Asn Ile Ile Thr
    370                 375                 380
Cys Ile Glu Lys Ser Tyr Lys Ser Ile Phe Val Leu Ser Pro Asn Phe
385                 390                 395                 400
Val Gln Ser Glu Trp Cys His Tyr Glu Leu Tyr Phe Ala His His Asn
                405                 410                 415
Leu Phe His Glu Gly Ser Asn Ser Leu Ile Leu Ile Leu Leu Glu Pro
                420                 425                 430
Ile Pro Gln Tyr Ser Ile Pro Ser Ser Tyr His Lys Leu Lys Ser Leu
                435                 440                 445
Met Ala Arg Arg Thr Tyr Leu Glu Trp Pro Lys Glu Lys Ser Lys Arg
    450                 455                 460
Gly Leu Phe Trp Ala Asn Leu Arg Ala Ala Ile Asn Ile Lys Leu Thr
465                 470                 475                 480
Glu Gln Ala Lys Lys Asp Ser Lys Ala Gly Met Glu Glu Asp His Thr
                485                 490                 495
Tyr Glu Gly Leu Asp Ile Asp Gln Thr Ala Thr Tyr Glu Asp Ile Val
                500                 505                 510
Thr Leu Arg Thr Gly Glu Val Lys Trp Ser Val Gly Glu His Pro Gly
                515                 520                 525
Gln Glu
    530

<210> SEQ ID NO 174
<211> LENGTH: 778
<212> TYPE: PRT
<213> ORGANISM: Artificial Sequence
<220> FEATURE:
<223> OTHER INFORMATION: CER126 protein
<220> FEATURE:
<221> NAME/KEY: sig_peptide
<222> LOCATION: 1...22

<400> SEQUENCE: 174

Met Ser Lys Gly Leu Leu Leu Leu Trp Leu Val Thr Glu Leu Trp Trp
1               5                   10                  15
Leu Tyr Leu Thr Pro Ala Ala Ser Glu Asp Thr Ile Ile Gly Phe Leu
                20                  25                  30
Gly Gln Pro Val Thr Leu Pro Cys His Tyr Leu Ser Trp Ser Gln Ser
                35                  40                  45
Arg Asn Ser Met Cys Trp Gly Lys Gly Ser Cys Pro Asn Ser Lys Cys
    50                  55                  60
Asn Ala Glu Leu Leu Arg Thr Asp Gly Thr Arg Ile Ile Ser Arg Lys
65                  70                  75                  80
Ser Thr Lys Tyr Thr Leu Leu Gly Lys Val Gln Phe Gly Glu Val Ser
                85                  90                  95
Leu Thr Ile Ser Asn Thr Asn Arg Gly Asp Ser Gly Val Tyr Cys Cys
                100                 105                 110
Arg Ile Glu Val Pro Gly Trp Phe Asn Asp Val Lys Lys Asn Val Arg
```

-continued

```
                115                 120                 125
Leu Glu Leu Arg Arg Ala Thr Thr Thr Lys Lys Pro Thr Thr Thr Thr
            130                 135                 140
Arg Pro Thr Thr Thr Pro Tyr Val Thr Thr Thr Thr Pro Glu Leu Leu
145                 150                 155                 160
Pro Thr Thr Val Met Thr Thr Ser Val Leu Pro Thr Thr Thr Pro Pro
                165                 170                 175
Gln Thr Leu Ala Thr Thr Ala Phe Ser Thr Ala Val Thr Thr Cys Pro
            180                 185                 190
Ser Thr Thr Pro Gly Ser Phe Ser Gln Glu Thr Thr Lys Gly Ser Ala
            195                 200                 205
Phe Thr Thr Glu Ser Glu Thr Leu Pro Ala Ser Asn His Ser Gln Arg
210                 215                 220
Ser Met Met Thr Ile Ser Thr Asp Ile Ala Val Leu Arg Pro Thr Gly
225                 230                 235                 240
Ser Asn Pro Gly Ile Leu Pro Ser Thr Ser Gln Leu Thr Thr Gln Lys
                245                 250                 255
Thr Thr Leu Thr Thr Ser Glu Ser Leu Gln Lys Thr Thr Lys Ser His
            260                 265                 270
Gln Ile Asn Ser Arg Gln Thr Ile Leu Ile Ile Ala Cys Cys Val Gly
            275                 280                 285
Phe Val Leu Met Val Leu Leu Phe Leu Ala Phe Leu His Arg Phe His
            290                 295                 300
Gly Leu Trp Tyr Met Lys Met Met Trp Ala Trp Leu Gln Ala Lys Arg
305                 310                 315                 320
Lys Pro Arg Lys Ala Pro Ser Arg Asn Ile Cys Tyr Asp Ala Phe Val
                325                 330                 335
Ser Tyr Ser Glu Arg Asp Ala Tyr Trp Val Glu Asn Leu Met Val Gln
            340                 345                 350
Glu Leu Glu Asn Phe Asn Pro Pro Phe Lys Leu Cys Leu His Lys Arg
            355                 360                 365
Asp Phe Ile Pro Gly Lys Trp Ile Ile Asp Asn Ile Asp Ser Ile
370                 375                 380
Glu Lys Ser His Lys Thr Val Phe Val Leu Ser Glu Asn Phe Val Lys
385                 390                 395                 400
Ser Glu Trp Cys Lys Tyr Glu Leu Asp Phe Ser His Phe Arg Leu Phe
                405                 410                 415
Asp Glu Asn Asn Asp Ala Ala Ile Leu Ile Leu Leu Glu Pro Ile Glu
            420                 425                 430
Lys Lys Ala Ile Pro Gln Arg Phe Cys Lys Leu Arg Lys Ile Met Asn
            435                 440                 445
Thr Lys Thr Tyr Leu Glu Trp Pro Met Asp Glu Ala Gln Arg Glu Gly
            450                 455                 460
Phe Trp Val Asn Leu Arg Ala Ala Ile Lys Ser Met Ala Ala Ala Ser
465                 470                 475                 480
Val Thr Pro Pro Gly Ser Leu Glu Leu Leu Gln Pro Gly Phe Ser Lys
                485                 490                 495
Thr Leu Leu Gly Thr Lys Leu Glu Ala Lys Tyr Leu Cys Ser Ala Cys
            500                 505                 510
Arg Asn Val Leu Arg Arg Pro Phe Gln Ala Gln Cys Gly His Arg Tyr
            515                 520                 525
Cys Ser Phe Cys Leu Ala Ser Ile Leu Ser Ser Gly Pro Gln Asn Cys
            530                 535                 540
```

```
Ala Ala Cys Val His Glu Gly Ile Tyr Glu Glu Gly Ile Ser Ile Leu
545                 550                 555                 560

Glu Ser Ser Ser Ala Phe Pro Asp Asn Ala Arg Arg Glu Val Glu
            565                 570                 575

Ser Leu Pro Ala Val Cys Pro Ser Asp Gly Cys Thr Trp Lys Gly Thr
        580                 585                 590

Leu Lys Glu Tyr Glu Ser Cys His Glu Gly Arg Cys Pro Leu Met Leu
            595                 600                 605

Thr Glu Cys Pro Ala Cys Lys Gly Leu Val Arg Leu Gly Glu Lys Glu
        610                 615                 620

Arg His Leu Glu His Glu Cys Pro Glu Arg Ser Leu Ser Cys Arg His
625                 630                 635                 640

Cys Arg Ala Pro Cys Cys Gly Ala Asp Val Lys Ala His His Glu Val
                645                 650                 655

Cys Pro Lys Phe Pro Leu Thr Cys Asp Gly Cys Gly Lys Lys Lys Ile
            660                 665                 670

Pro Arg Glu Lys Phe Gln Asp His Val Lys Thr Cys Gly Lys Cys Arg
        675                 680                 685

Val Pro Cys Arg Phe His Ala Ile Gly Cys Leu Glu Thr Val Glu Gly
            690                 695                 700

Glu Lys Gln Gln Glu His Glu Val Gln Trp Leu Arg Glu His Leu Ala
705                 710                 715                 720

Met Leu Leu Ser Ser Val Leu Glu Ala Lys Pro Leu Leu Gly Asp Gln
                725                 730                 735

Ser His Ala Gly Ser Glu Leu Leu Gln Arg Cys Glu Ser Leu Glu Lys
            740                 745                 750

Lys Thr Ala Thr Phe Glu Asn Ile Val Cys Val Leu Asn Arg Glu Val
        755                 760                 765

Glu Arg Val Ala Met Thr Ala Glu Ala Cys
    770                 775

<210> SEQ ID NO 175
<211> LENGTH: 778
<212> TYPE: PRT
<213> ORGANISM: Artificial Sequence
<220> FEATURE:
<223> OTHER INFORMATION: CER127 protein
<220> FEATURE:
<221> NAME/KEY: sig_peptide
<222> LOCATION: 1...22

<400> SEQUENCE: 175

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95

Leu Thr Ile Ser Asn Thr Asn Arg Gly Asp Ser Gly Val Tyr Cys Cys
            100                 105                 110
```

-continued

```
Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
                180                 185                 190

Ser Thr Thr Pro Gly Ser Phe Ser Gln Glu Thr Thr Lys Gly Ser Ala
                195                 200                 205

Phe Thr Thr Glu Ser Glu Thr Leu Pro Ala Ser Asn His Ser Gln Arg
                210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ile Ala Cys Cys Val Gly
                275                 280                 285

Phe Val Leu Met Val Leu Leu Phe Leu Ala Phe Leu Met Ala Ala Ala
                290                 295                 300

Ser Val Thr Pro Pro Gly Ser Leu Glu Leu Leu Gln Pro Gly Phe Ser
305                 310                 315                 320

Lys Thr Leu Leu Gly Thr Lys Leu Glu Ala Lys Tyr Leu Cys Ser Ala
                325                 330                 335

Cys Arg Asn Val Leu Arg Arg Pro Phe Gln Ala Gln Cys Gly His Arg
                340                 345                 350

Tyr Cys Ser Phe Cys Leu Ala Ser Ile Leu Ser Ser Gly Pro Gln Asn
                355                 360                 365

Cys Ala Ala Cys Val His Glu Gly Ile Tyr Glu Glu Gly Ile Ser Ile
                370                 375                 380

Leu Glu Ser Ser Ser Ala Phe Pro Asp Asn Ala Ala Arg Arg Glu Val
385                 390                 395                 400

Glu Ser Leu Pro Ala Val Cys Pro Ser Asp Gly Cys Thr Trp Lys Gly
                405                 410                 415

Thr Leu Lys Glu Tyr Glu Ser Cys His Glu Gly Arg Cys Pro Leu Met
                420                 425                 430

Leu Thr Glu Cys Pro Ala Cys Lys Gly Leu Val Arg Leu Gly Glu Lys
                435                 440                 445

Glu Arg His Leu Glu His Glu Cys Pro Glu Arg Ser Leu Ser Cys Arg
450                 455                 460

His Cys Arg Ala Pro Cys Cys Gly Ala Asp Val Lys Ala His His Glu
465                 470                 475                 480

Val Cys Pro Lys Phe Pro Leu Thr Cys Asp Gly Cys Gly Lys Lys Lys
                485                 490                 495

Ile Pro Arg Glu Lys Phe Gln Asp His Val Lys Thr Cys Gly Lys Cys
                500                 505                 510

Arg Val Pro Cys Arg Phe His Ala Ile Gly Cys Leu Glu Thr Val Glu
                515                 520                 525
```

```
Gly Glu Lys Gln Gln Glu His Glu Val Gln Trp Leu Arg Glu His Leu
            530                 535                 540
Ala Met Leu Leu Ser Ser Val Leu Glu Ala Lys Pro Leu Leu Gly Asp
545                 550                 555                 560
Gln Ser His Ala Gly Ser Glu Leu Leu Gln Arg Cys Glu Ser Leu Glu
                565                 570                 575
Lys Lys Thr Ala Thr Phe Glu Asn Ile Val Cys Val Leu Asn Arg Glu
            580                 585                 590
Val Glu Arg Val Ala Met Thr Ala Glu Ala Cys His Arg Phe His Gly
        595                 600                 605
Leu Trp Tyr Met Lys Met Met Trp Ala Trp Leu Gln Ala Lys Arg Lys
    610                 615                 620
Pro Arg Lys Ala Pro Ser Arg Asn Ile Cys Tyr Asp Ala Phe Val Ser
625                 630                 635                 640
Tyr Ser Glu Arg Asp Ala Tyr Trp Val Glu Asn Leu Met Val Gln Glu
                645                 650                 655
Leu Glu Asn Phe Asn Pro Pro Phe Lys Leu Cys Leu His Lys Arg Asp
            660                 665                 670
Phe Ile Pro Gly Lys Trp Ile Ile Asp Asn Ile Ile Asp Ser Ile Glu
        675                 680                 685
Lys Ser His Lys Thr Val Phe Val Leu Ser Glu Asn Phe Val Lys Ser
    690                 695                 700
Glu Trp Cys Lys Tyr Glu Leu Asp Phe Ser His Phe Arg Leu Phe Asp
705                 710                 715                 720
Glu Asn Asn Asp Ala Ala Ile Leu Ile Leu Leu Glu Pro Ile Glu Lys
                725                 730                 735
Lys Ala Ile Pro Gln Arg Phe Cys Lys Leu Arg Lys Ile Met Asn Thr
            740                 745                 750
Lys Thr Tyr Leu Glu Trp Pro Met Asp Glu Ala Gln Arg Glu Gly Phe
        755                 760                 765
Trp Val Asn Leu Arg Ala Ala Ile Lys Ser
    770                 775

<210> SEQ ID NO 176
<211> LENGTH: 796
<212> TYPE: PRT
<213> ORGANISM: Artificial Sequence
<220> FEATURE:
<223> OTHER INFORMATION: CER128 protein
<220> FEATURE:
<221> NAME/KEY: sig_peptide
<222> LOCATION: 1...22

<400> SEQUENCE: 176

Met Ser Lys Gly Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
    50                  55                  60

Asn Ala Glu Leu Leu Arg Thr Asp Gly Thr Arg Ile Ile Ser Arg Lys
65                  70                  75                  80

Ser Thr Lys Tyr Thr Leu Leu Gly Lys Val Gln Phe Gly Glu Val Ser
                85                  90                  95
```

-continued

```
Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
        115                 120                 125

Leu Glu Leu Arg Arg Ala Thr Thr Lys Lys Pro Thr Thr Thr Thr
    130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Thr Pro Pro
                165                 170                 175

Gln Thr Leu Ala Thr Thr Ala Phe Ser Thr Ala Val Thr Thr Cys Pro
        180                 185                 190

Ser Thr Thr Pro Gly Ser Phe Ser Gln Glu Thr Thr Lys Gly Ser Ala
        195                 200                 205

Phe Thr Thr Glu Ser Glu Thr Leu Pro Ala Ser Asn His Ser Gln Arg
        210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                245                 250                 255

Thr Thr Leu Thr Thr Ser Glu Ser Leu Gln Lys Thr Thr Lys Ser His
        260                 265                 270

Gln Ile Asn Ser Arg Gln Thr Ile Leu Ile Ala Cys Cys Val Gly
        275                 280                 285

Phe Val Leu Met Val Leu Leu Phe Leu Ala Phe Leu Met Ala Ala Ala
290                 295                 300

Ser Val Thr Pro Pro Gly Ser Leu Glu Leu Leu Gln Pro Gly Phe Ser
305                 310                 315                 320

Lys Thr Leu Leu Gly Thr Lys Leu Glu Ala Lys Tyr Leu Cys Ser Ala
                325                 330                 335

Cys Arg Asn Val Leu Arg Arg Pro Phe Gln Ala Gln Cys Gly His Arg
        340                 345                 350

Tyr Cys Ser Phe Cys Leu Ala Ser Ile Leu Ser Ser Gly Pro Gln Asn
        355                 360                 365

Cys Ala Ala Cys Val His Glu Gly Ile Tyr Glu Glu Gly Ile Ser Ile
        370                 375                 380

Leu Glu Ser Ser Ser Ala Phe Pro Asp Asn Ala Ala Arg Arg Glu Val
385                 390                 395                 400

Glu Ser Leu Pro Ala Val Cys Pro Ser Asp Gly Cys Thr Trp Lys Gly
                405                 410                 415

Thr Leu Lys Glu Tyr Glu Ser Cys His Glu Gly Arg Cys Pro Leu Met
        420                 425                 430

Leu Thr Glu Cys Pro Ala Cys Lys Gly Leu Val Arg Leu Gly Glu Lys
        435                 440                 445

Glu Arg His Leu Glu His Glu Cys Pro Glu Arg Ser Leu Ser Cys Arg
    450                 455                 460

His Cys Arg Ala Pro Cys Cys Gly Ala Asp Val Lys Ala His His Glu
465                 470                 475                 480

Val Cys Pro Lys Phe Pro Leu Thr Cys Asp Gly Cys Gly Lys Lys Lys
                485                 490                 495

Ile Pro Arg Glu Lys Phe Gln Asp His Val Lys Thr Cys Gly Lys Cys
        500                 505                 510

Arg Val Pro Cys Arg Phe His Ala Ile Gly Cys Leu Glu Thr Val Glu
```

```
            515                 520                 525
Gly Glu Lys Gln Gln Glu His Glu Val Gln Trp Leu Arg Glu His Leu
530                 535                 540

Ala Met Leu Leu Ser Ser Val Leu Glu Ala Lys Pro Leu Leu Gly Asp
545                 550                 555                 560

Gln Ser His Ala Gly Ser Glu Leu Leu Gln Arg Cys Glu Ser Leu Glu
                565                 570                 575

Lys Lys Thr Ala Thr Phe Glu Asn Ile Val Cys Val Leu Asn Arg Glu
            580                 585                 590

Val Glu Arg Val Ala Met Thr Ala Glu Ala Cys His His Leu Phe Tyr
        595                 600                 605

Trp Asp Val Trp Phe Ile Tyr Asn Val Cys Leu Ala Lys Val Lys Gly
    610                 615                 620

Tyr Arg Ser Leu Ser Thr Ser Gln Thr Phe Tyr Asp Ala Tyr Ile Ser
625                 630                 635                 640

Tyr Asp Thr Lys Asp Ala Ser Val Thr Asp Trp Val Ile Asn Glu Leu
                645                 650                 655

Arg Tyr His Leu Glu Glu Ser Arg Asp Lys Asn Val Leu Leu Cys Leu
            660                 665                 670

Glu Glu Arg Asp Trp Asp Pro Gly Leu Ala Ile Ile Asp Asn Leu Met
        675                 680                 685

Gln Ser Ile Asn Gln Ser Lys Lys Thr Val Phe Val Leu Thr Lys Lys
690                 695                 700

Tyr Ala Lys Ser Trp Asn Phe Lys Thr Ala Phe Tyr Leu Ala Leu Gln
705                 710                 715                 720

Arg Leu Met Asp Glu Asn Met Asp Val Ile Ile Phe Ile Leu Leu Glu
                725                 730                 735

Pro Val Leu Gln His Ser Gln Tyr Leu Arg Leu Arg Gln Arg Ile Cys
            740                 745                 750

Lys Ser Ser Ile Leu Gln Trp Pro Asp Asn Pro Lys Ala Glu Gly Leu
        755                 760                 765

Phe Trp Gln Thr Leu Arg Asn Val Val Leu Thr Glu Asn Asp Ser Arg
770                 775                 780

Tyr Asn Asn Met Tyr Val Asp Ser Ile Lys Gln Tyr
785                 790                 795

<210> SEQ ID NO 177
<211> LENGTH: 796
<212> TYPE: PRT
<213> ORGANISM: Artificial Sequence
<220> FEATURE:
<223> OTHER INFORMATION: CER129 protein
<220> FEATURE:
<221> NAME/KEY: sig_peptide
<222> LOCATION: 1...22

<400> SEQUENCE: 177

Met Ser Lys Gly Leu Leu Leu Leu Trp Leu Val Thr Glu Leu Trp Trp
1               5                   10                  15

Leu Tyr Leu Thr Pro Ala Ala Ser Glu Asp Thr Ile Ile Gly Phe Leu
            20                  25                  30

Gly Gln Pro Val Thr Leu Pro Cys His Tyr Leu Ser Trp Ser Gln Ser
        35                  40                  45

Arg Asn Ser Met Cys Trp Gly Lys Gly Ser Cys Pro Asn Ser Lys Cys
50                  55                  60

Asn Ala Glu Leu Leu Arg Thr Asp Gly Thr Arg Ile Ile Ser Arg Lys
```

```
                65                  70                  75                  80
Ser Thr Lys Tyr Thr Leu Leu Gly Lys Val Gln Phe Gly Glu Val Ser
                        85                  90                  95

Leu Thr Ile Ser Asn Thr Asn Arg Gly Asp Ser Gly Val Tyr Cys Cys
            100                 105                 110

Arg Ile Glu Val Pro Gly Trp Phe Asn Asp Val Lys Lys Asn Val Arg
            115                 120                 125

Leu Glu Leu Arg Arg Ala Thr Thr Lys Lys Pro Thr Thr Thr Thr
130                 135                 140

Arg Pro Thr Thr Thr Pro Tyr Val Thr Thr Thr Pro Glu Leu Leu
145                 150                 155                 160

Pro Thr Thr Val Met Thr Thr Ser Val Leu Pro Thr Thr Pro Pro
                    165                 170                 175

Gln Thr Leu Ala Thr Thr Ala Phe Ser Thr Ala Val Thr Cys Pro
                180                 185                 190

Ser Thr Thr Pro Gly Ser Phe Ser Gln Glu Thr Thr Lys Gly Ser Ala
                    195                 200                 205

Phe Thr Thr Glu Ser Glu Thr Leu Pro Ala Ser Asn His Ser Gln Arg
            210                 215                 220

Ser Met Met Thr Ile Ser Thr Asp Ile Ala Val Leu Arg Pro Thr Gly
225                 230                 235                 240

Ser Asn Pro Gly Ile Leu Pro Ser Thr Ser Gln Leu Thr Thr Gln Lys
                        245                 250                 255

Thr Thr Leu Thr Thr Ser Glu Ser Leu Gln Lys Thr Thr Lys Ser His
                260                 265                 270

Gln Ile Asn Ser Arg Gln Thr Ile Leu Ile Ala Cys Cys Val Gly
            275                 280                 285

Phe Val Leu Met Val Leu Leu Phe Leu Ala Phe Leu His His Leu Phe
            290                 295                 300

Tyr Trp Asp Val Trp Phe Ile Tyr Asn Val Cys Leu Ala Lys Val Lys
305                 310                 315                 320

Gly Tyr Arg Ser Leu Ser Thr Ser Gln Thr Phe Tyr Asp Ala Tyr Ile
                    325                 330                 335

Ser Tyr Asp Thr Lys Asp Ala Ser Val Thr Asp Trp Val Ile Asn Glu
                340                 345                 350

Leu Arg Tyr His Leu Glu Glu Ser Arg Asp Lys Asn Val Leu Leu Cys
            355                 360                 365

Leu Glu Glu Arg Asp Trp Asp Pro Gly Leu Ala Ile Ile Asp Asn Leu
370                 375                 380

Met Gln Ser Ile Asn Gln Ser Lys Lys Thr Val Phe Val Leu Thr Lys
385                 390                 395                 400

Lys Tyr Ala Lys Ser Trp Asn Phe Lys Thr Ala Phe Tyr Leu Ala Leu
                    405                 410                 415

Gln Arg Leu Met Asp Glu Asn Met Asp Val Ile Ile Phe Ile Leu Leu
                420                 425                 430

Glu Pro Val Leu Gln His Ser Gln Tyr Leu Arg Leu Arg Gln Arg Ile
            435                 440                 445

Cys Lys Ser Ser Ile Leu Gln Trp Pro Asp Asn Pro Lys Ala Glu Gly
            450                 455                 460

Leu Phe Trp Gln Thr Leu Arg Asn Val Val Leu Thr Glu Asn Asp Ser
465                 470                 475                 480

Arg Tyr Asn Asn Met Tyr Val Asp Ser Ile Lys Gln Tyr Met Ala Ala
                    485                 490                 495
```

```
Ala Ser Val Thr Pro Pro Gly Ser Leu Glu Leu Leu Gln Pro Gly Phe
            500                 505                 510

Ser Lys Thr Leu Leu Gly Thr Lys Leu Glu Ala Lys Tyr Leu Cys Ser
            515                 520                 525

Ala Cys Arg Asn Val Leu Arg Arg Pro Phe Gln Ala Gln Cys Gly His
            530                 535                 540

Arg Tyr Cys Ser Phe Cys Leu Ala Ser Ile Leu Ser Ser Gly Pro Gln
545                 550                 555                 560

Asn Cys Ala Ala Cys Val His Glu Gly Ile Tyr Glu Glu Gly Ile Ser
                565                 570                 575

Ile Leu Glu Ser Ser Ser Ala Phe Pro Asp Asn Ala Ala Arg Arg Glu
            580                 585                 590

Val Glu Ser Leu Pro Ala Val Cys Pro Ser Asp Gly Cys Thr Trp Lys
            595                 600                 605

Gly Thr Leu Lys Glu Tyr Glu Ser Cys His Glu Gly Arg Cys Pro Leu
            610                 615                 620

Met Leu Thr Glu Cys Pro Ala Cys Lys Gly Leu Val Arg Leu Gly Glu
625                 630                 635                 640

Lys Glu Arg His Leu Glu His Glu Cys Pro Glu Arg Ser Leu Ser Cys
                645                 650                 655

Arg His Cys Arg Ala Pro Cys Cys Gly Ala Asp Val Lys Ala His His
                660                 665                 670

Glu Val Cys Pro Lys Phe Pro Leu Thr Cys Asp Gly Cys Gly Lys Lys
            675                 680                 685

Lys Ile Pro Arg Glu Lys Phe Gln Asp His Val Lys Thr Cys Gly Lys
            690                 695                 700

Cys Arg Val Pro Cys Arg Phe His Ala Ile Gly Cys Leu Glu Thr Val
705                 710                 715                 720

Glu Gly Glu Lys Gln Gln Glu His Glu Val Gln Trp Leu Arg Glu His
                725                 730                 735

Leu Ala Met Leu Leu Ser Ser Val Leu Glu Ala Lys Pro Leu Leu Gly
            740                 745                 750

Asp Gln Ser His Ala Gly Ser Glu Leu Leu Gln Arg Cys Glu Ser Leu
            755                 760                 765

Glu Lys Lys Thr Ala Thr Phe Glu Asn Ile Val Cys Val Leu Asn Arg
            770                 775                 780

Glu Val Glu Arg Val Ala Met Thr Ala Glu Ala Cys
785                 790                 795
```